US012609184B2

(12) United States Patent
Miron

(10) Patent No.: US 12,609,184 B2
(45) Date of Patent: Apr. 21, 2026

(54) METHODS AND COMPOSITIONS FOR IMPROVED MULTIPLEX GENOTYPING AND SEQUENCING

(71) Applicant: COVARIANCE BIOSCIENCES, LLC, Cleveland, OH (US)

(72) Inventor: Alexander Miron, Pepper Pike, OH (US)

(73) Assignee: COVARIANCE BIOSCIENCES, LLC, Cleveland, OH (US)

( * ) Notice: Subject to any disclaimer, the term of this patent is extended or adjusted under 35 U.S.C. 154(b) by 1387 days.

(21) Appl. No.: 17/255,722

(22) PCT Filed: Jun. 28, 2019

(86) PCT No.: PCT/US2019/039921
§ 371 (c)(1),
(2) Date: Dec. 23, 2020

(87) PCT Pub. No.: WO2020/006475
PCT Pub. Date: Jan. 2, 2020

(65) Prior Publication Data
US 2022/0310203 A1      Sep. 29, 2022

Related U.S. Application Data

(60) Provisional application No. 62/692,293, filed on Jun. 29, 2018.

(51) Int. Cl.
*G16B 25/20*       (2019.01)
*C12Q 1/686*       (2018.01)
*G16B 40/00*       (2019.01)

(52) U.S. Cl.
CPC ............. *G16B 25/20* (2019.02); *C12Q 1/686* (2013.01); *G16B 40/00* (2019.02)

(58) Field of Classification Search
None
See application file for complete search history.

(56) References Cited

U.S. PATENT DOCUMENTS

| | | | |
|---|---|---|---|
| 6,892,141 | B1 | 5/2005 | Nakae et al. |
| 7,565,248 | B2 | 7/2009 | Peterson |
| 8,003,317 | B2 | 8/2011 | Beaulieu et al. |
| 8,349,566 | B2 | 1/2013 | Beaulieu et al. |
| 8,428,886 | B2 | 4/2013 | Wong et al. |
| 8,825,412 | B2 | 9/2014 | Rabinowitz et al. |
| 9,068,223 | B2 | 6/2015 | Beaulieu et al. |
| 9,896,724 | B2 | 2/2018 | Beaulieu et al. |
| 10,017,812 | B2 | 7/2018 | Rabinowitz et al. |
| 2003/0096277 | A1 | 5/2003 | Chen |
| 2003/0097223 | A1 | 5/2003 | Nakae et al. |
| 2003/0130802 | A1 | 7/2003 | Mei et al. |
| 2003/0198987 | A1 | 10/2003 | Matveeva |
| 2004/0009484 | A1 | 1/2004 | Wolber et al. |
| 2007/0259337 | A1 | 11/2007 | Hully et al. |
| 2009/0068664 | A1 | 3/2009 | Lyamichev et al. |
| 2010/0184153 | A1 | 7/2010 | Brookes |
| 2012/0058515 | A1 | 3/2012 | Morley et al. |
| 2013/0123113 | A1 | 5/2013 | Tao et al. |
| 2013/0123120 | A1 | 5/2013 | Zimmermann et al. |
| 2014/0141981 | A1 | 5/2014 | Zimmermann et al. |
| 2015/0354000 | A1 | 12/2015 | Borodina et al. |
| 2016/0068903 | A1 | 3/2016 | Zhou et al. |
| 2016/0098515 | A1 | 4/2016 | Dotson et al. |
| 2016/0306915 | A1 | 10/2016 | Kim et al. |
| 2016/0369333 | A1 | 12/2016 | Babiarz et al. |
| 2017/0051355 | A1 | 2/2017 | Zimmermann et al. |
| 2018/0004894 | A1 | 1/2018 | Dotson et al. |

FOREIGN PATENT DOCUMENTS

WO      2017109762 A1      6/2017

OTHER PUBLICATIONS

Fondevila, M., Børsting, C., Phillips, C., De La Puente, M., Carracedo, A., Morling, N., Lareu, M.V. and EN Consortium, 2017. Forensic SNP genotyping with SNAPshot: technical considerations for the development and optimization of multiplexed SNP assays. Forensic Sci Rev, 29(1), pp. 57-76. (Year: 2017).*
Kaplinski, L. and Remm, M., 2015. MultiPLX: Automatic grouping and evaluation of PCR primers. PCR Primer Design, pp. 127-142. (Year: 2015).*
Kitchen, J.L., Moore, J.D., Palmer, S.A. and Allaby, R.G., 2012. MCMC-ODPR: primer design optimization using Markov Chain Monte Carlo sampling. BMC bioinformatics, 13, pp. 1-10. (Year: 2012).*
Kayima et al., "Association of genetic variation with blood pressure traits among East Africans." Clinical genetics 92.5 (2017): 487-494.
Rawlins et al., "An Amish founder variant consolidates disruption of CEP55 as acause of hydranencephaly and renal dysplasia" European Journal of Human Genetics (2019) 27:657-662.
Soong et al., "Evidence for lineage continuity between early serousproliferations (ESPs) in the Fallopian tube and disseminatedhigh-grade serous carcinomas", J Pathol (2018); 246: 344-351.
Meserve et al., "Evidence of a Monoclonal Origin for Bilateral Serous Tubal Intraepithelial Neoplasia" Int J Gynecol Pathol. Sep. 2019;38(5):443-448.

(Continued)

*Primary Examiner* — G. Steven Vanni
*Assistant Examiner* — Meredith Abbott Vassell
(74) *Attorney, Agent, or Firm* — Nixon Peabody LLP; Mark J. FitzGerald; Alissa R. Young

(57) ABSTRACT

The technology described herein is directed to methods of designing primers for multiplex PCR amplification. Also described herein are methods for equalization of reads in these approaches. A variation is described herein that permits single base multiplexed sequencing on an NGS platform. Also described herein are methods to rapidly analyze NGS sequencing data to automatically provide genotype or sequencing results and methods to identify and quantify low abundance rare variants in clinically relevant genes in a minority of tumor cells from a complex mixture of cells.

17 Claims, 6 Drawing Sheets

Specification includes a Sequence Listing.

(56) References Cited

OTHER PUBLICATIONS

Beaucage et al. "Advances in the Synthesis of Oligonucleotides by the Phosphoramidite Approach." Tetrahedron 48 (12): 2223-2311 (1992).

Calinski et al. "A dendrite method for cluster analysis." Communications in Statistics 3(1): 1-27 (1974).

Caruthers. "The chemical synthesis of DNA/RNA: our gift to science." J Biol Chem. 288(2): 1420-1427 (2013).

Chang et al. "N-Dimension Golden Section Search: Its Variants and Limitations." 2nd International Conference on Biomedical Engineering and Informatics, Oct. 17-19, 2009.

Fraley et al. "How Many Clusters? Which Clustering Method? Answers Via Model-Based Cluster Analysis." The Computer Journal 41(8): 578-588 (1998).

Goedecker. "Minima hopping: An efficient search method for the global minimum of the potential energy surface of complex molecular systems." J. Chem. Phys. 120(21): 9911-9917 (2004).

Hansen et al. "Neural Network Ensembles." IEEE Transactions on Pattern Analysis & Machine Intelligence 12(10): 993-1001 (1990).

Mandic. "A Generalized Normalized Gradient Descent Algorithm." IEEE Signal Processing Letters 11(2): 115-118 (2004).

Metropolis et al. "The Monte Carlo Method." J Am Stat Assoc. 44(247): 335-41 (1949).

Nugent et al. "Clustering with Confidence: A Binning Approach." available on the world wide web at stat.cmu.edu/tr/tr870/tr870.pdf (2008).

Owczarzy et al. "IDT SciTools: a suite for analysis and design of nucleic acid oligomers." Nucleic Acids Res. 36 (Web Server issue): W163-W169 (2008).

Panjkovich et al. "Comparison of different melting temperature calculation methods for short DNA sequences." Bioinformatics 21(6): 711-722 (2005).

Rozen et al. "Primer3 on the WWW for general users and for biologist programmers." Methods Mol Biol. 132: 365-86 (2000).

Ruder. "An overview of gradient descent optimization algorithms." 2016, available on the world wide web at arxiv.org/abs/1609.04747.

Santalucia. "A unified view of polymer, dumbbell, and oligonucleotide DNA nearest-neighbor thermodynamics." Proc. Natl Acad. Sci. USA 95: 1460-1465 (1998).

Scott et al. "A Cluster Analysis Method for Grouping Means in the Analysis of Variance." Biometrics 30(3): 507-512 (1974).

Specht. "A general regression neural network." IEEE Transactions on Neural Networks 2(6): 568-576 (1991).

Sugimoto et al. "Thermodynamic parameters to predict stability of RNA/DNA hybrid duplexes." Biochemistry 34: 11211-11216 (1995).

Huang et al. "Integrated minimum-set primers and unique probe design algorithms for differential detection on symptom-related pathogens." Bioinformatics 21(24): 4330-4337 (2005).

Kaplinski et al. "MultiPLX: automatic grouping and evaluation of PCR primers." Bioinformatics 21(8): 1701-1702 (2004).

* cited by examiner

Assay Specific
2X PCR mix 1.5 uL

384 Amplicon MIX reactions

384 DNA Samples 1.5 uL

PCR

1x BARCODING MIX
(384 individual mixes)

3 uL

Barcoding
Reaction MIX

PCR 100 nL automated transfer
(disposable pin tool)

Mix All Wells

384 Amplicon MIX PCR Products

Purify and Quantitate

NGS

METHODS AND COMPOSITIONS FOR IMPROVED MULTIPLEX GENOTYPING AND SEQUENCING

CROSS-REFERENCE TO RELATED APPLICATIONS

This application is a 35 U.S.C. § 371 National Phase Entry Application of International Patent Application No. PCT/US2019/039921 filed on Jun. 28, 2019 which claims benefit under 35 U.S.C. § 119(e) of U.S. Provisional Application No. 62/692,293 filed Jun. 29, 2018, the contents of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Jun. 27, 2019, is named 079753-093010WOPT_SL.txt and is 389,212 bytes in size.

TECHNICAL FIELD

The technology described herein relates to methods and compositions for multiplexed genotyping and sequencing.

BACKGROUND

So-called "Next Generation Sequencing" (NGS) or "NextGen" nucleic acid sequencing has revolutionized nucleic acid analysis and bioinformatics. These sequencing approaches rely on the concept of massively parallel processing, in which millions of short sequence reads are generated in parallel, followed by in silico assembly of the resulting data into corresponding genomic, expressed gene or other relevant sequences.

While the details vary, most NGS approaches rely upon at least one multiplex amplification step. This is particularly true when NGS approaches are applied to the genotyping of known genomic sequence variations, including, but not limited to single nucleotide polymorphisms (SNPs). For such approaches, when hundreds to thousands of target variable sequences are genotyped in a single reaction, interactions between primers can result in products in which primers in the reaction serve as both template and primer to generate so-called "primer dimer" extension products.

SUMMARY

Described herein are improved methods of designing primers for multiplex PCR amplification. By minimizing primer:primer interactions, the primer-design methods described herein can dramatically improve throughput in NGS-based multiplex genotyping methods. Thus, provided herein are methods for primer design that permit large amplicon number multiplexing and genotype calling.

It has also been recognized that uneven amplification of genotyping targets reduces the efficiency, and therefore the throughput of NGS-based multiplex genotyping approaches. Accordingly, also described herein are methods for equalization of reads in these approaches. Embodiments of the methods use anti-sense oligos in various concentrations to inhibit high-performing amplicons from forming, and thereby allow poorer performing amplicons to produce more data. Some embodiments use anti-sense oligos with additional sequences on their 5'-end that permanently inactivate primers in solution once annealed and extended (inactivator oligos). Other embodiments use anti-sense oligos with reversible binding characteristics having only complementary sequences (attenuator oligos).

The methods described herein permit efficient sequencing and genotype calling in high multiplex. Thus, described herein are methods for performing multiplex PCR that results in even reads produced by NGS instruments for each amplicon (for 2-10,000 amplicons) and each sample (for 1-100,000 DNA samples). In one embodiment, a variation is described herein that permits single base multiplexed sequencing on an NGS platform, in order to avoid sequencing additional regions where this is beneficial.

Also described herein are methods to rapidly analyze NGS sequencing data using personalized software to automatically provide genotype or sequencing results, and methods to identify and quantify low abundance rare variants in clinically relevant genes in a minority of tumor cells from a complex mixture of cells.

In one aspect, described herein is a method for primer design that allows for large amplicon number multiplexing. In one embodiment, the method comprises the synthesis and use of a computer algorithm to perform steps as described herein to identify a primer set that permits large amplicon number multiplexing, which can be followed by synthesis of the designed primer set, e.g., for multiplex genotyping, among other uses. In one embodiment, the primer design algorithm is incorporated into the PlexForm™ software package.

In one aspect, described herein is a method of preparing a primer set for multiplex amplification or genotyping, the method comprising: A) for a given set N of variable genomic target sequences to be genotyped in a sample, designing a set of forward and reverse amplification primers that will amplify a sequence comprising each variable genomic target sequence in a multiplex amplification reaction, wherein the designing includes the steps of: 1) identifying all possible primers of 17 to 35 nucleotides within 100 base pairs of each genomic target sequence variation in set N of variable genomic target sequences; 2) for each member of set N, selecting a subset of primer pairs from the set of step (1) that satisfies the conditions for a primer selection algorithm; 3) evaluating specificity of primer pairs chosen in step (2) in the genome, keeping only those pairs predicted to be specific for their respective targets; 4) selecting a set of optimized primers for the amplification of target gene set N, where the optimal primers are selected to minimize primer-primer interactions with other primers in the set by iterative calculation of predicted ΔG (or delta G, Gibbs free energy) for interactions between primers to generate a fitness score and use of a fitness score optimization method selected from one or a combination of the group consisting of: a) a Monte Carlo random or pseudo-random selection method; b) a golden section search; c) gradient descent; d) minima hopping; e) genetic algorithm; f) neural networks; g) cluster analysis, in which substitution is picked to minimize score; and h) cluster analysis to create bins; and B) synthesizing the optimized primer set selected in step (4).

In another aspect, described herein is a method of preparing a primer set for multiplex amplification or genotyping, the method comprising: A) for a given set N of variable genomic target sequences to be genotyped in a sample, designing a set of forward and reverse amplification primers that will amplify a sequence comprising each variable genomic target sequence in a multiplex amplification reaction, wherein the designing includes the steps of: 1) identifying all possible primers of 17 to 35 nucleotides within 100 base pairs of each genomic target sequence variation in set N of variable genomic target sequences; 2) for the primers identified in step (1), randomly selecting a primer pair for each target in set N that satisfies the conditions for a primer selection algorithm; 3) evaluating specificity of primer pairs chosen in step (2) in the genome, keeping only those pairs predicted to be specific for their respective targets; 4) repeat step (2) on the primer pairs kept from step (3) to generate set P, a population of randomly selected primer sets for each target in set N; 5) generating a Fitness Score for each member of population P based upon ΔG for all possible interactions between candidate primers in each member of the population; 6) picking acceptable member(s) of the population P based on Fitness Score; 7) repeating steps (4)-(6) iteratively until a set of primer pairs for target genes identified in step (6) has a Fitness Score at a predetermined threshold; and B) synthesizing the primer set identified in step (7).

In one embodiment of this method, the Fitness Score is generated according to the rule: a) G=the set of ΔG's for all possible interactions determined for a given member of set P; and b) Fitness Score is calculated by: i) for each member of set P, calculating the sum, S, of |ΔG|$^Q$ for each ΔG value in that member, wherein Q is a weighting factor constant exponent that makes large ΔG absolute values much larger than small values; ii) S'=S/# of ΔG values in G; iii) H=T/S', wherein T is a constant that makes H small for large values of S' and H large for small values of S'; and iv) Fitness Score=H$^R$, wherein R is a weighting factor constant exponent that makes large values of H larger, and small values of H smaller.

In another aspect, described herein is a method of preparing a primer set for multiplex amplification or genotyping, the method comprising: A) for a given set N of variable genomic target sequences to be genotyped in a sample, designing a set of forward and reverse amplification primers that will amplify a sequence comprising each variable genomic target sequence in a multiplex amplification reaction, wherein the designing includes the steps of: 1) identifying all possible primers of 17 to 35 nucleotides within 100 base pairs of each genomic target sequence variation in set N of variable genomic target sequences; 2) for the primers identified in step (1), randomly selecting a primer pair for each target in set N that satisfies the conditions for a primer selection algorithm and is predicted to be specific for its target in the genome, or providing a primer pair for each target in set N, that has been selected to reduce potential for primer:primer interactions with other primers in the set and is predicted to be specific for its target in the genome; 3) repeat step (2) to generate population Z, of size 2 or greater, of primer pair sets for each target in set N; 4) generating a Fitness Score for each member of population Z based upon ΔG for all possible interactions between candidate primers in each member of the population; 5) selecting the worst members of population Z based on Fitness Scores as set W; 6) replacing a primer for a single target from W with another primer from step (2), and generating a Fitness Score for the resulting set; wherein if the change results in an improved Fitness Score relative to the Fitness Score generated in step (4), the resulting new set W' replaces set W, and if the change results in a no change in Fitness Score or a decreased Fitness Score, keeping set W; 7) iteratively repeating steps (4)-(6) on the set W or W' retained in each iteration of step (6) until a set of primer pairs for target genes in set N is identified that has a Fitness Score at a predetermined threshold, or, if a predetermined threshold is not reached by iteratively repeating steps (4)-(6), beginning again at step (2) and iteratively repeating steps (4)-(6) until a set of primer pairs for target genes in set N is identified that has a Fitness Score at the predetermined threshold; and B) synthesizing the primer set selected in step (7) that reaches the predetermined Fitness Score threshold.

In one embodiment of the aspect, the Fitness Score is generated according to the rule: a) G=the set of ΔG's for all possible interactions determined for a given member of set P; and b) Fitness Score is calculated by: i) for each member of set P, calculating the sum, S, of |ΔG|$^Q$ for each ΔG value in that member, wherein Q is a weighting factor constant exponent that makes large ΔG absolute values much larger than small values; ii) S'=S/# of ΔG values in G; iii) H=T/S', wherein T is a constant that makes H small for large values of S' and H large for small values of S'; and iv) Fitness Score=H$^R$, wherein R is a weighting factor constant exponent that makes large values of H larger, and small values of H smaller.

In another embodiment of the aspect, the step of providing a primer pair for each target in set N that has been selected to reduce potential for primer:primer interactions with other primers in the set provides primer sets selected using one or more of a Monte Carlo random or pseudo-random selection method, a golden section search, gradient descent, minima hopping, a genetic algorithm, neural networks, cluster analysis in which substitution is picked to minimize score, or cluster analysis to create bins.

In another aspect, described herein is a method of preparing a primer set for multiplex amplification or genotyping, the method comprising: A) for a given set N of variable genomic target sequences to be genotyped in a sample, designing a set of forward and reverse amplification primers that will amplify a sequence comprising each variable genomic target sequence in a multiplex amplification reaction, wherein the designing includes the steps of: 1) identifying all possible primers of 17 to 35 nucleotides within 100 base pairs of each genomic target sequence variation in set N of variable genomic target sequences; 2) generating primer set Z, including a primer pair for each member of set N either by: (a) randomly selecting from the primers identified in step (1) a primer pair for each target in set N that satisfies the conditions for a primer selection algorithm and is predicted to be specific for its target in the genome; or (b) providing a primer pair for each target in set N that is predicted to be specific for its target in the genome, and that has been selected to reduce potential for primer:primer interactions with other primers in the set; 3) generating a Fitness Score for primer set Z based upon ΔG for all possible interactions between candidate primers in each member of the population; 4) making a change to a primer for a single target from set Z to generate new set Z', and generating a Fitness Score for set Z', wherein if the change results in an improved Fitness Score relative to that generated in step (3), the resulting new set Z' replaces set Z, and if the change results in no change in Fitness Score or a decreased Fitness Score, keeping set Z; and 5) repeating step (4) iteratively until further iterations do not improve fitness of set Z; and B) synthesizing the primer set selected in step (5).

In one embodiment of the aspect, the Fitness Score is generated according to the rule: a) G=the set of ΔG's for all possible interactions determined for members of primer set Z; and b) Fitness Score is calculated by: i) calculating the sum, S, of |ΔG|$^Q$ for each ΔG value, wherein Q is a weighting factor constant exponent that makes large ΔG absolute values much larger than small values; ii) S'=S/# of ΔG values in G; iii) H=T/S', wherein T is a constant that makes H small for large values of S' and H large for small values of S'; and iv) Fitness Score=$H^R$, wherein R is a weighting factor constant exponent that makes large values of H larger, and small values of H smaller.

In another aspect, described herein is a method of preparing a primer set for multiplex amplification or genotyping, the method comprising: A) for a given set N of variable genomic target sequences to be genotyped in a sample, designing a set of forward and reverse amplification primers that will amplify a sequence comprising each variable genomic target sequence in a multiplex amplification reaction, wherein the designing includes the steps of: 1) identifying all possible primers of 17 to 35 nucleotides within 100 base pairs of each genomic target sequence variation in set N of variable genomic target sequences; 2) providing a set of optimized primer pairs for the amplification of target gene set N, where the optimal primer pairs are predicted to be specific for their target genes in the genome, and are selected to minimize primer-primer interactions with other primers in the set by iterative calculation of predicted ΔG for all possible interactions between primers to generate a Fitness Score and use of a Fitness Score optimization method selected from one or a combination of the group consisting of: a) a Monte Carlo random or pseudo-random selection method; b) a golden section search; c) gradient descent; d) minima hopping; e) genetic algorithm; f) neural networks; g) cluster analysis, in which substitution is picked to minimize score; and h) cluster analysis to create bins; 3) adding the set of optimized primers of step (2) to set M; 4) while maintaining a degree of dissimilarity from primer sets included in set M, selecting a primer pair for each target in set N from step (1) and designating it set Z, wherein the primer pairs satisfy the conditions for a primer selection algorithm, and are predicted to be specific for their target genes in the genome; 5) optimizing primer pairs of set Z for the amplification of target gene set N, to minimize primer-primer interactions with other primers in the set by iterative calculation of predicted ΔG for all possible interactions between primers to generate a Fitness Score and use of a Fitness Score optimization method selected from one or a combination of methods (a)-(h) of step (2); and 6) repeating steps (2)-(5) iteratively until a set of primer pairs for target gene set N identified in step (5) has a Fitness Score at a predetermined threshold; and B) synthesizing the optimized primer set selected in step (6).

In one embodiment of the aspect, the Fitness Score is generated according to the rule: a) G=the set of ΔG's for all possible interactions determined for members of primer set Z; and b) Fitness Score is calculated by: i) calculating the sum, S, of $|ΔG|^Q$ for each ΔG value, wherein Q is a weighting factor constant exponent that makes large ΔG absolute values much larger than small values; ii) S'=S/# of ΔG values in G; iii) H=T/S', wherein T is a constant that makes H small for large values of S' and H large for small values of S'; and iv) Fitness Score=$H^R$, wherein R is a weighting factor constant exponent that makes large values of H larger, and small values of H smaller.

In another aspect, described herein is a method of preparing a primer set for multiplex amplification or genotyping, the method comprising: A) for a given set N of variable genomic target sequences to be genotyped in a sample, designing a set of forward and reverse amplification primers that will amplify a sequence comprising each variable genomic target sequence in a multiplex amplification reaction, wherein the designing includes the steps of: 1) identifying all possible primers of 17 to 35 nucleotides within 100 base pairs of each genomic target sequence variation in set N of variable genomic target sequences; 2) For each primer identified in step (1) creating a node $P_{nz}$, such node connected to a node for the corresponding target (TO, wherein: (i) each node outputs its ID and a numeric value; (ii) each $T_n$ produces ID of one of the P nodes connected to it; (iii) each one of the $T_n$ nodes is connected to all others; and (iv) each node $T_n$ represents a multilayer neural network; 3) calculating a Fitness Score for output of the neural network, and on the basis of Fitness Score, the value produced by the network is compared to target, and neural network parameters for a plurality of the $T_n$ are changed; 4) calculating Fitness Score again for output of the neural network with parameters changed in step (3); 5) determining if a change was beneficial or not to the fitness of the resulting set, wherein if the change was beneficial, the direction of change is maintained with smaller increments, and wherein if the change was not beneficial, either direction is reversed or the parameters revert to a previous state; 6) repeating steps (3)-(5) iteratively, wherein at a plurality of iterations random changes are made to the parameters of the network, and wherein when the rate of fitness improvement decreases, the frequency of such random changes is increased, until a set of primer pairs for target genes in set N is identified that has a fitness score at a predetermined threshold; and B) synthesizing the optimized primer set selected in step (6).

In one embodiment of the aspect, the Fitness Score is generated according to the rule: a) G=the set of ΔG's for all possible interactions determined for members of a primer set for targets N; and b) Fitness Score is calculated by: i) calculating the sum, S, of $|ΔG|^Q$ for each ΔG value, wherein Q is a weighting factor constant exponent that makes large ΔG absolute values much larger than small values; ii) S'=S/# of ΔG values in G; iii) H=T/S', wherein T is a constant that makes H small for large values of S' and H large for small values of S'; and iv) Fitness Score=$H^R$, wherein R is a weighting factor constant exponent that makes large values of H larger, and small values of H smaller.

In another aspect, described herein is a method of preparing a primer set for multiplex amplification or genotyping, the method comprising: A) for a given set N of variable genomic target sequences to be genotyped in a sample, designing a set of forward and reverse amplification primers that will amplify a sequence comprising each variable genomic target sequence in a multiplex amplification reaction, wherein the designing includes the steps of: 1) identifying all possible primers of 17 to 35 nucleotides within 100 base pairs of each genomic target sequence variation in set N of variable genomic target sequences; 2) picking a target at random, as well as a primer for such target, and placing it in set R; 3) picking an additional target, and calculating a Fitness Score evaluating all primers for this target in combination with primers already in set R on the basis of ΔG for all potential interactions, wherein the primer that results in the best Fitness Score is added to set R; 4) if fitness of set R is below a predetermined threshold T, removing one of the primers from R according to the following: calculating a Fitness Score for set Ri, wherein $i^{th}$ target with its primer is removed from set R, and the set with the best Fitness Score determines the target with its primer to be removed from set R and placed back into the pool of primers of step (1); and 5) repeating steps (3) and (4) until all targets are assigned primers; and B) synthesizing the optimized primer set selected in step (5). In this embodiment, if one is trying to pick a next primer to add to set R and any primer that is picked does not decrease fitness to such level that it is below T, options include restarting the process with a different starting point (primer) or decreasing the initial threshold T.

In one embodiment of the aspect, the Fitness Score is generated according to the rule: a) G=the set of ΔG's for all possible interactions determined for members of a primer set; and b) Fitness Score is calculated by: i) calculating the sum, S, of $|\Delta G|^Q$ for each ΔG value, wherein Q is a weighting factor constant exponent that makes large ΔG absolute values much larger than small values; ii) S'=S/# of ΔG values in G; iii) H=T/S', wherein T is a constant that makes H small for large values of S' and H large for small values of S'; and iv) Fitness Score=$H^R$, wherein R is a weighting factor constant exponent that makes large values of H larger, and small values of H smaller.

In another aspect, described herein is a method of preparing a primer set for multiplex amplification or genotyping, the method comprising: A) for a given set N of variable genomic target sequences to be genotyped in a sample, designing a set of forward and reverse amplification primers that will amplify a sequence comprising each variable genomic target sequence in a multiplex amplification reaction, wherein the designing includes the steps of: 1) identifying all possible primers of 17 to 35 nucleotides within 100 base pairs of each genomic target sequence variation in set N of variable genomic target sequences; 2) picking a target at random, as well as a primer for such target, and placing it in set R; 3) picking an additional target, and calculating a Fitness Score evaluating all primers for this target in combination with primers already in set R on the basis of ΔG for all potential interactions, wherein the primer that results in the best Fitness Score is added to set R; 4) if fitness of set R is below a predetermined threshold T, removing one of the primers from R according to the following: calculating a Fitness Score for set Ri, wherein $i^{th}$ target with its primer is removed from set R, and the set with the best Fitness Score determines the target with its primer to be removed from set R and placed back into the pool of primers of step (1); 5) repeating steps (3) and (4) until all targets are assigned primers; 6) once all targets are assigned primers, designating set R as $R_1$, and its fitness as $F_t$, 7) creating empty set $R_{z+1}$, where Z is the number of sets, with fitness $F_{z+1}$; 8) for each set Rz, where z is an index from 1 to number of sets R, determining the element that is worst for the set's fitness, and removing this element, designated Target E; 9) recalculating Fz after removal of E; 10) for all Rz, determining where E can be added so as to maximize Fz and maximize the minimum of Fz; and 11) if the minimum of Fz is below the predetermined threshold, repeating steps (7)-(10) until the standard deviation of Fz is below the predetermined threshold, thereby designing a multiplex primer set; and B) synthesizing the optimized primer set designed in step (11). In one embodiment, the step of determining the element in step (8) that is worst for fitness is performed in a method analogous to step (4).

In another aspect, described herein is a method of preparing a primer set for multiplex amplification or genotyping, the method comprising: A) for a given set N of variable genomic target sequences to be genotyped in a sample, designing a set of forward and reverse amplification primers that will amplify a sequence comprising each variable genomic target sequence in a multiplex amplification reaction, wherein the designing includes the steps of: 1) identifying all possible primers of 17 to 35 nucleotides within 100 base pairs of each genomic target sequence variation in set N of variable genomic target sequences; 2) for each member of set N, selecting from the set of primers in step (1) a subset of primer pairs that satisfies the conditions for a primer selection algorithm and is predicted to be specific for its target; 3) repeating step (2) to generate set P, a population of randomly selected primer sets for each target gene in set N; 4) calculating a Fitness Score for each member of the population P; 5) placing members of population P into a pool of candidate primer sets on the basis of Fitness Scores; 6) randomly selecting a plurality of "parent" sets of candidate primers from the pool of step (5), each parent set including a different pair of candidate primer sets, parent A and parent B; 7) for each parent set of candidate primers, creating a crossover set of candidate primers by replacing a subset of candidate primer pairs of parent A with the corresponding subset of primer pairs of parent B; 8) randomly replacing one primer pair in crossover set A with a different primer pair for the corresponding target sequence generated in step (2) to create a Generation 2 population of primer sets for each target gene in set N; and 9) repeating steps (4)-(8) iteratively until a set of primer pairs for target genes in set N is identified that has a Fitness Score at a predetermined threshold, and runs for an additional set amount of iterations with no measurable improvement in the fitness of the best member, whereby an optimized primer set is designed; and B) synthesizing the optimized primer set designed in step (9).

In one embodiment of the aspect, the Fitness Score is generated according to the rule: a) G=the set of ΔG's for all possible interactions determined for members of a primer set; and b) Fitness Score is calculated by: i) calculating the sum, S, of $|\Delta G|^Q$ for each ΔG value, wherein Q is a weighting factor constant exponent that makes large ΔG absolute values much larger than small values; ii) S'=S/# of ΔG values in G; iii) H=T/S', wherein T is a constant that makes H small for large values of S' and H large for small values of S'; and iv) Fitness Score=$H^R$, wherein R is a weighting factor constant exponent that makes large values of H larger, and small values of H smaller.

In another aspect, described herein is a method of preparing a primer set for multiplex amplification or genotyping, the method comprising: A) for a given set N of variable genomic target sequences to be genotyped in a sample, designing a set of forward and reverse amplification primers that will amplify a sequence comprising each variable genomic target sequence in a multiplex amplification reaction, wherein the designing includes the steps of: 1) identifying all possible primers of 17 to 35 nucleotides within 100 base pairs of each genomic target sequence variation in set N of variable genomic target sequences; 2) selecting a primer set for the multiplex amplification and genotyping of the members of set N comprising: a) from the set of all possible primers for each genomic target sequence variation of step (1), randomly selecting set P, a population of sets of candidate primers, each individual set of candidate primers in population P including a primer pair for the amplification of each member of set N of variable genomic target sequences to be genotyped; b) calculating a fitness score for each member of the population of set P by calculating ΔG for all possible interactions between candidate primers in each member of the population of set P, and assigning each member of set P a Fitness Score according to the rule: i) G=the set of ΔG's for all possible interactions determined for a given member of set P; ii) Number of top scorers to go into next generation=1 . . . N, Number of distinct populations sets=1 . . . N, and Population size=1 . . . N such that number of top scorers to go into next generation is greater or equal to population size; wherein fitness score is calculated by: iii) for each member of set P, calculating the sum, S, of $|\Delta G|^Q$ for each ΔG value in that member, wherein Q is a weighting factor constant exponent that makes large ΔG absolute values much larger than small values; iv) S'=S/# of ΔG values in G; v) H=T/S', wherein T is a constant that makes H small for large values of S' and H large for small values of S'; vi) Fitness Score=H$^R$, wherein R is a weighting factor constant exponent that makes large values of H larger, and small values of H smaller; c) selecting a set of primers for the multiplex amplification and genotyping of members of set N by: i) randomly selecting a plurality of sets of "parent" sets of candidate primers, each having parent set A and parent set B, from set P based upon Fitness Scores; ii) for each member of the plurality of sets of parents, creating a crossover set of candidate primers by replacing a subset of candidate primers in parent set A with a corresponding subset of candidate primers in parent set B, resulting in two crossover sets, crossover set A and crossover set B; and iii) randomly replacing one primer pair in crossover set A with a different primer pair for the corresponding variable genomic target sequence to create a next generation population of candidate sets of primers, Generation 2; and d) iteratively repeating steps (a)-(c), whereby a primer set for the multiplex amplification and genotyping of set N of variable genomic target sequences is selected; and B) synthesizing the primer set designed in step (A).

In another aspect, described herein is a method for multiplex amplification, sequencing, and/or genotyping, the method comprising using a primer set designed according to any one of the preceding aspects.

In another aspect, described herein is a method for equalization of reads in a next generation sequencing method, the method comprising using anti-sense oligos in concentrations sufficient to inhibit high-performing amplicons from forming and thereby allowing poorer performing amplicons to produce more data.

In another aspect, described herein is a method for performing multiplex PCR that results in even reads produced by NGS instruments for each amplicon (for 2-10,000 amplicons) and each sample (for 1-100,000 DNA samples). Embodiments of this method benefit from improved primer design methods as described herein and, for example, the use of antisense oligonucleotides targeting a subset of amplicons that are high-performing or highly efficiently amplified to permit amplicons that amplify less efficiently to produce more data. Embodiments include the use of primers designed according to the methods described herein in multiplex PCR, high throughput genotyping, and other approaches using NGS.

In another aspect, described herein is a variation of NGS (e.g., PlexSeq™ sequencing) that permits single base multiplexed sequencing on an NGS platform in order to avoid sequencing additional regions, e.g., when this is beneficial. One embodiment comprises designing a multiplex genotyping primer set as described herein, and adding random nucleotides to the 5' end of the primers in the set that are shorter than the longest primer in the set, such that each primer in the set is the same length, N, and performing only N+1 cycles in an NGS sequencing run.

In another aspect, described herein is a method to rapidly analyze NGS data (e.g., PlexSeq™ sequencing data) using personalized software (e.g., PlexCall™ software) to automatically provide genotype or sequencing results.

In another aspect, described herein is a method of using NGS methodology (e.g., PlexSeq™ technology) to identify and quantify low abundance rare variants in clinically relevant genes in a minority of tumor cells from a complex mixture of cells.

DETAILED DESCRIPTION

Figure 1:
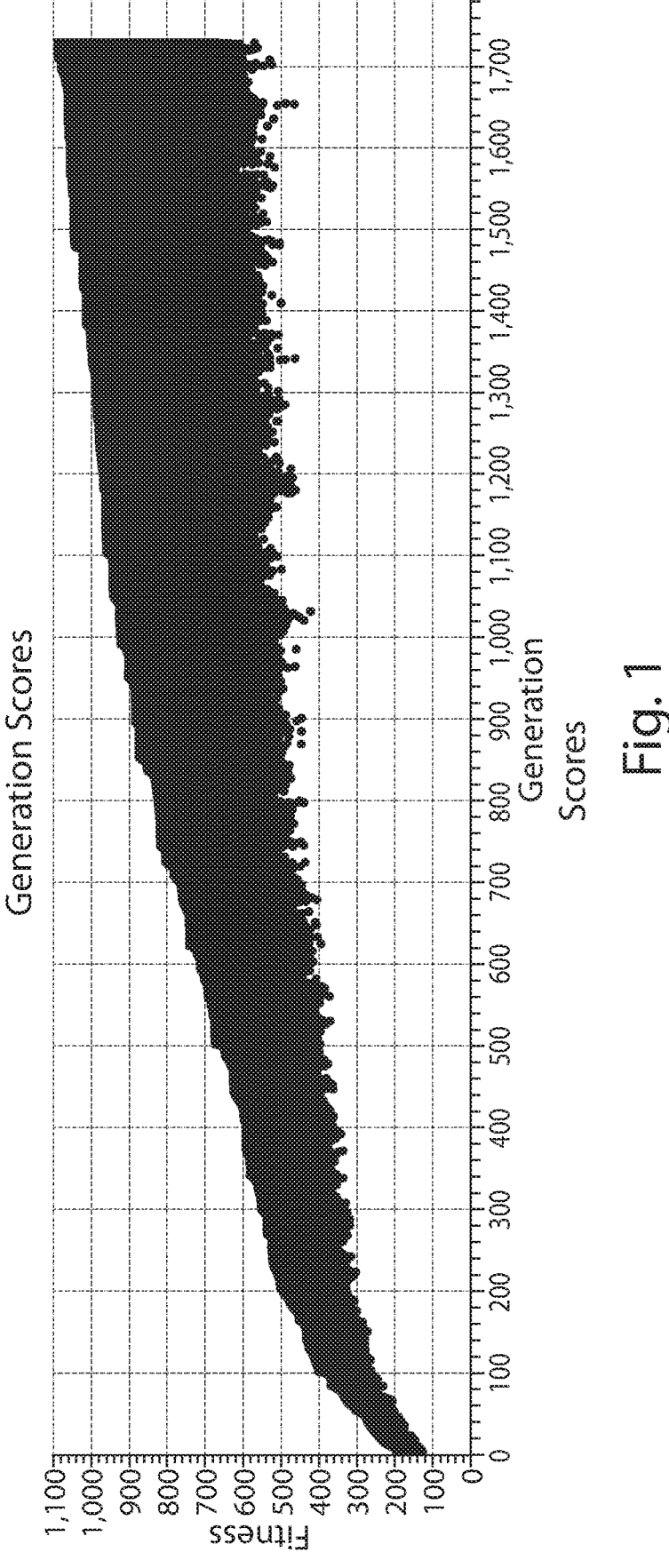
FIG. 1 is a PlexForm™ Fitness graph example demonstrating optimization of primer mix.

Described herein are methods that dramatically increase the degree of multiplexing achievable for multiplex PCR, based, in part, on improvements in primer design for multiplex amplification. The following sets out various approaches for design of primer sets for high multiplex amplification that avoid or minimize primer:primer interactions. Methods of using the primers so designed in, e.g., multiplex amplification, sequencing and genotyping are also provided and follow directly from the improved primer designs.

Multiplexed Genotyping

Described herein are improved methods of designing primers for multiplex PCR amplification (see e.g., Examples 1-11). As used herein, the term "primer" denotes a single-stranded nucleic acid that hybridizes to a nucleic acid region of interest and provides a starting point for nucleic acid synthesis, i.e. for enzymatic synthesis of a nucleic acid strand complementary to a template. In some embodiments of any of the aspects, the primer can be DNA, RNA, modified DNA, modified RNA, synthetic DNA, synthetic RNA, or another synthetic nucleic acid. In some embodiments, the primer is about 17-35 nucleotides long. As a non-limiting example, the primer is 17 nucleotides (nt) long, 18 nt, 19 nt, 20 nt, 21 nt, 22 nt, 23 nt, 24 nt, 25 nt, 26 nt, 27 nt, 28 nt, 29 nt, 30 nt, 31 nt, 32 nt, 33 nt, 34 nt, or 35 nt long.

In some embodiments of any of the aspects, the primer exhibits reverse complementarity to the coding strand of a nucleic acid region of interest. In some embodiments, the primer has 90-100% identity with the non-coding strand of a nucleic acid region of interest or the reverse complement of a nucleic acid region of interest. In some embodiments, the primer has about 90%, about 91%, about 92%, about 93%, about 94%, about 95%, about 96%, about 97%, about 98%, about 99%, or about 100% identity with the non-coding strand of a nucleic acid region of interest or the reverse complement of a nucleic acid region of interest.

In some embodiments of any of the aspects, the primer is within 100 base pairs (bp) of the nucleic acid region of interest. As a non-limiting example, the primer is within (i.e., hybridizes to a region) about 0 bp, about 1 bp, about 2 bp, about 3 bp, about 4 bp, about 5 bp, about 6 bp, about 7 bp, about 8 bp, about 9 bp, about 10 bp, about 11 bp, about 12 bp, about 13 bp, about 14 bp, about 15 bp, about 16 bp, about 17 bp, about 18 bp, about 19 bp, about 20 bp, about 21 bp, about 22 bp, about 23 bp, about 24 bp, about 25 bp, about 26 bp, about 27 bp, about 28 bp, about 29 bp, about 30 bp, about 31 bp, about 32 bp, about 33 bp, about 34 bp, about 35 bp, about 36 bp, about 37 bp, about 38 bp, about 39 bp, about 40 bp, about 41 bp, about 42 bp, about 43 bp, about 44 bp, about 45 bp, about 46 bp, about 47 bp, about 48 bp, about 49 bp, about 50 bp, about 51 bp, about 52 bp, about 53 bp, about 54 bp, about 55 bp, about 56 bp, about 57 bp, about 58 bp, about 59 bp, about 60 bp, about 61 bp, about 62 bp, about 63 bp, about 64 bp, about 65 bp, about 66 bp, about 67 bp, about 68 bp, about 69 bp, about 70 bp, about 71 bp, about 72 bp, about 73 bp, about 74 bp, about 75 bp, about 76 bp, about 77 bp, about 78 bp, about 79 bp, about 80 bp, about 81 bp, about 82 bp, about 83 bp, about 84 bp, about 85 bp, about 86 bp, about 87 bp, about 88 bp, about 89 bp, about 90 bp, about 91 bp, about 92 bp, about 93 bp, about 94 bp, about 95 bp, about 96 bp, about 97 bp, about 98 bp, about 99 bp, or about 100 bp of the nucleic acid region of interest. In some embodiments of any of the aspects, the primer is within about 80-90 bp, about 90-100 bp, about 100-110 bp, about 110-120 bp, about 120-130 bp, about 130-140 bp, about 140-150 bp, about 150-160 bp, about 160-170 bp, about 170-180 bp, about 180-190 bp, or about 190-200 bp of the nucleic acid region of interest.

In some embodiments of any of the aspects, the nucleic acid region of interest can also be referred to as the target, the target gene, the DNA target of interest, or the genomic target sequence. The nucleic acid region of interest can be DNA, RNA, genomic DNA (gDNA), complementary DNA (cDNA), messenger RNA (mRNA), or any nucleic acid of at least 20 bp. As a non-limiting example, the nucleic acid region of interest can comprise a gene, as known in the art. As a non-limiting example, the nucleic acid region of interest can be present in a non-coding region of the genome or larger nucleic acid. As a non-limiting example, the nucleic acid region of interest can comprise a single-nucleotide polymorphism (SNP). A SNP is a substitution of a single nucleotide that occurs at a specific position in the nucleic acid of interest, where each variation is present to some appreciable degree within a population. For example, a SNP can be an A/T, A/G, A/C, C/G, C/T, G/T, A/C/G, A/C/T, A/G/T, C/G/T, or A/C/G/T polymorphism, where A indicates adenosine, C indicates cytosine, G indicates guanine, T indicates thymine, and the groupings indicate the bases found at a specific SNP.

In some embodiments of any of the aspects, the nucleic acid region of interest can comprise a nucleotide deletion or a nucleotide insertion. As a non-limiting example, the nucleotide deletion or nucleotide insertion can be about 1 bp, about 2 bp, about 3 bp, about 4 bp, about 5 bp, about 6 bp, about 7 bp, about 8 bp, about 9 bp, about 10 bp, about 11 bp, about 12 bp, about 13 bp, about 14 bp, about 15 bp, about 16 bp, about 17 bp, about 18 bp, about 19 bp, about 20 bp, about 21 bp, about 22 bp, about 23 bp, about 24 bp, about 25 bp, about 26 bp, about 27 bp, about 28 bp, about 29 bp, or about 30 bp long. The specific genetic variation (e.g., SNP, insertion, deletion) found in an organism can be referred to as an allele.

In some embodiments of any of the aspects, the nucleic acid region of interest can be from a human, a mammal, a bird, a reptile, an amphibian, a fish, an animal, a plant, a fungus, a protist, a multicellular organism, a unicellular organism, a eukaryote, a bacterium, or an archaebacterium.

As a non-limiting example, the nucleic acid region of interest can be from one of the following plant species: corn (e.g., *Zea mays*), soybean (e.g., *Glycine max*), tomato (e.g., *Solanum lycopersicum*), squash (e.g., *Cucurbita argyro-*

*sperma, Cucurbita maxima, Cucurbita moschata, Cucurbita pepo*), cotton (e.g., *Gossypium hirsutum, Gossypium barbadense, Gossypium arboreum, Gossypium herbaceum*), wheat (e.g., *Triticum aestivum, Triticum aethiopicum, Triticum araraticum, Triticum boeoticum, Triticum carthlicum, Triticum compactum, Triticum dicoccoides, Triticum dicoccon, Triticum durum, Triticum ispahanicum, Triticum karamyschevii, Triticum macha, Triticum militinae, Triticum monococcum, Triticum polonicum, Triticum spelta, Triticum sphaerococcum, Triticum timopheevii, Triticum turanicum, Triticum turgidum, Triticum Urartu, Triticum vavilovii, Triticum zhukovskyi*), sunflower (e.g., *Helianthus annuus, Helianthis agrestis, Helianthus angustifolius, Helianthus anomalus, Helianthus argophyllus, Helianthus arizonensis, Helianthus atrorubens, Helianthus bolanderi, Helianthus californicus, Helianthus carnosus, Helianthus ciliaris, Helianthus cinereus, Helianthus cusickii, Helianthus debilis, Helianthus decapetalus, Helianthus deserticola, Helianthus divaricatus, Helianthus eggertii, Helianthus floridanus, Helianthus giganteus, Helianthus glaucophyllus, Helianthus gracilentus, Helianthus grosseserratus, Helianthus heterophyllus, Helianthus hirsutus, Helianthus laciniatus, Helianthus laetiflorus, Helianthus laevigatus, Helianthus longifolius, Helianthus maximiliani, Helianthus microcephalus, Helianthus mollis, Helianthus multiflorus, Helianthus neglectus, Helianthus niveus, Helianthus nuttallii, Helianthus occidentalis, Helianthus paradoxus, Helianthus pauciflorus, Helianthus petiolaris, Helianthus porter, Helianthus praecox, Helianthus praetermissus, Helianthus pumilus, Helianthus radula, Helianthus resinosus, Helianthus salicifolius, Helianthus schweinitzii, Helianthus silphioides, Helianthus simulans, Helianthus smithii, Helianthus strumosus, Helianthus tuberosus*), grape (e.g., *Vitis vinifera, Vitis vinifera, Vitis labrusca, Vitis riparia, Vitis rotundifolia, Vitis rupestris, Vitis aestivalis, Vitis mustangensis*, or any multi-species hybrids), cowpea (e.g., *Vigna unguiculata*), *Chrysanthemum* (e.g., *Chrysanthemum indicum*), *Eucalyptus* (e.g., *Eucalyptus obliqua* or any of the approximately 700 other species in the *Eucalyptus* genus), flax (e.g., *Phormium tenax, Phormium cookianum*), sesame (e.g., *Sesamum radiatum*), pepper (e.g., *Capsicum annuum, Capsicum baccatum, Capsicum chinense, Capsicum frutescens, Capsicum pubescens*), rice (e.g., *Oryza sativa*, including any one of the more than 40,000 varieties of this species), potato (e.g., *Solanum tuberosum*), cassava (e.g., *Manihot esculenta*), rye (e.g., *Secale cereale*), barley (e.g., *Hordeum vulgare*), alfalfa (e.g., *Medicago sativa*), or rapeseed (e.g., *Brassica napus*). A plant species can include any subspecies, cultivars, multi-species hybrids, strains, or any other variations or varieties that are known in the art.

As a non-limiting example, the nucleic acid region of interest can be from one of the following animal species: *Homo sapiens*, chicken (e.g., *Gallus gallus domesticus*), pig (e.g., *Sus ahoenobarbus, Sus amyus, Sus cebifrons, Sus barbatus, Sus celebensis, Sus oliveri, Sus philippensis, Sus scrofa, Sus verrucosus*) bovine (*Bos taurus*), sheep (e.g., *Ovis aries*), goat (e.g., *Capra aegagrus hircus*) deer (e.g. *Odocoileus virginianus, Odocoileus hemionus*), salmon (e.g., *Salmo salar, Oncorhynchus tshawytscha, Oncorhynchus keta, Oncorhynchus kisutch, Oncorhynchus masou, Oncorhynchus gorbuscha, Oncorhynchus nerka, Ampis trutta, Hucho hucho, Elagatis bipinnulata, Eleutheronema tetradactylum*) or other fish species (e.g., *Acetes japonicas, Ammodytes personatus, Anadara granosa, Brevoortia patronus, Brevoortia tyrannus, Carassius carassius, Catla catla, Cetengraulis mysticetus, Channa argus, Chanos chanos, Cirrhinus mrigala, Clupea bentincki, Clupea harengus,*

*Clupea pallasii, Cololabis saira, Crassostrea gigas, Ctenopharyngodon idellus, Cyprinus carpio, Dosidicus gigas, Engraulis capensis, Engraulis encrasicolus, Engraulis japonicus, Engraulis ringens, Eriocheir sinensis, Ethmalosa fimbriata, Euphausia superba, Euthynnus affinis, Gadus macrocephalus, Gadus morhua, Harpadon nehereus, Hypophthalmichthys molitrix, Hypophthalmichthys nobilis, Ictalurus punctatus, Illex argentinus, Katsuwonus pelamis, Labeo rohita, Larimichthys polyactis, Lates niloticus, Mallotus villosus, Megalobrama amblycephala, Melanogrammus aeglefinus, Merluccius hubbsi, Merluccius productus, Micromesistius poutassou, Misgumus anguillicaudatus, Monopterus albus, Muraenesox cinereus, Mylopharyngodon piceus, Oncorhynchus mykiss, Opisthonema libertate, Oreochromis niloticus, Oreochromis niloticus, Pandalus borealis, Pangasius hypophthalmus, Patinopecten yessoensis, Pelodiscus sinensis, Penaeus monodon, Penaeus monodon, Penaeus vannamei, Placopecten magellanicus, Pollachius virens, Portunus pelagicus, Portunus trituberculatus, Procambarus Rastrelliger brachysoma, Rastrelliger kanagurta, Rastrineobola argentea, Sardina pilchardus, Sardinella aurita, Sardinella gibbosa, Sardinella longiceps, Sardinella maderensis, Sardinops caeruleus, Sardinops melanostictus, Scomber japonicus, Scomber scombrus, Scomberomorus commerson, Selar crumenophthalmus, Selaroides leptolepis, Silurus asotus, Siniperca chuatsi, Sinonovacula constricta, Sprattus sprattus, Tachysurus fulvidraco, Tenualosa ilisha, Theragra chalcogramma, Thunnus alalunga, Thunnus albacares, Thunnus obesus, Thunnus tonggol, Todarodes pacificus, Trachurus capensis, Trachurus japonicus, Trachurus murphyi, Trachurus trachurus, Trachysalambria curvirostris, Trichiurus lepturus, Venerupis philippinarum).* An animal species can include any subspecies, strains, breeds, or any other variations or varieties that are known in the art.

Described herein are improved methods of multiplex PCR amplification. Polymerase chain reaction (PCR) is a method to make copies of a specific nucleic acid region of interest. As well known in the art, PCR functions by using a pair of primers to amplify a specific amplicon. As used here, an "amplicon" is the segment of DNA or RNA that is the source and/or product of an amplification, replication, and/or PCR event. The primer pair comprises a forward primer and a reverse primer that anneals a certain distance from the forward primer; the reverse primer anneals to the opposite strand to and opposite orientation to the forward primer, such that polymerization from one primer progresses towards the other primer.

In general, the PCR procedure describes a method of gene amplification which is comprised of (i) sequence-specific hybridization of primers to specific genes or sequences within a nucleic acid sample or library, (ii) subsequent amplification involving multiple rounds of annealing, elongation, and denaturation using a thermostable DNA polymerase, and, optionally, (iii) screening the PCR products for a band or bands of the correct size(s). As described herein, the primers used are oligonucleotides of sufficient length and appropriate sequence to provide initiation of polymerization, i.e. each primer is specifically designed to be complementary to a strand of the genomic locus to be amplified. Unless noted otherwise, all PCR reactions are carried out using standard PCR reaction conditions and reagents, as well known to those of skill in the art.

In some embodiments of any of the aspects, the forward primer and the reverse primer are about 20-100 bp apart. As a non-limiting example, the forward primer and the reverse primer are about 20 bp, about 21 bp, about 22 bp, about 23 bp, about 24 bp, about 25 bp, about 26 bp, about 27 bp, about 28 bp, about 29 bp, about 30 bp, about 31 bp, about 32 bp, about 33 bp, about 34 bp, about 35 bp, about 36 bp, about 37 bp, about 38 bp, about 39 bp, about 40 bp, about 41 bp, about 42 bp, about 43 bp, about 44 bp, about 45 bp, about 46 bp, about 47 bp, about 48 bp, about 49 bp, about 50 bp, about 51 bp, about 52 bp, about 53 bp, about 54 bp, about 55 bp, about 56 bp, about 57 bp, about 58 bp, about 59 bp, about 60 bp, about 61 bp, about 62 bp, about 63 bp, about 64 bp, about 65 bp, about 66 bp, about 67 bp, about 68 bp, about 69 bp, about 70 bp, about 71 bp, about 72 bp, about 73 bp, about 74 bp, about 75 bp, about 76 bp, about 77 bp, about 78 bp, about 79 bp, about 80 bp, about 81 bp, about 82 bp, about 83 bp, about 84 bp, about 85 bp, about 86 bp, about 87 bp, about 88 bp, about 89 bp, about 90 bp, about 91 bp, about 92 bp, about 93 bp, about 94 bp, about 95 bp, about 96 bp, about 97 bp, about 98 bp, about 99 bp, or about 100 bp apart. In some embodiments of any of the aspects, the forward primer and the reverse primer are about 80-90 bp, about 90-100 bp, about 100-110 bp, about 110-120 bp, about 120-130 bp, about 130-140 bp, about 140-150 bp, about 150-160 bp, about 160-170 bp, about 170-180 bp, about 180-190 bp, about 190-200 bp apart, about 200-210 bp apart, about 210-220 bp apart, about 220-230 bp apart, about 230-240 bp apart, or about 240-250 bp apart.

The length of the amplicon is the sum of the distance between the primers and the lengths of both primers. As a non-limiting example, the amplicon can be about 35 bp, about 36 bp, about 37 bp, about 38 bp, about 39 bp, about 40 bp, about 41 bp, about 42 bp, about 43 bp, about 44 bp, about 45 bp, about 46 bp, about 47 bp, about 48 bp, about 49 bp, about 50 bp, about 51 bp, about 52 bp, about 53 bp, about 54 bp, about 55 bp, about 56 bp, about 57 bp, about 58 bp, about 59 bp, about 60 bp, about 61 bp, about 62 bp, about 63 bp, about 64 bp, about 65 bp, about 66 bp, about 67 bp, about 68 bp, about 69 bp, about 70 bp, about 71 bp, about 72 bp, about 73 bp, about 74 bp, about 75 bp, about 76 bp, about 77 bp, about 78 bp, about 79 bp, about 80 bp, about 81 bp, about 82 bp, about 83 bp, about 84 bp, about 85 bp, about 86 bp, about 87 bp, about 88 bp, about 89 bp, about 90 bp, about 91 bp, about 92 bp, about 93 bp, about 94 bp, about 95 bp, about 96 bp, about 97 bp, about 98 bp, about 99 bp, or about 100 bp long. In some embodiments of any of the aspects, the amplicon can be about 80-90 bp, about 90-100 bp, about 100-110 bp, about 110-120 bp, about 120-130 bp, about 130-140 bp, about 140-150 bp, about 150-160 bp, about 160-170 bp, about 170-180 bp, about 180-190 bp, about 190-200 bp long, about 200-210 bp long, about 210-220 bp long, about 220-230 bp long, about 230-240 bp long, or about 240-250 bp long.

The amplicon can be detected by any method known to those of skill in the art. As a non-limiting example, the amplicon can be detected by gel electrophoresis, real time PCR, allele-specific PCR, an array-based method or next generation sequencing (NGS).

Described herein are methods of genotyping. As used herein, genotyping refers to the process of determining differences in the genetic make-up (e.g., genotype) of an individual by examining the individual's DNA sequence using biological assays and comparing it to another individual's sequence or a reference sequence. As used herein, the term "genotype calling" refers to the process of determining a subject's genotype with respect to members of a set of allelic markers, including but not limited to single nucleotide polymorphisms (see e.g., U.S. Pat. No. 8,428,886, which is incorporated herein by reference in its entirety). Biological assays used for genotyping can include but are not limited to PCR, restriction fragment length polymorphism identification (RFLPI) of genomic DNA, random amplified polymorphic detection (RAPD) of genomic DNA, amplified fragment length polymorphism detection (AFLPD), DNA sequencing, allele specific oligonucleotide (ASO) probes, or hybridization to DNA microarrays or beads. In some embodiments of any of the aspects, genotyping is performed on a nucleic acid region of interest, a gene, a non-coding region, a SNP, an insertion, a deletion, or any other region of nucleic acid. Genotyping can reveal the specific allele(s) present in an individual organism or population of organism. Genotyping can be used for in research of genes and gene variants associated with disease Described herein are methods of multiplexed genotyping and/or multiplexed PCR. As used herein, "multiplex" refers to a reaction in which multiple targets and/or targets in or from multiple samples are amplified or interrogated in the same reaction. In some embodiments of any of the aspects, a multiplexed genotyping reaction can comprise 1 to 100,000 samples. As a non-limiting example, a multiplexed genotyping reaction can comprise about 1 sample, about 2 samples, about 3 samples, about 4 samples, about 5 samples, about 6 samples, about 7 samples, about 8 samples, about 9 samples, about 10 samples, about 20 samples, about 30 samples, about 40 samples, about 50 samples, about 60 samples, about 70 samples, about 80 samples, about 90 samples, about 100-200 samples, about 200-300 samples, about 300-400 samples, about 400-500 samples, about 500-600 samples, about 600-700 samples, about 700-800 samples, about 800-900 samples, about 900-1,000 samples, about 1,000-10,000 samples, about 10,000-20,000 samples, about 20,000-30,000 samples, about 30,000-40,000 samples, about 40,000-50,000 samples, about 50,000-60,000 samples, about 60,000-70,000 samples, about 70,000-80,000 samples, about 80,000-90,000 samples, or about 90,000-100,000 samples.

In some embodiments of any of the aspects, a multiplexed genotyping reaction can comprise 2 to 10,000 amplicons from the same or different nucleic acid regions of interest. As a non-limiting example, the multiplexed genotyping reaction can comprise about 2 amplicons, about 3 amplicons, about 4 amplicons, about 5 amplicons, about 6 amplicons, about 7 amplicons, about 8 amplicons, about 9 amplicons, about 10 amplicons, about 20 amplicons, about 30 amplicons, about 40 amplicons, about 50 amplicons, about 60 amplicons, about 70 amplicons, about 80 amplicons, about 90 amplicons, about 100-200 amplicons, about 200-300 amplicons, about 300-400 amplicons, about 400-500 amplicons, about 500-600 amplicons, about 600-700 amplicons, about 700-800 amplicons, about 800-900 amplicons, about 900-1,000 amplicons, about 1,000-2,000 amplicons, about 2,000-3,000 amplicons, about 3,000-4,000 amplicons, about 4,000-5,000 amplicons, about 5,000-6,000 amplicons, about 6,000-7,000 amplicons, about 7,000-8,000 amplicons, about 8,000-9,000 amplicons, or about 9,000-10,000 amplicons from the same or different nucleic acid regions of interest.

As described herein, to generate a primer set, all possible primers (e.g., 17-35 nucleotides) are identified within about 100 base pairs of each target gene. Primers are chosen that satisfy standard PCR conditions for a primer selection algorithm (e.g., Primer 3™, Oligo Analyzer™, NetPrimer™, or Oligo Calculator™). See e.g., Rozen et al. Methods Mol Biol. 2000, 132:365-86; Owczarzy et al., Nucleic Acids Res. 2008 Jul. 1, 36 (Web Server issue): W163-9; each of which is incorporated by reference herein in its entirety.

As well known to those of skill in the art, standard PCR conditions or parameters can comprise preferred values for product (e.g., amplicon) size, primer size, primer $T_m$, $T_m$ difference, product $T_m$, and/or primer GC % (e.g., the percentage of G or C bases compared to total bases). As a non-limiting example, primer $T_m$ and/or product $T_m$ can be about 57° C., about 58° C., about 59° C., about 60° C., about 61° C., about 62° C., or about 63° C., with a preferred primer $T_m$ of about 60° C. As a non-limiting example, the max difference between the $T_m$'s of the forward primer, the reverse primer, and/or the amplicon can be about 0° C., about 1° C., about 2° C., about 3° C., about 4° C., about 5° C., about 6° C., about 7° C., about 8° C., about 9° C., or about 10° C. As a non-limiting example, GC % can be about 20%, about 25%, about 30%, about 35%, about 40%, about 45%, about 50%, about 55%, about 60%, about 65%, about 70%, about 75%, or about 80%. Methods for calculating $T_m$ are well known to those of skill in the art (see e.g., Panjkovich and Melo, Bioinformatics, Volume 21, Issue 6, 15 Mar. 2005, Pages 711-722, which is incorporated by reference herein in its entirety).

Additional PCR conditions that can be considered when necessary or desired during primer selection include but are not limited to primer self complementarity, primer 3' self complementarity, primer #N's (e.g., consecutive repeated nucleotides), primer mispriming similarity, primer sequence quality, primer 3' sequence quality, and/or primer 3' stability. Preferred values for each of the aforementioned conditions can be set or determined by one of skill in the art or by the specific primer selection algorithm (e.g., Primer 3™, Oligo Analyzer™, NetPrimer™, or Oligo Calculator™).

In some embodiments of any of the aspects, primers are compared for specificity versus the genome using alignment software (e.g., primer blast (NCBI™); isPCR (UCSC)). Only those primers predicted to be specific for their respective targets (e.g., hybridizing only to a single sequence or a single set of allelic sequences in the subject genome) are kept. While hybridization is influenced by GC content as well as overall complementarity, in general a primer that is specific for a single target in the genome should have no more than about 80% sequence identity with sequences that are not target sequences in the genome of interest. As a non-limiting example, the primer can have about 0%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, or about 80% or less sequence identity with a non-target sequence in the genome of interest.

Described herein, are methods of minimizing primer: primer interactions. As used herein, the term "primer-primer interactions" refers to inappropriate non-specific binding or non-specific hybridization of a primer with another primer in a reaction mixture, including a multiplex reaction mixture, as opposed to appropriate specific binding or specific hybridization with each primer's target of interest. Where primers are included in a reaction at many times the concentration of any given target sequence, even relatively inefficient primer-primer interactions can impact performance of the amplification. As a non-limiting example, primer-primer dimers are a potential byproduct in PCR, comprising primer molecules that have hybridized to each other due to regions of complementary bases. Primer-primer interactions reduce the availability of the interacting primers to hybridize productively with their intended targets and can lead to a competition for reaction reagents and potential inhibition of amplification of the targets of interest. In multiplex PCR and/or genotyping reactions, at least 2 pairs of primers are present in the same sample. As a non-limiting example, at least 3 pairs of primers, at least 4 pairs of primers, at least 5 pairs of primers, at least 6 pairs of primers, at least 7 pairs of primers, at least 8 pairs of primers, at least 9 pairs of primers, at least 10 pairs of primers, at least 20 pairs of primers, at least 30 pairs of primers, at least 40 pairs of primers, at least 50 pairs of primers, at least 60 pairs of primers, at least 70 pairs of primers, at least 80 pairs of primers, at least 90 pairs of primers, at least 100 pairs of primers, at least 110 pairs of primers, at least 120 pairs of primers, at least 130 pairs of primers, at least 140 pairs of primers, at least 150 pairs of primers, at least 160 pairs of primers, at least 170 pairs of primers, at least 180 pairs of primers, at least 190 pairs of primers, at least 200 pairs of primers, at least 250 pairs of primers, at least 300 pairs of primers, at least 350 pairs of primers, at least 400 pairs of primers, at least 450 pairs of primers, or least 500 pairs of primers are present in a reaction mixture, allowing for hundreds or thousands of potential inappropriate primer-primer interactions. The primer-design methods described herein can dramatically improve throughput in NGS-based multiplex genotyping methods.

Fitness Score

In some embodiments, a fitness score is calculated for a primer set, chromosome, or individual (see e.g., Example 2). As used in the context of a genetic algorithm, the terms "chromosome" or "individual" refer to a set of "X" primer pairs, where X is the number of targets being interrogated in a multiplex reaction. A primer set can comprise one primer pair for each target gene or nucleic acid region of interest in a multiplex set of target genes or nucleic acid regions of interest. The initial primer pairs for each primer set can be selected randomly or guided by a selection algorithm. As a non-limiting example, a primer set can comprise at least 2 primer pairs, at least 3 primer pairs, at least 4 primer pairs, at least 5 primer pairs, at least 6 primer pairs, at least 7 primer pairs, at least 8 primer pairs, at least 9 primer pairs, at least 10 primer pairs, at least 20 primer pairs, at least 30 primer pairs, at least 4 primer pairs, at least 50 primer pairs, at least 60 primer pairs, at least 70 primer pairs, at least 80 primer pairs, at least 90 primer pairs, at least 100 primer pairs, at least 110 primer pairs, at least 120 primer pairs, at least 130 primer pairs, at least 140 primer pairs, at least 150 primer pairs, at least 160 primer pairs, at least 170 primer pairs, at least 180 primer pairs, at least 190 primer pairs, at least 200 primer pairs, at least 250 primer pairs, at least 300 primer pairs, at least 350 primer pairs, at least 400 primer pairs, at least 450 primer pairs, or least 500 primer pairs.

In some embodiments, e.g., in the context of a genetic algorithm, a fitness score is calculated for a population (i.e. set) of individuals. As a non-limiting example, a population can comprise at least 2 individuals, at least 3 individuals, at least 4 individuals, at least 5 individuals, at least 6 individuals, at least 7 individuals, at least 8 individuals, at least 9 individuals, at least 10 individuals, at least 20 individuals, at least 30 individuals, at least 4 individuals, at least 50 individuals, at least 60 individuals, at least 70 individuals, at least 80 individuals, at least 90 individuals, at least 100 individuals, at least 110 individuals, at least 120 individuals, at least 130 individuals, at least 140 individuals, at least 150 individuals, at least 160 individuals, at least 170 individuals, at least 180 individuals, at least 190 individuals, at least 200 individuals, at least 250 individuals, at least 300 individuals, at least 350 individuals, at least 400 individuals, at least 450 individuals, or at least 500 individuals.

In some embodiments, the primers within each primer set are analyzed for $\Delta G$. In this context, "$\Delta G$" (or "delta G") refers to the change in Gibbs free energy, a measure of spontaneity. In some embodiments, $\Delta G$ represents the quantity of energy needed to fully break a secondary DNA structure (e.g., primer-primer interaction). $\Delta G$ can be measured in units of kilocalorie per mole (kcal/mol) or kilojoule per mole (kJ/mol). When $\Delta G$ is negative (i.e. less than zero), a process (e.g., primer-primer interactions) proceeds spontaneously and is referred to as exergonic. When $\Delta G$ is positive (i.e. greater than zero), a process (e.g., primer-primer interactions) does not proceed spontaneously and is referred to as endergonic. When $\Delta G$ is equal to zero, a process is referred to as in equilibrium. In some embodiments, $\Delta G$ is calculated using FORMULA 1:

FORMULA 1: $\Delta G = \Delta H - T\,\Delta S$, where "$\Delta H$" (or "delta H") refers to the change in enthalpy, "T" refers to the temperature of the reaction in degrees Kelvin (K), and "$\Delta S$" (or "delta S") refers to the change in entropy of the reaction.

When $\Delta H$ is negative (i.e. less than zero), a process (e.g., primer-primer interactions) releases heat and is referred to as exothermic. When $\Delta H$ is positive (i.e. greater than zero), a process (e.g., primer-primer interactions) absorbs heat and is referred to as endothermic. When $\Delta H$ is equal to zero, no heat is released or absorbed in a process (e.g., primer-primer interactions). $\Delta H$ can be measured in units of kilojoule per mole (kJ/mol) or kilocalorie per mole (kcal/mol). $\Delta H$ can be determined experimentally or calculated or closely approximated using various software packages, which, e.g., incorporate or account for enthalpy change for various short sequences hybridizing with their complementary sequences (for a discussion of nearest neighbor, see below). As well known to those of skill in the art, in some embodiments $\Delta H$ can be determined using the heats of formation for each compound in a reaction; for a nucleic acid duplex, the heat of formation refers to the heat of duplex formation.

As used herein, "$\Delta S$" (or "delta S") refers to the change in entropy and can be used as a measure of disorder and randomness. When $\Delta S$ is negative (i.e. less than zero), there is a decrease of disorder in a process (e.g., primer-primer interactions). When $\Delta S$ is positive (i.e. greater than zero), there is an increase of disorder in a process (e.g., primer-primer interactions). When $\Delta S$ is equal to zero, there is no change in disorder in a process (e.g., primer-primer interactions). $\Delta S$ can be measured in units of kilojoule per mole (kJ/mol) per Kelvin or kilocalorie per mole (kcal/mol) per Kelvin. $\Delta S$ can be determined experimentally or calculated or closely approximated by using various software packages, e.g., as for $\Delta H$.

As well known to those of skill in the art, in some embodiments $\Delta G$, $\Delta H$, and/or $\Delta S$ are known for each possible "nearest neighbor" nucleotide interaction (e.g., AA/TT, AT/TA, TA/AT, CA/GT, GT/CA, CT/GA, GA/CT, CG/GC, GC/CG, GG/CC; see e.g., TABLE 1). See e.g., SantaLucia. A unified view of polymer, dumbbell, and oligonucleotide DNA nearest-neighbor thermodynamics.

Proc. Natl Acad. Sci. USA 95, 1460-1465 (1998); Sugimoto et al. Thermodynamic parameters to predict stability of RNA/DNA hybrid duplexes. Biochemistry 34, 11211-11216 (1995); each of which is incorporated by reference herein in its entirety.

TABLE 1

| ΔH, ΔG, and ΔS for each possible nearest neighbor DNA nucleotide interaction (T ≈ 300K). | | | |
|---|---|---|---|
| Interaction | dH° (kcal/mol) | dS° (cal/mol per K) | dG° (kcal/mol) |
| AA/TT | −9.1 | −24.0 | −1.9 |
| AT/TA | −8.6 | −23.9 | −1.5 |
| TA/AT | −6.0 | −16.9 | −1.0 |
| CA/GT | −5.8 | −12.9 | −2.0 |
| GT/CA | −6.5 | −17.3 | −1.3 |
| CT/GA | −7.8 | −20.8 | −1.6 |
| GA/CT | −5.6 | −13.5 | −1.6 |
| CG/GC | −11.9 | −27.8 | −3.6 |
| GC/CG | −11.1 | −26.7 | −3.1 |
| GG/CC | −11.0 | −26.6 | −3.1 |

In some embodiments, the following Fitness Score (e.g., F) is calculated via FORMULA 2.

$$F = \{C/[\Sigma(|\Delta G|A)]/GB]\}^B \qquad \text{FORMULA 2}$$

In this context, "G" equals the set of ΔG's for primer interactions determined for that primer set. ΔG is calculated for all possible primer-primer interactions determined in an primer set or a subset of every possible primer-primer interaction determined in an individual or set of primers. "A" and "B" are weighting factors; A and/or B can be an exponential weighting factor constant that makes large values much larger than small values. In some embodiments of Fitness Score calculations, the weighting factor "A" is alternatively referred to as "Q," and/or the weighting factor "B" is alternatively referred to as "R." A and/or B can be a non-zero, positive number greater than 1. A and/or B can be an integer or a fraction/decimal. As a non-limiting example, A and/or B can equal 1, 2, 3, 4, 5, 6, 7, 8, 9, 10, 15, 20, 25, 30, 35, 40, 45, 50, 55, 60, 65, 70, 75, 80, 85, 90, 95, 100, or any integer or fraction/decimal from 1 to 100 or 100 to 1,000. "C" is a factor to create reciprocal scaled values. C causes large numbers to become small numbers. C causes small numbers to become large numbers. In some embodiments of Fitness Score calculations, the scaling factor is alternatively referred to as "T." In the context of Fitness score calculation, T should not be construed as referring to temperature, but to a scaling factor analogous to C described herein. As a non-limiting example, C can equal 1, 2, 3, 4, 5, 6, 7, 8, 9, 10, 15, 20, 25, 30, 35, 40, 45, 50, 55, 60, 65, 70, 75, 80, 85, 90, 95, 100, or any non-zero integer or fraction/decimal from 0 to 100 or 100 to 1,000. As a non-limiting example, A equals 5, B equals 2, and C equals 200.

In this Fitness Score F formula, the absolute value of each ΔG value is raised to the "A" power, and all such values are summed for a primer set, wherein E denotes a summation. The "A" exponent has the effect of spreading out the data values. In some embodiments, A (or Q) is a weighting factor constant exponent that makes large ΔG absolute values much larger than small values. The "A" exponent in effect "weights" or penalizes values proportional to the magnitude of "A". This sum is "S". See e.g., FORMULA 3: $S = \Sigma(|\Delta G|^A)$ In FORMULA 2, some embodiments, the sum is divided by the total number of ΔG values determined for that primer set or "$G_n$." The division by $G_n$ normalizes S, such that the sum is not inherently larger for larger numbers of primer sets or smaller for smaller numbers of primer sets. This normalized S value is referred to as "S'" (or "S prime"). See e.g., FORMULA 4: $S' = S/G_n$.

In calculating the Fitness Score F according to FORMULA 2, factor C (or T) is divided by S' resulting in the value referred to herein as "H" (not to be confused with DH). See e.g., FORMULA 5: H=C/S'.

In calculating the Fitness Score F, H is raised to the "B" power. B (or R), similar to A, has the effect of further spreading out the data, making the difference between large and small values even bigger. The value is referred to as the "Fitness Score" or F. See e.g., FORMULA 6: $F = H^B$.

In some embodiments, each primer set is assigned a Fitness Score (e.g., "F"). "F" can be calculated using FORMULA 2, which simplifies using FORMULAE 3, 4, and 5 to FORMULA 6.

In some embodiments, an alternative calculation or algorithm can be used to calculate a fitness score. As a non-limiting example, a fitness score can comprise any one of the values described herein, including but not limited to ΔG, ΔH, T, and/or ΔS for each primer interaction; any one of the constants described herein, including but not limited to A, B, C, Q, R, T, and/or other constants; and/or any permutation of these values and/or constants, including but not limited to addition, subtraction, multiplication, division, absolute value, summation, exponential power, logarithm, and the like.

Selection Methods

Provided herein are methods for primer design that permit large amplicon number multiplexing and genotype calling. In some embodiments, a set of primers is selected for each target through a specific selection method. In some embodiments, the selected primer set is referred to as "optimal." As used herein "optimal primer set" can refer to a primer set with a minimization of primer-primer interactions. An optimal primer set can be selected using any of several mathematical algorithms described herein.

In some embodiments, optimal primers or an optimal primer set are selected for each target based on the minimization of primer-primer interactions. In some embodiments, primer set selection is based on the maximization of a Fitness Score F for a primer set (see e.g., Example 2). In other embodiments, primer set selection is based on the set meeting a threshold Fitness Score. As non-limiting examples, a threshold Fitness Score can be at least 1, at least 100, at least 200, at least 300, at least 400, at least 500, at least 600, at least 700, at least 800, at least 900, at least 1000, at least 1100, at least 1200, at least 1300, at least 1400, at least 1500, at least 1600, at least 1700, at least 1800, at least 1900, at least 2000, at least 3000, at least 4000, at least 5000, at least 6000, at least 7000, at least 8000, at least 9000, or at least 10,000.

In some embodiments, a primer set is selected using any of several mathematical algorithms described herein and/or incorporated into the PlexForm™ process as described herein. In some embodiments, each sample point in the search space is a collection of primer pairs (e.g., one for each target) in one or more sets, where either highest chance of primer interaction or number of primers below a threshold of primer interaction within a set (e.g., or maximum value for multiple sets) provides a value that is being minimized. In some embodiments, the techniques use a model that can accurately predict the possibility of primer interaction between members of a collection of primer pairs.

In some embodiments, the search space for this task is too large to search for best solution (e.g., global minima). In some embodiments, the following techniques are employed iteratively, together, and/or separately to find an acceptable solution: Genetic Algorithm (see e.g., Example 3); a Monte Carlo random or pseudo-random selection method (see e.g., Example 4); Golden-section search (see e.g., Example 5); Gradient descent (see e.g., Example 6), Minima hopping (see e.g., Example 7); Neural Networks (see e.g., Example 8); Cluster analysis, in which substitution is picked to minimize score (see e.g., Example 9); or Cluster Analysis to create bins (see e.g., Example 10). Examples and detailed descriptions of each of these algorithmic approaches is described further herein.

In some embodiments, a Monte Carlo method can be used alone or iteratively, together, and/or separately with at least one other method to select an optimal primer set. In some embodiments, using random and/or pseudo random selection, one can achieve with a Monte Carlo method a uniform distribution of the sample points in the search space. Such a distribution can be augmented or replaced by selection of inputs near points of interest, that can be determined. See e.g., METROPOLIS et al., J Am Stat Assoc. 1949 September, 44(247):335-41.; Rubinstein and Kroese, Simulation and the Monte Carlo method, $3^{rd}$ Ed., John Wiley & Sons, Inc. Hoboken, N.J., ISBN: 978-1-118-63216-1, October 2016; each of which is incorporated herein by reference in its entirety.

In some embodiments, a Golden-section search method can be used alone or iteratively, together, and/or separately with at least one other method to select an optimal primer set. In some embodiments, using a Golden Section Search algorithm it is possible to pick two points (e.g., where some of the targets contain primer pairs that are the same and do not change during the progression of the search) and using the assumption that minima located between two of those pick a third and fourth point between first two and evaluate the model of each point. In some embodiments, using the assumption that in between two original points the function produced by the model is unimodal, one removes an outside point that has an additional point between it and a point with minimum value. A replacement for the removed point can be picked in-between the two outermost points. This process can be repeated until the distance between two outer most points is small enough to be within a previously determined margin.

As a non-limiting example, the previously determined margin can less than 1, less than 100, less than 200, less than 300, less than 400, less than 500, less than 600, less than 700, less than 800, less than 900, less than 1000, less than 1100, less than 1200, less than 1300, less than 1400, less than 1500, less than 1600, less than 1700, less than 1800, less than 1900, less than 2000, less than 3000, less than 4000, less than 5000, less than 6000, less than 7000, less than 8000, less than 9000, or less than 10,000. For an example involving a Golden Section search method, see e.g., Chang et al., N-Dimension Golden Section Search: Its Variants and Limitations, 2009 2nd International Conference on Biomedical Engineering and Informatics, 17-19 Oct. 2009, which is incorporated herein by reference in its entirety.

In some embodiments, a Gradient descent method can be used alone or iteratively, together, and/or separately with at least one other method to select an optimal primer set. In some embodiments, using a gradient descent algorithm it is possible to determine a gradient (e.g., that represents an increase or decrease in change of interaction between primers) in a given point by measuring a change in interaction with the change of a single primer pair for a given target. In some embodiments, measured change in primer interaction points to a change in primer pairs that produces the greatest reduction in primer interaction. The process is repeated until a point is achieved where any change increases primer interaction score (e.g., decreases the fitness score). Such a point can be referred to as a minima (e.g., where primer-primer interaction is least likely). See e.g., Ruder, An overview of gradient descent optimization algorithms, 2016, available on the world wide web at arxiv.org/abs/1609.04747; Mandic et al. IEEE Signal Processing Letters (Volume: 11, Issue: 2, February 2004), pp. 115-118; each of which is incorporated by reference herein in its entirety.

In some embodiments, a minima hopping method can be used alone or iteratively, together, and/or separately with at least one other method to select an optimal primer set. In some embodiments, to ensure that minima (e.g., where primer interaction is least likely) that are found are not local minima, minima hopping can be employed. Upon locating a minima, it is noted, and a new point in the search space is picked. The new point can be picked randomly or via deterministic method(s) that may be based on variety of factors such as completeness of the data, historical accuracy of predictions, coverage during present search, human guided suggestion, and random and pseudo random number generation, or any combination of those methods as well as others. See e.g., Goedecker, J. Chem. Phys. 120, 9911 (2004), which is incorporated by reference herein in its entirety.

In some embodiments, a genetic algorithm method can be used alone or iteratively, together, and/or separately with at least one other method to select an optimal primer set. In some embodiments, using a genetic algorithm it is possible to pick several valid points and evaluate points in such cohort. Few points that produce lowest chance of primer interaction move on to next iteration with rest of the population being replaced via combining points with lowest chance of primer interaction, random, pseudo random, and/or guided changes. Magnitude of the change can be correlated to fitness of the best point, average fitness, predetermined function, rate of improvement or other metrics. In some embodiments, this process comprising a genetic algorithm can be repeated. In some embodiments, repetition can be stopped when model of high enough fitness is obtained (e.g., a threshold fitness scores as described herein). In some embodiments, time limit and/or changes are insignificant. See e.g., Davis, Handbook of genetic algorithms, 1991, ISBN-13: 978-0442001735; Whitley, Statistics and Computing, June 1994, Volume 4, Issue 2, pp 65-85; each of which is incorporated herein by reference in its entirety.

In some embodiments, a neural network method can be used alone or iteratively, together, and/or separately with at least one other method to select an optimal primer set. In some embodiments, using a neural network it is possible to create a function (e.g., one or more per target) that gets inputs of all possible primer pairs. Such a function produces a recommendation based on internal values and/or functions. Once a recommendation has been made, an output of functions is fed back into the initial set of functions, with some causing output values to change. After the function settles on certain point, a primer interaction score (e.g., fitness score) is calculated. If this score is not satisfactory, changes are made to internal values and/or functions, and the process is repeated. Change to the internal values can be guided by a variety of algorithms. In some embodiments, it is possible to have internal values for the function to be picked in advance as well as adjusted or created just for the set of targets. In some embodiments, the neural network comprises a node. As used herein, "node" refers to the basic unit of computation in a neural network. A node can also be referred to as a neuron or unit. See e.g., Hansen et al., IEEE Transactions on Pattern Analysis & Machine Intelligence, October 1990, pp. 993-1001, vol. 12; Specht et al., IEEE Transactions on Neural Networks (Volume: 2, Issue: 6, November 1991), pp. 568-576; each of which is incorporated by reference herein in its entirety.

In some embodiments, a cluster analysis method can be used alone or iteratively, together, and/or separately with at least one other method to select an optimal primer set. In some embodiments, using a cluster analysis algorithm where all primer pair interactions are placed in a cluster, some members of the cluster that are outer most are candidates for substitution (e.g., either one of the primer pairs is replaced, or both). In some embodiments, substitution is picked in such way to minimize resulting interaction score (e.g., maximize the fitness score). See e.g., Scott et al., Biometrics Vol. 30, No. 3 (September, 1974), pp. 507-512; Calinski et al., Communications in Statistics Volume 3, 1974—Issue 1, pp. 1-27; Fraley et al., The Computer Journal, Volume 41, Issue 8, 1998, Pages 578-588; each of which is incorporated by reference herein in its entirety.

In some embodiments, Cluster Analysis to create bins method can be used alone or iteratively, together, and/or separately with at least one other method to select an optimal primer set. In some embodiments, if there is a situation where it becomes evident that the solution to produce a set of primers where primer interaction is below a certain threshold is not attainable, cluster analysis can be used to separate targets into two or more sets where targets that have primer pairs with high likelihood of primer interactions will be placed into separate sub set(s) once they are extracted. New subset is optimized using approaches listed above (e.g., a Monte Carlo random or pseudo-random selection method; a golden section search; gradient descent; minima hopping; genetic algorithm; neural networks; cluster analysis). In some embodiments, if a score for the new set is significantly lower, as compared to an original set, new elements may be added to even out the chance of interaction between multiple sets. See e.g., Nugent and Stuetzle, Clustering with Confidence: A Binning Approach, 2008, available on the world wide web at stat.cmu.edu/tr/tr870/tr870.pdf, which is incorporated by reference herein in its entirety.

Primer Synthesis

Described herein are methods of selecting and/or designing a primer set, e.g., for large amplicon number multiplexing. In some embodiments, the selected primer set is synthesized. Methods of oligonucleotide synthesis are well known to those of skill in the art. As used herein, "oligonucleotide synthesis" refers to the chemical synthesis of relatively short fragments of nucleic acids with defined chemical structure. As a non-limiting example, methods of oligonucleotide synthesis include phosphoramidite solid-phase synthesis, phosphoramidite synthesis, phosphodiester synthesis, phosphotriester synthesis, or phosphite triester synthesis. See e.g., Beaucage et al. Tetrahedron Volume 48, Issue 12, 20 Mar. 1992, Pages 2223-2311; Caruthers, J Biol Chem. 2013 Jan. 11, 288(2):1420-7.

In some embodiments, each primer is synthesized separately. In some embodiments, the entire primer set is synthesized in one reaction. In some embodiments, a subset of the entire primer set is synthesized in one reaction. In some embodiments, the entire primer set is synthesized in multiple, separate reactions. In some embodiments, reaction products are isolated, e.g., by high-performance liquid chromatography (HPLC), to obtain the desired oligonucleotides in high purity.

Equalization of Reads

It has been recognized that uneven amplification of genotyping targets reduces the efficiency, and therefore the throughput, of NGS-based multiplex genotyping approaches. Accordingly, described herein are methods for equalization of reads in these approaches (see e.g., Example 12). In some embodiments, anti-sense oligos are used to equalize reads. As used herein, the term "anti-sense oligo" (also referred to as a "blocker" or an "attenuator oligo") refers to an oligo that is complementary (i.e. anti-sense) to at least one amplicon in a reaction mixture.

In some embodiments the anti-sense oligo is at least 10 nucleotides (nt) long. As a non-limiting example, the anti-sense oligo is at least 10 nt, 11 nt, 12 nt, 13 nt, 14 nt, 15 nt, 16 nt, 17 nt, 18 nt, 19 nt, 20 nt, 21 nt, 22 nt, 23 nt, 24 nt, 25 nt, 26 nt, 27 nt, 28 nt, 29 nt, 30 nt, 31 nt, 32 nt, 33 nt, 34 nt, or at least 35 nt long. In some embodiments of any of the aspects, the anti-sense oligo is between 10 and 35 nucleotides in length, e.g., 10-30 nucleotides, 10-25 nucleotides, 10-20 nucleotides, 10-15 nucleotides, 15-35 nucleotides, 15-30 nucleotides, 15-25 nucleotides, 15-20 nucleotides, 20-35 nucleotides, 20-30 nucleotides, or 20-25 nucleotides long.

In some embodiments of any of the aspects, the anti-sense oligo exhibits reverse complementarity (i.e. is anti-sense) to an amplicon or part of an amplicon. The anti-sense oligo used must be capable of hybridizing to the target amplicon and thereby inhibiting amplification. In one embodiment, the anti-sense oligos lack a 3' hydroxyl moiety that permits extension by a polymerase. In another embodiment, the anti-sense oligos are fully complementary to at least a portion of the target amplicon. Alternatively, the anti-sense oligos can include some degree of non-complementarity, as long as they are still capable of hybridizing to the target amplicon under the conditions for the amplification reaction. The degree of non-complementarity tolerated can vary with the length and composition of the oligo and/or target, in that longer oligos tend to hybridize more efficiently than shorter ones, and G/C content affects efficiency as well. Keeping these and other variables in mind, in some embodiments, the anti-sense oligos have at least about 90%, about 91%, about 92%, about 93%, about 94%, about 95%, about 96%, about 97%, about 98%, about 99%, or about 100% identity with at least one target amplicon. In some embodiments, the anti-sense oligo hybridizes to at least one primer, especially during the early PCR cycles when the amplicon level is minimal.

In some embodiments, at least one anti-sense oligo is added to a reaction mixture. As a non-limiting example, 1 anti-sense oligo, 2 anti-sense oligos, 3 anti-sense oligos, 4 anti-sense oligos, 5 anti-sense oligos, 6 anti-sense oligos, 7 anti-sense oligos, 8 anti-sense oligos, 9 anti-sense oligos, or at least 10 anti-sense oligos are added or included in a reaction mixture. In some embodiments, each anti-sense oligo can be directed at a different amplicon. In some embodiments, a set of anti-sense oligo binds to and/or inhibits at least 1, at least 2, at least 3, at least 4, at least 5, at least 6, at least 7, at least 8, at least 9, or at least 10 primers and/or amplicons.

In some embodiments, the anti-sense oligo or set of anti-sense oligos is added to inhibit high-performing amplicons from forming and thereby allow poorer performing amplicons to produce more data. As used herein, "high performing" refers to an amplicon that has a higher number of reads than the average number of reads for all amplicons. As a non-limiting example, a high-performing amplicon can have at least 400 reads, at least 410 reads, at least 420 reads, at least 430 reads, at least 440 reads, at least 450 reads, at least 460 reads, at least 470 reads, at least 480 reads, at least 490 reads, at least 500 reads, at least 510 reads, at least 520 reads, at least 530 reads, at least 540 reads, at least 550 reads, at least 560 reads, at least 570 reads, at least 580 reads, at least 590 reads, at least 600 reads, at least 610 reads, at least 620 reads, at least 630 reads, at least 640 reads, at least 650 reads, at least 660 reads, at least 670 reads, at least 680 reads, at least 690 reads, or at least 700 reads in a sequencing reaction.

In some embodiments, a high-performing amplicon can have a number of reads that is at least 50% greater than the average number of reads for all amplicons. As a non-limiting example, a high-performing amplicon can have a number of reads that is at least 10%, at least 20%, at least 30%, at least 40%, at least 50%, at least 60%, at least 70%, at least 80%, at least 90%, at least 100%, at least 110%, at least 120%, at least 130%, at least 140%, at least 150%, at least 160%, at least 170%, at least 180%, at least 190%, or at least 200% greater than the average number of reads for all amplicons.

As used herein, "low performing amplicon" (or "poorer performing amplicon) refers to an amplicon that has a lower number of reads than the average number of reads for all amplicons. As a non-limiting example, a low-performing amplicon can have at most 100 reads, at most 110 reads, at most 120 reads, at most 130 reads, at most 140 reads, at most 150 reads, at most 160 reads, at most 170 reads, at most 180 reads, at most 190 reads, at most 200 reads, at most 210 reads, at most 220 reads, at most 230 reads, at most 240 reads, at most 250 reads, at most 260 reads, at most 270 reads, at most 280 reads, at most 290 reads, at most 300 reads, at most 310 reads, at most 320 reads, at most 330 reads, at most 340 reads, at most 350 reads, at most 360 reads, at most 370 reads, at most 380 reads, at most 390 reads, or at most 400 reads in a sequencing reaction.

In some embodiments, a low-performing amplicon can have a number of reads that is at least 50% less than the average number of reads for all amplicons. As a non-limiting example, a low-performing amplicon can have a number of reads that is at least 10%, at least 20%, at least 30%, at least 40%, at least 50%, at least 60%, at least 70%, at least 80%, at least 90%, at least 100%, at least 110%, at least 120%, at least 130%, at least 140%, at least 150%, at least 160%, at least 170%, at least 180%, at least 190%, or at least 200% less than the average number of reads for all amplicons.

In some embodiments, an anti-sense oligo or a set of anti-sense oligos is added at a specific concentration. In some embodiments, an anti-sense oligo or a set of anti-sense oligos can be added at a concentration that is higher than the concentration of the other primers or oligos. In some embodiments, an anti-sense oligo or a set of anti-sense oligos can be added at a concentration that is lower than the concentration of the other primers or oligos. In some embodiments, an anti-sense oligo or a set of anti-sense oligos can be added at a concentration that is the same as the concentration of the other primers or oligos. As a non-limiting example, an anti-sense oligo or a set of anti-sense oligos can be added at a concentration of about 0.01 μM, about 0.02 μM, about 0.03 μM, about 0.04 μM, about 0.05 μM, about 0.06 μM, about 0.07 μM, about 0.08 μM, about 0.09 μM, about 0.1 μM, about 0.2 μM, about 0.3 μM, about 0.4 μM, about 0.5 μM, about 0.6 μM, about 0.7 μM, about 0.8 μM, about 0.9 μM, or about 1.0 μM.

In some embodiments, anti-sense oligos can be used for performing multiplex PCR that results in even reads produced by NGS instruments for each amplicon (e.g., for 2-10,000 amplicons) and each sample (e.g., for 1-100,000 DNA samples).

In some embodiments, the anti-sense oligo further comprises an additional sequence on the 5'-end that permanently inactivate primers in solution once annealed and extended. Such anti-sense oligos with 5' primer-binding sequences are referred to as an inactivator oligos. Other embodiments use anti-sense oligos with reversible binding characteristics having only complementary sequences (e.g., attenuator oligos).

In some embodiments, the additional 5' sequence on an inactivator oligo can be at least 2 nt, 3 nt, 4 nt, 5 nt, 6 nt, 7 nt, 8 nt, 9 nt, 10 nt, 11 nt, 12 nt, 13 nt, 14 nt, 15 nt, 16 nt, 17 nt, 18 nt, 19 nt, 20 nt, 21 nt, 22 nt, 23 nt, 24 nt, 25 nt, 26 nt, 27 nt, 28 nt, 29 nt, 30 nt, 31 nt, 32 nt, 33 nt, 34 nt, or at least 35 nt long. In some embodiments, the inactivator oligo has about 90%, about 91%, about 92%, about 93%, about 94%, about 95%, about 96%, about 97%, about 98%, about 99%, or about 100% identity with at least one primer. At least one inactivator oligo can be added to a reaction mixture.

Barcode Primer Design

Described herein are methods of designing a primer set, e.g., for large amplicon number multiplexing. In some embodiments, the primers comprise barcodes that allow for large number multiplexing (see e.g., Example 13). As used herein, a "barcode" or "index" is a nucleotide sequence that can be used to identify a sample (e.g., a sample from a specific subject). As a non-limiting example, a barcode can be 5-10 nucleotides long. As a non-limiting example, barcode can be 2 nt, 3 nt, 4 nt, 5 nt, 6 nt, 7 nt, 8 nt, 9 nt, 10 nt, 11 nt, 12 nt, 13 nt, 14 nt, 15 nt, 16 nt, 17 nt, 18 nt, 19 nt, 20 nt, 21 nt, 22 nt, 23 nt, 24 nt, 25 nt, 26 nt, 27 nt, 28 nt, 29 nt, 30 nt, 31 nt, 32 nt, 33 nt, 34 nt, or at least 35 nt long.

In some embodiments, a barcode can be unique for each primer or amplicon. In some embodiments, a set of barcodes can comprise at least 2 unique barcode sequences. As a non-limiting example, a set of barcodes can comprise at least 2, at least 3, at least 4, at least 5, at least 6, at least 7, at least 8, at least 9, at least 10, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190, at least 200, at least 250, at least 300, at least 350, at least 400, at least 450, or least 500 unique barcode sequences. As a non-limiting example, a set of barcodes can comprise 144 unique barcode sequences that are each 10 nucleotides long.

In some embodiments, a primer can comprise at least 2 barcodes. As a non-limiting example, a primer can comprise 1 barcode, 2 barcodes, 3 barcodes, 4 barcodes, 5 barcodes, 6 barcodes, 7 barcodes, 8 barcodes, 9 barcodes, or 10 barcodes. In some embodiments, one set of barcodes can comprise Illumina™ I5 indexes, Illumina™ I7 indexes, and/or Ion Torrent barcode sequences. In some embodiments, barcodes be incorporated "in-line" (meaning sequentially or in the same primer) into I5 Illumina™ primers, I7 Illumina™ primers, Ion Torrent™ primers, or the primers for any other sequencing platform, as described herein. As a non-limiting example, a combination of in-line and I5/I7 barcodes on the Illumina™ platform can be used for greater than 100 samples, 500 samples, 1,000 samples, 10,000 samples, 20,000 samples, 30,000 samples, 40,000 samples, 50,000 samples, 60,000 samples, 70,000 samples, 80,000 samples, 90,000 samples, or 100,000 samples in the same sequencing run.

In some embodiments, the barcodes that allow for large number multiplexing (e.g., "in-line" barcodes) are used during the primary amplification. In some embodiments, the barcodes that allow for large number multiplexing are used during the secondary amplification. In some embodiments, the Illumina™, Ion Torrent, or other NGS barcodes or indexes are used during the primary amplification. In some embodiments, the Illumina™, Ion Torrent, or other NGS barcodes or indexes are used during the secondary amplification. In some embodiments, the barcodes that allows for large number multiplexing are used during a different amplification as the Illumina™, Ion Torrent, or other NGS barcodes or indexes. In some embodiments, the barcodes that allow for large number multiplexing are used during the same amplification as the Illumina™, Ion Torrent, or other NGS barcodes or indexes.

PCR Amplification Method

Described herein is a non-limiting example of a PCR amplification method (see e.g., Example 14). In some embodiments, the PCR amplification method comprises a primary (i.e. first) PCR amplification and a secondary PCR amplification. In some embodiments, the primary PCR amplification and the secondary PCR amplification are performed sequentially. In some embodiments, the primary amplification is performed with the primer mix or primer set designed using any one or combination of the methods described herein. In some embodiments, primers in the primary PCR amplification further comprise a 5' tail sequence, wherein "tail" denotes that the sequence does not hybridize to the target. In some embodiments, the 5' tail sequence of the primary PCR amplification primers comprises an appropriate number of bases such that all primers in the primer set are the same length (e.g., length N). In some embodiments, the 5' tail sequence of the primary PCR amplification primers comprises at 1 barcode or at least 2 barcodes.

In some embodiments, a secondary PCR amplification can be performed using the primary amplification as the source or template. In some embodiments, the secondary PCR amplification is performed using a different set of primers as the primary PCR amplification. In some embodiments, the secondary PCR amplification is performed using the same set of primers as the primary PCR amplification. In some embodiments, the secondary PCR amplification is performed using primers (e.g., from the primary PCR amplification, from a unique set of primers) further comprising a 5' tail sequence. In some embodiments, the 5' tail sequence of the secondary PCR amplification primers comprises an appropriate number of bases such that all primers in the primer set are the same length (e.g., length N). In some embodiments, the 5' tail sequence of the secondary PCR amplification primers comprises at 1 barcode or at least 2 barcodes.

In some embodiments, the primary PCR amplification reaction mixture is transferred into the secondary PCR amplification reaction mixture. As a non-limiting example, about 10 nanoliters (nL), about 20 nL, about 30 nL, about 40 nL, about 50 nL, about 60 nL, about 70 nL, about 80 nL, about 90 nL, about 100 nL, about 200 nL, about 300 nL, about 400 nL, about 500 nL, about 600 nL, about 700 nL, about 800 nL, about 900 nL, or about 1000 nL of the primary PCR amplification reaction mixture is transferred into the secondary PCR amplification reaction mixture. In some embodiments, the transfer can performed using a disposable plastic pintool, a pipette, an automated pintool, an automated pipette, or any other device or machine appropriate for this task. In some embodiments, the secondary amplicons are mixed into one sample and loaded onto a Next Generation Sequencer.

Single Base Multiplexed Sequencing

The methods described herein permit efficient sequencing and genotype calling in high multiplex. Thus, described herein are methods for performing multiplex PCR that results in even reads produced by NGS instruments for each amplicon (for 2-10,000 amplicons) and each sample (for 1-100,000 DNA samples). In one embodiment, a variation is described herein that permits single base multiplexed sequencing on an NGS platform, in order to avoid sequencing additional regions, e.g., when this is beneficial. In some embodiments, primers can be designed using an N+1 approach, meaning that all primers in a set end at the same number of nucleotides, N, away from a sequence of interest, e.g., a SNP. In this design, the NGS sequencing platform can be run for a maximum of N+1 cycles to interrogate the SNPs without reading beyond the SNP itself.

In some embodiments, a primer set is designed such that all primers in the primer set (e.g., of the primary PCR amplification and/or the secondary PCR amplification) are the same length (e.g., length N). As a non-limiting example, all primers in a primer set are 17 nt, 18 nt, 19 nt, 20 nt, 21 nt, 22 nt, 23 nt, 24 nt, 25 nt, 26 nt, 27 nt, 28 nt, 29 nt, 30 nt, 31 nt, 32 nt, 33 nt, 34 nt, or 35 nt long. In some embodiments, an additional set of bases are added to the 5' end of the primers (e.g., used in the primary amplification and/or the secondary PCR amplification) such that all are of length N. In some embodiments, the additional set of bases added to the 5' end of the primer can be referred to as a "5' tail", as described supra.

In some embodiments, a primer or a primer set is designed such that the 3' end of the primer binds or hybridizes a short distance from the nucleic acid region of interest (e.g., SNP). In some embodiments, a primer or a primer set is designed such that the 3' end of the primer binds or hybridizes immediately preceding the nucleic acid region of interest (e.g., SNP). In other words, the 3' end of the primer binds or hybridizes to a base and the nearest 3' neighbor of that base is the nucleic acid region of interest (e.g., SNP). As a non-limiting example, a primer can be designed such that the 3' end of the primer binds or hybridizes 1 bp, 2 bp, 3 bp, 4 bp, 5 bp, 6 bp, 7 bp, 8 bp, 9 bp, or 10 bp from the nucleic acid region of interest (e.g., SNP).

In some embodiments, single based multiplexed sequencing can be performed using a limited number of cycles on an NGS platform. As a non-limiting example, single based multiplexed sequencing can be performed using 1 cycle, 2 cycles, 3 cycles, 4 cycles, 5 cycles, 6 cycles, 7 cycles, 8 cycles, 9 cycles, 10 cycles, 11 cycles, 12 cycles, 13 cycles, 14 cycles, 15 cycles, 16 cycles, 17 cycles, 18 cycles, 19 cycles, 20 cycles, 21 cycles, 22 cycles, 23 cycles, 24 cycles, 25 cycles, 26 cycles, 27 cycles, 28 cycles, 29 cycles, 30 cycles, 31 cycles, 32 cycles, 33 cycles, 34 cycles, 35 cycles, 36 cycles, 37 cycles, 38 cycles, 39 cycles, 40 cycles, 41 cycles, 42 cycles, 43 cycles, 44 cycles, 45 cycles, 46 cycles, 47 cycles, 48 cycles, 49 cycles, or 50 cycles on an NGS platform.

Personalized Software

Also described herein are methods to rapidly analyze NGS sequencing data using personalized software to automatically provide genotype or sequencing results (see e.g., Example 16). In some embodiments, a primer set is designed using methods comprising PlexForm™. In some embodiments, a sequencing reaction is performed using a PlexSeq™ assay, and in some embodiments primers are used designed by Plexform™. In some embodiments, data from the PlexSeg™ assay is analyzed using PlexCall™.

In some embodiments, PlexCall™ provides automatic calling of genotypes and allele ratios. As a non-limiting example, PlexCall™ comprises a method of calling geno- types and allele ratios, comprising at least one of the following steps: determining a sample ID based on the barcode sequence, determining an amplicon ID based on the amplicon sequence, determining an allele ratio based on the number of reads per allele, and/or determining a genotype based on the allele ratio. In some embodiments, PlexCall™ can be personalized for each experiment and includes all barcode and SNP information. In some embodiments, Plex- Call™ can provide information on primer dimer (e.g., primer-primer interactions).

Low Abundance Rare Variants

Also described herein are methods to identify and quan- tify low abundance rare variants. As used herein, "low abundance rare variants" refers to variants or alleles for a specific gene that are present at a low level in a population. As a non-limiting example, a low abundance rare variant can represent at most 0.01%, at most 0.1%, at most 0.2%, at most 0.3%, at most 0.4%, at most 0.5%, at most 0.6%, at most 0.7%, at most 0.8%, at most 0.9%, at most 1.0%, at most 2.0%, at most 3.0%, at most 4.0%, at most 5.0%, at most 6.0%, at most 7.0%, at most 8.0%, at most 9.0%, at most 10.0%, at most 20.0%, at most 30.0%, at most 40.0% or at most 50.0% of the total variants or alleles for a specific gene in a population.

In some embodiments, low abundance rare variants can be identified and/or quantified in clinically relevant genes, as known in the art.

In some embodiments, genotyping (e.g., for low abun- dance rare variant(s)) can be performed on a minority of tumor cells from a complex mixture of cells. As used herein, "complex mixture of cells" denotes that many cells types other than the cell of interest (e.g., tumor cell) are present in the mixture. In some embodiments, the complex mixture of cells can comprise at most 0.01%, at most 0.1%, at most 0.2%, at most 0.3%, at most 0.4%, at most 0.5%, at most 0.6%, at most 0.7%, at most 0.8%, at most 0.9%, at most 1.0%, at most 2.0%, at most 3.0%, at most 4.0%, at most 5.0%, at most 6.0%, at most 7.0%, at most 8.0%, at most 9.0%, at most 10.0%, at most 20.0%, at most 30.0%, at most 40.0% or at most 50.0% tumor cells.

In some embodiments, the genotyping (e.g., PlexSeg™) analysis is performed in triplicate. As a non-limiting example, the genotyping analysis can be performed at least 1 time, at least 2 times, at least 3 times, at least 4 times, at least 5 times, at least 6 times, at least 7 times, at least 8 times, at least 9 times, or at least 10 times. In some embodiments, the mutant alleles are quantified and the quantification produces a mutant allele frequency. In some embodiments, the mutant allele frequency is used to determine or quantify the percent of tumor cells in the sample.

In some embodiments, such a method can be applied to the detection of cells collected from blood, urine, other body fluids, or an organ biopsy. In some embodiments, such a method can be applied to the detection of minimal residual disease immediately post-surgery or therapy. In some embodiments, such a method can be applied to follow-up weekly, monthly or yearly to determine success of therapy and track disease recurrence.

Nucleic Acid Samples

Methods and compositions described herein can comprise nucleic acids. In some embodiments the nucleic acids are synthetic (e.g., oligonucleotides, primers, amplicons). A nucleic acid can include nucleobase (often referred to in the art simply as "base") modifications or substitutions. As used herein, "unmodified" or "natural" nucleobases include the purine bases adenine (A) and guanine (G), and the pyrimi- dine bases thymine (T), cytosine (C) and uracil (U). Modi- fied nucleobases include other synthetic and natural nucle- obases such as 5-methylcytosine (5-me-C), 5-hydroxymethyl cytosine, xanthine, hypoxanthine, 2-ami- noadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hy- droxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deaz- aguanine and 7-daazaadenine and 3-deazaguanine and 3-deazaadenine. Certain of these nucleobases are particu- larly useful for increasing the binding affinity of the inhibi- tory nucleic acids featured in the invention. These include 5-substituted pyrimidines, 6-azapyrimidines and N-2, N-6 and 0-6 substituted purines, including 2-aminopropylad- enine, 5-propynyluracil and 5-propynylcytosine. 5-methyl- cytosine substitutions have been shown to increase nucleic acid duplex stability by 0.6-1.2° C. (Sanghvi, Y. S., Crooke, S. T. and Lebleu, B., Eds., dsRNA Research and Applica- tions, CRC Press, Boca Raton, 1993, pp. 276-278) and are exemplary base substitutions, even more particularly when combined with 2'-O-methoxyethyl sugar modifications. The preparation of the modified nucleobases described above are well known in the art. Nucleic acids can be indicated using a one-letter code, e.g., the ambiguity code developed by International Union of Pure and Applied Chemistry (IU- PAC).

TABLE 13

| shows IUPAC Ambiguity Codes. | | |
| --- | --- | --- |
| IUPAC Code | Meaning | Complement |
| A | A | T |
| C | C | G |
| G | G | C |
| T/U | T | A |
| M | A or C | K |
| R | A or G | Y |
| W | A or T | W |
| S | C or G | S |
| Y | C or T | R |
| K | G or T | M |
| V | A or C or G | B |
| H | A or C or T | D |

In some embodiments, nucleic acids are isolated from a sample. Nucleic acid and ribonucleic acid (RNA) molecules can be isolated from a particular biological sample using any of a number of procedures, which are well-known in the art, the particular isolation procedure chosen being appropriate for the particular biological sample. For example, freeze- thaw and alkaline lysis procedures can be useful for obtain- ing nucleic acid molecules from solid materials; heat and alkaline lysis procedures can be useful for obtaining nucleic acid molecules from urine; and proteinase K extraction can be used to obtain nucleic acid from blood (Roiff, A et al. PCR: Clinical Diagnostics and Research, Springer (1994)).

In some embodiments, a nucleic acid of interest (e.g., SNP) can be quantified and compared to a reference level.

A level which is less than a reference level can be a level which is less by at least about 10%, at least about 20%, at least about 50%, at least about 60%, at least about 80%, at least about 90%, or less relative to the reference level. In some embodiments of any of the aspects, a level which is less than a reference level can be a level which is statistically significantly less than the reference level.

A level which is more than a reference level can be a level which is greater by at least about 10%, at least about 20%, at least about 50%, at least about 60%, at least about 80%, at least about 90%, at least about 100%, at least about 200%, at least about 300%, at least about 500% or more than the reference level. In some embodiments of any of the aspects, a level which is more than a reference level can be a level which is statistically significantly greater than the reference level.

In some embodiments of any of the aspects, the reference can be a level of the target molecule in a population of subjects who do not have or are not diagnosed as having, and/or do not exhibit signs or symptoms of a specific disease (e.g., cancer). In some embodiments of any of the aspects, the reference can also be a level of expression of the target molecule in a control sample, a pooled sample of control individuals or a numeric value or range of values based on the same. In some embodiments of any of the aspects, the reference can be the level of a target molecule in a sample obtained from the same subject at an earlier point in time, e.g., the methods described herein can be used to determine if a subject's sensitivity or response to a given therapy is changing over time.

In some embodiments of the foregoing aspects, the quantification of a nucleic acid of interest (e.g., SNP) can be normalized relative to the expression level of one or more reference genes or reference proteins.

In some embodiments, the reference level can be the level in a sample of similar cell type, sample type, sample processing, and/or obtained from a subject of similar age, sex and other demographic parameters as the sample/subject for which the level of a nucleic acid region of interest (e.g., SNP) is to be determined. In some embodiments, the test sample and control reference sample are of the same type, that is, obtained from the same biological source, and comprising the same composition, e.g. the same number and type of cells.

The term "sample" or "test sample" as used herein denotes a sample taken or isolated from a biological organism, e.g., a blood or plasma sample from a subject. In some embodiments of any of the aspects, the present invention encompasses several examples of a biological sample. In some embodiments of any of the aspects, the biological sample is cells, or tissue, or peripheral blood, or bodily fluid. Exemplary biological samples include, but are not limited to, a biopsy, a tumor sample, biofluid sample; blood; serum; plasma; urine; sperm; mucus; tissue biopsy; organ biopsy; synovial fluid; bile fluid; cerebrospinal fluid; mucosal secretion; effusion; sweat; saliva; and/or tissue sample etc. The term also includes a mixture of the above-mentioned samples. The term "test sample" also includes untreated or pretreated (or pre-processed) biological samples. In some embodiments of any of the aspects, a test sample can comprise cells from a subject. In some embodiments of any of the aspects, the test sample can be a tumor biopsy. In some embodiments, the test sample can be a plant sample, including but not limited to a leaf, stem, root, bark, fruit, flower, seed, or other plant product.

The test sample can be obtained by removing a sample from a subject, but can also be accomplished by using a previously isolated sample (e.g. isolated at a prior time point and isolated by the same or another person).

In some embodiments of any of the aspects, the test sample can be an untreated test sample. As used herein, the phrase "untreated test sample" refers to a test sample that has not had any prior sample pre-treatment except for dilution and/or suspension in a solution. Exemplary methods for treating a test sample include, but are not limited to, centrifugation, filtration, sonication, homogenization, heating, freezing and thawing, and combinations thereof. In some embodiments of any of the aspects, the test sample can be a frozen test sample, e.g., a frozen tissue. The frozen sample can be thawed before employing methods, assays and systems described herein. After thawing, a frozen sample can be centrifuged before being subjected to methods, assays and systems described herein. In some embodiments of any of the aspects, the test sample is a clarified test sample, for example, by centrifugation and collection of a supernatant comprising the clarified test sample. In some embodiments of any of the aspects, a test sample can be a pre-processed test sample, for example, supernatant or filtrate resulting from a treatment selected from the group consisting of centrifugation, filtration, thawing, purification, and any combinations thereof. In some embodiments of any of the aspects, the test sample can be treated with a chemical and/or biological reagent. Chemical and/or biological reagents can be employed to protect and/or maintain the stability of the sample, including biomolecules (e.g., nucleic acid and protein) therein, during processing. One exemplary reagent is a protease inhibitor, which is generally used to protect or maintain the stability of protein during processing. The skilled artisan is well aware of methods and processes appropriate for pre-processing of biological samples required for determination of the level of an expression product as described herein.

In some embodiments of any of the aspects, the methods, assays, and systems described herein can further comprise a step of obtaining or having obtained a test sample from a subject. In some embodiments of any of the aspects, the subject can be a human subject. In some embodiments of any of the aspects, the subject can be a subject in need of treatment for (e.g. having or diagnosed as having) cancer or a subject at risk of or at increased risk of developing cancer as described elsewhere herein.

In some embodiments, a nucleic acid sample (e.g., an isolated nucleic acid) can be amplified using PCR. The PCR procedure describes a method of gene amplification which is comprised of (i) sequence-specific hybridization of primers to specific genes or sequences within a nucleic acid sample or library, (ii) subsequent amplification involving multiple rounds of annealing, elongation, and denaturation using a thermostable DNA polymerase, and (iii) screening the PCR products for a band of the correct size. The primers used are oligonucleotides of sufficient length and appropriate sequence to provide initiation of polymerization, i.e. each primer is specifically designed to be complementary to a strand of the genomic locus to be amplified. Unless noted otherwise, PCR reactions are conducted under standard conditions using standard reagents, as well known to those of skill in the art.

Next Generation Sequencing

In some embodiments as described further herein, nucleic acid samples (e.g., amplified nucleic acid samples) can be sequenced. Sequencing is the process of determining the order of monomers in a polymer. For example, DNA or RNA sequencing is the process of determining a nucleic acid sequence—the order of nucleotides in DNA or RNA, respectively, from a sample. DNA or RNA sequencing can also be referred to herein as "nucleic acid sequencing" or simply "sequencing."

Methods of sequencing a nucleic acid sequence are well known in the art. Briefly, a sample obtained from a subject can be contacted with one or more primers which specifically hybridize to a single-strand nucleic acid sequence flanking the target gene sequence and a complementary strand is synthesized. In some next-generation technologies, an adaptor (double or single-stranded) is ligated to nucleic acid molecules in the sample and synthesis proceeds from the adaptor or adaptor compatible primers. In some third-generation technologies, the sequence can be determined, e.g. by determining the location and pattern of the hybridization of probes, or measuring one or more characteristics of a single molecule as it passes through a sensor (e.g. the modulation of an electrical field as a nucleic acid molecule passes through a nanopore).

In some embodiments as described herein, nucleic acid sequence data can be obtained from a sequencing platform. The term "sequencing platform" refers not only to a particular machine or device used for sequencing, but also to the particular chemical and/or physical approaches applied to extract or derive the sequence information from a sample. Exemplary methods of sequencing include, but are not limited to, Sanger sequencing, dideoxy chain termination, high-throughput sequencing, next generation sequencing, pyrosequencing (e.g., 454), sequencing by ligation and detection (SOLiD™), polony sequencing, sequencing by synthesis (e.g., Illumina™), ion semiconductor sequencing (e.g., Ion Torrent™), sequencing by hybridization, nanopore sequencing, HeliScope single molecule sequencing, single-molecule real-time sequencing (SMRT), RNAP sequencing, combinatorial probe anchor synthesis (cPAS), nanopore sequencing, chain termination sequencing, DNA nanoball sequencing, and the like. Methods and protocols for performing these sequencing methods are known in the art, see, e.g. "Next Generation Genome Sequencing" Ed. Michal Janitz, Wiley-VCH; "High-Throughput Next Generation Sequencing" Eds. Kwon and Ricke, Humanna Press, 2011; and Sambrook et al., Molecular Cloning: A Laboratory Manual (4 ed.), Cold Spring Harbor Laboratory Press, Cold Spring Harbor, N.Y., USA (2012); which are incorporated by reference herein in their entireties.

Early methods of DNA sequencing, or "first generation sequencing," included Sanger sequencing (also known as chain terminator sequencing) and Maxam-Gilbert sequencing (also known as chemical sequencing). High-throughput sequencing methods have significantly reduced the cost and time to sequence nucleic acid samples. High-throughput sequencing can also be referred to herein as "next-generation sequencing", "second-generation sequencing", "third-generation sequencing", or "massively parallel signature sequencing (MPSS)".

Non-limiting examples of ion semiconductor sequencing platforms include Ion Torrent™ sequencing platforms comprising Ion S5™, Ion AmpliSeq™, Ion Proton™, Ion PGM™ (e.g., PGM 314™, PGM 316™, PGM 318™, PI™ or PII™), or Ion Chef™ platforms, from ThermoFisher™ (see e.g., U.S. Pat. Nos. 7,785,785, 8,552,771, 8,692,298B2, 8,731,847B2, 8,742,472B2, 8,841,217B1, 8,912,580B2, 8,912,005B1, 8,962,366B2, 8,963,216B2, 9,116,117B2, 9,128,044B2, 9,194,000B2, 9,239,313B2, 9,404,920B2, 9,841,398B2, 9,927,393B2, 9,944,981B2, 9,958,414B2, 9,960,253B2, which are incorporated herein by reference in their entireties).

Pyrosequencing, an example of sequencing by synthesis, can also be referred to as 454 Life Sciences™ sequencing, 454 sequencing, or 454 pyrosequencing. Non-limiting examples of 454 pyrosequencing platforms include Genome Sequencer FLX™, GS20™, or GS Junior™ sequencing platforms. Pyrosequencing can also be performed on any the following sequencing platforms from QIAGEN: PyroMark Q48 Autoprep™, PyroMark Q24 Advanced™, PyroMark Q24™, or PyroMark Q96 ID™ (see e.g., U.S. Pat. Nos. 6,210,891, 7,323,305, 8,748,102, 8,765,380, which are incorporated herein by reference in their entireties).

Sequencing by synthesis include, for example, Illumina™ sequencing or Solexa™ sequencing. Non-limiting examples of Illumina™ sequencing platforms include cBot™, Genome Analyzer (GA)™, MiniSeg™, NextSeg™, MiSeg™, HiSeq2500™, HiSeq3000™, HiSeq 4000™, HiSeq X™ (e.g., Hiseq Ten™), iSeg™ 100, HiScan™, and iScan™ Illumina platforms (see e.g., U.S. Pat. Nos. 7,414, 116, 7,329,860, 7,589,315, 7,960,685, 8,039,817, 8,071,962, 8,158,926, 8,241,573, 8,778,848, 8,778,849, 8,244,479, 8,315,817, 8,412,467, 8,422,031, 8,446,573, 8,914,241, 8,965,076, 9,012,022, 9,068,220, 9,121,063, 9,365,898, 9,410,977, 9,512,422, 9,540,690, 9,670,535, 9,752,186, 9,777,325, 9,994,687, 10,005,083, 10,053,730, 10,152,776, which are incorporated herein by reference in their entireties).

Additional non-limiting example of sequencing by synthesis platforms can comprise GeneReader™ from QIAGEN or Mini20™ from AZCO Biotech™, Inc.

Non-limiting examples of SMRT sequencing platforms include C1™, C2™, P4-XL™, P5-C3™, P6-C4™, RS™, RS II™, or Sequel™ platforms, all from PacBio™ sequencing. SMRT sequencing can also be referred to as PacBio™ sequencing.

Non-limiting examples of cPAS sequencing platforms includeBGISEQ-50™, MGISEQ 200™, BGISEQ500™, or MGISEQ2000™, cPAS platforms. cPas sequencing platforms can also utilize DNA nanoball sequencing methods (e.g., BGISEQ500™, or MGISEQ-2000™).

Non-limiting examples of SOLiD™ sequencing platforms include 5500xl SOLiD™, 5500 SOLiD™, SOLiD 5500xl Wildfire™, or SOLiD 5500 Wildfire™, from Thermo Fisher Scientific™.

Non-limiting examples of Nanopore sequencing platforms include SmidgeION™, MinION™, and PromethION™, all from Oxford Nanopore Technologies™.

Chain termination sequencing can also be referred to as Sanger sequencing. Non-limiting examples of chain termination sequencing platforms can comprise Microfluidic Sanger sequencing platforms or the Apollo100™ platform (Microchip Biotechnologies™, Inc.).

Non-limiting examples of Polony sequencing platforms include a Polonator™ platform (Dover™) or fluorescence microscope and a computer controlled flowcell.

Non-limiting examples of HeliScope single molecule sequencing platforms include Helicos® Genetic Analysis System platform or the HeliScope™ Sequencer.

Additional non-limiting examples of sequencing methods include tunneling currents DNA sequencing, sequencing by hybridization, sequencing with mass spectrometry, microscopy-based techniques, RNA polymerase (RNAP) sequencing, or in vitro virus high-throughput sequencing.

Kits

Another aspect of the technology described herein relates to kits for multiplex genotyping, among others. Described herein are kit components that can be included in one or more of the kits described herein.

In some embodiments, the kit comprises an effective amount of PCR reagents, primers, and/or sequencing reagents. PCR reagents can comprise a polymerase, dNTPs, and/or an appropriate reaction buffer. The PCR reagents can further comprise template DNA, such as including a reference template DNA. The kit can comprise a set of primers, e.g., primers for a multiplex genotyping reaction designed using methods as described herein. The sequencing reagents can comprise reagents sufficient for library preparation specific for the sequencing platform. As a non-limiting example, the sequencing reagents can comprise primers, adaptors, polymerase, ligase, blocking reagent, lysing reagent, an appropriate buffer, and any other reagents or enzymes necessary for the specific sequencing reaction. The kit can further comprise reagents necessary for nucleic acid isolation, as described further herein.

As will be appreciated by one of skill in the art, PCR reagents, primers, and/or sequencing reagents can be supplied in a lyophilized form or a concentrated form that can diluted prior to use with cultured cells. Preferred formulations include those that are non-toxic to the cells and/or does not affect growth rate or viability etc. PCR reagents, primers, and/or sequencing reagents can be supplied in aliquots or in unit doses.

In some embodiments, the components described herein can be provided singularly or in any combination as a kit. The kit includes the components described herein, e.g., a composition comprising PCR reagents, primers, and/or sequencing reagents. In addition, the kit optionally comprises informational material.

In some embodiments, the compositions in the kit can be provided in a watertight or gas tight container which in some embodiments is substantially free of other components of the kit. For example, a composition can be supplied in more than one container, e.g., it can be supplied in a container having sufficient reagent for a predetermined number of PCR and/or sequencing reactions, e.g., 1, 2, 3 or greater. One or more components as described herein can be provided in any form, e.g., liquid, dried or lyophilized form. It is preferred that the components described herein are substantially pure and/or sterile. When the components described herein are provided in a liquid solution, the liquid solution preferably is an aqueous solution, with a sterile aqueous solution being preferred.

The informational material can be descriptive, instructional, marketing or other material that relates to the methods described herein. The informational material of the kits is not limited in its form. In one embodiment, the informational material can include information about production of a primer set, concentration, date of expiration, batch or production site information, and so forth. In one embodiment, the informational material relates to methods for using or administering the components of the kit.

The kit will typically be provided with its various elements included in one package, e.g., a fiber-based, e.g., a cardboard, or polymeric, e.g., a Styrofoam box. The enclosure can be configured so as to maintain a temperature differential between the interior and the exterior, e.g., it can provide insulating properties to keep the reagents at a preselected temperature for a preselected time.

Cancer

As used herein, the term "cancer" relates generally to a class of diseases or conditions in which abnormal cells divide without control and can invade nearby tissues. Cancer cells can also spread to other parts of the body through the blood and lymph systems. There are several main types of cancer. Carcinoma is a cancer that begins in the skin or in tissues that line or cover internal organs. Sarcoma is a cancer that begins in bone, cartilage, fat, muscle, blood vessels, or other connective or supportive tissue. Leukemia is a cancer that starts in blood-forming tissue such as the bone marrow, and causes large numbers of abnormal blood cells to be produced and enter the blood. Lymphoma and multiple myeloma are cancers that begin in the cells of the immune system. Central nervous system cancers are cancers that begin in the tissues of the brain and spinal cord.

In some embodiments of any of the aspects, the cancer is a primary cancer. In some embodiments of any of the aspects, the cancer is a malignant cancer. As used herein, the term "malignant" refers to a cancer in which a group of tumor cells display one or more of uncontrolled growth (i.e., division beyond normal limits), invasion (i.e., intrusion on and destruction of adjacent tissues), and metastasis (i.e., spread to other locations in the body via lymph or blood). As used herein, the term "metastasize" refers to the spread of cancer from one part of the body to another. A tumor formed by cells that have spread is called a "metastatic tumor" or a "metastasis." The metastatic tumor contains cells that are like those in the original (primary) tumor. As used herein, the term "benign" or "non-malignant" refers to tumors that may grow larger but do not spread to other parts of the body. Benign tumors are self-limited and typically do not invade or metastasize.

A "cancer cell" or "tumor cell" refers to an individual cell of a cancerous growth or tissue. A tumor refers generally to a swelling or lesion formed by an abnormal growth of cells, which may be benign, pre-malignant, or malignant. Most cancer cells form tumors, but some, e.g., leukemia, do not necessarily form tumors. For those cancer cells that form tumors, the terms cancer (cell) and tumor (cell) are used interchangeably.

As used herein the term "neoplasm" refers to any new and abnormal growth of tissue, e.g., an abnormal mass of tissue, the growth of which exceeds and is uncoordinated with that of the normal tissues. Thus, a neoplasm can be a benign neoplasm, premalignant neoplasm, or a malignant neoplasm.

A subject that has a cancer or a tumor is a subject having objectively measurable cancer cells present in the subject's body. Included in this definition are malignant, actively proliferative cancers, as well as potentially dormant tumors or micrometastases. Cancers which migrate from their original location and seed other vital organs can eventually lead to the death of the subject through the functional deterioration of the affected organs.

Examples of cancer include but are not limited to, carcinoma, lymphoma, blastoma, sarcoma, leukemia, basal cell carcinoma, biliary tract cancer; bladder cancer; bone cancer; brain and CNS cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma (GBM); hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); lymphoma including Hodgkin's and non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; as well as other carcinomas and sarcomas; as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome A "cancer cell" is a cancerous, pre-cancerous, or transformed cell, either in vivo, ex vivo, or in tissue culture, that has spontaneous or induced phenotypic changes that do not necessarily involve the uptake of new genetic material. Although transformation can arise from infection with a transforming virus and incorporation of new genomic nucleic acid, or uptake of exogenous nucleic acid, it can also arise spontaneously or following exposure to a carcinogen, thereby mutating an endogenous gene. Transformation/cancer is associated with, e.g., morphological changes, immortalization of cells, aberrant growth control, foci formation, anchorage independence, malignancy, loss of contact inhibition and density limitation of growth, growth factor or serum independence, tumor specific markers, invasiveness or metastasis, and tumor growth in suitable animal hosts such as nude mice.

One of skill in the art can readily identify a chemotherapeutic agent of use (e.g. see Physicians' Cancer Chemotherapy Drug Manual 2014, Edward Chu, Vincent T. DeVita Jr., Jones & Bartlett Learning; Principles of Cancer Therapy, Chapter 85 in Harrison's Principles of Internal Medicine, 18th edition; Therapeutic Targeting of Cancer Cells: Era of Molecularly Targeted Agents and Cancer Pharmacology, Chs. 28-29 in Abeloff's Clinical Oncology, 2013 Elsevier; and Fischer D S (ed): The Cancer Chemotherapy Handbook, 4th ed. St. Louis, Mosby-Year Book, 2003).

In some embodiments, genotyping methods as described herein can be used to detect and/or quantify a cancer cell with a specific allele or set of alleles. In some embodiments, the detection or quantification of cancer cells can be used to provide or alter a treatment method.

Definitions

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

As used herein, a "subject" typically means a human, animal, or plant. Usually the animal is a vertebrate such as a primate, rodent, domestic animal or game animal. Primates include chimpanzees, cynomologus monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. In some embodiments, the subject is a plant, including but not limited to species of corn, soybean, tomato, squash, cotton, wheat, sunflower, grape, cowpea, *Chrysanthemum, Eucalyptus*, flax, sesame, pepper, and rice. In some embodiments, the subject is a fungus, bacteria, protest, archaea, virus, or other entity with a nucleic acid genome. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of cancer. A subject can be male or female.

A subject can be one who has been previously diagnosed with or identified as suffering from or having a condition in need of treatment (e.g. cancer) or one or more complications related to such a condition, and optionally, have already undergone treatment for cancer or the one or more complications related to cancer. Alternatively, a subject can also be one who has not been previously diagnosed as having cancer or one or more complications related to cancer. For example, a subject can be one who exhibits one or more risk factors for cancer or one or more complications related to cancer or a subject who does not exhibit risk factors.

A "subject in need" of treatment for a particular condition can be a subject having that condition, diagnosed as having that condition, or at risk of developing that condition.

In the various embodiments described herein, it is further contemplated that variants (naturally occurring or otherwise), alleles, homologs, conservatively modified variants, and/or conservative substitution variants of any of the particular nucleic acids described are encompassed. One of skill will recognize that individual substitutions, deletions or additions to a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid and retains the desired activity of the polypeptide. Such conservatively modified variants are in addition to and do not exclude polymorphic variants, interspecies homologs, and alleles consistent with the disclosure.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known.

A variant amino acid or DNA sequence can be at least 90%, at least 91%, at least 92%, at least 93%, at least 94%, at least 95%, at least 96%, at least 97%, at least 98%, at least 99%, or more, identical to a native or reference sequence. The degree of homology (percent identity) between a native and a mutant sequence can be determined, for example, by comparing the two sequences using freely available computer programs commonly employed for this purpose on the world wide web (e.g. BLASTp or BLASTn with default settings).

Alterations of the native amino acid sequence can be accomplished by any of a number of techniques known to one of skill in the art. Mutations can be introduced, for example, at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations are very well established and include, for example, those disclosed by Walder et al. (Gene 42:133, 1986); Bauer et al. (Gene 37:73, 1985); Craik (BioTechniques, January 1985, 12-19); Smith et al. (Genetic Engineering: Principles and Methods, Plenum Press, 1981); and U.S. Pat. Nos. 4,518,584 and 4,737,462, which are herein incorporated by reference in their entireties. Any cysteine residue not involved in maintaining the proper conformation of the polypeptide also can be substituted, generally with serine, to improve the oxidative stability of the molecule and prevent aberrant crosslinking. Conversely, cysteine bond(s) can be added to the polypeptide to improve its stability or facilitate oligomerization.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable DNA can include, e.g., genomic DNA or cDNA. Suitable RNA can include, e.g., mRNA.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. cancer. The term "treating" includes reducing or alleviating at least one adverse effect or symptom of a condition, disease or disorder associated with a cancer. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, "contacting" refers to any suitable means for delivering, or exposing, an agent to at least one cell. Exemplary delivery methods include, but are not limited to, direct delivery to cell culture medium, perfusion, injection, or other delivery method well known to one skilled in the art. In some embodiments, contacting comprises physical human activity, e.g., an injection; an act of dispensing, mixing, and/or decanting; and/or manipulation of a delivery device or machine.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

As used herein, the term "corresponding to" refers to an amino acid or nucleotide at the enumerated position in a first polypeptide or nucleic acid, or an amino acid or nucleotide that is equivalent to an enumerated amino acid or nucleotide in a second polypeptide or nucleic acid. Equivalent enumerated amino acids or nucleotides can be determined by alignment of candidate sequences using degree of homology programs known in the art, e.g., BLAST.

As used herein, the term "specific binding" (e.g., hybridize) refers to a chemical interaction between two molecules, compounds, cells and/or particles wherein the first entity binds to the second, target entity with greater specificity and affinity than it binds to a third entity which is a non-target. In some embodiments, specific binding can refer to an affinity of the first entity for the second target entity which is at least 10 times, at least 50 times, at least 100 times, at least 500 times, at least 1000 times or greater than the affinity for the third nontarget entity. A reagent specific for a given target is one that exhibits specific binding for that target under the conditions of the assay being utilized.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 20th Edition, published by Merck Sharp & Dohme Corp., 2018 (ISBN 0911910190, 978-0911910421); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), W. W. Norton & Company, 2016 (ISBN 0815345054, 978-0815345053); Lewin's Genes XI, published by Jones & Bartlett Publishers, 2014 (ISBN-1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. A method for primer design that allows for large amplicon number multiplexing using PlexForm™ software.

2. A method of preparing a primer set for multiplex genotyping, the method comprising:

A) for a given set N of variable genomic target sequences to be genotyped in a sample, designing a set of forward and reverse amplification primers that will amplify a sequence comprising each variable genomic target sequence in a multiplex amplification reaction, wherein the designing includes the steps of:

1) identifying all possible primers of 17 to 35 nucleotides within 100 base pairs of each genomic target sequence variation in set N of variable genomic target sequences;

2) for each member of set N, selecting a subset of primer pairs from the set of step (1) that satisfies the conditions for a primer selection algorithm;

3) evaluating specificity of primer pairs chosen in step (2) in the genome, keeping only those pairs predicted to be specific for their respective targets;

4) selecting a set of optimized primers for the amplification of target gene set N, where the optimal primers are selected to minimize primer-primer interactions with other primers in the set by iterative calculation of predicted $\Delta G$ for interactions between primers to generate a fitness score and use of a fitness score optimization method selected from one or a combination of the group consisting of:

a) a Monte Carlo random or pseudo-random selection method;

b) a golden section search;

c) gradient descent;

d) minima hopping;

e) genetic algorithm;

f) neural networks;

g) cluster analysis, in which substitution is picked to minimize score; and h) cluster analysis to create bins; and B) synthesizing the optimized primer set selected in step (4).

3. A method of preparing a primer set for multiplex genotyping, the method comprising:

A) for a given set N of variable genomic target sequences to be genotyped in a sample, designing a set of forward and reverse amplification primers that will amplify a sequence comprising each variable genomic target sequence in a multiplex amplification reaction, wherein the designing includes the steps of:

1) identifying all possible primers of 17 to 35 nucleotides within 100 base pairs of each genomic target sequence variation in set N of variable genomic target sequences;

2) for the primers identified in step (1), randomly selecting a primer pair for each target in set N that satisfies the conditions for a primer selection algorithm;

3) evaluating specificity of primer pairs chosen in step (2) in the genome, keeping only those pairs predicted to be specific for their respective targets;

4) repeat step (2) on the primer pairs kept from step (3) to generate set P, a population of randomly selected primer sets for each target in set N;

5) generating a Fitness Score for each member of population P based upon $\Delta G$ for all possible interactions between candidate primers in each member of the population;

6) picking acceptable member(s) of the population P based on Fitness Score;

7) repeating steps (4)-(6) iteratively until a set of primer pairs for target genes identified in step (6) has a Fitness Score at a predetermined threshold; and B) synthesizing the primer set identified in step (7).

4. The method of paragraph 3, wherein the Fitness Score is generated according to the rule:

a) G=the set of $\Delta G$'s for all possible interactions determined for a given member of set P; and b) Fitness Score is calculated by:

i) for each member of set P, calculating the sum, S, of $|\Delta G|^{Q}$ for each $\Delta G$ value in that member, wherein Q is a weighting factor constant exponent that makes large $\Delta G$ absolute values much larger than small values;

ii) S'=S/# of $\Delta G$ values in G;

iii) H=T/S', wherein T is a constant that makes H small for large values of S' and H large for small values of S'; and iv) Fitness Score=$H^{R}$, wherein R is a weighting factor constant exponent that makes large values of H larger, and small values of H smaller.

5. A method of preparing a primer set for multiplex genotyping, the method comprising:

A) for a given set N of variable genomic target sequences to be genotyped in a sample, designing a set of forward and reverse amplification primers that will amplify a sequence comprising each variable genomic target sequence in a multiplex amplification reaction, wherein the designing includes the steps of:

1) identifying all possible primers of 17 to 35 nucleotides within 100 base pairs of each genomic target sequence variation in set N of variable genomic target sequences;

2) for the primers identified in step (1), randomly selecting a primer pair for each target in set N that satisfies the conditions for a primer selection algorithm and is predicted to be specific for its target in the genome, or providing a primer pair for each target in set N, that has been selected to reduce potential for primer:primer interactions with other primers in the set and is predicted to be specific for its target in the genome;

3) repeat step (2) to generate population Z, of size 2 or greater, of primer pair sets for each target in set N;

4) generating a Fitness Score for each member of population Z based upon $\Delta G$ for all possible interactions between candidate primers in each member of the population;

5) selecting the worst members of population Z based on Fitness Scores as set W;

6) replacing a primer for a single target from W with another primer identified in step (2), and generating a Fitness Score for the resulting set; wherein if the change results in an improved Fitness Score relative to the Fitness Score generated in step (4), the resulting new set W' replaces set W, and if the change results in a no change in Fitness Score or a decreased Fitness Score, keeping set W;

7) iteratively repeating steps (4)-(6) on the set W or W' retained in each iteration of step (6) until a set of primer pairs for target genes in set N is identified that has a Fitness Score at a predetermined threshold, or, if a predetermined threshold is not reached by iteratively repeating steps (4)-(6), beginning again at step (2) and iteratively repeating steps (4)-(6) until a set of primer pairs for target genes in set N is identified that has a Fitness Score at the predetermined threshold; and B) synthesizing the primer set selected in step (7) that reaches the predetermined Fitness Score threshold.

6. The method of paragraph 5, wherein the Fitness Score is generated according to the rule:

a) G=the set of ΔG's for all possible interactions determined for a given member of set P; and b) Fitness Score is calculated by:

i) for each member of set P, calculating the sum, S, of $|\Delta G|^Q$ for each ΔG value in that member, wherein Q is a weighting factor constant exponent that makes large ΔG absolute values much larger than small values;

ii) S'=S/# of ΔG values in G;

iii) H=T/S', wherein T is a constant that makes H small for large values of S' and H large for small values of S'; and iv) Fitness Score=$H^R$, wherein R is a weighting factor constant exponent that makes large values of H larger, and small values of H smaller.

7. The method of paragraph 5, wherein the step of providing a primer pair for each target in set N that has been selected to reduce potential for primer:primer interactions with other primers in the set provides primer sets selected using one or more of a Monte Carlo random or pseudo-random selection method, a golden section search, gradient descent, minima hopping, a genetic algorithm, neural networks, cluster analysis in which substitution is picked to minimize score, or cluster analysis to create bins.

8. A method of preparing a primer set for multiplex genotyping, the method comprising:

A) for a given set N of variable genomic target sequences to be genotyped in a sample, designing a set of forward and reverse amplification primers that will amplify a sequence comprising each variable genomic target sequence in a multiplex amplification reaction, wherein the designing includes the steps of:

1) identifying all possible primers of 17 to 35 nucleotides within 100 base pairs of each genomic target sequence variation in set N of variable genomic target sequences;

2) generating primer set Z, including a primer pair for each member of set N either by: (a) randomly selecting from the primers identified in step (1) a primer pair for each target in set N that satisfies the conditions for a primer selection algorithm and is predicted to be specific for its target in the genome; or (b) providing a primer pair for each target in set N that is predicted to be specific for its target in the genome, and that has been selected to reduce potential for primer:primer interactions with other primers in the set;

3) generating a Fitness Score for primer set Z based upon ΔG for all possible interactions between candidate primers in each member of the population;

4) making a change to a primer for a single target from set Z to generate new set Z', and generating a Fitness Score for set Z', wherein if the change results in an improved Fitness Score relative to that generated in step (3), the resulting new set Z' replaces set Z, and if the change results in no change in Fitness Score or a decreased Fitness Score, keeping set Z; and 5) repeating step (4) iteratively until further iterations do not improve fitness of set Z; and B) synthesizing the primer set selected in step (5).

9. The method of paragraph 8, wherein the Fitness Score is generated according to the rule:

a) G=the set of ΔG's for all possible interactions determined for members of primer set Z; and b) Fitness Score is calculated by:

i) calculating the sum, S, of $|\Delta G|^Q$ for each ΔG value, wherein Q is a weighting factor constant exponent that makes large ΔG absolute values much larger than small values;

ii) S'=S/# of ΔG values in G;

iii) H=T/S', wherein T is a constant that makes H small for large values of S' and H large for small values of S'; and iv) Fitness Score=$H^R$, wherein R is a weighting factor constant exponent that makes large values of H larger, and small values of H smaller.

10. A method of preparing a primer set for multiplex genotyping, the method comprising:

A) for a given set N of variable genomic target sequences to be genotyped in a sample, designing a set of forward and reverse amplification primers that will amplify a sequence comprising each variable genomic target sequence in a multiplex amplification reaction, wherein the designing includes the steps of:

1) identifying all possible primers of 17 to 35 nucleotides within 100 base pairs of each genomic target sequence variation in set N of variable genomic target sequences;

2) providing a set of optimized primer pairs for the amplification of target gene set N, where the optimal primer pairs are predicted to be specific for their target genes in the genome, and are selected to minimize primer-primer interactions with other primers in the set by iterative calculation of predicted ΔG for all possible interactions between primers to generate a Fitness Score and use of a Fitness Score optimization method selected from one or a combination of the group consisting of:

a) a Monte Carlo random or pseudo-random selection method;

b) a golden section search;

c) gradient descent;

d) minima hopping;

e) genetic algorithm;

f) neural networks;

g) cluster analysis, in which substitution is picked to minimize score; and h) cluster analysis to create bins;

3) adding the set of optimized primers of step (2) to set M;

4) while maintaining a degree of dissimilarity from primer sets included in set M, selecting a primer pair for each target in set N from step (1) and designating it set Z, wherein the primer pairs satisfy the conditions for a primer selection algorithm, and are predicted to be specific for their target genes in the genome;

5) optimizing primer pairs of set Z for the amplification of target gene set N, to minimize primer-primer interactions with other primers in the set by iterative calculation of predicted ΔG for all possible interactions between primers to generate a Fitness Score and use of a Fitness Score optimization method selected from one or a combination of methods (a)-(h) of step (2); and 6) repeating steps (2)-(5) iteratively until a set of primer pairs for target gene set N identified in step (5) has a Fitness Score at a predetermined threshold; and B) synthesizing the optimized primer set selected in step (6).

11. The method of paragraph 10, wherein the Fitness Score is generated according to the rule:

a) G=the set of ΔG's for all possible interactions determined for members of primer set Z; and b) Fitness Score is calculated by:

i) calculating the sum, S, of $|\Delta G|^Q$ for each $\Delta G$ value, wherein Q is a weighting factor constant exponent that makes large $\Delta G$ absolute values much larger than small values;

ii) S'=S/# of $\Delta G$ values in G;

iii) H=T/S', wherein T is a constant that makes H small for large values of S' and H large for small values of S'; and iv) Fitness Score=$H^R$, wherein R is a weighting factor constant exponent that makes large values of H larger, and small values of H smaller.

12. A method of preparing a primer set for multiplex genotyping, the method comprising:

A) for a given set N of variable genomic target sequences to be genotyped in a sample, designing a set of forward and reverse amplification primers that will amplify a sequence comprising each variable genomic target sequence in a multiplex amplification reaction, wherein the designing includes the steps of:

1) identifying all possible primers of 17 to 35 nucleotides within 100 base pairs of each genomic target sequence variation in set N of variable genomic target sequences;

2) For each primer identified in step (1) creating a node $P_{nz}$, such node connected to a node for the corresponding target (TO, wherein:

(i) each node outputs its ID and a numeric value;

(ii) each $T_n$ produces ID of one of the P nodes connected to it;

(iii) each one of the $T_n$ nodes is connected to all others; and (iv) each node $T_n$ represents a multilayer neural network;

3) calculating a Fitness Score for output of the neural network, and on the basis of Fitness Score, the value produced by the network is compared to target, and neural network parameters for a plurality of the $T_n$ are changed;

4) calculating Fitness Score again for output of the neural network with parameters changed in step (3);

5) determining if a change was beneficial or not to the fitness of the resulting set, wherein if the change was beneficial, the direction of change is maintained with smaller increments, and wherein if the change was not beneficial, either direction is reversed or the parameters revert to a previous state;

6) repeating steps (3)-(5) iteratively, wherein at a plurality of iterations random changes are made to the parameters of the network, and wherein when the rate of fitness improvement decreases, the frequency of such random changes is increased, until a set of primer pairs for target genes in set N is identified that has a fitness score at a predetermined threshold; and B) synthesizing the optimized primer set selected in step (6).

13. The method of paragraph 12, wherein the Fitness Score is generated according to the rule:

a) G=the set of $\Delta G$'s for all possible interactions determined for members of a primer set for targets N; and b) Fitness Score is calculated by:

i) calculating the sum, S, of $|\Delta G|^Q$ for each $\Delta G$ value, wherein Q is a weighting factor constant exponent that makes large $\Delta G$ absolute values much larger than small values;

ii) S'=S/# of $\Delta G$ values in G;

iii) H=T/S', wherein T is a constant that makes H small for large values of S' and H large for small values of S'; and iv) Fitness Score=$H^R$, wherein R is a weighting factor constant exponent that makes large values of H larger, and small values of H smaller.

14. A method of preparing a primer set for multiplex genotyping, the method comprising:

A) for a given set N of variable genomic target sequences to be genotyped in a sample, designing a set of forward and reverse amplification primers that will amplify a sequence comprising each variable genomic target sequence in a multiplex amplification reaction, wherein the designing includes the steps of:

1) identifying all possible primers of 17 to 35 nucleotides within 100 base pairs of each genomic target sequence variation in set N of variable genomic target sequences;

2) picking a target at random, as well as a primer for such target, and placing it in set R;

3) picking an additional target, and calculating a Fitness Score evaluating all primers for this target in combination with primers already in set R on the basis of $\Delta G$ for all potential interactions, wherein the primer that results in the best Fitness Score is added to set R;

4) if fitness of set R is below a predetermined threshold T, removing one of the primers from R according to the following:

calculating a Fitness Score for set Ri, wherein the $i^{th}$ target with its primer is removed from set R, and the set with the best Fitness Score determines the target with its primer to be removed from set R and placed back into the pool of primers of step (1); and 5) repeating steps (3) and (4) until all targets are assigned primers; and B) synthesizing the optimized primer set selected in step (5).

15. The method of paragraph 14, wherein the Fitness Score is generated according to the rule:

a) G=the set of $\Delta G$'s for all possible interactions determined for members of a primer set; and b) Fitness Score is calculated by:

i) calculating the sum, S, of $|\Delta G|^Q$ for each $\Delta G$ value, wherein Q is a weighting factor constant exponent that makes large $\Delta G$ absolute values much larger than small values;

ii) S'=S/# of $\Delta G$ values in G;

iii) H=T/S', wherein T is a constant that makes H small for large values of S' and H large for small values of S'; and iv) Fitness Score=$H^R$, wherein R is a weighting factor constant exponent that makes large values of H larger, and small values of H smaller.

16. A method of preparing a primer set for multiplex genotyping, the method comprising:

A) for a given set N of variable genomic target sequences to be genotyped in a sample, designing a set of forward and reverse amplification primers that will amplify a sequence comprising each variable genomic target sequence in a multiplex amplification reaction, wherein the designing includes the steps of:

1) identifying all possible primers of 17 to 35 nucleotides within 100 base pairs of each genomic target sequence variation in set N of variable genomic target sequences;

2) picking a target at random, as well as a primer for such target, and placing it in set R;

3) picking an additional target, and calculating a Fitness Score evaluating all primers for this target in combination with primers already in set R on the basis of $\Delta G$ for all potential interactions, wherein the primer that results in the best Fitness Score is added to set R;

4) if fitness of set R is below a predetermined threshold T, removing one of the primers from R according to the following:

calculating a Fitness Score for set Ri, wherein the $i^{th}$ target with its primer is removed from set R, and the set with the best Fitness Score determines the target with its primer to be removed from set R and placed back into the pool of primers of step (1);

5) repeating steps (3) and (4) until all targets are assigned primers;

6) once all targets are assigned primers, designating set R as $R_1$, and its fitness as $F_1$, 7) creating empty set $R_{z+1}$, where Z is the number of sets, with fitness $F_{z+1}$;

8) for each set Rz, where z is an index from 1 to number of sets R, determining the element that is worst for the set's fitness, and removing this element, designated Target E;

9) recalculating Fz after removal of E;

10) for all Rz, determining where E can be added so as to maximize Fz and maximize the minimum of Fz; and 11) if the minimum of Fz is below the predetermined threshold, repeating steps (7)-(10) until the standard deviation of Fz is below the predetermined threshold, thereby designing a multiplex primer set; and B) synthesizing the optimized primer set designed in step (11).

17. The method of paragraph 16, wherein the step of determining the element in step (8) that is worst for fitness is performed in a method analogous to step (4).

18. A method of preparing a primer set for multiplex genotyping, the method comprising:

A) for a given set N of variable genomic target sequences to be genotyped in a sample, designing a set of forward and reverse amplification primers that will amplify a sequence comprising each variable genomic target sequence in a multiplex amplification reaction, wherein the designing includes the steps of:

1) identifying all possible primers of 17 to 35 nucleotides within 100 base pairs of each genomic target sequence variation in set N of variable genomic target sequences;

2) for each member of set N, selecting from the set of primers in step (1) a subset of primer pairs that satisfies the conditions for a primer selection algorithm and is predicted to be specific for its target;

3) repeating step (2) to generate set P, a population of randomly selected primer sets for each target gene in set N;

4) calculating a Fitness Score for each member of the population P;

5) placing members of population P into a pool of candidate primer sets on the basis of Fitness Scores;

6) randomly selecting a plurality of "parent" sets of candidate primers from the pool of step (5), each parent set including a different pair of candidate primer sets, parent A and parent B;

7) for each parent set of candidate primers, creating a crossover set of candidate primers by replacing a subset of candidate primer pairs of parent A with the corresponding subset of primer pairs of parent B;

8) randomly replacing one primer pair in crossover set A with a different primer pair for the corresponding target sequence generated in step (2) to create a Generation 2 population of primer sets for each target gene in set N; and 9) repeating steps (4)-(8) iteratively until a set of primer pairs for target genes in set N is identified that has a Fitness Score at a predetermined threshold, and runs for an additional set amount of iterations with no measurable improvement in the fitness of the best member, whereby an optimized primer set is designed; and B) synthesizing the optimized primer set designed in step (9).

19. The method of paragraph 18, wherein the Fitness Score is generated according to the rule:

a) G=the set of $\Delta G$'s for all possible interactions determined for members of a primer set; and b) Fitness Score is calculated by:

i) calculating the sum, S, of $|\Delta G|^Q$ for each $\Delta G$ value, wherein Q is a weighting factor constant exponent that makes large $\Delta G$ absolute values much larger than small values;

ii) S'=S/# of $\Delta G$ values in G;

iii) H=T/S', wherein T is a constant that makes H small for large values of S' and H large for small values of S'; and iv) Fitness Score=$H^R$, wherein R is a weighting factor constant exponent that makes large values of H larger, and small values of H smaller.

20. A method of preparing a primer set for multiplex genotyping, the method comprising:

A) for a given set N of variable genomic target sequences to be genotyped in a sample, designing a set of forward and reverse amplification primers that will amplify a sequence comprising each variable genomic target sequence in a multiplex amplification reaction, wherein the designing includes the steps of:

1) identifying all possible primers of 17 to 35 nucleotides within 100 base pairs of each genomic target sequence variation in set N of variable genomic target sequences;

2) selecting a primer set for the multiplex amplification and genotyping of the members of set N comprising:

a) from the set of all possible primers for each genomic target sequence variation of step (1), randomly selecting set P, a population of sets of candidate primers, each individual set of candidate primers in population P including a primer pair for the amplification of each member of set N of variable genomic target sequences to be genotyped;

b) calculating a fitness score for each member of the population of set P by calculating $\Delta G$ for all possible interactions between candidate primers in each member of the population of set P, and assigning each member of set P a Fitness Score according to the rule:

i) G=the set of $\Delta G$'s for all possible interactions determined for a given member of set P;

ii) Number of top scorers to go into next generation= 1 . . . N, Number of distinct populations sets=1 . . . N, and Population size=1 . . . N such that number of top scorers to go into next generation is greater or equal to population size;

wherein fitness score is calculated by:

iii) for each member of set P, calculating the sum, S, of $|\Delta G|^Q$ for each $\Delta G$ value in that member, wherein Q is a weighting factor constant exponent that makes large $\Delta G$ absolute values much larger than small values;

iv) S'=S/# of $\Delta G$ values in G;

v) H=T/S', wherein T is a constant that makes H small for large values of S' and H large for small values of S';

vi) Fitness Score=$H^R$, wherein R is a weighting factor constant exponent that makes large values of H larger, and small values of H smaller;

c) selecting a set of primers for the multiplex amplification and genotyping of members of set N by:

i) randomly selecting a plurality of sets of "parent" sets of candidate primers, each having parent set A and parent set B, from set P based upon Fitness Scores;

ii) for each member of the plurality of sets of parents, creating a crossover set of candidate primers by replacing a subset of candidate primers in parent set A with a corresponding subset of candidate primers in parent set B, resulting in two crossover sets, crossover set A and crossover set B; and iii) randomly replacing one primer pair in crossover set A with a different primer pair for the corresponding variable genomic target sequence to create a next generation population of candidate sets of primers, Generation 2; and d) iteratively repeating steps (a)-(c), whereby a primer set for the multiplex amplification and genotyping of set N of variable genomic target sequences is selected; and B) synthesizing the primer set designed in step (A).

21. A method of multiplex amplification, sequencing, and/or genotyping comprising using a primer set designed according to any one of the preceding paragraphs.

21. A method for equalization of NGS reads, the method comprising adding anti-sense oligonucleotides in concentrations sufficient to inhibit highly efficiently amplified amplicons from forming, thereby permitting less efficiently amplifying amplicons to produce more detectable data.

22. A method for performing multiplex PCR that results in substantially even reads produced by an NGS instrument for each of 2 to 10,000 amplicons and each of 1-100,000 samples in an NGS run.

23. A method for sequencing on an NGS instrument that permits single base multiplexed sequencing, without reading beyond a designated single base.

24. The method of paragraph 23, comprising designing a multiplex genotyping primer set as set out in any one of paragraphs 1-20, and adding random nucleotides to the 5' end of the primers in the set that are shorter than the longest primer in the set, such that each primer in the set is the same length, N, and performing only N+1 cycles in an NGS sequencing run.

25. A method to rapidly analyze NGS sequencing data using software specific to the sample and/or target sequence or gene set to automatically provide genotype or sequencing results.

26. A method of using NGS sequencing methodology to identify and quantify low abundance, rare variants in clinically relevant genes in a minority of tumor cells from a complex mixture of cells.

EXAMPLES

Example 1: Large Amplicon Number Multiplexing

PlexForm™ software can be used for primer design that allows for large amplicon number multiplexing. As an example, the following general primer design scheme can be followed to design multiplex primer sets.

A target gene set N comprises Genes 1 to N (e.g., Gene 1, Gene 2, Gene 3, . . . Gene N). The target genes or DNA targets of interest can be a SNP or another region of interest. All possible primers (e.g., 17-35 nucleotides) within 100 base pairs of each target gene. Primers are chosen that satisfy standard PCR conditions for a primer selection algorithm (e.g., Primer 3™, Oligo Analyzer™ NetPrimer™, or Oligo Calculator™). Primers are compared for specificity versus the genome using alignment software (e.g., primer blast (NCBI™); isPCR (UCSC)). Only those primers predicted to be specific for their respective targets are kept. In some embodiments, a fitness score is calculated for a primer set (see e.g., Example 2).

Optimal primers are selected for each target based on the minimization of primer-primer interactions (e.g., maximization of Fitness Score) using any of several mathematical algorithms incorporated into the PlexForm™ process. Each sample point in the search space is a collection of primer pairs (one for each target) in one or more sets, where either highest chance of primer interaction or number of primers below a threshold of primer interaction within a set (or maximum value for multiple sets) provides a value that is being minimized. All techniques use a model that can accurately predict the possibility of primer interaction between members of a collection of primer pairs.

Since search space for this task is too large to search for best solution (global minima), the following techniques are employed iteratively, together, and/or separately to find an acceptable solution: Genetic Algorithm (see e.g., Example 3); a Monte Carlo random or pseudo-random selection method (see e.g., Example 4); Golden-section search (see e.g., Example 5); Gradient descent (see e.g., Example 6), Minima hopping (see e.g., Example 7); Neural Networks (see e.g., Example 8); Cluster analysis, in which substitution is picked to minimize score (see e.g., Example 9); or Cluster Analysis to create bins (see e.g., Example 10). Examples and detailed descriptions of each of these algorithmic approaches is described further herein. In some embodiments, the optimal primer set selected is then synthesized.

As a non-limiting example, the following steps can be applied as a general primer design scheme on a target gene set N {Genes 1, 2, 3, . . . N}.

Step 1: Identify all possible primers 17-35 nt, within 100 bp of each target.

Step 2: For each member of set N, elect a subset of primer pairs from the set of step 1 that satisfies the conditions for a primer selection algorithm (such as Primer 3, Oligo Analyzer, NetPrimer, or Oligo Calculator).

Step 3: Evaluate specificity of primer pairs chosen in step 2 in the genome, keeping only those pairs predicted to be specific for their respective targets.

Step 4: Select a set of optimal primers for the amplification of target gene set N, where the optimal primers are selected to minimize primer-primer interactions with other primers in the set by iterative use of one or more of the following: a) a Monte Carlo random or pseudo-random selection method; b) a golden section search; c) gradient descent; d) minima hopping; e) genetic algorithm; f) neural networks; g) cluster analysis, in which substitution is picked to minimize score; or h) cluster analysis to create bins;

Step 5: Synthesize the optimal primer set selected in step 4.

Example 2: Fitness Score

In some embodiments, a fitness score is calculated for a primer set, chromosome, or individual. As used in the context of a genetic algorithm, a "chromosome" or "individual" is a set of "X" primer pairs. For example, if running analysis on 150 primer pairs, the chromosome or individual comprises 150 primer pairs. 100 different individuals are assembled randomly from the available primers. This set of 100 "individuals" comprises a "population". The primers within each primer set or within each of the 100 individuals within the population are analyzed for ΔG for all possible interactions. A "score" is then calculated for each primer set or for each individual in the population.

In some embodiments, the following Fitness Score (e.g., F) in FORMULA 2 is used:

$$F = \{C/[\Sigma(|\Delta G|^A))/G_n]\}^B \qquad \text{FORMULA 2}$$

G equals the set of ΔG's for all possible primer interactions determined for that individual or primer set. A and B are weighting factors. C is a factor to create reciprocal scaled values; large numbers become small and vice versa. As a non-limiting example, A equals 5, B equals 2, and C equals 200.

The absolute value of each ΔG value is raised to the "A" power, and all such values are summed for an individual or primer set. The "A" exponent has the effect of spreading out the data values; "A" expands the scale, making large values much larger than small values. This in effect "weights" or penalizes values proportional to the magnitude of "A". This sum is "S". See e.g., FORMULA 3.

$$S = \Sigma(|\Delta G|^A) \qquad \text{FORMULA 3}$$

his sum (e.g., "S") is divided by the number of ΔG values (e.g., "$G_n$"). This division by $G_n$ normalizes S, such that the sum is not inherently larger or smaller for larger or smaller numbers of SNPs, respectively. This normalized S value is "S'". See e.g., FORMULA 4.

$$S' = S/G_n \qquad \text{FORMULA 4}$$

C (a constant) is divided by S' resulting in value "H". C is a factor to create reciprocal scaled values; large numbers become small, and small numbers become large. See e.g., FORMULA 5.

$$H = C/S' \qquad \text{FORMULA 5}$$

Finally, H is raised to the "B" power. "B" once again has the effect of further spreading out the data, making the difference between large and small values even bigger. This value is the "Fitness Score" or F. See e.g., FORMULA 6.

$$F = H^B \qquad \text{FORMULA 6}$$

Each individual or primer set is assigned a fitness score (e.g., "F"). "F" can be calculated using FORMULA 1 or FORMULAS 3-6. FORMULA 2 is a combination of FORMULAS 3-6.

Example 3: Genetic Algorithm

PlexForm™ software can be used for primer design that allows for large amplicon number multiplexing. Included herein is a description of a genetic algorithm used as one approach in PlexForm™ In a genetic algorithm, it is possible to pick several valid points and evaluate points in such cohort. Few points that produce lowest chance of primer interaction move on to next iteration with rest of the population being replaced via combining points with lowest chance of primer interaction, random, pseudo random, and/ or guided changes. Magnitude of the change can be correlated to fitness of the best point, average fitness, predetermined function, rate of improvement or other metrics. This process is repeated. Repetition can be stopped when model of high enough fitness is obtained, time limit and/or changes are insignificant.

Such a genetic algorithm works on the input of multiple primers generated for each target (see e.g., Example 1). A fitness score for each individual can be calculated (see e.g., Example 2). An optimized set of primers is selected using a genetic algorithm (see below). The optimized primer set can then be synthesized. Described below is a non-limiting example using a genetic algorithm.

Each generation comprises a selection step and a mutation step. In the Selection step, the top 5 individuals (e.g., individuals with the 5 highest Fitness Scores, or "The Elite") are automatically passed through to the next generation. This is referred to as Elitism. All individuals are represented in a theoretical "pool" proportional to their fitness score. In this way, those individuals with a higher fitness score are more highly represented in this "pool", and those with very low fitness scores are minimally represented in this pool. Note that the Elite, though automatically passed to the next generation, remain represented in the pool. From this pool, two "parent" individuals are selected randomly. Note that the pool is not random itself as it is weighted to increase probability of selection of higher scoring individuals.

In the Mutation step, two "parent" individuals (or chromosomes) undergo a cross-over event. The result of one of those crossover events is retained. The resulting "child" individual then undergoes "mutation". Each individual has a fixed probability of undergoing a mutation. Thus, for the individual as a whole, there can be from 0 mutations up to any number of mutations. As used herein, mutation denotes that another primer pair for the same target is used to replace the existing one. 100 pairs of parents are selected from the existing generation score-based pool. This results in 100 Child individuals, all of which result from a crossover of parents and a subsequent mutation event. The resulting 100 child individuals then comprise the next Generation population, and the process is repeated over and over again.

As an example, a genetic algorithm was used over multiple generations to optimize a primer set. As an output, two files were written every 25 generations or cycles to record the ΔG scores and primer pairs. One could thus monitor the process graphically and halt as needed (see e.g., FIG. 1). At that point, the final result was written to an output file. The output files contain data for the individual with the best Fitness Score at that point. One file contains the SNP name and the sequence of the associated primers which are then used in the PlexSeg™ assay. The other file contains the ΔG values for all possible interactions between those primers.

As shown in FIG. 1, the X axis displays each generation and the Y Axis displays the Fitness score. The data points at each generation are all of the individuals within that generation. Each individual in Generation X is plotted as a function of that individual's Fitness Score.

As a non-limiting example, the following steps can be applied as a primer design scheme based on a genetic algorithm for a target gene set N {Genes 1, 2, 3, . . . N}.

Step 1: Identify all possible primers 17-35 nt, within 100 bp of each target.

Step 2: A) from the primers identified in step (1), randomly select a primer pair for each target; B) repeat step (A) to generate set P, a population of randomly selected primer sets for each target gene in set N; C) calculate a fitness score for each member of the population P, according to the noted rule/algorithm (see e.g., Example 2); D) on the basis of fitness scores, place members of population P into a pool of candidate primer sets; E) randomly select a plurality of "parent" sets of candidate primers from the pool of (D), each parent set including a different pair of candidate primer sets, parent A and parent B; F) for each parent set of candidate primers, create a "crossover" set of candidate primers by replacing a subset of candidate primer pairs of parent A with the corresponding subset of primer pairs of parent B; G)

randomly replace one primer pair in crossover set A with a different primer pair for the corresponding target sequence to create a Generation 2 population of primer sets for each target gene in set N; and H) repeat steps (C)-(G) iteratively until a set of primer pairs for target genes in set N is identified that has a fitness score at a desired threshold, and runs for and additional set amount of time with no measurable improvement in the fitness of the best member.

As another non-limiting example, described below is a method of preparing a primer set for multiplex genotyping, the method comprising:

A) for a given set N of variable genomic target sequences to be genotyped in a sample, designing a set of forward and reverse amplification primers that amplifies a sequence comprising each variable genomic target sequence in a multiplex amplification reaction, wherein the designing includes the steps of:

1) identifying all possible primers of 17 to 35 nucleotides within 100 base pairs of each genomic target sequence variation in set N of variable genomic target sequences;

2) selecting of a primer set for the multiplex amplification and genotyping of the members of set N comprising:

a) from the set of all possible primers for each genomic target sequence variation of step (1), randomly selecting set P, a population of sets of candidate primers, each individual set of candidate primers in population P including a primer pair for the amplification of each member of set N of variable genomic target sequences to be genotyped;

b) calculating a fitness score for each member of the population of set P by calculating ΔG for all possible interactions between candidate primers in each member of the population of set P, and assigning each member of set P a Fitness Score according to the rules: i) G=the set of ΔG's for all possible interactions determined for a given member of set P; ii) Number of top scorers to go into next generation=1 . . . N, Number of distinct populations sets=1 . . . N, and Population size=1 . . . N such that number of top scorers to go into next generation is greater or equal to population size; Where iii) for each member of set P, calculate the sum, S, of $|\Delta G|^A$ for each ΔG value in that member; iv) S'=S/# of ΔG values in G; v) H=C/S'; vi) Fitness Score=$H^B$; Better fitness score improves chances of specific set to move onto next generation, and/or be one of the parents for one or more sets in next generation.

c) selecting a set of primers for the multiplex amplification and genotyping of members of set N by: i) randomly selecting a plurality of sets of "parent" sets of candidate primers, each having parent set A and parent set B, from set P based upon Fitness Scores; ii) for each member of the plurality of sets of parents, creating a crossover set of candidate primers by replacing a subset of candidate primers in parent set A with a corresponding subset of candidate primers in parent set B, resulting in two crossover sets, crossover set A and crossover set B; and iii) randomly replacing one primer pair in crossover set A with a different primer pair for the corresponding variable genomic target sequence to create a next generation population of candidate sets of primers, Generation 2; and d) iteratively repeating steps (a)-(c) whereby a primer set for the multiplex amplification and genotyping of set N of variable genomic target sequences is selected; and B) synthesizing the primer set designed in step (A).

Example 4: Monte Carlo Algorithm

PlexForm™ software can be used for primer design that allows for large amplicon number multiplexing. Included herein is a description of a Monte Carlo algorithm used as one approach in PlexForm™. Using random and/or pseudo random selection, one can achieve with a Monte Carlo method a uniform distribution of the sample points in the search space. Such a distribution can be augmented or replaced by selection of inputs near points of interest, that can be determined.

Such a Monte Carlo algorithm works on the input of multiple primers generated for each target (see e.g., Example 1). A fitness score for each primer set can then be calculated (see e.g., Example 2). An optimized set of primers is selected using a Monte Carlo algorithm (see below). The optimized primer set can then be synthesized.

As a non-limiting example, the following steps can be applied as a primer design scheme based on a Monte Carlo method for a target gene set N {Genes 1, 2, 3, . . . N}.

Step 1: Identify all possible primers 17-35 nt, within 100 bp of each target.

Step 2: A) from the primers identified in step (1), randomly select a primer pair for each target; B) repeat step (A) to generate set P, a population of randomly selected primer sets for each target gene in set N; C) calculate a fitness score for each member of the population P, according to the noted rule/algorithm (see e.g., Example 2); D) based on the fitness score, pick the best (best fitness) member of the population; E) repeat steps (A)-(D) iteratively until a set of primer pairs for target genes identified in step D has a fitness score at a desired threshold.

Example 5: Golden Section Search

PlexForm™ software can be used for primer design that allows for large amplicon number multiplexing. Included herein is a description of a Golden Section Search algorithm used as one approach in PlexForm™. Using a Golden Section Search algorithm, it is possible to pick two points (where some of the targets contain primer pairs that are the same and do not change during the progression of the search) and using the assumption that minima located between two of those pick a third and fourth point between first two and evaluate the model of each point. Using the assumption that in between two original points the function produced by the model is unimodal, one removes an outside point that has an additional point between it and a point with minimum value. A replacement for the removed point can be picked in-between the two outermost points. This process is repeated until the distance between two outer most points is small enough to be within a previously determined margin.

Such a Golden Section Search algorithm works on the input of multiple primers generated for each target (see e.g., Example 1). A fitness score for each primer set can then be calculated (see e.g., Example 2). An optimized set of primers is selected using a Golden Section Search algorithm (see below). The optimized primer set can then be synthesized.

As a non-limiting example, the following steps can be applied as a primer design scheme based on a Golden Section Search method for a target gene set N {Genes 1, 2, 3, . . . N}.

Step 1: Identify all possible primers 17-35 nt, within 100 bp of each target.

Step 2: A) from the primers identified in step (1), randomly or based on results of other scheme select a primer pair for each target; B) repeat step (A) to generate population Z of size 2 or greater, a population of randomly selected primer sets for each target gene in set N; C) calculate a fitness score for each member of the population Z, according to the noted rule/algorithm (see e.g., Example 2); D) based on fitness scores, pick the worst members (e.g., lowest fitness score) of the population Z:W; E) make a change to a primer for a single target from W and evaluate fitness of resulting set, and if the fitness of the new set is better than fitness of W, new set (W') replaces W; F) repeat steps (C)-(E) iteratively until a set of primer pairs for target genes in set N is identified that has a fitness score at a desired threshold, or there is no improvement, or if threshold was not reached start again from step A.

Example 6: Gradient Descent

PlexForm™ software can be used for primer design that allows for large amplicon number multiplexing. Included herein is a description of a gradient descent algorithm used as one approach in PlexForm™. Using a gradient descent algorithm, it is possible to determine a gradient (that represents an increase or decrease in change of interaction between primers) in a given point by measuring a change in interaction with the change of a single primer pair for a given target. Measured change in primer interaction points to a change in primer pairs that produces the greatest reduction in primer interaction. The process is repeated until a point is achieved where any change increases primer interaction score. Such a point is declared minima (where interaction is least likely).

Such a gradient descent algorithm works on the input of multiple primers generated for each target (see e.g., Example 1). A fitness score for each primer set can then be calculated (see e.g., Example 2). An optimized set of primers is selected using a gradient descent algorithm (see below). The optimized primer set can then be synthesized.

As a non-limiting example, the following steps can be applied as a primer design scheme based on a gradient descent method for a target gene set N {Genes 1, 2, 3, . . . N}.

Step 1: Identify all possible primers 17-35 nt, within 100 bp of each target.

Step 2: A) from the primers identified in step (1), randomly or based on results of other scheme select a primer pair for each target calling such set of primers Z; B) calculate a fitness score for Z, according to the noted rule/algorithm (see e.g., Example 2); C) make a change to a primer for a single target from Z and evaluate the fitness of the resulting set (according to the noted rule/algorithm, see e.g., Example 2), if the fitness of the resulting set is better than fitness of Z, new set (Z') replaces Z; D) repeat step (C) iteratively until there is no improvement to fitness of Z.

Example 7: Minima Hopping

PlexForm™ software can be used for primer design that allows for large amplicon number multiplexing. Included herein is a description of a minima hopping algorithm used as one approach in PlexForm™. To ensure that minima (e.g., where primer interaction is least likely) that are found are not local minima, minima hopping can be employed. Upon locating a minima, it is noted, and a new point in the search space is picked. The new point can be picked randomly or via deterministic method(s) that may be based on variety of factors such as completeness of the data, historical accuracy of predictions, coverage during present search, human guided suggestion, and random and pseudo random number generation, or any combination of those methods as well as others.

Such a minima hopping algorithm works on the input of multiple primers generated for each target (see e.g., Example 1). A fitness score for each primer set can then be calculated (see e.g., Example 2). An optimized set of primers is selected using a minima hopping algorithm (see below). The optimized primer set can then be synthesized.

As a non-limiting example, the following steps can be applied as a primer design scheme based on a minima hopping method for a target gene set N {Genes 1, 2, 3, . . . N}.

Step 1: Identify all possible primers 17-35 nt, within 100 bp of each target.

Step 2: A) From the results of another scheme obtain a primer set where no marked improvement was achieved, add it to set M; B) Select a primer pair for each target, calling such set of primers Z, while maintaining a degree of dissimilarity from primers sets included in M; C) Use any other scheme to improve Z; D) Repeat step (A)-(C) iteratively until a set of primer pairs for target genes identified in step C has a fitness score at a desired threshold.

Example 8: Neural Networks

PlexForm™ software can be used for primer design that allows for large amplicon number multiplexing. Included herein is a description of a neural networks algorithm used as one approach in PlexForm™. Using neural networks, it is possible to create a function (one or more per target) that gets inputs of all possible primer pairs. Such a function produces a recommendation based on internal values and/or functions. Once a recommendation has been made, an output of functions is fed back into the initial set of functions, with some causing output values to change. After the function settles on certain point, primer interaction score is calculated. If this score is not satisfactory, changes are made to internal values and/or functions, and the process is repeated. Change to the internal values can be guided by a variety of algorithms. It is possible to have internal values for the function to be picked in advance as well as adjusted or created just for the set of targets.

Such a neural networks algorithm works on the input of multiple primers generated for each target (see e.g., Example 1). A fitness score for each primer set can then be calculated (see e.g., Example 2). An optimized set of primers is selected using a neural networks algorithm (see below). The optimized primer set can then be synthesized.

As a non-limiting example, the following steps can be applied as a primer design scheme based on a neural networks method for a target gene set N {Genes 1, 2, 3, . . . N}.

Step 1: Identify all possible primers 17-35 nt, within 100 bp of each target.

Step 2: A) For each primer identified in step 1 a node Pnz is created, such node is connected to a node for the corresponding target (Tn); B) Each node outputs its ID and a numeric value; each Tn produces ID of one of the Pnz nodes connected to it. Each one of the Tn nodes is connected to all others. C) Each node Tn represents a multilayer neural network. D) Calculate a fitness score as the output of the neural network is evaluated on the basis of fitness scores. The produced value is compared to target, and neural network parameters for some of the Tn are changed. E) Fitness score is calculated again for output of the neural network. F) Determination is made if change was beneficial or not to the fitness of the result set. If change was beneficial direction of change is maintained with smaller increments. If change was not beneficial either direction is reversed to revert to previous state. G) From time to time there are random changes that are be made to the parameters of the network; when there are no marked improvements in fitness rate of such changes may be increased. H) Repeat steps (E)-(G) iteratively until a set of primer pairs for target genes in set N is identified that has a fitness score at a desired threshold.

Example 9: Cluster Analysis

PlexForm™ software can be used for primer design that allows for large amplicon number multiplexing. Included herein is a description of a cluster analysis algorithm used as one approach in PlexForm™. Using a cluster analysis algorithm where all primer pair interactions are placed in a cluster, some members of the cluster that are outer most are candidates for substitution (either one of the primer pairs is replaced, or both). Substitution is picked in such way to minimize resulting score (or maximize the fitness score).

Such a cluster analysis algorithm works on the input of multiple primers generated for each target (see e.g., Example 1). A fitness score for each primer set can then be calculated (see e.g., Example 2). An optimized set of primers is selected using a cluster analysis algorithm (see below). The optimized primer set can then be synthesized.

As a non-limiting example, the following steps can be applied as a primer design scheme based on a cluster analysis method for a target gene set N {Genes 1, 2, 3, . . . N}.

Step 1: Identify all possible primers 17-35 nt, within 100 bp of each target.

Step 2: A) A target is picked at random, as well as a primer for such target. It is trivial that this target and primer produce a high fitness score. It is placed in set R. B) An additional target is picked, and all primers for this target are evaluated in combination with primers already in R. The primer that results in best fitness score (according to the noted rule/algorithm; see e.g., Example 2) is added to set R. C) If the fitness of set R is below threshold T, one of the primers is removed from R according to following: a fitness score is generated for set R, (where $i^{th}$ target with its primer is removed from R). The set with the best fitness core determines target with its primer to be removed from R and be placed in the pool of unassigned targets. D) Steps (B)-(C) are repeated until all primers are assigned. If there is an attempt to add element to the set R and if after several attempts fitness of the set R is below threshold T, either threshold T can be lowered, or the process from Step (A) is restart starting with different initial target.

Example 10: Cluster Analysis to Create Bins

PlexForm™ software can be used for primer design that allows for large amplicon number multiplexing. Included herein is a description of a cluster analysis to create bins used as one approach in PlexForm™. If there is a situation where it becomes evident that the solution to produce a set of primers where primer interaction is below a certain threshold is not attainable, cluster analysis can be used to separate targets into two or more sets where targets that have primer pairs with high likelihood of primer interactions will be placed into separate sub set(s) once they are extracted. New subset is optimized using approaches listed above (e.g., a Monte Carlo random or pseudo-random selection method; a golden section search; gradient descent; minima hopping; genetic algorithm; neural networks; cluster analysis). If a score for the new set is significantly lower, as compared to an original set, new elements may be added to even out the chance of interaction between multiple sets.

Such a cluster analysis to create bins works on the input of multiple primers generated for each target (see e.g., Example 1). A fitness score for each primer set can then be calculated (see e.g., Example 2). An optimized set of primers is selected using a cluster analysis to create bins (see below). The optimized primer set can then be synthesized.

As a non-limiting example, the following steps can be applied as a primer design scheme based on a cluster analysis to create bins method for a target gene set N {Genes 1, 2, 3, . . . N}.

Step 1: Identify all possible primers 17-35 nt, within 100 bp of each target.

Step 2: A) A target is picked at random, as well as a primer for such target. It is trivial that this produces a high fitness score. It is placed in set R. B) An additional target is picked, and all primers for this target are evaluated in combination with primers already in R. Primer that results in best fitness score (according to the noted rule/algorithm; see e.g., Example 2) is added to set R. C) If the fitness of set R is below threshold T, one of the primers is removed from R according to following: a fitness score is generated for set R, (where $i^{th}$ target with its primer is removed from R). The set with the best fitness core determines target with its primer to be removed from R and be placed in the pool of unassigned targets. D) Steps (B)-(C) are repeated until all primers are assigned. If there is an attempt to add element to the R, after several unsuccessful attempts threshold T can be lowered. E) Once all primers are assigned set R is marked as $R_1$, and its fitness is $F_1$. F) Empty set $R_{z+1}$ (where z is number of R sets) is created; its fitness is Fz+1. G) For each set $R_z$ (where z is an index from 1 to number of sets R) determine element that is the worst for its fitness. This can be done in a similar manner to step C. Once this element (Target E) is removed, recalculate $F_z$. H) For all Rz determine where E can be added in such a way as to maximize F. and maximize minimum of $F_z$. I) Once standard deviation of Fz is below threshold, this means that all bins have similar fitness level. If minimum of $F_z$ is below threshold steps (F)-(H) are repeated.

Example 11: Exemplary Primer Set #1

PlexForm™ software can be used for primer design that allows for large amplicon number multiplexing. Included herein is an exemplary primer set designed by PlexForm™ software for *Homo sapiens* SNP targets (see e.g., TABLE 2). TABLE 2 shows the input allelic target sequences for 81 SNP regions, comprising SEQ ID NOs: 1-167. SNP position indicated by bolded letters in TABLE 2. A lack of bolded nucleotide(s) in a target sequence in TABLE 2 indicates a deletion.

TABLE 2

Input target sequences for 81 SNP regions

| Target | Allele No. | SEQ ID NO: | Target Sequence |
|---|---|---|---|
| SNP001 | 1 | 1 | GCAAGGAATATATTAAATTTTTTCTTTCTTGCACAGAATTCAAT GTTAAACAAGTATGTTGCCATTCTGTGGAAGGCATTATTTTCCC CTTCCAAACTTTGAAACTCAAAAGTTTTCTAAGAAAAAAAATCA AATCC |
| SNP001 | 2 | 2 | GCAAGGAATATATTAAATTTTTTCTTTCTTGCACAGAATTCAAT GTTAAACAAGTATGTTGCCATTCTGTGGAATTAAAAAAAAAAA GGCATTATTTTCCCCTTCCAAACTTTGAAACTCAAAAGTTTTCTA AGAAAAAAAATCAAATCC |
| SNP002 | 1 | 3 | ATATAGTGTCAGGTTAAGCATTATTAGGTTAAGTTATAGCTATC TGTGGCAATAGCAAGCAGTTTCAAGGGATGAATCCATAGCTCA AAGCGGGGAATAGGACGTATAGCTCTCTCATTTTAATGTCTCTC TGGGCCTGATGATTTAAAAGACTCACACTCCTAAGATGAAAGTT ATTTTCTCATCTATGTAATGTGTTAA |
| SNP002 | 2 | 4 | ATATAGTGTCAGGTTAAGCATTATTAGGTTAAGTTATAGCTATC TGTGGCAATAGCAAGCAGTTTCAAGGGATGAATCCATAGCTCA AAGCGGGGAATAGGATGTATAGCTCTCTCATTTTAATGTCTCTC TGGGCCTGATGATTTAAAAGACTCACACTCCTAAGATGAAAGTT ATTTTCTCATCTATGTAATGTGTTAA |
| SNP003 | 1 | 5 | TAAGAACTGTTAGGTGACTGACACATCTAGGAGGAAAATGAGG GGTGTCCTGGCGCTTAGTTCTTCAAACCCGGTAGGAATAAGGCA AGCCTGGTCTACAGGAAACCATCTGTCCTGACTCCGGGAGGGT AAGATGGACAAGCAGGTCATTTTCAGCTCCTATTTCAGTTGCCC TATGGAACAGGGGTGATTCAAACTGTA |
| SNP003 | 2 | 6 | TAAGAACTGTTAGGTGACTGACACATCTAGGAGGAAAATGAGG GGTGTCCTGGCGCTTAGTTCTTCAAACCCGGTAGGAATAAGGCA AGCCTGGTCTACAGGGAACCATCTGTCCTGACTCCGGGAGGGT AAGATGGACAAGCAGGTCATTTTCAGCTCCTATTTCAGTTGCCC TATGGAACAGGGGTGATTCAAACTGTA |
| SNP004 | 1 | 7 | CTGCACAGGGCCGGGATCCCTGCCCTCTGGGAGTTGATGCTCTT GGGGTGGGAGGACACAGATGCTTCAGGATCCCTTAGTGCTTCA GGATTCTAGAGTCTCAGAATTTCCAAGCCAAGGCTTGGAGTGCC TCAGCTGATGTCACAGTGGAGGTTCTAGCAGAGTGGGTAGCAC ATATGTGTCATGTCCCTCTGGTCTG |
| SNP004 | 2 | 8 | CTGCACAGGGCCGGGATCCCTGCCCTCTGGGAGTTGATGCTCTT GGGGTGGGAGGACACAGATGCTTCAGGATCCCTTAGTGCTTCA GGATTCTAGAGTCTCTTAGAATTTCCAAGCCAAGGCTTGGAGTG CCTCAGCTGATGTCACAGTGGAGGTTCTAGCAGAGTGGGTAGC ACATATGTGTCATGTCCCTCTGGTCTG |
| SNP005 | 1 | 9 | GTGAGACTGCGTGTGCAGGTGTGTGTGGAGGGCTGTGGGGAGC TGTGTGTGGGGGGGGGTGTGTGTGTGAGGTTGGGGGCTGTGTGG GGTGTGTGTGAGGCTGCGTGTGGGGAGTGTGAGGCTGTGTGTG TGCGAGGGGGACTATGTGTGTCGGATGATGTCCCTGGCTGTGTG TGGGGATGTGTGTGTGTGTGTGTGTG |
| SNP005 | 2 | 10 | GTGAGACTGCGTGTGCAGGTGTGTGTGGAGGGCTGTGGGGAGC TGTGTGTGGGGGGGGGTGTGTGTGTGAGGTTGGGGGCTGTGTGG GGTGTGTGTGAGGCTGTGTGTGGGGAGTGTGAGGCTGTGTGTGT GCGAGGGGGACTATGTGTGTCGGATGATGTCCCTGGCTGTGTGT GGGGATGTGTGTGTGTGTGTGTGTG |
| SNP006 | 1 | 11 | CCAATACAGGAGCACTCAGATTCATAAAGCAAGTCCTTAGAGA CCTACAAAGAGACTTAGAACTCCCACACAATAATAATGGGAGA CTTCAACACCTCACTGCCAACATTAGACAGATAGAGACAGAAA GTTAACAAGGATATCCAGGAATTGAACTCAGGAATTGAACTCA GCTCTGCACCAAGCGGACCTAATAGACAT |
| SNP006 | 2 | 12 | CCAATACAGGAGCACTCAGATTCATAAAGCAAGTCCTTAGAGA CCTACAAAGAGACTTAGAACTCCCACACAATAATAATGGGAGA CTTCAACACCTCACTGTCAACATTAGACAGATAGAGACAGAAA GTTAACAAGGATATCCAGGAATTGAACTCAGGAATTGAACTCA GCTCTGCACCAAGCGGACCTAATAGACAT |
| SNP007 | 1 | 13 | CAAGTGAAACAACCAACTATGGCTGTAAGGATCATGAAAAACA GGGAATTCCCCCCCAGTTTACACAGACAACAAAAACTAAGTGT AGGTCACTATCTCATTGTACCCATGGATTTTAATTTATAGAGGT GACTGAGTGATGACATAGAAAGACCAATGCCATCGAAAGAATA ATTTATTACTTACAAGTCCTGGGAGAAG |

TABLE 2-continued

| | | | |
|---|---|---|---|
| | | | Input target sequences for 81 SNP regions |

| Target | Allele No. | SEQ ID NO: | Target Sequence |
|---|---|---|---|
| SNP007 | 2 | 14 | CAAGTGAAACAACCAACTATGGCTGTAAGGATCATGAAAAACA GGGAATTCCCCCCCAGTTTACACAGACAACAAAAACTAAGTGT AGGTCACTATCTCATTTTACCCATGGATTTTAATTTATAGAGGT GACTGAGTGATGACATAGAAAGACCAATGCCATCGAAAGAATA ATTTATTACTTACAAGTCCTGGGAGAAG |
| SNP008 | 1 | 15 | CTTTTGTCTCCCAGGCAAGATGCTATTAGGGGTCACTTCCCATG TACGGAGAAAACAATCTTCATGGATAATAATGATAAAACCTTA TGGAATGCAAAAACAACCAAAATATGTATTCTCGGATGACTGC ATTAGGGCCAAGTCAATATTAGTCCCACTTCACCCACGCATTGC ATAGTCTAAAAATGCTGTCAGCCTGAT |
| SNP008 | 2 | 16 | CTTTTGTCTCCCAGGCAAGATGCTATTAGGGGTCACTTCCCATG TACGGAGAAAACAATCTTCATGGATAATAATGATAAAACCTTA TGGAATGCAAAAACAGCCAAAATATGTATTCTCGGATGACTGC ATTAGGGCCAAGTCAATATTAGTCCCACTTCACCCACGCATTGC ATAGTCTAAAAATGCTGTCAGCCTGAT |
| SNP009 | 1 | 17 | CAACGTTTTTTAGATTCCTCATATGAGTGAGATCATGCTGTGAA TCTGTTTCTGGCTGATTTCACTTAGGAGGATGTCCTCCAAGCTC ATCCATGCTGTCCCAAAGGCTGAATAATATTCCATTGTATATAT CTCTCACATTTTCTTTATCCATTCATTCATCAACTTAGATTTTTTT CA |
| SNP009 | 2 | 18 | CAACGTTTTTTAGATTCCTCATATGAGTGAGATCATGCTGTGAA TCTGTTTCTGGCTGATTTCACTTAGGAGGATGTCCTCCAAGCTC ATCCATGCTGTCCCAAAGGGCAAGATCTCCTTTTTAAAGGCTG AATAATATTCCATTGTATATATCTCTCACATTTTCTTTATCCATT CATTCATCAACTTAGATTTTTTTCA |
| SNP010 | 1 | 19 | AGAGCAAGATAAGTAGAATCCAAAGCAATGATCTGACTGCTCA AAATCACCGATATTGACAACTGACTCCCAAATCCCTGCTTCATC TAACATATATTGCTAATACCATGCCCAGATAGAACACAAAGCA ATATTTATTATATGACAAATTCTCTCCATAATTTTAGAGAGTTTT CCCTAAGGAAAGAAAGGACTTTTTAA |
| SNP010 | 2 | 20 | AGAGCAAGATAAGTAGAATCCAAAGCAATGATCTGACTGCTCA AAATCACCGATATTGACAACTGACTCCCAAATCCCTGCTTCATC TAACATATATTGCTACTACCATGCCCAGATAGAACACAAAGCA ATATTTATTATATGACAAATTCTCTCCATAATTTTAGAGAGTTTT CCCTAAGGAAAGAAAGGACTTTTTAA |
| SNP011 | 1 | 21 | ATATTAGTAGACATAAAAATCACCTGGGGAGAGTGTAAAAAAA TAAAAATTCCCAGAAATTCTGGTTCAGTCATTTTGGGGCCAACC TAGTCATTTGCATTAATCAGCATGCACTCCCTGATGATTCTGAT ATAAATGAATCACATGTTGCAAAATGCTTTAGCCTGTTCCCTAA TCTAAATCTTATCTCTCTCCTCTCAG |
| SNP011 | 2 | 22 | ATATTAGTAGACATAAAAATCACCTGGGGAGAGTGTAAAAAAA TAAAAATTCCCAGAAATTCTGGTTCAGTCATTTTGGGGCCAACC TAGTCATTTGCATTAGTCAGCATGCACTCCCTGATGATTCTGAT ATAAATGAATCACATGTTGCAAAATGCTTTAGCCTGTTCCCTAA TCTAAATCTTATCTCTCTCCTCTCAG |
| SNP012 | 1 | 23 | ACTCAAGTGATCCTCCTGCCTTGGCCTCCCAAAGTGCTAGGATT ACAGGCATGAGCCACTGCGCCTGGCCCAGTTACTTATTTTAGAA GTTATATTTGAGCACCTATTCTGTGCCGAGCCCTGGCATGAGCT GTGAACAGGCCATATCTATCCTAGATGTGCACTAATGGGGCTTT GGAGGGTGGCAACAGGAGGCCCGGT |
| SNP012 | 2 | 24 | ACTCAAGTGATCCTCCTGCCTTGGCCTCCCAAAGTGCTAGGATT ACAGGCATGAGCCACTGCGCCTGGCCCAGTTACTTATTTTAGAA GTTATATTTGAGCATCTATTCTGTGCCGAGCCCTGGCATGAGCT GTGAACAGGCCATATCTATCCTAGATGTGCACTAATGGGGCTTT GGAGGGTGGCAACAGGAGGCCCGGT |
| SNP013 | 1 | 25 | CTTAAATGCAAATGGTAAATCTGAGGCAGCAGTAAGGTAGAGT GGAAAGGCTTTAGGGGAAAAAAAATAAAGTCTGAGAAACTGTC ACAGCAAGAGGACCCTAAGGAGACATGACAAGTAAATGTAATA TGGTGTCCTGGATGGCATCCTGGAAAAGAAAAGGGACATTAGA TAAAAACAAACCATGGACTTCAATAATAA |

TABLE 2-continued

| Input target sequences for 81 SNP regions | | | |
| --- | --- | --- | --- |
| Target | Allele No. | SEQ ID NO: | Target Sequence |
| SNP013 | 2 | 26 | CTTAAATGCAAATGGTAAATCTGAGGCAGCAGTAAGGTAGAGT GGAAAGGCTTTAGGGGAAAAAAAATAAAGTCTGAGAAACTGTC ACAGCAAGAGGACCCTGAGGAGACATGACAAGTAAATGTAATA TGGTGTCCTGGATGGCATCCTGGAAAAGAAAAGGGACATTAGA TAAAAACAAACCATGGACTTCAATAATAA |
| SNP014 | 1 | 27 | GCTAGCAAAAGGTTCATTGTCAGAGATAACCTAGGTCTGAGGA AGCAGAGGCCAATAGTTTTTACATGCATCAGAGTGTTAGACAAT AAGATGCAGTGTAAAAGTGTTTGTTCTCACTGCTAACCAAAGAC AGGCAAATTAAGACTATTAAAGTATCCTTTTCTACCCACTAAAA TAATTTTAGAGAAAATTTAAGATTAC |
| SNP014 | 2 | 28 | GCTAGCAAAAGGTTCATTGTCAGAGATAACCTAGGTCTGAGGA AGCAGAGGCCAATAGTTTTTACATGCATCAGAGTGTTAGACAAT AAGATGCAGTGTAAAGGTGTTTGTTCTCACTGCTAACCAAAGAC AGGCAAATTAAGACTATTAAAGTATCCTTTTCTACCCACTAAAA TAATTTTAGAGAAAATTTAAGATTAC |
| SNP015 | 1 | 29 | ATTTCTTAAATGGGTACGTTTTGTTTGTACCCATCTCAAGACCTT TGAGATAGCCATTCCACTTGATTTTTTTTTTTTTTTGAGATGGA GTCTTGCCCTGTCGCCAGGCTGGAGTGCGGTGGCGTGATCTCAA CTCAATGCAACCGCTGATTCCCTGGTTCAAGTGATTCTCCTGCC TCAGCCTCCCAAGTAGCTGGGAT |
| SNP015 | 2 | 30 | ATTTCTTAAATGGGTACGTTTTGTTTGTACCCATCTCAAGACCTT TGAGATAGCCATTCCACTTGATTTTTTTTTTTTTTTGAGATGGA GTCTTGCCCTGTTGCCAGGCTGGAGTGCGGTGGCGTGATCTCAA CTCAATGCAACCGCTGATTCCCTGGTTCAAGTGATTCTCCTGCC TCAGCCTCCCAAGTAGCTGGGAT |
| SNP016 | 1 | 31 | ATAAAGAAGCTTACTGTGGTCCTGTAGGGCCTACCATCCTGTGT TGGTATTGCTCCAAAGATAAGCATTTTTGATTAAATTGGAGATT GCCCTCATTTGGGGCAGGGAGGGGGGTGCTTAGTCCAGTGATTT CACAAGCATTTTGGTCTCAGGACCCTTTTTTAACTCTTAAAATTT GTTGAGAACAGCAAATAAATTGTT |
| SNP016 | 2 | 32 | ATAAAGAAGCTTACTGTGGTCCTGTAGGGCCTACCATCCTGTGT TGGTATTGCTCCAAAGATAAGCATTTTTGATTAAATTGGAGATT GCCCTCATTTGGGGTAGGGAGGGGGGTGCTTAGTCCAGTGATTT CACAAGCATTTTGGTCTCAGGACCCTTTTTTAACTCTTAAAATTT GTTGAGAACAGCAAATAAATTGTT |
| SNP017 | 1 | 33 | CTCCCGGAGTAGCTCTGGGAGCAAGGCCCTCCCTGGATCCCTCC CTCTTTCCCGGTGTGCCTGTCTTTCCCGCTCCATCCTCCAGCCTC CACCGGGAGGAACACGGCTGCATTGTTCCTCAGGAGGAGGCCC TGCCTCGGGGCCTGGCCCAGTGCCCAGGTGGGGGGCCAGGAAC AAAACTCTGAGATCGAGGGGCGGGGT |
| SNP017 | 2 | 34 | CTCCCGGAGTAGCTCTGGGAGCAAGGCCCTCCCTGGATCCCTCC CTCTTTCCCGGTGTGCCTGTCTTTCCCGCTCCATCCTCCAGCCTC CACCGGGAGGAACGCGGCTGCATTGTTCCTCAGGAGGAGGCCC TGCCTCGGGGCCTGGCCCAGTGCCCAGGTGGGGGGCCAGGAAC AAAACTCTGAGATCGAGGGGCGGGGT |
| SNP018 | 1 | 35 | AGAATCTGATTAATAATTGCCCAGTAGGGACCAGTTCCTGGGTC CTGCTGAGCGGAGGGGAGGGAGTTCTGGGCTGGTTCTGGCTGG CCAGCCGAGGAGAGGAGAGGAGCAAAGGTGACTTTGAGCTGCA GAGGGTGGCCGCTGGGGCCCAGAGCTGGCAGATCCCAGCGGCT GGCCTCCTTCCATGCTTCCCTGGTGGCT |
| SNP018 | 2 | 36 | AGAATCTGATTAATAATTGCCCAGTAGGGACCAGTTCCTGGGTC CTGCTGAGCGGAGGGGAGGGAGTTCTGGGCTGGTTCTGGCTGG CCAGCCGAGGAGAGGGGAGGAGCAAAGGTGACTTTGAGCTGC AGAGGGTGGCCGCTGGGGCCCAGAGCTGGCAGATCCCAGCGGC TGGCCTCCTTCCATGCTTCCCTGGTGGCT |
| SNP019 | 1 | 37 | ACCAAAAGTATGCTCTGGCTGGATTGCAGCTACTCAAAAGGAG AAGGAACTGGGATGAGGCTAGAGATGTAGTCAGACCCTATAAA TTTTTTTTTTTTTTTTGAGCATTGAGACCTCAGGAACAGGTTTTA ATGGGTGTTTGCTGGTGGAGGAGAGGGTGGAGTGACTTAACAT GATGAGACTTACTGTGTTG |

TABLE 2-continued

| | Allele | SEQ ID | |
|---|---|---|---|
| Target | No. | NO: | Target Sequence |

Input target sequences for 81 SNP regions

| Target | Allele No. | SEQ ID NO: | Target Sequence |
|---|---|---|---|
| SNP019 | 2 | 38 | ACCAAAAGTATGCTCTGGCTGGATTGCAGCTACTCAAAAGGAG AAGGAACTGGGATGAGGCTAGAGATGTAGTCAGACCCTATAAA TTTTTTTTTTTTTTTTTTGAGCATTGAGACCTCAGGAACAGGTTTT AATGGGTGTTTGCTGGTGGAGGAGAGGGTGGAGTGACTTAACA TGATGAGACTTACTGTGTTG |
| SNP019 | 3 | 39 | ACCAAAAGTATGCTCTGGCTGGATTGCAGCTACTCAAAAGGAG AAGGAACTGGGATGAGGCTAGAGATGTAGTCAGACCCTATAAA TTTTTTTTTTTTTTTTTTTTGAGCATTGAGACCTCAGGAACAGGTTT TAATGGGTGTTTGCTGGTGGAGGAGAGGGTGGAGTGACTTAAC ATGATGAGACTTACTGTGTTG |
| SNP019 | 4 | 40 | ACCAAAAGTATGCTCTGGCTGGATTGCAGCTACTCAAAAGGAG AAGGAACTGGGATGAGGCTAGAGATGTAGTCAGACCCTATAAA TTTTTTTTTTTTTTTTTTTTTGAGCATTGAGACCTCAGGAACAGGTT TTAATGGGTGTTTGCTGGTGGAGGAGAGGGTGGAGTGACTTAA CATGATGAGACTTACTGTGTTG |
| SNP020 | 1 | 41 | GGACCTGAGCGGTAGCCTTGGTCCACTGCAGACATCAGCAAGT TCTTAGATCAGGCGGGGAACCGGTCCACCCACTCATGCTCTGGT TTAGCTCCCTACTCTGCTTTCTGAGAGTCAGTTTGGAAGGGAAC CTAGCGGAGCTCCTCAGAGTCTCAGGGTCCTTGTCTTTGATGAA CTTTCTGCTTGGTCATAGGCAGCCTC |
| SNP020 | 2 | 42 | GGACCTGAGCGGTAGCCTTGGTCCACTGCAGACATCAGCAAGT TCTTAGATCAGGCGGGGAACCGGTCCACCCACTCATGCTCTGGT TTAGCTCCCTACTCTTCTTTCTGAGAGTCAGTTTGGAAGGGAAC CTAGCGGAGCTCCTCAGAGTCTCAGGGTCCTTGTCTTTGATGAA CTTTCTGCTTGGTCATAGGCAGCCTC |
| SNP021 | 1 | 43 | AAAATGCGTAGCATGGCTCCTGTAACTACGAGAGCTCCACAAA TGCAAACTATATGACAAGTGAGGAACATTAGATGACAGTCATG CTTCGATTTAAGTAAAGTTAATTGTAAAAATATAAACTTCCTAG AGGAAGTTGTTCTTCGTTCCTGCGGCTGTTGTTCTAACAAGTTA ATTCCTTTGGTGGATTTCCAGTAAGAT |
| SNP021 | 2 | 44 | AAAATGCGTAGCATGGCTCCTGTAACTACGAGAGCTCCACAAA TGCAAACTATATGACAAGTGAGGAACATTAGATGACAGTCATG CTTCGATTTAAGTAAATTTAATTGTAAAAATATAAACTTCCTAG AGGAAGTTGTTCTTCGTTCCTGCGGCTGTTGTTCTAACAAGTTA ATTCCTTTGGTGGATTTCCAGTAAGAT |
| SNP022 | 1 | 45 | CTGTCCAGTCAGGCAGCGCGCCAGTCAGCCTTCCTCCGTTTGCT GTTTCACCTTTCCAATCCCTCATTTTCACCCATTGGCTCCTAATG TGGGACACTGCTGAGGGCTTTGGTTTTCTACCTCAGTGAGCGTT CAACAGTCTGTTTTGACGCCTTGCTTTTAGAGCCAGGTTTAACA AAGCAAGGCATGGAATCATTTTCC |
| SNP022 | 2 | 46 | CTGTCCAGTCAGGCAGCGCGCCAGTCAGCCTTCCTCCGTTTGCT GTTTCACCTTTCCAATCCCTCATTTTCACCCATTGGCTCCTAATG TGGGACACTGCTGTGGGCTTTGGTTTTCTACCTCAGTGAGCGTT CAACAGTCTGTTTTGACGCCTTGCTTTTAGAGCCAGGTTTAACA AAGCAAGGCATGGAATCATTTTCC |
| SNP023 | 1 | 47 | TTTGGATTTCCTCTTGGCTGTGTTCATATCAATTTATCTCACCCC ACACCCCACAGTACTTGGTGTACCAGTTCTGGAACTACTGGTAT TTATTGCTGTGCCAAGGAGGCCCATTGCACAAGTCCTCCTAAAA GAGGCCATTGTCTCGATCACTTTAACATCTCCGCCCTGGGGAGC TTCAGGCTGAGAGATGGGCCTAAC |
| SNP023 | 2 | 48 | TTTGGATTTCCTCTTGGCTGTGTTCATATCAATTTATCTCACCCC ACACCCCACAGTACTTGGTGTACCAGTTCTGGAACTACTGGTAT TTATTGCTGTGCCGAGGAGGCCCATTGCACAAGTCCTCCTAAAA GAGGCCATTGTCTCGATCACTTTAACATCTCCGCCCTGGGGAGC TTCAGGCTGAGAGATGGGCCTAAC |
| SNP024 | 1 | 49 | ATTTTTGCTTTTTTTTTTTTTTTTTTTTTTTGTGGAGAGGGTGTTT CTCCATGTTGCCCAGGCTGGTCTCAAACTCCTGAGCTCAAGAGA TCTGCCTGCCTCAGCCTCCCAAAGTGCTAGGATTATAGGCATGA GCTACTGCGCCTGCCCAGAGCCTGCATTCTTTACCTTTACAGTCT AGACCCTGCTCCTATAGATCCC |

TABLE 2-continued

| | Allele | SEQ ID | |
|---|---|---|---|
| Target | No. | NO: | Target Sequence |

| | | | |
|---|---|---|---|
| SNP024 | 2 | 50 | ATTTTTGCTTTTTTTTTTTTTTTTTTTTTTTGTGGAGAGGGTGTTT |
| | | | CTCCATGTTGCCCAGGCTGGTCTCAAACTCCTGAGCTCAAGAGA |
| | | | TCTGCCTGCCTCGGCCTCCCAAAGTGCTAGGATTATAGGCATGA |
| | | | GCTACTGCGCCTGCCCAGAGCCTGCATTCTTTACCTTTACAGTCT |
| | | | AGACCCTGCTCCTATAGATCCC |
| SNP025 | 1 | 51 | TGGAACAAAGGTGGTGCTTATGGGATGTATGGAGCTGTGGGAT |
| | | | GTGGGAGAGGACAGGTTTAGCAGAGTGGCGTGGTGGAAAGTTT |
| | | | CCTCTCGCCGAGGAGGACAACTCCCCAGCGCCTGAGACAGCGG |
| | | | GAGCTCAGAGCGCCTAGAATGTGCCCAGATTCTAAAGTGAAGC |
| | | | AGGCTGTGGTGTGATGATGGCCCCCGAGG |
| SNP025 | 2 | 52 | TGGAACAAAGGTGGTGCTTATGGGATGTATGGAGCTGTGGGAT |
| | | | GTGGGAGAGGACAGGTTTAGCAGAGTGGCGTGGTGGAAAGTTT |
| | | | CCTCTCGCCGAGGAGGCCAACTCCCCAGCGCCTGAGACAGCGG |
| | | | GAGCTCAGAGCGCCTAGAATGTGCCCAGATTCTAAAGTGAAGC |
| | | | AGGCTGTGGTGTGATGATGGCCCCCGAGG |
| SNP026 | 1 | 53 | TGCCTGTCTTCTGCAGGGGCCTCTGCACCCACAGGCTTGGTCCA |
| | | | CAGCTGCCTCTTGGTTGTCCCTCCACCTCCCTGGCCTTTGAGACT |
| | | | CCCTCAGTGGCTTCGTCAGAGTTCTCTGAGCCCAGCTGTGGAGG |
| | | | AGAGTCTGAAACAGCTGCTCTGGGAGGCGGCAGCAGGAGTGTC |
| | | | CCAGCGCCGTGGGCTGGGCTGGTGC |
| SNP026 | 2 | 54 | TGCCTGTCTTCTGCAGGGGCCTCTGCACCCACAGGCTTGGTCCA |
| | | | CAGCTGCCTCTTGGTTGTCCCTCCACCTCCCTGGCCTTTGAGACT |
| | | | CCCTCAGTGGCTTTGTCAGAGTTCTCTGAGCCCAGCTGTGGAGG |
| | | | AGAGTCTGAAACAGCTGCTCTGGGAGGCGGCAGCAGGAGTGTC |
| | | | CCAGCGCCGTGGGCTGGGCTGGTGC |
| SNP027 | 1 | 55 | AGGCACTGAAGGGTGAGGCTGTGTGCCACTCCTTGGGCTGGCTC |
| | | | CAGCTGACAGGGTTGTCCACAGTAGAAAATGTGCCTGTGGGCA |
| | | | GTGGGGTCGGCCCCCAGCCCCACGTGGGAGGATGAACAACCCT |
| | | | CGGCACCATGCCATGCGCTTTGCTCAGATTCCCCTTCAGGAAAT |
| | | | TACTGATTTGGTTTCTTAGGAATTGGC |
| SNP027 | 2 | 56 | AGGCACTGAAGGGTGAGGCTGTGTGCCACTCCTTGGGCTGGCTC |
| | | | CAGCTGACAGGGTTGTCCACAGTAGAAAATGTGCCTGTGGGCA |
| | | | GTGGGGTCGGCCCCCGGCCCCACGTGGGAGGATGAACAACCCT |
| | | | CGGCACCATGCCATGCGCTTTGCTCAGATTCCCCTTCAGGAAAT |
| | | | TACTGATTTGGTTTCTTAGGAATTGGC |
| SNP028 | 1 | 57 | GGAGTCTTTCCCCCATTGCTTGCTTTTAATTGGCTTTGTTGAAGA |
| | | | TGAGATGGTTATAGTTGTGTTTTCTGAGTTCTTTATTCTGTTTCA |
| | | | TTGGTCTATGTTTTTTTTTTTTGTTTTTTTTTTTTTGAAAGTGTCTC |
| | | | ACTCTTTACCAAGGCTGGAGTGTAGTGGCATGATCACAGCTCAC |
| | | | TGAAGCCTCAGCCTTCAGGG |
| SNP028 | 2 | 58 | GGAGTCTTTCCCCCATTGCTTGCTTTTAATTGGCTTTGTTGAAGA |
| | | | TGAGATGGTTATAGTTGTGTTTTCTGAGTTCTTTATTCTGTTTCA |
| | | | TTGGTCTATGTTGTTTTTTTTGTTTTTTTTTTTTTTGAAAGTGTCT |
| | | | CACTCTTTACCAAGGCTGGAGTGTAGTGGCATGATCACAGCTCA |
| | | | CTGAAGCCTCAGCCTTCAGGG |
| SNP029 | 1 | 59 | CCCACTCATGAGAACTCTACCCCCATCCAATCACCTCCCACTTG |
| | | | GTCCCACCTCCAACATGGGGGATTATAACTGGACATGAGATTTA |
| | | | GTGGGGACAGAGATACAAATTATATCATTCCACCCCCAGCCCCT |
| | | | CCAAATTTCATGTCCTTCTCATATTGCAAAATACAATCATCCCTT |
| | | | CTCAACAGTCCCCCAAAGTCTTAT |
| SNP029 | 2 | 60 | CCCACTCATGAGAACTCTACCCCCATCCAATCACCTCCCACTTG |
| | | | GTCCCACCTCCAACATGGGGGATTATAACTGGACATGAGATTTA |
| | | | GTGGGGACAGAGATCCAAATTATATCATTCCACCCCCAGCCCCT |
| | | | CCAAATTTCATGTCCTTCTCATATTGCAAAATACAATCATCCCTT |
| | | | CTCAACAGTCCCCCAAAGTCTTAT |
| SNP030 | 1 | 61 | TTTGACGAGTTGAGAGAAGAAGGCTTCAGATGATCAAACTACT |
| | | | CCGAGCTACAGGAGGAAATTCAAACCAAAGGCAAAGAAGTTCA |
| | | | AAACTTTGAAAAAAATGTAGACGAATGTATAATTAGAATAACC |
| | | | AATACAGAAAAGTGCTTAAAGGAGCTGATGGAGCTGAAAGCCA |
| | | | AGGCTGGAGAACTACGTGAAGAATGCAGA |

TABLE 2-continued

| | | | |
|---|---|---|---|
| | | | Input target sequences for 81 SNP regions |
| Target | Allele No. | SEQ ID NO: | Target Sequence |
| SNP030 | 2 | 62 | TTTGACGAGTTGAGAGAAGAAGGCTTCAGATGATCAAACTACT CCGAGCTACAGGAGGAAATTCAAACCAAAGGCAAAGAAGTTCA AAACTTTGAAAAAATTTAGACGAATGTATAATTAGAATAACC AATACAGAAAAGTGCTTAAAGGAGCTGATGGAGCTGAAAGCCA AGGCTGGAGAACTACGTGAAGAATGCAGA |
| SNP031 | 1 | 63 | GATCCAGATTGTGAGGTCATGAAATGCTTATGAACAGAGAGCT TAAGAGTAACTAGACAGAAGAAGAAAGAATGTTACTTCTGTTA ATATGAATAGCATGTGAGAAAGCCCTGGGTCCATATGGAGCCT GACCTAATCAAGACACATAAGAAAGACCTATGTGACAGGAGCG CAAAAAAGTGAAGGAGAAAATGGTTGG |
| SNP031 | 2 | 64 | GATCCAGATTGTGAGGTCATGAAATGCTTATGAACAGAGAGCT TAAGAGTAACTAGACAGAAGAAGAAAGAATGTTACTTCTGTTA ATATGAATAGCATGTGCGAAAGCCCTGGGTCCATATGGAGCCT GACCTAATCAAGACACATAAGAAAGACCTATGTGACAGGAGCG CAAAAAAGTGAAGGAGAAAATGGTTGG |
| SNP031 | 3 | 65 | GATCCAGATTGTGAGGTCATGAAATGCTTATGAACAGAGAGCT TAAGAGTAACTAGACAGAAGAAGAAAGAATGTTACTTCTGTTA ATATGAATAGCATGTGTGAAAGCCCTGGGTCCATATGGAGCCT GACCTAATCAAGACACATAAGAAAGACCTATGTGACAGGAGCG CAAAAAAGTGAAGGAGAAAATGGTTGG |
| SNP032 | 1 | 66 | TGGTCATCAGGGGTCCAAGCTTCTTCATTCTGCCTCACCATCTC GCTTGCAGCTTCTGCCTAATGTTGACTTACAGTTCAAGATGGCT TCTGGAGTGCTACCATTACATCCATGTTGTAGGCTAGAAGGAAA AGGGCAATGGCCTGAAGAGGAAGGGAGAGTTCCTGTTAACTCA GCTTCCTTTAAACAGCCTCCCCAAAA |
| SNP032 | 2 | 67 | TGGTCATCAGGGGTCCAAGCTTCTTCATTCTGCCTCACCATCTC GCTTGCAGCTTCTGCCTAATGTTGACTTACAGTTCAAGATGGCT TCTGGAGTGCTACCGTTACATCCATGTTGTAGGCTAGAAGGAAA AGGGCAATGGCCTGAAGAGGAAGGGAGAGTTCCTGTTAACTCA GCTTCCTTTAAACAGCCTCCCCAAAA |
| SNP033 | 1 | 68 | CAGCCTTGGACTCCTGGTCCAAAGCAATCCTCCTGCTTCAGCCT CCTAAGTGGCTGGGAGCACAGGAGCAAGCCATCACACTTGACT AATTTTTTTTTTTTTGAGACAGAGTTTCACTCTTGTTGCCCAGGC TGCAGTGCAATGGTGCCATCTCAGCTCACTGAAACCTCTACTTC CCAGATTCGAGCGATTCTCTTGCC |
| SNP033 | 2 | 69 | CAGCCTTGGACTCCTGGTCCAAAGCAATCCTCCTGCTTCAGCCT CCTAAGTGGCTGGGAGCACAGGAGCAAGCCATCACACTTGACT AATTTTTTTTTTTTTTGAGACAGAGTTTCACTCTTGTTGCCCAGG CTGCAGTGCAATGGTGCCATCTCAGCTCACTGAAACCTCTACTT CCCAGATTCGAGCGATTCTCTTGCC |
| SNP034 | 1 | 70 | ATCATTTGAACATAAATCAGAGTCTCAGTACAAACAGAGTGCTC AGGACATCAAGATGGTTAACCAGAGAGCCTGGCCAGAATATCT GCGGTGGAGAGAAACAATCTTGTTGGGAGAAGGATGACAATAA TTGGGGACTTAGAATAAAGGCTAAAAATGATTCAAAGAGAATG CAAAAAGAATCAGGCACACATCCTTTAC |
| SNP034 | 2 | 71 | ATCATTTGAACATAAATCAGAGTCTCAGTACAAACAGAGTGCTC AGGACATCAAGATGGTTAACCAGAGAGCCTGGCCAGAATATCT GCGGTGGAGAGAAACGATCTTGTTGGGAGAAGGATGACAATAA TTGGGGACTTAGAATAAAGGCTAAAAATGATTCAAAGAGAATG CAAAAAGAATCAGGCACACATCCTTTAC |
| SNP035 | 1 | 72 | TAAGAAGCATCCTCAAGCTCCCAGTTAAGTAACTTGACTACTTT TATTTGGGAATTTCAGACTATAGAAGCTCTCTTATGTCCAGATT CTGTGACCACTAGTTACTGTATCAGAACTCATCAGGTACCCACT TATAAATAGCACTGATCTGGC |
| SNP035 | 2 | 73 | TAAGAAGCATCCTCAAGCTCCCAGTTAAGTAACTTGACTACTTT TATTTGGGAATTTCAGACTATAGAAGCTCTCTTATGTTTTATGT CCAGATTCTGTGACCACTAGTTACTGTATCAGAACTCATCAGGT ACCCACTTATAAATAGCACTGATCTGGC |

TABLE 2-continued

| | | | |
|---|---|---|---|
| | | | Input target sequences for 81 SNP regions |

| Target | Allele No. | SEQ ID NO: | Target Sequence |
|---|---|---|---|
| SNP036 | 1 | 74 | CTCTGCTCCAGGCTCTGGGCCGGGCACCAGCCTCTGGGAAAATG GAGGGGGTGGTGGTGAGGGCTCGGACAAGGAGCAGTGACTCCA TTCCAGGGACTCTGTCCAGAGGGACTGTCAGCTTAGGACGTGC GCGAAACACTCGGTTCACAGGGTTTAACACACTTTAGGGTAAA ACCTGGGAGAGCTTCCTAAGGAGGTGAC |
| SNP036 | 2 | 75 | CTCTGCTCCAGGCTCTGGGCCGGGCACCAGCCTCTGGGAAAATG GAGGGGGTGGTGGTGAGGGCTCGGACAAGGAGCAGTGACTCCA TTCCAGGGACTCTGTTCAGAGGGACTGTCAGCTTAGGACGTGCG CGAAACACTCGGTTCACAGGGTTTAACACACTTTAGGGTAAAA CCTGGGAGAGCTTCCTAAGGAGGTGAC |
| SNP037 | 1 | 76 | ACAAAAGAAACAAAAGACTGCTACTCCATAGGCAGAGCAGTCC TGAGAGCTGCTCGTGGCCTATTTTTATGGTTTTTTTTTTAAATTT TTATTTTAGGTTTGGGGGTACATGTGAAGGTTTTACATCGGTAA ACTTGTGCCACAGGGGTTTGTTGTACACATTGTTTCATTACCCA GGTATTAAGCCCAGTATCCGATAGT |
| SNP037 | 2 | 77 | ACAAAAGAAACAAAAGACTGCTACTCCATAGGCAGAGCAGTCC TGAGAGCTGCTCGTGGCCTATTTTTATGGTTTTTTTTTTAAATTT TTATTTTAGGTTTGTGGGTACATGTGAAGGTTTTACATCGGTAA ACTTGTGCCACAGGGGTTTGTTGTACACATTGTTTCATTACCCA GGTATTAAGCCCAGTATCCGATAGT |
| SNP038 | 1 | 78 | TTTCAAAAACGTGGCCACATCCATTTTCCCGCCATCAGCTTTCC AGACCACAGAATGCTCTGCTTTTGAGCTGCTCCTCAGCTGACAC CCTCCTTGAATCCACTTTGAGTTGCTCTTCCCTGGCCCCATTAGA AAATGTCGGCTCTGACTACACCATGCTTGCGAACAAAGGTGCA GAACAATTTTGGCTGCTTCGTCCAG |
| SNP038 | 2 | 79 | TTTCAAAAACGTGGCCACATCCATTTTCCCGCCATCAGCTTTCC AGACCACAGAATGCTCTGCTTTTGAGCTGCTCCTCAGCTGACAC CCTCCTTGAATCCATTTTGAGTTGCTCTTCCCTGGCCCCATTAGA AAATGTCGGCTCTGACTACACCATGCTTGCGAACAAAGGTGCA GAACAATTTTGGCTGCTTCGTCCAG |
| SNP039 | 1 | 80 | CTTCTAGAAGCGTAAGGTAACACTGGCATTCCTCTAGCCTCTGC TGGAGTGCAGTGAGGATTTTCTAGCATGTTGCTGCACTGTTCCC ATGCACATTATTCTAACTTTTTAGTAACTCACACGTGCATTCTTT TTTCAACGCTATCCTTAGAGTGAAAGTCAGAAAAAAAATACTAG AAACTAACTCAGGGCTGAGCGTGGT |
| SNP039 | 2 | 81 | CTTCTAGAAGCGTAAGGTAACACTGGCATTCCTCTAGCCTCTGC TGGAGTGCAGTGAGGATTTTCTAGCATGTTGCTGCACTGTTCCC ATGCACATTATTCTGACTTTTTAGTAACTCACACGTGCATTCTTT TTTCAACGCTATCCTTAGAGTGAAAGTCAGAAAAAAAATACTAG AAACTAACTCAGGGCTGAGCGTGGT |
| SNP040 | 1 | 82 | CTGAGCTCCCATCTCACACTGACATCTACAGAGTCCTATAGCTT CCATCTTGGAGTCCCACTCTGCCTTCTCAGAAAGCCACAGGTCA AATGAGGCTCCGCCGCACGCAGAACAGGGGACCTCCTGGACAG GAGTGGCTTTTATCCATCCCCACACCCACAGCTCCCAGCGCAGA CCCCGAAGAATTCATCCCAGGTGAGT |
| SNP040 | 2 | 83 | CTGAGCTCCCATCTCACACTGACATCTACAGAGTCCTATAGCTT CCATCTTGGAGTCCCACTCTGCCTTCTCAGAAAGCCACAGGTCA AATGAGGCTCCGCCTCACGCAGAACAGGGGACCTCCTGGACAG GAGTGGCTTTTATCCATCCCCACACCCACAGCTCCCAGCGCAGA CCCCGAAGAATTCATCCCAGGTGAGT |
| SNP041 | 1 | 84 | TTCTGACCTCAAGTGATCCGCCCGCCTCGGCCTCTGAAAGTGCT AGGATTGTAGGCATGAGCCACCGCGCCCGGCCTCGTACGGTAA TTCTGTGTGATGTTTAGGGACACGTCTCGGAGCTGGCGAACTGG ACTTGGGGTGGGAGGGAAAGGAAGCATTAAAG |
| SNP041 | 2 | 85 | TTCTGACCTCAAGTGATCCGCCCGCCTCGGCCTCTGAAAGTGCT AGGATTGTAGGCATGAGCCACCGCGCCCGGCCTCGTACGGTAA TTCTGTGTGATGTTTTGAGGAATTGCCACAATTTTTTCCTGCG CCTGCACCAGGGACACGTCTCGGAGCTGGCGAACTGGACTTGG GGTGGGAGGGAAAGGAAGCATTAAAG |

TABLE 2-continued

| | | | |
|---|---|---|---|
| Input target sequences for 81 SNP regions | | | |
| Target | Allele No. | SEQ ID NO: | Target Sequence |
| SNP042 | 1 | 86 | AACTGGCTGCCTCTATTCCAAAAATTATTTAGAAATTTTCAGAA TTTAAACTCATTAGCATGGCTTGGAACTTTCTCATCCCTAACGC AATCCCTGTGACCGATATAATGATGGTAATACTAAGAGTAAAG GGGAGAGACAGATCCTACTGATTATTAAAAAGTTATAGTCTGAT AATGAATGAGTGTTGTCAGGAATAGA |
| SNP042 | 2 | 87 | AACTGGCTGCCTCTATTCCAAAAATTATTTAGAAATTTTCAGAA TTTAAACTCATTAGCATGGCTTGGAACTTTCTCATCCCTAACGC AATCCCTGTGACCGGTATAATGATGGTAATACTAAGAGTAAAG GGGAGAGACAGATCCTACTGATTATTAAAAAGTTATAGTCTGAT AATGAATGAGTGTTGTCAGGAATAGA |
| SNP043 | 1 | 88 | AAACCCTGCGCACTGTGGTTCACGCCAGCAATCCCAGCCCTTTG GGAGGCTAAGGCAGGTGGATCACCTGAGTCCAGGAGTTCAAGA CCAGCCAGGATGACACAGCAAAACACCATCTCTACTAATAATA CAAAAACCAGCTGTGAATGGTGACACACAGCTGAAGTAGCAGC TACTAGGGAGACTGAAGCAGGAGGACTG |
| SNP043 | 2 | 89 | AAACCCTGCGCACTGTGGTTCACGCCAGCAATCCCAGCCCTTTG GGAGGCTAAGGCAGGTGGATCACCTGAGTCCAGGAGTTCAAGA CCAGCCAGGATGACATAGCAAAACACCATCTCTACTAATAATA CAAAAACCAGCTGTGAATGGTGACACACAGCTGAAGTAGCAGC TACTAGGGAGACTGAAGCAGGAGGACTG |
| SNP044 | 1 | 90 | TGCTATATCCATCTACATATATAAAGCCACCGGGAGAACTAGTC CACTTGGTGCAGTCTTCTATACTGTCCTTCACAGCTTAGATTCAA TCTTTCCTTAAAGTGTAGCCGGGATACACAGGAGTGTGATTCTG GGCTGACTCAAAGTTCTTCTCTTGAAGGCTTTTTCCTGTGGCACT GGCAGATGGCTGTGCTATCTTC |
| SNP044 | 2 | 91 | TGCTATATCCATCTACATATATAAAGCCACCGGGAGAACTAGTC CACTTGGTGCAGTCTTCTATACTGTCCTTCACAGCTTAGATTCAA TCTTTCCTTAAAGATGTAGCCGGGATACACAGGAGTGTGATTCT GGGCTGACTCAAAGTTCTTCTCTTGAAGGCTTTTTCCTGTGGCA CTGGCAGATGGCTGTGCTATCTTC |
| SNP045 | 1 | 92 | ATTTGCTGGAGATTGATGCTGGGAAAGGAAGCAAAATCTTTTGC AATCTGTGGTTCCTTGGTTGGACAAGAAAGAGTCTTCTGCCAGG CCTGAGGATCTTCCAGACACTCACAGTACTCATGGTACACTGGT CCTAGGGAAGGAAAACATGAAAAAGGCCGCACTCCATTAGCAA GCACCACAACACAGGGAGTCACTTCT |
| SNP045 | 2 | 93 | ATTTGCTGGAGATTGATGCTGGGAAAGGAAGCAAAATCTTTTGC AATCTGTGGTTCCTTGGTTGGACAAGAAAGAGTCTTCTGCCAGG CCTGAGGATCTTCCGGACACTCACAGTACTCATGGTACACTGGT CCTAGGGAAGGAAAACATGAAAAAGGCCGCACTCCATTAGCAA GCACCACAACACAGGGAGTCACTTCT |
| SNP046 | 1 | 94 | AATGACTGACACTCTCAAATTCCCCTCTGCATCATGGGCACTCA GCACTGTGCCTAGTGCATAGTAAGACTTCAACAAATATGTGCTG TTGTTATAATTCGGAATGACGATGGAGGTGCAGAGGTTTACCTG TGTTTTTATTATCTCTGGTTGACAAGGCGGCCACACCCAGGTTG CCTGTTCTGAAGCTGTCTCAAGACA |
| SNP046 | 2 | 95 | AATGACTGACACTCTCAAATTCCCCTCTGCATCATGGGCACTCA GCACTGTGCCTAGTGCATAGTAAGACTTCAACAAATATGTGCTG TTGTTATAATTCGGCATGACGATGGAGGTGCAGAGGTTTACCTG TGTTTTTATTATCTCTGGTTGACAAGGCGGCCACACCCAGGTTG CCTGTTCTGAAGCTGTCTCAAGACA |
| SNP047 | 1 | 96 | GGCATGCACCACCACGCCCAGCTAAATTTTTTTATTTTTAGTAG AGATGGGGTTTCACCATGTTGGCAAGGCTGGTCTCAAACTCCTG ACTTCATGATCCACCCCGCCTCGGCCTCTCAAAGTGCTGGGATTA CAGGTGTGAGCCACTGCAACCAGCCTGTTTTTTGTTTTTTTTGAG TAGGATGTGATCCGCTTATGTTTT |
| SNP047 | 2 | 97 | GGCATGCACCACCACGCCCAGCTAAATTTTTTTATTTTTAGTAG AGATGGGGTTTCACCATGTTGGCAAGGCTGGTCTCAAACTCCTG ACTTCATGATCCACCTCGCCTCGGCCTCTCAAAGTGCTGGGATTA CAGGTGTGAGCCACTGCAACCAGCCTGTTTTTTGTTTTTTTTGAG TAGGATGTGATCCGCTTATGTTTT |

TABLE 2-continued

Input target sequences for 81 SNP regions

| Target | Allele No. | SEQ ID NO: | Target Sequence |
|---|---|---|---|
| SNP048 | 1 | 98 | TTCACAGGTGTTTAGAAAAATTAGATTGTCACCTCTTGTTGGTC ACAGAATGATTACAATACTTTGCATTCGTGCCACAATAGTTTTT AGAGGGTTTTTGTACGTTATGTAGCTGAGCATTCCATTTGGTCT TTGGAGCCTGGGGGAAGAGGACCTTTAATGAGGACAAGAAGAT AGGAAAGTGCAAAAATACAAATGGAG |
| SNP048 | 2 | 99 | TTCACAGGTGTTTAGAAAAATTAGATTGTCACCTCTTGTTGGTC ACAGAATGATTACAATACTTTGCATTCGTGCCACAATAGTTTTT AGAGGGTTTTTGTATGTTATGTAGCTGAGCATTCCATTTGGTCTT TGGAGCCTGGGGGAAGAGGACCTTTAATGAGGACAAGAAGATA GGAAAGTGCAAAAATACAAATGGAG |
| SNP049 | 1 | 100 | ACTGTGTGACTCTAGTGATCTTTAACATACACAGAATGATCTAC AGTGATCTTTAACATACTCAGAAATATGAAAAATGTTTGAATAT GATCTTTAGGGACTGCTAATGAAAAGGGTATATGAAATGGGAA CAATAAATTCTGTACATGTATACAGTCCATATACACATTAAGTG TTTGTCATTTGGACAAATTGAAAACT |
| SNP049 | 2 | 101 | ACTGTGTGACTCTAGTGATCTTTAACATACACAGAATGATCTAC AGTGATCTTTAACATACTCAGAAATATGAAAAATGTTTGAATAT GATCTTTAGGGACTTCTAATGAAAAGGGTATATGAAATGGGAA CAATAAATTCTGTACATGTATACAGTCCATATACACATTAAGTG TTTGTCATTTGGACAAATTGAAAACT |
| SNP050 | 1 | 102 | ACTAGCCATGGACATGCAAATTTTAAAAACAATGAGCTACTGTT GCTCTCAATTGGGCAATATTTTTAGAAAACTGATAGCATCTAGG CCAGCCCTTCCCAACCGTCTGCACCTGGGAATCGCCTGGGGACC TTCAAGTAACTACTGATCCCCAGCTACCAATTTAATTGGTTTGG GGTATGGCCTGGGGTTCTACATTTT |
| SNP050 | 2 | 103 | ACTAGCCATGGACATGCAAATTTTAAAAACAATGAGCTACTGTT GCTCTCAATTGGGCAATATTTTTAGAAAACTGATAGCATCTAGG CCAGCCCTTCCCAATCGTCTGCACCTGGGAATCGCCTGGGGACC TTCAAGTAACTACTGATCCCCAGCTACCAATTTAATTGGTTTGG GGTATGGCCTGGGGTTCTACATTTT |
| SNP051 | 1 | 104 | ATCAGTGTTACAGTGAAACAAAGTTATTCAAGGACCTGCTGCTG TACATACTTTTGCTAAAAATCAGTTTCCAAGAACCTATTGTGGA TGTTAGGAGAGGAGCTACCATGCCACAATGACTCTGGGAGATG AAGCCATTTTATTCCCATGCTTGTTAACCTTGTGCAGGTGCGGG AATGCAGATGGCTGAGTAGGTCAGAT |
| SNP051 | 2 | 105 | ATCAGTGTTACAGTGAAACAAAGTTATTCAAGGACCTGCTGCTG TACATACTTTTGCTAAAAATCAGTTTCCAAGAACCTATTGTGGA TGTTAGGAGAGGAGTTACCATGCCACAATGACTCTGGGAGATG AAGCCATTTTATTCCCATGCTTGTTAACCTTGTGCAGGTGCGGG AATGCAGATGGCTGAGTAGGTCAGAT |
| SNP052 | 1 | 106 | CCTCCCAAAGTGTTGGGATTACAGGTATGAGCCACCACACCCA GCTGCATGTGGATTCTTAAGTGCAACAGTCAGCAGTAATCTCAC ATCTGTTAGCAGACACTTGCTGTAGTCACAACAATGCTTTCTTC TTCCCTGAACAGATACTCCACTTCTTGAAATATACTTAAGTAGG CACTGTATTTATACAGCTCTGAAAGC |
| SNP052 | 2 | 107 | CCTCCCAAAGTGTTGGGATTACAGGTATGAGCCACCACACCCA GCTGCATGTGGATTCTTAAGTGCAACAGTCAGCAGTAATCTCAC ATCTGTTAGCAGACATTTGCTGTAGTCACAACAATGCTTTCTTC TTCCCTGAACAGATACTCCACTTCTTGAAATATACTTAAGTAGG CACTGTATTTATACAGCTCTGAAAGC |
| SNP053 | 1 | 108 | AGGAAAGATTGATTCCAGGAAAAGGGACCAAATGTCCTAACAC TTTTAAATGCCTAACAGAAAAGTTTTTACCACAGACTACCATTT TTTTCTTTCTAAAGGCTGCTACCTTTGAGGCTTCATCTGCATAAC AAGACAGCTTTTGCTCACCATGCCTTTCCTCCCCTCTCCCTCCCA TAAAGCTGTTGCCACACTCCAAGC |
| SNP053 | 2 | 109 | AGGAAAGATTGATTCCAGGAAAAGGGACCAAATGTCCTAACAC TTTTAAATGCCTAACAGAAAAGTTTTTACCACAGACTACCATTT TTTTCTTTCTAAAGGTTGCTACCTTTGAGGCTTCATCTGCATAAC AAGACAGCTTTTGCTCACCATGCCTTTCCTCCCCTCTCCCTCCCA TAAAGCTGTTGCCACACTCCAAGC |

TABLE 2-continued

Input target sequences for 81 SNP regions

| Target | Allele No. | SEQ ID NO: | Target Sequence |
|--------|-----------|-----------|-----------------|
| SNP054 | 1 | 110 | TCTGTAACTACCAGATTTTACTCGCCTTCCTGGACTCTGTTCACA GGAAAGAAAGGAAACAAACAAACCTCATACATTATGAAGCATA GGGTATCAATGGCCCTGCTGATTATAGTGGGTGGGGGTGGCAT AAATACATGTACACCCCCACTGCTGCCCCATCCCCACTCCTCTG AGCACTGGGGTCAAGGAATATATATT |
| SNP054 | 2 | 111 | TCTGTAACTACCAGATTTTACTCGCCTTCCTGGACTCTGTTCACA GGAAAGAAAGGAAACAAACAAACCTCATACATTATGAAGCATA GGGTATCAATGGCCTTGCTGATTATAGTGGGTGGGGGTGGCAT AAATACATGTACACCCCCACTGCTGCCCCATCCCCACTCCTCTG AGCACTGGGGTCAAGGAATATATATT |
| SNP055 | 1 | 112 | ACACCTGAGGAAGGCTGGGCAGAATGGATCGGGGGTGTGTATT GGCTGCAGTCACCTCCCCTCTGCTCGTCTGTGTCCACATTCTGTC GTGGTTGAGACCGGATCCTGTGTGGACCGGGTGGGCTGGTGTG GAGTCCTGTCAGGAGACCTGGGGCGGTTTTGAGGCAAGCTCAC GGAGGCCTGCCGCAGGGCCCTGCGCTG |
| SNP055 | 2 | 113 | ACACCTGAGGAAGGCTGGGCAGAATGGATCGGGGGTGTGTATT GGCTGCAGTCACCTCCCCTCTGCTCGTCTGTGTCCACATTCTGTC GTGGTTGAGACCGGCTCCTGTGTGGACCGGGTGGGCTGGTGTG GAGTCCTGTCAGGAGACCTGGGGCGGTTTTGAGGCAAGCTCAC GGAGGCCTGCCGCAGGGCCCTGCGCTG |
| SNP056 | 1 | 114 | TTATCTTCCTAAGACATAAGGCAATTGCTGACATTTGCCTTCCTC AAGGGCCAAACAGCCAACCAACAGTGTCCTTGGGAGCAGAGCT GAGTTTCTAAACCTACGGCTAGAAACATGGAGATCCAAATCCA TATATGGAGATACTTCACAGAAGGAAAAAAAGCAGAAATAAAC TCTTGGGAAAGAAAGAATCAGACCCAC |
| SNP056 | 2 | 115 | TTATCTTCCTAAGACATAAGGCAATTGCTGACATTTGCCTTCCTC AAGGGCCAAACAGCCAACCAACAGTGTCCTTGGGAGCAGAGCT GAGTTTCTAAACCTGCGGCTAGAAACATGGAGATCCAAATCCA TATATGGAGATACTTCACAGAAGGAAAAAAAGCAGAAATAAAC TCTTGGGAAAGAAAGAATCAGACCCAC |
| SNP057 | 1 | 116 | CTTCACAGGTGAAATTGTTTGACCCATGAAAATCTGAAACATAT GAGGTCTCTTGTTTTCATTCAGCATATGCCAGTTAAGTGCCTAA TTGTTCACCCAGCAACCAGATCCTGACTCACAATTAATTTTATTT ATAGAGCCTCACTGCTTTGCTGCTTCCCTACTTGTTATTTTGACT GTGGGAGCAAAAAATGGTAAC |
| SNP057 | 2 | 117 | CTTCACAGGTGAAATTGTTTGACCCATGAAAATCTGAAACATAT GAGGTCTCTTGTTTTCATTCAGCATATGCCAGTTAAGTGCCTAA TTGTTCACCCAGCACCCAGATCCTGACTCACAATTAATTTTATTT ATAGAGCCTCACTGCTTTGCTGCTTCCCTACTTGTTATTTTGACT GTGGGAGCAAAAAATGGTAAC |
| SNP057 | 3 | 118 | CTTCACAGGTGAAATTGTTTGACCCATGAAAATCTGAAACATAT GAGGTCTCTTGTTTTCATTCAGCATATGCCAGTTAAGTGCCTAA TTGTTCACCCAGCATCCAGATCCTGACTCACAATTAATTTTATTT ATAGAGCCTCACTGCTTTGCTGCTTCCCTACTTGTTATTTTGACT GTGGGAGCAAAAAATGGTAAC |
| SNP058 | 1 | 119 | AGTATGTAAGGTGATGCTAAGAGAAGAGGCACAAAAGTATTCA CAATTGGGAGGGAGACAGATCCCAGGGCTCCTTGAAGAGGTTC TCCCTCACTACTCATGCCCTGCTTATCACACACTTGCACAGTTG GATTTCTTTTCAGGTGTGCAAATATATAAGCTTTTAAGTCATGA ATAGTATGTACCTTATCTGCACTGTTG |
| SNP058 | 2 | 120 | AGTATGTAAGGTGATGCTAAGAGAAGAGGCACAAAAGTATTCA CAATTGGGAGGGAGACAGATCCCAGGGCTCCTTGAAGAGGTTC TCCCTCACTACTCATGTCCTGCTTATCACACACTTGCACAGTTG GATTTCTTTTCAGGTGTGCAAATATATAAGCTTTTAAGTCATGA ATAGTATGTACCTTATCTGCACTGTTG |
| SNP059 | 1 | 121 | GAAGATAAGGGGAAACTGAAAAATGAGCATGGGAGGAAGTAG CCAGGGAGGGAGGAGGAAAACCAGGCGAACACTGTGTTCTAGA AGCCAAGCAAAGATGGACTTTCAAGAAGAAGAGAGTCATCAAC TGTGTCAAATGCTGCTTATAGGATGATAGAGGACCACTGATTGG ATTTAAGAAAGTGGAAGTCCTTGGCCACC |

TABLE 2-continued

Input target sequences for 81 SNP regions

| Target | Allele No. | SEQ ID NO: | Target Sequence |
|---|---|---|---|
| SNP059 | 2 | 122 | GAAGATAAGGGGAAACTGAAAAATGAGCATGGGAGGAAGTAG CCAGGGAGGGAGGAGGAGGAAAACCAGGCGAACACTGTGTTCTAGA AGCCAAGCAAAGATGGAGTTTCAAGAAGAAGAGAGTCATCAAC TGTGTCAAATGCTGCTTATAGGATGATAGAGGACCACTGATTGG ATTTAAGAAAGTGGAAGTCCTTGGCCACC |
| SNP060 | 1 | 123 | TTTCCTGACTTAGTCCCTTACCCTCAGAGACTGAACAAGAGCTG TAATTTTTACATGGGTGCCCAGGATGTGGCCTTGTCCCCTGTAT CCTTTCCAACCTAGATTTGAGCTGCTGCCTTCTATTAACTGCCTT TTCTGGCTAAGGTGGGAGGCAGAGCCCAAGCCGATCCCAGGAT GATGGGAGACCCCAGCCATGTTCCT |
| SNP060 | 2 | 124 | TTTCCTGACTTAGTCCCTTACCCTCAGAGACTGAACAAGAGCTG TAATTTTTACATGGGTGCCCAGGATGTGGCCTTGTCCCCTGTAT CCTTTCCAACCTAGCTTTGAGCTGCTGCCTTCTATTAACTGCCTT TTCTGGCTAAGGTGGGAGGCAGAGCCCAAGCCGATCCCAGGAT GATGGGAGACCCCAGCCATGTTCCT |
| SNP061 | 1 | 125 | CCTTCTAAAGCCACCGAAAGTTAATTGGTAGGATATCACAGGG GTGTTTTAACTTTTCTTTGAATTTTCTCCAATCTTAGTAACACAG CTGACTGGGGCAATCGCATCTCACTTCTACTTGATTTCTAAATA TTTGTTAACTAATATTCTTCATTTATGCTAAGATAGACAGTTTTT ACATTTAATAATTTTAGAATAAGA |
| SNP061 | 2 | 126 | CCTTCTAAAGCCACCGAAAGTTAATTGGTAGGATATCACAGGG GTGTTTTAACTTTTCTTTGAATTTTCTCCAATCTTAGTAACACAG CTGACTGGGGCAATGGCATCTCACTTCTACTTGATTTCTAAATA TTTGTTAACTAATATTCTTCATTTATGCTAAGATAGACAGTTTTT ACATTTAATAATTTTAGAATAAGA |
| SNP062 | 1 | 127 | TAACAGCAAGCAATAGTATCTATTTGAATAGAAACCAACACCT GTTATTTGAAGTTGAAGGTATGTGAGTTTGACCGTGATCCTTAA ATAGCAGCACAGACCCATTTGCAAACCGTGGATTGATGTGGCC CCAGCGGAGCAGGGGAGACGGAGATGCAGGGGGGGTGTTGTGT GCTTGGTGGAGGGACTGGGTTCTGCAGG |
| SNP062 | 2 | 128 | TAACAGCAAGCAATAGTATCTATTTGAATAGAAACCAACACCT GTTATTTGAAGTTGAAGGTATGTGAGTTTGACCGTGATCCTTAA ATAGCAGCACAGACCTATTTGCAAACCGTGGATTGATGTGGCC CCAGCGGAGCAGGGGAGACGGAGATGCAGGGGGGGTGTTGTGT GCTTGGTGGAGGGACTGGGTTCTGCAGG |
| SNP063 | 1 | 129 | ATTAATCAAAGTCCATACTGCAGGTAAGTGGCAGAACTGAGGT CTGAACCAAGGAAGTCTGACTCCAGTGCCTACGATCATAATCAC AAGTACCTCGAATACATTGGTAAGATGGCACATGACTGGTAGC TTTGCTGTAGAGGAATCTTACCTTGTCATACAAATCAATATGCC TTGTGAAAAATTTTTCAAATGCTTGAA |
| SNP063 | 2 | 130 | ATTAATCAAAGTCCATACTGCAGGTAAGTGGCAGAACTGAGGT CTGAACCAAGGAAGTCTGACTCCAGTGCCTACGATCATAATCAC AAGTACCTCGAATACGTTGGTAAGATGGCACATGACTGGTAGC TTTGCTGTAGAGGAATCTTACCTTGTCATACAAATCAATATGCC TTGTGAAAAATTTTTCAAATGCTTGAA |
| SNP064 | 1 | 131 | TCCTGCCTGCTGAAAGGAGCCCAGCGACTCCAACACCAACGTC ATTCATTAGGAAAACAAAACCGAAGACTCGCATGCACGTATAT GTACACACACAAAATGAACAAATAGTGGGAAGAATTATTGTAA GTCTTAAGTCACAGGAAATTTGATTTGCTTCAACTAAAACACCC GAGGATAGGCCGGCGTGGCGGGTCGCCC |
| SNP064 | 2 | 132 | TCCTGCCTGCTGAAAGGAGCCCAGCGACTCCAACACCAACGTC ATTCATTAGGAAAACAAAACCGAAGACTCGCATGCACGTATAT GTACACACACAAAATGCACAAATAGTGGGAAGAATTATTGTAA GTCTTAAGTCACAGGAAATTTGATTTGCTTCAACTAAAACACCC GAGGATAGGCCGGCGTGGCGGGTCGCCC |
| SNP065 | 1 | 133 | CACGCTCTGGTAGGCACTGAGGTTGGTGGTGAAACCCAGCTGG GAGATGGAGGCGCCCTTGTCCCGCAGCACTCGGTACTCCTCCCA GCAGTAGTAGATGCCATATGCCAGCACGCCCAGCACTCCCAGG ATCAGCACCAGCACCAGGGGCCCAGCCACCAGGCGCAGAAGCA AGATAAACAGTAGGCTCAAGACCAGAGC |

TABLE 2-continued

| | | | Input target sequences for 81 SNP regions |
|---|---|---|---|

| Target | Allele No. | SEQ ID NO: | Target Sequence |
|---|---|---|---|
| SNP065 | 2 | 134 | CACGCTCTGGTAGGCACTGAGGTTGGTGGTGAAACCCAGCTGG GAGATGGAGGCGCCCTTGTCCCGCAGCACTCGGTACTCCTCCCA GCAGTAGTAGATGCCGTATGCCAGCACGCCCAGCACTCCCAGG ATCAGCACCAGCACCAGGGGCCCAGCCACCAGGCGCAGAAGCA AGATAAACAGTAGGCTCAAGACCAGAGC |
| SNP066 | 1 | 135 | TATTTCCTATTTTAATTTCCCTAGTTGCCTCCAAAATACCTTTTA TAGCTATTTTTATTTTTTCCTGATCCAAGGTACAATCAAGACTCA TGCATTGCAAGGATAAATTTTTTTTTCCCTAAGTGATCTTCATTG GGAGAAGTAAAACAATTTTATGTTAAACTCTAAGTGAGGTGAT ATTTTGTTCTCAGATTTTGAACT |
| SNP066 | 2 | 136 | TATTTCCTATTTTAATTTCCCTAGTTGCCTCCAAAATACCTTTTA TAGCTATTTTTATTTTTTCCTGATCCAAGGTACAATCAAGACTCA TGCATTGCAAGGGTAAATTTTTTTTTCCCTAAGTGATCTTCATTG GGAGAAGTAAAACAATTTTATGTTAAACTCTAAGTGAGGTGAT ATTTTGTTCTCAGATTTTGAACT |
| SNP067 | 1 | 137 | ATCAAGATCTGCAGCTCCAGAGGTTGCCATTTCCCATGCCCAGA TAGTTGGCTTACAAGCCTAGCTTCAAAGCATGCCTTGGCTCACA GAGTCATCTCTTTTAGGGATGTCCCCACCCTGTACTCATCTCAA AGCCATCGAGAACCATCTCTAAATGTCATATCTGGCAGTGATCT CTCTTTTCTCTGATCCGTTGTCGCA |
| SNP067 | 2 | 138 | ATCAAGATCTGCAGCTCCAGAGGTTGCCATTTCCCATGCCCAGA TAGTTGGCTTACAAGCCTAGCTTCAAAGCATGCCTTGGCTCACA GAGTCATCTCTTTTTGGGATGTCCCCACCCTGTACTCATCTCAA AGCCATCGAGAACCATCTCTAAATGTCATATCTGGCAGTGATCT CTCTTTTCTCTGATCCGTTGTCGCA |
| SNP068 | 1 | 139 | CCTATGGACAACAAACTGTGCCTAATGAATTCTGGCCAGAGCC AAAACAATGAAATTATTTATCTCCACCTCCCCTATTGATGCACA GCAGAAATAAATATAAGGATCACCACCTTCTGTGCAAATGCAA ATAAGTATACTCGCAGAAACAAAAATTTCAACCTACAATTTCAG TTTTCCTCACCTTTTGCTTACACTCTA |
| SNP068 | 2 | 140 | CCTATGGACAACAAACTGTGCCTAATGAATTCTGGCCAGAGCC AAAACAATGAAATTATTTATCTCCACCTCCCCTATTGATGCACA GCAGAAATAAATATAGGGATCACCACCTTCTGTGCAAATGCAA ATAAGTATACTCGCAGAAACAAAAATTTCAACCTACAATTTCAG TTTTCCTCACCTTTTGCTTACACTCTA |
| SNP069 | 1 | 141 | AGGCATGAAGTAAGGGTCGAGGTCCAAGGGTGTGTGACACAAC ATTGCTACCATGTTATAGAGGGATATTCTAAACAAAATCTCTGC ATTCTTACCCCATGAACCCTATCTTCAGCCTTTACCACTGGAAA GCATCTTTCTAAATTCAAATCCTTGATTTGCTTCTGGTTTTGTAA TAAAGTCATGAGCAATAGGAATGCA |
| SNP069 | 2 | 142 | AGGCATGAAGTAAGGGTCGAGGTCCAAGGGTGTGTGACACAAC ATTGCTACCATGTTATAGAGGGATATTCTAAACAAAATCTCTGC ATTCTTACCCCATGAGCCCTATCTTCAGCCTTTACCACTGGAAA GCATCTTTCTAAATTCAAATCCTTGATTTGCTTCTGGTTTTGTAA TAAAGTCATGAGCAATAGGAATGCA |
| SNP070 | 1 | 143 | TCAGACCTCTAGGCCCTCCTTCCTTAGACTCCGGAGTCCCTCCT GCCTCTGACACTCACGAGGTCCAGACCCCAAGATAGCCCAGCC AGCAGGGACAGGGACAGGTAAGCCTCACATGCTGGGCTCTGCA GGAGAATGAGAGGGGCTGAAGCTGGGCCCCTCTCGCTTTCCTCT TTCTCTCTCCTCCCCTTCACACCTGAA |
| SNP070 | 2 | 144 | TCAGACCTCTAGGCCCTCCTTCCTTAGACTCCGGAGTCCCTCCT GCCTCTGACACTCACGAGGTCCAGACCCCAAGATAGCCCAGCC AGCAGGGACAGGGACGGGTAAGCCTCACATGCTGGGCTCTGCA GGAGAATGAGAGGGGCTGAAGCTGGGCCCCTCTCGCTTTCCTCT TTCTCTCTCCTCCCCTTCACACCTGAA |
| SNP071 | 1 | 145 | TAATGAACAGAATATTTACTAAATGCTAGAGAGTAAAAATCCTT TCTATCCTTTCACCAAATCCCTAGATTAGTTGTATGGGGAGGGG GCAGGAAGCAGTACATGGAAGAAAAGCTCTTACTAGGCTTTTC AGTAAGCAGAAAACATGAGCTCCTAGATAGGACGGCAAATTCA TTTTTAAATCAACGGCAATTCCTATGA |

TABLE 2-continued

| | Allele | SEQ ID | |
|---|---|---|---|
| Target | No. | NO: | Target Sequence |

Input target sequences for 81 SNP regions

| Target | Allele No. | SEQ ID NO: | Target Sequence |
|---|---|---|---|
| SNP071 | 2 | 146 | TAATGAACAGAATATTTACTAAATGCTAGAGAGTAAAAATCCTT TCTATCCTTTCACCAAATCCCTAGATTAGTTGTATGGGGAGGGG GCAGGAAGCAGTACGTGGAAGAAAAGCTCTTACTAGGCTTTTC AGTAAGCAGAAAACATGAGCTCCTAGATAGGACGGCAAATTCA TTTTTAAATCAACGGCAATTCCTATGA |
| SNP072 | 1 | 147 | GATCTATTAGGATTGAATATGCTTTGTAAACAGTAGCATAACCA GATATTTCTGACTCCATTCTATAGTATGTAGTCTTCAGTTATCAG GACAAGTATCTTTCATGCTGTAACTCAGCCTTGAGAACTCGTTG GCACATTGCTCGGTCAGTGATCTGGGAGTCCAGTCATTGCAACG GGGATGCACTGAGCACCTGCTGAT |
| SNP072 | 2 | 148 | GATCTATTAGGATTGAATATGCTTTGTAAACAGTAGCATAACCA GATATTTCTGACTCCATTCTATAGTATGTAGTCTTCAGTTATCAG GACAAGTATCTTTTATGCTGTAACTCAGCCTTGAGAACTCGTTG GCACATTGCTCGGTCAGTGATCTGGGAGTCCAGTCATTGCAACG GGGATGCACTGAGCACCTGCTGAT |
| SNP073 | 1 | 149 | TTGAAAGGGTGTTTAATAAGATAATTGGGCCGGGCACAGTGGC TCATGCCTGTAATCCCAGCATTTTGGGAGGCTGAGGAGGGCAG ATCATGAGGTCAGGAGGTTGAGACCAGCCTGACCAACATGGTG AAACCCCGTCTCTACTAAAAATACAAAAATTAGCCAGGCGTGG TGGCACACACCTGTAATCCCAGCTACTCA |
| SNP073 | 2 | 150 | TTGAAAGGGTGTTTAATAAGATAATTGGGCCGGGCACAGTGGC TCATGCCTGTAATCCCAGCATTTTGGGAGGCTGAGGAGGGCAG ATCATGAGGTCAGGAGTTTGAGACCAGCCTGACCAACATGGTG AAACCCCGTCTCTACTAAAAATACAAAAATTAGCCAGGCGTGG TGGCACACACCTGTAATCCCAGCTACTCA |
| SNP074 | 1 | 151 | GGGCCACAGCAAGCAAGGGGCAGCGGCTTTTGCCTCCCCACCC TGCCCTGGCCCCGTCACCTCCCAAGGAGGGAAAGGTGATGCAT ACGTGCCCGAAGAAACCGACCGCATAGGTTATTTTCACGCAGC CCCTCCAAGGCAGGCACTAACTGGACACCTGCTTTGCGTCTCAG CTGTTGAAATGCCATCCCCTGCCCCCAG |
| SNP074 | 2 | 152 | GGGCCACAGCAAGCAAGGGGCAGCGGCTTTTGCCTCCCCACCC TGCCCTGGCCCCGTCACCTCCCAAGGAGGGAAAGGTGATGCAT ACGTGCCCGAAGAAACTGACCGCATAGGTTATTTTCACGCAGC CCCTCCAAGGCAGGCACTAACTGGACACCTGCTTTGCGTCTCAG CTGTTGAAATGCCATCCCCTGCCCCCAG |
| SNP075 | 1 | 153 | GGGCACAGAAAGGACCCTAGAGGGTCATCTGACCTGGGCCCAG ACACCCTGAGACCCATGACCCCTGGACTCTTGCAGATGCCAGTT CAATCCCCCATTTCCCCTTTTTATTTAATCAGCACTTTTCTGAGC ATCAGCAGTGCTGGAGGCCCTGTGCCAGGCGCTTCCCATCAGCA GCTCGTTTAGACCTCACAGCTGTTC |
| SNP075 | 2 | 154 | GGGCACAGAAAGGACCCTAGAGGGTCATCTGACCTGGGCCCAG ACACCCTGAGACCCATGACCCCTGGACTCTTGCAGATGCCAGTT CAATCCCCCATTTCCTCTTTTTATTTAATCAGCACTTTTCTGAGC ATCAGCAGTGCTGGAGGCCCTGTGCCAGGCGCTTCCCATCAGCA GCTCGTTTAGACCTCACAGCTGTTC |
| SNP076 | 1 | 155 | TTGGGAAAGAATTTGAACTCATCTTCCAATATATCCTACTAACA AAATTTTTTTGAGATGATGAATAGATTTGTTCTTATAACCAGTG TGGAAAGTTAACTCCATGGGGCTAAACAAATTCTCTTAACGTCA ACACACAACACAGGACAGGAGACAAAAGTAATGTGAGATTAT ATTTTAGTATGCCATTAAAAATTTTG |
| SNP076 | 2 | 156 | TTGGGAAAGAATTTGAACTCATCTTCCAATATATCCTACTAACA AAATTTTTTTGAGATGATGAATAGATTTGTTCTTATAACCAGTG TGGAAAGTTAACTCTATGGGGCTAAACAAATTCTCTTAACGTCA ACACACAACACAGGACAGGAGACAAAAGTAATGTGAGATTAT ATTTTAGTATGCCATTAAAAATTTTG |
| SNP077 | 1 | 157 | GGAAGGTGGGCTGAGCCTGTGGGCAGGTGTTGGTGCTCCCCTCC CCGACGGGGCACGATGGGGACAGAGCATGGGAGGGAATATGA AGCAGGAGCTCTGTCTCGTACACATGGAATCTGAGGAGCTGAC AGATGACCTGTGGGGAGGGTGGTCCCGTGCCAATGTGTGCTGG AAGGACATGCCTGTGCGTTTATCAGCTCT |

TABLE 2-continued

| | Allele | SEQ ID | |
|---|---|---|---|
| Target | No. | NO: | Target Sequence |

Input target sequences for 81 SNP regions

| Target | Allele No. | SEQ ID NO: | Target Sequence |
|---|---|---|---|
| SNP077 | 2 | 158 | GGAAGGTGGGCTGAGCCTGTGGGCAGGTGTTGGTGCTCCCCTCC CCGACGGGGCACGATGGGGACAGAGCATGGGAGGGAATATGA AGCAGGAGCTCTGTCTTGTACACATGGAATCTGAGGAGCTGAC AGATGACCTGTGGGGAGGGTGGTCCCGTGCCAATGTGTGCTGG AAGGACATGCCTGTGCGTTTATCAGCTCT |
| SNP078 | 1 | 159 | AAGAAAATGTATGTTGTTTCTTAAATATCATTTACAGCTGTAAA ATATTCTGTTGAGGATGCCACCTAATTCAATTAACCATTCTCCT GTCCTCAAATATTTACTTCCTCCTTCTTTTGGGGTTTTATAAAGA ACAATATGGTAAACATCTGTGTGCATGTAAGTTCTTGCTTGCTT TCTTTTTTTTTTTTTTTTTTTTGAG |
| SNP078 | 2 | 160 | AAGAAAATGTATGTTGTTTCTTAAATATCATTTACAGCTGTAAA ATATTCTGTTGAGGATGCCACCTAATTCAATTAACCATTCTCCT GTCCTCAAATATTTCCTTCCTCCTTCTTTTGGGGTTTTATAAAGA ACAATATGGTAAACATCTGTGTGCATGTAAGTTCTTGCTTGCTT TCTTTTTTTTTTTTTTTTTTTTGAG |
| SNP079 | 1 | 161 | TTGTAGATGGGTAACAGCCCAGAGATGGGAAGGGACGTGCACA AGATGGGAATGGGCGTGCCCATGGTTGCACCGTGTGGTGTGGC AGAGCAGGAACTGGAACACAGGCGGCTGGAAGTGAAAGTGGA GCTCAGGCTTTTTAGCAGTTACTATGTGTGATTTCCTTTTCATCA TCACATCAACCCCATTTTTTTTTTTCAG |
| SNP079 | 2 | 162 | TTGTAGATGGGTAACAGCCCAGAGATGGGAAGGGACGTGCACA AGATGGGAATGGGCGTGCCCATGGTTGCACCGTGTGGTGTGGC AGAGCAGGAACTGGAATACAGGCGGCTGGAAGTGAAAGTGGA GCTCAGGCTTTTTAGCAGTTACTATGTGTGATTTCCTTTTCATCA TCACATCAACCCCATTTTTTTTTTTCAG |
| SNP080 | 1 | 163 | TCTAAAGCTTCCCTCTGAATGCTGCTTTGGAGGATTGTGAGAGG TAGTGACTCTTCAAAGTTTGTTTGTTTTCTTGAAGCTTTTACCTC TATGCAAATATGCAGTTTGGAGCAGGGAAGAAAGGTTAACTGT GATGGCGCCGGCTCTTAACGTGGAATGTCCTGAATTAATGTGGG TTTCAGTCCTCTGGCTCAGGATC |
| SNP080 | 2 | 164 | TCTAAAGCTTCCCTCTGAATGCTGCTTTGGAGGATTGTGAGAGG TAGTGACTCTTCAAAGTTTGTTTGTTTTCTTGAAGCTTTTACCTC TATGCAAATATGCGGTTTGGAGCAGGGAAGAAAGGTTAACTGT GATGGCGCCGGCTCTTAACGTGGAATGTCCTGAATTAATGTGGG TTTCAGTCCTCTGGCTCAGGATC |
| SNP080 | 3 | 165 | TCTAAAGCTTCCCTCTGAATGCTGCTTTGGAGGATTGTGAGAGG TAGTGACTCTTCAAAGTTTGTTTGTTTTCTTGAAGCTTTTACCTC TATGCAAATATGCTGTTTGGAGCAGGGAAGAAAGGTTAACTGT GATGGCGCCGGCTCTTAACGTGGAATGTCCTGAATTAATGTGGG TTTCAGTCCTCTGGCTCAGGATC |
| SNP081 | 1 | 166 | CAGGAGGGAGGGAAGAAGGAAGCCCAGCTCACTCATCCAACCG GAAGGACCCCTGCTCCAGGCAGGACTGGAATAACGCCAGGACT CCAAATGAGCAAGATAATCCCAGCCTGGCCTGCCTGGGATAAG GAGCGGGCAGGGAAACCCAGAGGAGAAGCACTGACTTTGGCA GGATGGGGCATGTGAGGGCACCTGGAAGGC |
| SNP081 | 2 | 167 | CAGGAGGGAGGGAAGAAGGAAGCCCAGCTCACTCATCCAACCG GAAGGACCCCTGCTCCAGGCAGGACTGGAATAACGCCAGGACT CCAAATGAGCAAGATAGTCCCAGCCTGGCCTGCCTGGGATAAG GAGCGGGCAGGGAAACCCAGAGGAGAAGCACTGACTTTGGCA GGATGGGGCATGTGAGGGCACCTGGAAGGC |

TABLE 3 shows the primers selected by PlexForm™ for the targets in TABLE 2. "F" in the primer name denotes a forward primer. "R" in the primer name denotes a reverse primer. TABLE 3 comurises SEO ID NO: 168-329. (See TABLE 13 for IUPAC nucleotide abbreviations.)

TABLE 3

| | | SEQ ID | |
|---|---|---|---|
| Target | Primer Name | NO: | Primer Sequence |

PlexForm primers selected (for the target sequences in TABLE 2)

| Target | Primer Name | SEQ ID NO: | Primer Sequence |
|---|---|---|---|
| SNP001 | SNP001-F | 168 | ACAAGTATGTTGCCATTCTGTGGA |
| SNP001 | SNP001-R | 169 | AGTTTCAAAGTTTGGAAGGGGAAAATAA |
| SNP002 | SNP002-F | 170 | CAAGGGATGAATCCATAGCTCAAAGC |
| SNP002 | SNP002-R | 171 | AGGCCCAGAGAGACATTAAAATGAGA |
| SNP003 | SNP003-F | 172 | CCCGGTAGGAATAAGGCAAGCC |
| SNP003 | SNP003-R | 173 | GTCCATCTTACCCTCCCGGAG |
| SNP004 | SNP004-F | 174 | TCCCTTAGTGCTTCAGGATTCTAGAG |
| SNP004 | SNP004-R | 175 | CTGTGACATCAGCTGAGGCAC |
| SNP005 | SNP005-F | 176 | GCTGTGTGGGGTGTGTGTGAG |
| SNP005 | SNP005-R | 177 | CTCGCACACACACAGCCTC |
| SNP006 | SNP006-F | 178 | ATGGGAGACTTCAACACCTCAC |
| SNP006 | SNP006-R | 179 | TGGATATCCTTGTTAACTTTCTGTCTCTATC |
| SNP007 | SNP007-F | 180 | ACAGACAACAAAAACTAAGTGTAGGTC |
| SNP007 | SNP007-R | 181 | TCATCACTCAGTCACCTCTATAAATTAAAATC |
| SNP008 | SNP008-F | 182 | CATGGATAATAATGATAAAACCTTATGGAATGC |
| SNP008 | SNP008-R | 183 | CCCTAATGCAGTCATCCGAGAATAC |
| SNP009 | SNP009-F | 184 | YTCCAAGCTCATCCATGCTGTC |
| SNP009 | SNP009-R | 185 | TGGATAAAGAAAATGTGAGAGATATATACAATGG |
| SNP010 | SNP010-F | 186 | TCCCAAATCCCTGCTTCATCTAACATATATTG |
| SNP010 | SNP010-R | 187 | GTCATATAATAAATATTGCTTTGTGTTCTATCTGG |
| SNP011 | SNP011-F | 188 | TGGGGCCAACCTAGTCATTTGC |
| SNP011 | SNP011-R | 189 | TGTGATTCATTTATATCAGAATCATCAGGGAG |
| SNP012 | SNP012-F | 190 | CTGGCCCAGTTACTTATTTTAGAAGTTATATTTG |
| SNP012 | SNP012-R | 191 | ACAGCTCATGCCAGGGCTC |
| SNP013 | SNP013-F | 192 | AGAAACTGTCACAGCAAGAGGAC |
| SNP013 | SNP013-R | 193 | TGCCATCCAGGACACCATATTAC |
| SNP014 | SNP014-F | 194 | CATCAGAGTGTTAGACAATAAGATGCAG |
| SNP014 | SNP014-R | 195 | GCCTGTCTTTGGTTAGCAGTGAG |
| SNP015 | SNP015-F | 196 | TTTGAGATGGAGTCTTGCCCTG |
| SNP015 | SNP015-R | 197 | GAGTTGAGATCACGCCACCG |
| SNP016 | SNP016-F | 198 | AAATTGGAGATTGCCCTCATTTGG |
| SNP016 | SNP016-R | 199 | TGAAATCACTGGACTAAGCACCC |
| SNP017 | SNP017-F | 200 | ATCCTCCAGCCTCCACCG |
| SNP017 | SNP017-R | 201 | GCAGGGCCTCCTCCTGAG |
| SNP018 | SNP018-F | 202 | TCTGGGCTGGTTCTGGCTG |
| SNP018 | SNP018-R | 203 | CACCCTCTGCAGCTCAAAGTC |
| SNP019 | SNP019-F | 204 | AGGCTAGAGATGTAGTCAGACCCTA |
| SNP019 | SNP019-R | 205 | CCATTAAAACCTGTTCCTGAGGTCT |

TABLE 3-continued

| Target | Primer Name | SEQ ID NO: | Primer Sequence |
|--------|-------------|------------|-----------------|

PlexForm primers selected (for the target sequences in TABLE 2)

| Target | Primer Name | SEQ ID NO: | Primer Sequence |
|--------|-------------|------------|-----------------|
| SNP020 | SNP020-F | 206 | GCTCTGGTTTAGCTCCCTACTC |
| SNP020 | SNP020-R | 207 | AGGTTCCCTTCCAAACTGACTC |
| SNP021 | SNP021-F | 208 | AGAYGACAGTCATGCTTCGATTTAAGT |
| SNP021 | SNP021-R | 209 | GGAACGAAGAACAACTTCCTCTAGGA |
| SNP022 | SNP022-F | 210 | TCACCCATTGGCTCCTAATGTG |
| SNP022 | SNP022-R | 211 | TGTTGAACGCTCACTGAGGTAG |
| SNP023 | SNP023-F | 212 | GTTCTGGAACTACTGGTATTTATTGCTG |
| SNP023 | SNP023-R | 213 | CTCTTTTAGGAGGACTTGTGCAATG |
| SNP024 | SNP024-F | 214 | GCTCAAGAGATCTGCCTGCCTC |
| SNP024 | SNP024-R | 215 | AAAGAATGCAGGCTCTGGGCAG |
| SNP025 | SNP025-F | 216 | AGTGGCGTGGTGGAAAGTTTC |
| SNP025 | SNP025-R | 217 | TCCCGCTGTCTCAGGCG |
| SNP026 | SNP026-F | 218 | CCTGGCCTTTGAGACTCCCTC |
| SNP026 | SNP026-R | 219 | TCCACAGCTGGGCTCAGAG |
| SNP027 | SNP027-F | 220 | CCACAGTAGAAAATGTGCCTGTGG |
| SNP027 | SNP027-R | 221 | TGCCGAGGGTTGTTCATCCTC |
| SNP028 | SNP028-F | 222 | GAGTTCTTTATTCYGTTTCATTGGTCTATGT |
| SNP028 | SNP028-R | 223 | CTTGGTAAAGAGTGAGACACTTTCAAAA |
| SNP029 | SNP029-F | 224 | ACATGAGATTTAGTGGGGACAGAG |
| SNP029 | SNP029-R | 225 | TGAAATTTGGAGGGGCTGGGG |
| SNP030 | SNP030-F | 226 | ACCAAAGGCAAAGAAGTTCAAAACT |
| SNP030 | SNP030-R | 227 | CAGCTCCTTTAAGCACTTTTCTGTAT |
| SNP031 | SNP031-F | 228 | GAAAGAATGTTACTTCTGTTAATATGAATAGCATG |
| SNP031 | SNP031-R | 229 | AGGTCAGGCTCCATATGGACC |
| SNP032 | SNP032-F | 230 | AAGATGGCTTCTGGAGTGCTAC |
| SNP032 | SNP032-R | 231 | TTGCCCTTTTCCTTCTAGCCTAC |
| SNP033 | SNP033-F | 232 | AGGAGCAAGCCATCACACTTGAC |
| SNP033 | SNP033-R | 233 | GCCTGGGCAACAAGAGTGAAAC |
| SNP034 | SNP034-F | 234 | AGCCTGGCCAGAATATCTGCG |
| SNP034 | SNP034-R | 235 | CCCCAATTATTGTCATCCTTCTCCC |
| SNP035 | SNP035-F | 236 | TGGGAATTTCAGACTATAGAAGCTCTC |
| SNP035 | SNP035-R | 237 | TGATGAGTTCTGATACAGTAACTAGTGGT |
| SNP036 | SNP036-F | 238 | AGGAGCAGTGACTCCACTCCAG |
| SNP036 | SNP036-R | 239 | CGCACGTCCTAAGCTGACAG |
| SNP037 | SNP037-F | 240 | ACAAGTTTACCGATGTAAAACCTTCAC |
| SNP037 | SNP037-R | 241 | GCTGCTCGTGGCCTATTTTTATG |
| SNP038 | SNP038-F | 242 | CAGCTGACACCCTCCTTGAATC |

TABLE 3-continued

PlexForm primers selected (for the target sequences in TABLE 2)

| Target | Primer Name | SEQ ID NO: | Primer Sequence |
|---|---|---|---|
| SNP038 | SNP038-R | 243 | TTTTCTAATGGGGCCAGGGAAG |
| SNP039 | SNP039-F | 244 | ATGTTGCTGCACTGTTCCCATG |
| SNP039 | SNP039-R | 245 | GAAAAAAGAATGCACGTSTGAGTTAC |
| SNP040 | SNP040-F | 246 | CCACAGGTCAAATGAGGCTCC |
| SNP040 | SNP040-R | 247 | GGATAAAAGCCACTCCTGTCCAG |
| SNP041 | SNP041-F | 248 | CCGGCCTCGTACGGTAATTC |
| SNP041 | SNP041-R | 249 | AGTTCGCCAGCTCCGAGAC |
| SNP042 | SNP042-F | 250 | TCCCTAACGCAATCCCTGTGAC |
| SNP042 | SNP042-R | 251 | GGATCTGTCTCTCCCCTTTACTCTTAG |
| SNP043 | SNP043-F | 252 | TTCAAGACCAGCCAGGATGAC |
| SNP043 | SNP043-R | 253 | CTGTGTGTCACCATTCACAGCTG |
| SNP044 | SNP044-F | 254 | TGTCCTTCACAGCTTAGATTCAATCTTTC |
| SNP044 | SNP044-R | 255 | GAGTCAGCCCAGAATCACACTC |
| SNP045 | SNP045-F | 256 | TGCCAGGCCTGAGGATCTTC |
| SNP045 | SNP045-R | 257 | TTCCCTAGGACCAGTGTACCATG |
| SNP046 | SNP046-F | 258 | AGACTTCAACAAATATGTGCTGTTGT |
| SNP046 | SNP046-R | 259 | TGTCAACCAGAGATAATAAAAACACAGGTA |
| SNP047 | SNP047-F | 260 | AGGCTGGTCTCAAACTCCTGAC |
| SNP047 | SNP047-R | 261 | ACCTGTAATCCCAGCACTTTGAGAG |
| SNP048 | SNP048-F | 262 | ACTTTGCATTCGTGCCACAATAG |
| SNP048 | SNP048-R | 263 | GGCTCCAAAGACCAAATGGAATG |
| SNP049 | SNP049-F | 264 | ATGAAAAATGTTTGAATATGATCTTTAGGGAC |
| SNP049 | SNP049-R | 265 | CATGTACAGAATTTATTGTTCCCATTTCATATAC |
| SNP050 | SNP050-F | 266 | CATCTAGGCCAGCCCTTCCC |
| SNP050 | SNP050-R | 267 | TACTTGAAGGTCCCCAGGCG |
| SNP051 | SNP051-F | 268 | AGAACCTATTGTGGATGTTAGGAGAG |
| SNP051 | SNP051-R | 269 | GGCTTCATCTCCCAGAGTCATTG |
| SNP052 | SNP052-F | 270 | ACAGTCAGCAGTAATCTCACATCTG |
| SNP052 | SNP052-R | 271 | GGGAAGAAGAAAGCATTGTTGTGAC |
| SNP053 | SNP053-F | 272 | ACAGAAAAGTTTTTACCACAGACTACCA |
| SNP053 | SNP053-R | 273 | TCTTGTTATGCAGATGAAGCCTCAA |
| SNP054 | SNP054-F | 274 | ACCTCAYACATTATGMAGCATAGGGTATC |
| SNP054 | SNP054-R | 275 | GGTGTACATGTATTTATGCCACCCC |
| SNP055 | SNP055-F | 276 | CCACATTCTGTCGTGGTTGAGAC |
| SNP055 | SNP055-R | 277 | CTCCTGACAGGACTCCACACC |
| SNP056 | SNP056-F | 278 | GGGAGCAGAGCTGAGTTTCTAAAC |
| SNP056 | SNP056-R | 279 | TCCTTCTGTGAAGTATCTCCAYATATGGATTTG |
| SNP057 | SNP057-F | 280 | AGTGCCTAATTGTTCACCCAGC |

TABLE 3-continued

| Target | Primer Name | SEQ ID NO: | Primer Sequence |
|---|---|---|---|
| | | | PlexForm primers selected (for the target sequences in TABLE 2) |
| SNP057 | SNP057-R | 281 | AVCAGTGAGGCTYTATAAATAAAATTAATTGTG |
| SNP058 | SNP058-F | 282 | GATCCCAGGGCTCCTTGAAGAG |
| SNP058 | SNP058-R | 283 | AAGAAATCCAACTGTGCAAGTGTG |
| SNP059 | SNP059-F | 284 | GTGTTCTAGAAGCCAAGCAAAGATG |
| SNP059 | SNP059-R | 285 | AGCAGCATTTGACACAGTTGATG |
| SNP060 | SNP060-F | 286 | GCCTTGTCCCCTGTATCCTTTC |
| SNP060 | SNP060-R | 287 | CCAGAAAAGGCAGTTAATAGAAGGC |
| SNP061 | SNP061-F | 288 | TTYTCTCCAATCTTAGTAACACAGCTGAC |
| SNP061 | SNP061-R | 289 | ACAAATATTTAGAAATCAAGTAGAAGTGAGATRC |
| SNP062 | SNP062-F | 290 | CCGTGATCCTTAAATAGCAGCACAG |
| SNP062 | SNP062-R | 291 | CTGGGGCCACATCAATCCACG |
| SNP063 | SNP063-F | 292 | CCTACGATCATAATCACAAGTACCTCG |
| SNP063 | SNP063-R | 293 | GCAAAGCTACCAGTCATGTGCC |
| SNP064 | SNP064-F | 294 | ACTCGCATGCACGTATATGTACAC |
| SNP064 | SNP064-R | 295 | CCTGTGACTTAAGACTTACAATAATTCTTCC |
| SNP065 | SNP065-F | 296 | ACTCCTCCCAGCAGTAGTAGATG |
| SNP065 | SNP065-R | 297 | TGCTGATCCTGGGAGTGCTG |
| SNP066 | SNP066-F | 298 | ACAATCAAGACTCATGCATTGCAAG |
| SNP066 | SNP066-R | 299 | ACTTCTCCCAATGAAGATCACTTAGG |
| SNP067 | SNP067-F | 300 | CCTTGGCTCACAGAGTCATCTC |
| SNP067 | SNP067-R | 301 | GCTTTGAGATGAGTACAGGGTGG |
| SNP068 | SNP068-F | 302 | CCTCCCCTATTGATGCACAGC |
| SNP068 | SNP068-R | 303 | TTCTGCGAGTATACTTATTTGCATTTGC |
| SNP069 | SNP069-F | 304 | CAAAATCTCTGCATTCTTACCCCATG |
| SNP069 | SNP069-R | 305 | AGATGCTTTCCAGTGGTAAAGGC |
| SNP070 | SNP070-F | 306 | CAAGATAGCCCAGCCAGCAG |
| SNP070 | SNP070-R | 307 | TGCAGAGCCCAGCATGTG |
| SNP071 | SNP071-F | 308 | GGGAGGGGGCAGGAAGC |
| SNP071 | SNP071-R | 309 | TCTAGGAGCTCATGTTTTCTGCTTAC |
| SNP072 | SNP072-F | 310 | TGTAGTCTTCAGTTATCAGGACAAGTATC |
| SNP072 | SNP072-R | 311 | TGTGCCAAYGAGTTCTCAAGG |
| SNP073 | SNP073-F | 312 | GAGGGCAGATCATGAGGTCAG |
| SNP073 | SNP073-R | 313 | ACGGGGTTTCACCATGTTGG |
| SNP074 | SNP074-F | 314 | AAGGAGGGAAAGGTGATGCATAC |
| SNP074 | SNP074-R | 315 | GGAGGGGCTGCGTGAAAATAAC |
| SNP075 | SNP075-F | 316 | TGCCAGTTCAATCCCCCATTT |
| SNP075 | SNP075-R | 317 | GGGCCTCCAGCACTGCT |

TABLE 3-continued

PlexForm primers selected (for the target sequences in TABLE 2)

| Target | Primer Name | SEQ ID NO: | Primer Sequence |
|---|---|---|---|
| SNP076 | SNP076-F | 318 | TTGTTCTTATAACCAGTGTGGAAAGTTAAC |
| SNP076 | SNP076-R | 319 | TCCTGTGTTGTGTGTTGACGTTAAG |
| SNP077 | SNP077-F | 320 | TGGGAGGGAATATGAAGCAGGAG |
| SNP077 | SNP077-R | 321 | CATCTGYCAGCTCCTCAGATTCC |
| SNP078 | SNP078-F | 322 | TCAATTAACCAKTCTCCTGTCCTCAA |
| SNP078 | SNP078-R | 323 | ACCATATTGTTCTTTATAAAACCCCAAAAGAA |
| SNP079 | SNP079-F | 324 | GGTGTGGCAGAGCAGGAAC |
| SNP079 | SNP079-R | 325 | GCCTGAGCTCCACTTTCACTTC |
| SNP080 | SNP080-F | 326 | TCTTGAAGCTTTTACCTCTATGCAAATAYG |
| SNP080 | SNP080-R | 327 | CGCCATCACAGTTAACCTTTCTTC |
| SNP081 | SNP081-F | 328 | GCCAGGACTCCAAATGAGCAAG |
| SNP081 | SNP081-R | 329 | CGCTCCTTATCCCAGGCAG |

The primers from TABLE 3 were synthesized and tested using NGS. TABLE 4 shows the number of total reads obtained on an Illumina sequencer, using the primers from TABLE 3. The data in TABLE 4 demonstrate even multiplexing in one reaction (average of 427, standard Deviation of 230).

TABLE 4

Number of total reads obtained on an Illumina sequencer (using the primers from TABLE 3)

| Target | PlexCall ™ Total Read # | Target | PlexCall ™ Total Read # | Target | PlexCall ™ Total Read # |
|---|---|---|---|---|---|
| SNP001 | 228.0 | SNP028 | 20.0 | SNP055 | 673.0 |
| SNP002 | 670.0 | SNP029 | 594.0 | SNP056 | 265.0 |
| SNP003 | 696.0 | SNP030 | 28.0 | SNP057 | 178.0 |
| SNP004 | 357.0 | SNP031 | 282.0 | SNP058 | 689.0 |
| SNP005 | 415.0 | SNP032 | 770.0 | SNP059 | 533.0 |
| SNP006 | 541.0 | SNP033 | 89.0 | SNP060 | 463.0 |
| SNP007 | 201.0 | SNP034 | 663.0 | SNP061 | 384.0 |
| SNP008 | 207.0 | SNP035 | 463.0 | SNP062 | 568.0 |
| SNP009 | 40.0 | SNP036 | 670.0 | SNP063 | 650.0 |
| SNP010 | 489.0 | SNP037 | 31.0 | SNP064 | 376.0 |
| SNP011 | 686.0 | SNP038 | 580.0 | SNP065 | 692.0 |
| SNP012 | 566.0 | SNP039 | 569.0 | SNP066 | 162.0 |
| SNP013 | 579.0 | SNP040 | 107.0 | SNP067 | 625.0 |
| SNP014 | 665.0 | SNP041 | 80.0 | SNP068 | 390.0 |
| SNP015 | 591.0 | SNP042 | 723.0 | SNP069 | 754.0 |
| SNP016 | 837.0 | SNP043 | 524.0 | SNP070 | 314.0 |
| SNP017 | 217.0 | SNP044 | 591.0 | SNP071 | 499.0 |
| SNP018 | 363.0 | SNP045 | 674.0 | SNP072 | 223.0 |
| SNP019 | 89.0 | SNP046 | 264.0 | SNP073 | 48.0 |
| SNP020 | 702.0 | SNP047 | 36.0 | SNP074 | 83.0 |
| SNP021 | 165.0 | SNP048 | 282.0 | SNP075 | 370.0 |
| SNP022 | 626.0 | SNP049 | 262.0 | SNP076 | 396.0 |
| SNP023 | 628.0 | SNP050 | 722.0 | SNP077 | 521.0 |
| SNP024 | 476.0 | SNP051 | 669.0 | SNP078 | 104.0 |
| SNP025 | 494.0 | SNP052 | 596.0 | SNP079 | 706.0 |
| SNP026 | 522.0 | SNP053 | 175.0 | SNP080 | 143.0 |
| SNP027 | 245.0 | SNP054 | 589.0 | SNP081 | 461.0 |

Example 12: Method for Equalization of Reads Using Anti-Sense Oligos

Due at least in part to differences in amplification efficiency, some sequence elements tend to be over-represented in multiplex amplification. This phenomenon reduces the dynamic range and accuracy of sequencing and genotyping based on NGS.

Described herein is a method for equalization of reads using anti-sense oligos in various concentrations to inhibit high-performing amplicons from forming and thereby allow poorer performing amplicons to produce more data. Anti-sense oligos can be produced with reversible binding characteristics using complementary sequences (e.g., attenuator oligos). Also described herein is a method for performing multiplex PCR that results in even reads produced by NGS instruments for each amplicon (for 2-10,000 amplicons) and each sample (for 1-100,000 DNA samples).

Figure 2:
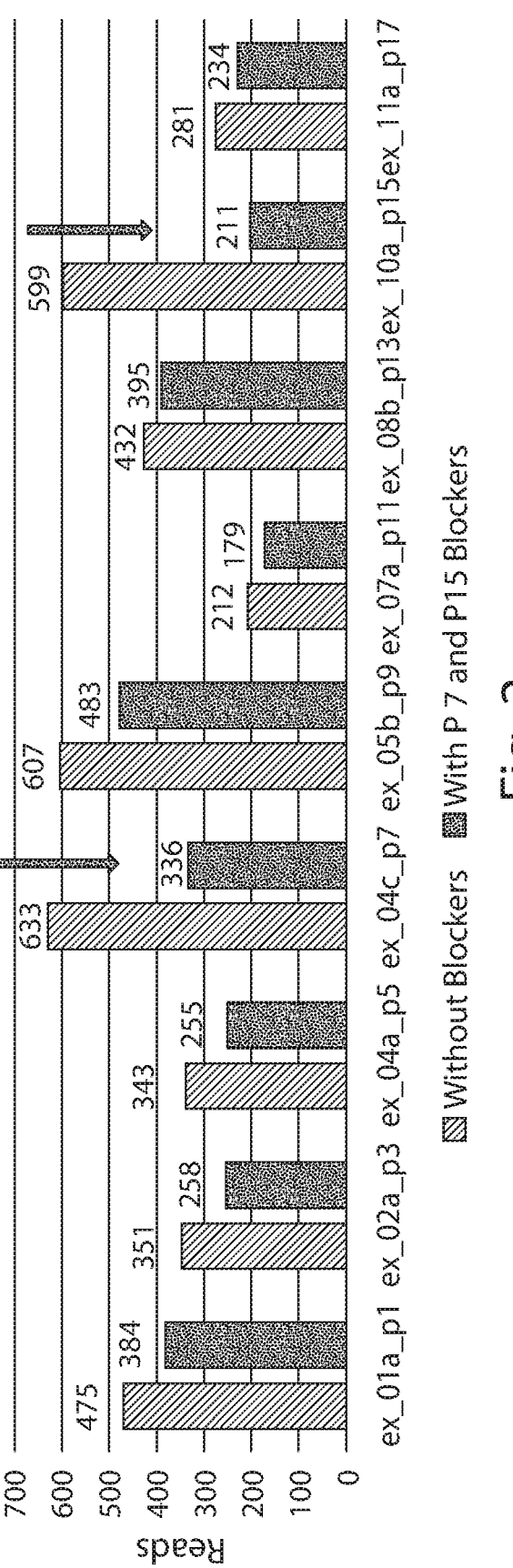
FIG. 2 is a bar graph showing a decrease in variance in read numbers in TP53 sequencing multiplex by addition of blockers to p7 and p15.

An exemplary process for equalization of reads is as follows: A) Initial multiplex is analyzed on a control sample and reads for each amplicon in the mix are obtained from PlexCall™ software; B) Anti-sense oligos targeting highly represented or over-represented amplicons in the reaction are added at a concentration needed to equalize number of reads for each amplicon (or target); and steps (A) and (B) are repeated as needed to improve evenness of assay. Amplicons that are represented at more than 2-fold greater than the average or median abundance for a set of amplicons can be targeted for reduction by anti-sense oligos. In one embodiment, the evenness of amplification and subsequent NGS reads can be improved by iteratively adding anti-sense oligos to reduce those amplicons with the highest representations until even reads are achieved. By "even reads" in this regard is meant that either the representation of all sequences is within 50% higher or lower relative to all others in a multiplex reaction. As a non-limiting example, see e.g., FIG. 2, which shows a decrease in variance in read numbers in TP53 sequencing multiplex by addition of blockers (e.g., anti-sense oligos) to targets p7 and p15.

Example 13: Barcode Primer Design

Described herein is a non-limiting example of barcode primer design. As a non-limiting example, two sets of 144 barcodes with a length of 10 bases each are used in every possible combination (20,736 combinations or 144$^2$), which allows for simultaneous analysis of 20,736 sample DNAs. These 10-base barcodes can be incorporated into custom Illumina™ primers for IS and 17. These 10-base barcodes can also be used in-line with other platforms such as Ion Torrent™. A combination of in-line and 15/17 barcodes on the Illumina™ platform can be used for greater than 100,000 samples in the same sequencing run.

Figure 5:
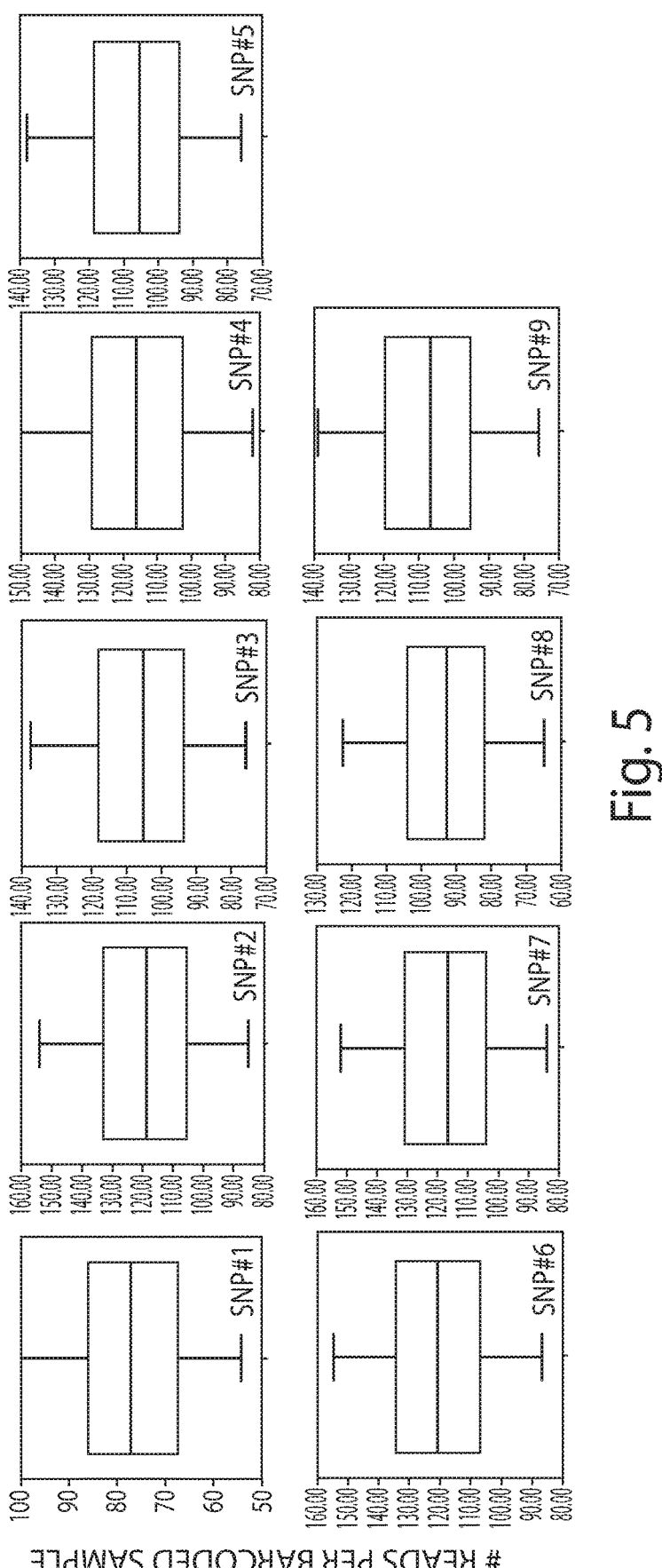
FIG. 5 is a series of box plots showing control DNA analysis of 9 multiplexed amplicons barcoded in 20,682 PlexSeg™ reactions and analyzed simultaneously on one NGS run. Box plots demonstrate even amplification across amplicon targets and 20,682 samples based on read depth (on Y-axis).

A non-limiting example showing barcode primer design is shown in FIG. 5. Control DNA was analyzed on 9 multiplexed amplicons barcoded in 20,682 PlexSeq™ reactions and analyzed simultaneously on one NGS run. Box plots demonstrate even amplification across amplicon targets and 20,682 samples based on read depth (see e.g., FIG. 5).

Example 14: PCR Amplification Method

Figure 3:
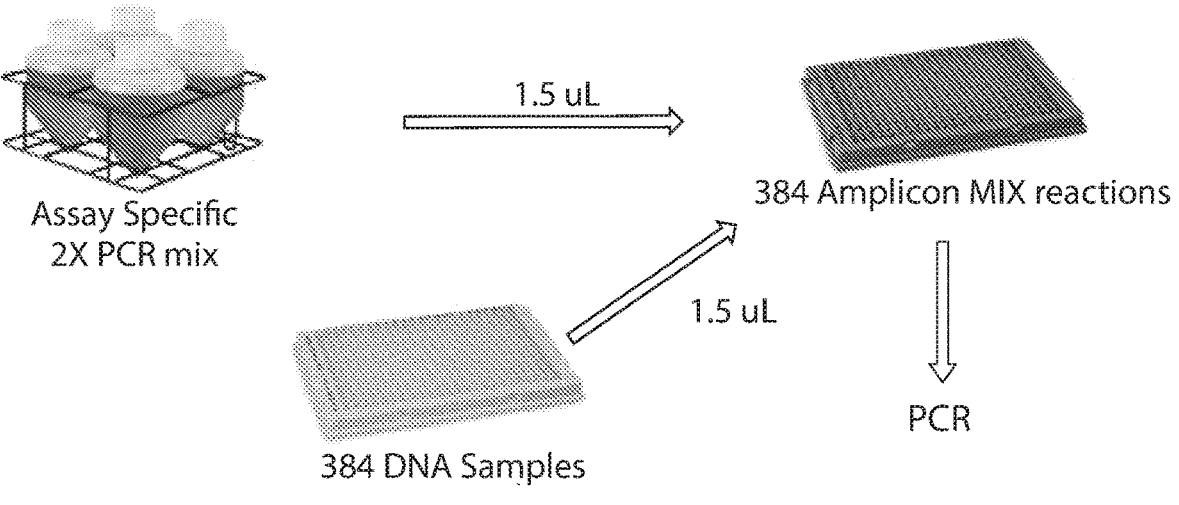
FIG. 3 is a schematic showing primary amplification using a 2×PCR mix and DNA samples.

Described herein is a non-limiting example of a PCR amplification method. A primary amplification with the primer mix designed by PlexForm™ that are extended with a tail sequence on the 5' end is first performed on each DNA sample using standard PCR conditions (see e.g., FIG. 3).

Figure 4:
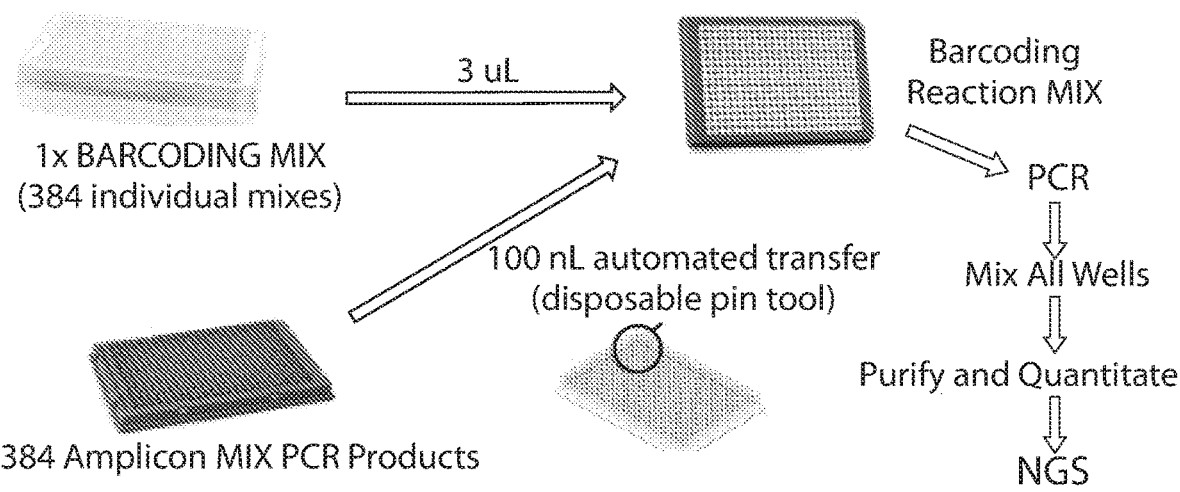
FIG. 4 is a schematic showing secondary amplification and barcoding reaction mixing, cleanup and NGS run.

A universal secondary amplification is then performed using primers and the primary amplification as the source. 100 nanoliters are transferred from primary to secondary reaction via a disposable plastic pintool (see e.g., FIG. 4). All secondary amplicons are mixed and loaded onto a Next Generation Sequencer.

Example 15: Single Base Sequencing

Described herein is a non-limiting example of single base sequencing. A variation of PlexSeg™ allows single base multiplexed sequencing on an NGS platform in order to avoid sequencing additional regions when this is beneficial. When data is needed for only one base pair, special primers are designed. An additional set of random bases are added to the 5' end of the primers used in the primary amplification such that all are of length N. The sequencer is set to sequence only N+1 thus insuring that no additional sequence except the target base is analyzed. Single base sequencing can be performed with the procedures of any one of or any combination of Examples 1-14.

Example 16: PlexCall™

Figure 6:
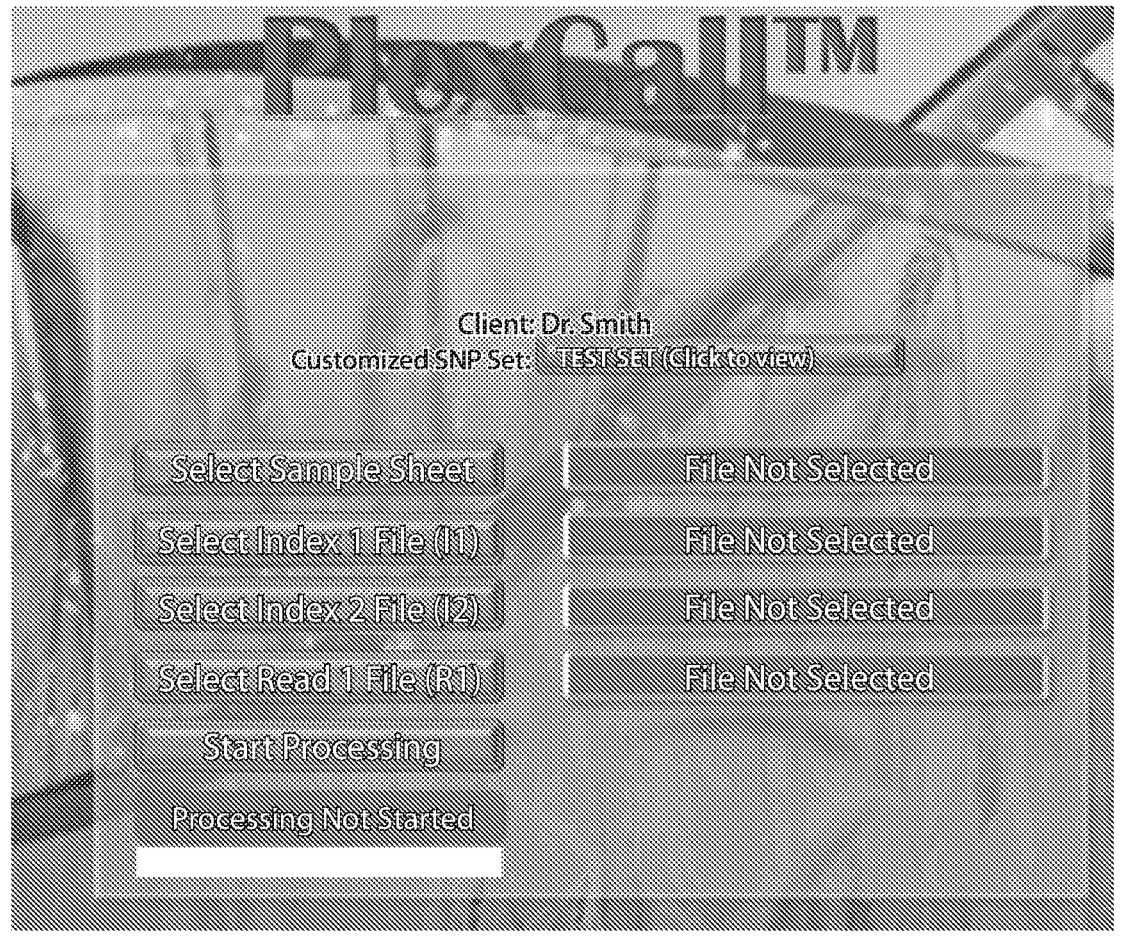
FIG. 6 is an image showing the PlexCall™ front-end, demonstrating simplicity of selecting output files from sequencer and simple sample sheet indicating locations to correlate with barcode positions for analysis.

Described herein is a method to rapidly analyze PlexSeg™ data using personalized PlexCall™ software to automatically provide genotype or sequencing results. As a non-limiting example, a PlexSeg™ experiment is run on a sequencer, and direct analysis is performed automatically. PlexCall™ provides automatic calling of genotypes and allele ratios. PlexCall™ is personalized for each experiment and includes all barcode and SNP information. PlexCall™ can provide information on primer dimer composition to assist with refinement of assay during development. FIG. 6 shows the front-end screen of PlexCall™, demonstrating simplicity of selecting output files from sequencer and simple sample sheet indicating locations to correlate with barcode positions for analysis.

Described herein is a non-limiting example of using PlexCall™ to analyze PlexSeg™ data, using an exemplary set of SNPs (e.g., SMITH_1, SMITH_2, SMITH_3, SMITH 4, SMITH_5), which each comprise 2 alleles.

TABLE 5 shows the specific nucleotides for Allele 1 and Allele 2 for each of the SMITH SNPs. In TABLE 6, the allele ratio output from PlexCall™ demonstrates simple allele counts for easy determination of genotype. TABLE 7 shows the final genotype call output from PlexCall™, using the information from TABLE 5 and TABLE 6.

TABLE 5

Alleles for the SMITH SNPs

| SNP name | SMITH_1 | SMITH_2 | SMITH_3 | SMITH_4 | SMITH_5 |
|---|---|---|---|---|---|
| PROJECT | Dr. Smith | Dr. Smith | Dr. Smith | Dr. Smith | Dr. Smith |
| Allele_1 | C | T | C | A | C |
| Allele_2 | G | C | T | T | T |

TABLE 6

Allele ratio output from PlexCall ™

| Sample Name | Index Plate Number | Well Position | SMITH_1 Allele_1/ Allele_2 | SMITH_2 Allele_1/ Allele_2 | SMITH_3 Allele_1/ Allele_2 | SMITH_4 Allele_1/ Allele_2 | SMITH_5 Allele_1/ Allele_2 |
|---|---|---|---|---|---|---|---|
| SAMPLE_1 | PL001 | A01 | 0/313 | 289/0 | 0/206 | 261/0 | 253/0 |
| SAMPLE_2 | PL001 | B01 | 0/262 | 255/0 | 0/179 | 268/0 | 235/0 |
| SAMPLE_3 | PL001 | C01 | 0/295 | 248/0 | 90/80 | 0/253 | 230/0 |
| SAMPLE_4 | PL001 | D01 | 0/301 | 244/0 | 134/110 | 0/230 | 263/0 |
| SAMPLE_5 | PL001 | E01 | 0/446 | 329/0 | 275/0 | 0/357 | 0/251 |
| SAMPLE_6 | PL001 | F01 | 0/285 | 0/246 | 126/140 | 213/0 | 236/0 |
| SAMPLE_7 | PL001 | G01 | 0/295 | 0/243 | 106/0 | 0/249 | 233/0 |
| SAMPLE_8 | PL001 | H01 | 0/363 | 284/0 | 170/0 | 0/280 | 223/0 |
| SAMPLE_9 | PL001 | A02 | 0/251 | 0/154 | 94/0 | 211/200 | 194/0 |
| SAMPLE_10 | PL001 | B02 | 0/317 | 207/0 | 130/0 | 240/220 | 215/0 |

TABLE 7

| | Index | | SMITH_1 | SMITH_2 | SMITH_3 | SMITH_4 | SMITH_5 |
| Sample | Plate | Well | Allele_1/ | Allele_1/ | Allele_1/ | Allele_1/ | Allele_1/ |
| Name | Number | Position | Allele_2 | Allele_2 | Allele_2 | Allele_2 | Allele_2 |
|---|---|---|---|---|---|---|---|
| SAMPLE_1 | PL001 | A01 | G | T | T | A | C |
| SAMPLE_2 | PL001 | B01 | G | T | T | A | C |
| SAMPLE_3 | PL001 | C01 | G | T | C/T | T | C |
| SAMPLE_4 | PL001 | D01 | G | T | C/T | T | C |
| SAMPLE_5 | PL001 | E01 | G | T | C | T | T |
| SAMPLE_6 | PL001 | F01 | G | C | C/T | A | C |
| SAMPLE_7 | PL001 | G01 | G | C | C | T | C |
| SAMPLE_8 | PL001 | H01 | G | T | C | T | C |
| SAMPLE_9 | PL001 | A02 | G | C | C | A/T | C |
| SAMPLE_10 | PL001 | B02 | G | T | C | A/T | C |

Final genotype call output from PlexCall ™

Example 17: Identification and Quantification of Low Abundance Rare Variants As described herein, PlexSeg™ methodology can be used to identify and quantify low abundance rare variants in clinically relevant genes in a minority of tumor cells from a complex mixture of cells.

Figure 7:
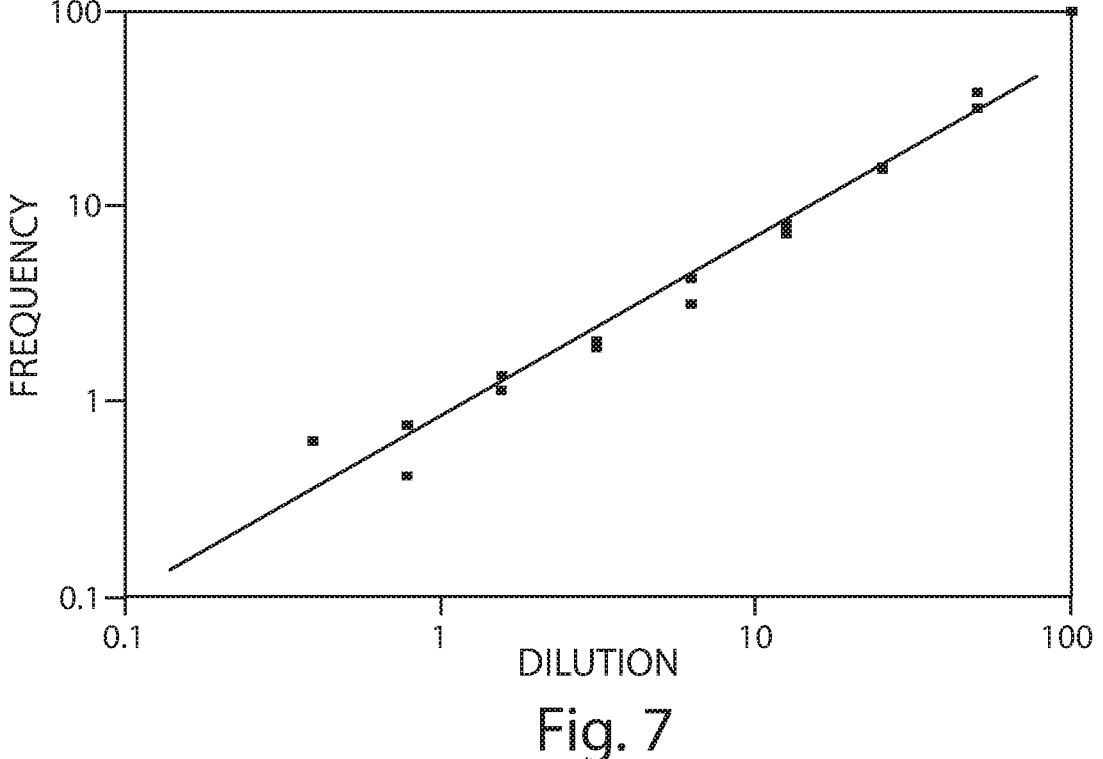
FIG. 7 is a scatterplot showing mutation frequency versus fold dilution from data in TABLE 4, demonstrating sensitivity of assay down to 1% or lower.

As a non-limiting example, TP53 analysis of the Arg273Cys mutation was performed in triplicate from a serial dilution of wild type DNA spiked with mutant DNA extracted from a cell line containing the mutation. TABLE 8 shows that the frequency of sequencing reads containing the Arg273Cys mutation is directly proportional to the amount of mutant DNA material present in the dilution series. The data from TABLE 8 is graphed in FIG. 7. As shown in FIG. 7, this process is linear down to 1% or lower.

quency is used to determine the percent of tumor cells in the sample.

Such a method can be applied to the detection of cells collected from blood, urine, other body fluids, or an organ biopsy. Such a method can be applied to the detection of minimal residual disease immediately post-surgery or therapy. Such a method can be applied to follow-up weekly, monthly or yearly to determine success of therapy and track disease recurrence.

Example 18: Exemplary Primer Set #2

PlexForm™ software can be used for primer design that allows for large amplicon number multiplexing. Included herein is an exemplary primer set designed by PlexForm'

TABLE 8

TP53 analysis of Arg273Cys mutation

| Object Label | DILUTION | FREQUENCY | MUTANT READS | TOTAL READS |
|---|---|---|---|---|
| CLINE-001-R0 | 100.00 | 99.14 | 1,720.00 | 1,735.00 |
| CLINE-001-R1 | 100.00 | 99.18 | 1,940.00 | 1,956.00 |
| CLINE-001-R2 | 100.00 | 99.21 | 2,005.00 | 2,021.00 |
| CLINE-002-R0 | 50.00 | 38.88 | 666.00 | 1,713.00 |
| CLINE-002-R1 | 50.00 | 32.04 | 837.00 | 2,612.00 |
| CLINE-002-R2 | 50.00 | 36.73 | 926.00 | 2,521.00 |
| CLINE-004-R0 | 25.00 | 15.47 | 318.00 | 2,056.00 |
| CLINE-004-R1 | 25.00 | 16.09 | 398.00 | 2,473.00 |
| CLINE-004-R2 | 25.00 | 15.08 | 409.00 | 2,713.00 |
| CLINE-008-R0 | 12.50 | 7.04 | 124.00 | 1,762.00 |
| CLINE-008-R1 | 12.50 | 8.20 | 170.00 | 2,074.00 |
| CLINE-008-R2 | 12.50 | 7.56 | 182.00 | 2,409.00 |
| CLINE-016-R0 | 6.25 | 4.13 | 75.00 | 1,815.00 |
| CLINE-016-R1 | 6.25 | 4.32 | 113.00 | 2,617.00 |
| CLINE-016-R2 | 6.25 | 3.09 | 77.00 | 2,493.00 |
| CLINE-032-R0 | 3.12 | 1.89 | 35.00 | 1,848.00 |
| CLINE-032-R1 | 3.12 | 1.88 | 44.00 | 2,337.00 |
| CLINE-032-R2 | 3.12 | 2.06 | 50.00 | 2,430.00 |
| CLINE-064-R0 | 1.56 | 1.13 | 21.00 | 1,855.00 |
| CLINE-064-R1 | 1.56 | 1.35 | 33.00 | 2,436.00 |
| CLINE-128-R0 | 0.78 | 0.76 | 14.00 | 1,838.00 |
| CLINE-128-R1 | 0.78 | 0.42 | 11.00 | 2,635.00 |
| CLINE-256-R2 | 0.39 | 0.63 | 15.00 | 2,381.00 |

As an example, the following method can be followed to identify and quantify low abundance rare variants, especially with regards to cancer variants. PlexSeg™ analysis is performed in triplicate on sets of clinical genes of interest. The mutant alleles are quantified. The mutant allele fresoftware for SNP targets from the tomato plant, *Solanum lycopersicum* (see e.g., TABLE 9). TABLE 9 shows the input allelic target sequences for 300 SNP regions (e.g., SNP100-SNP399), comprising SEQ ID NOs: 330-929. SNP position indicated by bolded letters in TABLE 9.

TABLE 9

| | | | |
|---|---|---|---|
| | | | Input target sequences for 300 SNP regions |

| Target | Allele # | SEQ ID NO: | Target Sequence |
|---|---|---|---|
| SNP100 | 1 | 330 | ACAATATACTCAGTGTATTAGAAGTGTGGCCTGGAGAGGGTAGGATGTACACGACCTTACCTCTACCTTTGAAGGGTGGAGAGGTTGTTTCCGATAGACCC |
| SNP100 | 2 | 331 | ACAATATACTCAGTGTATTAGAAGTGTGGCCTGGAGAGGGTAGGATGTACGCGACCTTACCTCTACCTTTGAAGGGTGGAGAGGTTGTTTCCGATAGACCC |
| SNP101 | 1 | 332 | TGAATTCGGATAATGGATCTGTTGTACTTCTTTCTTGCAGCTTTTGCCTGTTTTTCACGAAAAGATTTAGGAATCAATAATTTCGACTCCTCTAGTTTCTT |
| SNP101 | 2 | 333 | TGAATTCGGATAATGGATCTGTTGTACTTCTTTCTTGCAGCTTTTGCCTGCTTTTCACGAAAAGATTTAGGAATCAATAATTTCGACTCCTCTAGTTTCTT |
| SNP102 | 1 | 334 | TGTTTCTAAGTGATTGTGGAGGAAAAAGATACCCTTTGTTGCAACATCCAATTGCGCCAGATGGACCAGTTCTTTTTTTGCCATTTTTGAAGGGATGCAAG |
| SNP102 | 2 | 335 | TGTTTCTAAGTGATTGTGGAGGAAAAAGATACCCTTTGTTGCAACATCCAGTTGCGCCAGATGGACCAGTTCTTTTTTTGCCATTTTTGAAGGGATGCAAG |
| SNP103 | 1 | 336 | TCTCTGTTGCATTTGTAGATGGTGGTGAGGCTGGAAATGTAATCCCTGAAAGTGTGAAGTTTGGTGGAACATTCCGGTTCTTGACGTTTGAGGGTCATTCC |
| SNP103 | 2 | 337 | TCTCTGTTGCATTTGTAGATGGTGGTGAGGCTGGAAATGTAATCCCTGAAGGTGTGAAGTTTGGTGGAACATTCCGGTTCTTGACGTTTGAGGGTCATTCC |
| SNP104 | 1 | 338 | GGTGAGAAAGTTGCGGAGCCACTATACAAGATGGAGGCTGGTAAGACGTATAGGTATAGATTTTGCAATGTAGGTATGAGGACATCAGTGAATGTTAGGAT |
| SNP104 | 2 | 339 | GGTGAGAAAGTTGCGGAGCCACTATACAAGATGGAGGCTGGTAAGACGTACAGGTATAGATTTTGCAATGTAGGTATGAGGACATCAGTGAATGTTAGGAT |
| SNP105 | 1 | 340 | TTTGTTCTATCTCTTCGCGTAACATTTGTGTCCAACGAAATCTTTTTGCCTCGCCACTTAAAAAGCCAAGCTATCATTGTACTGTTGTCTGTCTTGCGCTT |
| SNP105 | 2 | 341 | TTTGTTCTATCTCTTCGCGTAACATTTGTGTCCAACGAAATCTTTTTGCCGCGCCACTTAAAAAGCCAAGCTATCATTGTACTGTTGTCTGTCTTGCGCTT |
| SNP106 | 1 | 342 | TTACCGATATGTCAGACAGTAAGATGGAGAATTTTGTTCCTGCTTATGAAATCGTCAAATTTTACCTGTTTTTCGAGAAATGGAGGCGTGGAGAGATAGAG |
| SNP106 | 2 | 343 | TTACCGATATGTCAGACAGTAAGATGGAGAATTTTGTTCCTGCTTATGAATTCGTCAAATTTTACCTGTTTTTCGAGAAATGGAGGCGTGGAGAGATAGAG |
| SNP107 | 1 | 344 | TTTGACGCGGAAAAGTGAAGATAGCCTCCAAGCATTTCAATGCCGTCTCCACTTTTGCTTGGAGTGAGATTACCCCCGAACATAAGAAGAGAATAATCGGA |
| SNP107 | 2 | 345 | TTTGACGCGGAAAAGTGAAGATAGCCTCCAAGCATTTCAATGCCGTCTCCTCTTTTGCTTGGAGTGAGATTACCCCCGAACATAAGAAGAGAATAATCGGA |
| SNP108 | 1 | 346 | GGAGGTAGCAATAACAACAACAACAACAACGGGGCCCACCACCACCATCATCAGAACCAGTTTGATAACAATAACAACAACAACCTCATTGGCTCGTC |
| SNP108 | 2 | 347 | GGAGGTAGCAATAACAACAACAACAACAACGGGGCCCACCACCACCACCATCAGAACCAGTTTGATAACAATAACAACAACAACCTCATTGGCTCGTC |
| SNP109 | 1 | 348 | ATGCCCAGCCCATTGAACAGCATGGCAATGCTGTGGCAATGAAATCTGAAATCACTGACGCAATGATGGAAATTCCTGCTAAGGCTGTGCTAGTCAGTCC |
| SNP109 | 2 | 349 | ATGCCCAGCCCATTGAACAGCATGGCAATGCTGTGGCAATGAAATCTGAAGTCACTGACGCAATGATGGAAATTCCTGCTAAGGCTGTGCTAGTCAGTCCC |
| SNP110 | 1 | 350 | CCTTTATTTGTGTGATTATTTTATGGTTTTCAATTAGGTCTCATGATGCCAATGAGTTATGGATATTACTGANGCTTTGTGATTAGGTAAAGGTGATCACACTTTGTCAATCAAGAGACAAGGATGGCGAAGATGGTAATAAAAGCAACCATTTCTTTTTTCGAGTGCTTTCTTCCAGTTTAGATTATAAAAGTTCCTCTT |
| SNP110 | 2 | 351 | CCTTTATTTGTGTGATTATTTTATGGTTTTCAATTAGGTCTCATGATGCCAATGAGTTATGGATATTACTGANGCTTTGTGATTAGGTAAAGGTGATCACTCTTTGTCAATCAAGAGACAAGGATGGCGAAGATGGTAATAAAAGCAACCATTTCTTTTTTCGAGTGCTTTCTTCCAGTTTAGATTATAAAAGTTCCTCTT |
| SNP111 | 1 | 352 | AATCGTTGTACATGCTATATTTTCGCTTGTGCCTCTTCTCCCATGGACTTAGAAAGTATGTTTTTGCTAGTGTAAGAGGAATGCAACGGGATCGTTTCGTT |
| SNP111 | 2 | 353 | AATCGTTGTACATGCTATATTTTCGCTTGTGCCTCTTCTCCCATGGACTTGGAAAGTATGTTTTTGCTAGTGTAAGAGGAATGCAACGGGATCGTTTCGTT |

TABLE 9-continued

| | | | |
|---|---|---|---|
| | | Input target sequences for 300 SNP regions | |

| Target | Allele # | SEQ ID NO: | Target Sequence |
|---|---|---|---|
| SNP112 | 1 | 354 | CAAATGCATGTAATTTGCAGAAACAACTGCATCCACTGAAGCTCTATTACTGATACAGAAATATTAGGGGTAGAGAATATTCCAGTATTAATTAAATTGAC |
| SNP112 | 2 | 355 | CAAATGCATGTAATTTGCAGAAACAACTGCATCCACTGAAGCTCTATTACCGATACAGAAATATTAGGGGTAGAGAATATTCCAGTATTAATTAAATTGAC |
| SNP113 | 1 | 356 | GATGATATCGGTCGTCTCATGGATGATGATATCTCTAAGGTTTCTTCTGTTCTCTCTGTTTCCAGAACTGATGCATCTGCTTTACTCCGTCGGTATAACTG |
| SNP113 | 2 | 357 | GATGATATCGGTCGTCTCATGGATGATGATATCTCTAAGGTTTCTTCTGTCCTCTCTGTTTCCAGAACTGATGCATCTGCTTTACTCCGTCGGTATAACTG |
| SNP114 | 1 | 358 | TCAAGCGCTGAACTTCTTGCCACCTTCTGTGACAACATTCTCAAAAAAGGAGGGAGTGAGAAATTGAGTGATGAAGCTATTGAAGAAACGTTGGAAAAGGT |
| SNP114 | 2 | 359 | TCAAGCGCTGAACTTCTTGCCACCTTCTGTGACAACATTCTCAAAAAAGGCGGGAGTGAGAAATTGAGTGATGAAGCTATTGAAGAAACGTTGGAAAAGGT |
| SNP115 | 1 | 360 | CAAAATTTGGGAGAGCTGAAGCAGAGTTTCCCACTCAAGGTAAATGTATATAGCTAGTCAAAAGTATGCCAGTTGTGTCCTGTTGCTTGTGTATATAGTTC |
| SNP115 | 2 | 361 | CAAAATTTGGGAGAGCTGAAGCAGAGTTTCCCACTCAAGGTAAATGTATAGAGCTAGTCAAAAGTATGCCAGTTGTGTCCTGTTGCTTGTGTATATAGTTC |
| SNP116 | 1 | 362 | GTAGAGTTATGTTGGTGGAAGGAAGTACAGAGAAGAAGCATAGAGATGTTTGAGAATTGGGTGGGAGATTGTTTTTTCCAGAGCTCCAACTATATGATATA |
| SNP116 | 2 | 363 | GTAGAGTTATGTTGGTGGAAGGAAGTACAGAGAAGAAGCATAGAGATGTTCGAGAATTGGGTGGGAGATTGTTTTTTCCAGAGCTCCAACTATATGATATA |
| SNP117 | 1 | 364 | CTGCTTTGGCTTTTCCTCTACAACAGGAACATCGTCAACACCTTGAAAACTTGTGTCTGTGGAGGAACTATTTTCGCCAGAAATCTGAATGATCTGCTTCA |
| SNP117 | 2 | 365 | CTGCTTTGGCTTTTCCTCTACAACAGGAACATCGTCAACACCTTGAAAACCTGTGTCTGTGGAGGAACTATTTTCGCCAGAAATCTGAATGATCTGCTTCA |
| SNP118 | 1 | 366 | GTACTGGTTTTGGTTTAAAAAAATGAAGACATCAATGATTGACAGTGCTCATCCTACTATCATGCTCATTACCAGGGTGGGAAGAAGCTCCTATCATCAGA |
| SNP118 | 2 | 367 | GTACTGGTTTTGGTTTAAAAAAATGAAGACATCAATGATTGACAGTGCTCGTCCTACTATCATGCTCATTACCAGGGTGGGAAGAAGCTCCTATCATCAGA |
| SNP119 | 1 | 368 | GTGAAATTGCACTGTTTCCCCTTTCATCTTGAGGGAGCTCACATGCTTCATTTATAGACCCCGATTTCAGATCAGCTGGTGGGATGAAGCAGTCTACTGAT |
| SNP119 | 2 | 369 | GTGAAATTGCACTGTTTCCCCTTTCATCTTGAGGGAGCTCACATGCTTCACTTATAGACCCCGATTTCAGATCAGCTGGTGGGATGAAGCAGTCTACTGAT |
| SNP120 | 1 | 370 | TAAGTTTTTGACTCTATTAACTCTGTGTGGCCTGACAATGTAATTTGTCTTAGCTAGAGAAAAGTTCAGTCAGAAAATAAATTTCCCATCTCTCTCATTGT |
| SNP120 | 2 | 371 | TAAGTTTTTGACTCTATTAACTCTGTGTGGCCTGACAATGTAATTTGTCTCAGCTAGAGAAAAGTTCAGTCAGAAAATAAATTTCCCATCTCTCTCATTGT |
| SNP121 | 1 | 372 | AATAAAATGGTGAAATGGTGTCCAAGTATCCCTCATTGTGGGAATGCTATACGAGTAGAGACCGATGAGTTCTGTGAAGTAGAATGTTCATGTGGTTTACA |
| SNP121 | 2 | 373 | AATAAAATGGTGAAATGGTGTCCAAGTATCCCTCATTGTGGGAATGCTATTCGAGTAGAGACCGATGAGTTCTGTGAAGTAGAATGTTCATGTGGTTTACA |
| SNP122 | 1 | 374 | TACATTGACAATGGCAATTTGGAGCAATGGCTACACGGTGATGTAGGGTCAGTTAGTCCTCTAACTTGGGAAATCAGACTGAGAATTGCAATTGGAACTGC |
| SNP122 | 2 | 375 | TACATTGACAATGGCAATTTGGAGCAATGGCTACACGGTGATGTAGGGTCTGTTAGTCCTCTAACTTGGGAAATCAGACTGAGAATTGCAATTGGAACTGC |
| SNP123 | 1 | 376 | GGAGACACTGTGAAGAGAATATGATGAGAGGAGTGCTCCGGAAACTTGGGTCGATATGCACATTGACATTATTTGCTAGAGCATTCACATGCACTTGGCAT |
| SNP123 | 2 | 377 | GGAGACACTGTGAAGAGAATATGATGAGAGGAGTGCTCCGGAAACTTGGGGCGATATGCACATTGACATTATTTGCTAGAGCATTCACATGCACTTGGCAT |
| SNP124 | 1 | 378 | GTATGCAGCTCACAACTACTAAACGGTCAATTTTAAGTGAGCATAGTGCCATTGCCAATTCCCATTTCTCTAAATATCAAACCAGAAAACATATTTAACGT |

TABLE 9-continued

| | | | |
|---|---|---|---|
| | | | Input target sequences for 300 SNP regions |

| Target | Allele # | SEQ ID NO: | Target Sequence |
|---|---|---|---|
| SNP124 | 2 | 379 | GTATGCAGCTCACAACTACTAAACGGTCAATTTTAAGTGAGCATAGTGCCGT<br>TGCCAATTCCCATTTCTCTAAATATCAAACCAGAAAACATATTTAACGT |
| SNP125 | 1 | 380 | GAGGAACATAAACCACTGAAGCATTAGCCTTTGTCTCTACTTTTGCCTCTACA<br>ACAGTATTAAAAACAGGTAGCCCCAAATGTTCTGTTCCACCCTTCTTG |
| SNP125 | 2 | 381 | GAGGAACATAAACCACTGAAGCATTAGCCTTTGTCTCTACTTTTGCCTCTGCA<br>ACAGTATTAAAAACAGGTAGCCCCAAATGTTCTGTTCCACCCTTCTTG |
| SNP126 | 1 | 382 | CCTCTTTGAAAATGTTTAAGATCTCGGCGAGCTTGGTGACCTCTAAAACAACT<br>TTGAACACATAAGATGCCATGGAGAGTGCGATTTCTTGTATCTTCAAG |
| SNP126 | 2 | 383 | CCTCTTTGAAAATGTTTAAGATCTCGGCGAGCTTGGTGACCTCTAAAACAGC<br>TTTGAACACATAAGATGCCATGGAGAGTGCGATTTCTTGTATCTTCAAG |
| SNP127 | 1 | 384 | TCAGCTTATTGGTGATTCCTGTTCATAGATTTGGCTGTATTTTATGTCTTCTAT<br>TGCCTTAAATTCGTGTATGGACTATAAAAAACTGATTGTTTGTTGGA |
| SNP127 | 2 | 385 | TCAGCTTATTGGTGATTCCTGTTCATAGATTTGGCTGTATTTTATGTCTTGTAT<br>TGCCTTAAATTCGTGTATGGACTATAAAAAACTGATTGTTTGTTGGA |
| SNP128 | 1 | 386 | AACGATAATCTTCTTACTTCTTCAATAAACCTCAGGAATTCTTTGGAGAATGG<br>GACGCCATTGACGTTGATTCCGATGATGATAGCCATGGCTCCTTGAAT |
| SNP128 | 2 | 387 | AACGATAATCTTCTTACTTCTTCAATAAACCTCAGGAATTCTTTGGAGAACGG<br>GACGCCATTGACGTTGATTCCGATGATGATAGCCATGGCTCCTTGAAT |
| SNP129 | 1 | 388 | AGGTTGAGATGGATGATTGGTTGTTCGAGTTTGCTCAGTTATTCAGGACTTAT<br>GTTGGCATTGATCCGGATGCCCACATTGACCTGCACGAGCTTGGGATG |
| SNP129 | 2 | 389 | AGGTTGAGATGGATGATTGGTTGTTCGAGTTTGCTCAGTTATTCAGGACTCAT<br>GTTGGCATTGATCCGGATGCCCACATTGACCTGCACGAGCTTGGGATG |
| SNP130 | 1 | 390 | CATATCCATTAAAGAAAGAGTTTAGATCCAAGACTGTGAATTAGGGCATTTA<br>ATTACTCCACATGGCAAGATAGAAAGTATGTCACCCGGATTTAGAAGAT |
| SNP130 | 2 | 391 | CATATCCATTAAAGAAAGAGTTTAGATCCAAGACTGTGAATTAGGGCATTGA<br>ATTACTCCACATGGCAAGATAGAAAGTATGTCACCCGGATTTAGAAGAT |
| SNP131 | 1 | 392 | TCAGATAGAAACAGTCAAGGCCAACAGGGAACAAGAGACTAAAGGCCTCAA<br>TGATAAAATTTCTAGGATAGAGGCTGAACTTCAAGCTGCTGAATCTATCA |
| SNP131 | 2 | 393 | TCAGATAGAAACAGTCAAGGCCAACAGGGAACAAGAGACTAAAGGCCTCAG<br>TGATAAAATTTCTAGGATAGAGGCTGAACTTCAAGCTGCTGAATCTATCA |
| SNP132 | 1 | 394 | CAACCGAGCCACCGGACTTGAGAATAAAGCGAAATTCCTCTTTGATTCACTG<br>ATCAAAGAGCAGATTTCAACCTAACAGTTGAATCCATGCACAACTCAAT |
| SNP132 | 2 | 395 | CAACCGAGCCACCGGACTTGAGAATAAAGCGAAATTCCTCTTTGATTCACCG<br>ATCAAAGAGCAGATTTCAACCTAACAGTTGAATCCATGCACAACTCAAT |
| SNP133 | 1 | 396 | TTCATTTTGTTGAAACCAAAATTATACATAGAATATCTGTCCAACATTTAATA<br>GGCTCTCATGAGGGACATTGAAGATTACACTATTTTCCCTGCATATTT |
| SNP133 | 2 | 397 | TTCATTTTGTTGAAACCAAAATTATACATAGAATATCTGTCCAACATTTACTA<br>GGCTCTCATGAGGGACATTGAAGATTACACTATTTTCCCTGCATATTT |
| SNP134 | 1 | 398 | TCCCTGTGTAGTATCATTTTGAAAGATACAAAGCAAACAAGATTGATTAGTC<br>CCGCTTGCACGAATTTGTAAGATTTTTATATCTAGAACAGGATGATAGT |
| SNP134 | 2 | 399 | TCCCTGTGTAGTATCATTTTGAAAGATACAAAGCAAACAAGATTGATTAGCC<br>CCGCTTGCACGAATTTGTAAGATTTTTATATCTAGAACAGGATGATAGT |
| SNP135 | 1 | 400 | ATTTAGAAAATCAGGATAGTAAACATTCCCTGGCCAAACAACCCCTTGGTAG<br>GGCATATTATCGCGTTTTATGAAGACATCTGCTTCCATGCCTCTCCTAT |
| SNP135 | 2 | 401 | ATTTAGAAAATCAGGATAGTAAACATTCCCTGGCCAAACAACCCCTTGGTGG<br>GGCATATTATCGCGTTTTATGAAGACATCTGCTTCCATGCCTCTCCTAT |
| SNP136 | 1 | 402 | TGAGAGAAGGAGTGGCGAAGCAGAGGAAGGATTTTGCGAAGGAGGCTAAAA<br>AGTTTACTAATATTAGGCATCCTAATGTAGTAGGATTAAGAGGTTACTAC |
| SNP136 | 2 | 403 | TGAGAGAAGGAGTGGCGAAGCAGAGGAAGGATTTTGCGAAGGAGGCTAAA<br>GAGTTTACTAATATTAGGCATCCTAATGTAGTAGGATTAAGAGGTTACTAC |

TABLE 9-continued

| | | | |
|---|---|---|---|
| | | | Input target sequences for 300 SNP regions |

| Target | Allele # | SEQ ID NO: | Target Sequence |
|---|---|---|---|
| SNP137 | 1 | 404 | CATATGACAAGATGGAGCAACAATTGTCAAAGACTCGTAACCTGCATTGTTA GATCAACTGTGAACAGGTGTTTTTTCTTCTCTTTTGCTTCATTTATTTA |
| SNP137 | 2 | 405 | CATATGACAAGATGGAGCAACAATTGTCAAAGACTCGTAACCTGCATTGTCA GATCAACTGTGAACAGGTGTTTTTTCTTCTCTTTTGCTTCATTTATTTA |
| SNP138 | 1 | 406 | GCCAAAGAGCAAGCTGAATCTGCTCAAGAGGAGGCAGAGGAGTGGAAACGT AAGTACGGCATTGCTGCCAAGGAAGCAAAGAATGCTCTTGAGAAGGCAGC |
| SNP138 | 2 | 407 | GCCAAAGAGCAAGCTGAATCTGCTCAAGAGGAGGCAGAGGAGTGGAAACGC AAGTACGGCATTGCTGCCAAGGAAGCAAAGAATGCTCTTGAGAAGGCAGC |
| SNP139 | 1 | 408 | ACCATGGACAGATGACCTTTTATGGCAGTACCACGAAGCTTGACAAGTTCAT GCAGCACAGTTTTCACCATTCTTAAAGGTTTATCATCGGCTCCCGCTCT |
| SNP139 | 2 | 409 | ACCATGGACAGATGACCTTTTATGGCAGTACCACGAAGCTTGACAAGTTCGT GCAGCACAGTTTTCACCATTCTTAAAGGTTTATCATCGGCTCCCGCTCT |
| SNP140 | 1 | 410 | GAAGATTTGTGGGTATTGATGCAAAAGAAGAATGTTGATGCTGACTTGGGAA GTTACACCATTAGATTACAAGGATTGGTTGCGAATAACCAGGTTAACGA |
| SNP140 | 2 | 411 | GAAGATTTGTGGGTATTGATGCAAAAGAAGAATGTTGATGCTGACTTGGGGA GTTACACCATTAGATTACAAGGATTGGTTGCGAATAACCAGGTTAACGA |
| SNP141 | 1 | 412 | AGACGTTATTGTGTTCTGAACCAGTGTAATTATGTTGTTCTTGATGAAGCTGA CCGTATGATTGACATGGGTTTTGAGCCTCAAGTTGTTGGTGTACTGGA |
| SNP141 | 2 | 413 | AGACGTTATTGTGTTCTGAACCAGTGTAATTATGTTGTTCTTGATGAAGCGGA CCGTATGATTGACATGGGTTTTGAGCCTCAAGTTGTTGGTGTACTGGA |
| SNP142 | 1 | 414 | CCCATATTGCTAATGCAGATCAAAGAGCGGGAGGATTAAGCTTCTATAGTAG AAGATATCCATCAAATGGAGTAGCAAACAAGCAATGTACCACAATATTA |
| SNP142 | 2 | 415 | CCCATATTGCTAATGCAGATCAAAGAGCGGGAGGATTAAGCTTCTATAGTCG AAGATATCCATCAAATGGAGTAGCAAACAAGCAATGTACCACAATATTA |
| SNP143 | 1 | 416 | TCACTTGATTTGATAGCAGAAGCAAAGTAGATCCAGAATCCAGGTTAATAG AACATTTATTGCTTGTAAAAGATTTCTGGTTCTGACCAGAAGATGGATC |
| SNP143 | 2 | 417 | TCACTTGATTTGATAGCAGAAGCAAAGTAGATCCAGAATCCAGGTTAATTG AACATTTATTGCTTGTAAAAGATTTCTGGTTCTGACCAGAAGATGGATC |
| SNP144 | 1 | 418 | GGAGGTCAGGCTGGGCAATTGGGAGTTGGGCCATTAAATGGATTCTTTTCAT GCAAGCTCAATGAATCTGAGATGATGCTCCGAAATATACCAGTGTTGGT |
| SNP144 | 2 | 419 | GGAGGTCAGGCTGGGCAATTGGGAGTTGGGCCATTAAATGGATTCTTTTCCT GCAAGCTCAATGAATCTGAGATGATGCTCCGAAATATACCAGTGTTGGT |
| SNP145 | 1 | 420 | GTGTAATACGATCTGCCAGACCGTGGTGGGCAGGGGATTCTGTTAGCTGATA ATGCTCCGTACGAAATGTAGTACTTGAATTTGTTCCACAATAGAGATCT |
| SNP145 | 2 | 421 | GTGTAATACGATCTGCCAGACCGTGGTGGGCAGGGGATTCTGTTAGCTGACA ATGCTCCGTACGAAATGTAGTACTTGAATTTGTTCCACAATAGAGATCT |
| SNP146 | 1 | 422 | CGTCGATCAAAATACTCTTCCAAACCTACCGCAAAAGATAATAGCAGGCAAT AACAACAAAGATTAATCTCCCCCCTATATATGACTTGAGTTGTCAGGAA |
| SNP146 | 2 | 423 | CGTCGATCAAAATACTCTTCCAAACCTACCGCAAAAGATAATAGCAGGCAGT AACAACAAAGATTAATCTCCCCCCTATATATGACTTGAGTTGTCAGGAA |
| SNP147 | 1 | 424 | CCAGGATCACCCCTCTAGTAGCCAGCCAAGTGAAAAAGCACACCTTCATCAG CACTTTGGAAATGTAAACTGCATCAAAACTTCCTCTTCCTAACCAAAAG |
| SNP147 | 2 | 425 | CCAGGATCACCCCTCTAGTAGCCAGCCAAGTGAAAAAGCACACCTTCATCGG CACTTTGGAAATGTAAACTGCATCAAAACTTCCTCTTCCTAACCAAAAG |
| SNP148 | 1 | 426 | ACTCCAAGGGACCAAATAAGCTTTGCCATTGTAAGAGATAAGATCATGTCAA AGACAAATTGGACTGTGAATATGTTCTTAGACTGCGAACGGCGTAACTT |
| SNP148 | 2 | 427 | ACTCCAAGGGACCAAATAAGCTTTGCCATTGTAAGAGATAAGATCATGTCCA AGACAAATTGGACTGTGAATATGTTCTTAGACTGCGAACGGCGTAACTT |
| SNP149 | 1 | 428 | CGGGTGTGCATGTTTCAATACTGACAAAAAAGGGCCTTCAATGGTGTTGATC GCGCTAGTGAGAAATGAATTTGGTGGTTCTCTGTGCCTTCTTTCCGCTA |

TABLE 9-continued

| | Allele | SEQ ID | |
|---|---|---|---|
| Target | # | NO: | Target Sequence |

| | | | |
|---|---|---|---|
| SNP149 | 2 | 429 | CGGGTGTGCATGTTTCAATACTGACAAAAAAGGGCCTTCAATGGTGTTGACC GCGCTAGTGAGAAATGAATTTGGTGGTTCTCTGTGCCTTCTTTCCGCTA |
| SNP150 | 1 | 430 | AATTCCGCCAGCCATTTCTTCGCCGGCTTTTTCCCCCTCAACATCTCCGGTGA TGTCACGTTATCTATCAAATAGGGGAGGAACTCAAGTACAAAAGGTTC |
| SNP150 | 2 | 431 | AATTCCGCCAGCCATTTCTTCGCCGGCTTTTTCCCCCTCAACATCTCCGGCGA TGTCACGTTATCTATCAAATAGGGGAGGAACTCAAGTACAAAAGGTTC |
| SNP151 | 1 | 432 | ACAGCTCTACAACTATTGCTCCGTTCATTCCTTCCTAGCACTTTTGAGGCAAA GCTAGGAGGCTTAAGCTTCTCAACTTGACTCTGCAGAGATCCATGGCT |
| SNP151 | 2 | 433 | ACAGCTCTACAACTATTGCTCCGTTCATTCCTTCCTAGCACTTTTGAGGCTAA GCTAGGAGGCTTAAGCTTCTCAACTTGACTCTGCAGAGATCCATGGCT |
| SNP152 | 1 | 434 | ACTCTTGAACCATTTGAAAGAGACCACGCTTGTGTTGTTGGTGCCTATCGTGT ACCAAAGAAGCAAAAGGCTGCTGCCTAGAAAATTTAAGCTTATGATTT |
| SNP152 | 2 | 435 | ACTCTTGAACCATTTGAAAGAGACCACGCTTGTGTTGTTGGTGCCTATCGCGT ACCAAAGAAGCAAAAGGCTGCTGCCTAGAAAATTTAAGCTTATGATTT |
| SNP153 | 1 | 436 | AAACAGAAATTCGGGTTTCGGTTCAGAAAAACATCAATGAACAAAGTATCA ATCAAGCAATTAACTTGAATGGCACCCCTTTTGTTCTTCCAGAGTTTTTC |
| SNP153 | 2 | 437 | AAACAGAAATTCGGGTTTCGGTTCAGAAAAACATCAATGAACAAAGTATCG ATCAAGCAATTAACTTGAATGGCACCCCTTTTGTTCTTCCAGAGTTTTTC |
| SNP154 | 1 | 438 | CTCTCCTCTTTTGTTAATTCATCAATTTTTTCCTGCATCAGTTTCATTAGTGAT ACAACTTCTTCAGGCCTTCGCTTGAAGTTATCAATGCTGAATGCATA |
| SNP154 | 2 | 439 | CTCTCCTCTTTTGTTAATTCATCAATTTTTTCCTGCATCAGTTTCATTAGCGAT ACAACTTCTTCAGGCCTTCGCTTGAAGTTATCAATGCTGAATGCATA |
| SNP155 | 1 | 440 | GGGCGTGACTCAAACACTTGGGAAGATGCATTATCTTTCAGGCCAGAGCGAT TTCTCAACTCTAATGTGGATTTCAGGGGTCAAGATTTCGAGTTCATACC |
| SNP155 | 2 | 441 | GGGCGTGACTCAAACACTTGGGAAGATGCATTATCTTTCAGGCCAGAGCGGT TTCTCAACTCTAATGTGGATTTCAGGGGTCAAGATTTCGAGTTCATACC |
| SNP156 | 1 | 442 | GAAGAGTATGCTCTTCGACGTCTAAGGCTTTTGCAGCACATCTGCTAACGTG GAGCATATTTGTTCTCTCATCGCATCCCTGTTATTTGCATCAAGTGTAA |
| SNP156 | 2 | 443 | GAAGAGTATGCTCTTCGACGTCTAAGGCTTTTGCAGCACATCTGCTAACGCG GAGCATATTTGTTCTCTCATCGCATCCCTGTTATTTGCATCAAGTGTAA |
| SNP157 | 1 | 444 | TTCCATCAGCTTATGAACTCCAAACGTTGTTTGTCAATGAGTTGTGCTAAATA CTACCTCTTTGACCATCAGTTCATTTACCAGGCAAATCAACAGGGCAA |
| SNP157 | 2 | 445 | TTCCATCAGCTTATGAACTCCAAACGTTGTTTGTCAATGAGTTGTGCTAAGTA CTACCTCTTTGACCATCAGTTCATTTACCAGGCAAATCAACAGGGCAA |
| SNP158 | 1 | 446 | AAGTCCATTGAATCCAATATCGAGGCAGGGTTGCCCTGGGTGAGATCTACAG TAGTTATGGACTCTAAATTAGCAGACTCTGGTGAGAAGTTTGCAATATT |
| SNP158 | 2 | 447 | AAGTCCATTGAATCCAATATCGAGGCAGGGTTGCCCTGGGTGAGATCTACTG TAGTTATGGACTCTAAATTAGCAGACTCTGGTGAGAAGTTTGCAATATT |
| SNP159 | 1 | 448 | GAATGGAACTATCACCACAAGTACACAACTAAAGCTTTGATGAAAACACCA GAGCTGTTTCAGTCTTGACGAACATACCAACCGCATTCTAGTGCTTGAAA |
| SNP159 | 2 | 449 | GAATGGAACTATCACCACAAGTACACAACTAAAGCTTTGATGAAAACACCG GAGCTGTTTCAGTCTTGACGAACATACCAACCGCATTCTAGTGCTTGAAA |
| SNP160 | 1 | 450 | CCCTACTGATGTTGAGCTGATAATGTACTATCTAAAGCGGAAGATCATGGTG AAAAAGATCCTTTTTGAAGTCATATCAGAACTCAACATTTATAAGTTCT |
| SNP160 | 2 | 451 | CCCTACTGATGTTGAGCTGATAATGTACTATCTAAAGCGGAAGATCATGGGG AAAAAGATCCTTTTTGAAGTCATATCAGAACTCAACATTTATAAGTTCT |
| SNP161 | 1 | 452 | AGATTTTGAAGTTCACCCAACTCTTCAATTCTTGAATCACTAAATGCACCTAC GACAAATCTTGTTGAATAAGAAAGTAGGAGAATCTGTAACTTGCTTTT |
| SNP161 | 2 | 453 | AGATTTTGAAGTTCACCCAACTCTTCAATTCTTGAATCACTAAATGCACCCAC GACAAATCTTGTTGAATAAGAAAGTAGGAGAATCTGTAACTTGCTTTT |

TABLE 9-continued

| | Allele | SEQ ID | |
|---|---|---|---|
| Target | # | NO: | Target Sequence |

| | | | |
|---|---|---|---|
| SNP162 | 1 | 454 | ATAATGCAAGTCTCACATTTTTCGTGCAGATAAAGTATACCCCTTGATATATC<br>CAATGCAAGTCTCATCCTTTGCTCCCAAGAAGGTCTTGTTTCAGAACT |
| SNP162 | 2 | 455 | ATAATGCAAGTCTCACATTTTTCGTGCAGATAAAGTATACCCCTTGATATGTC<br>CAATGCAAGTCTCATCCTTTGCTCCCAAGAAGGTCTTGTTTCAGAACT |
| SNP163 | 1 | 456 | TACCAATAGATTCTCCGATCAAAGAGTTTTCCTTGGGCTCAAGCACACCGTC<br>GGACTTTGACAAGATCAAAAACAATTTTTTTGCATCGTCGTCAGTTAAC |
| SNP163 | 2 | 457 | TACCAATAGATTCTCCGATCAAAGAGTTTTCCTTGGGCTCAAGCACACCGCC<br>GGACTTTGACAAGATCAAAAACAATTTTTTTGCATCGTCGTCAGTTAAC |
| SNP164 | 1 | 458 | GCTATCAACTGGTGTATATGCAAGGGTACAATTCCTATCCCTGGAATCAAAT<br>CTGTAAAACAAACTGAAGAGAACCTAGGAGCCCTTGGTTGGCAACTCAG |
| SNP164 | 2 | 459 | GCTATCAACTGGTGTATATGCAAGGGTACAATTCCTATCCCTGGAATCAAGT<br>CTGTAAAACAAACTGAAGAGAACCTAGGAGCCCTTGGTTGGCAACTCAG |
| SNP165 | 1 | 460 | TCATGCTGGCAGAGGAAGTGAGAGAAATTATGTCTCAACTTGGTTTCAGAAC<br>ACTTACTGAAATGGTTGGCCGTTCAGACATGCTTGAAATGGACAATGAT |
| SNP165 | 2 | 461 | TCATGCTGGCAGAGGAAGTGAGAGAAATTATGTCTCAACTTGGTTTCAGAGC<br>ACTTACTGAAATGGTTGGCCGTTCAGACATGCTTGAAATGGACAATGAT |
| SNP166 | 1 | 462 | AAAAGCCATCCTTAAGTTTCCGTTCGATGCCGGAAATTTAATACCGCAGGAG<br>ACGATTGGCCGGAAGAGGAGAATTGATCAGTGATGCACTTAGTTGAGTG |
| SNP166 | 2 | 463 | AAAAGCCATCCTTAAGTTTCCGTTCGATGCCGGAAATTTAATACCGCAGGTG<br>ACGATTGGCCGGAAGAGGAGAATTGATCAGTGATGCACTTAGTTGAGTG |
| SNP167 | 1 | 464 | CAAAACATAGAATATCATGCAAGTTGCTGGTTAAGTGCCAAGAACATGGATG<br>TTCATTGCATGTTTAATTAACTCTTTCGGGTGAGATCAAAATCTCTGGT |
| SNP167 | 2 | 465 | CAAAACATAGAATATCATGCAAGTTGCTGGTTAAGTGCCAAGAACATGGAC<br>GTTCATTGCATGTTTAATTAACTCTTTCGGGTGAGATCAAAATCTCTGGT |
| SNP168 | 1 | 466 | TCGCAACTCTTATACTATGATGGGTGTTCAATTATTGAGATGTGTACCAAATG<br>CTTGTAACTGCTCACTTTAAGATGAAAAGCTGCCTTCACTGGTTAGTG |
| SNP168 | 2 | 467 | TCGCAACTCTTATACTATGATGGGTGTTCAATTATTGAGATGTGTACCAAGTG<br>CTTGTAACTGCTCACTTTAAGATGAAAAGCTGCCTTCACTGGTTAGTG |
| SNP169 | 1 | 468 | TGATGTAAGCAAATTTTCAAGTCGCCATGTGGTGAGTGCTGCATATGATCAC<br>ACAATAAAAGTTTGGGATCTGCAGAAGGGTTACTGTAACAACACTATCA |
| SNP169 | 2 | 469 | TGATGTAAGCAAATTTTCAAGTCGCCATGTGGTGAGTGCTGCATATGATCGC<br>ACAATAAAAGTTTGGGATCTGCAGAAGGGTTACTGTAACAACACTATCA |
| SNP170 | 1 | 470 | AGGAGGTGGCATCTGGGGTGGGAAGTAGGGGAATGGTTCAATTGGGAAACA<br>ACCGGGAGGAACTGGAGCTCCATAAGGTGGCCCTCCGGGTGGCCCTCTAT |
| SNP170 | 2 | 471 | AGGAGGTGGCATCTGGGGTGGGAAGTAGGGGAATGGTTCAATTGGGAAACC<br>ACCGGGAGGAACTGGAGCTCCATAAGGTGGCCCTCCGGGTGGCCCTCTAT |
| SNP171 | 1 | 472 | AGCGGCTGAGATAAAGGATTAAATCTACAAAACGAAGCGGAACTGGACGGC<br>TTGTGAGGCTTCTTAGGGAGTGAAATTGACGGAGAAAACGAGATTGCTGT |
| SNP171 | 2 | 473 | AGCGGCTGAGATAAAGGATTAAATCTACAAAACGAAGCGGAACTGGACGGG<br>TTGTGAGGCTTCTTAGGGAGTGAAATTGACGGAGAAAACGAGATTGCTGT |
| SNP172 | 1 | 474 | CTCCAAATATTGCAGCACCTGTTGCATTGTAGGTCTATCATCTGGATTTGAAT<br>CAGTGCATCTTGCAGCTATTTCTATAATTGCTTCTACTGTCTCTGCAT |
| SNP172 | 2 | 475 | CTCCAAATATTGCAGCACCTGTTGCATTGTAGGTCTATCATCTGGATTTGCAT<br>CAGTGCATCTTGCAGCTATTTCTATAATTGCTTCTACTGTCTCTGCAT |
| SNP173 | 1 | 476 | GGTAACCTAACTCCGGCTGAGACTCATCAGAATCCGCCGTCAAATCCACCAC<br>TTCCGTCTCCATCACCTTCGCCGGTGACGGAGAAGCTGTAATTTCTTCT |
| SNP173 | 2 | 477 | GGTAACCTAACTCCGGCTGAGACTCATCAGAATCCGCCGTCAAATCCACCGC<br>TTCCGTCTCCATCACCTTCGCCGGTGACGGAGAAGCTGTAATTTCTTCT |
| SNP174 | 1 | 478 | AACGAATCGAAATCATGACTCGTGGTGCAAAACTCGGAGCTATCATCGTCAT<br>CGGTGAGATCGTACAACAGATTCTCCTTGAGTTTCTTCACTTCCGGTGA |

TABLE 9-continued

| | Allele | SEQ ID | |
|---|---|---|---|
| Target | # | NO: | Target Sequence |

SNP174    2    479    AACGAATCGAAATCATGACTCGTGGTGCAAAACTCGGAGCTATCATCGTCGT
                      CGGTGAGATCGTACAACAGATTCTCCTTGAGTTTCTTCACTTCCGGTGA

SNP175    1    480    CTAAAATCAATTATCTTGAGCTGTGAACATTGAGACAGTTGAGATGGAATTG
                      GACCATAAAGTGAGTTATCAGGTGCTCTCAGCTCTTCCAATGATGAAGC

SNP175    2    481    CTAAAATCAATTATCTTGAGCTGTGAACATTGAGACAGTTGAGATGGAATCG
                      GACCATAAAGTGAGTTATCAGGTGCTCTCAGCTCTTCCAATGATGAAGC

SNP176    1    482    ATCGAAGCCAGAAATTGTGATTATTGATTGTGGATTAAGGAATTTTGGTGTG
                      GAGTTGAAATGGATGGGAATAATTGGAGGGCCGCTCAGGCTCAGGCTCC

SNP176    2    483    ATCGAAGCCAGAAATTGTGATTATTGATTGTGGATTAAGGAATTTTGGTGCG
                      GAGTTGAAATGGATGGGAATAATTGGAGGGCCGCTCAGGCTCAGGCTCC

SNP177    1    484    TCTCCGGCGACCGGAGAATCCTACGCCTGTAAATCTATCGATAAAAACCTTC
                      TCATTGATTCCACCGACCGTGAGTGTCTCGATAAAGAACCCAAAATTCT

SNP177    2    485    TCTCCGGCGACCGGAGAATCCTACGCCTGTAAATCTATCGATAAAAACCTCC
                      TCATTGATTCCACCGACCGTGAGTGTCTCGATAAAGAACCCAAAATTCT

SNP178    1    486    GATCGAAGGTCAATTGAGAGAAGCAGAAGAGACTATGACAGGAGCAGGAGC
                      CGTAGTAGGAGTAGAAGCCACAGCCGAAGCTTGCATGATCAAGGTACAAG

SNP178    2    487    GATCGAAGGTCAATTGAGAGAAGCAGAAGAGACTATGACAGGAGCAGGAG
                      GCGTAGTAGGAGTAGAAGCCACAGCCGAAGCTTGCATGATCAAGGTACAAG

SNP179    1    488    CTATATGGGTCAATATTTCCCTGCTCATGATCTGCAAGAAGAAGAGCTTTAGT
                      ACAATCAGTGGAAGGATGTTCAGACGATCCTGTGTCACATGTTATCTG

SNP179    2    489    CTATATGGGTCAATATTTCCCTGCTCATGATCTGCAAGAAGAAGAGCTTTGG
                      TACAATCAGTGGAAGGATGTTCAGACGATCCTGTGTCACATGTTATCTG

SNP180    1    490    TGGCCCAAATGAAGATATGACACCAGAAAATCGATCTGTTCTGTGCGTGCCA
                      CTAGAGGAAAACGGGATAAACTTACCCCCACCCGGAGAGCCACCAAAGG

SNP180    2    491    TGGCCCAAATGAAGATATGACACCAGAAAATCGATCTGTTCTGTGCGTGCGA
                      CTAGAGGAAAACGGGATAAACTTACCCCCACCCGGAGAGCCACCAAAGG

SNP181    1    492    ATAGACTCGAAGCATTTCTTCGTGCCTTCAGGAAATGCAGCTGTTGAATTAAT
                      AGGAGGAAGGGAAACAGGCATTGCACAGACGATACGTACAATCCCAAA

SNP181    2    493    ATAGACTCGAAGCATTTCTTCGTGCCTTCAGGAAATGCAGCTGTTGAATTGA
                      TAGGAGGAAGGGAAACAGGCATTGCACAGACGATACGTACAATCCCAAA

SNP182    1    494    CTTCAGCAACTTTACCATCTTCATTCACTTTATTCTTCCCTTTGAAGCCACAAC
                      CAAAAACAAATGTGTCATTCAGTTTTGGACCCTGATACTCTGGTTCC

SNP182    2    495    CTTCAGCAACTTTACCATCTTCATTCACTTTATTCTTCCCTTTGAAGCCAGAA
                      CCAAAAACAAATGTGTCATTCAGTTTTGGACCCTGATACTCTGGTTCC

SNP183    1    496    CCATTCAGAAAATAGATTCTTAAAAGTTGTGAGCCATCAAATCTCCAGCTTTT
                      CAGTTTTGGGGTTGTAGTTTTCGGACTCTACATGTTATAACTACAATA

SNP183    2    497    CCATTCAGAAAATAGATTCTTAAAAGTTGTGAGCCATCAAATCTCCAGCTCT
                      TCAGTTTTGGGGTTGTAGTTTTCGGACTCTACATGTTATAACTACAATA

SNP184    1    498    TTTATAAAATGTGATCTTGTATACTTCCTGGACAACCATCAACCATCCATTTG
                      TTCTGCCTTTGTGTAGCCCTCACCTGGTTTTTTATTAACCGCTCCCAG

SNP184    2    499    TTTATAAAATGTGATCTTGTATACTTCCTGGACAACCATCAACCATCCATCTG
                      TTCTGCCTTTGTGTAGCCCTCACCTGGTTTTTTATTAACCGCTCCCAG

SNP185    1    500    GAGAGACCACACAGATGCCGACGGCGATAGACAGCCGAATACTTTGTGTAA
                      GCGTGCTCTGAAGCTCTCATCGTCCATGCCTTACCACTTTCTACTTCCTG

SNP185    2    501    GAGAGACCACACAGATGCCGACGGCGATAGACAGCCGAATACTTTGTGTAC
                      GCGTGCTCTGAAGCTCTCATCGTCCATGCCTTACCACTTTCTACTTCCTG

SNP186    1    502    CCCGACTGTCATCAGCCAAACGATAAATATTCCTTCGAGAAAAGAAATGGAG
                      TTTGTAAACATTTTGCCTCGTCTGGCTATCTGAACCTAGAAGAAACTCC

SNP186    2    503    CCCGACTGTCATCAGCCAAACGATAAATATTCCTTCGAGAAAAGAAATGGGG
                      TTTGTAAACATTTTGCCTCGTCTGGCTATCTGAACCTAGAAGAAACTCC

TABLE 9-continued

| | | | |
|---|---|---|---|
| | | | Input target sequences for 300 SNP regions |

| Target | Allele # | SEQ ID NO: | Target Sequence |
|---|---|---|---|
| SNP187 | 1 | 504 | GACGCTCATTGCATCTCGCACTGATGGTGGCAAATTCCTCAAGATCTTGGTAGATTTATGCTATCCAAAGTGGGCACTGGAAGCATTTGTCATTGCAAATG |
| SNP187 | 2 | 505 | GACGCTCATTGCATCTCGCACTGATGGTGGCAAATTCCTCAAGATCTTGGCAGATTTATGCTATCCAAAGTGGGCACTGGAAGCATTTGTCATTGCAAATG |
| SNP188 | 1 | 506 | GAGCTTCGTCAGAGAGGTACTTCTGTTGTACCTCCAGGTGAAGTGTATGGAAGATGGGGTGGCATGGAATTTAAAGATAAAGAAATTGTGTGGCCACCAAT |
| SNP188 | 2 | 507 | GAGCTTCGTCAGAGAGGTACTTCTGTTGTACCTCCAGGTGAAGTGTATGGGAGATGGGGTGGCATGGAATTTAAAGATAAAGAAATTGTGTGGCCACCAAT |
| SNP189 | 1 | 508 | GTATGATGATCGAGCCATTTGCAATGTTTTAGTTGGTGACCTAAGAATTCTTGGTCTTCTAAAAGGTGCAAGCATGCGTTGTCTAATTCAGAAGAAACAAC |
| SNP189 | 2 | 509 | GTATGATGATCGAGCCATTTGCAATGTTTTAGTTGGTGACCTAAGAATTCCTGGTCTTCTAAAAGGTGCAAGCATGCGTTGTCTAATTCAGAAGAAACAAC |
| SNP190 | 1 | 510 | GGATGAATGGAGAGGGACATGGTCAATATCGATGCATCGCCCAAATGTTCTGTTTTTCCCCTTGGTGATTGTTCAATTATGATTTATGTACAATATATATA |
| SNP190 | 2 | 511 | GGATGAATGGAGAGGGACATGGTCAATATCGATGCATCGCCCAAATGTTCGGTTTTTCCCCTTGGTGATTGTTCAATTATGATTTATGTACAATATATATA |
| SNP191 | 1 | 512 | AACTTAATCAGCAGACATCTTTATACAAGAAAATGTGGCTAGCATACAAGTAATAAAGTCAAATAAATAACAAATTGGCACAACAAAACAATTTGCTTAAA |
| SNP191 | 2 | 513 | AACTTAATCAGCAGACATCTTTATACAAGAAAATGTGGCTAGCATACAAGCAATAAAGTCAAATAAATAACAAATTGGCACAACAAAACAATTTGCTTAAA |
| SNP192 | 1 | 514 | AATTGGCCGCATCTACATAATGCCCAGTTTTTCGTCTATGCCGACTATAATCTGATACAAACCTAAAAGTCAGTCCACAACCCTCAACCTTGCACTTGTAT |
| SNP192 | 2 | 515 | AATTGGCCGCATCTACATAATGCCCAGTTTTTCGTCTATGCCGACTATAACCTGATACAAACCTAAAAGTCAGTCCACAACCCTCAACCTTGCACTTGTAT |
| SNP193 | 1 | 516 | GAGAAAGCTAGAGAAGCCAGAGCTTCCTGCTAGCATTATTGAGATGAGTATATTGATGTCGATAGTATTTTCTTCAACTCTATTTACCTGACAGACTTTGA |
| SNP193 | 2 | 517 | GAGAAAGCTAGAGAAGCCAGAGCTTCCTGCTAGCATTATTGAGATGAGTAGATTGATGTCGATAGTATTTTCTTCAACTCTATTTACCTGACAGACTTTGA |
| SNP194 | 1 | 518 | TCCCCCTATACATTAGCCTTGGAATGACTCCTCTTCATCTGGCAAGACAATAGCTAGTAAAGAGAACTTAACACGAAGAGAAATCTTAGCCTTGTCCACTA |
| SNP194 | 2 | 519 | TCCCCCTATACATTAGCCTTGGAATGACTCCTCTTCATCTGGCAAGACAACAGCTAGTAAAGAGAACTTAACACGAAGAGAAATCTTAGCCTTGTCCACTA |
| SNP195 | 1 | 520 | ATTCTCAAAGTGGAGCTTTCGAGTGCTTCAATTGTTCAAAAAAGAGAGTGTGGCTCTTATTGGCTGGCTCCCATCTGTTGTTGTTTGCCTAAGGACAAAAG |
| SNP195 | 2 | 521 | ATTCTCAAAGTGGAGCTTTCGAGTGCTTCAATTGTTCAAAAAAGAGAGTGCGGCTCTTATTGGCTGGCTCCCATCTGTTGTTGTTTGCCTAAGGACAAAAG |
| SNP196 | 1 | 522 | AAGTAGAAAGTACTGCCAATGAAGTTCCAAATGATCCTTCCAAGATCACAAACATCAAAGAAATTGCCACCTATGACAGTAAAGACATGCCTTCACTTGAACTTAGTTTGAAGCAACTTCGAGATGTTGGAGAGAATGGGACTGGTGTGCAAGAGCGAAATATACTCAGGCATTCAGATCTGTCAGCGTTCTCTAGGCATG |
| SNP196 | 2 | 523 | AAGTAGAAAGTACTGCCAATGAAGTTCCAAATGATCCTTCCAAGATCACAAACATCAAAGAAATTGCCACCTATGACAGTAAAGACATGCCTTCACTTGAGCTTAGTTTGAAGCAACTTCGAGATGTTGGAGAGAATGGGACTGGTGTGCAAGAGCGAAATATACTCAGGCATTCAGATCTGTCAGCGTTCTCTAGGCATG |
| SNP197 | 1 | 524 | TTTTCGCCTATAGAGTCAGGTATTAAGAAAGTGGCAAAGGATTTTGAGCATTGTTGGCCTGGTAAAGCTGAGAGTTGTACTAGTAGTGGGTATGGATTAGA |
| SNP197 | 2 | 525 | TTTTCGCCTATAGAGTCAGGTATTAAGAAAGTGGCAAAGGATTTTGAGCACTGTTGGCCTGGTAAAGCTGAGAGTTGTACTAGTAGTGGGTATGGATTAGA |
| SNP198 | 1 | 526 | CTGAACCAAAACAATGGACTGATGGTAAATTGAGCAAGAGAATCGGAAGGAGAGGAACTCCATTTGTATTGAGACTGCTAATTGCTGTTTTCCCATTCTTA |

TABLE 9-continued

| | Allele | SEQ ID | |
|---|---|---|---|
| Target | # | NO: | Target Sequence |

SNP198    2    527    CTGAACCAAAACAATGGACTGATGGTAAATTGAGCAAGAGAATCGGAAGGG
GAGGAACTCCATTTGTATTGAGACTGCTAATTGCTGTTTTCCCATTCTTA

SNP199    1    528    TGACCATGAGAGGGAGAAATAATATTGTGATATATGAAGAAGAGCTTGGCT
AATAGTGGTGGAAGTCACAGATGAACCAATCTTAGGCTTCAAAAGATTGT

SNP199    2    529    TGACCATGAGAGGGAGAAATAATATTGTGATATATGAAGAAGAGCTTGGCG
AATAGTGGTGGAAGTCACAGATGAACCAATCTTAGGCTTCAAAAGATTGT

SNP200    1    530    ATAATAAGAATTGGGAAACAATTGGAGTACTTTGAACAATATCAAAGGAGA
GTAAGTGGTTTAATTGGAGCAGCACAAACAGAGCAGCTAGTAAACAGTGC

SNP200    2    531    ATAATAAGAATTGGGAAACAATTGGAGTACTTTGAACAATATCAAAGGAGG
GTAAGTGGTTTAATTGGAGCAGCACAAACAGAGCAGCTAGTAAACAGTGC

SNP201    1    532    TCATATCGATCTGCATGTCTAAGCTTAAGCCTAATTGACGAATTCCCATATGA
TTTTGCAGTTGTGTGCCAGACACCGGTAACAGCATATCGACTCCCTGA

SNP201    2    533    TCATATCGATCTGCATGTCTAAGCTTAAGCCTAATTGACGAATTCCCATACGA
TTTTGCAGTTGTGTGCCAGACACCGGTAACAGCATATCGACTCCCTGA

SNP202    1    534    ACAAGCAACAGCAGCATGTATTTAACAAACAAGGAACTATGTACGGTTAGA
GTCCTTAATGCTGTCAGTCAAGATGAAGTCACTGTAAGTATATTAATGGT

SNP202    2    535    ACAAGCAACAGCAGCATGTATTTAACAAACAAGGAACTATGTACGGTTAGG
GTCCTTAATGCTGTCAGTCAAGATGAAGTCACTGTAAGTATATTAATGGT

SNP203    1    536    TTTTTGTTTAATCAGATATTTTGAATTCGAGCTTTGTTCGTTAAAATGTTTTTG
CTAGGGAACGTTTTATGCTAATGTATATTTGAAATGATGTGCTAGAA

SNP203    2    537    TTTTTGTTTAATCAGATATTTTGAATTCGAGCTTTGTTCGTTAAAATGTTCTTG
CTAGGGAACGTTTTATGCTAATGTATATTTGAAATGATGTGCTAGAA

SNP204    1    538    CTAGAAGCAAAAGGGTAACTAGCAGCAACAGAAGCAGCAGCAGCTGTGGTA
GCCAACTTGGCTGAGAAAATACCATAAGAATGAAGGGTTTGACCATTAAA

SNP204    2    539    CTAGAAGCAAAAGGGTAACTAGCAGCAACAGAAGCAGCAGCAGCTGTGGTT
GCCAACTTGGCTGAGAAAATACCATAAGAATGAAGGGTTTGACCATTAAA

SNP205    1    540    GATGTAACCTGAATGTCTCCTTGAGCACTAGTTCTAAGTATTCCAACTTAAGT
AAGTCATCTTCCTCAACCATTCTATCAAGTCCTACAATAGAAGTCAAC

SNP205    2    541    GATGTAACCTGAATGTCTCCTTGAGCACTAGTTCTAAGTATTCCAACTTAGGT
AAGTCATCTTCCTCAACCATTCTATCAAGTCCTACAATAGAAGTCAAC

SNP206    1    542    CTGTGTCATTTTTTTTTCTAACACTATACTAGTCTTTTTGCCGCCGGCGGTATG
AGTTTATTCAGGTAAAAGGGAAAAGGGTATTCATATATAAGCCTAAA

SNP206    2    543    CTGTGTCATTTTTTTTTCTAACACTATACTAGTCTTTTTGCCGCCGGCGGGATG
AGTTTATTCAGGTAAAAGGGAAAAGGGTATTCATATATAAGCCTAAA

SNP207    1    544    AGGGCAATATTACTCCCCTTGATCGCCATTGTAGACCTTTGTGAAATAGAAC
AGTTTCCACTCACTTTACGTTTTACTTCTGAGAAAGTAAGCGCCCATTT

SNP207    2    455    AGGGCAATATTACTCCCCTTGATCGCCATTGTAGACCTTTGTGAAATAGAGC
AGTTTCCACTCACTTTACGTTTTACTTCTGAGAAAGTAAGCGCCCATTT

SNP208    1    546    AACTGCACATTGTTTGCATTCAGAAGGTTTTGGAATTCACTGTAGTCTATTCT
ATGAGAATTTTCAGGATCCCACTCTGTCCCCTTCAGCTTTCCCTGCAT

SNP208    2    547    AACTGCACATTGTTTGCATTCAGAAGGTTTTGGAATTCACTGTAGTCTATCCT
ATGAGAATTTTCAGGATCCCACTCTGTCCCCTTCAGCTTTCCCTGCAT

SNP209    1    548    GAAGCAAATAGTGTGCAGAGGAAGAGAAAATAGAGATGTCGAAGACGCTAC
TTCAGCCTGTAGGCCAAAAGAGACTTACCAATGTTGCTGTTGTGCGCTC

SNP209    2    549    GAAGCAAATAGTGTGCAGAGGAAGAGAAAATAGAGATGTCGAAGACGCTAG
TTCAGCCTGTAGGCCAAAAGAGACTTACCAATGTTGCTGTTGTGCGCTC

SNP210    1    550    GTTCCCATAGTACCCAAAGAAAAGAAGGTCCCTCCAACTGGTGACAAGGTAA
AAAATGGAGATTTCTCAGGTGACAATAATAATGTCAAAAAAATGAAAGTT

SNP210    2    551    GTTCCCATAGTACCCAAAGAAAAGAAGGTCCCTCCAACTGGTGACAAGGTCA
AAAATGGAGATTTCTCAGGTGACAATAATAATGTCAAAAAAATGAAAGTT

TABLE 9-continued

| | | | Input target sequences for 300 SNP regions | |
|---|---|---|---|---|

| Target | Allele # | SEQ ID NO: | Target Sequence |
|---|---|---|---|
| SNP211 | 1 | 552 | TCAATACAATACCTTTACCACTATTATAAAGAAAAAGGACAACCAGGTGCACGAAACATCACATGTTCACGCATGGTCTGAGGAAGGGCCACATTCCAAGG |
| SNP211 | 2 | 553 | TCAATACAATACCTTTACCACTATTATAAAGAAAAAGGACAACCAGGTGCGCGAAACATCACATGTTCACGCATGGTCTGAGGAAGGGCCACATTCCAAGG |
| SNP212 | 1 | 554 | GACTCTAGTGGAGTTGAAGTAGGAGCAATGTTGGTGATGGTTATTGGATATAGGGTGTTAGCCTACTTCCTCCTAAGAAAAATGAAACCAAGAACAAGCAA |
| SNP212 | 2 | 555 | GACTCTAGTGGAGTTGAAGTAGGAGCAATGTTGGTGATGGTTATTGGATACAGGGTGTTAGCCTACTTCCTCCTAAGAAAAATGAAACCAAGAACAAGCAA |
| SNP213 | 1 | 556 | TAATATTATTTGTTCATTTTAAGATGAATAAAGAATTAAGTCTGCAAGATCTTTATGGTCAAACCACTACCCTTGGAACTCATTGAGATTAGATCTTATAT |
| SNP213 | 2 | 557 | TAATATTATTTGTTCATTTTAAGATGAATAAAGAATTAAGTCTGCAAGATGTTTATGGTCAAACCACTACCCTTGGAACTCATTGAGATTAGATCTTATAT |
| SNP214 | 1 | 558 | ATGTTTTACCAAGTACTATCTGCTGCAAGTTGTTTTTTCTTTAATCTAGACACTCCAGATCAAGTTTATTTAGAACACAAAAAACCATAGAAGAAAAAGGT |
| SNP214 | 2 | 559 | ATGTTTTACCAAGTACTATCTGCTGCAAGTTGTTTTTTCTTTAATCTAGAGACTCCAGATCAAGTTTATTTAGAACACAAAAAACCATAGAAGAAAAAGGT |
| SNP215 | 1 | 560 | TGATTACACGTGCAATCCTCTGGAGAAGCTCCAATACTAGAGAAGGCGACAAATTTGTCCTAGATGTCGCAACAAAAAGCAGACCAACTACCTTCACATGG |
| SNP215 | 2 | 561 | TGATTACACGTGCAATCCTCTGGAGAAGCTCCAATACTAGAGAAGGCGACCAATTTGTCCTAGATGTCGCAACAAAAAGCAGACCAACTACCTTCACATGG |
| SNP216 | 1 | 562 | TGGACTTCCAAACCAACTGGTGCCTTTATACTTGCTGTGTATGTTGCGTCTTCTTGTCCTACGTTAGTTACAGTTCTTGTTACTTTCTTGATTTCATTTTC |
| SNP216 | 2 | 563 | TGGACTTCCAAACCAACTGGTGCCTTTATACTTGCTGTGTATGTTGCGTCGTCTTGTCCTACGTTAGTTACAGTTCTTGTTACTTTCTTGATTTCATTTTC |
| SNP217 | 1 | 564 | TGTTTTTTTATCATATTGCTCTGAAAAACAAAATATGGAGTGATGGAGCATTGTGGACAAGTAAACTCCACCCCATCCAAATAATACACCAGAAAAGTACA |
| SNP217 | 2 | 565 | TGTTTTTTTATCATATTGCTCTGAAAAACAAAATATGGAGTGATGGAGCAGTGTGGACAAGTAAACTCCACCCCATCCAAATAATACACCAGAAAAGTACA |
| SNP218 | 1 | 566 | AGATATTTTTAAAATTGGATGATTTTTTTTCGAGTGATTTTGGGCGTTCCATTTTCCTGGGTTTATTGAGTTTCTTCCTCTGTTTGATCTGACCAATGCAC |
| SNP218 | 2 | 567 | AGATATTTTTAAAATTGGATGATTTTTTTTCGAGTGATTTTGGGCGTTCCGTTTTCCTGGGTTTATTGAGTTTCTTCCTCTGTTTGATCTGACCAATGCAC |
| SNP219 | 1 | 568 | TCCAGGTAGTCTTTTGGTACTTCCATTTCAGATAGTGTGCTGGCATTGATTGCCTGAGCTGCCTTGAAAATTTGATTTGTGCATTCCCTACACTGCCGCAA |
| SNP219 | 2 | 569 | TCCAGGTAGTCTTTTGGTACTTCCATTTCAGATAGTGTGCTGGCATTGATCGCCTGAGCTGCCTTGAAAATTTGATTTGTGCATTCCCTACACTGCCGCAA |
| SNP220 | 1 | 570 | CCGGTTCACATTTCGTCATTCAGCTAAATCTCTGGCCAAAGTTGACGCCATTCACTCTCCTTTGCTCCTTCCGATCTCAATCTCCGGTGAACTCCTGCGTG |
| SNP220 | 2 | 571 | CCGGTTCACATTTCGTCATTCAGCTAAATCTCTGGCCAAAGTTGACGCCACTCACTCTCCTTTGCTCCTTCCGATCTCAATCTCCGGTGAACTCCTGCGTG |
| SNP221 | 1 | 572 | ACCAAATAAACAAGAAAAAAAATGATTTTTGGAGCTCAGAAGAAAGAAGAACCAAAAGGGTCGATTCCTTTTCCTTCTAGAAATGTAAAAACCTAATTATT |
| SNP221 | 2 | 573 | ACCAAATAAACAAGAAAAAAAATGATTTTTGGAGCTCAGAAGAAAGAAGAGCCAAAAGGGTCGATTCCTTTTCCTTCTAGAAATGTAAAAACCTAATTATT |
| SNP222 | 1 | 574 | ATTGGCTTGGTCTAAATGAGTTCTCTGATTTGAGCCATGATGAGTTTAAGAAAATGTATTTAGGACTGAAAGTTGATCAAGAGTTGCTTAATAAAAGAGAG |
| SNP222 | 2 | 575 | ATTGGCTTGGTCTAAATGAGTTCTCTGATTTGAGCCATGATGAGTTTAAGGAAATGTATTTAGGACTGAAAGTTGATCAAGAGTTGCTTAATAAAAGAGAG |
| SNP223 | 1 | 576 | AACTTGCTATTAGGATTGTTCCAAGCAGGTGCAGCTGCTTTTAGAAAAAGAAAAACCCCTCTTTCATTGACTGGTTGTGATGACTACTATCATTCGCCATA |

TABLE 9-continued

| Target | Allele # | SEQ ID NO: | Target Sequence |
|---|---|---|---|
| SNP223 | 2 | 577 | AACTTGCTATTAGGATTGTTCCAAGCAGGTGCAGCTGCTTTTAGAAAAAGGA AAACCCCTCTTTCATTGACTGGTTGTGATGACTACTATCATTCGCCATA |
| SNP224 | 1 | 578 | TCTGGAAGACATGTTGGAGGATCGTACGTGTATGGTTCAAAGGGATTGTCTA ACAGAAAATAACTGGACGACGGGCTGCATGAGTTATCACATTGATAGGA |
| SNP224 | 2 | 579 | TCTGGAAGACATGTTGGAGGATCGTACGTGTATGGTTCAAAGGGATTGTCGA ACAGAAAATAACTGGACGACGGGCTGCATGAGTTATCACATTGATAGGA |
| SNP225 | 1 | 580 | AGCGATTTCAGGGACGAAGAATGCTCAAAACAATAAGGGATGTTCTTGAGAT GCTGGCATCTTTTCAGTTCCAAGCGTTCAAGGCATGGAAAGGCATCATC |
| SNP225 | 2 | 581 | AGCGATTTCAGGGACGAAGAATGCTCAAAACAATAAGGGATGTTCTTGAGG TGCTGGCATCTTTTCAGTTCCAAGCGTTCAAGGCATGGAAAGGCATCATC |
| SNP226 | 1 | 582 | CCTTTGGCAAGTTATCTTACGATAGAACAGAAAACATTGCACTGAAAGAATT GCCAAGATATAGATCTCCCAAAATCAGCAATCTTCTCTGCAACTTCAAC |
| SNP226 | 2 | 583 | CCTTTGGCAAGTTATCTTACGATAGAACAGAAAACATTGCACTGAAAGAACT GCCAAGATATAGATCTCCCAAAATCAGCAATCTTCTCTGCAACTTCAAC |
| SNP227 | 1 | 584 | ATTCAACTATAGCATGGGTTGGTTGTGTGGGCAAAGGCAGAGTCCCTAACAT GAGCTACGCGTACAAGACAACAAGTTCAGTGGACTACATGTTCCGCGTC |
| SNP227 | 2 | 585 | ATTCAACTATAGCATGGGTTGGTTGTGTGGGCAAAGGCAGAGTCCCTAACGT GAGCTACGCGTACAAGACAACAAGTTCAGTGGACTACATGTTCCGCGTC |
| SNP228 | 1 | 586 | CAAAATCCCAAAATTACCCTTCCTCCTACACCGCCCTATCCTACACACTTATG TCCTCATTCGTCTTTTTACAATCTGAGTCTCACTGTCTCCAACTCACT |
| SNP228 | 2 | 587 | CAAAATCCCAAAATTACCCTTCCTCCTACACCGCCCTATCCTACACACTTGTG TCCTCATTCGTCTTTTTACAATCTGAGTCTCACTGTCTCCAACTCACT |
| SNP229 | 1 | 588 | ATTCTACTACTGTTCCATAACCCATTGTGTTCAATTGGACTCATTTTGAGATC CATGAATCGCCAGAGCTTTCGATTAGATCCTCTTTTTTTTCTTTGTTT |
| SNP229 | 2 | 589 | ATTCTACTACTGTTCCATAACCCATTGTGTTCAATTGGACTCATTTTGAGCTC CATGAATCGCCAGAGCTTTCGATTAGATCCTCTTTTTTTTCTTTGTTT |
| SNP230 | 1 | 590 | AATGAAGTTGAAGCAATATCTTTCGAGAATGATGAGATTTCTCCTGAATCAA TTGAGAAAGTTCTGTCGTTGGATCACTTATCTATCATTTTGAACTCTGA |
| SNP230 | 2 | 591 | AATGAAGTTGAAGCAATATCTTTCGAGAATGATGAGATTTCTCCTGAATCGA TTGAGAAAGTTCTGTCGTTGGATCACTTATCTATCATTTTGAACTCTGA |
| SNP231 | 1 | 592 | ATTTCCCGCCAAATCCTCATCGATCCGATCAAATCGACTACCGTCACCACTG GCGCGAACATCTCTATTTCCGTGCGGTTGAAAATTCCAGCCGAATTCGG |
| SNP231 | 2 | 593 | ATTTCCCGCCAAATCCTCATCGATCCGATCAAATCGACTACCGTCACCACCG GCGCGAACATCTCTATTTCCGTGCGGTTGAAAATTCCAGCCGAATTCGG |
| SNP232 | 1 | 594 | ATGTTTCAAAAGCTGCTGCTGAAGCAAGGAAAAAATCGAAAATTCTTCAGTC AGTGGTGAGAAACAAAGAACCTTACATTCTTGAAACAAATAGCAGTTTA |
| SNP232 | 2 | 595 | ATGTTTCAAAAGCTGCTGCTGAAGCAAGGAAAAAATCGAAAATTCTTCAGCC AGTGGTGAGAAACAAAGAACCTTACATTCTTGAAACAAATAGCAGTTTA |
| SNP233 | 1 | 596 | AAATACGAGTTTGCATATTTTCGTCCATGTTTTTAATCTTTTCAATGTGCTTGT TGTGATATGACTTTCTATGCAATCATTGGTTCTTGAGTGAATTCACT |
| SNP233 | 2 | 597 | AAATACGAGTTTGCATATTTTCGTCCATGTTTTTAATCTTTTCAATGTGCCTGT TGTGATATGACTTTCTATGCAATCATTGGTTCTTGAGTGAATTCACT |
| SNP234 | 1 | 598 | ATGACCAAGTTGTGGGTAGCTGAAGGGTTTGTACAAGCAAACAACGAAAAA GGACAAGAAGATACCGCACAAGGTTTCTTGGACGATCTTATTGGTAGGAA |
| SNP234 | 2 | 599 | ATGACCAAGTTGTGGGTAGCTGAAGGGTTTGTACAAGCAAACAACGAAAT GGACAAGAAGATACCGCACAAGGTTTCTTGGACGATCTTATTGGTAGGAA |
| SNP235 | 1 | 600 | CAGGGGCAATGTAGCCTATATTTCCTCTCACTACTGTGCTAAGATGGGTTAG ATCAAGCTCGGGCATTGTCTTAGATATTCCAAAATCAGTAATTTTTGGC |
| SNP235 | 2 | 601 | CAGGGGCAATGTAGCCTATATTTCCTCTCACTACTGTGCTAAGATGGGTTTGA TCAAGCTCGGGCATTGTCTTAGATATTCCAAAATCAGTAATTTTTGGC |

TABLE 9-continued

| | | | |
|---|---|---|---|
| | | Input target sequences for 300 SNP regions | |

| Target | Allele # | SEQ ID NO: | Target Sequence |
|---|---|---|---|
| SNP236 | 1 | 602 | GTTAATGCCAGTGAAAAGTCTACTTCCACTTCTCCTGTGGATCTATTAGGTTT GGCTAACTATGCGTCAGATGATGAGGATGACAATGAAATCCAGAGTTC |
| SNP236 | 2 | 603 | GTTAATGCCAGTGAAAAGTCTACTTCCACTTCTCCTGTGGATCTATTAGGCTT GGCTAACTATGCGTCAGATGATGAGGATGACAATGAAATCCAGAGTTC |
| SNP237 | 1 | 604 | GAGCTGCTAACCAAGGCTCCACCATAGAAGCCCCAAATCCATCCACAATTTG CCTTCCCCTATGCTTCTCTTCATTAACAATCCTCTTATCCAAACTTGAC |
| SNP237 | 2 | 605 | GAGCTGCTAACCAAGGCTCCACCATAGAAGCCCCAAATCCATCCACAATTCG CCTTCCCCTATGCTTCTCTTCATTAACAATCCTCTTATCCAAACTTGAC |
| SNP238 | 1 | 606 | CGGTTATTGAAGAACAGTTCTTCAGCATTTTCAAATCTGGTGGCAGAATTTTT GCGGAGATCATCCAAGGGGTTAACCTAAAAGCATAGCACATTTGATAG |
| SNP238 | 2 | 607 | CGGTTATTGAAGAACAGTTCTTCAGCATTTTCAAATCTGGTGGCAGAATTCTT GCGGAGATCATCCAAGGGGTTAACCTAAAAGCATAGCACATTTGATAG |
| SNP239 | 1 | 608 | TGGGATGCTTCCAAACTATGTCGTCTATCATGAATTAATAGTTACATCACACC CATTTATGCGTAATGTATGTGCAGTTGAGATGCGATGGGTTGCACCAA |
| SNP239 | 2 | 609 | TGGGATGCTTCCAAACTATGTCGTCTATCATGAATTAATAGTTACATCACGCC CATTTATGCGTAATGTATGTGCAGTTGAGATGCGATGGGTTGCACCAA |
| SNP240 | 1 | 610 | ATGCCTCTGAGAGATTCTAACCCTGGTAATACAGCAAGTACGACTGGTTATG CAGTTCCTGGCATGATGCAAGTAATAGCTACCACTAGTGGAGATAGACC |
| SNP240 | 2 | 611 | ATGCCTCTGAGAGATTCTAACCCTGGTAATACAGCAAGTACGACTGGTTACG CAGTTCCTGGCATGATGCAAGTAATAGCTACCACTAGTGGAGATAGACC |
| SNP241 | 1 | 612 | TCACTTTCATAGATCTCCTCAATCGATTCGGGAATATCTGCTTGAAACTGTGG CCCAACAGGTATTCTCTTTCTGCGCTGCTTCCACCAAAAACCAATTGC |
| SNP241 | 2 | 613 | TCACTTTCATAGATCTCCTCAATCGATTCGGGAATATCTGCTTGAAACTGCGG CCCAACAGGTATTCTCTTTCTGCGCTGCTTCCACCAAAAACCAATTGC |
| SNP242 | 1 | 614 | TAATAAAATGGATTTGGAGACGAGTGAGATTTCAAATTACAAGTCATCAGTA GTTTTGTCTAAGTTGGCTAGTAACGAACAACATGGTGAAAACTCACCAT |
| SNP242 | 2 | 615 | TAATAAAATGGATTTGGAGACGAGTGAGATTTCAAATTACAAGTCATCAGCA GTTTTGTCTAAGTTGGCTAGTAACGAACAACATGGTGAAAACTCACCAT |
| SNP243 | 1 | 616 | GCGATTGCAAAATTTATGGAGAAAACAAGAGGTGGTAAGGTTAAGTTTGAT GCTAAACGTGTAGTAATGGCTGGTGGAGCTACTGGAGCTAATGAGACTCT |
| SNP243 | 2 | 617 | GCGATTGCAAAATTTATGGAGAAAACAAGAGGTGGTAAGGTTAAGTTTGAC GCTAAACGTGTAGTAATGGCTGGTGGAGCTACTGGAGCTAATGAGACTCT |
| SNP244 | 1 | 618 | CTGCGTTCTATGCACTTCCTTCATCACATTGTTGTGCAACATCGCTAAACACA GTTGGATTAATGCAACATTTTCGAAGAAAAGCCAACAACTCCTCTTTA |
| SNP244 | 2 | 619 | CTGCGTTCTATGCACTTCCTTCATCACATTGTTGTGCAACATCGCTAAACTCA GTTGGATTAATGCAACATTTTCGAAGAAAAGCCAACAACTCCTCTTTA |
| SNP245 | 1 | 620 | TAAGGTTTCCAGACAATTGTGGTCTCAGCAATCATGGATGTAACAGTGTAAG GATCCATGTTCGAAGCAGGCCTCCTGTCCTCGAAATATCCCTTCCCTGC |
| SNP245 | 2 | 621 | TAAGGTTTCCAGACAATTGTGGTCTCAGCAATCATGGATGTAACAGTGTAGG GATCCATGTTCGAAGCAGGCCTCCTGTCCTCGAAATATCCCTTCCCTGC |
| SNP246 | 1 | 622 | TTACTATGCAATTTCAAGAAAAGGGTTCATGAACTAGAAGCTGAAGTAGCAA ATAGACGATTAACGGAGTCCAAAATATTCGATTCGTTGGCCTCACAGAC |
| SNP246 | 2 | 623 | TTACTATGCAATTTCAAGAAAAGGGTTCATGAACTAGAAGCTGAAGTAGCGA ATAGACGATTAACGGAGTCCAAAATATTCGATTCGTTGGCCTCACAGAC |
| SNP247 | 1 | 624 | AATTCAATTGGTCTTGTTTGTTTGGCCCAATAGGCCAATGTGGAGTGTTAATA TAATTGGAGATTCGGGGTTTTTTCTTCTTCTTTTCAATTGTGGGGGAT |
| SNP247 | 2 | 625 | AATTCAATTGGTCTTGTTTGTTTGGCCCAATAGGCCAATGTGGAGTGTTACTA TAATTGGAGATTCGGGGTTTTTTCTTCTTCTTTTCAATTGTGGGGGAT |
| SNP248 | 1 | 626 | CAAAGTTATCCTCCCGGAGTGCAATCTCATAATAGTGCTCCTGTTCAATCTCT TCCTAGTTATGCCTATGGCAATTCCGTCGCTGCAATGCCACCCCATAC |

TABLE 9-continued

| | | | Input target sequences for 300 SNP regions | | |
|---|---|---|---|

| Target | Allele # | SEQ ID NO: | Target Sequence |
|---|---|---|---|
| SNP248 | 2 | 627 | CAAAGTTATCCTCCCGGAGTGCAATCTCATAATAGTGCTCCTGTTCAATCGCT TCCTAGTTATGCCTATGGCAATTCCGTCGCTGCAATGCCACCCCATAC |
| SNP249 | 1 | 628 | CTAATTCCCTGTTTAACTGAAAAATGGGGAGATTTACCACTAAAAGTCGATG ATTCCGAAGATATGGTAATTTACGGTCTATTAAAAGACGCTCTAAGCGT |
| SNP249 | 2 | 629 | CTAATTCCCTGTTTAACTGAAAAATGGGGAGATTTACCACTAAAAGTCGACG ATTCCGAAGATATGGTAATTTACGGTCTATTAAAAGACGCTCTAAGCGT |
| SNP250 | 1 | 630 | TCGGATGTTATCAGTGTGTGTACAGTAAAACCTCTGGTCTTATGTGTACTATG GAGTATCATTGTAATAGCAGTACAAGCTTTGAAATGGACTCTACTTGT |
| SNP250 | 2 | 631 | TCGGATGTTATCAGTGTGTGTACAGTAAAACCTCTGGTCTTATGTGTACTGTG GAGTATCATTGTAATAGCAGTACAAGCTTTGAAATGGACTCTACTTGT |
| SNP251 | 1 | 632 | TACACTTTGTGCTATTTTCAGATGAAATTTATGATGCATGGGTGACAGCAACG AATGAACAGTTGAATTGATTAGTATGTTTACGAGTATTTGCAAGACGG |
| SNP251 | 2 | 633 | TACACTTTGTGCTATTTTCAGATGAAATTTATGATGCATGGGTGACAGCAGC GAATGAACAGTTGAATTGATTAGTATGTTTACGAGTATTTGCAAGACGG |
| SNP252 | 1 | 634 | TAATAAACCTTAGCAAAGTTGCCTTGACCTAATAATCTCCCCAAATCGTATTT TTCCATCAGTACATTTCCTTTTTTCTCCATTTGAACCAACAATTCTTG |
| SNP252 | 2 | 635 | TAATAAACCTTAGCAAAGTTGCCTTGACCTAATAATCTCCCCAAATCGTACTT TTCCATCAGTACATTTCCTTTTTTCTCCATTTGAACCAACAATTCTTG |
| SNP253 | 1 | 636 | CAATTTTAACTCAATAACAGGAAATCACACCTAATCCAGGACACGACGCTTG TTCAGATGTATCTACGGAATAATAGCAACCACAGATAACACGACCCCAA |
| SNP253 | 2 | 637 | CAATTTTAACTCAATAACAGGAAATCACACCTAATCCAGGACACGACGCTCG TTCAGATGTATCTACGGAATAATAGCAACCACAGATAACACGACCCCAA |
| SNP254 | 1 | 638 | GGCCCTAGCAAATTATTCGCCATCTCCCTTAGCACATGCTTCAGTTCATTCCC ATCATTAATTACTGAACACCCGCTCAAAGGTGAACCATAAGTGTTGTC |
| SNP254 | 2 | 639 | GGCCCTAGCAAATTATTCGCCATCTCCCTTAGCACATGCTTCAGTTCATTGCC ATCATTAATTACTGAACACCCGCTCAAAGGTGAACCATAAGTGTTGTC |
| SNP255 | 1 | 640 | AAATTCCGGTTTTGTATACCGATGATGAAAACACTCTAGCTAGGTGTGTTATG GGGTTTAAACTTTTTTGGGGTATTTGATGTCCATTGTTGATTTTGAAC |
| SNP255 | 2 | 641 | AAATTCCGGTTTTGTATACCGATGATGAAAACACTCTAGCTAGGTGTGTTGT GGGGTTTAAACTTTTTTGGGGTATTTGATGTCCATTGTTGATTTTGAAC |
| SNP256 | 1 | 642 | TACTCTGTTGAACCTGCTGAAAGCAGGAGGCCTTTCCGTGCTCTCTTGGATGT CGGCCTCTTAAGAACTACTACAGGGAACCGTGTTTTTGGTGCTCTCAA |
| SNP256 | 2 | 643 | TACTCTGTTGAACCTGCTGAAAGCAGGAGGCCTTTCCGTGCTCTCTTGGACGT CGGCCTCTTAAGAACTACTACAGGGAACCGTGTTTTTGGTGCTCTCAA |
| SNP257 | 1 | 644 | ATATAGATCTGTGTGAAAGGCATCATATGTTAGCTCTCTGTTATTACGGAAA AGGAGATAATTTCACCGCCTTGAACTTGTTGCGGAAACTATTGAGTAGT |
| SNP257 | 2 | 645 | ATATAGATCTGTGTGAAAGGCATCATATGTTAGCTCTCTGTTATTACGGAGA AGGAGATAATTTCACCGCCTTGAACTTGTTGCGGAAACTATTGAGTAGT |
| SNP258 | 1 | 646 | CGGCGAAATTCCAGTAGACATTCAGGGTCTGAGTAATTTGAGAGCATTGAAC TTGGGGAGAAATAAGTTCATGGGTGAAATTCCAGATGAAATTGGAGGTT |
| SNP258 | 2 | 647 | CGGCGAAATTCCAGTAGACATTCAGGGTCTGAGTAATTTGAGAGCATTGAGC TTGGGGAGAAATAAGTTCATGGGTGAAATTCCAGATGAAATTGGAGGTT |
| SNP259 | 1 | 648 | ACAATACATGAGAGGAACAAATTAAGTAAGATCATCTTCCTCAAGCTCCTTC GCCTTCAATGTTTCCTTGACTCTTAGAAGTAGTGTTGTCCTCCAAGCAT |
| SNP259 | 2 | 649 | ACAATACATGAGAGGAACAAATTAAGTAAGATCATCTTCCTCAAGCTCCTCC GCCTTCAATGTTTCCTTGACTCTTAGAAGTAGTGTTGTCCTCCAAGCAT |
| SNP260 | 1 | 650 | ATAAGTGTCCACTTGACCATAATGCCCTTGTGAGATGGGTGTGGAGGATGAG TCCCACATGTTCAAGGGCATAGGTTGGTGATGCTGATGAGGTGGACCAA |
| SNP260 | 2 | 651 | ATAAGTGTCCACTTGACCATAATGCCCTTGTGAGATGGGTGTGGAGGATGGG TCCCACATGTTCAAGGGCATAGGTTGGTGATGCTGATGAGGTGGACCAA |

TABLE 9-continued

| | | | |
|---|---|---|---|
| | | | Input target sequences for 300 SNP regions |

| Target | Allele # | SEQ ID NO: | Target Sequence |
|---|---|---|---|
| SNP261 | 1 | 652 | CCCATTCTTTGTTTCTACACACAATTCAAAATCCCCTCCTCCCTCTCTTTTCCC CCCTTTGAACTCTGCAGCCGTACGCCACTCTCATTTTCCTGCGAATT |
| SNP261 | 2 | 653 | CCCATTCTTTGTTTCTACACACAATTCAAAATCCCCTCCTCCCTCTCTTTCCCC CCCTTTGAACTCTGCAGCCGTACGCCACTCTCATTTTCCTGCGAATT |
| SNP262 | 1 | 654 | CAGTAAAAATGCTTGCAAAGGGCAGAAGACCTCCCACCAGAGAAATAACAT ATGGTCTTAGGTACCATTTCTTCTCAGGGATAGGACGCGGAATATTCTTA |
| SNP262 | 2 | 655 | CAGTAAAAATGCTTGCAAAGGGCAGAAGACCTCCCACCAGAGAAATAACAG ATGGTCTTAGGTACCATTTCTTCTCAGGGATAGGACGCGGAATATTCTTA |
| SNP263 | 1 | 656 | ATCATCTTTCTTCTCCGGATTGGGAGAAAATACCCCTGCTGTAACAAGTGTG GTAAGTACAAGAGAAATGGCGAAAACATTCATCATCTTTTCCAATTAGT |
| SNP263 | 2 | 657 | ATCATCTTTCTTCTCCGGATTGGGAGAAAATACCCCTGCTGTAACAAGTGCG GTAAGTACAAGAGAAATGGCGAAAACATTCATCATCTTTTCCAATTAGT |
| SNP264 | 1 | 658 | TGGGTGCTCAATGGTCAGATGACCATCTGAGTGTGAGAAATATGCACTCCTT CACAAGCAGCAGGCCTATCAGAGTGCTGCTCATGCGTGGTTCAGCAGAG |
| SNP264 | 2 | 659 | TGGGTGCTCAATGGTCAGATGACCATCTGAGTGTGAGAAATATGCACTCCGT CACAAGCAGCAGGCCTATCAGAGTGCTGCTCATGCGTGGTTCAGCAGAG |
| SNP265 | 1 | 660 | GTGCATTTTTTCCATGATGGACAAGGTTTCATGTCTGTTGAGTTGACACCAAC AGAGGCTGAGATCAAATATTATGATGTTTTTGGTAGAATTAGACATAG |
| SNP265 | 2 | 661 | GTGCATTTTTTCCATGATGGACAAGGTTTCATGTCTGTTGAGTTGACACCGAC AGAGGCTGAGATCAAATATTATGATGTTTTTGGTAGAATTAGACATAG |
| SNP266 | 1 | 662 | AGTTAATTCTTGTGCTGCTTGCTATATTTTGAGGCCTGTTGGACGCAACAAAC TAGTAAAATAGGATCTTAGTCATGTATTGCCTCAAGAATTTGTGTTTC |
| SNP266 | 2 | 663 | AGTTAATTCTTGTGCTGCTTGCTATATTTTGAGGCCTGTTGGACGCAACATAC TAGTAAAATAGGATCTTAGTCATGTATTGCCTCAAGAATTTGTGTTTC |
| SNP267 | 1 | 664 | GGCCCGGATAAGATTAGTAAAATATATGGCGACTGGATTGATGACATCGAAT GAAGGAGTTGTCATAATTAGCTACTGATCTGTTTAGCTAGACACAAATA |
| SNP267 | 2 | 665 | GGCCCGGATAAGATTAGTAAAATATATGGCGACTGGATTGATGACATCGAGT GAAGGAGTTGTCATAATTAGCTACTGATCTGTTTAGCTAGACACAAATA |
| SNP268 | 1 | 666 | GGTCGGAAGCAATTGATGGGGCAAGAATCGGTCGGAAATGGAGTTCTAGGA CATTTATCTTCGTCGTCTTGATGAGAAGGTAGTGGATTTAAACCGTTTAA |
| SNP268 | 2 | 667 | GGTCGGAAGCAATTGATGGGGCAAGAATCGGTCGGAAATGGAGTTCTAGGG CATTTATCTTCGTCGTCTTGATGAGAAGGTAGTGGATTTAAACCGTTTAA |
| SNP269 | 1 | 668 | TATGTAGCTAGGAAGAGAGTTGAAAAGACCTAGCTTACAAAAGATGGGGGA AAAAAGGGGGAGATGATAAATAAGGTATAAGTTTTTGAGAGATGAATGAA |
| SNP269 | 2 | 669 | TATGTAGCTAGGAAGAGAGTTGAAAAGACCTAGCTTACAAAAGATGGGGGG AAAAAGGGGGAGATGATAAATAAGGTATAAGTTTTTGAGAGATGAATGAA |
| SNP270 | 1 | 670 | CAACACCTGTACAGGATACATCTGCAGAAGAATTGTTGTCCAGAAAGATGAC AGGCAATAGGTTGGCAGAATCTTTATGGCCCTCAACAATGAGGAGTCTG |
| SNP270 | 2 | 671 | CAACACCTGTACAGGATACATCTGCAGAAGAATTGTTGTCCAGAAAGATGGC AGGCAATAGGTTGGCAGAATCTTTATGGCCCTCAACAATGAGGAGTCTG |
| SNP271 | 1 | 672 | GTCTCCTATGCTCTTCCTGTCTCCTTTGTTTCAAGTGGTATCATGCGTTCAGAG ACAGAAGTTGAGGAGAAATCAATCGAAACAACCCAGACAACCACCAT |
| SNP271 | 2 | 673 | GTCTCCTATGCTCTTCCTGTCTCCTTTGTTTCAAGTGGTATCATGCGTTCGGAG ACAGAAGTTGAGGAGAAATCAATCGAAACAACCCAGACAACCACCAT |
| SNP272 | 1 | 674 | ATCTCAGGAACTTCTCTAAAGAACGTATCTTGTCTTCCAGGATTTGCATGATC TCACCAGGAAGTCGGCAGACAACTACTACATTGTCAAATGCTTCTGAA |
| SNP272 | 2 | 675 | ATCTCAGGAACTTCTCTAAAGAACGTATCTTGTCTTCCAGGATTTGCATGGTC TCACCAGGAAGTCGGCAGACAACTACTACATTGTCAAATGCTTCTGAA |
| SNP273 | 1 | 676 | GACAGCTCCACTTGCAGCAGAAAGTGTGACTCCAACAAAGCGAAACAGAAA ATCTTCAGCTTCTAAGGAGGACGTGAAAGACAAAAAGAACAGGAAGAAA |

TABLE 9-continued

| | Allele | SEQ ID | |
|---|---|---|---|
| Target | # | NO: | Target Sequence |
| SNP273 | 2 | 677 | GACAGCTCCACTTGCAGCAGAAAGTGTGACTCCAACAAAGCGAAACAGAAG ATCTTCAGCTTCTAAGAAGGACGTGAAAGACAAAAAGAACAGGAAGAAA |
| SNP274 | 1 | 678 | CATGAAGTTGGGATACACGAATGCATATAAAGCTTTTGATCCAAGTCGATCA AAATCTTGGTCCTTCCCCGCACTACCAGTTTCACATCGTTGGATGCTGA |
| SNP274 | 2 | 679 | CATGAAGTTGGGATACACGAATGCATATAAAGCTTTTGATCCAAGTCGATGA AAATCTTGGTCCTTCCCCGCACTACCAGTTTCACATCGTTGGATGCTGA |
| SNP275 | 1 | 680 | TCTTTTGTCAGAAGGAATCAACTCGGGGGTTGATGGAGCCAGAAGCATCTAG TGGTGGTTAGCTAGGCTGTTAATCATCCAACAAAGTTGTTAGATGATC |
| SNP275 | 2 | 681 | TCTTTTGTCAGAAGGAATCAACTCGGGGGTTGATGGAGCCAGAAGCATCTCG TGGTGGTTAGCTAGGCTGTTAATCATCCAACAAAGTTGTTAGATGATC |
| SNP276 | 1 | 682 | CTACTCTTTCACAATACATTCAAGTGGTGAAGTTCACATAGTGTGCCTCATCA CTTTTATTCATGCTACATGCATTACTTAATTTTATTCATAAGTTACAC |
| SNP276 | 2 | 683 | CTACTCTTTCACAATACATTCAAGTGGTGAAGTTCACATAGTGTGCCTCACCA CTTTTATTCATGCTACATGCATTACTTAATTTTATTCATAAGTTACAC |
| SNP277 | 1 | 684 | ACCTTCCTCCATGCCACAAAGTTCCCAGAACCTCCACCACGATAAGTTCTAGT ATCACAGAAGTCGAAGTTGAAGAAATAACTATTTTGGGAGCTTATTGG |
| SNP277 | 2 | 685 | ACCTTCCTCCATGCCACAAAGTTCCCAGAACCTCCACCACGATAAGTTCTGG TATCACAGAAGTCGAAGTTGAAGAAATAACTATTTTGGGAGCTTATTGG |
| SNP278 | 1 | 686 | TTGATCTTTAACCCTGCAACCGAAGCTATTGACTGTGAAAACTTCACCAACA AGCATTTGATCAATGACCTCCTCCCTCTTCGACCCAGTCAACTTGTGCA |
| SNP278 | 2 | 687 | TTGATCTTTAACCCTGCAACCGAAGCTATTGACTGTGAAAACTTCACCAAGA AGCATTTGATCAATGACCTCCTCCCTCTTCGACCCAGTCAACTTGTGCA |
| SNP279 | 1 | 688 | CCTGAAGAAGCTGTTTCGACTGATACTATTAATGGTGGGGGGCAGAACCCAG TTTTCGATCAGAGTCTTCGACTTAATGTCAAGACTATTGAAACATCAGT |
| SNP279 | 2 | 689 | CCTGAAGAAGCTGTTTCGACTGATACTATTAATGGTGGGGGGCAGAACCCGG TTTTCGATCAGAGTCTTCGACTTAATGTCAAGACTATTGAAACATCAGT |
| SNP280 | 1 | 690 | CACTCCGAAACTTTGTCAGAACAGGGAAGTGTCAAATCAATTGGGACTACTC CGGTAACCCAACTGCCCAGGCTGCACAAGAATGTCAGCGACTCAATGTT |
| SNP280 | 2 | 691 | CACTCCGAAACTTTGTCAGAACAGGGAAGTGTCAAATCAATTGGGACTACCC CGGTAACCCAACTGCCCAGGCTGCACAAGAATGTCAGCGACTCAATGTT |
| SNP281 | 1 | 692 | TCAGGCTGGATTCTTGGTTTATTCGAAGCGGTTAGTCACAGTAAGATAAGTTT TGTTGTATAAGCGGTGGGTAAAGCGGTTGTCGGTTTGCTGAACATGCC |
| SNP281 | 2 | 693 | TCAGGCTGGATTCTTGGTTTATTCGAAGCGGTTAGTCACAGTAAGATAAGCT TTGTTGTATAAGCGGTGGGTAAAGCGGTTGTCGGTTTGCTGAACATGCC |
| SNP282 | 1 | 694 | CAACTTTAAGTCGAGGATGAAGGGTGGTGGTGATTTGGCTGTTGCATCTATT ACGAATGGAAAAGATAGATATGTTCCGTTTGATGTGGAGAACGGTTCTA |
| SNP282 | 2 | 695 | CAACTTTAAGTCGAGGATGAAGGGTGGTGGTGATTTGGCTGTTGCATCTACT ACGAATGGAAAAGATAGATATGTTCCGTTTGATGTGGAGAACGGTTCTA |
| SNP283 | 1 | 696 | GTGAGGCTACTGTCGGGTTACCCGGTGGGTGTGACATTGGGGCCCGACCCAT TGATTTTTACATTCATGGTCTACGTGCTCTTGGTGCTACGGTTGAGTTG |
| SNP283 | 2 | 697 | GTGAGGCTACTGTCGGGTTACCCGGTGGGTGTGACATTGGGGCCCGACCCGT TGATTTTTACATTCATGGTCTACGTGCTCTTGGTGCTACGGTTGAGTTG |
| SNP284 | 1 | 698 | CAGACGACAATACTGTTGGACCAACTTGCATTTTCGGGATCACCTTTGTCTGG CAAGCAACCTTTTCTGAAACTTGCTTAGGTGATTTTCTTCTTCCCTGT |
| SNP284 | 2 | 699 | CAGACGACAATACTGTTGGACCAACTTGCATTTTCGGGATCACCTTTGTCCG GCAAGCAACCTTTTCTGAAACTTGCTTAGGTGATTTTCTTCTTCCCTGT |
| SNP285 | 1 | 700 | CAAAAAGTTTTCAAACCGTGTGATTTCTGGTGAACCTGATCCAGATCGTCAT GTAGTTGCACCAATCAAGTCAGACAAAAAGTTTTCATACCCAGATCTTC |
| SNP285 | 2 | 701 | CAAAAAGTTTTCAAACCGTGTGATTTCTGGTGAACCTGATCCAGATCGTCCT GTAGTTGCACCAATCAAGTCAGACAAAAAGTTTTCATACCCAGATCTTC |

TABLE 9-continued

| | Allele | SEQ ID | |
|---|---|---|---|
| Target | # | NO: | Target Sequence |

Input target sequences for 300 SNP regions

| Target | Allele # | SEQ ID NO: | Target Sequence |
|---|---|---|---|
| SNP286 | 1 | 702 | CGGTGGCGGCAACAGCGGAGGAGAATCGGCGTGGTAGGGAGGGTTTGAAGA<br>TTGGGTTTACCGTTTTGAGTGATGAAGGTTTTGGAATTCGCGGAAGCAGA |
| SNP286 | 2 | 703 | CGGTGGCGGCAACAGCGGAGGAGAATCGGCGTGGTAGGGAGGGTTTGAAGG<br>TTGGGTTTACCGTTTTGAGTGATGAAGGTTTTGGAATTCGCGGAAGCAGA |
| SNP287 | 1 | 704 | GAGTTTTTTTTGCGGAGTTGAACGAAGTGCTTACAAGAGAGTTGGCGGAGAA<br>TGGTTACTCGGGAGTTGAAGTTAGGGTTACTCCCGTGCGAACTGAAATC |
| SNP287 | 2 | 705 | GAGTTTTTTTTGCGGAGTTGAACGAAGTGCTTACAAGAGAGTTGGCGGAGGA<br>TGGTTACTCGGGAGTTGAAGTTAGGGTTACTCCCGTGCGAACTGAAATC |
| SNP288 | 1 | 706 | AACAAAACTTGAAGAGCAATTTAAGGAAGTGAAGTTGGAAGAAAGAGCAGT<br>CCGTAGGGAAGCCAGAAGGAAGATGTATGGTTGGTCACCAAAATCAGAGG |
| SNP288 | 2 | 707 | AACAAAACTTGAAGAGCAATTTAAGGAAGTGAAGTTGGAAGAAAGAGCAGC<br>CCGTAGGGAAGCCAGAAGGAAGATGTATGGTTGGTCACCAAAATCAGAGG |
| SNP289 | 1 | 708 | CAGGACCAAGTCTCCGATCTTTCTGGATTAAACGGGAAACTGCATCCATAAC<br>CTCATTACTAATGTCAAGAGGCTTAGATGCAGCCCGAACACTTGGGATA |
| SNP289 | 2 | 709 | CAGGACCAAGTCTCCGATCTTTCTGGATTAAACGGGAAACTGCATCCATAGC<br>CTCATTACTAATGTCAAGAGGCTTAGATGCAGCCCGAACACTTGGGATA |
| SNP290 | 1 | 710 | TCTGTCATGCGTTAATCGTGTTAACATTTCCTTTAAGGTATGACGATGAGTTC<br>TGGCATCCGATTTACATGCCCGGACTGTTTTTTGATGGCAAAGTTTCT |
| SNP290 | 2 | 711 | TCTGTCATGCGTTAATCGTGTTAACATTTCCTTTAAGGTATGACGATGAGCTC<br>TGGCATCCGATTTACATGCCCGGACTGTTTTTTGATGGCAAAGTTTCT |
| SNP291 | 1 | 712 | CATATTAGTAAAGGCCTAATGGAAGGGACACGATAAACTTGCTCCTCAATTA<br>GCTCGTTGCCTGTTGTGGTTCCAAGTTGGTCCCTGGTTGTCTCAGTCTC |
| SNP291 | 2 | 713 | CATATTAGTAAAGGCCTAATGGAAGGGACACGATAAACTTGCTCCTCAATCA<br>GCTCGTTGCCTGTTGTGGTTCCAAGTTGGTCCCTGGTTGTCTCAGTCTC |
| SNP292 | 1 | 714 | TTAATAGGTGCTACTCCGAGGTTCTTCGGTAGGTATTGCTTGCTAGAGGATA<br>AACTCGAACGGATTAAAATTTATTGCTACAGGCGCTGTGCGTCTATGTT |
| SNP292 | 2 | 715 | TTAATAGGTGCTACTCCGAGGTTCTTCGGTAGGTATTGCTTGCTAGAGGACA<br>AACTCGAACGGATTAAAATTTATTGCTACAGGCGCTGTGCGTCTATGTT |
| SNP293 | 1 | 716 | CCATCCGCTAAATCCAAAAATTTCGTTGAATATTAGGTTACCTGCAAAAAAG<br>CAAAAGGCAACCCATCTGAATCCCTTCGCGGAACTTTCTATATTTGGTA |
| SNP293 | 2 | 717 | CCATCCGCTAAATCCAAAAATTTCGTTGAATATTAGGTTACCTGCAAAAAGG<br>CAAAAGGCAACCCATCTGAATCCCTTCGCGGAACTTTCTATATTTGGTA |
| SNP294 | 1 | 718 | TCATCGACTAATTCAAATTCACGCTCCTTGCCTCAGTCACATTAAGGACTAGG<br>CCGGTGTCGATCCGCAAATCGATTAACCAAAGCAAGTGCATTACTAGT |
| SNP294 | 2 | 719 | TCATCGACTAATTCAAATTCACGCTCCTTGCCTCAGTCACATTAAGGACTTGG<br>CCGGTGTCGATCCGCAAATCGATTAACCAAAGCAAGTGCATTACTAGT |
| SNP295 | 1 | 720 | ATCAACGCCGCCGACACTGAATGAAGCTCCGAGTGTGATTCGGGTCGGGTTG<br>GAAACGACATTTCCGGTTCGAGAAAATCACCTAAACCAAAAACAGTGAA |
| SNP295 | 2 | 721 | ATCAACGCCGCCGACACTGAATGAAGCTCCGAGTGTGATTCGGGTCGGGTCG<br>GAAACGACATTTCCGGTTCGAGAAAATCACCTAAACCAAAAACAGTGAA |
| SNP296 | 1 | 722 | GAACACTATGAAGATGAGACCCCAGATGACACCGAAGATGACGATGAGGGT<br>GGAAAAGAAGCATCTCTTGGGCGTTATTGTGTCTTCTGTAGTAAACTTGA |
| SNP296 | 2 | 723 | GAACACTATGAAGATGAGACCCCAGATGACACCGAAGATGACGATGAGGGG<br>GGAAAAGAAGCATCTCTTGGGCGTTATTGTGTCTTCTGTAGTAAACTTGA |
| SNP297 | 1 | 724 | ACTGCAAGTAAAAATGTTTCATATACGGATGCTGCAGCTGTTGAAGAAAAAA<br>AATCCTGGTCTTCTTCTGCATGCCCATACAACCTGTAGAGGACACGCAA |
| SNP297 | 2 | 725 | ACTGCAAGTAAAAATGTTTCATATACGGATGCTGCAGCTGTTGAAGAAAGA<br>AATCCTGGTCTTCTTCTGCATGCCCATACAACCTGTAGAGGACACGCAA |
| SNP298 | 1 | 726 | GTTCAGTATCCCGAAATTCAAAGGTTTGCTTTTCGGCTCCTTAGTCAGACATG<br>CAATGGTGCTTCACATTATAGGCTGAAAAGGAGCTTGGTCGAGACATT |

TABLE 9-continued

| | | | Input target sequences for 300 SNP regions |
|---|---|---|---|
| Target | Allele # | SEQ ID NO: | Target Sequence |

| Target | Allele # | SEQ ID NO: | Target Sequence |
|---|---|---|---|
| SNP298 | 2 | 727 | GTTCAGTATCCCGAAATTCAAAGGTTTGCTTTTCGGCTCCTTAGTCAGACTTG CAATGGTGCTTCACATTATAGGCTGAAAAGGAGCTTGGTCGAGACATT |
| SNP299 | 1 | 728 | ACTATAGCGTGCATGGGAAACAGAAAATTGAGTTTGATCCTTGATGATTGAA AATGAAGGATCAGCAGAACCGTCTTTGCTCTGAGAAACAACAAAAGGTG |
| SNP299 | 2 | 729 | ACTATAGCGTGCATGGGAAACAGAAAATTGAGTTTGATCCTTGATGATTGGA AATGAAGGATCAGCAGAACCGTCTTTGCTCTGAGAAACAACAAAAGGTG |
| SNP300 | 1 | 730 | TAACCACAGCATCAGACAAAGACATAAAGAGGCTGCGATGAGGAGAAAAAA ATATGGAGTAGACACACTACTCCCAATATTCCACTTCAAATTATTAACCC |
| SNP300 | 2 | 731 | TAACCACAGCATCAGACAAAGACATAAAGAGGCTGCGATGAGGAGAAAAAC ATATGGAGTAGACACACTACTCCCAATATTCCACTTCAAATTATTAACCC |
| SNP301 | 1 | 732 | TGGTGTTCTAACATTTGAAAGCAAATTCTGCAACCTTTCCACACTCATTCTAG CACATGATGCGATGTCTTCTTTGGTTGGATGACGATTGCCTTGTCGAA |
| SNP301 | 2 | 733 | TGGTGTTCTAACATTTGAAAGCAAATTCTGCAACCTTTCCACACTCATTCCAG CACATGATGCGATGTCTTCTTTGGTTGGATGACGATTGCCTTGTCGAA |
| SNP302 | 1 | 734 | CGTTTGCATGACCGTCTGTGGCTGCATTCGTAGATGTTGAATTTGCTTTCAGT ACCAAACTTTTGTATGACAGACGACATAACTTCTGTCATATTTCCAGG |
| SNP302 | 2 | 735 | CGTTTGCATGACCGTCTGTGGCTGCATTCGTAGATGTTGAATTTGCTTTCGGT ACCAAACTTTTGTATGACAGACGACATAACTTCTGTCATATTTCCAGG |
| SNP303 | 1 | 736 | CCATCCCAGAAGACATAATTTGTAGCATTGGAGCATGTTCCGATGGACCTAG CATTACAAAGGAATGATGTTTCTAGTGTACCAGTCCCGCAGCAAGCCTT |
| SNP303 | 2 | 737 | CCATCCCAGAAGACATAATTTGTAGCATTGGAGCATGTTCCGATGGACCTGG CATTACAAAGGAATGATGTTTCTAGTGTACCAGTCCCGCAGCAAGCCTT |
| SNP304 | 1 | 738 | GAATTCTTGCATTTGAAATTGCAACTTTGATGTCTAAGGTGGTTAACTTGTGG CAGTGTCTAAGTGAAAGGCGANTCGACAAGTTAAGAGAAGAAATCTCAAGT TCACTTGGCATTCAGAAGCTTGTTGCTGAAGATGACAAATATCTTATGGATCT TGCTNTTGCTGAGATAATTGACAATTTGGGATCTCTGACGAAGT |
| SNP304 | 2 | 739 | GAATTCTTGCATTTGAAATTGCAACTTTGATGTCTAAGGTGGTTAACTTGTGG CAGTGTCTAAGTGAAAGGCGANTCGACAAGTTAAGAGAAGAAATCTCGAGT TCACTTGGCATTCAGAAGCTTGTTGCTGAAGATGACAAATATCTTATGGATCT TGCTNTTGCTGAGATAATTGACAATTTGGGATCTCTGACGAAGT |
| SNP305 | 1 | 740 | CCCACAAAATAGCTGGTAGAGAATCATTGATTGGCTCAATTTAGCCTCTATA ACACATTTTGCAAGAACTGAAAGATTGATAAGTAACCATCCCATCATAC |
| SNP305 | 2 | 741 | CCCACAAAATAGCTGGTAGAGAATCATTGATTGGCTCAATTTAGCCTCTACA ACACATTTTGCAAGAACTGAAAGATTGATAAGTAACCATCCCATCATAC |
| SNP306 | 1 | 742 | AATGATGTCATTGAGATCTTTAGTGGATAGTAAAATGGTGGGTTCTTAAGTA AAATGGTAAAGAGGTGCGCTGTTCGTGATGTGGGCTTGTAGATAAAGCT |
| SNP306 | 2 | 743 | AATGATGTCATTGAGATCTTTAGTGGATAGTAAAATGGTGGGTTCTTAAGGA AAATGGTAAAGAGGTGCGCTGTTCGTGATGTGGGCTTGTAGATAAAGCT |
| SNP307 | 1 | 744 | CAAAACCCGCATGCTGGTGACGTTTTGGTTGATTCTATGAAAAGGTATTATG GAAAGTTACCTGCAGTCGTTGAACTGTTTAGTCAAGTTGGAGCACAGGT |
| SNP307 | 2 | 745 | CAAAACCCGCATGCTGGTGACGTTTTGGTTGATTCTATGAAAAGGTATTACG GAAAGTTACCTGCAGTCGTTGAACTGTTTAGTCAAGTTGGAGCACAGGT |
| SNP308 | 1 | 746 | ACACTCATGAACATTGCTGATAACCCGACGAATGTCCAACTCCCCGGTATAT ACAACAAGCAAGAGAATGCCAGGGTACCTATTATTGTCACTGGTAACGA |
| SNP308 | 2 | 747 | ACACTCATGAACATTGCTGATAACCCGACGAATGTCCAACTCCCCGGTATGT ACAACAAGCAAGAGAATGCCAGGGTACCTATTATTGTCACTGGTAACGA |
| SNP309 | 1 | 748 | TTAATGCATCACAGACAGGATGTAAACCACACCCTACGCGTATAGATATTAT CAGCCCATTATCCAATTTGTTGAAGCGTTTGCAAGTTAGGGATACAGAG |
| SNP309 | 2 | 749 | TTAATGCATCACAGACAGGATGTAAACCACACCCTACGCGTATAGATATTCT CAGCCCATTATCCAATTTGTTGAAGCGTTTGCAAGTTAGGGATACAGAG |

TABLE 9-continued

| | | | Input target sequences for 300 SNP regions |
|---|---|---|---|

| Target | Allele # | SEQ ID NO: | Target Sequence |
|---|---|---|---|
| SNP310 | 1 | 750 | TCTTTTGGTAGAAGAGATGTGCCATCTTTCCAATTTTCATCAATATATTCAAG AATCACTAGAGACTCAGGAATTGGATTTCCCTTGTGCAAAAATACAGG |
| SNP310 | 2 | 751 | TCTTTTGGTAGAAGAGATGTGCCATCTTTCCAATTTTCATCAATATATTCCAG AATCACTAGAGACTCAGGAATTGGATTTCCCTTGTGCAAAAATACAGG |
| SNP311 | 1 | 752 | GAGTAGAAGAAGAATCAAAAAGCAAAAATGGTGAAAGACAGAACCATTGGT GTGGCTGTAGATTTTTCAAAGAGCAGCAAAACAGCTTTGAAATGGGCAAT |
| SNP311 | 2 | 753 | GAGTAGAAGAAGAATCAAAAAGCAAAAATGGTGAAAGACAGAACCATTGG CGTGGCTGTAGATTTTTCAAAGAGCAGCAAAACAGCTTTGAAATGGGCAAT |
| SNP312 | 1 | 754 | TCGCTCATCTACCCTTCTCCACTTAAATAGTTTACGGGCAAGACTCGTACAGT GCATCCCGCAGTGGGGACACAAGTATGTGTCTTTCATTTGGTTCTTAA |
| SNP312 | 2 | 755 | TCGCTCATCTACCCTTCTCCACTTAAATAGTTTACGGGCAAGACTCGTACCGT GCATCCCGCAGTGGGGACACAAGTATGTGTCTTTCATTTGGTTCTTAA |
| SNP313 | 1 | 756 | TACAGATCCTCTGTTTTCTTCAAACAACAAATGTCTCTTATTCCAAGCTTTTTT GGTGGTCGGAGGAGCAATATCTTCGACCCATTTTCCCTTGACTTATG |
| SNP313 | 2 | 757 | TACAGATCCTCTGTTTTCTTCAAACAACAAATGTCTCTTATTCCAAGCTTCTTT GGTGGTCGGAGGAGCAATATCTTCGACCCATTTTCCCTTGACTTATG |
| SNP314 | 1 | 758 | TCCAAATCCATAAGTGGTTGTTACTTCACTTGAACACCATTCCCCTTCTTAGC TGAATTTGTGTTGCATCACCTTTTTCCGTAGTGCATGCTCCTCTTGGT |
| SNP314 | 2 | 759 | TCCAAATCCATAAGTGGTTGTTACTTCACTTGAACACCATTCCCCTTCTTCGC TGAATTTGTGTTGCATCACCTTTTTCCGTAGTGCATGCTCCTCTTGGT |
| SNP315 | 1 | 760 | CAGGAAGACATAATCACAACACTTTTGAATCTGTCCATCCATGACAACAATA AGAAGCTTGTCGCGGAGACTCCAAAAGTTATTCCACTTCTTGTGGAGGC |
| SNP315 | 2 | 761 | CAGGAAGACATAATCACAACACTTTTGAATCTGTCCATCCATGACAACAACA AGAAGCTTGTCGCGGAGACTCCAAAAGTTATTCCACTTCTTGTGGAGGC |
| SNP316 | 1 | 762 | GATGGAATTACACACAACCTCAGATGAATATGAGAGACAGCTACATACCTAA TTGGTCTGCATCGCGTAATCCTGGGCATTATTCTGGCTATCGTGGTCCT |
| SNP316 | 2 | 763 | GATGGAATTACACACAACCTCAGATGAATATGAGAGACAGCTACATACCTG ATTGGTCTGCATCGCGTAATCCTGGGCATTATTCTGGCTATCGTGGTCCT |
| SNP317 | 1 | 764 | CCAGCATAAATTTAAGAATGGAGTAGAATCCAATTGACAAAAGAGAGCAGT TATTAACGCACCTAAACATCCTTACCCGCACTGCAATTAATGCATTTATC |
| SNP317 | 2 | 765 | CCAGCATAAATTTAAGAATGGAGTAGAATCCAATTGACAAAAGAGAGCAGC TATTAACGCACCTAAACATCCTTACCCGCACTGCAATTAATGCATTTATC |
| SNP318 | 1 | 766 | ACTGCTGGACCTGGCATTGACATGTCCATGGCACATAATCATGCTATTTTTCA GAGTCTCCCGGAAGCTACGAGGCAAAATTTACAGATGGCCGCAGCAGC |
| SNP318 | 2 | 767 | ACTGCTGGACCTGGCATTGACATGTCCATGGCACATAATCATGCTATTTTCCA GAGTCTCCCGGAAGCTACGAGGCAAAATTTACAGATGGCCGCAGCAGC |
| SNP319 | 1 | 768 | GATTTATTCACAGATAACGAAGAGGATGATATGGAAAATGCTGATATCAGTA TCAAGGGAAGGAGGAGAGAAGACGATGGCATCTTTTTACGACTCAGGAT |
| SNP319 | 2 | 769 | GATTTATTCACAGATAACGAAGAGGATGATATGGAAAATGCTGATATCAGCA TCAAGGGAAGGAGGAGAGAAGACGATGGCATCTTTTTACGACTCAGGAT |
| SNP320 | 1 | 770 | AAATCGGCAGAGAAGGAAGTCGAGATATTGACCAAATTTGCTCCACTCAAA GGATTCTCCATCTAATTGAACTTTCTGTTGTACAGTTTAGTTCAGTATCT |
| SNP320 | 2 | 771 | AAATCGGCAGAGAAGGAAGTCGAGATATTGACCAAATTTGCTCCACTCAAG GGATTCTCCATCTAATTGAACTTTCTGTTGTACAGTTTAGTTCAGTATCT |
| SNP321 | 1 | 772 | AGTTCAAGCAAGGTGACATACTAATCAACACGTTCGTGCAATCGTTGCTCAA TTGAGCAACAACTCCAGAACAGATCATCGCAAACATAATCGCGAAAAAA |
| SNP321 | 2 | 773 | AGTTCAAGCAAGGTGACATACTAATCAACACGTTCGTGCAATCGTTGCTCGA TTGAGCAACAACTCCAGAACAGATCATCGCAAACATAATCGCGAAAAAA |
| SNP322 | 1 | 774 | CAATACAGATATGGGAGAAAACTAAAGATCTGAAGGCACAAGTGGAGACGT ACTATAAATCCTTAAAATTCACTCCATCGCAATTCCCCACTGTTGGTGGA |

TABLE 9-continued

| | Allele | SEQ ID | |
|--------|---|-----|---|
| Target | # | NO: | Target Sequence |

SNP322   2   775   CAATACAGATATGGGAGAAAACTAAAGATCTGAAGGCACAAGTGGAGACGC
ACTATAAATCCTTAAAATTCACTCCATCGCAATTCCCCACTGTTGGTGGA

SNP323   1   776   GATGAAAAGATTGCAACTCATTTTCAAGTTGCCGTCAGCTCAATTGCACAAT
CTCTCAGAACTCAGATTATTAATAGGTCTTATGATGAAGTTTCTATATG

SNP323   2   777   GATGAAAAGATTGCAACTCATTTTCAAGTTGCCGTCAGCTCAATTGCACAGT
CTCTCAGAACTCAGATTATTAATAGGTCTTATGATGAAGTTTCTATATG

SNP324   1   778   ACAAGTTCTTCTTTGAAACGGAGATATTCAGGAACCGTCAATTGTTCAACAC
TCAGATCATATACGTTCACACGAACATATTCCCAAACACCTGGCCTTGG

SNP324   2   779   ACAAGTTCTTCTTTGAAACGGAGATATTCAGGAACCGTCAATTGTTCAACGC
TCAGATCATATACGTTCACACGAACATATTCCCAAACACCTGGCCTTGG

SNP325   1   780   GCTCGAGTCCTCAAATGAGGAATCAGCTGATTCGAGGGGTCTCCCTTCAATC
CACGTTCTAACAGACTTGTTCTTCAGTTGGTAGGTGTAGTACACTTCTT

SNP325   2   781   GCTCGAGTCCTCAAATGAGGAATCAGCTGATTCGAGGGGTCTCCCTTCAACC
CACGTTCTAACAGACTTGTTCTTCAGTTGGTAGGTGTAGTACACTTCTT

SNP326   1   782   GAGTCAAGATGAGATTGCAAAAAAGGACTCTTCAACCAGGAAGAGACCGCT
TTTTGTCAATCCTCAAAGGCCAATGAGACCAAGTACTATTGCTGCAGCTA

SNP326   2   783   GAGTCAAGATGAGATTGCAAAAAAGGACTCTTCAACCAGGAAGAGACCGCC
TTTTGTCAATCCTCAAAGGCCAATGAGACCAAGTACTATTGCTGCAGCTA

SNP327   1   784   TGGAGATGTACTCTAGATCTTAACTGTGATGTTCTGAGCTGTAAAAGTACTA
ACTCCGATCATCAGTCAGATCAACGTCCCTATTACTTTGTAACGATGTC

SNP327   2   785   TGGAGATGTACTCTAGATCTTAACTGTGATGTTCTGAGCTGTAAAAGTACCA
ACTCCGATCATCAGTCAGATCAACGTCCCTATTACTTTGTAACGATGTC

SNP328   1   786   TGAAGATTGTGTATGGTGATACTAAAGTGGATTTAAAAGGCGAAAACGACAT
AAACATGGGTGCAGGGGAAGTTGTTGGTTTTGTTCTGGAGAATAGGAAG

SNP328   2   787   TGAAGATTGTGTATGGTGATACTAAAGTGGATTTAAAAGGCGAAAACGACGT
AAACATGGGTGCAGGGGAAGTTGTTGGTTTTGTTCTGGAGAATAGGAAG

SNP329   1   788   GGATATGAAAGGTAAGAAGTTAACCGTCATTGGTACAGTTGATCCAGTGAAC
GTAGTGAGTAGGCTACGTAAGTTTTGGTGGACAGAGATACTCATAGTAG

SNP329   2   789   GGATATGAAAGGTAAGAAGTTAACCGTCATTGGTACAGTTGATCCAGTGAGC
GTAGTGAGTAGGCTACGTAAGTTTTGGTGGACAGAGATACTCATAGTAG

SNP330   1   790   AAAGAGTAAACCGGTGCACAAAGTATCCTACGTCAACAAGCTTCGGGGAAA
GCCGCACCCCAAGAAGCATAAGTAGATTCATAACCACAAAGTGATACTAT

SNP330   2   791   AAAGAGTAAACCGGTGCACAAAGTATCCTACGTCAACAAGCTTCGGGGAAG
GCCGCACCCCAAGAAGCATAAGTAGATTCATAACCACAAAGTGATACTAT

SNP331   1   792   CTTTAGCTGTCTTGATCTTCTGAAGTCTCACTTACAGTGCGTCAACTTCACTC
AGCTCTAGACTGCCCAGCTCGGGAAGACAAGATAATGCCAACAATAAG

SNP331   2   793   CTTTAGCTGTCTTGATCTTCTGAAGTCTCACTTACAGTGCGTCAACTTCAGTC
AGCTCTAGACTGCCCAGCTCGGGAAGACAAGATAATGCCAACAATAAG

SNP332   1   794   CCATAAGAGAACAACAGATTGGTGGCATTGTTCAGGTGATTGATTGATTTAT
TCCTGGATGTTTTAAACAACTTATCATGTCGATTTCTTGTGGATTACTC

SNP332   2   795   CCATAAGAGAACAACAGATTGGTGGCATTGTTCAGGTGATTGATTGATTTGT
TCCTGGATGTTTTAAACAACTTATCATGTCGATTTCTTGTGGATTACTC

SNP333   1   796   AAACCCTTATCGGCGCAAGAATGGGAAAATCTAATCGACGATTACAACCACG
GTGGTTCACGGCGGCTCCGGTGGACTTCCATCAACTACGCCGCCGTTCCTCTT
CTTGACCTCACACTTTCATCACTTCTCCGGAAAGATATCCCTCACAATC

SNP333   2   797   AAACCCTTATCGGCGCAAGAATGGGAAAATCTAATCGACGATTACAACCACG
GCGGTTCACGGCGGCTCCGGTGGACTTCCATCAACTACGCCGCCGTTCCTCTT
CTTGACCTCACACTTTCATCACTTCTCCGGAAAGATATCCCTCACAATC

SNP334   1   798   GAAAGGGGGATTTTGGTAAGAGATTGGGCACCTCAATTGGAGATCTTGTCAC
ATTGTTCGACTGGTGGATTCTTGAGTCACTGTGGGTGGAATTCATGCAT

TABLE 9-continued

| | Allele | SEQ ID | |
|---|---|---|---|
| Target | # | NO: | Target Sequence |

Input target sequences for 300 SNP regions

| Target | Allele # | SEQ ID NO: | Target Sequence |
|---|---|---|---|
| SNP334 | 2 | 799 | GAAAGGGGGATTTTGGTAAGAGATTGGGCACCTCAATTGGAGATCTTGTCGC ATTGTTCGACTGGTGGATTCTTGAGTCACTGTGGGTGGAATTCATGCAT |
| SNP335 | 1 | 800 | TAACCAACCACTTTGGTATCTGTTAGTCCACCAACATGACTATGAGTAATTCG ACTATTGAAACTGAAGATACTTTTGCCAGCTTGCTTGAACTTGCTGCC |
| SNP335 | 2 | 801 | TAACCAACCACTTTGGTATCTGTTAGTCCACCAACATGACTATGAGTAATCC GACTATTGAAACTGAAGATACTTTTGCCAGCTTGCTTGAACTTGCTGCC |
| SNP336 | 1 | 802 | CCACGTTGGACTAACGAAATTTTAACCATCATAGAAATGACTTCCGCGCGTT CCTTCACTGGAATTCAATTTCTTATAGTGGGACCCACTTTCCGATCTGT |
| SNP336 | 2 | 803 | CCACGTTGGACTAACGAAATTTTAACCATCATAGAAATGACTTCCGCGCGCT CCTTCACTGGAATTCAATTTCTTATAGTGGGACCCACTTTCCGATCTGT |
| SNP337 | 1 | 804 | TTTGCTGAAGAGAGCAGGATTTTTATGTGGCAGTTGCTAGACTGCAGTATAA ACTCCTTTTGCAGTTTCTTTCGTTACATTTATGTTGCCGTCTTTATCAT |
| SNP337 | 2 | 805 | TTTGCTGAAGAGAGCAGGATTTTTATGTGGCAGTTGCTAGACTGCAGTATGA ACTCCTTTTGCAGTTTCTTTCGTTACATTTATGTTGCCGTCTTTATCAT |
| SNP338 | 1 | 806 | AAGGGAAGAGAATGTGCTTTGCTAGTAGTTTGAAGGAGTCTTTTTTGGTGTTT TGAGGGTTTGATTCTTTTTGTAATGGGCTGTGAATAAAGTGAAGTGCT |
| SNP338 | 2 | 807 | AAGGGAAGAGAATGTGCTTTGCTAGTAGTTTGAAGGAGTCTTTTTTGGTGCT TTGAGGGTTTGATTCTTTTTGTAATGGGCTGTGAATAAAGTGAAGTGCT |
| SNP339 | 1 | 808 | TTTTGAGTTAAATTCGAATAATTTCAAAGTTTACACAATAATTTTGATGTTGG TGGTTGTTCAGGTTCAATGTAACAATGAGGTAATTCAACAGCATTGTAACGG ACCTGTACAAAAATTAAAGCGATTTCTTATAAAGAAATTGAAACGTAATGTT TCTGTTGTTCGACAAAAGAAAGGTAATNAATCATGCAGCCGNTA |
| SNP339 | 2 | 809 | TTTTGAGTTAAATTCGAATAATTTCAAAGTTTACACAATAATTTTGATGTTGG TGGTTGTTCAGGTTCAATGTAACAATGAGGTAATTCAACAGCATTGTGACGG ACCTGTACAAAAATTAAAGCGATTTCTTATAAAGAAATTGAAACGTAATGTT TCTGTTGTTCGACAAAAGAAAGGTAATNAATCATGCAGCCGNTA |
| SNP340 | 1 | 810 | TCACCATATAACCACGAAATACCTTCTGGATCCTTAACGCTGAAGCAGATCT TCTATCAGGCGCCTCCGCCTGCGCCAACTCATCAGGTTTCTGTGACCGA |
| SNP340 | 2 | 811 | TCACCATATAACCACGAAATACCTTCTGGATCCTTAACGCTGAAGCAGATGT TCTATCAGGCGCCTCCGCCTGCGCCAACTCATCAGGTTTCTGTGACCGA |
| SNP341 | 1 | 812 | CCAGCTTGAAAAGCAGAGACATTAACGTTTCATTCACCCGTACCCTTTCCATT TCGTCTCTCCGAATCAACTCCGCCGTTTCGCCGAATAAAAGCTTCCGT |
| SNP341 | 2 | 813 | CCAGCTTGAAAAGCAGAGACATTAACGTTTCATTCACCCGTACCCTTTCCCTT TCGTCTCTCCGAATCAACTCCGCCGTTTCGCCGAATAAAAGCTTCCGT |
| SNP342 | 1 | 814 | GTTGCGCTCTATGTATTTTACTGTCTATATACACCATTCACTGCTGCTTCAAC GTGGACTGCGTTACCATCTTCCATGATCATCCCGTTGATTTGTGTTCT |
| SNP342 | 2 | 815 | GTTGCGCTCTATGTATTTTACTGTCTATATACACCATTCACTGCTGCTTCGAC GTGGACTGCGTTACCATCTTCCATGATCATCCCGTTGATTTGTGTTCT |
| SNP343 | 1 | 816 | ATTTGAGCTGTGAAAGGAGTTGCAGATTTGGGATAGTTAGGGCTTCTTGTAC CGAGGAGGTGGTGGTGGATGATCATGAGATTGATGACGTGGAGAGGAAG |
| SNP343 | 2 | 817 | ATTTGAGCTGTGAAAGGAGTTGCAGATTTGGGATAGTTAGGGCTTCTTGTGC CGAGGAGGTGGTGGTGGATGATCATGAGATTGATGACGTGGAGAGGAAG |
| SNP344 | 1 | 818 | CCTCTCTGCATCATACAGTTGATCGTGGGGGAACACACATATTTCTAGTTTCA GTAATATTCCTTTTGTATCTTGCATGCAGTCATTCAGAAAGAGATAGG |
| SNP344 | 2 | 819 | CCTCTCTGCATCATACAGTTGATCGTGGGGGAACACACATATTTCTAGTTCCA GTAATATTCCTTTTGTATCTTGCATGCAGTCATTCAGAAAGAGATAGG |
| SNP345 | 1 | 820 | GTCGATCGAACGTTATTGATAACGAGAACAACGATCTTTTCTCATGTGCATG CAAATCAGGCCTTGATATACGAGATGTGTCTATTTACGATGGTTTTCCT |
| SNP345 | 2 | 821 | GTCGATCGAACGTTATTGATAACGAGAACAACGATCTTTTCTCATGTGCACG CAAATCAGGCCTTGATATACGAGATGTGTCTATTTACGATGGTTTTCCT |
| SNP346 | 1 | 822 | ACTTAATCCAAGAAAGAGAGGAAATTGTGGCTTGTGGAATTTCAAATCAATA ATAACCCCAAAAAGAACTGCTAAAAACCGTAAGCAAGATACCACAGAGA |

TABLE 9-continued

| | | | |
|---|---|---|---|
| | | | Input target sequences for 300 SNP regions |
| Target | Allele # | SEQ ID NO: | Target Sequence |
| SNP346 | 2 | 823 | ACTTAATCCAAGAAAGAGAGGAAATTGTGGCTTGTGGAATTTCAAATCAACA ATAACCCCAAAAAGAACTGCTAAAAACCGTAAGCAAGATACCACAGAGA |
| SNP347 | 1 | 824 | GTGGAGCTCAATTTGGGGCTTATTTACAGAGGAGCACAGATACTCCTGCAAA TGGGAGTTGCGGTAGAATTGAAGCCACCGGAGAAAACCCAGTTTGGGAA |
| SNP347 | 2 | 825 | GTGGAGCTCAATTTGGGGCTTATTTACAGAGGAGCACAGATACTCCTGCACA TGGGAGTTGCGGTAGAATTGAAGCCACCGGAGAAAACCCAGTTTGGGAA |
| SNP348 | 1 | 826 | TCCTTGTCTTGAATCTTAGCTTTGACATTATCAATGGTGTCAGAACTCTCAAC CTCAAGAGTGATGGTCTTTCCGGTGAGTGTCTTAACAAATATCTGCAT |
| SNP348 | 2 | 827 | TCCTTGTCTTGAATCTTAGCTTTGACATTATCAATGGTGTCAGAACTCTCGAC CTCAAGAGTGATGGTCTTTCCGGTGAGTGTCTTAACAAATATCTGCAT |
| SNP349 | 1 | 828 | ATATCTTTGTTTTGCAAAACTCATGAATTTAAGCTTGTTCAAGCAAACGATGG AAGACGGAGGTCGTGAAATTAGAGTCCCTGTGGCATCAAGCTTCTCCA |
| SNP349 | 2 | 829 | ATATCTTTGTTTTGCAAAACTCATGAATTTAAGCTTGTTCAAGCAAACGACGG AAGACGGAGGTCGTGAAATTAGAGTCCCTGTGGCATCAAGCTTCTCCA |
| SNP350 | 1 | 830 | TTGAAGTTTGTGGATTTTGTCAGTAGGATGGTACTTGTTAGGACCCGAAATG CCAAGCAACTCGCGTCTCATGATCATAAGAGCAATATCGTCAATTATAA |
| SNP350 | 2 | 831 | TTGAAGTTTGTGGATTTTGTCAGTAGGATGGTACTTGTTAGGACCCGAAACG CCAAGCAACTCGCGTCTCATGATCATAAGAGCAATATCGTCAATTATAA |
| SNP351 | 1 | 832 | TAGTTTGATTGTTTGATCAAGCAGCAAGAACAAGTGCTTTTATTGTCCCTTGA CTGTTTGCTGTAACAATGGTTGGGCTGTCACGTTTCCAACAAACAGCA |
| SNP351 | 2 | 833 | TAGTTTGATTGTTTGATCAAGCAGCAAGAACAAGTGCTTTTATTGTCCCTCGA CTGTTTGCTGTAACAATGGTTGGGCTGTCACGTTTCCAACAAACAGCA |
| SNP352 | 1 | 834 | ATAGAGCAAAGAACCCTGACCATTCTAAGCAGCAACCACCTCTTGAGCACAT CTAGACTCCAACCATGATGTAGCTGCAACCTTCGTGGTCAAAAACCACC |
| SNP352 | 2 | 835 | ATAGAGCAAAGAACCCTGACCATTCTAAGCAGCAACCACCTCTTGAGCACGT CTAGACTCCAACCATGATGTAGCTGCAACCTTCGTGGTCAAAAACCACC |
| SNP353 | 1 | 836 | GCAACCTCAACTTCTAATTGTTTCTCTGTGTCACGGACTGAAGTAGTTGGTGA TGAGTCAAATTGCTCGTCCACATCTTGGACAACTGACACATCTGGGAT |
| SNP353 | 2 | 837 | GCAACCTCAACTTCTAATTGTTTCTCTGTGTCACGGACTGAAGTAGTTGGCGA TGAGTCAAATTGCTCGTCCACATCTTGGACAACTGACACATCTGGGAT |
| SNP354 | 1 | 838 | TCAAATGAGGAGCAAAAATTGGGTTTAAACACCAAAAAAATGCAGCAGCAA CAGCAGCCTTAAAAGGCCGAAACTGAAGAGCAAAAAATGGGTTTAAACTC |
| SNP354 | 2 | 839 | TCAAATGAGGAGCAAAAATTGGGTTTAAACACCAAAAAAATGCAGCAGCAG CAGCAGCCTTAAAAGGCCGAAACTGAAGAGCAAAAAATGGGTTTAAACTC |
| SNP355 | 1 | 840 | CCCATTACCAACACAGTGGCATCAGCATGCCTTGCAGCCACTTCTGCTAATC CAAAGTTTTGATTCCCTGGACAAGCTACTCCCATACATCCTTGTTGGTG |
| SNP355 | 2 | 841 | CCCATTACCAACACAGTGGCATCAGCATGCCTTGCAGCCACTTCTGCTAACC CAAAGTTTTGATTCCCTGGACAAGCTACTCCCATACATCCTTGTTGGTG |
| SNP356 | 1 | 842 | GCTTTAAAGGGTCCTAAAGATGTCTCTGATGGCCTAAGGAAACTTGATAAAC TAATAGAGAAAAGTGATGGACCAGAAAAGTTCCAGCTTGCTCGTGGACT |
| SNP356 | 2 | 843 | GCTTTAAAGGGTCCTAAAGATGTCTCTGATGGCCTAAGGAAACTTGATAAGC TAATAGAGAAAAGTGATGGACCAGAAAAGTTCCAGCTTGCTCGTGGACT |
| SNP357 | 1 | 844 | TTCTCAAGTCATCCCACTCATTATAGTTATCATTCCACACATCATCCAGGACA ACAAGAAACTTCTTCCCTTCGGGCTTTCTTTCAATTGACCTATAGCTT |
| SNP357 | 2 | 845 | TTCTCAAGTCATCCCACTCATTATAGTTATCATTCCACACATCATCCAGGGCA ACAAGAAACTTCTTCCCTTCGGGCTTTCTTTCAATTGACCTATAGCTT |
| SNP358 | 1 | 846 | TATTAGGAGACAGGTGTGATTTCACCTCTGGAATAATTTTCTTGTGAAACTGA CGATCATCATGAGATTCAACAAAACGCTGGGTCATATTGGAGGCTTGA |
| SNP358 | 2 | 847 | TATTAGGAGACAGGTGTGATTTCACCTCTGGAATAATTTTCTTGTGAAACCG ACGATCATCATGAGATTCAACAAAACGCTGGGTCATATTGGAGGCTTGA |

TABLE 9-continued

| Input target sequences for 300 SNP regions |||||
|---|---|---|---|
| Target | Allele # | SEQ ID NO: | Target Sequence |
| SNP359 | 1 | 848 | GATATGTTGGAACAAAGTCGGCACATGTCCTATTACAGAGGAGAAGATGGTC ACTTTGAGAAATTGAAACAACTCTCTGAATCAGAGCAGCTGAGGACATT |
| SNP359 | 2 | 849 | GATATGTTGGAACAAAGTCGGCACATGTCCTATTACAGAGGAGAAGATGGC CACTTTGAGAAATTGAAACAACTCTCTGAATCAGAGCAGCTGAGGACATT |
| SNP360 | 1 | 850 | TGAGTGGATCTTTGTCGTGTGCATCTGTATGTGTGTGGTACATGCGTGCTTTT CTTCATCAATTTAGATGACAGTGAGACTACTCCAAAGATCATGCATTA |
| SNP360 | 2 | 851 | TGAGTGGATCTTTGTCGTGTGCATCTGTATGTGTGTGGTACATGCGTGCTCTT CTTCATCAATTTAGATGACAGTGAGACTACTCCAAAGATCATGCATTA |
| SNP361 | 1 | 852 | ATACTAGAGGGAGGTATATGGCCTATTGTCCAGGTGGCCAACTTCCGCTATA TACCAGTTAGGTATCAGCTCCTTTACGTCAATTTCTTCTGCTTGCTTGA |
| SNP361 | 2 | 853 | ATACTAGAGGGAGGTATATGGCCTATTGTCCAGGTGGCCAACTTCCGCTACA TACCAGTTAGGTATCAGCTCCTTTACGTCAATTTCTTCTGCTTGCTTGA |
| SNP362 | 1 | 854 | GGGTCTGGGGAGGACTTTACCCCTACCTTGGGAGGTAGAGAGTTGTTTTCAA TAGAACCTCGGCTCAAAACTAACTTGAAAAGATGCTTGGTATTACTGAG |
| SNP362 | 2 | 855 | GGGTCTGGGGAGGACTTTACCCCTACCTTGGGAGGTAGAGAGTTGTTTTCTA TAGAACCTCGGCTCAAAACTAACTTGAAAAGATGCTTGGTATTACTGAG |
| SNP363 | 1 | 856 | GAAAACTGAAGTTTGTCCTCCAAGTTTATGTGATAACCCAATTATATTATTGC TGTCCTCATCTTCTTCATAGTGTTGCAAACTGTGACCACTCAAACTAT |
| SNP363 | 2 | 857 | GAAAACTGAAGTTTGTCCTCCAAGTTTATGTGATAACCCAATTATATTATCGC TGTCCTCATCTTCTTCATAGTGTTGCAAACTGTGACCACTCAAACTAT |
| SNP364 | 1 | 858 | TCCAGGTCCTCAAGGCCTTTGCGAATACTGGAATTGAGCTTATGATTGGGATT CCAAACTCAGACTTGTTGGCGTTTTCTCAATTCGAGTCTAATGCCAAT |
| SNP364 | 2 | 859 | TCCAGGTCCTCAAGGCCTTTGCGAATACTGGAATTGAGCTTATGATTGGGGT TCCAAACTCAGACTTGTTGGCGTTTTCTCAATTCGAGTCTAATGCCAAT |
| SNP365 | 1 | 860 | AGAAAGCATTTCATATGGGCAAAGCTACGTTTGATTTTATATGTTCTGAAATA GAATCAGTAGTGACAAAAAAGGACACGATGTTACGTATGGCGATACCT |
| SNP365 | 2 | 861 | AGAAAGCATTTCATATGGGCAAAGCTACGTTTGATTTTATATGTTCTGAATTA GAATCAGTAGTGACAAAAAAGGACACGATGTTACGTATGGCGATACCT |
| SNP366 | 1 | 862 | ATGGCAAGGGTGGTTGTCGACCCATATTTCGTATTTATGGACAGGATCCATT CATAGTTTCTGATCGGTCTCCGAAAAGCTTGTTCTCAACACAAAGAAA |
| SNP366 | 2 | 863 | ATGGCAAGGGTGGTTGTCGACCCATATTTCGTATTTATGGACAGGATCCACT CATAGTTTCTGATCGGTCTCCGAAAAGCTTGTTCTCAACACAAAGAAA |
| SNP367 | 1 | 864 | TCTCTAATTGAAAAACCTTGTCCACCTCCACCTCCACCTCCACCACTTCCTGA GAAGCATGTGAAGGAAGATTTTTCTCTAACCGAAAAACTATGTCCACC |
| SNP367 | 2 | 865 | TCTCTAATTGAAAAACCTTGTCCACCTCCACCTCCACCTCCACCACTTCCCGA GAAGCATGTGAAGGAAGATTTTTCTCTAACCGAAAAACTATGTCCACC |
| SNP368 | 1 | 866 | GAGCTTCACGAAGTTATGGCAAGCAAAACGAAGATTTACTTCGCCATGGAAT ACGTTAAAGGCGGTGAATTGTTCGAAAAAGTAGCTAAAGGTAAGCTTAG |
| SNP368 | 2 | 867 | GAGCTTCACGAAGTTATGGCAAGCAAAACGAAGATTTACTTCGCCATGGAGT ACGTTAAAGGCGGTGAATTGTTCGAAAAAGTAGCTAAAGGTAAGCTTAG |
| SNP369 | 1 | 868 | TACTATATCTACTACTAATCTTGGTCCTTCATTCACTTGAGATGTCTTTGTGTA GACCTCCACTTCCTCGACTTCTGCTGAATAACGTCTCGTGTATGAGA |
| SNP369 | 2 | 869 | TACTATATCTACTACTAATCTTGGTCCTTCATTCACTTGAGATGTCTTTGCGTA GACCTCCACTTCCTCGACTTCTGCTGAATAACGTCTCGTGTATGAGA |
| SNP370 | 1 | 870 | CAACAATATAGGGACGAGGTCAATAACAACGAGCACAACAACAACAACAAT AATAGTAACGTTTGGGATCAGAGTGAAAAATACAAAGCGGATATTTAAA |
| SNP370 | 2 | 871 | CAACAATATAGGGACGAGGTCAATAACAACGAGCACAACAACAACAACAAC AATAGTAACGTTTGGGATCAGAGTGAAAAATACAAAGCGGATATTTAAA |
| SNP371 | 1 | 872 | ATAATAGGAGGCCAACAAGCCTTATAAGACGCAACTCGTGCTCTTGGTGATC CTCCCTTAGCTGTTCCATTGCCATATCCGAAAATGTTAGCTCCCTCGAC |

TABLE 9-continued

| | Allele | SEQ ID | |
|---|---|---|---|
| Target | # | NO: | Target Sequence |

SNP371   2   873   ATAATAGGAGGCCAACAAGCCTTATAAGACGCAACTCGTGCTCTTGGTGACC
CTCCCTTAGCTGTTCCATTGCCATATCCGAAAATGTTAGCTCCCTCGAC

SNP372   1   874   CTTGCCAAACAAGAGTATAAGTTCCACAATGGAAATGCCAAGAGCAGGGGT
CTTCTCACAGCAGCAAGGAACCAGGAATTTTCAATCTGGAAGTTCACCGC

SNP372   2   875   CTTGCCAAACAAGAGTATAAGTTCCACAATGGAAATGCCAAGAGCAGGGGC
CTTCTCACAGCAGCAAGGAACCAGGAATTTTCAATCTGGAAGTTCACCGC

SNP373   1   876   ATTCAGATTTCGAGCTACAACTTTTCTTACTTTCCAGTATCCTCTACTGCTTGA
ACCCGAGATTTAACGTCTGATTCGGACATTGGATCCCGAATTGATCC

SNP373   2   877   ATTCAGATTTCGAGCTACAACTTTTCTTACTTTCCAGTATCCTCTACTGCCTG
AACCCGAGATTTAACGTCTGATTCGGACATTGGATCCCGAATTGATCC

SNP374   1   878   CATTTAGTTCACACTGATCTGATCAGCTGCTAAACACGCGAGTACAAGGAAG
CAGAGGTAACATTTCAGATTATTCACTTTCGAGTACATTCTGTCTAAGA

SNP374   2   879   CATTTAGTTCACACTGATCTGATCAGCTGCTAAACACGCGAGTACAAGGAGG
CAGAGGTAACATTTCAGATTATTCACTTTCGAGTACATTCTGTCTAAGA

SNP375   1   880   TTAACAATACCAGCATTAATGTTGAACAGATCATCACGGGTCATACCAGGTT
TCCGTGGCACACCAGCTGGAATAATGACAACATCAGCTCCCTCCAAAGC

SNP375   2   881   TTAACAATACCAGCATTAATGTTGAACAGATCATCACGGGTCATACCAGGCT
TCCGTGGCACACCAGCTGGAATAATGACAACATCAGCTCCCTCCAAAGC

SNP376   1   882   CAATCCAAGTTTACATTATAAAGATCTGGAAGAAGCCTACTTGTGGAAGTAA
CATTTTCATCTTTACCAGGTACAGATACTGAGACTGAAGAATCACTCCA

SNP376   2   883   CAATCCAAGTTTACATTATAAAGATCTGGAAGAAGCCTACTTGTGGAAGTTA
CATTTTCATCTTTACCAGGTACAGATACTGAGACTGAAGAATCACTCCA

SNP377   1   884   TTAAAATTTGTTCATTTTGCTTGGTAGTGAAGTTGAGGCCTCCGTTAATCTGT
GGTCATCAAACCCGATTCTTAACATACCTCATATATTTGGCAGAAGAG

SNP377   2   885   TTAAAATTTGTTCATTTTGCTTGGTAGTGAAGTTGAGGCCTCCGTTAATCCGT
GGTCATCAAACCCGATTCTTAACATACCTCATATATTTGGCAGAAGAG

SNP378   1   886   CAGGGTGGTTTGCATGGCTATTTTCCGTCATCTAAGGTTCTTGTTTGGTGTGA
TTCCAAGTGATCACGGTGCAACCGAGACTACTGTGAACCTTGGAAGGA

SNP378   2   887   CAGGGTGGTTTGCATGGCTATTTTCCGTCATCTAAGGTTCTTGTTTGGTGGGA
TTCCAAGTGATCACGGTGCAACCGAGACTACTGTGAACCTTGGAAGGA

SNP379   1   888   AATAAAAAAACAAATCAAATCGACAAACAATACATATCTGGTTAACTGAGT
GAAGATGAGATGCCATTCTTGTTGCCACTGACAGACGAGGGTTTTCCAAC

SNP379   2   889   AATAAAAAAACAAATCAAATCGACAAACAATACATATCTGGTTAACTGAGC
GAAGATGAGATGCCATTCTTGTTGCCACTGACAGACGAGGGTTTTCCAAC

SNP380   1   890   CAGAGAGACCGGCCAGCATTGGGAACCAAAAATGCTCTGTGACGTCACACC
TCTCATCTTCAGTAGTGTCAACTGGCTTCAGAGCACCACCAGGTATAAGA

SNP380   2   891   CAGAGAGACCGGCCAGCATTGGGAACCAAAAATGCTCTGTGACGTCACACG
TCTCATCTTCAGTAGTGTCAACTGGCTTCAGAGCACCACCAGGTATAAGA

SNP381   1   892   GAACTAGGAGCAGGACATCCAAGAAGAGCAAAGCTTTCAGTATTAGTGGTA
TCAATAACTTCACTTGTAATTGGTGCATTATTGACAATATTACTCTTACT

SNP381   2   893   GAACTAGGAGCAGGACATCCAAGAAGAGCAAAGCTTTCAGTATTAGTGGTG
TCAATAACTTCACTTGTAATTGGTGCATTATTGACAATATTACTCTTACT

SNP382   1   894   TAGAGGGTCTTCAGGAGATAAAGGTAGTCCGAGTCAAACTGTATCAAGCTTC
CATGCAACACCATATGAAGTTCCATTACAAACCCAGAATAGATTTCTTT

SNP382   2   895   TAGAGGGTCTTCAGGAGATAAAGGTAGTCCGAGTCAAACTGTATCAAGCTCC
CATGCAACACCATATGAAGTTCCATTACAAACCCAGAATAGATTTCTTT

SNP383   1   896   GAGGACATTATGGAGCGCATAACAGCCATGAACTTGATGAAACCTCAAAAA
TGTAGGCTCAAACGAACACCAAGTCATCCTCGAAAACAGAAACAAGTAAG

SNP383   2   897   GAGGACATTATGGAGCGCATAACAGCCATGAACTTGATGAAACCTCAAAAC
TGTAGGCTCAAACGAACACCAAGTCATCCTCGAAAACAGAAACAAGTAAG

TABLE 9-continued

| | | | |
|---|---|---|---|
| Input target sequences for 300 SNP regions | | | |

| Target | Allele # | SEQ ID NO: | Target Sequence |
|---|---|---|---|
| SNP384 | 1 | 898 | GATGAAAGCCCTGGCAGAAAATCAATTGTGTTCTCTCAATTCAGGAAGTTTTT TGCTCCTACTTGAAGAGCCGCTTAAAGCAGCTGGTTTTAAGATATTGCG |
| SNP384 | 2 | 899 | GATGAAAGCCCTGGCAGAAAATCAATTGTGTTCTCTCAATTCAGGAAGTTGT TGCTCCTACTTGAAGAGCCGCTTAAAGCAGCTGGTTTTAAGATATTGCG |
| SNP385 | 1 | 900 | TAACATCTATGGTACGTTTCAAAGCACGCCAAAGAATTAGTGCAAAGACAAC TTTAGCACATCCATACTTTGATAGAGAAGGTCTTCTAGCCCTGTCCTTC |
| SNP385 | 2 | 901 | TAACATCTATGGTACGTTTCAAAGCACGCCAAAGAATTAGTGCAAAGACAGC TTTAGCACATCCATACTTTGATAGAGAAGGTCTTCTAGCCCTGTCCTTC |
| SNP386 | 1 | 902 | CTTTCTTGAGCCTAGCTGCCTGAATGTCATCAAACATGTGTGTCCTTCTCTCC TTCCTTGTTAGCATGAAATATATATGTATACATCTGTTTATTTTGTCT |
| SNP386 | 2 | 903 | CTTTCTTGAGCCTAGCTGCCTGAATGTCATCAAACATGTGTGTCCTTCTCCCC TTCCTTGTTAGCATGAAATATATATGTATACATCTGTTTATTTTGTCT |
| SNP387 | 1 | 904 | CAATAGGAACAGAAATTGATGGGCACTAAGCTGTCACATCAAATGTAATGA AAGCTGTCCAATGTTCAACGTGTTGGCCACTTATGCCTTATCAAGAAATA |
| SNP387 | 2 | 905 | CAATAGGAACAGAAATTGATGGGCACTAAGCTGTCACATCAAATGTAATGTA AGCTGTCCAATGTTCAACGTGTTGGCCACTTATGCCTTATCAAGAAATA |
| SNP388 | 1 | 906 | AGGGAGGTTGTTTCCGATAGTCCCATAGTTTATTCCGACACCATGAACATTGT AGTTAATAAGAGAGAGGAGAATGAAGAGGGATAAGACAAGAGTACAAA |
| SNP388 | 2 | 907 | AGGGAGGTTGTTTCCGATAGTCCCATAGTTTATTCCGACACCATGAACATCG TAGTTAATAAGAGAGAGGAGAATGAAGAGGGATAAGACAAGAGTACAAA |
| SNP389 | 1 | 908 | GAAAAGGAGCATCGAAGCAACAGTAAAGTTGTCTCTGAGTGAATTATAGGT AAGGGGTTTAAGCCGTCAGAATAGTCACTAATACTTGTAATTAGGATAGA |
| SNP389 | 2 | 909 | GAAAAGGAGCATCGAAGCAACAGTAAAGTTGTCTCTGAGTGAATTATAGGC AAGGGGTTTAAGCCGTCAGAATAGTCACTAATACTTGTAATTAGGATAGA |
| SNP390 | 1 | 910 | CAGCGGTTGATGAAACTGAACTGCTAGGAACATCTGACACTTCTCCTGCCAC AGTTCCCACATCTTTCTTTTTGGTCATGAAAAGATAAGCTACATAAATT |
| SNP390 | 2 | 911 | CAGCGGTTGATGAAACTGAACTGCTAGGAACATCTGACACTTCTCCTGCCTC AGTTCCCACATCTTTCTTTTTGGTCATGAAAAGATAAGCTACATAAATT |
| SNP391 | 1 | 912 | AACTTCACTGAAACTTCAATCAAAAAAACCATCTTCTTCGGTAACCCAACAA ACAAACTTCTCAGAGTATTGCCGGTGCATCTGCTTACTCACTTTAGCAT |
| SNP391 | 2 | 913 | AACTTCACTGAAACTTCAATCAAAAAAACCATCTTCTTCGGTAACCCAACGA ACAAACTTCTCAGAGTATTGCCGGTGCATCTGCTTACTCACTTTAGCAT |
| SNP392 | 1 | 914 | CACCTCTATACTGCTGTAGACAAGCAGAGTCCAATCCAGAGGATGTTTCTAA GAACACTTGTTAGACAATCAACATCAGATGACAGTTTACTAGCGTATCA |
| SNP392 | 2 | 915 | CACCTCTATACTGCTGTAGACAAGCAGAGTCCAATCCAGAGGATGTTTCTCA GAACACTTGTTAGACAATCAACATCAGATGACAGTTTACTAGCGTATCA |
| SNP393 | 1 | 916 | GTTCTTCAGCTTACGTTCTTCAGCTCAGCAACAGTTCGTCCGCAAGAGCTAAG CTCAGCTCAGCTCTTCAGTCTTCTGCTTCCTCTCTTCGATCTTCAGTA |
| SNP393 | 2 | 917 | GTTCTTCAGCTTACGTTCTTCAGCTCAGCAACAGTTCGTCCGCAAGAGCTGAG CTCAGCTCAGCTCTTCAGTCTTCTGCTTCCTCTCTTCGATCTTCAGTA |
| SNP394 | 1 | 918 | CCTGTTTTATTTGTTGGACATCTTTCGAAAACTTCCACCTTGATCATAGATAA ACCTTGGATTCAAGTGGTTAAAACTCTTGATGCTCAACCAGTTCACAG |
| SNP394 | 2 | 919 | CCTGTTTTATTTGTTGGACATCTTTCGAAAACTTCCACCTTGATCATAGACAA ACCTTGGATTCAAGTGGTTAAAACTCTTGATGCTCAACCAGTTCACAG |
| SNP395 | 1 | 920 | TATCCAGGGATTAAGGGCGAAGGTCCTGAATCAGGTGAGAAGTCTCTCCGAA GAGGCTGGAGGCAAAGGGTCTGCCAAGAAGGACCTAAACAGTCAAAGAA |
| SNP395 | 2 | 921 | TATCCAGGGATTAAGGGCGAAGGTCCTGAATCAGGTGAGAAGTCTCTCCGTA GAGGCTGGAGGCAAAGGGTCTGCCAAGAAGGACCTAAACAGTCAAAGAA |
| SNP396 | 1 | 922 | TCCGAAACTGTTGAAGTGTCTGCACTATTCATATTTTGATTCGAACCAACTGA ACCTTCAAGCCATACAGTTGGATTTCTTGACGCCTTTGTACTGGCACG |

TABLE 9-continued

| | Allele | SEQ ID | |
|---|---|---|---|
| Target | # | NO: | Target Sequence |

| | | | |
|---|---|---|---|
| SNP396 | 2 | 923 | TCCGAAACTGTTGAAGTGTCTGCACTATTCATATTTTGATTCGAACCAACCGA ACCTTCAAGCCATACAGTTGGATTTCTTGACGCCTTTGTACTGGCACG |
| SNP397 | 1 | 924 | GCAATCGGGTATGGGCAACGAGTGCCCATACGATTTAAGGTTGCGGGGCGA GTGGATATAAATTTGGTCACGGTAACAATGGTTGCACCTGGATTTAACAC |
| SNP397 | 2 | 925 | GCAATCGGGTATGGGCAACGAGTGCCCATACGATTTAAGGTTGCGGGGCGG GTGGATATAAATTTGGTCACGGTAACAATGGTTGCACCTGGATTTAACAC |
| SNP398 | 1 | 926 | AACCAATGGCCCCAACCTAGGTGAGAGAACTCAGGCAAACCAGAGAGAGGA GATGGGACGTTTGCAGGATGTGAAGGATGATTTAGTGTTCCGGCAACTTC |
| SNP398 | 2 | 927 | AACCAATGGCCCCAACCTAGGTGAGAGAACTCAGGCAAACCAGAGAGAGGG GATGGGACGTTTGCAGGATGTGAAGGATGATTTAGTGTTCCGGCAACTTC |
| SNP399 | 1 | 928 | CAACAACACAAAAATGGTTTACGCACACGCCATGGGTTAGAAAATAATCAA GAATTTCAACATCAACCGTATAAAAATGGTTTAGGCCCACGTCACGGGTT |
| SNP399 | 2 | 929 | CAACAACACAAAAATGGTTTACGCACACGCCATGGGTTAGAAAATAATCAG GAATTTCAACATCAACCGTATAAAAATGGTTTAGGCCCACGTCACGGGTT |

TABLE 10 shows the primers selected by PlexForm™ for the targets in TABLE 9. "F" in the primer name denotes a forward primer. "R" in the primer name denotes a reverse primer. TABLE 10 comprises SEQ ID NOs: 930-1529.

TABLE 10

PlexForm primers selected (for the target sequences in TABLE 9)

| Target | Primer Name | SEQ ID NO: | Primer Sequence |
|---|---|---|---|
| SNP100 | SNP100-F | 930 | TGTGGCCTGGAGAGGGTAGG |
| SNP100 | SNP100-R | 931 | TCTCCACCCTTCAAAGGTAGAGG |
| SNP101 | SNP101-F | 932 | GATCTGTTGTACTTCTTTCTTGCAGC |
| SNP101 | SNP101-R | 933 | GTCGAAATTATTGATTCCTAAATCTTTTCGTG |
| SNP102 | SNP102-F | 934 | GGAGGAAAAGATACCCTTTGTTGC |
| SNP102 | SNP102-R | 935 | CTTGCATCCCTTCAAAAATGGCAA |
| SNP103 | SNP103-F | 936 | GTGGTGAGGCTGGAAATGTAATCC |
| SNP103 | SNP103-R | 937 | ACGTCAAGAACCGGAATGTTCC |
| SNP104 | SNP104-F | 938 | CCACTATACAAGATGGAGGCTGGTAAG |
| SNP104 | SNP104-R | 939 | ATGTCCTCATACCTACATTGCAAAATC |
| SNP105 | SNP105-F | 940 | CGCGTAACATTTGTGTCCAACG |
| SNP105 | SNP105-R | 941 | GACAGACAACAGTACAATGATAGCTTGG |
| SNP106 | SNP106-F | 942 | GACAGTAAGATGGAGAATTTTGTTCCTG |
| SNP106 | SNP106-R | 943 | CTCCACGCCTCCATTTCTCG |
| SNP107 | SNP107-F | 944 | AGTGAAGATAGCCTCCAAGCATTTC |
| SNP107 | SNP107-R | 945 | ATGTTCGGGGGTAATCTCACTCC |
| SNP108 | SNP108-F | 946 | AACAACAACAACGGGGCCC |
| SNP108 | SNP108-R | 947 | GGTTGTTGTTGTTATTGTTATCAAACTGG |
| SNP109 | SNP109-F | 948 | CCCATTGAACAGCATGGCAATG |
| SNP109 | SNP109-R | 949 | TTAGCAGGAATTTCCATCATTGCG |
| SNP110 | SNP110-F | 950 | GCTTTGTGATTAGGTAAAGGTGATCAC |

TABLE 10-continued

| PlexForm primers selected (for the target sequences in TABLE 9) | | | |
|---|---|---|---|
| Target | Primer Name | SEQ ID NO: | Primer Sequence |
| SNP110 | SNP110-R | 951 | ACCATCTTCGCCATCCTTGTCT |
| SNP111 | SNP111-F | 952 | TTTCGCTTGTGCCTCTTCTCCC |
| SNP111 | SNP111-R | 953 | CCCGTTGCATTCCTCTTACACTAG |
| SNP112 | SNP112-F | 954 | CAGAAACAACTGCATCCACTGAAG |
| SNP112 | SNP112-R | 955 | ACTGGAATATTCTCTACCCCTAATATTTCTG |
| SNP113 | SNP113-F | 956 | GTCGTCTCATGGATGATGATATCTCTAAG |
| SNP113 | SNP113-R | 957 | GCAGATGCATCAGTTCTGGAAAC |
| SNP114 | SNP114-F | 958 | GCTGAACTTCTTGCCACCTTCTG |
| SNP114 | SNP114-R | 959 | TCTTCAATAGCTTCATCACTCAATTTCTCAC |
| SNP115 | SNP115-F | 960 | GAGCTGAAGCAGAGTTTCCCAC |
| SNP115 | SNP115-R | 961 | CAGGACACAACTGGCATACTTTTG |
| SNP116 | SNP116-F | 962 | GTGGAAGGAAGTACAGAGAAGAAGC |
| SNP116 | SNP116-R | 963 | GCTCTGGAAAAAACAATCTCCCAC |
| SNP117 | SNP117-F | 964 | ACAGGAACATCGTCAACACCTTG |
| SNP117 | SNP117-R | 965 | TTCTGGCGAAAATAGTTCCTCCAC |
| SNP118 | SNP118-F | 966 | TGAAGACATCAATGATTGACAGTGCT |
| SNP118 | SNP118-R | 967 | TAGGAGCTTCTTCCCACCCTGG |
| SNP119 | SNP119-F | 968 | TTCATCTTGAGGGAGCTCACATG |
| SNP119 | SNP119-R | 969 | CACCAGCTGATCTGAAATCGGGG |
| SNP120 | SNP120-F | 970 | AACTCTGTGTGGCCTGACAATG |
| SNP120 | SNP120-R | 971 | GGGAAATTTATTTTCTGACTGAACTTTTCTC |
| SNP121 | SNP121-F | 972 | TGTCCAAGTATCCCTCATTGTGGG |
| SNP121 | SNP121-R | 973 | TTCTACTTCACAGAACTCATCGGTC |
| SNP122 | SNP122-F | 974 | ACAATGGCAATTTGGAGCAATGG |
| SNP122 | SNP122-R | 975 | TCAGTCTGATTTCCCAAGTTAGAGG |
| SNP123 | SNP123-F | 976 | CACTGTGAAGAGAATATGATGAGAGGA |
| SNP123 | SNP123-R | 977 | GCTCTAGCAAATAATGTCAATGTGCA |
| SNP124 | SNP124-F | 978 | CAACTACTAAACGGTCAATTTTAAGTGAGC |
| SNP124 | SNP124-R | 979 | TGTTTTCTGGTTTGATATTTAGAGAAATGGG |
| SNP125 | SNP125-F | 980 | CACTGAAGCATTAGCCTTTGTCTC |
| SNP125 | SNP125-R | 981 | GGAACAGAACATTTGGGGCTACC |
| SNP126 | SNP126-F | 982 | ATCTCGGCGAGCTTGGTGAC |
| SNP126 | SNP126-R | 983 | CGCACTCTCCATGGCATCTTATG |
| SNP127 | SNP127-F | 984 | TGGTGATTCCTGTTCATAGATTTGGC |
| SNP127 | SNP127-R | 985 | CAGTTTTTTATAGTCCATACACGAATTTAAGGC |
| SNP128 | SNP128-F | 986 | TTCTTACTTCTTCAATAAACCTCAGGAATTC |
| SNP128 | SNP128-R | 987 | ATCGGAATCAACGTCAATGGCG |
| SNP129 | SNP129-F | 988 | ATTGGTTGTTCGAGTTTGCTCAG |

TABLE 10-continued

PlexForm primers selected (for the target sequences in TABLE 9)

| Target | Primer Name | SEQ ID NO: | Primer Sequence |
|---|---|---|---|
| SNP129 | SNP129-R | 989 | GGGCATCCGGATCAATGCC |
| SNP130 | SNP130-F | 990 | AGAGTTTAGATCCAAGACTGTGAATTAGG |
| SNP130 | SNP130-R | 991 | TGACATACTTTCTATCTTGCCATGTGG |
| SNP131 | SNP131-F | 992 | GCCAACAGGGAACAAGAGACTAAAGG |
| SNP131 | SNP131-R | 993 | CAGCTTGAAGTTCAGCCTCTATCC |
| SNP132 | SNP132-F | 994 | GACTTGAGAATAAAGCGAAATTCCTCTTTG |
| SNP132 | SNP132-R | 995 | TGTGCATGGATTCAACTGTTAGGTTG |
| SNP133 | SNP133-F | 996 | TGTTGAAACCAAAATTATACATAGAATATCTGTCC |
| SNP133 | SNP133-R | 997 | GTGTAATCTTCAATGTCCCTCATGAGAG |
| SNP134 | SNP134-F | 998 | AGTATCATTTTGAAAGATACAAAGCAAACAAG |
| SNP134 | SNP134-R | 999 | TTCTAGATATAAAAATCTTACAAATTCGTGCAAG |
| SNP135 | SNP135-F | 1000 | TCCCTGGCCAAACAACCCC |
| SNP135 | SNP135-R | 1001 | AGGCATGGAAGCAGATGTCTTC |
| SNP136 | SNP136-F | 1002 | AAGGATTTTGCGAAGGAGGCTAAA |
| SNP136 | SNP136-R | 1003 | CCTCTTAATCCTACTACATTAGGATGCCT |
| SNP137 | SNP137-F | 1004 | CAATTGTCAAAGACTCGTAACCTGC |
| SNP137 | SNP137-R | 1005 | GCAAAAGAGAAGAAAAAACACCTGTTC |
| SNP138 | SNP138-F | 1006 | CAAGAGGAGGCAGAGGAGTGG |
| SNP138 | SNP138-R | 1007 | TTTGCTTCCTTGGCAGCAATGC |
| SNP139 | SNP139-F | 1008 | GGCAGTACCACGAAGCTTGAC |
| SNP139 | SNP139-R | 1009 | AAACCTTTAAGAATGGTGAAAACTGTGC |
| SNP140 | SNP140-F | 1010 | TGATGCAAAAGAAGAATGTTGATGCTG |
| SNP140 | SNP140-R | 1011 | TCGCAACCAATCCTTGTAATCTAATGG |
| SNP141 | SNP141-F | 1012 | GTTCTGAACCAGTGTAATTATGTTGTTCTTG |
| SNP141 | SNP141-R | 1013 | AGGCTCAAAACCCATGTCAATCATAC |
| SNP142 | SNP142-F | 1014 | ATCAAAGAGCGGGAGGATTAAGC |
| SNP142 | SNP142-R | 1015 | TTGCTTGTTTGCTACTCCATTTGATG |
| SNP143 | SNP143-F | 1016 | GAAGCAAAAGTAGATCCAGAATCCAG |
| SNP143 | SNP143-R | 1017 | GGTCAGAACCAGAAATCTTTTACAAGC |
| SNP144 | SNP144-F | 1018 | GGCAATTGGGAGTTGGGCC |
| SNP144 | SNP144-R | 1019 | GGAGCATCATCTCAGATTCATTGAGC |
| SNP145 | SNP145-F | 1020 | TGGTGGGCAGGGGATTCTG |
| SNP145 | SNP145-R | 1021 | TGTGGAACAAATTCAAGTACTACATTTCG |
| SNP146 | SNP146-F | 1022 | ACTCTTCCAAACCTACCGCAAAAGA |
| SNP146 | SNP146-R | 1023 | TCCTGACAACTCAAGTCATATATAGGGG |
| SNP147 | SNP147-F | 1024 | CCCCTCTAGTAGCCAGCCAAG |
| SNP147 | SNP147-R | 1025 | GGAAGTTTTGATGCAGTTTACATTTCC |
| SNP148 | SNP148-F | 1026 | ATAAGCTTTGCCATTGTAAGAGATAAGATC |

TABLE 10-continued

PlexForm primers selected (for the target sequences in TABLE 9)

| Target | Primer Name | SEQ ID NO: | Primer Sequence |
|---|---|---|---|
| SNP148 | SNP148-R | 1027 | AGTCTAAGAACATATTCACAGTCCAATTTG |
| SNP149 | SNP149-F | 1028 | ACTGACAAAAAAGGGCCTTCAATGG |
| SNP149 | SNP149-R | 1029 | GGCACAGAGAACCACCAAATTC |
| SNP150 | SNP150-F | 1030 | GCCAGCCATTTCTTCGCCG |
| SNP150 | SNP150-R | 1031 | GAGTTCCTCCCCTATTTGATAGATAACG |
| SNP151 | SNP151-F | 1032 | GCTCCGTTCATTCCTTCCTAGC |
| SNP151 | SNP151-R | 1033 | GCAGAGTCAAGTTGAGAAGCTTAAGC |
| SNP152 | SNP152-F | 1034 | CGCTTGTGTTGTTGGTGCC |
| SNP152 | SNP152-R | 1035 | TAAGCTTAAATTTTCTAGGCAGCAGC |
| SNP153 | SNP153-F | 1036 | CAGAAATTCGGGTTTCGGTTCAG |
| SNP153 | SNP153-R | 1037 | AAGGGGTGCCATTCAAGTTAATTG |
| SNP154 | SNP154-F | 1038 | ATTCATCAATTTTTTCCTGCATCAGTTTC |
| SNP154 | SNP154-R | 1039 | TCAAGCGAAGGCCTGAAGAAG |
| SNP155 | SNP155-F | 1040 | GCATTATCTTTCAGGCCAGAGCG |
| SNP155 | SNP155-R | 1041 | TGAACTCGAAATCTTGACCCCTGA |
| SNP156 | SNP156-F | 1042 | CTTCGACGTCTAAGGCTTTTGC |
| SNP156 | SNP156-R | 1043 | CAGGGATGCGATGAGAGAACAAATATG |
| SNP157 | SNP157-F | 1044 | ATCAGCTTATGAACTCCAAACGTTGTTTG |
| SNP157 | SNP157-R | 1045 | CTGGTAAATGAACTGATGGTCAAAGAG |
| SNP158 | SNP158-F | 1046 | ATCCAATATCGAGGCAGGGTTG |
| SNP158 | SNP158-R | 1047 | TCTCACCAGAGTCTGCTAATTTAGAGTC |
| SNP159 | SNP159-F | 1048 | ACCACAAGTACACAACTAAAGCTTTG |
| SNP159 | SNP159-R | 1049 | GTTGGTATGTTCGTCAAGACTGAAAC |
| SNP160 | SNP160-F | 1050 | TGAGCTGATAATGTACTATCTAAAGCGG |
| SNP160 | SNP160-R | 1051 | AATGTTGAGTTCTGATATGACTTCAAAAAGG |
| SNP161 | SNP161-F | 1052 | GTTCACCCAACTCTTCAATTCTTGAATC |
| SNP161 | SNP161-R | 1053 | ACAGATTCTCCTACTTTCTTATTCAACAAGATTTG |
| SNP162 | SNP162-F | 1054 | TCACATTTTTCGTGCAGATAAAGTATACC |
| SNP162 | SNP162-R | 1055 | GGGAGCAAAGGATGAGACTTGC |
| SNP163 | SNP163-F | 1056 | AGAGTTTTCCTTGGGCTCAAGCA |
| SNP163 | SNP163-R | 1057 | AAAAATTGTTTTTGATCTTGTCAAAGTCCG |
| SNP164 | SNP164-F | 1058 | GCAAGGGTACAATTCCTATCCCTGG |
| SNP164 | SNP164-R | 1059 | CCAAGGGCTCCTAGGTTCTCTTC |
| SNP165 | SNP165-F | 1060 | CTGAACGGCCAACCATTTCAG |
| SNP165 | SNP165-R | 1061 | CATGCTGGCAGAGGAAGTGAGAG |
| SNP166 | SNP166-F | 1062 | TAAGTTTCCGTTCGATGCCGG |
| SNP166 | SNP166-R | 1063 | TGATCAATTCTCCTCTTCCGGC |
| SNP167 | SNP167-F | 1064 | TGCAAGTTGCTGGTTAAGTGCC |

TABLE 10-continued

| PlexForm primers selected (for the target sequences in TABLE 9) | | | |
|---|---|---|---|
| Target | Primer Name | SEQ ID NO: | Primer Sequence |
| SNP167 | SNP167-R | 1065 | TCACCCGAAAGAGTTAATTAAACATGC |
| SNP168 | SNP168-F | 1066 | TGATGGGTGTTCAATTATTGAGATGTG |
| SNP168 | SNP168-R | 1067 | GGCAGCTTTTCATCTTAAAGTGAGC |
| SNP169 | SNP169-F | 1068 | GCCATGTGGTGAGTGCTGC |
| SNP169 | SNP169-R | 1069 | TTGTTACAGTAACCCTTCTGCAGATCC |
| SNP170 | SNP170-F | 1070 | CTGGGGTGGGAAGTAGGGGAAT |
| SNP170 | SNP170-R | 1071 | TATGGAGCTCCAGTTCCTCCCG |
| SNP171 | SNP171-F | 1072 | AAATCTACAAAACGAAGCGGAACTG |
| SNP171 | SNP171-R | 1073 | CGTCAATTTCACTCCCTAAGAAGCC |
| SNP172 | SNP172-F | 1074 | CTGTTGCATTGTAGGTCTATCATCTGG |
| SNP172 | SNP172-R | 1075 | AGAAGCAATTATAGAAATAGCTGCAAGATG |
| SNP173 | SNP173-F | 1076 | CTGAGACTCATCAGAATCCGCC |
| SNP173 | SNP173-R | 1077 | CCGGCGAAGGTGATGGAGAC |
| SNP174 | SNP174-F | 1078 | CTCGTGGTGCAAAACTCGGAG |
| SNP174 | SNP174-R | 1079 | TCAAGGAGAATCTGTTGTACGATCTC |
| SNP175 | SNP175-F | 1080 | GCTGTGAACATTGAGACAGTTGAG |
| SNP175 | SNP175-R | 1081 | CTGAGAGCACCTGATAACTCACTTTATG |
| SNP176 | SNP176-F | 1082 | AAGCCAGAAATTGTGATTATTGATTGTGG |
| SNP176 | SNP176-R | 1083 | GGCCCTCCAATTATTCCCATCC |
| SNP177 | SNP177-F | 1084 | CGGCGACCGGAGAATCCTAC |
| SNP177 | SNP177-R | 1085 | TCGAGACACTCACGGTCGG |
| SNP178 | SNP178-F | 1086 | AGAAGCAGAAGAGACTATGACAGGAG |
| SNP178 | SNP178-R | 1087 | CGGCTGTGGCTTCTACTCCTAC |
| SNP179 | SNP179-F | 1088 | TTCCCTGCTCATGATCTGCAAG |
| SNP179 | SNP179-R | 1089 | AGGATCGTCTGAACATCCTTCCAC |
| SNP180 | SNP180-F | 1090 | CACCAGAAAATCGATCTGTTCTGTG |
| SNP180 | SNP180-R | 1091 | CGGGTGGGGGTAAGTTTATCC |
| SNP181 | SNP181-F | 1092 | CGTGCCTTCAGGAAATGCAGC |
| SNP181 | SNP181-R | 1093 | TGTGCAATGCCTGTTTCCCTTC |
| SNP182 | SNP182-F | 1094 | CCATCTTCATTCACTTTATTCTTCCCTTTG |
| SNP182 | SNP182-R | 1095 | TCAGGGTCCAAAACTGAATGACAC |
| SNP183 | SNP183-F | 1096 | TCTTAAAAGTTGTGAGCCATCAAATCTC |
| SNP183 | SNP183-R | 1097 | GTAGAGTCCGAAAACTACAACCCC |
| SNP184 | SNP184-F | 1098 | TACTTCCTGGACAACCATCAACC |
| SNP184 | SNP184-R | 1099 | GGTGAGGGCTACACAAAGGCAG |
| SNP185 | SNP185-F | 1100 | ACCACACAGATGCCGACGG |
| SNP185 | SNP185-R | 1101 | GCATGGACGATGAGAGCTTCAG |
| SNP186 | SNP186-F | 1102 | CAGCCAAACGATAAATATTCCTTCGAG |

TABLE 10-continued

| PlexForm primers selected (for the target sequences in TABLE 9) | | | |
|---|---|---|---|
| Target | Primer Name | SEQ ID NO: | Primer Sequence |
| SNP186 | SNP186-R | 1103 | TAGGTTCAGATAGCCAGACGAGG |
| SNP187 | SNP187-F | 1104 | CGCACTGATGGTGGCAAATTC |
| SNP187 | SNP187-R | 1105 | TCCAGTGCCCACTTTGGATAGC |
| SNP188 | SNP188-F | 1106 | TTTATCTTTAAATTCCATGCCACCCC |
| SNP188 | SNP188-R | 1107 | GCTTCGTCAGAGAGGTACTTCTG |
| SNP189 | SNP189-F | 1108 | GCCATTTGCAATGTTTTAGTTGGTG |
| SNP189 | SNP189-R | 1109 | CTGAATTAGACAACGCATGCTTGC |
| SNP190 | SNP190-F | 1110 | GACATGGTCAATATCGATGCATCGC |
| SNP190 | SNP190-R | 1111 | AAATCATAATTGAACAATCACCAAGGGG |
| SNP191 | SNP191-F | 1112 | AGCAGACATCTTTATACAAGAAAATGTGGC |
| SNP191 | SNP191-R | 1113 | TTTTGTTGTGCCAATTTGTTATTTATTTGAC |
| SNP192 | SNP192-F | 1114 | GCCGCATCTACATAATGCCCAG |
| SNP192 | SNP192-R | 1115 | GGTTGTGGACTGACTTTTAGGTTTG |
| SNP193 | SNP193-F | 1116 | GCTTCCTGCTAGCATTATTGAGATGA |
| SNP193 | SNP193-R | 1117 | AGGTAAATAGAGTTGAAGAAAATACTATCGACAT |
| SNP194 | SNP194-F | 1118 | CTTGGAATGACTCCTCTTCATCTGG |
| SNP194 | SNP194-R | 1119 | AAGATTTCTCTTCGTGTTAAGTTCTCTTTAC |
| SNP195 | SNP195-F | 1120 | GGAGCTTTCGAGTGCTTCAATTGTTC |
| SNP195 | SNP195-R | 1121 | CAGATGGGAGCCAGCCAATAAG |
| SNP196 | SNP196-F | 1122 | TGCCACCTATGACAGTAAAGACATG |
| SNP196 | SNP196-R | 1123 | CTCTCCAACATCTCGAAGTTGCTTC |
| SNP197 | SNP197-F | 1124 | GAGTCAGGTATTAAGAAAGTGGCAAAG |
| SNP197 | SNP197-R | 1125 | ACAACTCTCAGCTTTACCAGGC |
| SNP198 | SNP198-F | 1126 | ACTGATGGTAAATTGAGCAAGAGAATCG |
| SNP198 | SNP198-R | 1127 | GCAATTAGCAGTCTCAATACAAATGGAG |
| SNP199 | SNP199-F | 1128 | GGGAGAAATAATATTGTGATATATGAAGAAGAGC |
| SNP199 | SNP199-R | 1129 | TTGGTTCATCTGTGACTTCCACC |
| SNP200 | SNP200-F | 1130 | GGAAACAATTGGAGTACTTTGAACAATATC |
| SNP200 | SNP200-R | 1131 | GTTTGTGCTGCTCCAATTAAACCAC |
| SNP201 | SNP201-F | 1132 | TGCATGTCTAAGCTTAAGCCTAATTGAC |
| SNP201 | SNP201-R | 1133 | ATATGCTGTTACCGGTGTCTGG |
| SNP202 | SNP202-F | 1134 | GCAGCATGTATTTAACAAACAAGGAAC |
| SNP202 | SNP202-R | 1135 | CAGTGACTTCATCTTGACTGACAGC |
| SNP203 | SNP203-F | 1136 | CAGATATTTTGAATTCGAGCTTTGTTCG |
| SNP203 | SNP203-R | 1137 | TCATTTCAAATATACATTAGCATAAAACGTTCCC |
| SNP204 | SNP204-F | 1138 | ACTAGCAGCAACAGAAGCAGC |
| SNP204 | SNP204-R | 1139 | CCTTCATTCTTATGGTATTTTCTCAGCC |
| SNP205 | SNP205-F | 1140 | GTCTCCTTGAGCACTAGTTCTAAGTATTC |

TABLE 10-continued

| PlexForm primers selected (for the target sequences in TABLE 9) | | | |
| --- | --- | --- | --- |
| Target | Primer Name | SEQ ID NO: | Primer Sequence |
| SNP205 | SNP205-R | 1141 | ACTTGATAGAATGGTTGAGGAAGATGAC |
| SNP206 | SNP206-F | 1142 | TAACACTATACTAGTCTTTTTGCCGCC |
| SNP206 | SNP206-R | 1143 | ACCCTTTTCCCTTTTACCTGAATAAAC |
| SNP207 | SNP207-F | 1144 | CCCTTGATCGCCATTGTAGACC |
| SNP207 | SNP207-R | 1145 | CTCAGAAGTAAAACGTAAAGTGAGTGG |
| SNP208 | SNP208-F | 1146 | TTCAGAAGGTTTTGGAATTCACTGTAG |
| SNP208 | SNP208-R | 1147 | GAAGGGGACAGAGTGGGATCC |
| SNP209 | SNP209-F | 1148 | GTGTGCAGAGGAAGAGAAAATAGAGATG |
| SNP209 | SNP209-R | 1149 | GGTAAGTCTCTTTTGGCCTACAGG |
| SNP210 | SNP210-F | 1150 | GAAAAGAAGGTCCCTCCAACTGG |
| SNP210 | SNP210-R | 1151 | TGACATTATTATTGTCACCTGAGAAATCTCC |
| SNP211 | SNP211-F | 1152 | CCTTTACCACTATTATAAAGAAAAAGGACAACC |
| SNP211 | SNP211-R | 1153 | GACCATGCGTGAACATGTGATG |
| SNP212 | SNP212-F | 1154 | TGAAGTAGGAGCAATGTTGGTGATG |
| SNP212 | SNP212-R | 1155 | CATTTTTCTTAGGAGGAAGTAGGCTAAC |
| SNP213 | SNP213-F | 1156 | TGTTCATTTTAAGATGAATAAAGAATTAAGTCTGC |
| SNP213 | SNP213-R | 1157 | AATGAGTTCCAAGGGTAGTGGTTTG |
| SNP214 | SNP214-F | 1158 | AAGTACTATCTGCTGCAAGTTGTTTTTTC |
| SNP214 | SNP214-R | 1159 | TATGGTTTTTTGTGTTCTAAATAAACTTGATCTG |
| SNP215 | SNP215-F | 1160 | CGTGCAATCCTCTGGAGAAGC |
| SNP215 | SNP215-R | 1161 | GTTGGTCTGCTTTTTGTTGCGAC |
| SNP216 | SNP216-F | 1162 | TGGTGCCTTTATACTTGCTGTGTATG |
| SNP216 | SNP216-R | 1163 | AGTAACAAGAACTGTAACTAACGTAGGAC |
| SNP217 | SNP217-F | 1164 | TTGCTCTGAAAAACAAAATATGGAGTGATG |
| SNP217 | SNP217-R | 1165 | TTGGATGGGGTGGAGTTTACTTG |
| SNP218 | SNP218-F | 1166 | TTCGAGTGATTTTGGGCGTTCC |
| SNP218 | SNP218-R | 1167 | TGCATTGGTCAGATCAAACAGAGGA |
| SNP219 | SNP219-F | 1168 | TCCATTTCAGATAGTGTGCTGGC |
| SNP219 | SNP219-R | 1169 | ATGCACAAATCAAATTTTCAAGGCAG |
| SNP220 | SNP220-F | 1170 | TTCAGCTAAATCTCTGGCCAAAGTTG |
| SNP220 | SNP220-R | 1171 | GAGATCGGAAGGAGCAAAGGAG |
| SNP221 | SNP221-F | 1172 | TGATTTTTGGAGCTCAGAAGAAAGAAGA |
| SNP221 | SNP221-R | 1173 | TCTAGAAGGAAAAGGAATCGACCCT |
| SNP222 | SNP222-F | 1174 | GTTCTCTGATTTGAGCCATGATGAG |
| SNP222 | SNP222-R | 1175 | GCAACTCTTGATCAACTTTCAGTCC |
| SNP223 | SNP223-F | 1176 | CAAGCAGGTGCAGCTGCTTTTAG |
| SNP223 | SNP223-R | 1177 | TCACAACCAGTCAATGAAAGAGGGG |
| SNP224 | SNP224-F | 1178 | AGGATCGTACGTGTATGGTTCAAAGG |

TABLE 10-continued

| Target | Primer Name | SEQ ID NO: | Primer Sequence |
|---|---|---|---|
| SNP224 | SNP224-R | 1179 | AGCCCGTCGTCCAGTTATTTTC |
| SNP225 | SNP225-F | 1180 | GGACGAAGAATGCTCAAAACAATAAGG |
| SNP225 | SNP225-R | 1181 | ACGCTTGGAACTGAAAAGATGC |
| SNP226 | SNP226-F | 1182 | ACGATAGAACAGAAAACATTGCACTG |
| SNP226 | SNP226-R | 1183 | GTTGCAGAGAAGATTGCTGATTTTGG |
| SNP227 | SNP227-F | 1184 | GTTGTGTGGGCAAAGGCAGAG |
| SNP227 | SNP227-R | 1185 | GAACTTGTTGTCTTGTACGCGTAG |
| SNP228 | SNP228-F | 1186 | CTCCTACACCGCCCTATCCTAC |
| SNP228 | SNP228-R | 1187 | AGTTGGAGACAGTGAGACTCAGATTG |
| SNP229 | SNP229-F | 1188 | TCCATAACCCATTGTGTTCAATTGGAC |
| SNP229 | SNP229-R | 1189 | TCTAATCGAAAGCTCTGGCGATTC |
| SNP230 | SNP230-F | 1190 | GAAGTTGAAGCAATATCTTTCGAGAATGATG |
| SNP230 | SNP230-R | 1191 | GATAAGTGATCCAACGACAGAACTTTC |
| SNP231 | SNP231-F | 1192 | AATCCTCATCGATCCGATCAAATCG |
| SNP231 | SNP231-R | 1193 | CCGCACGGAAATAGAGATGTTCG |
| SNP232 | SNP232-F | 1194 | GCTGAAGCAAGGAAAAAATCGAAAATTC |
| SNP232 | SNP232-R | 1195 | TTTCAAGAATGTAAGGTTCTTTGTTTCTCACC |
| SNP233 | SNP233-F | 1196 | AGTTTGCATATTTTCGTCCATGTTTTTAATC |
| SNP233 | SNP233-R | 1197 | AACCAATGATTGCATAGAAAGTCATATCAC |
| SNP234 | SNP234-F | 1198 | GTGGGTAGCTGAAGGGTTTGTACAAG |
| SNP234 | SNP234-R | 1199 | CAAGAAACCTTGTGCGGTATCTTC |
| SNP235 | SNP235-F | 1200 | GCCTATATTTCCTCTCACTACTGTGC |
| SNP235 | SNP235-R | 1201 | GGAATATCTAAGACAATGCCCGAGC |
| SNP236 | SNP236-F | 1202 | GAAAAGTCTACTTCCACTTCTCCTGTG |
| SNP236 | SNP236-R | 1203 | CATCCTCATCATCTGACGCATAGTTAG |
| SNP237 | SNP237-F | 1204 | TCCACCATAGAAGCCCCAAATCC |
| SNP237 | SNP237-R | 1205 | GGATTGTTAATGAAGAGAAGCATAGGGG |
| SNP238 | SNP238-F | 1206 | TCAGCATTTTCAAATCTGGTGGC |
| SNP238 | SNP238-R | 1207 | AGGTTAACCCCTTGGATGATCTCC |
| SNP239 | SNP239-F | 1208 | GCTTCCAAACTATGTCGTCTATCATG |
| SNP239 | SNP239-R | 1209 | CATCTCAACTGCACATACATTACGC |
| SNP240 | SNP240-F | 1210 | CCCTGGTAATACAGCAAGTACGAC |
| SNP240 | SNP240-R | 1211 | GGTAGCTATTACTTGCATCATGCCAG |
| SNP241 | SNP241-F | 1212 | TCAATCGATTCGGGAATATCTGCTTG |
| SNP241 | SNP241-R | 1213 | AAGCAGCGCAGAAAGAGAATACC |
| SNP242 | SNP242-F | 1214 | GAGACGAGTGAGATTTCAAATTACAAGTC |
| SNP242 | SNP242-R | 1215 | CATGTTGTTCGTTACTAGCCAACTTAG |
| SNP243 | SNP243-F | 1216 | TGGAGAAAACAAGAGGTGGTAAGG |

TABLE 10-continued

PlexForm primers selected (for the target sequences in TABLE 9)

| Target | Primer Name | SEQ ID NO: | Primer Sequence |
|--------|-------------|------------|-----------------|
| SNP243 | SNP243-R | 1217 | GCTCCACCAGCCATTACTACACG |
| SNP244 | SNP244-F | 1218 | ATGCACTTCCTTCATCACATTGTTG |
| SNP244 | SNP244-R | 1219 | GGCTTTTCTTCGAAAATGTTGCATTAATCC |
| SNP245 | SNP245-F | 1220 | TTGTGGTCTCAGCAATCATGGATG |
| SNP245 | SNP245-R | 1221 | AGGCCTGCTTCGAACATGG |
| SNP246 | SNP246-F | 1222 | GAAAAGGGTTCATGAACTAGAAGCTG |
| SNP246 | SNP246-R | 1223 | ATCGAATATTTTGGACTCCGTTAATCG |
| SNP247 | SNP247-F | 1224 | TGGTCTTGTTTGTTTGGCCCAATAG |
| SNP247 | SNP247-R | 1225 | AGAAGAAGAAAAAACCCCGAATCTCC |
| SNP248 | SNP248-F | 1226 | GGAGTGCAATCTCATAATAGTGCTCCTG |
| SNP248 | SNP248-R | 1227 | AGCGACGGAATTGCCATAGG |
| SNP249 | SNP249-F | 1228 | TTTAACTGAAAAATGGGGAGATTTACCAC |
| SNP249 | SNP249-R | 1229 | TTTAATAGACCGTAAATTACCATATCTTCGG |
| SNP250 | SNP250-F | 1230 | TGTGTGTACAGTAAAACCTCTGGTC |
| SNP250 | SNP250-R | 1231 | GAGTCCATTTCAAAGCTTGTACTGC |
| SNP251 | SNP251-F | 1232 | TTCAGATGAAATTTATGATGCATGGGTG |
| SNP251 | SNP251-R | 1233 | GCAAATACTCGTAAACATACTAATCAATTCAAC |
| SNP252 | SNP252-F | 1234 | AAGTTGCCTTGACCTAATAATCTCCC |
| SNP252 | SNP252-R | 1235 | ATGGAGAAAAAGGAAATGTACTGATGG |
| SNP253 | SNP253-F | 1236 | CTCAATAACAGGAAATCACACCTAATCC |
| SNP253 | SNP253-R | 1237 | TGTGGTTGCTATTATTCCGTAGATACATC |
| SNP254 | SNP254-F | 1238 | TCGCCATCTCCCTTAGCACATG |
| SNP254 | SNP254-R | 1239 | TTGAGCGGGTGTTCAGTAATTAATG |
| SNP255 | SNP255-F | 1240 | TACCGATGATGAAACACTCTAGCTAG |
| SNP255 | SNP255-R | 1241 | AATCAACAATGGACATCAAATACCCC |
| SNP256 | SNP256-F | 1242 | GAGGCCTTTCCGTGCTCTC |
| SNP256 | SNP256-R | 1243 | ACGGTTCCCTGTAGTAGTTCTTAAGAG |
| SNP257 | SNP257-F | 1244 | TGTGAAAGGCATCATATGTTAGCTCTC |
| SNP257 | SNP257-R | 1245 | ACAAGTTCAAGGCGGTGAAATTATC |
| SNP258 | SNP258-F | 1246 | TCAGGGTCTGAGTAATTTGAGAGC |
| SNP258 | SNP258-R | 1247 | GAATTTCACCCATGAACTTATTTCTCCC |
| SNP259 | SNP259-F | 1248 | GGAACAAATTAAGTAAGATCATCTTCCTCAAG |
| SNP259 | SNP259-R | 1249 | AGGACAACACTACTTCTAAGAGTCAAGG |
| SNP260 | SNP260-F | 1250 | ATGCCCTTGTGAGATGGGTGTG |
| SNP260 | SNP260-R | 1251 | CAACCTATGCCCTTGAACATGTG |
| SNP261 | SNP261-F | 1252 | ACACAATTCAAAATCCCCTCCTCC |
| SNP261 | SNP261-R | 1253 | CGTACGGCTGCAGAGTTCAAAG |
| SNP262 | SNP262-F | 1254 | GCAGAAGACCTCCCACCAGAG |

TABLE 10-continued

| | PlexForm primers selected (for the target sequences in TABLE 9) | | |
|---|---|---|---|
| Target | Primer Name | SEQ ID NO: | Primer Sequence |
| SNP262 | SNP262-R | 1255 | ATCCCTGAGAAGAAATGGTACCTAAG |
| SNP263 | SNP263-F | 1256 | TTGGGAGAAAATACCCCTGCTG |
| SNP263 | SNP263-R | 1257 | TGAATGTTTTCGCCATTTCTCTTGTAC |
| SNP264 | SNP264-F | 1258 | TGACCATCTGAGTGTGAGAAATATGC |
| SNP264 | SNP264-R | 1259 | AGCACTCTGATAGGCCTGCTG |
| SNP265 | SNP265-F | 1260 | GACAAGGTTTCATGTCTGTTGAGTTG |
| SNP265 | SNP265-R | 1261 | CTACCAAAAACATCATAATATTTGATCTCAGC |
| SNP266 | SNP266-F | 1262 | GCTATATTTTGAGGCCTGTTGGAC |
| SNP266 | SNP266-R | 1263 | AAACACAAATTCTTGAGGCAATACATGAC |
| SNP267 | SNP267-F | 1264 | TAAAATATATGGCGACTGGATTGATGAC |
| SNP267 | SNP267-R | 1265 | ACAGATCAGTAGCTAATTATGACAACTCC |
| SNP268 | SNP268-F | 1266 | GGGCAAGAATCGGTCGGAAATG |
| SNP268 | SNP268-R | 1267 | CCACTACCTTCTCATCAAGACGAC |
| SNP269 | SNP269-F | 1268 | CTAGGAAGAGAGTTGAAAAGACCTAGC |
| SNP269 | SNP269-R | 1269 | AAAAACTTATACCTTATTTATCATCTCCCCC |
| SNP270 | SNP270-F | 1270 | CATCTGCAGAAGAATTGTTGTCCAG |
| SNP270 | SNP270-R | 1271 | GGCCATAAAGATTCTGCCAACC |
| SNP271 | SNP271-F | 1272 | TGTCTCCTTTGTTTCAAGTGGTATCATG |
| SNP271 | SNP271-R | 1273 | TGTTTCGATTGATTTCTCCTCAACTTC |
| SNP272 | SNP272-F | 1274 | TAGTTGTCTGCCGACTTCCTGG |
| SNP272 | SNP272-R | 1275 | CTCAGGAACTTCTCTAAAGAACGTATCTTG |
| SNP273 | SNP273-F | 1276 | AGAAAGTGTGACTCCAACAAAGCG |
| SNP273 | SNP273-R | 1277 | TCTTTCACGTCCTTCTTAGAAGCTG |
| SNP274 | SNP274-F | 1278 | CGAATGCATATAAAGCTTTTGATCCAAG |
| SNP274 | SNP274-R | 1279 | TAGTGCGGGGAAGGACCAAG |
| SNP275 | SNP275-F | 1280 | CAGAAGGAATCAACTCGGGGGT |
| SNP275 | SNP275-R | 1281 | TAACAGCCTAGCTAACCACCAC |
| SNP276 | SNP276-F | 1282 | TTCAAGTGGTGAAGTTCACATAGTGTG |
| SNP276 | SNP276-R | 1283 | AAAATTAAGTAATGCATGTAGCATGAATAAAAGTG |
| SNP277 | SNP277-F | 1284 | ACAAAGTTCCCAGAACCTCCAC |
| SNP277 | SNP277-R | 1285 | TAGTTATTTCTTCAACTTCGACTTCTGTG |
| SNP278 | SNP278-F | 1286 | CTGCAACCGAAGCTATTGACTGTG |
| SNP278 | SNP278-R | 1287 | CGAAGAGGGAGGAGGTCATTGATC |
| SNP279 | SNP279-F | 1288 | GCTGTTTCGACTGATACTATTAATGGTGG |
| SNP279 | SNP279-R | 1289 | TGACATTAAGTCGAAGACTCTGATCGA |
| SNP280 | SNP280-F | 1290 | GAACAGGGAAGTGTCAAATCAATTGGG |
| SNP280 | SNP280-R | 1291 | TGCAGCCTGGGCAGTTG |
| SNP281 | SNP281-F | 1292 | TTCGAAGCGGTTAGTCACAGTAAG |

TABLE 10-continued

PlexForm primers selected (for the target sequences in TABLE 9)

| Target | Primer Name | SEQ ID NO: | Primer Sequence |
|--------|-------------|------------|-----------------|
| SNP281 | SNP281-R | 1293 | AACCGCTTTACCCACCGC |
| SNP282 | SNP282-F | 1294 | GAAGGGTGGTGGTGATTTGGC |
| SNP282 | SNP282-R | 1295 | ACATCAAACGGAACATATCTATCTTTTCC |
| SNP283 | SNP283-F | 1296 | GTGGGTGTGACATTGGGGCC |
| SNP283 | SNP283-R | 1297 | CACCAAGAGCACGTAGACCATG |
| SNP284 | SNP284-F | 1298 | TTGGACCAACTTGCATTTTCGGG |
| SNP284 | SNP284-R | 1299 | CACCTAAGCAAGTTTCAGAAAAGGTTG |
| SNP285 | SNP285-F | 1300 | GTGATTTCTGGTGAACCTGATCCAG |
| SNP285 | SNP285-R | 1301 | TTTGTCTGACTTGATTGGTGCAAC |
| SNP286 | SNP286-F | 1302 | GAATCGGCGTGGTAGGGAGG |
| SNP286 | SNP286-R | 1303 | AACCTTCATCACTCAAAACGGTAAAC |
| SNP287 | SNP287-F | 1304 | TGAACGAAGTGCTTACAAGAGAGTTG |
| SNP287 | SNP287-R | 1305 | GAGTAACCCTAACTTCAACTCCCG |
| SNP288 | SNP288-F | 1306 | AGGAAGTGAAGTTGGAAGAAAGAGCAG |
| SNP288 | SNP288-R | 1307 | ACCAACCATACATCTTCCTTCTGGC |
| SNP289 | SNP289-F | 1308 | GATCTTTCTGGATTAAACGGGAAACTG |
| SNP289 | SNP289-R | 1309 | GCTGCATCTAAGCCTCTTGACATTAG |
| SNP290 | SNP290-F | 1310 | TCGTGTTAACATTTCCTTTAAGGTATGACG |
| SNP290 | SNP290-R | 1311 | TCCGGGCATGTAAATCGGATGC |
| SNP291 | SNP291-F | 1312 | AAGGGACACGATAAACTTGCTCC |
| SNP291 | SNP291-R | 1313 | ACCAACTTGGAACCACAACAGG |
| SNP292 | SNP292-F | 1314 | GAGGTTCTTCGGTAGGTATTGCTTG |
| SNP292 | SNP292-R | 1315 | GCGCCTGTAGCAATAAATTTTAATCCG |
| SNP293 | SNP293-F | 1316 | ATCCAAAAATTTCGTTGAATATTAGGTTACCTG |
| SNP293 | SNP293-R | 1317 | GCGAAGGGATTCAGATGGGTTG |
| SNP294 | SNP294-F | 1318 | ACGCTCCTTGCCTCAGTCAC |
| SNP294 | SNP294-R | 1319 | GCTTTGGTTAATCGATTTGCGGATC |
| SNP295 | SNP295-F | 1320 | GACACTGAATGAAGCTCCGAGTG |
| SNP295 | SNP295-R | 1321 | GATTTTCTCGAACCGGAAATGTCG |
| SNP296 | SNP296-F | 1322 | ACCCCAGATGACACCGAAGATG |
| SNP296 | SNP296-R | 1323 | AGACACAATAACGCCCAAGAGATG |
| SNP297 | SNP297-F | 1324 | TCATATACGGATGCTGCAGCTG |
| SNP297 | SNP297-R | 1325 | GGGCATGCAGAAGAAGACCAG |
| SNP298 | SNP298-F | 1326 | CAAAGGTTTGCTTTTCGGCTCC |
| SNP298 | SNP298-R | 1327 | TTTTCAGCCTATAATGTGAAGCACC |
| SNP299 | SNP299-F | 1328 | GCATGGGAAACAGAAAATTGAGTTTG |
| SNP299 | SNP299-R | 1329 | AAAGACGGTTCTGCTGATCCTTC |
| SNP300 | SNP300-F | 1330 | CATAAAGAGGCTGCGATGAGGAG |

TABLE 10-continued

PlexForm primers selected (for the target sequences in TABLE 9)

| Target | Primer Name | SEQ ID NO: | Primer Sequence |
|---|---|---|---|
| SNP300 | SNP300-R | 1331 | AGTGGAATATTGGGAGTAGTGTGTC |
| SNP301 | SNP301-F | 1332 | CAAATTCTGCAACCTTTCCACACT |
| SNP301 | SNP301-R | 1333 | CCAACCAAAGAAGACATCGCATC |
| SNP302 | SNP302-F | 1334 | TGGCTGCATTCGTAGATGTTGAATTTG |
| SNP302 | SNP302-R | 1335 | AGTTATGTCGTCTGTCATACAAAAGTTTG |
| SNP303 | SNP303-F | 1336 | TGTAGCATTGGAGCATGTTCCG |
| SNP303 | SNP303-R | 1337 | CGGGACTGGTACACTAGAAACATC |
| SNP304 | SNP304-F | 1338 | CAGCAACAAGCTTCTGAATGCCA |
| SNP304 | SNP304-R | 1339 | GGCAGTGTCTAAGTGAAAGGCGA |
| SNP305 | SNP305-F | 1340 | GCTGGTAGAGAATCATTGATTGGCTC |
| SNP305 | SNP305-R | 1341 | TGGTTACTTATCAATCTTTCAGTTCTTGC |
| SNP306 | SNP306-F | 1342 | TCTTTAGTGGATAGTAAAATGGTGGGTTC |
| SNP306 | SNP306-R | 1343 | CATCACGAACAGCGCACCTC |
| SNP307 | SNP307-F | 1344 | TGGTGACGTTTTGGTTGATTCTATG |
| SNP307 | SNP307-R | 1345 | CTAAACAGTTCAACGACTGCAGG |
| SNP308 | SNP308-F | 1346 | AACCCGACGAATGTCCAACTC |
| SNP308 | SNP308-R | 1347 | AGGTACCCTGGCATTCTCTTGC |
| SNP309 | SNP309-F | 1348 | TAAACCACACCCTACGCGTATAG |
| SNP309 | SNP309-R | 1349 | ACGCTTCAACAAATTGGATAATGGG |
| SNP310 | SNP310-F | 1350 | ATGTGCCATCTTTCCAATTTTCATCA |
| SNP310 | SNP310-R | 1351 | GGAAATCCAATTCCTGAGTCTCTAGTG |
| SNP311 | SNP311-F | 1352 | AGCAAAAATGGTGAAAGACAGAACC |
| SNP311 | SNP311-R | 1353 | CTGTTTTGCTGCTCTTTGAAAAATCTAC |
| SNP312 | SNP312-F | 1354 | CCACTTAAATAGTTTACGGGCAAGAC |
| SNP312 | SNP312-R | 1355 | TACTTGTGTCCCCACTGCGG |
| SNP313 | SNP313-F | 1356 | GTTTTCTTCAAACAACAAATGTCTCTTATTCC |
| SNP313 | SNP313-R | 1357 | CGAAGATATTGCTCCTCCGACCAC |
| SNP314 | SNP314-F | 1358 | GTTACTTCACTTGAACACCATTCCC |
| SNP314 | SNP314-R | 1359 | CAAGAGGAGCATGCACTACGG |
| SNP315 | SNP315-F | 1360 | ACACTTTTGAATCTGTCCATCCATGAC |
| SNP315 | SNP315-R | 1361 | TTGGAGTCTCCGCGACAAGC |
| SNP316 | SNP316-F | 1362 | CCCAGGATTACGCGATGCAG |
| SNP316 | SNP316-R | 1363 | GATGGAATTACACACAACCTCAGATG |
| SNP317 | SNP317-F | 1364 | CGGGTAAGGATGTTTAGGTGCGT |
| SNP317 | SNP317-R | 1365 | CCAGCATAAATTTAAGAATGGAGTAGAATCC |
| SNP318 | SNP318-F | 1366 | GACCTGGCATTGACATGTCCATG |
| SNP318 | SNP318-R | 1367 | CCTCGTAGCTTCCGGGAGAC |
| SNP319 | SNP319-F | 1368 | AACGAAGAGGATGATATGGAAAATGC |

TABLE 10-continued

| PlexForm primers selected (for the target sequences in TABLE 9) | | | |
|---|---|---|---|
| Target | Primer Name | SEQ ID NO: | Primer Sequence |
| SNP319 | SNP319-R | 1369 | ATCGTCTTCTCTCCTCCTTCCC |
| SNP320 | SNP320-F | 1370 | AGTCGAGATATTGACCAAATTTGCTC |
| SNP320 | SNP320-R | 1371 | TGTACAACAGAAAGTTCAATTAGATGGAG |
| SNP321 | SNP321-F | 1372 | AATCAACACGTTCGTGCAATCG |
| SNP321 | SNP321-R | 1373 | GATGATCTGTTCTGGAGTTGTTGC |
| SNP322 | SNP322-F | 1374 | ACTAAAGATCTGAAGGCACAAGTGG |
| SNP322 | SNP322-R | 1375 | GGGAATTGCGATGGAGTGAATTTTAAGG |
| SNP323 | SNP323-F | 1376 | TCATTTTCAAGTTGCCGTCAGC |
| SNP323 | SNP323-R | 1377 | AACTTCATCATAAGACCTATTAATAATCTGAGTTC |
| SNP324 | SNP324-F | 1378 | CGGAGATATTCAGGAACCGTCAATTG |
| SNP324 | SNP324-R | 1379 | GCCAGGTGTTTGGGAATATGTTC |
| SNP325 | SNP325-F | 1380 | CAGCTGATTCGAGGGGTCTC |
| SNP325 | SNP325-R | 1381 | ACCAACTGAAGAACAAGTCTGTTAGAAC |
| SNP326 | SNP326-F | 1382 | TGCAAAAAAGGACTCTTCAACCAG |
| SNP326 | SNP326-R | 1383 | GGTCTCATTGGCCTTTGAGGATTG |
| SNP327 | SNP327-F | 1384 | CTAGATCTTAACTGTGATGTTCTGAGCTG |
| SNP327 | SNP327-R | 1385 | ACGTTGATCTGACTGATGATCGG |
| SNP328 | SNP328-F | 1386 | GGTGATACTAAAGTGGATTTAAAAGGCG |
| SNP328 | SNP328-R | 1387 | ACCAACAACTTCCCCTGCACC |
| SNP329 | SNP329-F | 1388 | ACCGTCATTGGTACAGTTGATCC |
| SNP329 | SNP329-R | 1389 | CCACCAAAACTTACGTAGCCTACTC |
| SNP330 | SNP330-F | 1390 | AAGTATCCTACGTCAACAAGCTTCG |
| SNP330 | SNP330-R | 1391 | TGAATCTACTTATGCTTCTTGGGGTG |
| SNP331 | SNP331-F | 1392 | TGTCTTGATCTTCTGAAGTCTCACTTAC |
| SNP331 | SNP331-R | 1393 | CCGAGCTGGGCAGTCTAGAG |
| SNP332 | SNP332-F | 1394 | TGGTGGCATTGTTCAGGTGATTG |
| SNP332 | SNP332-R | 1395 | AGAAATCGACATGATAAGTTGTTTAAAACATC |
| SNP333 | SNP333-F | 1396 | TGGGAAAATCTAATCGACGATTACAAC |
| SNP333 | SNP333-R | 1397 | GGCGGCGTAGTTGATGGAAG |
| SNP334 | SNP334-F | 1398 | GGGGATTTTGGTAAGAGATTGGGC |
| SNP334 | SNP334-R | 1399 | CACAGTGACTCAAGAATCCACCAG |
| SNP335 | SNP335-F | 1400 | TATCTGTTAGTCCACCAACATGACTATG |
| SNP335 | SNP335-R | 1401 | CAAGCTGGCAAAAGTATCTTCAGTTTC |
| SNP336 | SNP336-F | 1402 | TAACGAAATTTTAACCATCATAGAAATGACTTCC |
| SNP336 | SNP336-R | 1403 | TGGGTCCCACTATAAGAAATTGAATTCC |
| SNP337 | SNP337-F | 1404 | GGATTTTTATGTGGCAGTTGCTAGAC |
| SNP337 | SNP337-R | 1405 | ACATAAATGTAACGAAAGAAACTGCAAAAG |
| SNP338 | SNP338-F | 1406 | GTGCTTTGCTAGTAGTTTGAAGGAG |

TABLE 10-continued

PlexForm primers selected (for the target sequences in TABLE 9)

| Target | Primer Name | SEQ ID NO: | Primer Sequence |
|---|---|---|---|
| SNP338 | SNP338-R | 1407 | CAGCCCATTACAAAAAGAATCAAACCC |
| SNP339 | SNP339-F | 1408 | CAATGTAACAATGAGGTAATTCAACAGC |
| SNP339 | SNP339-R | 1409 | TCTTTATAAGAAATCGCTTTAATTTTTGTACAGG |
| SNP340 | SNP340-F | 1410 | TACCTTCTGGATCCTTAACGCTG |
| SNP340 | SNP340-R | 1411 | ACCTGATGAGTTGGCGCAGG |
| SNP341 | SNP341-F | 1412 | AACGTTTCATTCACCCGTACCC |
| SNP341 | SNP341-R | 1413 | ACGGCGGAGTTGATTCGGAG |
| SNP342 | SNP342-F | 1414 | ATTTTACTGTCTATATACACCATTCACTGC |
| SNP342 | SNP342-R | 1415 | GATCATGGAAGATGGTAACGCAGTC |
| SNP343 | SNP343-F | 1416 | TTGCAGATTTGGGATAGTTAGGGC |
| SNP343 | SNP343-R | 1417 | CATGATCATCCACCACCACCTCC |
| SNP344 | SNP344-F | 1418 | GCATCATACAGTTGATCGTGGGG |
| SNP344 | SNP344-R | 1419 | ATGACTGCATGCAAGATACAAAAGG |
| SNP345 | SNP345-F | 1420 | ATTGATAACGAGAACAACGATCTTTTCTC |
| SNP345 | SNP345-R | 1421 | GACACATCTCGTATATCAAGGCCTG |
| SNP346 | SNP346-F | 1422 | GAAAGAGAGGAAATTGTGGCTTGTG |
| SNP346 | SNP346-R | 1423 | CGGTTTTTAGCAGTTCTTTTTGGGG |
| SNP347 | SNP347-F | 1424 | TTGGGGCTTATTTACAGAGGAGC |
| SNP347 | SNP347-R | 1425 | TGGCTTCAATTCTACCGCAACTC |
| SNP348 | SNP348-F | 1426 | TCACCGGAAAGACCATCACTCTTG |
| SNP348 | SNP348-R | 1427 | CCTTGTCTTGAATCTTAGCTTTGACATTATC |
| SNP349 | SNP349-F | 1428 | AAACTCATGAATTTAAGCTTGTTCAAGC |
| SNP349 | SNP349-R | 1429 | ACAGGGACTCTAATTTCACGACC |
| SNP350 | SNP350-F | 1430 | TGTCAGTAGGATGGTACTTGTTAGGAC |
| SNP350 | SNP350-R | 1431 | TTGCTCTTATGATCATGAGACGCG |
| SNP351 | SNP351-F | 1432 | ATCAAGCAGCAAGAACAAGTGC |
| SNP351 | SNP351-R | 1433 | GTGACAGCCCAACCATTGTTACAG |
| SNP352 | SNP352-F | 1434 | CCATTCTAAGCAGCAACCACCTC |
| SNP352 | SNP352-R | 1435 | TGCAGCTACATCATGGTTGGAG |
| SNP353 | SNP353-F | 1436 | TAATTGTTTCTCTGTGTCACGGACTG |
| SNP353 | SNP353-R | 1437 | CAAGATGTGGACGAGCAATTTGAC |
| SNP354 | SNP354-F | 1438 | GGAGCAAAAATTGGGTTTAAACACC |
| SNP354 | SNP354-R | 1439 | TTGCTCTTCAGTTTCGGCCTTTTAAG |
| SNP355 | SNP355-F | 1440 | CCAACACAGTGGCATCAGCATG |
| SNP355 | SNP355-R | 1441 | GGGAGTAGCTTGTCCAGGGAATC |
| SNP356 | SNP356-F | 1442 | TGTCTCTGATGGCCTAAGGAAAC |
| SNP356 | SNP356-R | 1443 | GCTGGAACTTTTCTGGTCCATCAC |
| SNP357 | SNP357-F | 1444 | CACTCATTATAGTTATCATTCCACACATCAT |

TABLE 10-continued

| Target | Primer Name | SEQ ID NO: | Primer Sequence |
|---|---|---|---|
| SNP357 | SNP357-R | 1445 | AGGTCAATTGAAAGAAAGCCCGAAG |
| SNP358 | SNP358-F | 1446 | TGTGATTTCACCTCTGGAATAATTTTCTTG |
| SNP358 | SNP358-R | 1447 | ATGACCCAGCGTTTTGTTGAATCTC |
| SNP359 | SNP359-F | 1448 | GTCGGCACATGTCCTATTACAGAGG |
| SNP359 | SNP359-R | 1449 | TCTGATTCAGAGAGTTGTTTCAATTTCTC |
| SNP360 | SNP360-F | 1450 | GCATCTGTATGTGTGTGGTACATG |
| SNP360 | SNP360-R | 1451 | TTGGAGTAGTCTCACTGTCATCTAAATTG |
| SNP361 | SNP361-F | 1452 | CCTATTGTCCAGGTGGCCAAC |
| SNP361 | SNP361-R | 1453 | ACGTAAAGGAGCTGATACCTAACTG |
| SNP362 | SNP362-F | 1454 | GGAGGACTTTACCCCTACCTTGG |
| SNP362 | SNP362-R | 1455 | CATCTTTTCAAGTTAGTTTTGAGCCGAGG |
| SNP363 | SNP363-F | 1456 | TGTCCTCCAAGTTTATGTGATAACCC |
| SNP363 | SNP363-R | 1457 | GTGGTCACAGTTTGCAACACTATGAAG |
| SNP364 | SNP364-F | 1458 | GCCTTTGCGAATACTGGAATTGAG |
| SNP364 | SNP364-R | 1459 | TTGAGAAAACGCCAACAAGTCTGAG |
| SNP365 | SNP365-F | 1460 | ATGGGCAAAGCTACGTTTGATTTTATATG |
| SNP365 | SNP365-R | 1461 | CATCGTGTCCTTTTTTGTCACTACTG |
| SNP366 | SNP366-F | 1462 | GTCGACCCATATTTCGTATTTATGGACAG |
| SNP366 | SNP366-R | 1463 | TGAGAACAAGCTTTTCGGAGACC |
| SNP367 | SNP367-F | 1464 | TCCACCTCCACCTCCACCTC |
| SNP367 | SNP367-R | 1465 | CGGTTAGAGAAAAATCTTCCTTCACATG |
| SNP368 | SNP368-F | 1466 | ACGAAGTTATGGCAAGCAAAACG |
| SNP368 | SNP368-R | 1467 | AGCTACTTTTTCGAACAATTCACCG |
| SNP369 | SNP369-F | 1468 | CTTGGTCCTTCATTCACTTGAGATG |
| SNP369 | SNP369-R | 1469 | AGCAGAAGTCGAGGAAGTGGAG |
| SNP370 | SNP370-F | 1470 | GGACGAGGTCAATAACAACGAGC |
| SNP370 | SNP370-R | 1471 | TTTTTCACTCTGATCCCAAACGTTAC |
| SNP371 | SNP371-F | 1472 | ACAAGCCTTATAAGACGCAACTCG |
| SNP371 | SNP371-R | 1473 | AACATTTTCGGATATGGCAATGGAAC |
| SNP372 | SNP372-F | 1474 | TCCTGGTTCCTTGCTGCTGTG |
| SNP372 | SNP372-R | 1475 | TTGCCAAACAAGAGTATAAGTTCCAC |
| SNP373 | SNP373-F | 1476 | GCTACAACTTTTCTTACTTTCCAGTATCCTC |
| SNP373 | SNP373-R | 1477 | CCGAATCAGACGTTAAATCTCGGG |
| SNP374 | SNP374-F | 1478 | TGATCAGCTGCTAAACACGCG |
| SNP374 | SNP374-R | 1479 | GTACTCGAAAGTGAATAATCTGAAATGTTACC |
| SNP375 | SNP375-F | 1480 | TGTTGAACAGATCATCACGGGTC |
| SNP375 | SNP375-R | 1481 | ATTATTCCAGCTGGTGTGCCAC |
| SNP376 | SNP376-F | 1482 | AGATCTGGAAGAAGCCTACTTGTG |

TABLE 10-continued

| PlexForm primers selected (for the target sequences in TABLE 9) | | | |
|---|---|---|---|
| Target | Primer Name | SEQ ID NO: | Primer Sequence |
| SNP376 | SNP376-R | 1483 | CAGTCTCAGTATCTGTACCTGGTAAAG |
| SNP377 | SNP377-F | 1484 | TTGGTAGTGAAGTTGAGGCCTC |
| SNP377 | SNP377-R | 1485 | TGAGGTATGTTAAGAATCGGGTTTGATG |
| SNP378 | SNP378-F | 1486 | TGCATGGCTATTTTCCGTCATCTAAGG |
| SNP378 | SNP378-R | 1487 | GGTTGCACCGTGATCACTTGG |
| SNP379 | SNP379-F | 1488 | TCAAATCGACAAACAATACATATCTGGTTA |
| SNP379 | SNP379-R | 1489 | AACCCTCGTCTGTCAGTGGC |
| SNP380 | SNP380-F | 1490 | TGAAGCCAGTTGACACTACTGAAG |
| SNP380 | SNP380-R | 1491 | GAGAGACCGGCCAGCATTG |
| SNP381 | SNP381-F | 1492 | GCAGGACATCCAAGAAGAGCAAAG |
| SNP381 | SNP381-R | 1493 | TGTCAATAATGCACCAATTACAAGTGAAG |
| SNP382 | SNP382-F | 1494 | AAGGTAGTCCGAGTCAAACTGTATC |
| SNP382 | SNP382-R | 1495 | TCTGGGTTTGTAATGGAACTTCATATGG |
| SNP383 | SNP383-F | 1496 | GCATAACAGCCATGAACTTGATGAAAC |
| SNP383 | SNP383-R | 1497 | GACTTGGTGTTCGTTTGAGCC |
| SNP384 | SNP384-F | 1498 | CAGAAAATCAATTGTGTTCTCTCAATTCAG |
| SNP384 | SNP384-R | 1499 | GCTTTAAGCGGCTCTTCAAGTAGG |
| SNP385 | SNP385-F | 1500 | TTCAAAGCACGCCAAAGAATTAGTG |
| SNP385 | SNP385-R | 1501 | ACCTTCTCTATCAAAGTATGGATGTGC |
| SNP386 | SNP386-F | 1502 | CTGCCTGAATGTCATCAAACATGTG |
| SNP386 | SNP386-R | 1503 | ACAGATGTATACATATATATTTCATGCTAACAAGG |
| SNP387 | SNP387-F | 1504 | ATGGGCACTAAGCTGTCACATC |
| SNP387 | SNP387-R | 1505 | GCCAACACGTTGAACATTGGAC |
| SNP388 | SNP388-F | 1506 | AGTCCCATAGTTTATTCCGACACC |
| SNP388 | SNP388-R | 1507 | TCTTGTCTTATCCCTCTTCATTCTCCTC |
| SNP389 | SNP389-F | 1508 | TAGTGACTATTCTGACGGCTTAAACC |
| SNP389 | SNP389-R | 1509 | AAAGGAGCATCGAAGCAACAGTAAAG |
| SNP390 | SNP390-F | 1510 | GAACTGCTAGGAACATCTGACACTTC |
| SNP390 | SNP390-R | 1511 | TCATGACCAAAAAGAAAGATGTGGG |
| SNP391 | SNP391-F | 1512 | AACCATCTTCTTCGGTAACCCAAC |
| SNP391 | SNP391-R | 1513 | AAGCAGATGCACCGGCAATACT |
| SNP392 | SNP392-F | 1514 | GCAGAGTCCAATCCAGAGGATG |
| SNP392 | SNP392-R | 1515 | GTCATCTGATGTTGATTGTCTAACAAGTG |
| SNP393 | SNP393-F | 1516 | CAGCTCAGCAACAGTTCGTCC |
| SNP393 | SNP393-R | 1517 | AGCAGAAGACTGAAGAGCTGAGC |
| SNP394 | SNP394-F | 1518 | ACATCTTTCGAAAACTTCCACCTTGATC |
| SNP394 | SNP394-R | 1519 | GCATCAAGAGTTTTAACCACTTGAATCC |
| SNP395 | SNP395-F | 1520 | GGGCGAAGGTCCTGAATCAG |

TABLE 10-continued

| PlexForm primers selected (for the target sequences in TABLE 9) | | | |
|---|---|---|---|
| Target | Primer Name | SEQ ID NO: | Primer Sequence |
| SNP395 | SNP395-R | 1521 | GCAGACCCTTTGCCTCCAGC |
| SNP396 | SNP396-F | 1522 | GTGTCTGCACTATTCATATTTTGATTCGA |
| SNP396 | SNP396-R | 1523 | GTCAAGAAATCCAACTGTATGGCTTG |
| SNP397 | SNP397-F | 1524 | TGCCCATACGATTTAAGGTTGCG |
| SNP397 | SNP397-R | 1525 | CAGGTGCAACCATTGTTACCGTG |
| SNP398 | SNP398-F | 1526 | CCCCAACCTAGGTGAGAGAACTC |
| SNP398 | SNP398-R | 1527 | TCCTTCACATCCTGCAAACGTCC |
| SNP399 | SNP399-F | 1528 | TTACGCACACGCCATGGGTTAG |
| SNP399 | SNP399-R | 1529 | CGTGACGTGGGCCTAAACC |

The primers from TABLE 10 were synthesized and tested using NGS. Anti-sense oligos were not added to the reaction mixture. TABLE 11 shows the average number of reads obtained on an NGS sequencer (AVG) using the primers from TABLE 10, as well as the standard deviation (STD) and coefficient of variance (% CV) for each target. All calculations were based on the average of 3 replicates for each SNP. The data in TABLE 11 is summarized in TABLE 12, demonstrating even multiplexing in one reaction.

TABLE 11

| Average number of reads obtained on an NGS sequencer (using the primers from TABLE 10) | | | |
|---|---|---|---|
| SNP | AVG | STD | CV % |
| 100 | 341 | 141 | 41.2% |
| 101 | 92 | 36 | 39.3% |
| 102 | 31 | 17 | 53.8% |
| 103 | 330 | 144 | 43.7% |
| 104 | 131 | 42 | 32.2% |
| 105 | 108 | 42 | 38.8% |
| 106 | 60 | 30 | 50.7% |
| 107 | 35 | 11 | 30.7% |
| 108 | 356 | 163 | 45.6% |
| 109 | 25 | 5 | 18.3% |
| 110 | 353 | 144 | 40.9% |
| 111 | 285 | 110 | 38.7% |
| 112 | 77 | 33 | 42.7% |
| 113 | 34 | 15 | 43.7% |
| 114 | 156 | 57 | 36.9% |
| 115 | 270 | 116 | 42.9% |
| 116 | 138 | 51 | 36.8% |
| 117 | 440 | 186 | 42.3% |
| 118 | 438 | 175 | 40.0% |
| 119 | 408 | 180 | 44.1% |
| 120 | 40 | 17 | 41.9% |
| 121 | 363 | 160 | 44.0% |
| 122 | 85 | 23 | 26.8% |
| 123 | 46 | 13 | 29.5% |
| 124 | 191 | 85 | 44.3% |
| 125 | 117 | 41 | 35.1% |
| 126 | 426 | 176 | 41.3% |
| 127 | 164 | 61 | 37.1% |
| 128 | 198 | 75 | 38.0% |
| 129 | 560 | 203 | 36.2% |
| 130 | 171 | 51 | 29.5% |
| 131 | 111 | 41 | 36.4% |
| 132 | 45 | 18 | 39.6% |
| 133 | 91 | 32 | 35.4% |
| 134 | 34 | 17 | 49.9% |

TABLE 11-continued

| Average number of reads obtained on an NGS sequencer (using the primers from TABLE 10) | | | |
|---|---|---|---|
| SNP | AVG | STD | CV % |
| 135 | 235 | 89 | 37.9% |
| 136 | 127 | 50 | 39.9% |
| 137 | 186 | 61 | 32.8% |
| 138 | 444 | 168 | 37.9% |
| 139 | 471 | 194 | 41.2% |
| 140 | 171 | 72 | 42.2% |
| 141 | 360 | 129 | 36.0% |
| 142 | 41 | 13 | 32.6% |
| 143 | 65 | 25 | 37.9% |
| 144 | 203 | 85 | 41.7% |
| 145 | 30 | 14 | 46.8% |
| 146 | 52 | 14 | 26.8% |
| 147 | 129 | 58 | 44.5% |
| 148 | 37 | 14 | 38.9% |
| 149 | 152 | 57 | 37.7% |
| 150 | 237 | 84 | 35.3% |
| 151 | 175 | 66 | 37.9% |
| 152 | 289 | 107 | 37.1% |
| 153 | 45 | 15 | 32.9% |
| 154 | 139 | 44 | 31.5% |
| 155 | 327 | 135 | 41.2% |
| 156 | 172 | 63 | 36.5% |
| 157 | 38 | 15 | 40.2% |
| 158 | 99 | 41 | 41.3% |
| 159 | 84 | 27 | 32.2% |
| 160 | 84 | 44 | 52.6% |
| 161 | 32 | 10 | 31.9% |
| 162 | 213 | 78 | 36.5% |
| 163 | 566 | 258 | 45.6% |
| 164 | 147 | 52 | 35.3% |
| 165 | 82 | 30 | 36.9% |
| 166 | 259 | 106 | 41.1% |
| 167 | 298 | 125 | 41.9% |
| 168 | 188 | 64 | 34.1% |
| 169 | 380 | 161 | 42.4% |
| 170 | 365 | 163 | 44.6% |
| 171 | 491 | 184 | 37.5% |
| 172 | 101 | 42 | 41.7% |
| 173 | 470 | 202 | 43.1% |
| 174 | 324 | 147 | 45.5% |
| 175 | 95 | 31 | 33.3% |
| 176 | 50 | 14 | 27.4% |
| 177 | 45 | 19 | 41.3% |
| 178 | 407 | 170 | 41.7% |
| 179 | 302 | 131 | 43.5% |
| 180 | 211 | 90 | 42.7% |
| 181 | 453 | 168 | 37.1% |

TABLE 11-continued

| Average number of reads obtained on an NGS sequencer (using the primers from TABLE 10) | | | |
|---|---|---|---|
| SNP | AVG | STD | CV % |
| 182 | 63 | 26 | 41.6% |
| 183 | 393 | 162 | 41.4% |
| 184 | 445 | 184 | 41.2% |
| 185 | 84 | 35 | 41.9% |
| 186 | 94 | 39 | 41.4% |
| 187 | 310 | 114 | 36.6% |
| 188 | 76 | 27 | 36.2% |
| 189 | 108 | 33 | 30.7% |
| 190 | 301 | 123 | 41.0% |
| 191 | 44 | 12 | 26.3% |
| 192 | 87 | 32 | 36.3% |
| 193 | 28 | 13 | 45.9% |
| 194 | 188 | 62 | 32.8% |
| 195 | 302 | 101 | 33.6% |
| 196 | 131 | 56 | 43.1% |
| 197 | 324 | 139 | 43.1% |
| 198 | 172 | 73 | 42.5% |
| 199 | 228 | 91 | 40.0% |
| 200 | 112 | 46 | 41.0% |
| 201 | 172 | 65 | 37.8% |
| 202 | 102 | 42 | 41.4% |
| 203 | 145 | 42 | 29.0% |
| 204 | 322 | 146 | 45.5% |
| 205 | 138 | 53 | 38.0% |
| 206 | 216 | 81 | 37.3% |
| 207 | 164 | 56 | 34.1% |
| 208 | 120 | 44 | 37.0% |
| 209 | 106 | 47 | 44.2% |
| 210 | 177 | 67 | 37.6% |
| 211 | 118 | 40 | 34.2% |
| 212 | 206 | 84 | 40.8% |
| 213 | 83 | 32 | 38.0% |
| 214 | 46 | 8 | 18.3% |
| 215 | 157 | 64 | 40.6% |
| 216 | 248 | 95 | 38.5% |
| 217 | 95 | 33 | 34.3% |
| 218 | 142 | 49 | 34.3% |
| 219 | 391 | 179 | 45.8% |
| 220 | 26 | 11 | 42.3% |
| 221 | 142 | 50 | 35.0% |
| 222 | 87 | 30 | 34.9% |
| 223 | 202 | 73 | 36.1% |
| 224 | 439 | 167 | 38.1% |
| 225 | 80 | 33 | 41.2% |
| 226 | 57 | 21 | 36.6% |
| 227 | 389 | 161 | 41.4% |
| 228 | 208 | 69 | 33.5% |
| 229 | 263 | 119 | 45.3% |
| 230 | 47 | 22 | 46.3% |
| 231 | 325 | 131 | 40.2% |
| 232 | 138 | 61 | 44.3% |
| 233 | 29 | 14 | 48.4% |
| 234 | 263 | 92 | 34.9% |
| 235 | 338 | 141 | 41.7% |
| 236 | 326 | 122 | 37.4% |
| 237 | 348 | 160 | 46.0% |
| 238 | 551 | 235 | 42.6% |
| 239 | 50 | 29 | 58.4% |
| 240 | 431 | 184 | 42.6% |
| 241 | 304 | 116 | 38.3% |
| 242 | 127 | 49 | 38.8% |
| 243 | 74 | 22 | 29.6% |
| 244 | 121 | 51 | 42.1% |
| 245 | 387 | 149 | 38.6% |
| 246 | 180 | 71 | 39.2% |
| 247 | 36 | 13 | 35.6% |
| 248 | 227 | 76 | 33.6% |
| 249 | 41 | 13 | 31.0% |
| 250 | 111 | 46 | 41.5% |
| 251 | 33 | 13 | 38.1% |
| 252 | 75 | 28 | 37.7% |
| 253 | 58 | 25 | 44.1% |
| 254 | 211 | 101 | 48.0% |
| 255 | 27 | 13 | 47.5% |
| 256 | 182 | 65 | 35.6% |

TABLE 11-continued

| Average number of reads obtained on an NGS sequencer (using the primers from TABLE 10) | | | |
|---|---|---|---|
| SNP | AVG | STD | CV % |
| 257 | 167 | 67 | 39.9% |
| 258 | 373 | 169 | 45.4% |
| 259 | 30 | 13 | 42.9% |
| 260 | 289 | 121 | 42.0% |
| 261 | 138 | 40 | 28.9% |
| 262 | 35 | 15 | 42.2% |
| 263 | 50 | 18 | 35.9% |
| 264 | 292 | 115 | 39.6% |
| 265 | 261 | 97 | 37.0% |
| 266 | 27 | 15 | 54.8% |
| 267 | 287 | 126 | 44.0% |
| 268 | 239 | 85 | 35.7% |
| 269 | 50 | 18 | 35.7% |
| 270 | 267 | 89 | 33.3% |
| 271 | 135 | 43 | 31.8% |
| 272 | 97 | 40 | 41.5% |
| 273 | 133 | 56 | 41.9% |
| 274 | 47 | 22 | 45.7% |
| 275 | 114 | 43 | 38.0% |
| 276 | 49 | 17 | 34.4% |
| 277 | 242 | 104 | 43.0% |
| 278 | 92 | 27 | 29.1% |
| 279 | 167 | 71 | 42.8% |
| 280 | 256 | 93 | 36.3% |
| 281 | 129 | 48 | 37.0% |
| 282 | 119 | 37 | 31.0% |
| 283 | 281 | 105 | 37.4% |
| 284 | 352 | 153 | 43.3% |
| 285 | 388 | 170 | 43.9% |
| 286 | 200 | 75 | 37.5% |
| 287 | 373 | 157 | 42.1% |
| 288 | 383 | 160 | 41.7% |
| 289 | 79 | 26 | 33.2% |
| 290 | 400 | 175 | 43.7% |
| 291 | 513 | 239 | 46.7% |
| 292 | 213 | 85 | 40.1% |
| 293 | 224 | 103 | 46.1% |
| 294 | 345 | 150 | 43.6% |
| 295 | 321 | 120 | 37.2% |
| 296 | 227 | 90 | 39.9% |
| 297 | 101 | 39 | 38.4% |
| 298 | 453 | 182 | 40.1% |
| 299 | 29 | 12 | 41.5% |
| 300 | 85 | 32 | 38.2% |
| 301 | 86 | 26 | 30.5% |
| 302 | 196 | 72 | 36.7% |
| 303 | 123 | 48 | 39.3% |
| 304 | 194 | 89 | 45.8% |
| 305 | 39 | 8 | 20.2% |
| 306 | 106 | 43 | 40.6% |
| 307 | 36 | 17 | 46.5% |
| 308 | 440 | 179 | 40.6% |
| 309 | 141 | 40 | 28.4% |
| 310 | 28 | 7 | 25.9% |
| 311 | 75 | 30 | 40.5% |
| 312 | 465 | 193 | 41.6% |
| 313 | 169 | 72 | 42.5% |
| 314 | 86 | 38 | 43.5% |
| 315 | 227 | 99 | 43.5% |
| 316 | 31 | 16 | 51.8% |
| 317 | 32 | 10 | 30.4% |
| 318 | 81 | 30 | 37.6% |
| 319 | 155 | 52 | 33.3% |
| 320 | 33 | 9 | 27.2% |
| 321 | 91 | 31 | 34.6% |
| 322 | 56 | 15 | 27.2% |
| 323 | 89 | 36 | 40.6% |
| 324 | 56 | 23 | 42.1% |
| 325 | 285 | 111 | 38.9% |
| 326 | 222 | 102 | 46.0% |
| 327 | 271 | 118 | 43.4% |
| 328 | 274 | 113 | 41.2% |
| 329 | 377 | 153 | 40.5% |
| 330 | 478 | 180 | 37.6% |
| 331 | 224 | 79 | 35.0% |

TABLE 11-continued

Average number of reads obtained on an NGS
sequencer (using the primers from TABLE 10)

| SNP | AVG | STD | CV % |
|---|---|---|---|
| 332 | 67 | 26 | 38.4% |
| 333 | 28 | 9 | 31.6% |
| 334 | 292 | 113 | 38.7% |
| 335 | 51 | 21 | 40.0% |
| 336 | 79 | 25 | 32.2% |
| 337 | 115 | 41 | 35.8% |
| 338 | 209 | 89 | 42.6% |
| 339 | 199 | 83 | 41.5% |
| 340 | 64 | 33 | 51.8% |
| 341 | 570 | 245 | 42.9% |
| 342 | 356 | 158 | 44.5% |
| 343 | 538 | 216 | 40.2% |
| 344 | 138 | 59 | 42.7% |
| 345 | 393 | 152 | 38.7% |
| 346 | 231 | 89 | 38.3% |
| 347 | 311 | 118 | 38.1% |
| 348 | 48 | 21 | 44.0% |
| 349 | 149 | 47 | 31.5% |
| 350 | 301 | 108 | 36.1% |
| 351 | 174 | 75 | 43.3% |
| 352 | 477 | 205 | 43.0% |
| 353 | 413 | 191 | 46.4% |
| 354 | 135 | 50 | 37.3% |
| 355 | 102 | 38 | 37.3% |
| 356 | 143 | 53 | 37.4% |
| 357 | 108 | 43 | 39.5% |
| 358 | 74 | 28 | 37.4% |
| 359 | 67 | 29 | 42.7% |
| 360 | 207 | 85 | 41.0% |
| 361 | 205 | 73 | 35.6% |
| 362 | 224 | 85 | 37.9% |
| 363 | 39 | 14 | 36.3% |
| 364 | 164 | 65 | 39.7% |
| 365 | 90 | 35 | 38.6% |
| 366 | 291 | 121 | 41.4% |
| 367 | 235 | 88 | 37.4% |
| 368 | 92 | 33 | 35.5% |
| 369 | 314 | 115 | 36.8% |
| 370 | 88 | 37 | 42.6% |
| 371 | 253 | 109 | 43.0% |
| 372 | 103 | 48 | 46.1% |
| 373 | 418 | 184 | 44.0% |
| 374 | 237 | 95 | 40.2% |
| 375 | 560 | 237 | 42.4% |
| 376 | 36 | 13 | 36.5% |
| 377 | 442 | 185 | 42.0% |
| 378 | 384 | 179 | 46.8% |

TABLE 11-continued

Average number of reads obtained on an NGS
sequencer (using the primers from TABLE 10)

| SNP | AVG | STD | CV % |
|---|---|---|---|
| 379 | 42 | 14 | 33.1% |
| 380 | 81 | 27 | 34.0% |
| 381 | 25 | 16 | 64.3% |
| 382 | 251 | 101 | 40.2% |
| 383 | 357 | 152 | 42.7% |
| 384 | 93 | 33 | 35.1% |
| 385 | 145 | 45 | 31.2% |
| 386 | 32 | 11 | 34.5% |
| 387 | 276 | 102 | 36.9% |
| 388 | 152 | 64 | 42.3% |
| 389 | 71 | 25 | 34.8% |
| 390 | 307 | 99 | 32.3% |
| 391 | 292 | 118 | 40.3% |
| 392 | 124 | 48 | 39.0% |
| 393 | 140 | 50 | 35.9% |
| 394 | 131 | 56 | 43.0% |
| 395 | 371 | 150 | 40.3% |
| 396 | 102 | 35 | 34.8% |
| 397 | 119 | 44 | 36.8% |
| 398 | 238 | 100 | 41.8% |
| 399 | 32 | 12 | 38.7% |

TABLE 12

Statistical Summary of TABLE 11

| | |
|---|---|
| Total Amplicons | 300 |
| Minimum Reads across 300 SNPs | 25 |
| Maximum Reads across 300 SNPs | 570 |
| Average Reads for all 300 SNPs | 193 |
| Standard Deviation of Average Reads for all 300 SNPs | 137 |
| CV % | 70.7% |
| # SNPS with > 10 reads | 300 |
| # SNPS with > 20 reads | 300 |
| # SNPS with > 50 reads | 254 |
| # SNPS with > 100 reads | 202 |
| # SNPS with > 200 reads | 123 |

What is claimed herein is:

1. A method of preparing an optimized primer set for multiplex genotyping, the method comprising:

A) for a given set N of variable genomic target sequences of a genome to be genotyped in a sample, designing an initial set of forward and reverse amplification primers that will amplify a sequence comprising each variable genomic target sequence in a multiplex amplification reaction, wherein the designing includes the steps of:

1) identifying all possible primers of 17 to 35 nucleotides within 100 base pairs of each genomic target sequence variation in set N of variable genomic target sequences from a pool of primers;

2) for each member of set N, selecting a subset of primer pairs from the set of step (1) that satisfies the conditions of a primer selection algorithm;

3) evaluating specificity of primer pairs chosen in step (2) in the genome, keeping only those pairs predicted to be specific for their respective targets;

4) selecting a set of optimized primers for the amplification of target gene set N, where the optimal primers are selected to minimize primer-primer interactions with other primers in the set by iterative calculation of predicted $\Delta G$ for interactions between primers to generate a fitness score and use of a fitness score optimization method selected from one or a combination of the group consisting of:

a) a Monte Carlo random or pseudo-random selection method;

b) a golden section search;

c) gradient descent;

d) minima hopping;

e) genetic algorithm;

f) neural networks;

g) cluster analysis, in which substitution is picked to minimize score; and h) cluster analysis to create bins; and wherein the Fitness Score is generated according to the method:

a) determining G=the set of $\Delta G$'s for all possible interactions for members of the initial primer set; and b) calculating the Fitness Score by:

i) determining the sum, S, of $|\Delta G|^Q$ for each $\Delta G$ value, wherein Q is a weighting factor constant exponent that makes large $\Delta G$ absolute values much larger than small values;

ii) determining S'=S/# of $\Delta G$ values in G;

iii) determining H=T/S', wherein T is a constant that makes H small for large values of S' and H large for small values of S'; and iv) determining the Fitness Score=$H^R$, wherein R is a weighting factor constant exponent that makes large values of H larger, and small values of H smaller; and B) synthesizing the optimized primer set selected in step (4).

2. The method of claim 1, wherein steps (2)-(4) comprise:

a) for the primers identified in step (1), randomly selecting a primer pair for each target in set N that satisfies the conditions of the primer selection algorithm;

b) evaluating specificity of primer pairs chosen in step (a) in the genome, keeping only those pairs predicted to be specific for their respective targets;

c) repeating step (a) on the primer pairs kept from step (b) to generate set P, a population of randomly selected primer sets for each target in set N;

d) generating the Fitness Score for each member of population P based upon $\Delta G$ for all possible interactions between the primers in each member of the population;

e) picking member(s) of the population P based on Fitness Score;

f) repeating steps (c)-(e) iteratively until a set of primer pairs for target genes identified in step (e) has the Fitness Score at a predetermined threshold.

3. The method of claim 1, wherein steps (2)-(4) comprise:

a) for the primers identified in step (1), randomly selecting a primer pair for each target in set N that satisfies the conditions of the primer selection algorithm and is predicted to be specific for its target in the genome, or providing a primer pair for each target in set N, that has been selected to reduce potential for primer: primer interactions with other primers in the set and is predicted to be specific for its target in the genome;

b) repeating step (a) to generate population Z, of size 2 or greater, of primer pair sets for each target in set N;

c) generating the Fitness Score for each member of population Z based upon $\Delta G$ for all possible interactions between the primers in each member of the population;

d) selecting the members of population Z with the lowest Fitness Scores as set W;

e) replacing a primer for a single target from W with another primer identified in step (a), and generating the Fitness Score for the resulting set; wherein if the change results in an improved Fitness Score relative to the Fitness Score generated in step (c), the resulting new set W' replaces set W, and if the change results in a no change in Fitness Score or a decreased Fitness Score, keeping set W;

f) iteratively repeating steps (c)-(e) on the set W or W' retained in each iteration of step (e) until a set of primer pairs for target genes in set N is identified that has the Fitness Score at a predetermined threshold, or, if a predetermined threshold is not reached by iteratively repeating steps (c)-(e), beginning again at step (a) and iteratively repeating steps (c)-(e) until a set of primer pairs for target genes in set N is identified that has the Fitness Score at the predetermined threshold.

4. The method of claim 3, wherein the step of providing a primer pair for each target in set N that has been selected to reduce potential for primer: primer interactions with other primers in the set provides primer sets selected using one or more of a Monte Carlo random or pseudo-random selection method, a golden section search, gradient descent, minima hopping, a genetic algorithm, neural networks, cluster analysis in which substitution is picked to minimize score, or cluster analysis to create bins.

5. The method of claim 1, wherein steps (2)-(4) comprise:

a) generating primer set Z, including a primer pair for each member of set N either by: (i) randomly selecting from the primers identified in step (1) a primer pair for each target in set N that satisfies the conditions of the primer selection algorithm and is predicted to be specific for its target in the genome; or (ii) providing a primer pair for each target in set N that is predicted to be specific for its target in the genome, and that has been selected to reduce potential for primer: primer interactions with other primers in the set;

b) generating the Fitness Score for primer set Z based upon ΔG for all possible interactions between the primers in each member of the population;

c) making a change to a primer for a single target from set Z to generate new set Z', and generating the Fitness Score for set Z', wherein if the change results in an improved Fitness Score relative to that generated in step (b), the resulting new set Z' replaces set Z, and if the change results in no change in Fitness Score or a decreased Fitness Score, keeping set Z; and d) repeating step (c) iteratively until further iterations do not improve fitness of set Z.

6. The method of claim 1, wherein steps (2)-(4) comprise:

a) providing a set of optimized primer pairs for the amplification of target gene set N, where the optimal primer pairs are predicted to be specific for their target genes in the genome, and are selected to minimize primer-primer interactions with other primers in the set by iterative calculation of predicted ΔG for all possible interactions between primers to generate the Fitness Score and use of the Fitness Score optimization method selected from one or a combination of the group consisting of:

i) a Monte Carlo random or pseudo-random selection method;

ii) a golden section search;

iii) gradient descent;

iv) minima hopping;

v) genetic algorithm;

vi) neural networks;

vii) cluster analysis, in which substitution is picked to minimize score; and viii) cluster analysis to create bins;

b) adding the set of optimized primers of step a to set M;

c) while maintaining a degree of dissimilarity from primer sets included in set M, selecting a primer pair for each target in set N from step (1) and designating it set Z, wherein the primer pairs satisfy the conditions of the primer selection algorithm, and are predicted to be specific for their target genes in the genome;

d) optimizing primer pairs of set Z for the amplification of target gene set N, to minimize primer-primer interactions with other primers in the set by iterative calculation of predicted ΔG for all possible interactions between primers to generate the Fitness Score and use of the Fitness Score optimization method selected from one or a combination of methods (i)-(viii) of step (a); and e) repeating steps (a)-(d) iteratively until a set of primer pairs for target gene set N identified in step (d) has the Fitness Score at a predetermined threshold.

7. The method of claim 1, wherein steps (2)-(4) comprise:

a) for a multilayer neural network, for each primer identified in step (1) creating a node Pnz comprised by the neural network, such node connected to a node for a corresponding target (Tn), wherein (i) each node outputs its identifier (ID) and a numeric value;

(ii) each $T_n$ produces the ID of one of the $P_{nz}$ nodes connected to it;

(iii) each one of the $T_n$ nodes is connected to all others; and (iv) each node Tn is comprised by the multilayer neural network;

b) calculating the Fitness Score for output of the neural network, and on the basis of Fitness Score, the value produced by the network is compared to target, and neural network parameters for a plurality of the $T_n$ are changed;

c) calculating Fitness Score again for output of the neural network with parameters changed in step (b);

d) determining if a change was beneficial or not to the fitness of the resulting set, wherein if the change was beneficial, the direction of change is maintained with smaller increments, and wherein if the change was not beneficial, either direction is reversed or the parameters revert to a previous state;

e) repeating steps (b)-(d) iteratively, wherein at a plurality of iterations random changes are made to the parameters of the network, and wherein when the rate of fitness improvement decreases, the frequency of such random changes is increased, until a set of primer pairs for target genes in set N is identified that has the fitness score at a predetermined threshold.

8. The method of claim 1, wherein steps (2)-(4) comprise:

a) picking the target at random, as well as a primer for such target, and placing it in set R;

b) picking an additional target, and calculating the Fitness Score evaluating all primers for this target in combination with primers already in set R on the basis of ΔG for all potential interactions, wherein the primer that results in the best Fitness Score is added to set R;

c) if fitness of set R is below a predetermined threshold T, removing one of the primers from R according to the following:

calculating the Fitness Score for set Ri, wherein the $i^{th}$ target with its primer is removed from set R, and the set with the best Fitness Score determines the target with its primer to be removed from set R and placed back into the pool of primers of step (1); and d) repeating steps (b) and (c) until all targets have optimized are assigned primers.

9. The method of claim 1, wherein steps (2)-(4) comprise:

a) picking the target at random, as well as a primer for such target, and placing it in set R;

b) picking an additional target, and calculating the Fitness Score evaluating all primers for this target in combination with primers already in set R on the basis of ΔG for all potential interactions, wherein the primer that results in the best Fitness Score is added to set R;

c) if fitness of set R is below a predetermined threshold T, removing one of the primers from R according to the following:

calculating the Fitness Score for set Ri, wherein the $i^{th}$ target with its primer is removed from set R, and the set with the best Fitness Score determines the target with its primer to be removed from set R and placed back into the pool of primers of step (1);

d) repeating steps (b) and (c) until all targets have optimized primers;

e) once all targets have optimized primers, designating set R as $R_1$, and its fitness as $F_1$;

f) creating empty set $R_{z+1}$, where Z is the number of sets, with fitness $F_{z+1}$;

g) for each set Rz, where z is an index from 1 to number of sets R, determining the element that is worst for the set's fitness, and removing this element, designated Target E;

h) recalculating Fz after removal of Target E;

i) for all Rz, determining where Target E can be added so as to maximize Fz and maximize the minimum of Fz; and j) if the minimum of Fz is below the predetermined threshold, repeating steps (f)-(i) until the standard deviation of Fz is below the predetermined threshold, thereby designing the multiplex primer set.

10. The method of claim 9, wherein the step of determining the element in step (g) that is worst for fitness is performed in a method according to step (4).

11. A method of multiplex amplification, sequencing, and/or genotyping comprising using an optimized primer set designed according to claim 2.

12. The method of claim 1, wherein the optimized primer set has decreased primer-primer interactions with other primers in the set, compared to the initial set of forward and reverse amplification primers.

13. The method of claim 1, wherein the Fitness Score of the optimized primer set is increased compared to the initial set of forward and reverse amplification primers.

14. The method of claim 1, wherein the Fitness Score of the optimized primer set is a threshold Fitness Score of at least 400.

15. The method of claim 1, wherein the fitness score optimization method is a method of genetic algorithm, wherein steps (2) and (3) comprise:

i) for each member of set N, selecting from the set of primers in step (1) a subset of primer pairs that satisfies the conditions for a primer selection algorithm and is predicted to be specific for its target; and ii) repeating step (i) to generate set P, a population of randomly selected primer sets for each target gene in set N; and

708 wherein step (4) comprises:

iii) calculating a Fitness Score for each member of the population P; and iv) placing members of population P into a pool of candidate primer sets on the basis of Fitness Scores; and v) randomly selecting a plurality of "parent" sets of candidate primers from the pool of step (iv), each parent set including a different pair of candidate primer sets, parent A and parent B; and vi) for each parent set of candidate primers, creating a crossover set of candidate primers by replacing a subset of candidate primer pairs of parent A with the corresponding subset of primer pairs of parent B; and vii) randomly replacing one primer pair in crossover set A with a different primer pair for the corresponding target sequence generated in step (i) to create a Generation 2 population of primer sets for each target gene in set N; and viii) repeating steps (iii)-(vii) iteratively until a set of primer pairs for target genes in set N is identified that has a Fitness Score at a predetermined threshold, and runs for an additional set amount of iterations with no measurable improvement in the fitness of the best member, whereby an optimized primer set is designed.

16. A method of preparing an optimized primer set for multiplex genotyping, the method comprising:

A) for a given set N of variable genomic target sequences to be genotyped in a sample, designing a set of forward and reverse amplification primers that will amplify a sequence comprising each variable genomic target sequence in a multiplex amplification reaction, wherein the designing includes the steps of:

1) identifying all possible primers of 17 to 35 nucleotides within 100 base pairs of each genomic target sequence variation in set N of variable genomic target sequences;

2) For each member of set N, selecting from the set of primers in step (1) a subset of primer pairs that satisfies the conditions of a primer selection algorithm and is predicted to be specific for its target;

3) Repeating step (2) to generate set P, a population of randomly selected primer sets for each target gene in set N;

4) calculating a Fitness Score for each member of the population P;

wherein the Fitness Score is generated according to the method:

a) determining G=the set of ΔG's for all possible interactions determined for members of the primer set; and b) calculating the Fitness Score by:

i) determining the sum, S, of $|\Delta G|^Q$ for each ΔG value, wherein Q is a weighting factor constant exponent that makes large ΔG absolute values much larger than small values;

ii) determining S'=S/# of ΔG values in G;

iii) determining H=T/S', wherein T is a constant that makes H small for large values of S' and H large for small values of S'; and iv) determining the Fitness Score=$H^R$, wherein R is a weighting factor constant exponent that makes large values of H larger, and small values of H smaller;

5) Placing members of population P into a pool of candidate primer sets on the basis of Fitness Scores;

6) randomly selecting a plurality of "parent" sets of candidate primers from the pool of step (5), each parent set including a different pair of candidate primer sets, parent A and parent B;

7) For each parent set of candidate primers, creating a crossover set of candidate primers by replacing a subset of candidate primer pairs of parent A with the corresponding subset of primer pairs of parent B;

8) Randomly replacing one primer pair in crossover set A with a different primer pair for the corresponding target sequence generated in step (2) to create a Generation 2 population of primer sets for each target gene in set N; and 9) repeating steps (4)-(8) iteratively until a set of primer pairs for target genes in set N is identified that has a Fitness Score at a predetermined threshold, and runs for an additional set amount of iterations with no measurable improvement in the fitness of the best member, whereby an optimized primer set is designed; and B) synthesizing the optimized primer set designed in step (9).

17. A method of preparing a primer set for multiplex genotyping, the method comprising:

A) for a given set N of variable genomic target sequences to be genotyped in a sample, designing a set of forward and reverse amplification primers that will amplify a sequence comprising each variable genomic target sequence in a multiplex amplification reaction, wherein the designing includes the steps of:

1) identifying all possible primers of 17 to 35 nucleotides within 100 base pairs of each genomic target sequence variation in set N of variable genomic target sequences;

2) Selecting a primer set for the multiplex amplification and genotyping of the members of set N comprising:

a) from the set of all possible primers for each genomic target sequence variation of step (1), randomly selecting set P, a population of sets of candidate primers, each individual set of candidate primers in population P including a primer pair for the amplification of each member of set N of variable genomic target sequences to be genotyped;

b) calculating a fitness score for each member of the population of set P by calculating ΔG for all possible interactions between candidate primers in each member of the population of set P, and assigning each member of set P a Fitness Score according to the rule:

i) G=the set of ΔG's for all possible interactions determined for a given member of set P;

ii) Number of top scorers to go into next generation= 1 . . . N, Number of distinct populations sets=1 . . . N, and Population size=1 . . . N such that number of top scorers to go into next generation is greater or equal to population size;

wherein the fitness score is calculated by:

iii) for each member of set P, calculating the sum, S, of $|\Delta G|^Q$ for each ΔG value in that member, wherein Q is a weighting factor constant exponent that makes large ΔG absolute values much larger than small values;

iv) S'=S/# of ΔG values in G;

v) H=T/S', wherein T is a constant that makes H small for large values of S' and H large for small values of S';

vi) Fitness Score=$H^R$, wherein R is a weighting factor constant exponent that makes large values of H larger, and small values of H smaller;

c) selecting a set of primers for the multiplex amplification and genotyping of members of set N by:

i) randomly selecting a plurality of sets of "parent" sets of candidate primers, each having parent set A and parent set B, from set P based upon Fitness Scores;

ii) for each member of the plurality of sets of parents, creating a crossover set of candidate primers by replacing a subset of candidate primers in parent set A with a corresponding subset of candidate primers in parent set B, resulting in two crossover sets, crossover set A and crossover set B; and iii) randomly replacing one primer pair in crossover set A with a different primer pair for the corresponding variable genomic target sequence to create a next generation population of candidate sets of primers, Generation 2; and d) iteratively repeating steps (a)-(c), whereby a primer set for the multiplex amplification and genotyping of set N of variable genomic target sequences is selected; and B) synthesizing the primer set designed in step (A).

\* \* \* \* \*

SEQUENCE LISTING

<160> NUMBER OF SEQ ID NOS: 1529

<210> SEQ ID NO 1
<211> LENGTH: 137
<212> TYPE: DNA
<213> ORGANISM: Unknown
<220> FEATURE:
<223> OTHER INFORMATION: Description of Unknown:
     target sequence

<400> SEQUENCE: 1
gcaaggaata tattaaattt tttctttctt gcacagaatt caatgttaaa caagtatgtt        60
gccattctgt ggaaggcatt attttcccct tccaaacttt gaaactcaaa agttttctaa       120
gaaaaaaaat caaatcc                                                     137

<210> SEQ ID NO 2
<211> LENGTH: 150

-continued

```
<212> TYPE: DNA
<213> ORGANISM: Unknown
<220> FEATURE:
<223> OTHER INFORMATION: Description of Unknown:
      target sequence

<400> SEQUENCE: 2
gcaaggaata tattaaattt tttctttctt gcacagaatt caatgttaaa caagtatgtt        60
gccattctgt ggaattaaaa aaaaaaaggc attattttcc ccttccaaac tttgaaactc       120
aaaagttttc taagaaaaaa aatcaaatcc                                        150

<210> SEQ ID NO 3
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 3
atatagtgtc aggttaagca ttattaggtt aagttatagc tatctgtggc aatagcaagc        60
agtttcaagg gatgaatcca tagctcaaag cggggaatag gacgtatagc tctctcattt       120
taatgtctct ctgggcctga tgatttaaaa gactcacact cctaagatga aagttatttt       180
ctcatctatg taatgtgtta a                                                 201

<210> SEQ ID NO 4
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 4
atatagtgtc aggttaagca ttattaggtt aagttatagc tatctgtggc aatagcaagc        60
agtttcaagg gatgaatcca tagctcaaag cggggaatag gatgtatagc tctctcattt       120
taatgtctct ctgggcctga tgatttaaaa gactcacact cctaagatga aagttatttt       180
ctcatctatg taatgtgtta a                                                 201

<210> SEQ ID NO 5
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 5
taagaactgt taggtgactg acacatctag gaggaaaatg aggggtgtcc tggcgcttag        60
ttcttcaaac ccggtaggaa taaggcaagc ctggtctaca ggaaaccatc tgtcctgact       120
ccgggagggt aagatggaca agcaggtcat tttcagctcc tatttcagtt gccctatgga       180
acaggggtga ttcaaactgt a                                                 201

<210> SEQ ID NO 6
<211> LENGTH: 201
<212> TYPE: DNA
<213> ORGANISM: Unknown
<220> FEATURE:
<223> OTHER INFORMATION: Description of Unknown:
      target sequence
```

<400> SEQUENCE: 6
taagaactgt taggtgactg acacatctag gaggaaaatg aggggtgtcc tggcgcttag          60
ttcttcaaac ccggtaggaa taaggcaagc ctggtctaca gggaaccatc tgtcctgact         120
ccgggagggt aagatggaca agcaggtcat tttcagctcc tatttcagtt gccctatgga         180
acaggggtga ttcaaactgt a                                                   201

<210> SEQ ID NO 7
<211> LENGTH: 199
<212> TYPE: DNA
<213> ORGANISM: Unknown
<220> FEATURE:
<223> OTHER INFORMATION: Description of Unknown:
      target sequence

<400> SEQUENCE: 7
ctgcacaggg ccgggatccc tgccctctgg gagttgatgc tcttggggtg ggaggacaca          60
gatgcttcag gatcccttag tgcttcagga ttctagagtc tcagaatttc caagccaagg         120
cttggagtgc ctcagctgat gtcacagtgg aggttctagc agagtgggta gcacatatgt         180
gtcatgtccc tctggtctg                                                      199

<210> SEQ ID NO 8
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 8
ctgcacaggg ccgggatccc tgccctctgg gagttgatgc tcttggggtg ggaggacaca          60
gatgcttcag gatcccttag tgcttcagga ttctagagtc tcttagaatt tccaagccaa         120
ggcttggagt gcctcagctg atgtcacagt ggaggttcta gcagagtggg tagcacatat         180
gtgtcatgtc cctctggtct g                                                   201

<210> SEQ ID NO 9
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 9
gtgagactgc gtgtgcaggt gtgtgtggag ggctgtgggg agctgtgtgt gggggggtg          60 tgtgtgtgag gttgggggct gtgtggggtg tgtgtgaggc tgcgtgtggg gagtgtgagg         120
ctgtgtgtgt gcgagggga ctatgtgtgt cggatgatgt ccctggctgt gtgtggggat          180
gtgtgtgtgt gtgtgtgtgt g                                                   201

<210> SEQ ID NO 10
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 10

-continued

```
gtgagactgc gtgtgcaggt gtgtgtggag ggctgtgggg agctgtgtgt gggggggggtg      60 tgtgtgtgag gttggggggct gtgtggggtg tgtgtgaggc tgtgtgtggg gagtgtgagg     120
ctgtgtgtgt gcgagggggga ctatgtgtgt cggatgatgt ccctggctgt gtgtgggggat    180 gtgtgtgtgt gtgtgtgtgt g                                                 201

<210> SEQ ID NO 11
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 11
ccaatacagg agcactcaga ttcataaagc aagtccttag agacctacaa agagacttag      60
aactcccaca caataataat gggagacttc aacacctcac tgccaacatt agacagatag     120
agacagaaag ttaacaagga tatccaggaa ttgaactcag gaattgaact cagctctgca     180
ccaagcggac ctaatagaca t                                                201

<210> SEQ ID NO 12
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 12
ccaatacagg agcactcaga ttcataaagc aagtccttag agacctacaa agagacttag      60
aactcccaca caataataat gggagacttc aacacctcac tgtcaacatt agacagatag     120
agacagaaag ttaacaagga tatccaggaa ttgaactcag gaattgaact cagctctgca     180
ccaagcggac ctaatagaca t                                                201

<210> SEQ ID NO 13
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 13
caagtgaaac aaccaactat ggctgtaagg atcatgaaaa acagggaatt cccccccagt      60
ttacacagac aacaaaaact aagtgtaggt cactatctca ttgtacccat ggattttaat     120
ttatagaggt gactgagtga tgacatagaa agaccaatgc catcgaaaga ataatttatt     180
acttacaagt cctgggagaa g                                                201

<210> SEQ ID NO 14
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 14
caagtgaaac aaccaactat ggctgtaagg atcatgaaaa acagggaatt cccccccagt      60
ttacacagac aacaaaaact aagtgtaggt cactatctca ttttacccat ggattttaat     120
```

-continued

```
ttatagaggt gactgagtga tgacatagaa agaccaatgc catcgaaaga ataatttatt      180
acttacaagt cctgggagaa g                                                201

<210> SEQ ID NO 15
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 15
cttttgtctc ccaggcaaga tgctattagg ggtcacttcc catgtacgga gaaaacaatc      60
ttcatggata ataatgataa aaccttatgg aatgcaaaaa caaccaaaat atgtattctc      120
ggatgactgc attagggcca agtcaatatt agtcccactt cacccacgca ttgcatagtc      180
taaaaatgct gtcagcctga t                                                201

<210> SEQ ID NO 16
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 16
cttttgtctc ccaggcaaga tgctattagg ggtcacttcc catgtacgga gaaaacaatc      60
ttcatggata ataatgataa aaccttatgg aatgcaaaaa cagccaaaat atgtattctc      120
ggatgactgc attagggcca agtcaatatt agtcccactt cacccacgca ttgcatagtc      180
taaaaatgct gtcagcctga t                                                201

<210> SEQ ID NO 17
<211> LENGTH: 180
<212> TYPE: DNA
<213> ORGANISM: Unknown
<220> FEATURE:
<223> OTHER INFORMATION: Description of Unknown:
      target sequence

<400> SEQUENCE: 17
caacgttttt tagattcctc atatgagtga gatcatgctg tgaatctgtt tctggctgat      60
ttcacttagg aggatgtcct ccaagctcat ccatgctgtc ccaaaggctg aataatattc      120
cattgtatat atctctcaca ttttctttat ccattcattc atcaacttag atttttttca      180

<210> SEQ ID NO 18
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 18
caacgttttt tagattcctc atatgagtga gatcatgctg tgaatctgtt tctggctgat      60
ttcacttagg aggatgtcct ccaagctcat ccatgctgtc ccaaagggca agatctcctt      120
tttaaaggct gaataatatt ccattgtata tatctctcac attttcttta tccattcatt      180
catcaactta gatttttttc a                                                201
```

<210> SEQ ID NO 19
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 19
agagcaagat aagtagaatc caaagcaatg atctgactgc tcaaaatcac cgatattgac          60
aactgactcc caaatccctg cttcatctaa catatattgc taataccatg cccagataga         120
acacaaagca atatttatta tatgacaaat tctctccata attttagaga gttttcccta         180
aggaaagaaa ggactttta a                                                     201

<210> SEQ ID NO 20
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 20
agagcaagat aagtagaatc caaagcaatg atctgactgc tcaaaatcac cgatattgac          60
aactgactcc caaatccctg cttcatctaa catatattgc tactaccatg cccagataga         120
acacaaagca atatttatta tatgacaaat tctctccata attttagaga gttttcccta         180
aggaaagaaa ggactttta a                                                     201

<210> SEQ ID NO 21
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 21
atattagtag acataaaaat cacctgggga gagtgtaaaa aaataaaaat tcccagaaat          60
tctggttcag tcattttggg gccaacctag tcatttgcat taatcagcat gcactccctg         120
atgattctga tataaatgaa tcacatgttg caaaatgctt tagcctgttc cctaatctaa         180
atcttatctc tctcctctca g                                                    201

<210> SEQ ID NO 22
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 22
atattagtag acataaaaat cacctgggga gagtgtaaaa aaataaaaat tcccagaaat          60
tctggttcag tcattttggg gccaacctag tcatttgcat tagtcagcat gcactccctg         120
atgattctga tataaatgaa tcacatgttg caaaatgctt tagcctgttc cctaatctaa         180
atcttatctc tctcctctca g                                                    201

<210> SEQ ID NO 23
<211> LENGTH: 201

<212> TYPE: DNA
<213> ORGANISM: Unknown
<220> FEATURE:
<223> OTHER INFORMATION: Description of Unknown:
        target sequence

<400> SEQUENCE: 23
actcaagtga tcctcctgcc ttggcctccc aaagtgctag gattacaggc atgagccact      60
gcgcctggcc cagttactta ttttagaagt tatatttgag cacctattct gtgccgagcc     120
ctggcatgag ctgtgaacag gccatatcta tcctagatgt gcactaatgg ggctttggag     180
ggtggcaaca ggaggcccgg t                                              201

<210> SEQ ID NO 24
<211> LENGTH: 201
<212> TYPE: DNA
<213> ORGANISM: Unknown
<220> FEATURE:
<223> OTHER INFORMATION: Description of Unknown:
        target sequence

<400> SEQUENCE: 24
actcaagtga tcctcctgcc ttggcctccc aaagtgctag gattacaggc atgagccact      60
gcgcctggcc cagttactta ttttagaagt tatatttgag catctattct gtgccgagcc     120
ctggcatgag ctgtgaacag gccatatcta tcctagatgt gcactaatgg ggctttggag     180
ggtggcaaca ggaggcccgg t                                              201

<210> SEQ ID NO 25
<211> LENGTH: 201
<212> TYPE: DNA
<213> ORGANISM: Unknown
<220> FEATURE:
<223> OTHER INFORMATION: Description of Unknown:
        target sequence

<400> SEQUENCE: 25
cttaaatgca aatggtaaat ctgaggcagc agtaaggtag agtggaaagg ctttagggga      60
aaaaaaataa agtctgagaa actgtcacag caagaggacc ctaaggagac atgacaagta     120
aatgtaatat ggtgtcctgg atggcatcct ggaaaagaaa agggacatta gataaaaaca     180
aaccatggac ttcaataata a                                              201

<210> SEQ ID NO 26
<211> LENGTH: 201
<212> TYPE: DNA
<213> ORGANISM: Unknown
<220> FEATURE:
<223> OTHER INFORMATION: Description of Unknown:
        target sequence

<400> SEQUENCE: 26
cttaaatgca aatggtaaat ctgaggcagc agtaaggtag agtggaaagg ctttagggga      60
aaaaaaataa agtctgagaa actgtcacag caagaggacc ctgaggagac atgacaagta     120
aatgtaatat ggtgtcctgg atggcatcct ggaaaagaaa agggacatta gataaaaaca     180
aaccatggac ttcaataata a                                              201

<210> SEQ ID NO 27
<211> LENGTH: 201
<212> TYPE: DNA
<213> ORGANISM: Unknown
<220> FEATURE:

-continued

```
<223> OTHER INFORMATION: Description of Unknown:
      target sequence

<400> SEQUENCE: 27
gctagcaaaa ggttcattgt cagagataac ctaggtctga ggaagcagag gccaatagtt        60
tttacatgca tcagagtgtt agacaataag atgcagtgta aaagtgtttg ttctcactgc       120
taaccaaaga caggcaaatt aagactatta aagtatcctt ttctacccac taaaataatt       180
ttagagaaaa tttaagatta c                                                 201

<210> SEQ ID NO 28
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 28
gctagcaaaa ggttcattgt cagagataac ctaggtctga ggaagcagag gccaatagtt        60
tttacatgca tcagagtgtt agacaataag atgcagtgta aaggtgtttg ttctcactgc       120
taaccaaaga caggcaaatt aagactatta aagtatcctt ttctacccac taaaataatt       180
ttagagaaaa tttaagatta c                                                 201

<210> SEQ ID NO 29
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 29
atttcttaaa tgggtacgtt ttgtttgtac ccatctcaag acctttgaga tagccattcc        60
acttgatttt tttttttttt ttgagatgga gtcttgccct gtcgccaggc tggagtgcgg       120
tggcgtgatc tcaactcaat gcaaccgctg attccctggt tcaagtgatt ctcctgcctc       180
agcctcccaa gtagctggga t                                                 201

<210> SEQ ID NO 30
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 30
atttcttaaa tgggtacgtt ttgtttgtac ccatctcaag acctttgaga tagccattcc        60
acttgatttt tttttttttt ttgagatgga gtcttgccct gttgccaggc tggagtgcgg       120
tggcgtgatc tcaactcaat gcaaccgctg attccctggt tcaagtgatt ctcctgcctc       180
agcctcccaa gtagctggga t                                                 201

<210> SEQ ID NO 31
<211> LENGTH: 201
<212> TYPE: DNA
<213> ORGANISM: Unknown
<220> FEATURE:
<223> OTHER INFORMATION: Description of Unknown:
      target sequence
```

```
<400> SEQUENCE: 31
ataaagaagc ttactgtggt cctgtagggc ctaccatcct gtgttggtat tgctccaaag      60
ataagcattt ttgattaaat tggagattgc cctcatttgg ggcagggagg ggggtgctta     120
gtccagtgat ttcacaagca ttttggtctc aggacccttt tttaactctt aaaatttgtt     180
gagaacagca aataaattgt t                                               201

<210> SEQ ID NO 32
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 32
ataaagaagc ttactgtggt cctgtagggc ctaccatcct gtgttggtat tgctccaaag      60
ataagcattt ttgattaaat tggagattgc cctcatttgg ggtagggagg ggggtgctta     120
gtccagtgat ttcacaagca ttttggtctc aggacccttt tttaactctt aaaatttgtt     180
gagaacagca aataaattgt t                                               201

<210> SEQ ID NO 33
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 33
ctcccggagt agctctggga gcaaggccct ccctggatcc ctccctcttt cccggtgtgc      60
ctgtctttcc cgctccatcc tccagcctcc accgggagga acacggctgc attgttcctc     120
aggaggaggc cctgcctcgg ggcctggccc agtgcccagg tgggggggcca ggaacaaaac    180 tctgagatcg aggggcgggg t                                               201

<210> SEQ ID NO 34
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 34
ctcccggagt agctctggga gcaaggccct ccctggatcc ctccctcttt cccggtgtgc      60
ctgtctttcc cgctccatcc tccagcctcc accgggagga acgcggctgc attgttcctc     120
aggaggaggc cctgcctcgg ggcctggccc agtgcccagg tgggggggcca ggaacaaaac    180 tctgagatcg aggggcgggg t                                               201

<210> SEQ ID NO 35
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 35
agaatctgat taataattgc ccagtaggga ccagttcctg ggtcctgctg agcggagggg      60
```

-continued

```
agggagttct gggctggttc tggctggcca gccgaggaga ggagaggagc aaaggtgact        120
ttgagctgca gagggtggcc gctggggccc agagctggca gatcccagcg gctggcctcc        180
ttccatgctt ccctggtggc t                                                  201

<210> SEQ ID NO 36
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 36
agaatctgat taataattgc ccagtaggga ccagttcctg ggtcctgctg agcggagggg         60
agggagttct gggctggttc tggctggcca gccgaggaga gggggaggagc aaaggtgact       120 ttgagctgca gagggtggcc gctggggccc agagctggca gatcccagcg gctggcctcc        180
ttccatgctt ccctggtggc t                                                  201

<210> SEQ ID NO 37
<211> LENGTH: 193
<212> TYPE: DNA
<213> ORGANISM: Unknown
<220> FEATURE:
<223> OTHER INFORMATION: Description of Unknown:
      target sequence

<400> SEQUENCE: 37
accaaaagta tgctctggct ggattgcagc tactcaaaag gagaaggaac tgggatgagg         60
ctagagatgt agtcagaccc tataaatttt ttttttttt ttgagcattg agacctcagg        120
aacaggtttt aatgggtgtt tgctggtgga ggagagggtg gagtgactta acatgatgag        180
acttactgtg ttg                                                           193

<210> SEQ ID NO 38
<211> LENGTH: 194
<212> TYPE: DNA
<213> ORGANISM: Unknown
<220> FEATURE:
<223> OTHER INFORMATION: Description of Unknown:
      target sequence

<400> SEQUENCE: 38
accaaaagta tgctctggct ggattgcagc tactcaaaag gagaaggaac tgggatgagg         60
ctagagatgt agtcagaccc tataaatttt ttttttttt tttgagcatt gagacctcag        120
gaacaggttt taatgggtgt ttgctggtgg aggagagggt ggagtgactt aacatgatga        180
gacttactgt gttg                                                          194

<210> SEQ ID NO 39
<211> LENGTH: 195
<212> TYPE: DNA
<213> ORGANISM: Unknown
<220> FEATURE:
<223> OTHER INFORMATION: Description of Unknown:
      target sequence

<400> SEQUENCE: 39
accaaaagta tgctctggct ggattgcagc tactcaaaag gagaaggaac tgggatgagg         60
ctagagatgt agtcagaccc tataaatttt ttttttttt ttttgagcat tgagacctca       120
```

-continued

```
ggaacaggtt ttaatgggtg tttgctggtg gaggagaggg tggagtgact taacatgatg        180
agacttactg tgttg                                                          195
```

```
<210> SEQ ID NO 40
<211> LENGTH: 196
<212> TYPE: DNA
<213> ORGANISM: Unknown
<220> FEATURE:
<223> OTHER INFORMATION: Description of Unknown:
      target sequence

<400> SEQUENCE: 40
accaaaagta tgctctggct ggattgcagc tactcaaaag gagaaggaac tgggatgagg         60
ctagagatgt agtcagaccc tataaatttt ttttttttt tttttgagca ttgagacctc        120
aggaacaggt tttaatgggt gtttgctggt ggaggagagg gtggagtgac ttaacatgat        180
gagacttact gtgttg                                                        196
```

```
<210> SEQ ID NO 41
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 41
ggacctgagc ggtagccttg gtccactgca gacatcagca agttcttaga tcaggcgggg         60
aaccggtcca cccactcatg ctctggttta gctccctact ctgctttctg agagtcagtt        120
tggaagggaa cctagcggag ctcctcagag tctcagggtc cttgtctttg atgaactttc        180
tgcttggtca taggcagcct c                                                  201
```

```
<210> SEQ ID NO 42
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 42
ggacctgagc ggtagccttg gtccactgca gacatcagca agttcttaga tcaggcgggg         60
aaccggtcca cccactcatg ctctggttta gctccctact cttctttctg agagtcagtt        120
tggaagggaa cctagcggag ctcctcagag tctcagggtc cttgtctttg atgaactttc        180
tgcttggtca taggcagcct c                                                  201
```

```
<210> SEQ ID NO 43
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 43
aaaatgcgta gcatggctcc tgtaactacg agagctccac aaatgcaaac tatatgacaa         60
gtgaggaaca ttagatgaca gtcatgcttc gatttaagta aagttaattg taaaaatata        120
aacttcctag aggaagttgt tcttcgttcc tgcggctgtt gttctaacaa gttaattcct        180
ttggtggatt tccagtaaga t                                                  201
```

-continued

<210> SEQ ID NO 44
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 44
aaaatgcgta gcatggctcc tgtaactacg agagctccac aaatgcaaac tatatgacaa      60
gtgaggaaca ttagatgaca gtcatgcttc gatttaagta aatttaattg taaaaatata     120
aacttcctag aggaagttgt tcttcgttcc tgcggctgtt gttctaacaa gttaattcct     180
ttggtggatt tccagtaaga t                                                201

<210> SEQ ID NO 45
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 45
ctgtccagtc aggcagcgcg ccagtcagcc ttcctccgtt tgctgtttca cctttccaat      60
ccctcatttt cacccattgg ctcctaatgt gggacactgc tgagggcttt ggttttctac     120
ctcagtgagc gttcaacagt ctgttttgac gccttgcttt tagagccagg tttaacaaag     180
caaggcatgg aatcattttc c                                                201

<210> SEQ ID NO 46
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 46
ctgtccagtc aggcagcgcg ccagtcagcc ttcctccgtt tgctgtttca cctttccaat      60
ccctcatttt cacccattgg ctcctaatgt gggacactgc tgtgggcttt ggttttctac     120
ctcagtgagc gttcaacagt ctgttttgac gccttgcttt tagagccagg tttaacaaag     180
caaggcatgg aatcattttc c                                                201

<210> SEQ ID NO 47
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 47
tttggatttc ctcttggctg tgttcatatc aatttatctc accccacacc ccacagtact      60
tggtgtacca gttctggaac tactggtatt tattgctgtg ccaaggaggc ccattgcaca     120
agtcctccta aaagaggcca ttgtctcgat cactttaaca tctccgccct ggggagcttc     180
aggctgagag atgggcctaa c                                                201

<210> SEQ ID NO 48

<211> LENGTH: 201
<212> TYPE: DNA
<213> ORGANISM: Unknown
<220> FEATURE:
<223> OTHER INFORMATION: Description of Unknown:
     target sequence

<400> SEQUENCE: 48
tttggatttc ctcttggctg tgttcatatc aatttatctc accccacacc ccacagtact      60
tggtgtacca gttctggaac tactggtatt tattgctgtg ccgaggaggc ccattgcaca     120
agtcctccta aaagaggcca ttgtctcgat cactttaaca tctccgccct ggggagcttc     180
aggctgagag atgggcctaa c                                               201

<210> SEQ ID NO 49
<211> LENGTH: 201
<212> TYPE: DNA
<213> ORGANISM: Unknown
<220> FEATURE:
<223> OTHER INFORMATION: Description of Unknown:
     target sequence

<400> SEQUENCE: 49 attttttgctt tttttttttt tttttttttt tgtggagagg gtgtttctcc atgttgccca      60
ggctggtctc aaactcctga gctcaagaga tctgcctgcc tcagcctccc aaagtgctag     120
gattataggc atgagctact gcgcctgccc agagcctgca ttctttacct ttacagtcta     180
gaccctgctc ctatagatcc c                                               201

<210> SEQ ID NO 50
<211> LENGTH: 201
<212> TYPE: DNA
<213> ORGANISM: Unknown
<220> FEATURE:
<223> OTHER INFORMATION: Description of Unknown:
     target sequence

<400> SEQUENCE: 50 attttttgctt tttttttttt tttttttttt tgtggagagg gtgtttctcc atgttgccca      60
ggctggtctc aaactcctga gctcaagaga tctgcctgcc tcggcctccc aaagtgctag     120
gattataggc atgagctact gcgcctgccc agagcctgca ttctttacct ttacagtcta     180
gaccctgctc ctatagatcc c                                               201

<210> SEQ ID NO 51
<211> LENGTH: 201
<212> TYPE: DNA
<213> ORGANISM: Unknown
<220> FEATURE:
<223> OTHER INFORMATION: Description of Unknown:
     target sequence

<400> SEQUENCE: 51
tggaacaaag gtggtgctta tgggatgtat ggagctgtgg gatgtgggag aggacaggtt      60
tagcagagtg gcgtggtgga aagtttcctc tcgccgagga ggacaactcc ccagcgcctg     120
agacagcggg agctcagagc gcctagaatg tgcccagatt ctaaagtgaa gcaggctgtg     180
gtgtgatgat ggcccccgag g                                               201

<210> SEQ ID NO 52
<211> LENGTH: 201
<212> TYPE: DNA
<213> ORGANISM: Unknown

<220> FEATURE:
<223> OTHER INFORMATION: Description of Unknown:
      target sequence

<400> SEQUENCE: 52
tggaacaaag gtggtgctta tgggatgtat ggagctgtgg gatgtgggag aggacaggtt      60
tagcagagtg gcgtggtgga aagtttcctc tcgccgagga ggccaactcc ccagcgcctg     120
agacagcggg agctcagagc gcctagaatg tgcccagatt ctaaagtgaa gcaggctgtg     180
gtgtgatgat ggcccccgag g                                               201

<210> SEQ ID NO 53
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 53
tgcctgtctt ctgcaggggc ctctgcaccc acaggcttgg tccacagctg cctcttggtt      60
gtccctccac ctccctggcc tttgagactc cctcagtggc ttcgtcagag ttctctgagc     120
ccagctgtgg aggagagtct gaaacagctg ctctgggagg cggcagcagg agtgtcccag     180
cgccgtgggc tgggctggtg c                                               201

<210> SEQ ID NO 54
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 54
tgcctgtctt ctgcaggggc ctctgcaccc acaggcttgg tccacagctg cctcttggtt      60
gtccctccac ctccctggcc tttgagactc cctcagtggc tttgtcagag ttctctgagc     120
ccagctgtgg aggagagtct gaaacagctg ctctgggagg cggcagcagg agtgtcccag     180
cgccgtgggc tgggctggtg c                                               201

<210> SEQ ID NO 55
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 55
aggcactgaa gggtgaggct gtgtgccact ccttgggctg gctccagctg acagggttgt      60
ccacagtaga aaatgtgcct gtgggcagtg gggtcggccc ccagccccac gtgggaggat     120
gaacaaccct cggcaccatg ccatgcgctt tgctcagatt ccccttcagg aaattactga     180
tttggtttct taggaattgg c                                               201

<210> SEQ ID NO 56
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 56
aggcactgaa gggtgaggct gtgtgccact ccttgggctg gctccagctg acagggttgt        60
ccacagtaga aaatgtgcct gtgggcagtg gggtcggccc ccggccccac gtgggaggat       120
gaacaaccct cggcaccatg ccatgcgctt tgctcagatt cccccttcagg aaattactga      180 tttggtttct taggaattgg c                                                 201

<210> SEQ ID NO 57
<211> LENGTH: 200
<212> TYPE: DNA
<213> ORGANISM: Unknown
<220> FEATURE:
<223> OTHER INFORMATION: Description of Unknown:
      target sequence

<400> SEQUENCE: 57
ggagtctttc ccccattgct tgcttttaat tggctttgtt gaagatgaga tggttatagt        60
tgtgttttct gagttcttta ttctgtttca ttggtctatg tttttttttt gtttttttt       120 tttttgaaag tgtctcactc tttaccaagg ctggagtgta gtggcatgat cacagctcac      180
tgaagcctca gccttcaggg                                                   200

<210> SEQ ID NO 58
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 58
ggagtctttc ccccattgct tgcttttaat tggctttgtt gaagatgaga tggttatagt        60
tgtgttttct gagttcttta ttctgtttca ttggtctatg ttgtttttt tgtttttttt       120 ttttttgaaa gtgtctcact ctttaccaag gctggagtgt agtggcatga tcacagctca      180
ctgaagcctc agccttcagg g                                                 201

<210> SEQ ID NO 59
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 59
cccactcatg agaactctac ccccatccaa tcacctccca cttggtccca cctccaacat        60
gggggattat aactggacat gagatttagt ggggacagag atacaaatta tatcattcca       120
cccccagccc ctccaaattt catgtccttc tcatattgca aaatacaatc atcccttctc       180
aacagtcccc caaagtctta t                                                 201

<210> SEQ ID NO 60
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 60

-continued

```
cccactcatg agaactctac ccccatccaa tcacctccca cttggtccca cctccaacat      60
gggggattat aactggacat gagatttagt ggggacagag atccaaatta tatcattcca     120
cccccagccc ctccaaattt catgtccttc tcatattgca aaatacaatc atcccttctc     180
aacagtcccc caaagtctta t                                             201
```

<210> SEQ ID NO 61
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 61

```
tttgacgagt tgagagaaga aggcttcaga tgatcaaact actccgagct acaggaggaa      60
attcaaacca aaggcaaaga agttcaaaac tttgaaaaaa atgtagacga atgtataatt     120
agaataacca atacagaaaa gtgcttaaag gagctgatgg agctgaaagc caaggctgga     180
gaactacgtg aagaatgcag a                                             201
```

<210> SEQ ID NO 62
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 62

```
tttgacgagt tgagagaaga aggcttcaga tgatcaaact actccgagct acaggaggaa      60
attcaaacca aaggcaaaga agttcaaaac tttgaaaaaa atttagacga atgtataatt     120
agaataacca atacagaaaa gtgcttaaag gagctgatgg agctgaaagc caaggctgga     180
gaactacgtg aagaatgcag a                                             201
```

<210> SEQ ID NO 63
<211> LENGTH: 199
<212> TYPE: DNA
<213> ORGANISM: Unknown
<220> FEATURE:
<223> OTHER INFORMATION: Description of Unknown:
      target sequence

<400> SEQUENCE: 63

```
gatccagatt gtgaggtcat gaaatgctta tgaacagaga gcttaagagt aactagacag      60
aagaagaaag aatgttactt ctgttaatat gaatagcatg tgagaaagcc ctgggtccat     120
atggagcctg acctaatcaa gacacataag aaagacctat gtgacaggag cgcaaaaaag     180
tgaaggagaa aatggttgg                                                199
```

<210> SEQ ID NO 64
<211> LENGTH: 199
<212> TYPE: DNA
<213> ORGANISM: Unknown
<220> FEATURE:
<223> OTHER INFORMATION: Description of Unknown:
      target sequence

<400> SEQUENCE: 64

```
gatccagatt gtgaggtcat gaaatgctta tgaacagaga gcttaagagt aactagacag      60
aagaagaaag aatgttactt ctgttaatat gaatagcatg tgcgaaagcc ctgggtccat     120
```
atggagcctg acctaatcaa gacacataag aaagacctat gtgacaggag cgcaaaaaag      180
tgaaggagaa aatggttgg                                                   199

<210> SEQ ID NO 65
<211> LENGTH: 199
<212> TYPE: DNA
<213> ORGANISM: Unknown
<220> FEATURE:
<223> OTHER INFORMATION: Description of Unknown:
      target sequence

<400> SEQUENCE: 65
gatccagatt gtgaggtcat gaaatgctta tgaacagaga gcttaagagt aactagacag       60
aagaagaaag aatgttactt ctgttaatat gaatagcatg tgtgaaagcc ctgggtccat      120
atggagcctg acctaatcaa gacacataag aaagacctat gtgacaggag cgcaaaaaag      180
tgaaggagaa aatggttgg                                                   199

<210> SEQ ID NO 66
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 66
tggtcatcag gggtccaagc ttcttcattc tgcctcacca tctcgcttgc agcttctgcc       60
taatgttgac ttacagttca agatggcttc tggagtgcta ccattacatc catgttgtag      120
gctagaagga aaagggcaat ggcctgaaga ggaagggaga gttcctgtta actcagcttc      180
ctttaaacag cctccccaaa a                                                201

<210> SEQ ID NO 67
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 67
tggtcatcag gggtccaagc ttcttcattc tgcctcacca tctcgcttgc agcttctgcc       60
taatgttgac ttacagttca agatggcttc tggagtgcta ccgttacatc catgttgtag      120
gctagaagga aaagggcaat ggcctgaaga ggaagggaga gttcctgtta actcagcttc      180
ctttaaacag cctccccaaa a                                                201

<210> SEQ ID NO 68
<211> LENGTH: 200
<212> TYPE: DNA
<213> ORGANISM: Unknown
<220> FEATURE:
<223> OTHER INFORMATION: Description of Unknown:
      target sequence

<400> SEQUENCE: 68
cagccttgga ctcctggtcc aaagcaatcc tcctgcttca gcctcctaag tggctgggag       60
cacaggagca agccatcaca cttgactaat tttttttttt ttgagacaga gtttcactct      120
tgttgcccag gctgcagtgc aatggtgcca tctcagctca ctgaaacctc tacttcccag      180

-continued

```
attcgagcga ttctcttgcc                                              200

<210> SEQ ID NO 69
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 69
cagccttgga ctcctggtcc aaagcaatcc tcctgcttca gcctcctaag tggctgggag     60
cacaggagca agccatcaca cttgactaat tttttttttt tttgagacag agtttcactc    120
ttgttgccca ggctgcagtg caatggtgcc atctcagctc actgaaacct ctacttccca    180
gattcgagcg attctcttgc c                                             201

<210> SEQ ID NO 70
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 70
atcatttgaa cataaatcag agtctcagta caaacagagt gctcaggaca tcaagatggt     60
taaccagaga gcctggccag aatatctgcg gtggagagaa acaatcttgt tgggagaagg    120
atgacaataa ttggggactt agaataaagg ctaaaaatga ttcaaagaga atgcaaaaag    180
aatcaggcac acatccttta c                                             201

<210> SEQ ID NO 71
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 71
atcatttgaa cataaatcag agtctcagta caaacagagt gctcaggaca tcaagatggt     60
taaccagaga gcctggccag aatatctgcg gtggagagaa acgatcttgt tgggagaagg    120
atgacaataa ttggggactt agaataaagg ctaaaaatga ttcaaagaga atgcaaaaag    180
aatcaggcac acatccttta c                                             201

<210> SEQ ID NO 72
<211> LENGTH: 153
<212> TYPE: DNA
<213> ORGANISM: Unknown
<220> FEATURE:
<223> OTHER INFORMATION: Description of Unknown:
      target sequence

<400> SEQUENCE: 72
taagaagcat cctcaagctc ccagttaagt aacttgacta cttttatttg ggaatttcag     60
actatagaag ctctcttatg tccagattct gtgaccacta gttactgtat cagaactcat    120
caggtaccca cttataaata gcactgatct ggc                                153

<210> SEQ ID NO 73
<211> LENGTH: 160
```

<212> TYPE: DNA
<213> ORGANISM: Unknown
<220> FEATURE:
<223> OTHER INFORMATION: Description of Unknown:
     target sequence

<400> SEQUENCE: 73
taagaagcat cctcaagctc ccagttaagt aacttgacta cttttatttg ggaatttcag        60
actatagaag ctctcttatg ttttatgtcc agattctgtg accactagtt actgtatcag       120
aactcatcag gtacccactt ataaatagca ctgatctggc                             160

<210> SEQ ID NO 74
<211> LENGTH: 201
<212> TYPE: DNA
<213> ORGANISM: Unknown
<220> FEATURE:
<223> OTHER INFORMATION: Description of Unknown:
     target sequence

<400> SEQUENCE: 74
ctctgctcca ggctctgggc cgggcaccag cctctgggaa aatggagggg gtggtggtga        60
gggctcggac aaggagcagt gactccattc cagggactct gtccagaggg actgtcagct       120
taggacgtgc gcgaaacact cggttcacag ggtttaacac actttagggt aaaacctggg       180
agagcttcct aaggaggtga c                                                 201

<210> SEQ ID NO 75
<211> LENGTH: 201
<212> TYPE: DNA
<213> ORGANISM: Unknown
<220> FEATURE:
<223> OTHER INFORMATION: Description of Unknown:
     target sequence

<400> SEQUENCE: 75
ctctgctcca ggctctgggc cgggcaccag cctctgggaa aatggagggg gtggtggtga        60
gggctcggac aaggagcagt gactccattc cagggactct gttcagaggg actgtcagct       120
taggacgtgc gcgaaacact cggttcacag ggtttaacac actttagggt aaaacctggg       180
agagcttcct aaggaggtga c                                                 201

<210> SEQ ID NO 76
<211> LENGTH: 201
<212> TYPE: DNA
<213> ORGANISM: Unknown
<220> FEATURE:
<223> OTHER INFORMATION: Description of Unknown:
     target sequence

<400> SEQUENCE: 76
acaaaagaaa caaaagactg ctactccata ggcagagcag tcctgagagc tgctcgtggc        60
ctatttttat ggtttttttt ttaaattttt attttaggtt tgggggtaca tgtgaaggtt       120
ttacatcggt aaacttgtgc cacaggggtt tgttgtacac attgtttcat tacccaggta       180
ttaagcccag tatccgatag t                                                 201

<210> SEQ ID NO 77
<211> LENGTH: 201
<212> TYPE: DNA
<213> ORGANISM: Unknown
<220> FEATURE:
<223> OTHER INFORMATION: Description of Unknown:
     target sequence -continued

<400> SEQUENCE: 77
acaaaagaaa caaaagactg ctactccata ggcagagcag tcctgagagc tgctcgtggc        60
ctatttttat ggtttttttt ttaaattttt attttaggtt tgtgggtaca tgtgaaggtt       120
ttacatcggt aaacttgtgc cacaggggtt tgttgtacac attgtttcat tacccaggta       180
ttaagcccag tatccgatag t                                                 201

<210> SEQ ID NO 78
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 78
tttcaaaaac gtggccacat ccattttccc gccatcagct ttccagacca cagaatgctc        60
tgcttttgag ctgctcctca gctgacaccc tccttgaatc cactttgagt tgctcttccc       120
tggccccatt agaaaatgtc ggctctgact acaccatgct tgcgaacaaa ggtgcagaac       180
aattttggct gcttcgtcca g                                                 201

<210> SEQ ID NO 79
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 79
tttcaaaaac gtggccacat ccattttccc gccatcagct ttccagacca cagaatgctc        60
tgcttttgag ctgctcctca gctgacaccc tccttgaatc cattttgagt tgctcttccc       120
tggccccatt agaaaatgtc ggctctgact acaccatgct tgcgaacaaa ggtgcagaac       180
aattttggct gcttcgtcca g                                                 201

<210> SEQ ID NO 80
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 80
cttctagaag cgtaaggtaa cactggcatt cctctagcct ctgctggagt gcagtgagga        60
ttttctagca tgttgctgca ctgttcccat gcacattatt ctaacttttt agtaactcac       120
acgtgcattc ttttttcaac gctatcctta gagtgaaagt cagaaaaaaa tactagaaac       180
taactcaggg ctgagcgtgg t                                                 201

<210> SEQ ID NO 81
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 81

```
cttctagaag cgtaaggtaa cactggcatt cctctagcct ctgctggagt gcagtgagga        60 tttttctagca tgttgctgca ctgttcccat gcacattatt ctgacttttt agtaactcac      120
acgtgcattc tttttttcaac gctatcctta gagtgaaagt cagaaaaaaa tactagaaac     180
taactcaggg ctgagcgtgg t                                                  201

<210> SEQ ID NO 82
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 82
ctgagctccc atctcacact gacatctaca gagtcctata gcttccatct tggagtccca        60
ctctgccttc tcagaaagcc acaggtcaaa tgaggctccg ccgcacgcag aacaggggac      120
ctcctggaca ggagtggctt ttatccatcc ccacacccac agctcccagc gcagaccccg      180
aagaattcat cccaggtgag t                                                  201

<210> SEQ ID NO 83
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 83
ctgagctccc atctcacact gacatctaca gagtcctata gcttccatct tggagtccca        60
ctctgccttc tcagaaagcc acaggtcaaa tgaggctccg cctcacgcag aacaggggac      120
ctcctggaca ggagtggctt ttatccatcc ccacacccac agctcccagc gcagaccccg      180
aagaattcat cccaggtgag t                                                  201

<210> SEQ ID NO 84
<211> LENGTH: 163
<212> TYPE: DNA
<213> ORGANISM: Unknown
<220> FEATURE:
<223> OTHER INFORMATION: Description of Unknown:
      target sequence

<400> SEQUENCE: 84
ttctgacctc aagtgatccg cccgcctcgg cctctgaaag tgctaggatt gtaggcatga        60
gccaccgcgc ccggcctcgt acggtaattc tgtgtgatgt ttagggacac gtctcggagc      120
tggcgaactg gacttggggt gggagggaaa ggaagcatta aag                         163

<210> SEQ ID NO 85
<211> LENGTH: 199
<212> TYPE: DNA
<213> ORGANISM: Unknown
<220> FEATURE:
<223> OTHER INFORMATION: Description of Unknown:
      target sequence

<400> SEQUENCE: 85
ttctgacctc aagtgatccg cccgcctcgg cctctgaaag tgctaggatt gtaggcatga        60
gccaccgcgc ccggcctcgt acggtaattc tgtgtgatgt tttgaggaat tgccacaatt      120
ttttcctgcg cctgcaccag ggacacgtct cggagctggc gaactggact tggggtggga      180
```

-continued

```
gggaaaggaa gcattaaag                                                  199

<210> SEQ ID NO 86
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 86
aactggctgc ctctattcca aaaattattt agaaattttc agaatttaaa ctcattagca     60
tggcttggaa ctttctcatc cctaacgcaa tccctgtgac cgatataatg atggtaatac    120
taagagtaaa ggggagagac agatcctact gattattaaa aagttatagt ctgataatga    180
atgagtgttg tcaggaatag a                                             201

<210> SEQ ID NO 87
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 87
aactggctgc ctctattcca aaaattattt agaaattttc agaatttaaa ctcattagca     60
tggcttggaa ctttctcatc cctaacgcaa tccctgtgac cggtataatg atggtaatac    120
taagagtaaa ggggagagac agatcctact gattattaaa aagttatagt ctgataatga    180
atgagtgttg tcaggaatag a                                             201

<210> SEQ ID NO 88
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 88
aaaccctgcg cactgtggtt cacgccagca atcccagccc tttgggaggc taaggcaggt     60
ggatcacctg agtccaggag ttcaagacca gccaggatga cacagcaaaa caccatctct    120
actaataata caaaaaccag ctgtgaatgg tgacacacag ctgaagtagc agctactagg    180
gagactgaag caggaggact g                                             201

<210> SEQ ID NO 89
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 89
aaaccctgcg cactgtggtt cacgccagca atcccagccc tttgggaggc taaggcaggt     60
ggatcacctg agtccaggag ttcaagacca gccaggatga catagcaaaa caccatctct    120
actaataata caaaaaccag ctgtgaatgg tgacacacag ctgaagtagc agctactagg    180
gagactgaag caggaggact g                                             201
```

```
<210> SEQ ID NO 90
<211> LENGTH: 200
<212> TYPE: DNA
<213> ORGANISM: Unknown
<220> FEATURE:
<223> OTHER INFORMATION: Description of Unknown:
      target sequence

<400> SEQUENCE: 90
tgctatatcc atctacatat ataaagccac cgggagaact agtccacttg gtgcagtctt        60
ctatactgtc cttcacagct tagattcaat ctttccttaa agtgtagccg ggatacacag       120
gagtgtgatt ctgggctgac tcaaagttct tctcttgaag gcttttttcct gtggcactgg      180 cagatggctg tgctatcttc                                                    200

<210> SEQ ID NO 91
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 91
tgctatatcc atctacatat ataaagccac cgggagaact agtccacttg gtgcagtctt        60
ctatactgtc cttcacagct tagattcaat ctttccttaa agatgtagcc gggatacaca       120
ggagtgtgat tctgggctga ctcaaagttc ttctcttgaa ggcttttttcc tgtggcactg      180 gcagatggct gtgctatctt c                                                  201

<210> SEQ ID NO 92
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 92
atttgctgga gattgatgct gggaaaggaa gcaaaatctt ttgcaatctg tggttccttg        60
gttggacaag aaagagtctt ctgccaggcc tgaggatctt ccagacactc acagtactca       120
tggtacactg gtcctaggga aggaaaacat gaaaaaggcc gcactccatt agcaagcacc       180
acaacacagg gagtcacttc t                                                  201

<210> SEQ ID NO 93
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 93
atttgctgga gattgatgct gggaaaggaa gcaaaatctt ttgcaatctg tggttccttg        60
gttggacaag aaagagtctt ctgccaggcc tgaggatctt ccggacactc acagtactca       120
tggtacactg gtcctaggga aggaaaacat gaaaaaggcc gcactccatt agcaagcacc       180
acaacacagg gagtcacttc t                                                  201

<210> SEQ ID NO 94
<211> LENGTH: 201
```

```
<212> TYPE: DNA
<213> ORGANISM: Unknown
<220> FEATURE:
<223> OTHER INFORMATION: Description of Unknown:
      target sequence

<400> SEQUENCE: 94
aatgactgac actctcaaat tcccctctgc atcatgggca ctcagcactg tgcctagtgc      60
atagtaagac ttcaacaaat atgtgctgtt gttataattc ggaatgacga tggaggtgca     120
gaggtttacc tgtgttttta ttatctctgg ttgacaaggc ggccacaccc aggttgcctg     180
ttctgaagct gtctcaagac a                                               201

<210> SEQ ID NO 95
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 95
aatgactgac actctcaaat tcccctctgc atcatgggca ctcagcactg tgcctagtgc      60
atagtaagac ttcaacaaat atgtgctgtt gttataattc ggcatgacga tggaggtgca     120
gaggtttacc tgtgttttta ttatctctgg ttgacaaggc ggccacaccc aggttgcctg     180
ttctgaagct gtctcaagac a                                               201

<210> SEQ ID NO 96
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 96
ggcatgcacc accacgccca gctaaatttt tttattttta gtagagatgg ggtttcacca      60
tgttggcaag gctggtctca aactcctgac ttcatgatcc acccgcctcg gcctctcaaa     120
gtgctgggat tacaggtgtg agccactgca accagcctgt tttttgtttt ttttgagtag     180
gatgtgatcc gcttatgttt t                                               201

<210> SEQ ID NO 97
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 97
ggcatgcacc accacgccca gctaaatttt tttattttta gtagagatgg ggtttcacca      60
tgttggcaag gctggtctca aactcctgac ttcatgatcc actcgcctcg gcctctcaaa     120
gtgctgggat tacaggtgtg agccactgca accagcctgt tttttgtttt ttttgagtag     180
gatgtgatcc gcttatgttt t                                               201

<210> SEQ ID NO 98
<211> LENGTH: 201
<212> TYPE: DNA
<213> ORGANISM: Unknown
<220> FEATURE:
```

```
<223> OTHER INFORMATION: Description of Unknown:
      target sequence

<400> SEQUENCE: 98
ttcacaggtg tttagaaaaa ttagattgtc acctcttgtt ggtcacagaa tgattacaat      60
actttgcatt cgtgccacaa tagtttttag agggtttttg tacgttatgt agctgagcat     120
tccatttggt ctttggagcc tggggggaaga ggacctttaa tgaggacaag aagataggaa    180
agtgcaaaaa tacaaatgga g                                               201

<210> SEQ ID NO 99
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 99
ttcacaggtg tttagaaaaa ttagattgtc acctcttgtt ggtcacagaa tgattacaat      60
actttgcatt cgtgccacaa tagtttttag agggtttttg tatgttatgt agctgagcat     120
tccatttggt ctttggagcc tggggggaaga ggacctttaa tgaggacaag aagataggaa    180
agtgcaaaaa tacaaatgga g                                               201

<210> SEQ ID NO 100
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 100
actgtgtgac tctagtgatc tttaacatac acagaatgat ctacagtgat ctttaacata      60
ctcagaaata tgaaaaatgt ttgaatatga tctttaggga ctgctaatga aaagggtata     120
tgaaatggga acaataaatt ctgtacatgt atacagtcca tatacacatt aagtgtttgt     180
catttggaca aattgaaaac t                                               201

<210> SEQ ID NO 101
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 101
actgtgtgac tctagtgatc tttaacatac acagaatgat ctacagtgat ctttaacata      60
ctcagaaata tgaaaaatgt ttgaatatga tctttaggga cttctaatga aaagggtata     120
tgaaatggga acaataaatt ctgtacatgt atacagtcca tatacacatt aagtgtttgt     180
catttggaca aattgaaaac t                                               201

<210> SEQ ID NO 102
<211> LENGTH: 201
<212> TYPE: DNA
<213> ORGANISM: Unknown
<220> FEATURE:
<223> OTHER INFORMATION: Description of Unknown:
      target sequence
```

```
<400> SEQUENCE: 102
actagccatg gacatgcaaa ttttaaaaac aatgagctac tgttgctctc aattgggcaa        60
tatttttaga aaactgatag catctaggcc agcccttccc aaccgtctgc acctgggaat       120
cgcctgggga ccttcaagta actactgatc cccagctacc aatttaattg gtttgggta        180 tggcctgggg ttctacattt t                                                 201

<210> SEQ ID NO 103
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 103
actagccatg gacatgcaaa ttttaaaaac aatgagctac tgttgctctc aattgggcaa        60
tatttttaga aaactgatag catctaggcc agcccttccc aatcgtctgc acctgggaat       120
cgcctgggga ccttcaagta actactgatc cccagctacc aatttaattg gtttggggta        180
tggcctgggg ttctacattt t                                                 201

<210> SEQ ID NO 104
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 104
atcagtgtta cagtgaaaca aagttattca aggacctgct gctgtacata cttttgctaa        60
aaatcagttt ccaagaacct attgtggatg ttaggagagg agctaccatg ccacaatgac       120
tctgggagat gaagccattt tattcccatg cttgttaacc ttgtgcaggt gcgggaatgc       180
agatggctga gtaggtcaga t                                                 201

<210> SEQ ID NO 105
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 105
atcagtgtta cagtgaaaca aagttattca aggacctgct gctgtacata cttttgctaa        60
aaatcagttt ccaagaacct attgtggatg ttaggagagg agttaccatg ccacaatgac       120
tctgggagat gaagccattt tattcccatg cttgttaacc ttgtgcaggt gcgggaatgc       180
agatggctga gtaggtcaga t                                                 201

<210> SEQ ID NO 106
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 106
cctcccaaag tgttgggatt acaggtatga gccaccacac ccagctgcat gtggattctt        60
```

-continued

```
aagtgcaaca gtcagcagta atctcacatc tgttagcaga cacttgctgt agtcacaaca     120
atgctttctt cttccctgaa cagatactcc acttcttgaa atatacttaa gtaggcactg     180
tatttataca gctctgaaag c                                               201

<210> SEQ ID NO 107
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 107
cctcccaaag tgttgggatt acaggtatga gccaccacac ccagctgcat gtggattctt      60
aagtgcaaca gtcagcagta atctcacatc tgttagcaga catttgctgt agtcacaaca     120
atgctttctt cttccctgaa cagatactcc acttcttgaa atatacttaa gtaggcactg     180
tatttataca gctctgaaag c                                               201

<210> SEQ ID NO 108
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 108
aggaaagatt gattccagga aaagggacca aatgtcctaa cacttttaaa tgcctaacag      60
aaaagttttt accacagact accatttttt tctttctaaa ggctgctacc tttgaggctt     120
catctgcata acaagacagc ttttgctcac catgcctttc ctccctctc cctcccataa      180 agctgttgcc acactccaag c                                               201

<210> SEQ ID NO 109
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 109
aggaaagatt gattccagga aaagggacca aatgtcctaa cactttaaa tgcctaacag       60 aaaagttttt accacagact accatttttt tctttctaaa ggttgctacc tttgaggctt     120
catctgcata acaagacagc ttttgctcac catgcctttc ctccctctc cctcccataa      180 agctgttgcc acactccaag c                                               201

<210> SEQ ID NO 110
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 110
tctgtaacta ccagattta ctcgccttcc tggactctgt tcacaggaaa gaaaggaaac       60
aaacaaacct catacattat gaagcatagg gtatcaatgg ccctgctgat tatagtgggt     120
```

-continued

```
gggggtggca taaatacatg tacacccccca ctgctgcccc atccccactc ctctgagcac    180
tggggtcaag gaatatatat t                                               201

<210> SEQ ID NO 111
<211> LENGTH: 201
<212> TYPE: DNA
<213> ORGANISM: Unknown
<220> FEATURE:
<223> OTHER INFORMATION: Description of Unknown:
     target sequence

<400> SEQUENCE: 111
tctgtaacta ccagatttta ctcgccttcc tggactctgt tcacaggaaa gaaaggaaac     60
aaacaaacct catacattat gaagcatagg gtatcaatgg ccttgctgat tatagtgggt    120
gggggtggca taaatacatg tacacccccca ctgctgcccc atccccactc ctctgagcac    180
tggggtcaag gaatatatat t                                               201

<210> SEQ ID NO 112
<211> LENGTH: 201
<212> TYPE: DNA
<213> ORGANISM: Unknown
<220> FEATURE:
<223> OTHER INFORMATION: Description of Unknown:
     target sequence

<400> SEQUENCE: 112
acacctgagg aaggctgggc agaatggatc gggggtgtgt attggctgca gtcacctccc     60
ctctgctcgt ctgtgtccac attctgtcgt ggttgagacc ggatcctgtg tggaccgggt    120
gggctggtgt ggagtcctgt caggagacct ggggcggttt tgaggcaagc tcacggaggc    180
ctgccgcagg gccctgcgct g                                               201

<210> SEQ ID NO 113
<211> LENGTH: 201
<212> TYPE: DNA
<213> ORGANISM: Unknown
<220> FEATURE:
<223> OTHER INFORMATION: Description of Unknown:
     target sequence

<400> SEQUENCE: 113
acacctgagg aaggctgggc agaatggatc gggggtgtgt attggctgca gtcacctccc     60
ctctgctcgt ctgtgtccac attctgtcgt ggttgagacc ggctcctgtg tggaccgggt    120
gggctggtgt ggagtcctgt caggagacct ggggcggttt tgaggcaagc tcacggaggc    180
ctgccgcagg gccctgcgct g                                               201

<210> SEQ ID NO 114
<211> LENGTH: 201
<212> TYPE: DNA
<213> ORGANISM: Unknown
<220> FEATURE:
<223> OTHER INFORMATION: Description of Unknown:
     target sequence

<400> SEQUENCE: 114
ttatcttcct aagacataag gcaattgctg acatttgcct tcctcaaggg ccaaacagcc     60
aaccaacagt gtccttggga gcagagctga gtttctaaac ctacggctag aaacatggag    120
atccaaatcc atatatggag atacttcaca gaaggaaaaa aagcagaaat aaactcttgg    180
gaaagaaaga atcagaccca c                                               201
```

-continued

<210> SEQ ID NO 115
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 115
ttatcttcct aagacataag gcaattgctg acatttgcct tcctcaaggg ccaaacagcc        60
aaccaacagt gtccttggga gcagagctga gtttctaaac ctgcggctag aaacatggag       120
atccaaatcc atatatggag atacttcaca gaaggaaaaa aagcagaaat aaactcttgg       180
gaaagaaaga atcagaccca c                                                 201

<210> SEQ ID NO 116
<211> LENGTH: 199
<212> TYPE: DNA
<213> ORGANISM: Unknown
<220> FEATURE:
<223> OTHER INFORMATION: Description of Unknown:
      target sequence

<400> SEQUENCE: 116
cttcacaggt gaaattgttt gacccatgaa aatctgaaac atatgaggtc tcttgttttc        60
attcagcata tgccagttaa gtgcctaatt gttcacccag caaccagatc ctgactcaca       120 attaattta tttatagagc ctcactgctt tgctgcttcc ctacttgtta ttttgactgt        180
gggagcaaaa aatggtaac                                                    199

<210> SEQ ID NO 117
<211> LENGTH: 199
<212> TYPE: DNA
<213> ORGANISM: Unknown
<220> FEATURE:
<223> OTHER INFORMATION: Description of Unknown:
      target sequence

<400> SEQUENCE: 117
cttcacaggt gaaattgttt gacccatgaa aatctgaaac atatgaggtc tcttgttttc        60
attcagcata tgccagttaa gtgcctaatt gttcacccag cacccagatc ctgactcaca       120 attaattta tttatagagc ctcactgctt tgctgcttcc ctacttgtta ttttgactgt        180
gggagcaaaa aatggtaac                                                    199

<210> SEQ ID NO 118
<211> LENGTH: 199
<212> TYPE: DNA
<213> ORGANISM: Unknown
<220> FEATURE:
<223> OTHER INFORMATION: Description of Unknown:
      target sequence

<400> SEQUENCE: 118
cttcacaggt gaaattgttt gacccatgaa aatctgaaac atatgaggtc tcttgttttc        60
attcagcata tgccagttaa gtgcctaatt gttcacccag catccagatc ctgactcaca       120 attaattta tttatagagc ctcactgctt tgctgcttcc ctacttgtta ttttgactgt        180
gggagcaaaa aatggtaac                                                    199

<210> SEQ ID NO 119

```
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 119
agtatgtaag gtgatgctaa gagaagaggc acaaaagtat tcacaattgg gagggagaca     60
gatcccaggg ctccttgaag aggttctccc tcactactca tgccctgctt atcacacact    120
tgcacagttg gatttctttt caggtgtgca aatatataag cttttaagtc atgaatagta    180
tgtaccttat ctgcactgtt g                                              201

<210> SEQ ID NO 120
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 120
agtatgtaag gtgatgctaa gagaagaggc acaaaagtat tcacaattgg gagggagaca     60
gatcccaggg ctccttgaag aggttctccc tcactactca tgtcctgctt atcacacact    120
tgcacagttg gatttctttt caggtgtgca aatatataag cttttaagtc atgaatagta    180
tgtaccttat ctgcactgtt g                                              201

<210> SEQ ID NO 121
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 121
gaagataagg ggaaactgaa aaatgagcat gggaggaagt agccagggag ggaggaggaa     60
aaccaggcga acactgtgtt ctagaagcca agcaaagatg gactttcaag aagaagagag    120
tcatcaactg tgtcaaatgc tgcttatagg atgatagagg accactgatt ggatttaaga    180
aagtggaagt ccttggccac c                                              201

<210> SEQ ID NO 122
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 122
gaagataagg ggaaactgaa aaatgagcat gggaggaagt agccagggag ggaggaggaa     60
aaccaggcga acactgtgtt ctagaagcca agcaaagatg gagtttcaag aagaagagag    120
tcatcaactg tgtcaaatgc tgcttatagg atgatagagg accactgatt ggatttaaga    180
aagtggaagt ccttggccac c                                              201

<210> SEQ ID NO 123
<211> LENGTH: 201
<212> TYPE: DNA
<213> ORGANISM: Unknown
```

-continued

```
<220> FEATURE:
<223> OTHER INFORMATION: Description of Unknown:
      target sequence

<400> SEQUENCE: 123
tttcctgact tagtccctta ccctcagaga ctgaacaaga gctgtaattt ttacatgggt     60
gcccaggatg tggccttgtc ccctgtatcc tttccaacct agatttgagc tgctgccttc    120
tattaactgc cttttctggc taaggtggga ggcagagccc aagccgatcc caggatgatg    180
ggagacccca gccatgttcc t                                              201

<210> SEQ ID NO 124
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 124
tttcctgact tagtccctta ccctcagaga ctgaacaaga gctgtaattt ttacatgggt     60
gcccaggatg tggccttgtc ccctgtatcc tttccaacct agctttgagc tgctgccttc    120
tattaactgc cttttctggc taaggtggga ggcagagccc aagccgatcc caggatgatg    180
ggagacccca gccatgttcc t                                              201

<210> SEQ ID NO 125
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 125
ccttctaaag ccaccgaaag ttaattggta ggatatcaca ggggtgtttt aacttttctt     60
tgaattttct ccaatcttag taacacagct gactggggca atcgcatctc acttctactt    120
gatttctaaa tatttgttaa ctaatattct tcatttatgc taagatagac agttttaca     180 tttaataatt ttagaataag a                                              201

<210> SEQ ID NO 126
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 126
ccttctaaag ccaccgaaag ttaattggta ggatatcaca ggggtgtttt aacttttctt     60
tgaattttct ccaatcttag taacacagct gactggggca atggcatctc acttctactt    120
gatttctaaa tatttgttaa ctaatattct tcatttatgc taagatagac agttttaca     180 tttaataatt ttagaataag a                                              201

<210> SEQ ID NO 127
<211> LENGTH: 201
<212> TYPE: DNA
<213> ORGANISM: Unknown
<220> FEATURE:
<223> OTHER INFORMATION: Description of Unknown:
      target sequence
```

-continued

<400> SEQUENCE: 127
taacagcaag caatagtatc tatttgaata gaaaccaaca cctgttattt gaagttgaag      60
gtatgtgagt ttgaccgtga tccttaaata gcagcacaga cccatttgca aaccgtggat     120
tgatgtggcc ccagcggagc aggggagacg gagatgcagg gggggtgttg tgtgcttggt     180
ggagggactg ggttctgcag g                                                201

<210> SEQ ID NO 128
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 128
taacagcaag caatagtatc tatttgaata gaaaccaaca cctgttattt gaagttgaag      60
gtatgtgagt ttgaccgtga tccttaaata gcagcacaga cctatttgca aaccgtggat     120
tgatgtggcc ccagcggagc aggggagacg gagatgcagg gggggtgttg tgtgcttggt     180
ggagggactg ggttctgcag g                                                201

<210> SEQ ID NO 129
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 129
attaatcaaa gtccatactg caggtaagtg gcagaactga ggtctgaacc aaggaagtct      60
gactccagtg cctacgatca taatcacaag tacctcgaat acattggtaa gatggcacat     120
gactggtagc tttgctgtag aggaatctta ccttgtcata caaatcaata tgccttgtga     180
aaaatttttc aaatgcttga a                                                201

<210> SEQ ID NO 130
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 130
attaatcaaa gtccatactg caggtaagtg gcagaactga ggtctgaacc aaggaagtct      60
gactccagtg cctacgatca taatcacaag tacctcgaat acgttggtaa gatggcacat     120
gactggtagc tttgctgtag aggaatctta ccttgtcata caaatcaata tgccttgtga     180
aaaatttttc aaatgcttga a                                                201

<210> SEQ ID NO 131
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 131

-continued

```
tcctgcctgc tgaaaggagc ccagcgactc caacaccaac gtcattcatt aggaaaacaa        60
aaccgaagac tcgcatgcac gtatatgtac acacacaaaa tgaacaaata gtgggaagaa       120
ttattgtaag tcttaagtca caggaaattt gatttgcttc aactaaaaca cccgaggata       180
ggccggcgtg gcgggtcgcc c                                                 201

<210> SEQ ID NO 132
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 132
tcctgcctgc tgaaaggagc ccagcgactc caacaccaac gtcattcatt aggaaaacaa        60
aaccgaagac tcgcatgcac gtatatgtac acacacaaaa tgcacaaata gtgggaagaa       120
ttattgtaag tcttaagtca caggaaattt gatttgcttc aactaaaaca cccgaggata       180
ggccggcgtg gcgggtcgcc c                                                 201

<210> SEQ ID NO 133
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 133
cacgctctgg taggcactga ggttggtggt gaaacccagc tgggagatgg aggcgccctt        60
gtcccgcagc actcggtact cctcccagca gtagtagatg ccatatgcca gcacgcccag       120
cactcccagg atcagcacca gcaccagggg cccagccacc aggcgcagaa gcaagataaa       180
cagtaggctc aagaccagag c                                                 201

<210> SEQ ID NO 134
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 134
cacgctctgg taggcactga ggttggtggt gaaacccagc tgggagatgg aggcgccctt        60
gtcccgcagc actcggtact cctcccagca gtagtagatg ccgtatgcca gcacgcccag       120
cactcccagg atcagcacca gcaccagggg cccagccacc aggcgcagaa gcaagataaa       180
cagtaggctc aagaccagag c                                                 201

<210> SEQ ID NO 135
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 135
tatttcctat tttaatttcc ctagttgcct ccaaaatacc ttttatagct atttttattt        60
tttcctgatc caaggtacaa tcaagactca tgcattgcaa ggataaattt tttttttccct       120
```

-continued

```
aagtgatctt cattgggaga agtaaaacaa ttttatgtta aactctaagt gaggtgatat      180
tttgttctca gattttgaac t                                               201

<210> SEQ ID NO 136
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 136
tatttcctat tttaatttcc ctagttgcct ccaaaatacc ttttatagct atttttattt       60
tttcctgatc caaggtacaa tcaagactca tgcattgcaa gggtaaattt ttttttccct      120
aagtgatctt cattgggaga agtaaaacaa ttttatgtta aactctaagt gaggtgatat      180
tttgttctca gatttgaac t                                                201

<210> SEQ ID NO 137
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 137
atcaagatct gcagctccag aggttgccat ttcccatgcc cagatagttg gcttacaagc       60
ctagcttcaa agcatgcctt ggctcacaga gtcatctctt ttagggatgt ccccaccctg      120
tactcatctc aaagccatcg agaaccatct ctaaatgtca tatctggcag tgatctctct      180
tttctctgat ccgttgtcgc a                                                201

<210> SEQ ID NO 138
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 138
atcaagatct gcagctccag aggttgccat ttcccatgcc cagatagttg gcttacaagc       60
ctagcttcaa agcatgcctt ggctcacaga gtcatctctt tttgggatgt ccccaccctg      120
tactcatctc aaagccatcg agaaccatct ctaaatgtca tatctggcag tgatctctct      180
tttctctgat ccgttgtcgc a                                                201

<210> SEQ ID NO 139
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 139
cctatggaca acaaactgtg cctaatgaat tctggccaga gccaaaacaa tgaaattatt       60
tatctccacc tcccctattg atgcacagca gaaataaata taaggatcac caccttctgt      120
gcaaatgcaa ataagtatac tcgcagaaac aaaaatttca acctacaatt tcagtttttcc     180
```
tcaccttttg cttacactct a                                          201

<210> SEQ ID NO 140
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 140
cctatggaca acaaactgtg cctaatgaat tctggccaga gccaaaacaa tgaaattatt      60
tatctccacc tcccctattg atgcacagca gaaataaaata tagggatcac caccttctgt     120
gcaaatgcaa ataagtatac tcgcagaaac aaaaatttca acctacaatt tcagttttcc     180
tcaccttttg cttacactct a                                          201

<210> SEQ ID NO 141
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 141
aggcatgaag taagggtcga ggtccaaggg tgtgtgacac aacattgcta ccatgttata      60
gagggatatt ctaaacaaaa tctctgcatt cttaccccat gaaccctatc ttcagccttt     120
accactggaa agcatctttc taaattcaaa tccttgattt gcttctggtt ttgtaataaa     180
gtcatgagca ataggaatgc a                                          201

<210> SEQ ID NO 142
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 142
aggcatgaag taagggtcga ggtccaaggg tgtgtgacac aacattgcta ccatgttata      60
gagggatatt ctaaacaaaa tctctgcatt cttaccccat gagccctatc ttcagccttt     120
accactggaa agcatctttc taaattcaaa tccttgattt gcttctggtt ttgtaataaa     180
gtcatgagca ataggaatgc a                                          201

<210> SEQ ID NO 143
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 143
tcagacctct aggccctcct tccttagact ccggagtccc tcctgcctct gacactcacg      60
aggtccagac cccaagatag cccagccagc agggacaggg acaggtaagc ctcacatgct     120
gggctctgca ggagaatgag aggggctgaa gctgggcccc tctcgctttc ctctttctct     180
ctcctcccct tcacacctga a                                          201

<210> SEQ ID NO 144
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 144
tcagacctct aggccctcct tccttagact ccggagtccc tcctgcctct gacactcacg        60
aggtccagac cccaagatag cccagccagc agggacaggg acgggtaagc ctcacatgct       120
gggctctgca ggagaatgag aggggctgaa gctgggcccc tctcgctttc ctctttctct       180
ctcctcccct tcacacctga a                                                 201

<210> SEQ ID NO 145
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 145
taatgaacag aatatttact aaatgctaga gagtaaaaat cctttctatc ctttcaccaa        60
atccctagat tagttgtatg gggagggggc aggaagcagt acatggaaga aaagctctta       120
ctaggctttt cagtaagcag aaaacatgag ctcctagata ggacggcaaa ttcatttta        180 aatcaacggc aattcctatg a                                                 201

<210> SEQ ID NO 146
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 146
taatgaacag aatatttact aaatgctaga gagtaaaaat cctttctatc ctttcaccaa        60
atccctagat tagttgtatg gggagggggc aggaagcagt acgtggaaga aaagctctta       120
ctaggctttt cagtaagcag aaaacatgag ctcctagata ggacggcaaa ttcatttta        180 aatcaacggc aattcctatg a                                                 201

<210> SEQ ID NO 147
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 147
gatctattag gattgaatat gctttgtaaa cagtagcata accagatatt tctgactcca        60
ttctatagta tgtagtcttc agttatcagg acaagtatct ttcatgctgt aactcagcct       120
tgagaactcg ttggcacatt gctcggtcag tgatctggga gtccagtcat tgcaacgggg       180
atgcactgag cacctgctga t                                                 201

<210> SEQ ID NO 148
<211> LENGTH: 201
<212> TYPE: DNA

<213> ORGANISM: Unknown
<220> FEATURE:
<223> OTHER INFORMATION: Description of Unknown:
      target sequence

<400> SEQUENCE: 148
gatctattag gattgaatat gctttgtaaa cagtagcata accagatatt tctgactcca        60
ttctatagta tgtagtcttc agttatcagg acaagtatct tttatgctgt aactcagcct       120
tgagaactcg ttggcacatt gctcggtcag tgatctggga gtccagtcat tgcaacgggg       180
atgcactgag cacctgctga t                                                 201

<210> SEQ ID NO 149
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 149
ttgaaagggt gtttaataag ataattgggc cgggcacagt ggctcatgcc tgtaatccca        60
gcattttggg aggctgagga gggcagatca tgaggtcagg aggttgagac cagcctgacc       120
aacatggtga aacccgtct ctactaaaaa tacaaaaatt agccaggcgt ggtggcacac        180
acctgtaatc ccagctactc a                                                 201

<210> SEQ ID NO 150
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 150
ttgaaagggt gtttaataag ataattgggc cgggcacagt ggctcatgcc tgtaatccca        60
gcattttggg aggctgagga gggcagatca tgaggtcagg agtttgagac cagcctgacc       120
aacatggtga aacccgtct ctactaaaaa tacaaaaatt agccaggcgt ggtggcacac        180
acctgtaatc ccagctactc a                                                 201

<210> SEQ ID NO 151
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 151
gggccacagc aagcaagggg cagcggcttt tgcctcccca ccctgccctg gccccgtcac        60
ctcccaagga gggaaaggtg atgcatacgt gcccgaagaa accgaccgca taggttattt       120
tcacgcagcc cctccaaggc aggcactaac tggacacctg ctttgcgtct cagctgttga       180
aatgccatcc cctgcccca g                                                  201

<210> SEQ ID NO 152
<211> LENGTH: 201
<212> TYPE: DNA
<213> ORGANISM: Unknown
<220> FEATURE:
<223> OTHER INFORMATION: Description of Unknown:

-continued

```
     target sequence

<400> SEQUENCE: 152
gggccacagc aagcaagggg cagcggcttt tgcctcccca ccctgccctg gccccgtcac         60
ctcccaagga gggaaaggtg atgcatacgt gcccgaagaa actgaccgca taggttattt        120
tcacgcagcc cctccaaggc aggcactaac tggacacctg ctttgcgtct cagctgttga        180
aatgccatcc cctgcccca g                                                    201

<210> SEQ ID NO 153
<211> LENGTH: 201
<212> TYPE: DNA
<213> ORGANISM: Unknown
<220> FEATURE:
<223> OTHER INFORMATION: Description of Unknown:
     target sequence

<400> SEQUENCE: 153
gggcacagaa aggaccctag agggtcatct gacctgggcc cagacaccct gagacccatg         60
acccctggac tcttgcagat gccagttcaa tccccattt ccccttttta tttaatcagc         120
acttttctga gcatcagcag tgctggaggc cctgtgccag gcgcttccca tcagcagctc        180
gtttagacct cacagctgtt c                                                   201

<210> SEQ ID NO 154
<211> LENGTH: 201
<212> TYPE: DNA
<213> ORGANISM: Unknown
<220> FEATURE:
<223> OTHER INFORMATION: Description of Unknown:
     target sequence

<400> SEQUENCE: 154
gggcacagaa aggaccctag agggtcatct gacctgggcc cagacaccct gagacccatg         60
acccctggac tcttgcagat gccagttcaa tccccattt cctcttttta tttaatcagc         120
acttttctga gcatcagcag tgctggaggc cctgtgccag gcgcttccca tcagcagctc        180
gtttagacct cacagctgtt c                                                   201

<210> SEQ ID NO 155
<211> LENGTH: 201
<212> TYPE: DNA
<213> ORGANISM: Unknown
<220> FEATURE:
<223> OTHER INFORMATION: Description of Unknown:
     target sequence

<400> SEQUENCE: 155
ttgggaaaga atttgaactc atcttccaat atatcctact aacaaaattt ttttgagatg         60
atgaatagat ttgttcttat aaccagtgtg gaaagttaac tccatggggc taaacaaatt        120
ctcttaacgt caacacacaa cacaggacag gagacaaaaa gtaatgtgag attatatttt        180
agtatgccat taaaaatttt g                                                   201

<210> SEQ ID NO 156
<211> LENGTH: 201
<212> TYPE: DNA
<213> ORGANISM: Unknown
<220> FEATURE:
<223> OTHER INFORMATION: Description of Unknown:
     target sequence

<400> SEQUENCE: 156
```

-continued

```
ttgggaaaga atttgaactc atcttccaat atatcctact aacaaaattt ttttgagatg      60
atgaatagat ttgttcttat aaccagtgtg gaaagttaac tctatggggc taaacaaatt     120
ctcttaacgt caacacacaa cacaggacag gagacaaaaa gtaatgtgag attatatttt     180
agtatgccat taaaaatttt g                                              201

<210> SEQ ID NO 157
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 157
ggaaggtggg ctgagcctgt gggcaggtgt tggtgctccc ctccccgacg gggcacgatg      60
gggacagagc atgggaggga atatgaagca ggagctctgt ctcgtacaca tggaatctga     120
ggagctgaca gatgacctgt ggggagggtg gtcccgtgcc aatgtgtgct ggaaggacat     180
gcctgtgcgt ttatcagctc t                                              201

<210> SEQ ID NO 158
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 158
ggaaggtggg ctgagcctgt gggcaggtgt tggtgctccc ctccccgacg gggcacgatg      60
gggacagagc atgggaggga atatgaagca ggagctctgt cttgtacaca tggaatctga     120
ggagctgaca gatgacctgt ggggagggtg gtcccgtgcc aatgtgtgct ggaaggacat     180
gcctgtgcgt ttatcagctc t                                              201

<210> SEQ ID NO 159
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 159
aagaaaatgt atgttgtttc ttaaatatca tttacagctg taaaatattc tgttgaggat      60
gccacctaat tcaattaacc attctcctgt cctcaaatat ttacttcctc cttcttttgg     120
ggttttataa agaacaatat ggtaaacatc tgtgtgcatg taagttcttg cttgctttct     180
tttttttttt tttttttga g                                              201

<210> SEQ ID NO 160
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 160
aagaaaatgt atgttgtttc ttaaatatca tttacagctg taaaatattc tgttgaggat      60
```
gccacctaat tcaattaacc attctcctgt cctcaaatat ttccttcctc cttcttttgg          120
ggttttataa agaacaatat ggtaaacatc tgtgtgcatg taagttcttg cttgctttct          180
tttttttttt tttttttttga g                                                  201

<210> SEQ ID NO 161
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 161
ttgtagatgg gtaacagccc agagatggga agggacgtgc acaagatggg aatgggcgtg           60
cccatggttg caccgtgtgg tgtggcagag caggaactgg aacacaggcg gctggaagtg          120
aaagtggagc tcaggctttt tagcagttac tatgtgtgat ttccttttca tcatcacatc          180
aaccccattt ttttttttca g                                                   201

<210> SEQ ID NO 162
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 162
ttgtagatgg gtaacagccc agagatggga agggacgtgc acaagatggg aatgggcgtg           60
cccatggttg caccgtgtgg tgtggcagag caggaactgg aatacaggcg gctggaagtg          120
aaagtggagc tcaggctttt tagcagttac tatgtgtgat ttccttttca tcatcacatc          180
aaccccattt ttttttttca g                                                   201

<210> SEQ ID NO 163
<211> LENGTH: 199
<212> TYPE: DNA
<213> ORGANISM: Unknown
<220> FEATURE:
<223> OTHER INFORMATION: Description of Unknown:
      target sequence

<400> SEQUENCE: 163
tctaaagctt ccctctgaat gctgctttgg aggattgtga gaggtagtga ctcttcaaag           60
tttgtttgtt ttcttgaagc ttttacctct atgcaaatat gcagtttgga gcagggaaga          120
aaggttaact gtgatggcgc cggctcttaa cgtggaatgt cctgaattaa tgtgggtttc          180
agtcctctgg ctcaggatc                                                      199

<210> SEQ ID NO 164
<211> LENGTH: 199
<212> TYPE: DNA
<213> ORGANISM: Unknown
<220> FEATURE:
<223> OTHER INFORMATION: Description of Unknown:
      target sequence

<400> SEQUENCE: 164
tctaaagctt ccctctgaat gctgctttgg aggattgtga gaggtagtga ctcttcaaag           60
tttgtttgtt ttcttgaagc ttttacctct atgcaaatat gcggtttgga gcagggaaga          120
aaggttaact gtgatggcgc cggctcttaa cgtggaatgt cctgaattaa tgtgggtttc          180
agtcctctgg ctcaggatc                                                                                              199

<210> SEQ ID NO 165
<211> LENGTH: 199
<212> TYPE: DNA
<213> ORGANISM: Unknown
<220> FEATURE:
<223> OTHER INFORMATION: Description of Unknown:
      target sequence

<400> SEQUENCE: 165
tctaaagctt ccctctgaat gctgctttgg aggattgtga gaggtagtga ctcttcaaag         60
tttgtttgtt ttcttgaagc ttttacctct atgcaaatat gctgtttgga gcagggaaga        120
aaggttaact gtgatggcgc cggctcttaa cgtggaatgt cctgaattaa tgtgggtttc        180
agtcctctgg ctcaggatc                                                                                              199

<210> SEQ ID NO 166
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 166
caggagggag ggaagaagga agcccagctc actcatccaa ccggaaggac ccctgctcca         60
ggcaggactg gaataacgcc aggactccaa atgagcaaga taatcccagc ctggcctgcc        120
tgggataagg agcgggcagg gaaacccaga ggagaagcac tgactttggc aggatggggc        180
atgtgagggc acctggaagg c                                                                                           201

<210> SEQ ID NO 167
<211> LENGTH: 201
<212> TYPE: DNA
<213> ORGANISM: Unknown
<220> FEATURE:
<223> OTHER INFORMATION: Description of Unknown:
      target sequence

<400> SEQUENCE: 167
caggagggag ggaagaagga agcccagctc actcatccaa ccggaaggac ccctgctcca         60
ggcaggactg gaataacgcc aggactccaa atgagcaaga tagtcccagc ctggcctgcc        120
tgggataagg agcgggcagg gaaacccaga ggagaagcac tgactttggc aggatggggc        180
atgtgagggc acctggaagg c                                                                                           201

<210> SEQ ID NO 168
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 168
acaagtatgt tgccattctg tgga                                                                                        24

<210> SEQ ID NO 169
<211> LENGTH: 28
<212> TYPE: DNA
<213> ORGANISM: Artificial Sequence
<220> FEATURE:

-continued

<223> OTHER INFORMATION: Description of Artificial Sequence: Synthetic
     primer

<400> SEQUENCE: 169
agtttcaaag tttggaaggg gaaaataa                                    28

<210> SEQ ID NO 170
<211> LENGTH: 26
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 170
caagggatga atccatagct caaagc                                      26

<210> SEQ ID NO 171
<211> LENGTH: 26
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 171
aggcccagag agacattaaa atgaga                                      26

<210> SEQ ID NO 172
<211> LENGTH: 22
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 172
cccggtagga ataaggcaag cc                                          22

<210> SEQ ID NO 173
<211> LENGTH: 21
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 173
gtccatctta ccctcccgga g                                           21

<210> SEQ ID NO 174
<211> LENGTH: 26
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 174
tcccttagtg cttcaggatt ctagag                                      26

<210> SEQ ID NO 175
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 175
ctgtgacatc agctgaggca c                                                  21

<210> SEQ ID NO 176
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 176
gctgtgtggg gtgtgtgtga g                                                  21

<210> SEQ ID NO 177
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 177
ctcgcacaca cacagcctc                                                     19

<210> SEQ ID NO 178
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 178
atgggagact caacacctc ac                                                  22

<210> SEQ ID NO 179
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 179
tggatatcct tgttaacttt ctgtctctat c                                       31

<210> SEQ ID NO 180
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 180
acagacaaca aaaactaagt gtaggtc                                            27

<210> SEQ ID NO 181
<211> LENGTH: 32
<212> TYPE: DNA
<213> ORGANISM: Artificial Sequence
<220> FEATURE:
<223> OTHER INFORMATION: Description of Artificial Sequence: Synthetic
      primer -continued

```
<400> SEQUENCE: 181
tcatcactca gtcacctcta taaattaaaa tc                                    32

<210> SEQ ID NO 182
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 182
catggataat aatgataaaa ccttatggaa tgc                                   33

<210> SEQ ID NO 183
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 183
ccctaatgca gtcatccgag aatac                                            25

<210> SEQ ID NO 184
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 184
ytccaagctc atccatgctg tc                                               22

<210> SEQ ID NO 185
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 185
tggataaaga aaatgtgaga gatatataca atgg                                  34

<210> SEQ ID NO 186
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 186
tcccaaatcc ctgcttcatc taacatatat tg                                    32

<210> SEQ ID NO 187
<211> LENGTH: 35
<212> TYPE: DNA
<213> ORGANISM: Artificial Sequence
<220> FEATURE:
<223> OTHER INFORMATION: Description of Artificial Sequence: Synthetic
      primer
```

-continued

<400> SEQUENCE: 187
gtcatataat aaatattgct ttgtgttcta tctgg                                35

<210> SEQ ID NO 188
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 188
tggggccaac ctagtcattt gc                                               22

<210> SEQ ID NO 189
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 189
tgtgattcat ttatatcaga atcatcaggg ag                                   32

<210> SEQ ID NO 190
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 190
ctggcccagt tacttatttt agaagttata tttg                                 34

<210> SEQ ID NO 191
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 191
acagctcatg ccagggctc                                                  19

<210> SEQ ID NO 192
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 192
agaaactgtc acagcaagag gac                                             23

<210> SEQ ID NO 193
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 193

-continued tgccatccag gacaccatat tac                                           23

<210> SEQ ID NO 194
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 194
catcagagtg ttagacaata agatgcag                                      28

<210> SEQ ID NO 195
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 195
gcctgtcttt ggttagcagt gag                                           23

<210> SEQ ID NO 196
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 196
tttgagatgg agtcttgccc tg                                            22

<210> SEQ ID NO 197
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 197
gagttgagat cacgccaccg                                               20

<210> SEQ ID NO 198
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 198
aaattggaga ttgccctcat ttgg                                          24

<210> SEQ ID NO 199
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 199

-continued

```
tgaaatcact ggactaagca ccc                                        23

<210> SEQ ID NO 200
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 200
atcctccagc ctccaccg                                              18

<210> SEQ ID NO 201
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 201
gcagggcctc ctcctgag                                              18

<210> SEQ ID NO 202
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 202
tctgggctgg ttctggctg                                             19

<210> SEQ ID NO 203
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 203
caccctctgc agctcaaagt c                                          21

<210> SEQ ID NO 204
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 204
aggctagaga tgtagtcaga cccta                                      25

<210> SEQ ID NO 205
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 205
ccattaaaac ctgttcctga ggtct                                      25
```

```
<210> SEQ ID NO 206
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 206
gctctggttt agctccctac tc                                              22

<210> SEQ ID NO 207
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 207
aggttccctt ccaaactgac tc                                              22

<210> SEQ ID NO 208
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 208
agaygacagt catgcttcga tttaagt                                         27

<210> SEQ ID NO 209
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 209
ggaacgaaga acaacttcct ctagga                                          26

<210> SEQ ID NO 210
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 210
tcacccattg gctcctaatg tg                                              22

<210> SEQ ID NO 211
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 211
tgttgaacgc tcactgaggt ag                                              22
```

-continued

<210> SEQ ID NO 212
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 212
gttctggaac tactggtatt tattgctg                                        28

<210> SEQ ID NO 213
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 213
ctcttttagg aggacttgtg caatg                                           25

<210> SEQ ID NO 214
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 214
gctcaagaga tctgcctgcc tc                                              22

<210> SEQ ID NO 215
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 215
aaagaatgca ggctctgggc ag                                              22

<210> SEQ ID NO 216
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 216
agtggcgtgg tggaaagttt c                                               21

<210> SEQ ID NO 217
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 217
tcccgctgtc tcaggcg                                                    17

-continued

```
<210> SEQ ID NO 218
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 218
cctggccttt gagactccct c                                              21

<210> SEQ ID NO 219
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 219
tccacagctg ggctcagag                                                 19

<210> SEQ ID NO 220
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 220
ccacagtaga aaatgtgcct gtgg                                           24

<210> SEQ ID NO 221
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 221
tgccgagggt tgttcatcct c                                              21

<210> SEQ ID NO 222
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 222
gagttcttta ttcygtttca ttggtctatg t                                  31

<210> SEQ ID NO 223
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 223
cttggtaaag agtgagacac tttcaaaa                                       28

<210> SEQ ID NO 224
```

```
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 224
acatgagatt tagtggggac agag                                            24

<210> SEQ ID NO 225
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 225
tgaaatttgg aggggctggg g                                               21

<210> SEQ ID NO 226
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 226
accaaaggca aagaagttca aaact                                           25

<210> SEQ ID NO 227
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 227
cagctccttt aagcactttt ctgtat                                          26

<210> SEQ ID NO 228
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 228
gaaagaatgt tacttctgtt aatatgaata gcatg                                35

<210> SEQ ID NO 229
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 229
aggtcaggct ccatatggac c                                               21

<210> SEQ ID NO 230
<211> LENGTH: 22
```

-continued

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 230
aagatggctt ctggagtgct ac                                                     22

<210> SEQ ID NO 231
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 231
ttgccctttt ccttctagcc tac                                                    23

<210> SEQ ID NO 232
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 232
aggagcaagc catcacactt gac                                                    23

<210> SEQ ID NO 233
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 233
gcctgggcaa caagagtgaa ac                                                     22

<210> SEQ ID NO 234
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 234
agcctggcca gaatatctgc g                                                      21

<210> SEQ ID NO 235
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 235
ccccaattat tgtcatcctt ctccc                                                  25

<210> SEQ ID NO 236
<211> LENGTH: 27
<212> TYPE: DNA

-continued

```
<213> ORGANISM: Artificial Sequence
<220> FEATURE:
<223> OTHER INFORMATION: Description of Artificial Sequence: Synthetic
      primer

<400> SEQUENCE: 236
tgggaatttc agactataga agctctc                                          27

<210> SEQ ID NO 237
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 237
tgatgagttc tgatacagta actagtggt                                        29

<210> SEQ ID NO 238
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 238
aggagcagtg actccactcc ag                                               22

<210> SEQ ID NO 239
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 239
cgcacgtcct aagctgacag                                                  20

<210> SEQ ID NO 240
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 240
acaagtttac cgatgtaaaa ccttcac                                          27

<210> SEQ ID NO 241
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 241
gctgctcgtg gcctattttt atg                                              23

<210> SEQ ID NO 242
<211> LENGTH: 22
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 242
cagctgacac cctccttgaa tc                                        22

<210> SEQ ID NO 243
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 243
ttttctaatg gggccaggga ag                                        22

<210> SEQ ID NO 244
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 244
atgttgctgc actgttccca tg                                        22

<210> SEQ ID NO 245
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 245
gaaaaaagaa tgcacgtstg agttac                                    26

<210> SEQ ID NO 246
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 246
ccacaggtca aatgaggctc c                                         21

<210> SEQ ID NO 247
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 247
ggataaaagc cactcctgtc cag                                       23

<210> SEQ ID NO 248
<211> LENGTH: 20
<212> TYPE: DNA
<213> ORGANISM: Artificial Sequence
<220> FEATURE:
```

-continued

<223> OTHER INFORMATION: Description of Artificial Sequence: Synthetic
       primer

<400> SEQUENCE: 248
ccggcctcgt acggtaattc                                                    20

<210> SEQ ID NO 249
<211> LENGTH: 19
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 249
agttcgccag ctccgagac                                                     19

<210> SEQ ID NO 250
<211> LENGTH: 22
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 250
tccctaacgc aatccctgtg ac                                                 22

<210> SEQ ID NO 251
<211> LENGTH: 27
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 251
ggatctgtct ctccccttta ctcttag                                            27

<210> SEQ ID NO 252
<211> LENGTH: 21
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 252
ttcaagacca gccaggatga c                                                  21

<210> SEQ ID NO 253
<211> LENGTH: 23
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 253
ctgtgtgtca ccattcacag ctg                                                23

<210> SEQ ID NO 254
<211> LENGTH: 29
<212> TYPE: DNA
<213> ORGANISM: Artificial Sequence
<220> FEATURE:
<223> OTHER INFORMATION: Description of Artificial Sequence: Synthetic -continued primer

<400> SEQUENCE: 254
tgtccttcac agcttagatt caatctttc                                    29

<210> SEQ ID NO 255
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 255
gagtcagccc agaatcacac tc                                           22

<210> SEQ ID NO 256
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 256
tgccaggcct gaggatcttc                                              20

<210> SEQ ID NO 257
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 257
ttccctagga ccagtgtacc atg                                          23

<210> SEQ ID NO 258
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 258
agacttcaac aaatatgtgc tgttgt                                       26

<210> SEQ ID NO 259
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 259
tgtcaaccag agataataaa aacacaggta                                   30

<210> SEQ ID NO 260
<211> LENGTH: 22
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 260
aggctggtct caaactcctg ac                                    22

<210> SEQ ID NO 261
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 261
acctgtaatc ccagcacttt gagag                                 25

<210> SEQ ID NO 262
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 262
actttgcatt cgtgccacaa tag                                   23

<210> SEQ ID NO 263
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 263
ggctccaaag accaaatgga atg                                   23

<210> SEQ ID NO 264
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 264
atgaaaaatg tttgaatatg atctttaggg ac                         32

<210> SEQ ID NO 265
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 265
catgtacaga atttattgtt cccatttcat atac                       34

<210> SEQ ID NO 266
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 266
catctaggcc agcccttccc                                                    20

<210> SEQ ID NO 267
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 267
tacttgaagg tccccaggcg                                                    20

<210> SEQ ID NO 268
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 268
agaacctatt gtggatgtta ggagag                                             26

<210> SEQ ID NO 269
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 269
ggcttcatct cccagagtca ttg                                                23

<210> SEQ ID NO 270
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 270
acagtcagca gtaatctcac atctg                                              25

<210> SEQ ID NO 271
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 271
gggaagaaga aagcattgtt gtgac                                              25

<210> SEQ ID NO 272
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 272
```

```
acagaaaagt ttttaccaca gactacca                                      28

<210> SEQ ID NO 273
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 273
tcttgttatg cagatgaagc ctcaa                                         25

<210> SEQ ID NO 274
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 274
acctcayaca ttatgmagca tagggtatc                                     29

<210> SEQ ID NO 275
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 275
ggtgtacatg tatttatgcc acccc                                         25

<210> SEQ ID NO 276
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 276
ccacattctg tcgtggttga gac                                           23

<210> SEQ ID NO 277
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 277
ctcctgacag gactccacac c                                             21

<210> SEQ ID NO 278
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 278
```

-continued

```
gggagcagag ctgagtttct aaac                                               24

<210> SEQ ID NO 279
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 279
tccttctgtg aagtatctcc ayatatggat ttg                                    33

<210> SEQ ID NO 280
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 280
agtgcctaat tgttcaccca gc                                                 22

<210> SEQ ID NO 281
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 281
avcagtgagg ctytataaat aaaattaatt gtg                                     33

<210> SEQ ID NO 282
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 282
gatcccaggg ctccttgaag ag                                                 22

<210> SEQ ID NO 283
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 283
aagaaatcca actgtgcaag tgtg                                               24

<210> SEQ ID NO 284
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 284
gtgttctaga agccaagcaa agatg                                              25
```

-continued

```
<210> SEQ ID NO 285
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 285
agcagcattt gacacagttg atg                                               23

<210> SEQ ID NO 286
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 286
gccttgtccc ctgtatcctt tc                                                22

<210> SEQ ID NO 287
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 287
ccagaaaagg cagttaatag aaggc                                             25

<210> SEQ ID NO 288
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 288
ttytctccaa tcttagtaac acagctgac                                         29

<210> SEQ ID NO 289
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 289
acaaatattt agaaatcaag tagaagtgag atrc                                   34

<210> SEQ ID NO 290
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 290
ccgtgatcct taaatagcag cacag                                             25
```

```
<210> SEQ ID NO 291
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 291
ctggggccac atcaatccac g                                                      21

<210> SEQ ID NO 292
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 292
cctacgatca taatcacaag tacctcg                                                27

<210> SEQ ID NO 293
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 293
gcaaagctac cagtcatgtg cc                                                     22

<210> SEQ ID NO 294
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 294
actcgcatgc acgtatatgt acac                                                   24

<210> SEQ ID NO 295
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 295
cctgtgactt aagacttaca ataattcttc c                                           31

<210> SEQ ID NO 296
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 296
actcctccca gcagtagtag atg                                                    23
```

```
<210> SEQ ID NO 297
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 297
tgctgatcct gggagtgctg                                                    20

<210> SEQ ID NO 298
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 298
acaatcaaga ctcatgcatt gcaag                                              25

<210> SEQ ID NO 299
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 299
acttctccca atgaagatca cttagg                                             26

<210> SEQ ID NO 300
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 300
ccttggctca cagagtcatc tc                                                 22

<210> SEQ ID NO 301
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 301
gctttgagat gagtacaggg tgg                                                23

<210> SEQ ID NO 302
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 302
cctcccctat tgatgcacag c                                                  21

<210> SEQ ID NO 303
```

```
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 303
ttctgcgagt atacttattt gcatttgc                                            28

<210> SEQ ID NO 304
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 304
caaaatctct gcattcttac cccatg                                              26

<210> SEQ ID NO 305
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 305
agatgctttc cagtggtaaa ggc                                                 23

<210> SEQ ID NO 306
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 306
caagatagcc cagccagcag                                                     20

<210> SEQ ID NO 307
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 307
tgcagagccc agcatgtg                                                       18

<210> SEQ ID NO 308
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 308 gggaggggc aggaagc                                                         17

<210> SEQ ID NO 309
<211> LENGTH: 26
```

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 309
tctaggagct catgttttct gcttac                                              26

<210> SEQ ID NO 310
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 310
tgtagtcttc agttatcagg acaagtatc                                           29

<210> SEQ ID NO 311
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 311
tgtgccaayg agttctcaag g                                                   21

<210> SEQ ID NO 312
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 312
gagggcagat catgaggtca g                                                   21

<210> SEQ ID NO 313
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 313
acggggtttc accatgttgg                                                     20

<210> SEQ ID NO 314
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 314
aaggagggaa aggtgatgca tac                                                 23

<210> SEQ ID NO 315
<211> LENGTH: 22
<212> TYPE: DNA

<213> ORGANISM: Artificial Sequence
<220> FEATURE:
<223> OTHER INFORMATION: Description of Artificial Sequence: Synthetic
      primer

<400> SEQUENCE: 315
ggaggggctg cgtgaaaata ac                                                22

<210> SEQ ID NO 316
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 316
tgccagttca atcccccatt t                                                 21

<210> SEQ ID NO 317
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 317
gggcctccag cactgct                                                      17

<210> SEQ ID NO 318
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 318
ttgttcttat aaccagtgtg gaaagttaac                                        30

<210> SEQ ID NO 319
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 319
tcctgtgttg tgtgttgacg ttaag                                             25

<210> SEQ ID NO 320
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 320
tgggagggaa tatgaagcag gag                                               23

<210> SEQ ID NO 321
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 321
catctgycag ctcctcagat tcc                                                      23

<210> SEQ ID NO 322
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 322
tcaattaacc aktctcctgt cctcaa                                                   26

<210> SEQ ID NO 323
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 323
accatattgt tctttataaa accccaaaag aa                                            32

<210> SEQ ID NO 324
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 324
ggtgtggcag agcaggaac                                                           19

<210> SEQ ID NO 325
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 325
gcctgagctc cactttcact tc                                                       22

<210> SEQ ID NO 326
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 326
tcttgaagct tttacctcta tgcaaatayg                                               30

<210> SEQ ID NO 327
<211> LENGTH: 24
<212> TYPE: DNA
<213> ORGANISM: Artificial Sequence
<220> FEATURE:

-continued

```
<223> OTHER INFORMATION: Description of Artificial Sequence: Synthetic
      primer

<400> SEQUENCE: 327
cgccatcaca gttaaccttt cttc                                              24

<210> SEQ ID NO 328
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 328
gccaggactc caaatgagca ag                                                22

<210> SEQ ID NO 329
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 329
cgctccttat cccaggcag                                                    19

<210> SEQ ID NO 330
<211> LENGTH: 101
<212> TYPE: DNA
<213> ORGANISM: Solanum lycopersicum

<400> SEQUENCE: 330
acaatatact cagtgtatta gaagtgtggc ctggagaggg taggatgtac acgaccttac       60
ctctaccttt gaagggtgga gaggttgttt ccgatagacc c                          101

<210> SEQ ID NO 331
<211> LENGTH: 101
<212> TYPE: DNA
<213> ORGANISM: Solanum lycopersicum

<400> SEQUENCE: 331
acaatatact cagtgtatta gaagtgtggc ctggagaggg taggatgtac gcgaccttac       60
ctctaccttt gaagggtgga gaggttgttt ccgatagacc c                          101

<210> SEQ ID NO 332
<211> LENGTH: 101
<212> TYPE: DNA
<213> ORGANISM: Solanum lycopersicum

<400> SEQUENCE: 332
tgaattcgga taatggatct gttgtacttc tttcttgcag cttttgcctg tttttcacga       60
aaagatttag gaatcaataa tttcgactcc tctagtttct t                          101

<210> SEQ ID NO 333
<211> LENGTH: 101
<212> TYPE: DNA
<213> ORGANISM: Solanum lycopersicum

<400> SEQUENCE: 333
tgaattcgga taatggatct gttgtacttc tttcttgcag cttttgcctg cttttcacga       60
```

-continued

```
aaagatttag gaatcaataa tttcgactcc tctagtttct t                        101

<210> SEQ ID NO 334
<211> LENGTH: 101
<212> TYPE: DNA
<213> ORGANISM: Solanum lycopersicum

<400> SEQUENCE: 334
tgtttctaag tgattgtgga ggaaaaagat accctttgtt gcaacatcca attgcgccag     60
atggaccagt tctttttttg ccatttttga agggatgcaa g                        101

<210> SEQ ID NO 335
<211> LENGTH: 101
<212> TYPE: DNA
<213> ORGANISM: Solanum lycopersicum

<400> SEQUENCE: 335
tgtttctaag tgattgtgga ggaaaaagat accctttgtt gcaacatcca gttgcgccag     60
atggaccagt tctttttttg ccatttttga agggatgcaa g                        101

<210> SEQ ID NO 336
<211> LENGTH: 101
<212> TYPE: DNA
<213> ORGANISM: Solanum lycopersicum

<400> SEQUENCE: 336
tctctgttgc atttgtagat ggtggtgagg ctggaaatgt aatccctgaa agtgtgaagt     60
ttggtggaac attccggttc ttgacgtttg agggtcattc c                        101

<210> SEQ ID NO 337
<211> LENGTH: 101
<212> TYPE: DNA
<213> ORGANISM: Solanum lycopersicum

<400> SEQUENCE: 337
tctctgttgc atttgtagat ggtggtgagg ctggaaatgt aatccctgaa ggtgtgaagt     60
ttggtggaac attccggttc ttgacgtttg agggtcattc c                        101

<210> SEQ ID NO 338
<211> LENGTH: 101
<212> TYPE: DNA
<213> ORGANISM: Solanum lycopersicum

<400> SEQUENCE: 338
ggtgagaaag ttgcggagcc actatacaag atggaggctg gtaagacgta taggtataga     60
ttttgcaatg taggtatgag gacatcagtg aatgttagga t                        101

<210> SEQ ID NO 339
<211> LENGTH: 101
<212> TYPE: DNA
<213> ORGANISM: Solanum lycopersicum

<400> SEQUENCE: 339
ggtgagaaag ttgcggagcc actatacaag atggaggctg gtaagacgta caggtataga     60
ttttgcaatg taggtatgag gacatcagtg aatgttagga t                        101

<210> SEQ ID NO 340
<211> LENGTH: 101
<212> TYPE: DNA
<213> ORGANISM: Solanum lycopersicum
```

-continued

<400> SEQUENCE: 340
tttgttctat ctcttcgcgt aacatttgtg tccaacgaaa tcttttttgcc tcgccactta      60 aaaagccaag ctatcattgt actgttgtct gtcttgcgct t                          101

<210> SEQ ID NO 341
<211> LENGTH: 101
<212> TYPE: DNA
<213> ORGANISM: Solanum lycopersicum

<400> SEQUENCE: 341
tttgttctat ctcttcgcgt aacatttgtg tccaacgaaa tcttttttgcc gcgccactta      60 aaaagccaag ctatcattgt actgttgtct gtcttgcgct t                          101

<210> SEQ ID NO 342
<211> LENGTH: 101
<212> TYPE: DNA
<213> ORGANISM: Solanum lycopersicum

<400> SEQUENCE: 342
ttaccgatat gtcagacagt aagatggaga attttgttcc tgcttatgaa atcgtcaaat      60
tttacctgtt tttcgagaaa tggaggcgtg gagagataga g                          101

<210> SEQ ID NO 343
<211> LENGTH: 101
<212> TYPE: DNA
<213> ORGANISM: Solanum lycopersicum

<400> SEQUENCE: 343
ttaccgatat gtcagacagt aagatggaga attttgttcc tgcttatgaa ttcgtcaaat      60
tttacctgtt tttcgagaaa tggaggcgtg gagagataga g                          101

<210> SEQ ID NO 344
<211> LENGTH: 101
<212> TYPE: DNA
<213> ORGANISM: Solanum lycopersicum

<400> SEQUENCE: 344
tttgacgcgg aaaagtgaag atagcctcca agcatttcaa tgccgtctcc acttttgctt      60
ggagtgagat taccccccgaa cataagaaga gaataatcgg a                          101

<210> SEQ ID NO 345
<211> LENGTH: 101
<212> TYPE: DNA
<213> ORGANISM: Solanum lycopersicum

<400> SEQUENCE: 345
tttgacgcgg aaaagtgaag atagcctcca agcatttcaa tgccgtctcc tcttttgctt      60
ggagtgagat taccccccgaa cataagaaga gaataatcgg a                          101

<210> SEQ ID NO 346
<211> LENGTH: 101
<212> TYPE: DNA
<213> ORGANISM: Solanum lycopersicum

<400> SEQUENCE: 346
ggaggtagca ataacaacaa caacaacaac aacggggccc accaccacca tcatcagaac      60
cagtttgata acaataacaa caacaacctc attggctcgt c                          101

-continued

```
<210> SEQ ID NO 347
<211> LENGTH: 101
<212> TYPE: DNA
<213> ORGANISM: Solanum lycopersicum

<400> SEQUENCE: 347
ggaggtagca ataacaacaa caacaacaac aacggggccc accaccacca ccatcagaac      60
cagtttgata acaataacaa caacaacctc attggctcgt c                        101

<210> SEQ ID NO 348
<211> LENGTH: 101
<212> TYPE: DNA
<213> ORGANISM: Solanum lycopersicum

<400> SEQUENCE: 348
atgcccagcc cattgaacag catggcaatg ctgtggcaat gaaatctgaa atcactgacg      60
caatgatgga aattcctgct aaggctgtgc tagtcagtcc c                        101

<210> SEQ ID NO 349
<211> LENGTH: 101
<212> TYPE: DNA
<213> ORGANISM: Solanum lycopersicum

<400> SEQUENCE: 349
atgcccagcc cattgaacag catggcaatg ctgtggcaat gaaatctgaa gtcactgacg      60
caatgatgga aattcctgct aaggctgtgc tagtcagtcc c                        101

<210> SEQ ID NO 350
<211> LENGTH: 201
<212> TYPE: DNA
<213> ORGANISM: Solanum lycopersicum
<220> FEATURE:
<221> NAME/KEY: modified_base
<222> LOCATION: (73)..(73)
<223> OTHER INFORMATION: a, c, t, g, unknown or other

<400> SEQUENCE: 350
cctttatttg tgtgattatt ttatggtttt caattaggtc tcatgatgcc aatgagttat      60
ggatattact gangctttgt gattaggtaa aggtgatcac actttgtcaa tcaagagaca     120
aggatggcga agatggtaat aaaagcaacc atttcttttt tcgagtgctt tcttccagtt     180
tagattataa aagttcctct t                                             201

<210> SEQ ID NO 351
<211> LENGTH: 201
<212> TYPE: DNA
<213> ORGANISM: Solanum lycopersicum
<220> FEATURE:
<221> NAME/KEY: modified_base
<222> LOCATION: (73)..(73)
<223> OTHER INFORMATION: a, c, t, g, unknown or other

<400> SEQUENCE: 351
cctttatttg tgtgattatt ttatggtttt caattaggtc tcatgatgcc aatgagttat      60
ggatattact gangctttgt gattaggtaa aggtgatcac tctttgtcaa tcaagagaca     120
aggatggcga agatggtaat aaaagcaacc atttcttttt tcgagtgctt tcttccagtt     180
tagattataa aagttcctct t                                             201

<210> SEQ ID NO 352
<211> LENGTH: 101
```

-continued

```
<212> TYPE: DNA
<213> ORGANISM: Solanum lycopersicum

<400> SEQUENCE: 352
aatcgttgta catgctatat tttcgcttgt gcctcttctc ccatggactt agaaagtatg        60
tttttgctag tgtaagagga atgcaacggg atcgtttcgt t                           101

<210> SEQ ID NO 353
<211> LENGTH: 101
<212> TYPE: DNA
<213> ORGANISM: Solanum lycopersicum

<400> SEQUENCE: 353
aatcgttgta catgctatat tttcgcttgt gcctcttctc ccatggactt ggaaagtatg        60
tttttgctag tgtaagagga atgcaacggg atcgtttcgt t                           101

<210> SEQ ID NO 354
<211> LENGTH: 101
<212> TYPE: DNA
<213> ORGANISM: Solanum lycopersicum

<400> SEQUENCE: 354
caaatgcatg taatttgcag aaacaactgc atccactgaa gctctattac tgatacagaa        60
atattagggg tagagaatat tccagtatta attaaattga c                           101

<210> SEQ ID NO 355
<211> LENGTH: 101
<212> TYPE: DNA
<213> ORGANISM: Solanum lycopersicum

<400> SEQUENCE: 355
caaatgcatg taatttgcag aaacaactgc atccactgaa gctctattac cgatacagaa        60
atattagggg tagagaatat tccagtatta attaaattga c                           101

<210> SEQ ID NO 356
<211> LENGTH: 101
<212> TYPE: DNA
<213> ORGANISM: Solanum lycopersicum

<400> SEQUENCE: 356
gatgatatcg gtcgtctcat ggatgatgat atctctaagg tttcttctgt tctctctgtt        60
tccagaactg atgcatctgc tttactccgt cggtataact g                           101

<210> SEQ ID NO 357
<211> LENGTH: 101
<212> TYPE: DNA
<213> ORGANISM: Solanum lycopersicum

<400> SEQUENCE: 357
gatgatatcg gtcgtctcat ggatgatgat atctctaagg tttcttctgt cctctctgtt        60
tccagaactg atgcatctgc tttactccgt cggtataact g                           101

<210> SEQ ID NO 358
<211> LENGTH: 101
<212> TYPE: DNA
<213> ORGANISM: Solanum lycopersicum

<400> SEQUENCE: 358
tcaagcgctg aacttcttgc caccttctgt gacaacattc tcaaaaaagg agggagtgag        60
```

-continued

```
aaattgagtg atgaagctat tgaagaaacg ttggaaaagg t                  101

<210> SEQ ID NO 359
<211> LENGTH: 101
<212> TYPE: DNA
<213> ORGANISM: Solanum lycopersicum

<400> SEQUENCE: 359
tcaagcgctg aacttcttgc caccttctgt gacaacattc tcaaaaaagg cgggagtgag       60
aaattgagtg atgaagctat tgaagaaacg ttggaaaagg t                  101

<210> SEQ ID NO 360
<211> LENGTH: 101
<212> TYPE: DNA
<213> ORGANISM: Solanum lycopersicum

<400> SEQUENCE: 360
caaaatttgg gagagctgaa gcagagtttc ccactcaagg taaatgtata tagctagtca       60
aaagtatgcc agttgtgtcc tgttgcttgt gtatatagtt c                  101

<210> SEQ ID NO 361
<211> LENGTH: 101
<212> TYPE: DNA
<213> ORGANISM: Solanum lycopersicum

<400> SEQUENCE: 361
caaaatttgg gagagctgaa gcagagtttc ccactcaagg taaatgtata gagctagtca       60
aaagtatgcc agttgtgtcc tgttgcttgt gtatatagtt c                  101

<210> SEQ ID NO 362
<211> LENGTH: 101
<212> TYPE: DNA
<213> ORGANISM: Solanum lycopersicum

<400> SEQUENCE: 362
gtagagttat gttggtggaa ggaagtacag agaagaagca tagagatgtt tgagaattgg       60
gtgggagatt gttttttcca gagctccaac tatatgatat a                  101

<210> SEQ ID NO 363
<211> LENGTH: 101
<212> TYPE: DNA
<213> ORGANISM: Solanum lycopersicum

<400> SEQUENCE: 363
gtagagttat gttggtggaa ggaagtacag agaagaagca tagagatgtt cgagaattgg       60
gtgggagatt gttttttcca gagctccaac tatatgatat a                  101

<210> SEQ ID NO 364
<211> LENGTH: 101
<212> TYPE: DNA
<213> ORGANISM: Solanum lycopersicum

<400> SEQUENCE: 364
ctgctttggc ttttcctcta caacaggaac atcgtcaaca ccttgaaaac ttgtgtctgt       60
ggaggaacta ttttcgccag aaatctgaat gatctgcttc a                  101

<210> SEQ ID NO 365
<211> LENGTH: 101
<212> TYPE: DNA
<213> ORGANISM: Solanum lycopersicum
```

-continued

<400> SEQUENCE: 365
ctgctttggc ttttcctcta caacaggaac atcgtcaaca ccttgaaaac ctgtgtctgt        60
ggaggaacta ttttcgccag aaatctgaat gatctgcttc a                          101

<210> SEQ ID NO 366
<211> LENGTH: 101
<212> TYPE: DNA
<213> ORGANISM: Solanum lycopersicum

<400> SEQUENCE: 366
gtactggttt tggtttaaaa aaatgaagac atcaatgatt gacagtgctc atcctactat        60
catgctcatt accagggtgg gaagaagctc ctatcatcag a                          101

<210> SEQ ID NO 367
<211> LENGTH: 101
<212> TYPE: DNA
<213> ORGANISM: Solanum lycopersicum

<400> SEQUENCE: 367
gtactggttt tggtttaaaa aaatgaagac atcaatgatt gacagtgctc gtcctactat        60
catgctcatt accagggtgg gaagaagctc ctatcatcag a                          101

<210> SEQ ID NO 368
<211> LENGTH: 101
<212> TYPE: DNA
<213> ORGANISM: Solanum lycopersicum

<400> SEQUENCE: 368
gtgaaattgc actgtttccc ctttcatctt gagggagctc acatgcttca tttatagacc        60
ccgatttcag atcagctggt gggatgaagc agtctactga t                          101

<210> SEQ ID NO 369
<211> LENGTH: 101
<212> TYPE: DNA
<213> ORGANISM: Solanum lycopersicum

<400> SEQUENCE: 369
gtgaaattgc actgtttccc ctttcatctt gagggagctc acatgcttca cttatagacc        60
ccgatttcag atcagctggt gggatgaagc agtctactga t                          101

<210> SEQ ID NO 370
<211> LENGTH: 101
<212> TYPE: DNA
<213> ORGANISM: Solanum lycopersicum

<400> SEQUENCE: 370
taagtttttg actctattaa ctctgtgtgg cctgacaatg taatttgtct tagctagaga        60
aaagttcagt cagaaaataa atttcccatc tctctcattg t                          101

<210> SEQ ID NO 371
<211> LENGTH: 101
<212> TYPE: DNA
<213> ORGANISM: Solanum lycopersicum

<400> SEQUENCE: 371
taagtttttg actctattaa ctctgtgtgg cctgacaatg taatttgtct cagctagaga        60
aaagttcagt cagaaaataa atttcccatc tctctcattg t                          101

-continued

```
<210> SEQ ID NO 372
<211> LENGTH: 101
<212> TYPE: DNA
<213> ORGANISM: Solanum lycopersicum

<400> SEQUENCE: 372
aataaaatgg tgaaatggtg tccaagtatc cctcattgtg ggaatgctat acgagtagag      60
accgatgagt tctgtgaagt agaatgttca tgtggtttac a                         101

<210> SEQ ID NO 373
<211> LENGTH: 101
<212> TYPE: DNA
<213> ORGANISM: Solanum lycopersicum

<400> SEQUENCE: 373
aataaaatgg tgaaatggtg tccaagtatc cctcattgtg ggaatgctat tcgagtagag      60
accgatgagt tctgtgaagt agaatgttca tgtggtttac a                         101

<210> SEQ ID NO 374
<211> LENGTH: 101
<212> TYPE: DNA
<213> ORGANISM: Solanum lycopersicum

<400> SEQUENCE: 374
tacattgaca atggcaattt ggagcaatgg ctacacggtg atgtagggtc agttagtcct      60
ctaacttggg aaatcagact gagaattgca attggaactg c                         101

<210> SEQ ID NO 375
<211> LENGTH: 101
<212> TYPE: DNA
<213> ORGANISM: Solanum lycopersicum

<400> SEQUENCE: 375
tacattgaca atggcaattt ggagcaatgg ctacacggtg atgtagggtc tgttagtcct      60
ctaacttggg aaatcagact gagaattgca attggaactg c                         101

<210> SEQ ID NO 376
<211> LENGTH: 101
<212> TYPE: DNA
<213> ORGANISM: Solanum lycopersicum

<400> SEQUENCE: 376
ggagacactg tgaagagaat atgatgagag gagtgctccg gaaacttggg tcgatatgca      60
cattgacatt atttgctaga gcattcacat gcacttggca t                         101

<210> SEQ ID NO 377
<211> LENGTH: 101
<212> TYPE: DNA
<213> ORGANISM: Solanum lycopersicum

<400> SEQUENCE: 377
ggagacactg tgaagagaat atgatgagag gagtgctccg gaaacttggg gcgatatgca      60
cattgacatt atttgctaga gcattcacat gcacttggca t                         101

<210> SEQ ID NO 378
<211> LENGTH: 101
<212> TYPE: DNA
<213> ORGANISM: Solanum lycopersicum

<400> SEQUENCE: 378
```

-continued

```
gtatgcagct cacaactact aaacggtcaa ttttaagtga gcatagtgcc attgccaatt      60
cccatttctc taaatatcaa accagaaaac atatttaacg t                        101

<210> SEQ ID NO 379
<211> LENGTH: 101
<212> TYPE: DNA
<213> ORGANISM: Solanum lycopersicum

<400> SEQUENCE: 379
gtatgcagct cacaactact aaacggtcaa ttttaagtga gcatagtgcc gttgccaatt      60
cccatttctc taaatatcaa accagaaaac atatttaacg t                        101

<210> SEQ ID NO 380
<211> LENGTH: 101
<212> TYPE: DNA
<213> ORGANISM: Solanum lycopersicum

<400> SEQUENCE: 380
gaggaacata aaccactgaa gcattagcct ttgtctctac ttttgcctct acaacagtat      60
taaaaacagg tagccccaaa tgttctgttc cacccttctt g                        101

<210> SEQ ID NO 381
<211> LENGTH: 101
<212> TYPE: DNA
<213> ORGANISM: Solanum lycopersicum

<400> SEQUENCE: 381
gaggaacata aaccactgaa gcattagcct ttgtctctac ttttgcctct gcaacagtat      60
taaaaacagg tagccccaaa tgttctgttc cacccttctt g                        101

<210> SEQ ID NO 382
<211> LENGTH: 101
<212> TYPE: DNA
<213> ORGANISM: Solanum lycopersicum

<400> SEQUENCE: 382
cctctttgaa aatgtttaag atctcggcga gcttggtgac ctctaaaaca actttgaaca      60
cataagatgc catggagagt gcgatttctt gtatcttcaa g                        101

<210> SEQ ID NO 383
<211> LENGTH: 101
<212> TYPE: DNA
<213> ORGANISM: Solanum lycopersicum

<400> SEQUENCE: 383
cctctttgaa aatgtttaag atctcggcga gcttggtgac ctctaaaaca gctttgaaca      60
cataagatgc catggagagt gcgatttctt gtatcttcaa g                        101

<210> SEQ ID NO 384
<211> LENGTH: 101
<212> TYPE: DNA
<213> ORGANISM: Solanum lycopersicum

<400> SEQUENCE: 384
tcagcttatt ggtgattcct gttcatagat ttggctgtat tttatgtctt ctattgcctt      60
aaattcgtgt atggactata aaaaactgat tgtttgttgg a                        101

<210> SEQ ID NO 385
```

-continued

```
<211> LENGTH: 101
<212> TYPE: DNA
<213> ORGANISM: Solanum lycopersicum

<400> SEQUENCE: 385
tcagcttatt ggtgattcct gttcatagat ttggctgtat tttatgtctt gtattgcctt      60
aaattcgtgt atggactata aaaaactgat tgtttgttgg a                          101

<210> SEQ ID NO 386
<211> LENGTH: 101
<212> TYPE: DNA
<213> ORGANISM: Solanum lycopersicum

<400> SEQUENCE: 386
aacgataatc ttcttacttc ttcaataaac ctcaggaatt ctttggagaa tgggacgcca      60
ttgacgttga ttccgatgat gatagccatg gctccttgaa t                          101

<210> SEQ ID NO 387
<211> LENGTH: 101
<212> TYPE: DNA
<213> ORGANISM: Solanum lycopersicum

<400> SEQUENCE: 387
aacgataatc ttcttacttc ttcaataaac ctcaggaatt ctttggagaa cgggacgcca      60
ttgacgttga ttccgatgat gatagccatg gctccttgaa t                          101

<210> SEQ ID NO 388
<211> LENGTH: 101
<212> TYPE: DNA
<213> ORGANISM: Solanum lycopersicum

<400> SEQUENCE: 388
aggttgagat ggatgattgg ttgttcgagt ttgctcagtt attcaggact tatgttggca      60
ttgatccgga tgcccacatt gacctgcacg agcttgggat g                          101

<210> SEQ ID NO 389
<211> LENGTH: 101
<212> TYPE: DNA
<213> ORGANISM: Solanum lycopersicum

<400> SEQUENCE: 389
aggttgagat ggatgattgg ttgttcgagt ttgctcagtt attcaggact catgttggca      60
ttgatccgga tgcccacatt gacctgcacg agcttgggat g                          101

<210> SEQ ID NO 390
<211> LENGTH: 101
<212> TYPE: DNA
<213> ORGANISM: Solanum lycopersicum

<400> SEQUENCE: 390
catatccatt aaagaaagag tttagatcca agactgtgaa ttagggcatt taattactcc      60
acatggcaag atagaaagta tgtcacccgg atttagaaga t                          101

<210> SEQ ID NO 391
<211> LENGTH: 101
<212> TYPE: DNA
<213> ORGANISM: Solanum lycopersicum

<400> SEQUENCE: 391
catatccatt aaagaaagag tttagatcca agactgtgaa ttagggcatt gaattactcc      60
```

-continued

```
acatggcaag atagaaagta tgtcacccgg atttagaaga t                101

<210> SEQ ID NO 392
<211> LENGTH: 101
<212> TYPE: DNA
<213> ORGANISM: Solanum lycopersicum

<400> SEQUENCE: 392
tcagatagaa acagtcaagg ccaacaggga acaagagact aaaggcctca atgataaaat     60
ttctaggata gaggctgaac ttcaagctgc tgaatctatc a                101

<210> SEQ ID NO 393
<211> LENGTH: 101
<212> TYPE: DNA
<213> ORGANISM: Solanum lycopersicum

<400> SEQUENCE: 393
tcagatagaa acagtcaagg ccaacaggga acaagagact aaaggcctca gtgataaaat     60
ttctaggata gaggctgaac ttcaagctgc tgaatctatc a                101

<210> SEQ ID NO 394
<211> LENGTH: 101
<212> TYPE: DNA
<213> ORGANISM: Solanum lycopersicum

<400> SEQUENCE: 394
caaccgagcc accggacttg agaataaagc gaaattcctc tttgattcac tgatcaaaga     60
gcagatttca acctaacagt tgaatccatg cacaactcaa t                101

<210> SEQ ID NO 395
<211> LENGTH: 101
<212> TYPE: DNA
<213> ORGANISM: Solanum lycopersicum

<400> SEQUENCE: 395
caaccgagcc accggacttg agaataaagc gaaattcctc tttgattcac cgatcaaaga     60
gcagatttca acctaacagt tgaatccatg cacaactcaa t                101

<210> SEQ ID NO 396
<211> LENGTH: 101
<212> TYPE: DNA
<213> ORGANISM: Solanum lycopersicum

<400> SEQUENCE: 396
ttcattttgt tgaaaccaaa attatacata gaatatctgt ccaacattta ataggctctc     60
atgagggaca ttgaagatta cactattttc cctgcatatt t                101

<210> SEQ ID NO 397
<211> LENGTH: 101
<212> TYPE: DNA
<213> ORGANISM: Solanum lycopersicum

<400> SEQUENCE: 397
ttcattttgt tgaaaccaaa attatacata gaatatctgt ccaacattta ctaggctctc     60
atgagggaca ttgaagatta cactattttc cctgcatatt t                101

<210> SEQ ID NO 398
<211> LENGTH: 101
<212> TYPE: DNA
```

-continued

```
<213> ORGANISM: Solanum lycopersicum

<400> SEQUENCE: 398
tccctgtgta gtatcatttt gaaagataca aagcaaacaa gattgattag tcccgcttgc        60
acgaatttgt aagattttta tatctagaac aggatgatag t                           101

<210> SEQ ID NO 399
<211> LENGTH: 101
<212> TYPE: DNA
<213> ORGANISM: Solanum lycopersicum

<400> SEQUENCE: 399
tccctgtgta gtatcatttt gaaagataca aagcaaacaa gattgattag ccccgcttgc        60
acgaatttgt aagattttta tatctagaac aggatgatag t                           101

<210> SEQ ID NO 400
<211> LENGTH: 101
<212> TYPE: DNA
<213> ORGANISM: Solanum lycopersicum

<400> SEQUENCE: 400
atttagaaaa tcaggatagt aaacattccc tggccaaaca accccttggt agggcatatt        60
atcgcgtttt atgaagacat ctgcttccat gcctctccta t                           101

<210> SEQ ID NO 401
<211> LENGTH: 101
<212> TYPE: DNA
<213> ORGANISM: Solanum lycopersicum

<400> SEQUENCE: 401
atttagaaaa tcaggatagt aaacattccc tggccaaaca accccttggt ggggcatatt        60
atcgcgtttt atgaagacat ctgcttccat gcctctccta t                           101

<210> SEQ ID NO 402
<211> LENGTH: 101
<212> TYPE: DNA
<213> ORGANISM: Solanum lycopersicum

<400> SEQUENCE: 402
tgagagaagg agtggcgaag cagaggaagg attttgcgaa ggaggctaaa aagtttacta        60
atattaggca tcctaatgta gtaggattaa gaggttacta c                           101

<210> SEQ ID NO 403
<211> LENGTH: 101
<212> TYPE: DNA
<213> ORGANISM: Solanum lycopersicum

<400> SEQUENCE: 403
tgagagaagg agtggcgaag cagaggaagg attttgcgaa ggaggctaaa gagtttacta        60
atattaggca tcctaatgta gtaggattaa gaggttacta c                           101

<210> SEQ ID NO 404
<211> LENGTH: 101
<212> TYPE: DNA
<213> ORGANISM: Solanum lycopersicum

<400> SEQUENCE: 404
catatgacaa gatggagcaa caattgtcaa agactcgtaa cctgcattgt tagatcaact        60
gtgaacaggt gttttttctt ctctttttgct tcatttattt a                          101
```

<210> SEQ ID NO 405
<211> LENGTH: 101
<212> TYPE: DNA
<213> ORGANISM: Solanum lycopersicum

<400> SEQUENCE: 405
catatgacaa gatggagcaa caattgtcaa agactcgtaa cctgcattgt cagatcaact      60
gtgaacaggt gttttttctt ctcttttgct tcatttattt a      101

<210> SEQ ID NO 406
<211> LENGTH: 101
<212> TYPE: DNA
<213> ORGANISM: Solanum lycopersicum

<400> SEQUENCE: 406
gccaaagagc aagctgaatc tgctcaagag gaggcagagg agtggaaacg taagtacggc      60
attgctgcca aggaagcaaa gaatgctctt gagaaggcag c      101

<210> SEQ ID NO 407
<211> LENGTH: 101
<212> TYPE: DNA
<213> ORGANISM: Solanum lycopersicum

<400> SEQUENCE: 407
gccaaagagc aagctgaatc tgctcaagag gaggcagagg agtggaaacg caagtacggc      60
attgctgcca aggaagcaaa gaatgctctt gagaaggcag c      101

<210> SEQ ID NO 408
<211> LENGTH: 101
<212> TYPE: DNA
<213> ORGANISM: Solanum lycopersicum

<400> SEQUENCE: 408
accatggaca gatgaccttt tatggcagta ccacgaagct tgacaagttc atgcagcaca      60
gttttcacca ttcttaaagg tttatcatcg gctcccgctc t      101

<210> SEQ ID NO 409
<211> LENGTH: 101
<212> TYPE: DNA
<213> ORGANISM: Solanum lycopersicum

<400> SEQUENCE: 409
accatggaca gatgaccttt tatggcagta ccacgaagct tgacaagttc gtgcagcaca      60
gttttcacca ttcttaaagg tttatcatcg gctcccgctc t      101

<210> SEQ ID NO 410
<211> LENGTH: 101
<212> TYPE: DNA
<213> ORGANISM: Solanum lycopersicum

<400> SEQUENCE: 410
gaagatttgt gggtattgat gcaaaagaag aatgttgatg ctgacttggg aagttacacc      60
attagattac aaggattggt tgcgaataac caggttaacg a      101

<210> SEQ ID NO 411
<211> LENGTH: 101
<212> TYPE: DNA
<213> ORGANISM: Solanum lycopersicum -continued

```
<400> SEQUENCE: 411
gaagatttgt gggtattgat gcaaaagaag aatgttgatg ctgacttggg gagttacacc        60
attagattac aaggattggt tgcgaataac caggttaacg a                            101

<210> SEQ ID NO 412
<211> LENGTH: 101
<212> TYPE: DNA
<213> ORGANISM: Solanum lycopersicum

<400> SEQUENCE: 412
agacgttatt gtgttctgaa ccagtgtaat tatgttgttc ttgatgaagc tgaccgtatg        60
attgacatgg gttttgagcc tcaagttgtt ggtgtactgg a                            101

<210> SEQ ID NO 413
<211> LENGTH: 101
<212> TYPE: DNA
<213> ORGANISM: Solanum lycopersicum

<400> SEQUENCE: 413
agacgttatt gtgttctgaa ccagtgtaat tatgttgttc ttgatgaagc ggaccgtatg        60
attgacatgg gttttgagcc tcaagttgtt ggtgtactgg a                            101

<210> SEQ ID NO 414
<211> LENGTH: 101
<212> TYPE: DNA
<213> ORGANISM: Solanum lycopersicum

<400> SEQUENCE: 414
cccatattgc taatgcagat caaagagcgg gaggattaag cttctatagt agaagatatc        60
catcaaatgg agtagcaaac aagcaatgta ccacaatatt a                            101

<210> SEQ ID NO 415
<211> LENGTH: 101
<212> TYPE: DNA
<213> ORGANISM: Solanum lycopersicum

<400> SEQUENCE: 415
cccatattgc taatgcagat caaagagcgg gaggattaag cttctatagt cgaagatatc        60
catcaaatgg agtagcaaac aagcaatgta ccacaatatt a                            101

<210> SEQ ID NO 416
<211> LENGTH: 101
<212> TYPE: DNA
<213> ORGANISM: Solanum lycopersicum

<400> SEQUENCE: 416
tcacttgatt tgatagcaga agcaaaagta gatccagaat ccaggttaat agaacattta        60
ttgcttgtaa aagatttctg gttctgacca gaagatggat c                            101

<210> SEQ ID NO 417
<211> LENGTH: 101
<212> TYPE: DNA
<213> ORGANISM: Solanum lycopersicum

<400> SEQUENCE: 417
tcacttgatt tgatagcaga agcaaaagta gatccagaat ccaggttaat tgaacattta        60
ttgcttgtaa aagatttctg gttctgacca gaagatggat c                            101
```

-continued

```
<210> SEQ ID NO 418
<211> LENGTH: 101
<212> TYPE: DNA
<213> ORGANISM: Solanum lycopersicum

<400> SEQUENCE: 418
ggaggtcagg ctgggcaatt gggagttggg ccattaaatg gattcttttc atgcaagctc      60
aatgaatctg agatgatgct ccgaaatata ccagtgttgg t                        101

<210> SEQ ID NO 419
<211> LENGTH: 101
<212> TYPE: DNA
<213> ORGANISM: Solanum lycopersicum

<400> SEQUENCE: 419
ggaggtcagg ctgggcaatt gggagttggg ccattaaatg gattcttttc ctgcaagctc      60
aatgaatctg agatgatgct ccgaaatata ccagtgttgg t                        101

<210> SEQ ID NO 420
<211> LENGTH: 101
<212> TYPE: DNA
<213> ORGANISM: Solanum lycopersicum

<400> SEQUENCE: 420
gtgtaatacg atctgccaga ccgtggtggg caggggattc tgttagctga taatgctccg      60
tacgaaatgt agtacttgaa tttgttccac aatagagatc t                        101

<210> SEQ ID NO 421
<211> LENGTH: 101
<212> TYPE: DNA
<213> ORGANISM: Solanum lycopersicum

<400> SEQUENCE: 421
gtgtaatacg atctgccaga ccgtggtggg caggggattc tgttagctga caatgctccg      60
tacgaaatgt agtacttgaa tttgttccac aatagagatc t                        101

<210> SEQ ID NO 422
<211> LENGTH: 101
<212> TYPE: DNA
<213> ORGANISM: Solanum lycopersicum

<400> SEQUENCE: 422
cgtcgatcaa aatactcttc caaacctacc gcaaaagata atagcaggca ataacaacaa      60
agattaatct cccccctata tatgacttga gttgtcagga a                        101

<210> SEQ ID NO 423
<211> LENGTH: 101
<212> TYPE: DNA
<213> ORGANISM: Solanum lycopersicum

<400> SEQUENCE: 423
cgtcgatcaa aatactcttc caaacctacc gcaaaagata atagcaggca gtaacaacaa      60
agattaatct cccccctata tatgacttga gttgtcagga a                        101

<210> SEQ ID NO 424
<211> LENGTH: 101
<212> TYPE: DNA
<213> ORGANISM: Solanum lycopersicum

<400> SEQUENCE: 424
```

-continued

```
ccaggatcac ccctctagta gccagccaag tgaaaaagca caccttcatc agcactttgg      60
aaatgtaaac tgcatcaaaa cttcctcttc ctaaccaaaa g                        101

<210> SEQ ID NO 425
<211> LENGTH: 101
<212> TYPE: DNA
<213> ORGANISM: Solanum lycopersicum

<400> SEQUENCE: 425
ccaggatcac ccctctagta gccagccaag tgaaaaagca caccttcatc ggcactttgg      60
aaatgtaaac tgcatcaaaa cttcctcttc ctaaccaaaa g                        101

<210> SEQ ID NO 426
<211> LENGTH: 101
<212> TYPE: DNA
<213> ORGANISM: Solanum lycopersicum

<400> SEQUENCE: 426
actccaaggg accaaataag ctttgccatt gtaagagata agatcatgtc aaagacaaat      60
tggactgtga atatgttctt agactgcgaa cggcgtaact t                        101

<210> SEQ ID NO 427
<211> LENGTH: 101
<212> TYPE: DNA
<213> ORGANISM: Solanum lycopersicum

<400> SEQUENCE: 427
actccaaggg accaaataag ctttgccatt gtaagagata agatcatgtc caagacaaat      60
tggactgtga atatgttctt agactgcgaa cggcgtaact t                        101

<210> SEQ ID NO 428
<211> LENGTH: 101
<212> TYPE: DNA
<213> ORGANISM: Solanum lycopersicum

<400> SEQUENCE: 428
cgggtgtgca tgtttcaata ctgacaaaaa agggccttca atggtgttga tcgcgctagt      60
gagaaatgaa tttggtggtt ctctgtgcct tctttccgct a                        101

<210> SEQ ID NO 429
<211> LENGTH: 101
<212> TYPE: DNA
<213> ORGANISM: Solanum lycopersicum

<400> SEQUENCE: 429
cgggtgtgca tgtttcaata ctgacaaaaa agggccttca atggtgttga ccgcgctagt      60
gagaaatgaa tttggtggtt ctctgtgcct tctttccgct a                        101

<210> SEQ ID NO 430
<211> LENGTH: 101
<212> TYPE: DNA
<213> ORGANISM: Solanum lycopersicum

<400> SEQUENCE: 430
aattccgcca gccatttctt cgccggcttt ttccccctca acatctccgg tgatgtcacg      60
ttatctatca aataggggag gaactcaagt acaaaaggtt c                        101

<210> SEQ ID NO 431
<211> LENGTH: 101
```

```
<212> TYPE: DNA
<213> ORGANISM: Solanum lycopersicum

<400> SEQUENCE: 431
aattccgcca gccatttctt cgccggcttt ttccccctca acatctccgg cgatgtcacg     60
ttatctatca aatagggggag gaactcaagt acaaaaggtt c                       101

<210> SEQ ID NO 432
<211> LENGTH: 101
<212> TYPE: DNA
<213> ORGANISM: Solanum lycopersicum

<400> SEQUENCE: 432
acagctctac aactattgct ccgttcattc cttcctagca cttttgaggc aaagctagga     60
ggcttaagct tctcaacttg actctgcaga gatccatggc t                       101

<210> SEQ ID NO 433
<211> LENGTH: 101
<212> TYPE: DNA
<213> ORGANISM: Solanum lycopersicum

<400> SEQUENCE: 433
acagctctac aactattgct ccgttcattc cttcctagca cttttgaggc taagctagga     60
ggcttaagct tctcaacttg actctgcaga gatccatggc t                       101

<210> SEQ ID NO 434
<211> LENGTH: 101
<212> TYPE: DNA
<213> ORGANISM: Solanum lycopersicum

<400> SEQUENCE: 434
actcttgaac catttgaaag agaccacgct tgtgttgttg gtgcctatcg tgtaccaaag     60
aagcaaaagg ctgctgccta gaaaatttaa gcttatgatt t                       101

<210> SEQ ID NO 435
<211> LENGTH: 101
<212> TYPE: DNA
<213> ORGANISM: Solanum lycopersicum

<400> SEQUENCE: 435
actcttgaac catttgaaag agaccacgct tgtgttgttg gtgcctatcg cgtaccaaag     60
aagcaaaagg ctgctgccta gaaaatttaa gcttatgatt t                       101

<210> SEQ ID NO 436
<211> LENGTH: 101
<212> TYPE: DNA
<213> ORGANISM: Solanum lycopersicum

<400> SEQUENCE: 436
aaacagaaat tcgggtttcg gttcagaaaa acatcaatga acaaagtatc aatcaagcaa     60
ttaacttgaa tggcacccct tttgttcttc cagagttttt c                       101

<210> SEQ ID NO 437
<211> LENGTH: 101
<212> TYPE: DNA
<213> ORGANISM: Solanum lycopersicum

<400> SEQUENCE: 437
aaacagaaat tcgggtttcg gttcagaaaa acatcaatga acaaagtatc gatcaagcaa     60
```

-continued

```
ttaacttgaa tggcaccct tttgttcttc cagagttttt c                           101

<210> SEQ ID NO 438
<211> LENGTH: 101
<212> TYPE: DNA
<213> ORGANISM: Solanum lycopersicum

<400> SEQUENCE: 438
ctctcctctt ttgttaattc atcaatttt tcctgcatca gtttcattag tgatacaact       60
tcttcaggcc ttcgcttgaa gttatcaatg ctgaatgcat a                          101

<210> SEQ ID NO 439
<211> LENGTH: 101
<212> TYPE: DNA
<213> ORGANISM: Solanum lycopersicum

<400> SEQUENCE: 439
ctctcctctt ttgttaattc atcaatttt tcctgcatca gtttcattag cgatacaact       60
tcttcaggcc ttcgcttgaa gttatcaatg ctgaatgcat a                          101

<210> SEQ ID NO 440
<211> LENGTH: 101
<212> TYPE: DNA
<213> ORGANISM: Solanum lycopersicum

<400> SEQUENCE: 440
gggcgtgact caaacacttg ggaagatgca ttatctttca ggccagagcg atttctcaac      60
tctaatgtgg atttcagggg tcaagatttc gagttcatac c                          101

<210> SEQ ID NO 441
<211> LENGTH: 101
<212> TYPE: DNA
<213> ORGANISM: Solanum lycopersicum

<400> SEQUENCE: 441
gggcgtgact caaacacttg ggaagatgca ttatctttca ggccagagcg gtttctcaac      60
tctaatgtgg atttcagggg tcaagatttc gagttcatac c                          101

<210> SEQ ID NO 442
<211> LENGTH: 101
<212> TYPE: DNA
<213> ORGANISM: Solanum lycopersicum

<400> SEQUENCE: 442
gaagagtatg ctcttcgacg tctaaggctt ttgcagcaca tctgctaacg tggagcatat      60
ttgttctctc atcgcatccc tgttatttgc atcaagtgta a                          101

<210> SEQ ID NO 443
<211> LENGTH: 101
<212> TYPE: DNA
<213> ORGANISM: Solanum lycopersicum

<400> SEQUENCE: 443
gaagagtatg ctcttcgacg tctaaggctt ttgcagcaca tctgctaacg cggagcatat      60
ttgttctctc atcgcatccc tgttatttgc atcaagtgta a                          101

<210> SEQ ID NO 444
<211> LENGTH: 101
<212> TYPE: DNA
<213> ORGANISM: Solanum lycopersicum
```

-continued

<400> SEQUENCE: 444
ttccatcagc ttatgaactc caaacgttgt ttgtcaatga gttgtgctaa atactacctc       60
tttgaccatc agttcattta ccaggcaaat caacagggca a                          101

<210> SEQ ID NO 445
<211> LENGTH: 101
<212> TYPE: DNA
<213> ORGANISM: Solanum lycopersicum

<400> SEQUENCE: 445
ttccatcagc ttatgaactc caaacgttgt ttgtcaatga gttgtgctaa gtactacctc       60
tttgaccatc agttcattta ccaggcaaat caacagggca a                          101

<210> SEQ ID NO 446
<211> LENGTH: 101
<212> TYPE: DNA
<213> ORGANISM: Solanum lycopersicum

<400> SEQUENCE: 446
aagtccattg aatccaatat cgaggcaggg ttgccctggg tgagatctac agtagttatg       60
gactctaaat tagcagactc tggtgagaag tttgcaatat t                          101

<210> SEQ ID NO 447
<211> LENGTH: 101
<212> TYPE: DNA
<213> ORGANISM: Solanum lycopersicum

<400> SEQUENCE: 447
aagtccattg aatccaatat cgaggcaggg ttgccctggg tgagatctac tgtagttatg       60
gactctaaat tagcagactc tggtgagaag tttgcaatat t                          101

<210> SEQ ID NO 448
<211> LENGTH: 101
<212> TYPE: DNA
<213> ORGANISM: Solanum lycopersicum

<400> SEQUENCE: 448
gaatggaact atcaccacaa gtacacaact aaagctttga tgaaaacacc agagctgttt       60
cagtcttgac gaacatacca accgcattct agtgcttgaa a                          101

<210> SEQ ID NO 449
<211> LENGTH: 101
<212> TYPE: DNA
<213> ORGANISM: Solanum lycopersicum

<400> SEQUENCE: 449
gaatggaact atcaccacaa gtacacaact aaagctttga tgaaaacacc ggagctgttt       60
cagtcttgac gaacatacca accgcattct agtgcttgaa a                          101

<210> SEQ ID NO 450
<211> LENGTH: 101
<212> TYPE: DNA
<213> ORGANISM: Solanum lycopersicum

<400> SEQUENCE: 450
ccctactgat gttgagctga taatgtacta tctaaagcgg aagatcatgg tgaaaaagat       60 ccttttgaa gtcatatcag aactcaacat ttataagttc t                          101

```
<210> SEQ ID NO 451
<211> LENGTH: 101
<212> TYPE: DNA
<213> ORGANISM: Solanum lycopersicum

<400> SEQUENCE: 451
ccctactgat gttgagctga taatgtacta tctaaagcgg aagatcatgg ggaaaaagat       60 ccttttttgaa gtcatatcag aactcaacat ttataagttc t                        101

<210> SEQ ID NO 452
<211> LENGTH: 101
<212> TYPE: DNA
<213> ORGANISM: Solanum lycopersicum

<400> SEQUENCE: 452
agattttgaa gttcacccaa ctcttcaatt cttgaatcac taaatgcacc tacgacaaat       60
cttgttgaat aagaaagtag gagaatctgt aacttgcttt t                        101

<210> SEQ ID NO 453
<211> LENGTH: 101
<212> TYPE: DNA
<213> ORGANISM: Solanum lycopersicum

<400> SEQUENCE: 453
agattttgaa gttcacccaa ctcttcaatt cttgaatcac taaatgcacc cacgacaaat       60
cttgttgaat aagaaagtag gagaatctgt aacttgcttt t                        101

<210> SEQ ID NO 454
<211> LENGTH: 101
<212> TYPE: DNA
<213> ORGANISM: Solanum lycopersicum

<400> SEQUENCE: 454
ataatgcaag tctcacattt ttcgtgcaga taaagtatac cccttgatat atccaatgca       60
agtctcatcc tttgctccca agaaggtctt gtttcagaac t                        101

<210> SEQ ID NO 455
<211> LENGTH: 101
<212> TYPE: DNA
<213> ORGANISM: Solanum lycopersicum

<400> SEQUENCE: 455
ataatgcaag tctcacattt ttcgtgcaga taaagtatac cccttgatat gtccaatgca       60
agtctcatcc tttgctccca agaaggtctt gtttcagaac t                        101

<210> SEQ ID NO 456
<211> LENGTH: 101
<212> TYPE: DNA
<213> ORGANISM: Solanum lycopersicum

<400> SEQUENCE: 456
taccaataga ttctccgatc aaagagtttt ccttgggctc aagcacaccg tcggactttg       60
acaagatcaa aaacaatttt tttgcatcgt cgtcagttaa c                        101

<210> SEQ ID NO 457
<211> LENGTH: 101
<212> TYPE: DNA
<213> ORGANISM: Solanum lycopersicum

<400> SEQUENCE: 457
```

-continued

```
taccaataga ttctccgatc aaagagtttt ccttgggctc aagcacaccg ccggactttg     60
acaagatcaa aaacaatttt tttgcatcgt cgtcagttaa c                        101

<210> SEQ ID NO 458
<211> LENGTH: 101
<212> TYPE: DNA
<213> ORGANISM: Solanum lycopersicum

<400> SEQUENCE: 458
gctatcaact ggtgtatatg caagggtaca attcctatcc ctggaatcaa atctgtaaaa     60
caaactgaag agaacctagg agcccttggt tggcaactca g                        101

<210> SEQ ID NO 459
<211> LENGTH: 101
<212> TYPE: DNA
<213> ORGANISM: Solanum lycopersicum

<400> SEQUENCE: 459
gctatcaact ggtgtatatg caagggtaca attcctatcc ctggaatcaa gtctgtaaaa     60
caaactgaag agaacctagg agcccttggt tggcaactca g                        101

<210> SEQ ID NO 460
<211> LENGTH: 101
<212> TYPE: DNA
<213> ORGANISM: Solanum lycopersicum

<400> SEQUENCE: 460
tcatgctggc agaggaagtg agagaaatta tgtctcaact tggtttcaga acacttactg     60
aaatggttgg ccgttcagac atgcttgaaa tggacaatga t                        101

<210> SEQ ID NO 461
<211> LENGTH: 101
<212> TYPE: DNA
<213> ORGANISM: Solanum lycopersicum

<400> SEQUENCE: 461
tcatgctggc agaggaagtg agagaaatta tgtctcaact tggtttcaga gcacttactg     60
aaatggttgg ccgttcagac atgcttgaaa tggacaatga t                        101

<210> SEQ ID NO 462
<211> LENGTH: 101
<212> TYPE: DNA
<213> ORGANISM: Solanum lycopersicum

<400> SEQUENCE: 462
aaaagccatc cttaagtttc cgttcgatgc cggaaattta ataccgcagg agacgattgg     60
ccggaagagg agaattgatc agtgatgcac ttagttgagt g                        101

<210> SEQ ID NO 463
<211> LENGTH: 101
<212> TYPE: DNA
<213> ORGANISM: Solanum lycopersicum

<400> SEQUENCE: 463
aaaagccatc cttaagtttc cgttcgatgc cggaaattta ataccgcagg tgacgattgg     60
ccggaagagg agaattgatc agtgatgcac ttagttgagt g                        101

<210> SEQ ID NO 464
```

-continued

```
<211> LENGTH: 101
<212> TYPE: DNA
<213> ORGANISM: Solanum lycopersicum

<400> SEQUENCE: 464
caaaacatag aatatcatgc aagttgctgg ttaagtgcca agaacatgga tgttcattgc        60
atgtttaatt aactctttcg ggtgagatca aaatctctgg t                          101

<210> SEQ ID NO 465
<211> LENGTH: 101
<212> TYPE: DNA
<213> ORGANISM: Solanum lycopersicum

<400> SEQUENCE: 465
caaaacatag aatatcatgc aagttgctgg ttaagtgcca agaacatgga cgttcattgc        60
atgtttaatt aactctttcg ggtgagatca aaatctctgg t                          101

<210> SEQ ID NO 466
<211> LENGTH: 101
<212> TYPE: DNA
<213> ORGANISM: Solanum lycopersicum

<400> SEQUENCE: 466
tcgcaactct tatactatga tgggtgttca attattgaga tgtgtaccaa atgcttgtaa        60
ctgctcactt taagatgaaa agctgccttc actggttagt g                          101

<210> SEQ ID NO 467
<211> LENGTH: 101
<212> TYPE: DNA
<213> ORGANISM: Solanum lycopersicum

<400> SEQUENCE: 467
tcgcaactct tatactatga tgggtgttca attattgaga tgtgtaccaa gtgcttgtaa        60
ctgctcactt taagatgaaa agctgccttc actggttagt g                          101

<210> SEQ ID NO 468
<211> LENGTH: 101
<212> TYPE: DNA
<213> ORGANISM: Solanum lycopersicum

<400> SEQUENCE: 468
tgatgtaagc aaattttcaa gtcgccatgt ggtgagtgct gcatatgatc acacaataaa        60
agtttgggat ctgcagaagg gttactgtaa caacactatc a                          101

<210> SEQ ID NO 469
<211> LENGTH: 101
<212> TYPE: DNA
<213> ORGANISM: Solanum lycopersicum

<400> SEQUENCE: 469
tgatgtaagc aaattttcaa gtcgccatgt ggtgagtgct gcatatgatc gcacaataaa        60
agtttgggat ctgcagaagg gttactgtaa caacactatc a                          101

<210> SEQ ID NO 470
<211> LENGTH: 101
<212> TYPE: DNA
<213> ORGANISM: Solanum lycopersicum

<400> SEQUENCE: 470
aggaggtggc atctggggtg ggaagtaggg gaatggttca attgggaaac aaccgggagg        60
```

-continued

```
aactggagct ccataaggtg gccctccggg tggccctcta t                         101

<210> SEQ ID NO 471
<211> LENGTH: 101
<212> TYPE: DNA
<213> ORGANISM: Solanum lycopersicum

<400> SEQUENCE: 471
aggaggtggc atctggggtg ggaagtaggg gaatggttca attgggaaac caccgggagg     60
aactggagct ccataaggtg gccctccggg tggccctcta t                         101

<210> SEQ ID NO 472
<211> LENGTH: 101
<212> TYPE: DNA
<213> ORGANISM: Solanum lycopersicum

<400> SEQUENCE: 472
agcggctgag ataaaggatt aaatctacaa aacgaagcgg aactggacgg cttgtgaggc     60
ttcttaggga gtgaaattga cggagaaaac gagattgctg t                         101

<210> SEQ ID NO 473
<211> LENGTH: 101
<212> TYPE: DNA
<213> ORGANISM: Solanum lycopersicum

<400> SEQUENCE: 473
agcggctgag ataaaggatt aaatctacaa aacgaagcgg aactggacgg gttgtgaggc     60
ttcttaggga gtgaaattga cggagaaaac gagattgctg t                         101

<210> SEQ ID NO 474
<211> LENGTH: 101
<212> TYPE: DNA
<213> ORGANISM: Solanum lycopersicum

<400> SEQUENCE: 474
ctccaaatat tgcagcacct gttgcattgt aggtctatca tctggatttg aatcagtgca     60
tcttgcagct atttctataa ttgcttctac tgtctctgca t                         101

<210> SEQ ID NO 475
<211> LENGTH: 101
<212> TYPE: DNA
<213> ORGANISM: Solanum lycopersicum

<400> SEQUENCE: 475
ctccaaatat tgcagcacct gttgcattgt aggtctatca tctggatttg catcagtgca     60
tcttgcagct atttctataa ttgcttctac tgtctctgca t                         101

<210> SEQ ID NO 476
<211> LENGTH: 101
<212> TYPE: DNA
<213> ORGANISM: Solanum lycopersicum

<400> SEQUENCE: 476
ggtaacctaa ctccggctga gactcatcag aatccgccgt caaatccacc acttccgtct     60
ccatcacctt cgccggtgac ggagaagctg taatttcttc t                         101

<210> SEQ ID NO 477
<211> LENGTH: 101
<212> TYPE: DNA
```

-continued

<213> ORGANISM: Solanum lycopersicum

<400> SEQUENCE: 477

```
ggtaacctaa ctccggctga gactcatcag aatccgccgt caaatccacc gcttccgtct      60
ccatcacctt cgccggtgac ggagaagctg taatttcttc t                        101
```

<210> SEQ ID NO 478
<211> LENGTH: 101
<212> TYPE: DNA
<213> ORGANISM: Solanum lycopersicum

<400> SEQUENCE: 478

```
aacgaatcga aatcatgact cgtggtgcaa aactcggagc tatcatcgtc atcggtgaga      60
tcgtacaaca gattctcctt gagtttcttc acttccggtg a                        101
```

<210> SEQ ID NO 479
<211> LENGTH: 101
<212> TYPE: DNA
<213> ORGANISM: Solanum lycopersicum

<400> SEQUENCE: 479

```
aacgaatcga aatcatgact cgtggtgcaa aactcggagc tatcatcgtc gtcggtgaga      60
tcgtacaaca gattctcctt gagtttcttc acttccggtg a                        101
```

<210> SEQ ID NO 480
<211> LENGTH: 101
<212> TYPE: DNA
<213> ORGANISM: Solanum lycopersicum

<400> SEQUENCE: 480

```
ctaaaatcaa ttatcttgag ctgtgaacat tgagacagtt gagatggaat tggaccataa      60
agtgagttat caggtgctct cagctcttcc aatgatgaag c                        101
```

<210> SEQ ID NO 481
<211> LENGTH: 101
<212> TYPE: DNA
<213> ORGANISM: Solanum lycopersicum

<400> SEQUENCE: 481

```
ctaaaatcaa ttatcttgag ctgtgaacat tgagacagtt gagatggaat cggaccataa      60
agtgagttat caggtgctct cagctcttcc aatgatgaag c                        101
```

<210> SEQ ID NO 482
<211> LENGTH: 101
<212> TYPE: DNA
<213> ORGANISM: Solanum lycopersicum

<400> SEQUENCE: 482

```
atcgaagcca gaaattgtga ttattgattg tggattaagg aattttggtg tggagttgaa      60
atggatggga ataattggag ggccgctcag gctcaggctc c                        101
```

<210> SEQ ID NO 483
<211> LENGTH: 101
<212> TYPE: DNA
<213> ORGANISM: Solanum lycopersicum

<400> SEQUENCE: 483

```
atcgaagcca gaaattgtga ttattgattg tggattaagg aattttggtg cggagttgaa      60
atggatggga ataattggag ggccgctcag gctcaggctc c                        101
```

-continued

```
<210> SEQ ID NO 484
<211> LENGTH: 101
<212> TYPE: DNA
<213> ORGANISM: Solanum lycopersicum

<400> SEQUENCE: 484
tctccggcga ccggagaatc ctacgcctgt aaatctatcg ataaaaacct tctcattgat      60
tccaccgacc gtgagtgtct cgataaagaa cccaaaattc t                        101

<210> SEQ ID NO 485
<211> LENGTH: 101
<212> TYPE: DNA
<213> ORGANISM: Solanum lycopersicum

<400> SEQUENCE: 485
tctccggcga ccggagaatc ctacgcctgt aaatctatcg ataaaaacct cctcattgat      60
tccaccgacc gtgagtgtct cgataaagaa cccaaaattc t                        101

<210> SEQ ID NO 486
<211> LENGTH: 101
<212> TYPE: DNA
<213> ORGANISM: Solanum lycopersicum

<400> SEQUENCE: 486
gatcgaaggt caattgagag aagcagaaga gactatgaca ggagcaggag ccgtagtagg      60
agtagaagcc acagccgaag cttgcatgat caaggtacaa g                        101

<210> SEQ ID NO 487
<211> LENGTH: 101
<212> TYPE: DNA
<213> ORGANISM: Solanum lycopersicum

<400> SEQUENCE: 487
gatcgaaggt caattgagag aagcagaaga gactatgaca ggagcaggag gcgtagtagg      60
agtagaagcc acagccgaag cttgcatgat caaggtacaa g                        101

<210> SEQ ID NO 488
<211> LENGTH: 101
<212> TYPE: DNA
<213> ORGANISM: Solanum lycopersicum

<400> SEQUENCE: 488
ctatatgggt caatatttcc ctgctcatga tctgcaagaa gaagagcttt agtacaatca      60
gtggaaggat gttcagacga tcctgtgtca catgttatct g                        101

<210> SEQ ID NO 489
<211> LENGTH: 101
<212> TYPE: DNA
<213> ORGANISM: Solanum lycopersicum

<400> SEQUENCE: 489
ctatatgggt caatatttcc ctgctcatga tctgcaagaa gaagagcttt ggtacaatca      60
gtggaaggat gttcagacga tcctgtgtca catgttatct g                        101

<210> SEQ ID NO 490
<211> LENGTH: 101
<212> TYPE: DNA
<213> ORGANISM: Solanum lycopersicum
```

<400> SEQUENCE: 490
tggcccaaat gaagatatga caccagaaaa tcgatctgtt ctgtgcgtgc cactagagga        60
aaacgggata aacttacccc cacccggaga gccaccaaag g                            101

<210> SEQ ID NO 491
<211> LENGTH: 101
<212> TYPE: DNA
<213> ORGANISM: Solanum lycopersicum

<400> SEQUENCE: 491
tggcccaaat gaagatatga caccagaaaa tcgatctgtt ctgtgcgtgc gactagagga        60
aaacgggata aacttacccc cacccggaga gccaccaaag g                            101

<210> SEQ ID NO 492
<211> LENGTH: 101
<212> TYPE: DNA
<213> ORGANISM: Solanum lycopersicum

<400> SEQUENCE: 492
atagactcga agcatttctt cgtgccttca ggaaatgcag ctgttgaatt aataggagga        60
agggaaacag gcattgcaca gacgatacgt acaatcccaa a                            101

<210> SEQ ID NO 493
<211> LENGTH: 101
<212> TYPE: DNA
<213> ORGANISM: Solanum lycopersicum

<400> SEQUENCE: 493
atagactcga agcatttctt cgtgccttca ggaaatgcag ctgttgaatt gataggagga        60
agggaaacag gcattgcaca gacgatacgt acaatcccaa a                            101

<210> SEQ ID NO 494
<211> LENGTH: 101
<212> TYPE: DNA
<213> ORGANISM: Solanum lycopersicum

<400> SEQUENCE: 494
cttcagcaac tttaccatct tcattcactt tattcttccc tttgaagcca caaccaaaaa        60
caaatgtgtc attcagtttt ggaccctgat actctggttc c                            101

<210> SEQ ID NO 495
<211> LENGTH: 101
<212> TYPE: DNA
<213> ORGANISM: Solanum lycopersicum

<400> SEQUENCE: 495
cttcagcaac tttaccatct tcattcactt tattcttccc tttgaagcca gaaccaaaaa        60
caaatgtgtc attcagtttt ggaccctgat actctggttc c                            101

<210> SEQ ID NO 496
<211> LENGTH: 101
<212> TYPE: DNA
<213> ORGANISM: Solanum lycopersicum

<400> SEQUENCE: 496
ccattcagaa aatagattct taaaagttgt gagccatcaa atctccagct tttcagtttt        60
ggggttgtag ttttcggact ctacatgtta taactacaat a                            101

-continued

<210> SEQ ID NO 497
<211> LENGTH: 101
<212> TYPE: DNA
<213> ORGANISM: Solanum lycopersicum

<400> SEQUENCE: 497
ccattcagaa aatagattct taaaagttgt gagccatcaa atctccagct cttcagtttt      60
ggggttgtag ttttcggact ctacatgtta taactacaat a                        101

<210> SEQ ID NO 498
<211> LENGTH: 101
<212> TYPE: DNA
<213> ORGANISM: Solanum lycopersicum

<400> SEQUENCE: 498
tttataaaat gtgatcttgt atacttcctg gacaaccatc aaccatccat ttgttctgcc      60
tttgtgtagc cctcacctgg ttttttatta accgctccca g                        101

<210> SEQ ID NO 499
<211> LENGTH: 101
<212> TYPE: DNA
<213> ORGANISM: Solanum lycopersicum

<400> SEQUENCE: 499
tttataaaat gtgatcttgt atacttcctg gacaaccatc aaccatccat ctgttctgcc      60
tttgtgtagc cctcacctgg ttttttatta accgctccca g                        101

<210> SEQ ID NO 500
<211> LENGTH: 101
<212> TYPE: DNA
<213> ORGANISM: Solanum lycopersicum

<400> SEQUENCE: 500
gagagaccac acagatgccg acggcgatag acagccgaat actttgtgta agcgtgctct      60
gaagctctca tcgtccatgc cttaccactt tctacttcct g                        101

<210> SEQ ID NO 501
<211> LENGTH: 101
<212> TYPE: DNA
<213> ORGANISM: Solanum lycopersicum

<400> SEQUENCE: 501
gagagaccac acagatgccg acggcgatag acagccgaat actttgtgta cgcgtgctct      60
gaagctctca tcgtccatgc cttaccactt tctacttcct g                        101

<210> SEQ ID NO 502
<211> LENGTH: 101
<212> TYPE: DNA
<213> ORGANISM: Solanum lycopersicum

<400> SEQUENCE: 502
cccgactgtc atcagccaaa cgataaatat tccttcgaga aaagaaatgg agtttgtaaa      60
cattttgcct cgtctggcta tctgaaccta gaagaaactc c                        101

<210> SEQ ID NO 503
<211> LENGTH: 101
<212> TYPE: DNA
<213> ORGANISM: Solanum lycopersicum

<400> SEQUENCE: 503

```
cccgactgtc atcagccaaa cgataaatat tccttcgaga aaagaaatgg ggtttgtaaa        60
cattttgcct cgtctggcta tctgaaccta gaagaaactc c                           101

<210> SEQ ID NO 504
<211> LENGTH: 101
<212> TYPE: DNA
<213> ORGANISM: Solanum lycopersicum

<400> SEQUENCE: 504
gacgctcatt gcatctcgca ctgatggtgg caaattcctc aagatcttgg tagatttatg        60
ctatccaaag tgggcactgg aagcatttgt cattgcaaat g                           101

<210> SEQ ID NO 505
<211> LENGTH: 101
<212> TYPE: DNA
<213> ORGANISM: Solanum lycopersicum

<400> SEQUENCE: 505
gacgctcatt gcatctcgca ctgatggtgg caaattcctc aagatcttgg cagatttatg        60
ctatccaaag tgggcactgg aagcatttgt cattgcaaat g                           101

<210> SEQ ID NO 506
<211> LENGTH: 101
<212> TYPE: DNA
<213> ORGANISM: Solanum lycopersicum

<400> SEQUENCE: 506
gagcttcgtc agagaggtac ttctgttgta cctccaggtg aagtgtatgg aagatggggt        60
ggcatggaat ttaaagataa agaaattgtg tggccaccaa t                           101

<210> SEQ ID NO 507
<211> LENGTH: 101
<212> TYPE: DNA
<213> ORGANISM: Solanum lycopersicum

<400> SEQUENCE: 507
gagcttcgtc agagaggtac ttctgttgta cctccaggtg aagtgtatgg gagatggggt        60
ggcatggaat ttaaagataa agaaattgtg tggccaccaa t                           101

<210> SEQ ID NO 508
<211> LENGTH: 101
<212> TYPE: DNA
<213> ORGANISM: Solanum lycopersicum

<400> SEQUENCE: 508
gtatgatgat cgagccattt gcaatgtttt agttggtgac ctaagaattc ttggtcttct        60
aaaaggtgca agcatgcgtt gtctaattca gaagaaacaa c                           101

<210> SEQ ID NO 509
<211> LENGTH: 101
<212> TYPE: DNA
<213> ORGANISM: Solanum lycopersicum

<400> SEQUENCE: 509
gtatgatgat cgagccattt gcaatgtttt agttggtgac ctaagaattc ctggtcttct        60
aaaaggtgca agcatgcgtt gtctaattca gaagaaacaa c                           101

<210> SEQ ID NO 510
<211> LENGTH: 101
```

-continued

```
<212> TYPE: DNA
<213> ORGANISM: Solanum lycopersicum

<400> SEQUENCE: 510
ggatgaatgg agagggacat ggtcaatatc gatgcatcgc ccaaatgttc tgtttttccc       60
cttggtgatt gttcaattat gatttatgta caatatatat a                         101

<210> SEQ ID NO 511
<211> LENGTH: 101
<212> TYPE: DNA
<213> ORGANISM: Solanum lycopersicum

<400> SEQUENCE: 511
ggatgaatgg agagggacat ggtcaatatc gatgcatcgc ccaaatgttc ggtttttccc       60
cttggtgatt gttcaattat gatttatgta caatatatat a                         101

<210> SEQ ID NO 512
<211> LENGTH: 101
<212> TYPE: DNA
<213> ORGANISM: Solanum lycopersicum

<400> SEQUENCE: 512
aacttaatca gcagacatct ttatacaaga aaatgtggct agcatacaag taataaagtc       60
aaataaataa caaattggca caacaaaaca atttgcttaa a                         101

<210> SEQ ID NO 513
<211> LENGTH: 101
<212> TYPE: DNA
<213> ORGANISM: Solanum lycopersicum

<400> SEQUENCE: 513
aacttaatca gcagacatct ttatacaaga aaatgtggct agcatacaag caataaagtc       60
aaataaataa caaattggca caacaaaaca atttgcttaa a                         101

<210> SEQ ID NO 514
<211> LENGTH: 101
<212> TYPE: DNA
<213> ORGANISM: Solanum lycopersicum

<400> SEQUENCE: 514
aattggccgc atctacataa tgcccagttt ttcgtctatg ccgactataa tctgatacaa       60
acctaaaagt cagtccacaa ccctcaacct tgcacttgta t                         101

<210> SEQ ID NO 515
<211> LENGTH: 101
<212> TYPE: DNA
<213> ORGANISM: Solanum lycopersicum

<400> SEQUENCE: 515
aattggccgc atctacataa tgcccagttt ttcgtctatg ccgactataa cctgatacaa       60
acctaaaagt cagtccacaa ccctcaacct tgcacttgta t                         101

<210> SEQ ID NO 516
<211> LENGTH: 101
<212> TYPE: DNA
<213> ORGANISM: Solanum lycopersicum

<400> SEQUENCE: 516
gagaaagcta gagaagccag agcttcctgc tagcattatt gagatgagta tattgatgtc       60
```

-continued

```
gatagtattt tcttcaactc tatttacctg acagactttg a                        101

<210> SEQ ID NO 517
<211> LENGTH: 101
<212> TYPE: DNA
<213> ORGANISM: Solanum lycopersicum

<400> SEQUENCE: 517
gagaaagcta gagaagccag agcttcctgc tagcattatt gagatgagta gattgatgtc    60
gatagtattt tcttcaactc tatttacctg acagactttg a                        101

<210> SEQ ID NO 518
<211> LENGTH: 101
<212> TYPE: DNA
<213> ORGANISM: Solanum lycopersicum

<400> SEQUENCE: 518 tcccccctata cattagcctt ggaatgactc ctcttcatct ggcaagacaa tagctagtaa   60
agagaactta acacgaagag aaatcttagc cttgtccact a                        101

<210> SEQ ID NO 519
<211> LENGTH: 101
<212> TYPE: DNA
<213> ORGANISM: Solanum lycopersicum

<400> SEQUENCE: 519 tcccccctata cattagcctt ggaatgactc ctcttcatct ggcaagacaa cagctagtaa   60
agagaactta acacgaagag aaatcttagc cttgtccact a                        101

<210> SEQ ID NO 520
<211> LENGTH: 101
<212> TYPE: DNA
<213> ORGANISM: Solanum lycopersicum

<400> SEQUENCE: 520
attctcaaag tggagctttc gagtgcttca attgttcaaa aaagagagtg tggctcttat     60
tggctggctc ccatctgttg ttgtttgcct aaggacaaaa g                         101

<210> SEQ ID NO 521
<211> LENGTH: 101
<212> TYPE: DNA
<213> ORGANISM: Solanum lycopersicum

<400> SEQUENCE: 521
attctcaaag tggagctttc gagtgcttca attgttcaaa aaagagagtg cggctcttat     60
tggctggctc ccatctgttg ttgtttgcct aaggacaaaa g                         101

<210> SEQ ID NO 522
<211> LENGTH: 201
<212> TYPE: DNA
<213> ORGANISM: Solanum lycopersicum

<400> SEQUENCE: 522
aagtagaaag tactgccaat gaagttccaa atgatccttc caagatcaca aacatcaaag     60
aaattgccac ctatgacagt aaagacatgc cttcacttga acttagtttg aagcaacttc    120
gagatgttgg agagaatggg actggtgtgc aagagcgaaa tatactcagg cattcagatc    180
tgtcagcgtt ctctaggcat g                                              201
```

-continued

```
<210> SEQ ID NO 523
<211> LENGTH: 201
<212> TYPE: DNA
<213> ORGANISM: Solanum lycopersicum

<400> SEQUENCE: 523
aagtagaaag tactgccaat gaagttccaa atgatccttc caagatcaca aacatcaaag      60
aaattgccac ctatgacagt aaagacatgc cttcacttga gcttagtttg aagcaacttc     120
gagatgttgg agagaatggg actggtgtgc aagagcgaaa tatactcagg cattcagatc     180
tgtcagcgtt ctctaggcat g                                             201

<210> SEQ ID NO 524
<211> LENGTH: 101
<212> TYPE: DNA
<213> ORGANISM: Solanum lycopersicum

<400> SEQUENCE: 524
ttttcgccta tagagtcagg tattaagaaa gtggcaaagg attttgagca ttgttggcct      60
ggtaaagctg agagttgtac tagtagtggg tatggattag a                       101

<210> SEQ ID NO 525
<211> LENGTH: 101
<212> TYPE: DNA
<213> ORGANISM: Solanum lycopersicum

<400> SEQUENCE: 525
ttttcgccta tagagtcagg tattaagaaa gtggcaaagg attttgagca ctgttggcct      60
ggtaaagctg agagttgtac tagtagtggg tatggattag a                       101

<210> SEQ ID NO 526
<211> LENGTH: 101
<212> TYPE: DNA
<213> ORGANISM: Solanum lycopersicum

<400> SEQUENCE: 526
ctgaaccaaa acaatggact gatggtaaat tgagcaagag aatcggaagg agaggaactc      60
catttgtatt gagactgcta attgctgttt tcccattctt a                       101

<210> SEQ ID NO 527
<211> LENGTH: 101
<212> TYPE: DNA
<213> ORGANISM: Solanum lycopersicum

<400> SEQUENCE: 527
ctgaaccaaa acaatggact gatggtaaat tgagcaagag aatcggaagg ggaggaactc      60
catttgtatt gagactgcta attgctgttt tcccattctt a                       101

<210> SEQ ID NO 528
<211> LENGTH: 101
<212> TYPE: DNA
<213> ORGANISM: Solanum lycopersicum

<400> SEQUENCE: 528
tgaccatgag agggagaaat aatattgtga tatatgaaga agagcttggc taatagtggt      60
ggaagtcaca gatgaaccaa tcttaggctt caaaagattg t                       101

<210> SEQ ID NO 529
<211> LENGTH: 101
<212> TYPE: DNA
```

-continued

```
<213> ORGANISM: Solanum lycopersicum

<400> SEQUENCE: 529
tgaccatgag agggagaaat aatattgtga tatatgaaga agagcttggc gaatagtggt        60
ggaagtcaca gatgaaccaa tcttaggctt caaaagattg t                          101

<210> SEQ ID NO 530
<211> LENGTH: 101
<212> TYPE: DNA
<213> ORGANISM: Solanum lycopersicum

<400> SEQUENCE: 530
ataataagaa ttgggaaaca attggagtac tttgaacaat atcaaaggag agtaagtggt        60
ttaattggag cagcacaaac agagcagcta gtaaacagtg c                          101

<210> SEQ ID NO 531
<211> LENGTH: 101
<212> TYPE: DNA
<213> ORGANISM: Solanum lycopersicum

<400> SEQUENCE: 531
ataataagaa ttgggaaaca attggagtac tttgaacaat atcaaaggag ggtaagtggt        60
ttaattggag cagcacaaac agagcagcta gtaaacagtg c                          101

<210> SEQ ID NO 532
<211> LENGTH: 101
<212> TYPE: DNA
<213> ORGANISM: Solanum lycopersicum

<400> SEQUENCE: 532
tcatatcgat ctgcatgtct aagcttaagc ctaattgacg aattcccata tgattttgca        60
gttgtgtgcc agacaccggt aacagcatat cgactccctg a                          101

<210> SEQ ID NO 533
<211> LENGTH: 101
<212> TYPE: DNA
<213> ORGANISM: Solanum lycopersicum

<400> SEQUENCE: 533
tcatatcgat ctgcatgtct aagcttaagc ctaattgacg aattcccata cgattttgca        60
gttgtgtgcc agacaccggt aacagcatat cgactccctg a                          101

<210> SEQ ID NO 534
<211> LENGTH: 101
<212> TYPE: DNA
<213> ORGANISM: Solanum lycopersicum

<400> SEQUENCE: 534
acaagcaaca gcagcatgta tttaacaaac aaggaactat gtacggttag agtccttaat        60
gctgtcagtc aagatgaagt cactgtaagt atattaatgg t                          101

<210> SEQ ID NO 535
<211> LENGTH: 101
<212> TYPE: DNA
<213> ORGANISM: Solanum lycopersicum

<400> SEQUENCE: 535
acaagcaaca gcagcatgta tttaacaaac aaggaactat gtacggttag ggtccttaat        60
gctgtcagtc aagatgaagt cactgtaagt atattaatgg t                          101
```

<210> SEQ ID NO 536
<211> LENGTH: 101
<212> TYPE: DNA
<213> ORGANISM: Solanum lycopersicum

<400> SEQUENCE: 536
tttttgttta atcagatatt ttgaattcga gctttgttcg ttaaaatgtt tttgctaggg    60
aacgttttat gctaatgtat atttgaaatg atgtgctaga a    101

<210> SEQ ID NO 537
<211> LENGTH: 101
<212> TYPE: DNA
<213> ORGANISM: Solanum lycopersicum

<400> SEQUENCE: 537
tttttgttta atcagatatt ttgaattcga gctttgttcg ttaaaatgtt cttgctaggg    60
aacgttttat gctaatgtat atttgaaatg atgtgctaga a    101

<210> SEQ ID NO 538
<211> LENGTH: 101
<212> TYPE: DNA
<213> ORGANISM: Solanum lycopersicum

<400> SEQUENCE: 538
ctagaagcaa aagggtaact agcagcaaca gaagcagcag cagctgtggt agccaacttg    60
gctgagaaaa taccataaga atgaagggtt tgaccattaa a    101

<210> SEQ ID NO 539
<211> LENGTH: 101
<212> TYPE: DNA
<213> ORGANISM: Solanum lycopersicum

<400> SEQUENCE: 539
ctagaagcaa aagggtaact agcagcaaca gaagcagcag cagctgtggt tgccaacttg    60
gctgagaaaa taccataaga atgaagggtt tgaccattaa a    101

<210> SEQ ID NO 540
<211> LENGTH: 101
<212> TYPE: DNA
<213> ORGANISM: Solanum lycopersicum

<400> SEQUENCE: 540
gatgtaacct gaatgtctcc ttgagcacta gttctaagta ttccaactta agtaagtcat    60
cttcctcaac cattctatca agtcctacaa tagaagtcaa c    101

<210> SEQ ID NO 541
<211> LENGTH: 101
<212> TYPE: DNA
<213> ORGANISM: Solanum lycopersicum

<400> SEQUENCE: 541
gatgtaacct gaatgtctcc ttgagcacta gttctaagta ttccaactta ggtaagtcat    60
cttcctcaac cattctatca agtcctacaa tagaagtcaa c    101

<210> SEQ ID NO 542
<211> LENGTH: 101
<212> TYPE: DNA
<213> ORGANISM: Solanum lycopersicum -continued

```
<400> SEQUENCE: 542
ctgtgtcatt tttttttcta acactatact agtctttttg ccgccggcgg tatgagttta       60
ttcaggtaaa agggaaaagg gtattcatat ataagcctaa a                          101

<210> SEQ ID NO 543
<211> LENGTH: 101
<212> TYPE: DNA
<213> ORGANISM: Solanum lycopersicum

<400> SEQUENCE: 543
ctgtgtcatt tttttttcta acactatact agtctttttg ccgccggcgg gatgagttta       60
ttcaggtaaa agggaaaagg gtattcatat ataagcctaa a                          101

<210> SEQ ID NO 544
<211> LENGTH: 101
<212> TYPE: DNA
<213> ORGANISM: Solanum lycopersicum

<400> SEQUENCE: 544
agggcaatat tactcccctt gatcgccatt gtagaccttt gtgaaataga acagtttcca       60
ctcactttac gttttacttc tgagaaagta agcgcccatt t                          101

<210> SEQ ID NO 545
<211> LENGTH: 101
<212> TYPE: DNA
<213> ORGANISM: Solanum lycopersicum

<400> SEQUENCE: 545
agggcaatat tactcccctt gatcgccatt gtagaccttt gtgaaataga gcagtttcca       60
ctcactttac gttttacttc tgagaaagta agcgcccatt t                          101

<210> SEQ ID NO 546
<211> LENGTH: 101
<212> TYPE: DNA
<213> ORGANISM: Solanum lycopersicum

<400> SEQUENCE: 546
aactgcacat tgtttgcatt cagaaggttt tggaattcac tgtagtctat tctatgagaa       60
ttttcaggat cccactctgt ccccttcagc tttccctgca t                          101

<210> SEQ ID NO 547
<211> LENGTH: 101
<212> TYPE: DNA
<213> ORGANISM: Solanum lycopersicum

<400> SEQUENCE: 547
aactgcacat tgtttgcatt cagaaggttt tggaattcac tgtagtctat cctatgagaa       60
ttttcaggat cccactctgt ccccttcagc tttccctgca t                          101

<210> SEQ ID NO 548
<211> LENGTH: 101
<212> TYPE: DNA
<213> ORGANISM: Solanum lycopersicum

<400> SEQUENCE: 548
gaagcaaata gtgtgcagag gaagagaaaa tagagatgtc gaagacgcta cttcagcctg       60
taggccaaaa gagacttacc aatgttgctg ttgtgcgtct c                          101
```

-continued

<210> SEQ ID NO 549
<211> LENGTH: 101
<212> TYPE: DNA
<213> ORGANISM: Solanum lycopersicum

<400> SEQUENCE: 549
gaagcaaata gtgtgcagag gaagagaaaa tagagatgtc gaagacgcta gttcagcctg        60
taggccaaaa gagacttacc aatgttgctg ttgtgcgtct c                           101

<210> SEQ ID NO 550
<211> LENGTH: 101
<212> TYPE: DNA
<213> ORGANISM: Solanum lycopersicum

<400> SEQUENCE: 550
gttcccatag tacccaaaga aaagaaggtc cctccaactg gtgacaaggt aaaaaatgga        60
gatttctcag gtgacaataa taatgtcaaa aaatgaaagt t                           101

<210> SEQ ID NO 551
<211> LENGTH: 101
<212> TYPE: DNA
<213> ORGANISM: Solanum lycopersicum

<400> SEQUENCE: 551
gttcccatag tacccaaaga aaagaaggtc cctccaactg gtgacaaggt caaaaatgga        60
gatttctcag gtgacaataa taatgtcaaa aaatgaaagt t                           101

<210> SEQ ID NO 552
<211> LENGTH: 101
<212> TYPE: DNA
<213> ORGANISM: Solanum lycopersicum

<400> SEQUENCE: 552
tcaatacaat acctttacca ctattataaa gaaaaaggac aaccaggtgc acgaaacatc        60
acatgttcac gcatggtctg aggaagggcc acattccaag g                           101

<210> SEQ ID NO 553
<211> LENGTH: 101
<212> TYPE: DNA
<213> ORGANISM: Solanum lycopersicum

<400> SEQUENCE: 553
tcaatacaat acctttacca ctattataaa gaaaaaggac aaccaggtgc gcgaaacatc        60
acatgttcac gcatggtctg aggaagggcc acattccaag g                           101

<210> SEQ ID NO 554
<211> LENGTH: 101
<212> TYPE: DNA
<213> ORGANISM: Solanum lycopersicum

<400> SEQUENCE: 554
gactctagtg gagttgaagt aggagcaatg ttggtgatgg ttattggata tagggtgtta        60
gcctacttcc tcctaagaaa aatgaaacca agaacaagca a                           101

<210> SEQ ID NO 555
<211> LENGTH: 101
<212> TYPE: DNA
<213> ORGANISM: Solanum lycopersicum

<400> SEQUENCE: 555

-continued

```
gactctagtg gagttgaagt aggagcaatg ttggtgatgg ttattggata cagggtgtta        60
gcctacttcc tcctaagaaa aatgaaacca agaacaagca a                           101

<210> SEQ ID NO 556
<211> LENGTH: 101
<212> TYPE: DNA
<213> ORGANISM: Solanum lycopersicum

<400> SEQUENCE: 556
taatattatt tgttcatttt aagatgaata aagaattaag tctgcaagat ctttatggtc        60
aaaccactac ccttggaact cattgagatt agatcttata t                           101

<210> SEQ ID NO 557
<211> LENGTH: 101
<212> TYPE: DNA
<213> ORGANISM: Solanum lycopersicum

<400> SEQUENCE: 557
taatattatt tgttcatttt aagatgaata aagaattaag tctgcaagat gtttatggtc        60
aaaccactac ccttggaact cattgagatt agatcttata t                           101

<210> SEQ ID NO 558
<211> LENGTH: 101
<212> TYPE: DNA
<213> ORGANISM: Solanum lycopersicum

<400> SEQUENCE: 558 atgtttacc aagtactatc tgctgcaagt tgtttttttct ttaatctaga cactccagat        60
caagtttatt tagaacacaa aaaaccatag aagaaaaagg t                           101

<210> SEQ ID NO 559
<211> LENGTH: 101
<212> TYPE: DNA
<213> ORGANISM: Solanum lycopersicum

<400> SEQUENCE: 559 atgtttacc aagtactatc tgctgcaagt tgtttttttct ttaatctaga gactccagat        60
caagtttatt tagaacacaa aaaaccatag aagaaaaagg t                           101

<210> SEQ ID NO 560
<211> LENGTH: 101
<212> TYPE: DNA
<213> ORGANISM: Solanum lycopersicum

<400> SEQUENCE: 560
tgattacacg tgcaatcctc tggagaagct ccaatactag agaaggcgac aaatttgtcc        60
tagatgtcgc aacaaaaagc agaccaacta ccttcacatg g                           101

<210> SEQ ID NO 561
<211> LENGTH: 101
<212> TYPE: DNA
<213> ORGANISM: Solanum lycopersicum

<400> SEQUENCE: 561
tgattacacg tgcaatcctc tggagaagct ccaatactag agaaggcgac caatttgtcc        60
tagatgtcgc aacaaaaagc agaccaacta ccttcacatg g                           101

<210> SEQ ID NO 562
<211> LENGTH: 101
```

-continued

```
<212> TYPE: DNA
<213> ORGANISM: Solanum lycopersicum

<400> SEQUENCE: 562
tggacttcca aaccaactgg tgcctttata cttgctgtgt atgttgcgtc ttcttgtcct      60
acgttagtta cagttcttgt tactttcttg atttcatttt c                        101

<210> SEQ ID NO 563
<211> LENGTH: 101
<212> TYPE: DNA
<213> ORGANISM: Solanum lycopersicum

<400> SEQUENCE: 563
tggacttcca aaccaactgg tgcctttata cttgctgtgt atgttgcgtc gtcttgtcct      60
acgttagtta cagttcttgt tactttcttg atttcatttt c                        101

<210> SEQ ID NO 564
<211> LENGTH: 101
<212> TYPE: DNA
<213> ORGANISM: Solanum lycopersicum

<400> SEQUENCE: 564
tgttttttta tcatattgct ctgaaaaaca aaatatggag tgatggagca ttgtggacaa      60
gtaaactcca ccccatccaa ataatacacc agaaaagtac a                        101

<210> SEQ ID NO 565
<211> LENGTH: 101
<212> TYPE: DNA
<213> ORGANISM: Solanum lycopersicum

<400> SEQUENCE: 565
tgttttttta tcatattgct ctgaaaaaca aaatatggag tgatggagca gtgtggacaa      60
gtaaactcca ccccatccaa ataatacacc agaaaagtac a                        101

<210> SEQ ID NO 566
<211> LENGTH: 101
<212> TYPE: DNA
<213> ORGANISM: Solanum lycopersicum

<400> SEQUENCE: 566
agatattttt aaaattggat gatttttttt cgagtgattt tgggcgttcc attttcctgg      60
gtttattgag tttcttcctc tgtttgatct gaccaatgca c                        101

<210> SEQ ID NO 567
<211> LENGTH: 101
<212> TYPE: DNA
<213> ORGANISM: Solanum lycopersicum

<400> SEQUENCE: 567
agatattttt aaaattggat gatttttttt cgagtgattt tgggcgttcc gttttcctgg      60
gtttattgag tttcttcctc tgtttgatct gaccaatgca c                        101

<210> SEQ ID NO 568
<211> LENGTH: 101
<212> TYPE: DNA
<213> ORGANISM: Solanum lycopersicum

<400> SEQUENCE: 568
tccaggtagt cttttggtac ttccatttca gatagtgtgc tggcattgat tgcctgagct      60
```

-continued

```
gccttgaaaa tttgatttgt gcattcccta cactgccgca a                            101

<210> SEQ ID NO 569
<211> LENGTH: 101
<212> TYPE: DNA
<213> ORGANISM: Solanum lycopersicum

<400> SEQUENCE: 569
tccaggtagt cttttggtac ttccatttca gatagtgtgc tggcattgat cgcctgagct        60
gccttgaaaa tttgatttgt gcattcccta cactgccgca a                            101

<210> SEQ ID NO 570
<211> LENGTH: 101
<212> TYPE: DNA
<213> ORGANISM: Solanum lycopersicum

<400> SEQUENCE: 570
ccggttcaca tttcgtcatt cagctaaatc tctggccaaa gttgacgcca ttcactctcc        60
tttgctcctt ccgatctcaa tctccggtga actcctgcgt g                            101

<210> SEQ ID NO 571
<211> LENGTH: 101
<212> TYPE: DNA
<213> ORGANISM: Solanum lycopersicum

<400> SEQUENCE: 571
ccggttcaca tttcgtcatt cagctaaatc tctggccaaa gttgacgcca ctcactctcc        60
tttgctcctt ccgatctcaa tctccggtga actcctgcgt g                            101

<210> SEQ ID NO 572
<211> LENGTH: 101
<212> TYPE: DNA
<213> ORGANISM: Solanum lycopersicum

<400> SEQUENCE: 572
accaaataaa caagaaaaaa aatgattttt ggagctcaga agaaagaaga accaaaaggg        60
tcgattcctt ttccttctag aaatgtaaaa acctaattat t                            101

<210> SEQ ID NO 573
<211> LENGTH: 101
<212> TYPE: DNA
<213> ORGANISM: Solanum lycopersicum

<400> SEQUENCE: 573
accaaataaa caagaaaaaa aatgattttt ggagctcaga agaaagaaga gccaaaaggg        60
tcgattcctt ttccttctag aaatgtaaaa acctaattat t                            101

<210> SEQ ID NO 574
<211> LENGTH: 101
<212> TYPE: DNA
<213> ORGANISM: Solanum lycopersicum

<400> SEQUENCE: 574
attggcttgg tctaaatgag ttctctgatt tgagccatga tgagtttaag aaaatgtatt        60
taggactgaa agttgatcaa gagttgctta ataaaagaga g                            101

<210> SEQ ID NO 575
<211> LENGTH: 101
<212> TYPE: DNA
<213> ORGANISM: Solanum lycopersicum
```

-continued

<400> SEQUENCE: 575
attggcttgg tctaaatgag ttctctgatt tgagccatga tgagtttaag gaaatgtatt        60
taggactgaa agttgatcaa gagttgctta ataaaagaga g        101

<210> SEQ ID NO 576
<211> LENGTH: 101
<212> TYPE: DNA
<213> ORGANISM: Solanum lycopersicum

<400> SEQUENCE: 576
aacttgctat taggattgtt ccaagcaggt gcagctgctt ttagaaaaag aaaaacccct        60 cttttcattga ctggttgtga tgactactat cattcgccat a        101

<210> SEQ ID NO 577
<211> LENGTH: 101
<212> TYPE: DNA
<213> ORGANISM: Solanum lycopersicum

<400> SEQUENCE: 577
aacttgctat taggattgtt ccaagcaggt gcagctgctt ttagaaaaag aaaaacccct        60 cttttcattga ctggttgtga tgactactat cattcgccat a        101

<210> SEQ ID NO 578
<211> LENGTH: 101
<212> TYPE: DNA
<213> ORGANISM: Solanum lycopersicum

<400> SEQUENCE: 578
tctggaagac atgttggagg atcgtacgtg tatggttcaa agggattgtc taacagaaaa        60
taactggacg acgggctgca tgagttatca cattgatagg a        101

<210> SEQ ID NO 579
<211> LENGTH: 101
<212> TYPE: DNA
<213> ORGANISM: Solanum lycopersicum

<400> SEQUENCE: 579
tctggaagac atgttggagg atcgtacgtg tatggttcaa agggattgtc gaacagaaaa        60
taactggacg acgggctgca tgagttatca cattgatagg a        101

<210> SEQ ID NO 580
<211> LENGTH: 101
<212> TYPE: DNA
<213> ORGANISM: Solanum lycopersicum

<400> SEQUENCE: 580
agcgatttca gggacgaaga atgctcaaaa caataaggga tgttcttgag atgctggcat        60
cttttcagtt ccaagcgttc aaggcatgga aaggcatcat c        101

<210> SEQ ID NO 581
<211> LENGTH: 101
<212> TYPE: DNA
<213> ORGANISM: Solanum lycopersicum

<400> SEQUENCE: 581
agcgatttca gggacgaaga atgctcaaaa caataaggga tgttcttgag gtgctggcat        60
cttttcagtt ccaagcgttc aaggcatgga aaggcatcat c        101

-continued

```
<210> SEQ ID NO 582
<211> LENGTH: 101
<212> TYPE: DNA
<213> ORGANISM: Solanum lycopersicum

<400> SEQUENCE: 582
cctttggcaa gttatcttac gatagaacag aaaacattgc actgaaagaa ttgccaagat       60
atagatctcc caaaatcagc aatcttctct gcaacttcaa c                          101

<210> SEQ ID NO 583
<211> LENGTH: 101
<212> TYPE: DNA
<213> ORGANISM: Solanum lycopersicum

<400> SEQUENCE: 583
cctttggcaa gttatcttac gatagaacag aaaacattgc actgaaagaa ctgccaagat       60
atagatctcc caaaatcagc aatcttctct gcaacttcaa c                          101

<210> SEQ ID NO 584
<211> LENGTH: 101
<212> TYPE: DNA
<213> ORGANISM: Solanum lycopersicum

<400> SEQUENCE: 584
attcaactat agcatgggtt ggttgtgtgg gcaaaggcag agtccctaac atgagctacg       60
cgtacaagac aacaagttca gtggactaca tgttccgcgt c                          101

<210> SEQ ID NO 585
<211> LENGTH: 101
<212> TYPE: DNA
<213> ORGANISM: Solanum lycopersicum

<400> SEQUENCE: 585
attcaactat agcatgggtt ggttgtgtgg gcaaaggcag agtccctaac gtgagctacg       60
cgtacaagac aacaagttca gtggactaca tgttccgcgt c                          101

<210> SEQ ID NO 586
<211> LENGTH: 101
<212> TYPE: DNA
<213> ORGANISM: Solanum lycopersicum

<400> SEQUENCE: 586
caaaatccca aaattaccct tcctcctaca ccgccctatc ctacacactt atgtcctcat       60
tcgtcttttt acaatctgag tctcactgtc tccaactcac t                          101

<210> SEQ ID NO 587
<211> LENGTH: 101
<212> TYPE: DNA
<213> ORGANISM: Solanum lycopersicum

<400> SEQUENCE: 587
caaaatccca aaattaccct tcctcctaca ccgccctatc ctacacactt gtgtcctcat       60
tcgtcttttt acaatctgag tctcactgtc tccaactcac t                          101

<210> SEQ ID NO 588
<211> LENGTH: 101
<212> TYPE: DNA
<213> ORGANISM: Solanum lycopersicum

<400> SEQUENCE: 588
```

```
attctactac tgttccataa cccattgtgt tcaattggac tcattttgag atccatgaat        60
cgccagagct ttcgattaga tcctcttttt tttctttgtt t                          101

<210> SEQ ID NO 589
<211> LENGTH: 101
<212> TYPE: DNA
<213> ORGANISM: Solanum lycopersicum

<400> SEQUENCE: 589
attctactac tgttccataa cccattgtgt tcaattggac tcattttgag ctccatgaat        60
cgccagagct ttcgattaga tcctcttttt tttctttgtt t                          101

<210> SEQ ID NO 590
<211> LENGTH: 101
<212> TYPE: DNA
<213> ORGANISM: Solanum lycopersicum

<400> SEQUENCE: 590
aatgaagttg aagcaatatc tttcgagaat gatgagattt ctcctgaatc aattgagaaa        60
gttctgtcgt tggatcactt atctatcatt ttgaactctg a                          101

<210> SEQ ID NO 591
<211> LENGTH: 101
<212> TYPE: DNA
<213> ORGANISM: Solanum lycopersicum

<400> SEQUENCE: 591
aatgaagttg aagcaatatc tttcgagaat gatgagattt ctcctgaatc gattgagaaa        60
gttctgtcgt tggatcactt atctatcatt ttgaactctg a                          101

<210> SEQ ID NO 592
<211> LENGTH: 101
<212> TYPE: DNA
<213> ORGANISM: Solanum lycopersicum

<400> SEQUENCE: 592
atttcccgcc aaatcctcat cgatccgatc aaatcgacta ccgtcaccac tggcgcgaac        60
atctctattt ccgtgcggtt gaaaattcca gccgaattcg g                          101

<210> SEQ ID NO 593
<211> LENGTH: 101
<212> TYPE: DNA
<213> ORGANISM: Solanum lycopersicum

<400> SEQUENCE: 593
atttcccgcc aaatcctcat cgatccgatc aaatcgacta ccgtcaccac cggcgcgaac        60
atctctattt ccgtgcggtt gaaaattcca gccgaattcg g                          101

<210> SEQ ID NO 594
<211> LENGTH: 101
<212> TYPE: DNA
<213> ORGANISM: Solanum lycopersicum

<400> SEQUENCE: 594
atgtttcaaa agctgctgct gaagcaagga aaaaatcgaa aattcttcag tcagtggtga        60
gaaacaaaga accttacatt cttgaaacaa atagcagttt a                          101

<210> SEQ ID NO 595
```

```
<211> LENGTH: 101
<212> TYPE: DNA
<213> ORGANISM: Solanum lycopersicum

<400> SEQUENCE: 595
atgtttcaaa agctgctgct gaagcaagga aaaaatcgaa aattcttcag ccagtggtga      60
gaaacaaaga accttacatt cttgaaacaa atagcagttt a                         101

<210> SEQ ID NO 596
<211> LENGTH: 101
<212> TYPE: DNA
<213> ORGANISM: Solanum lycopersicum

<400> SEQUENCE: 596
aaatacgagt ttgcatattt tcgtccatgt ttttaatctt ttcaatgtgc ttgttgtgat      60
atgactttct atgcaatcat tggttcttga gtgaattcac t                        101

<210> SEQ ID NO 597
<211> LENGTH: 101
<212> TYPE: DNA
<213> ORGANISM: Solanum lycopersicum

<400> SEQUENCE: 597
aaatacgagt ttgcatattt tcgtccatgt ttttaatctt ttcaatgtgc ctgttgtgat      60
atgactttct atgcaatcat tggttcttga gtgaattcac t                        101

<210> SEQ ID NO 598
<211> LENGTH: 101
<212> TYPE: DNA
<213> ORGANISM: Solanum lycopersicum

<400> SEQUENCE: 598
atgaccaagt tgtgggtagc tgaagggttt gtacaagcaa acaacgaaaa aggacaagaa      60
gataccgcac aaggtttctt ggacgatctt attggtagga a                        101

<210> SEQ ID NO 599
<211> LENGTH: 101
<212> TYPE: DNA
<213> ORGANISM: Solanum lycopersicum

<400> SEQUENCE: 599
atgaccaagt tgtgggtagc tgaagggttt gtacaagcaa acaacgaaaa tggacaagaa      60
gataccgcac aaggtttctt ggacgatctt attggtagga a                        101

<210> SEQ ID NO 600
<211> LENGTH: 101
<212> TYPE: DNA
<213> ORGANISM: Solanum lycopersicum

<400> SEQUENCE: 600 cagggggcaat gtagcctata tttcctctca ctactgtgct aagatgggtt agatcaagct     60
cgggcattgt cttagatatt ccaaaatcag taatttttgg c                        101

<210> SEQ ID NO 601
<211> LENGTH: 101
<212> TYPE: DNA
<213> ORGANISM: Solanum lycopersicum

<400> SEQUENCE: 601 cagggggcaat gtagcctata tttcctctca ctactgtgct aagatgggtt tgatcaagct     60
```

```
cgggcattgt cttagatatt ccaaaatcag taatttttgg c                          101

<210> SEQ ID NO 602
<211> LENGTH: 101
<212> TYPE: DNA
<213> ORGANISM: Solanum lycopersicum

<400> SEQUENCE: 602
gttaatgcca gtgaaaagtc tacttccact tctcctgtgg atctattagg tttggctaac      60
tatgcgtcag atgatgagga tgacaatgaa atccagagtt c                          101

<210> SEQ ID NO 603
<211> LENGTH: 101
<212> TYPE: DNA
<213> ORGANISM: Solanum lycopersicum

<400> SEQUENCE: 603
gttaatgcca gtgaaaagtc tacttccact tctcctgtgg atctattagg cttggctaac      60
tatgcgtcag atgatgagga tgacaatgaa atccagagtt c                          101

<210> SEQ ID NO 604
<211> LENGTH: 101
<212> TYPE: DNA
<213> ORGANISM: Solanum lycopersicum

<400> SEQUENCE: 604
gagctgctaa ccaaggctcc accatagaag ccccaaatcc atccacaatt tgccttcccc      60
tatgcttctc ttcattaaca atcctcttat ccaaacttga c                          101

<210> SEQ ID NO 605
<211> LENGTH: 101
<212> TYPE: DNA
<213> ORGANISM: Solanum lycopersicum

<400> SEQUENCE: 605
gagctgctaa ccaaggctcc accatagaag ccccaaatcc atccacaatt cgccttcccc      60
tatgcttctc ttcattaaca atcctcttat ccaaacttga c                          101

<210> SEQ ID NO 606
<211> LENGTH: 101
<212> TYPE: DNA
<213> ORGANISM: Solanum lycopersicum

<400> SEQUENCE: 606
cggttattga agaacagttc ttcagcattt tcaaatctgg tggcagaatt tttgcggaga      60
tcatccaagg ggttaaccta aaagcatagc acatttgata g                          101

<210> SEQ ID NO 607
<211> LENGTH: 101
<212> TYPE: DNA
<213> ORGANISM: Solanum lycopersicum

<400> SEQUENCE: 607
cggttattga agaacagttc ttcagcattt tcaaatctgg tggcagaatt cttgcggaga      60
tcatccaagg ggttaaccta aaagcatagc acatttgata g                          101

<210> SEQ ID NO 608
<211> LENGTH: 101
<212> TYPE: DNA
```

-continued

<213> ORGANISM: Solanum lycopersicum

<400> SEQUENCE: 608
tgggatgctt ccaaactatg tcgtctatca tgaattaata gttacatcac acccatttat        60
gcgtaatgta tgtgcagttg agatgcgatg ggttgcacca a        101

<210> SEQ ID NO 609
<211> LENGTH: 101
<212> TYPE: DNA
<213> ORGANISM: Solanum lycopersicum

<400> SEQUENCE: 609
tgggatgctt ccaaactatg tcgtctatca tgaattaata gttacatcac gcccatttat        60
gcgtaatgta tgtgcagttg agatgcgatg ggttgcacca a        101

<210> SEQ ID NO 610
<211> LENGTH: 101
<212> TYPE: DNA
<213> ORGANISM: Solanum lycopersicum

<400> SEQUENCE: 610
atgcctctga gagattctaa ccctggtaat acagcaagta cgactggtta tgcagttcct        60
ggcatgatgc aagtaatagc taccactagt ggagatagac c        101

<210> SEQ ID NO 611
<211> LENGTH: 101
<212> TYPE: DNA
<213> ORGANISM: Solanum lycopersicum

<400> SEQUENCE: 611
atgcctctga gagattctaa ccctggtaat acagcaagta cgactggtta cgcagttcct        60
ggcatgatgc aagtaatagc taccactagt ggagatagac c        101

<210> SEQ ID NO 612
<211> LENGTH: 101
<212> TYPE: DNA
<213> ORGANISM: Solanum lycopersicum

<400> SEQUENCE: 612
tcactttcat agatctcctc aatcgattcg ggaatatctg cttgaaactg tggcccaaca        60
ggtattctct ttctgcgctg cttccaccaa aaaccaattg c        101

<210> SEQ ID NO 613
<211> LENGTH: 101
<212> TYPE: DNA
<213> ORGANISM: Solanum lycopersicum

<400> SEQUENCE: 613
tcactttcat agatctcctc aatcgattcg ggaatatctg cttgaaactg cggcccaaca        60
ggtattctct ttctgcgctg cttccaccaa aaaccaattg c        101

<210> SEQ ID NO 614
<211> LENGTH: 101
<212> TYPE: DNA
<213> ORGANISM: Solanum lycopersicum

<400> SEQUENCE: 614
taataaaatg gatttggaga cgagtgagat ttcaaattac aagtcatcag tagttttgtc        60
taagttggct agtaacgaac aacatggtga aaactcacca t        101

-continued

```
<210> SEQ ID NO 615
<211> LENGTH: 101
<212> TYPE: DNA
<213> ORGANISM: Solanum lycopersicum

<400> SEQUENCE: 615
taataaaatg gatttggaga cgagtgagat ttcaaattac aagtcatcag cagttttgtc      60
taagttggct agtaacgaac aacatggtga aaactcacca t                        101

<210> SEQ ID NO 616
<211> LENGTH: 101
<212> TYPE: DNA
<213> ORGANISM: Solanum lycopersicum

<400> SEQUENCE: 616
gcgattgcaa aatttatgga gaaaacaaga ggtggtaagg ttaagtttga tgctaaacgt      60
gtagtaatgg ctggtggagc tactggagct aatgagactc t                        101

<210> SEQ ID NO 617
<211> LENGTH: 101
<212> TYPE: DNA
<213> ORGANISM: Solanum lycopersicum

<400> SEQUENCE: 617
gcgattgcaa aatttatgga gaaaacaaga ggtggtaagg ttaagtttga cgctaaacgt      60
gtagtaatgg ctggtggagc tactggagct aatgagactc t                        101

<210> SEQ ID NO 618
<211> LENGTH: 101
<212> TYPE: DNA
<213> ORGANISM: Solanum lycopersicum

<400> SEQUENCE: 618
ctgcgttcta tgcacttcct tcatcacatt gttgtgcaac atcgctaaac acagttggat      60
taatgcaaca ttttcgaaga aaagccaaca actcctcttt a                        101

<210> SEQ ID NO 619
<211> LENGTH: 101
<212> TYPE: DNA
<213> ORGANISM: Solanum lycopersicum

<400> SEQUENCE: 619
ctgcgttcta tgcacttcct tcatcacatt gttgtgcaac atcgctaaac tcagttggat      60
taatgcaaca ttttcgaaga aaagccaaca actcctcttt a                        101

<210> SEQ ID NO 620
<211> LENGTH: 101
<212> TYPE: DNA
<213> ORGANISM: Solanum lycopersicum

<400> SEQUENCE: 620
taaggtttcc agacaattgt ggtctcagca atcatggatg taacagtgta aggatccatg      60
ttcgaagcag gcctcctgtc ctcgaaatat cccttccctg c                        101

<210> SEQ ID NO 621
<211> LENGTH: 101
<212> TYPE: DNA
<213> ORGANISM: Solanum lycopersicum
```

-continued

```
<400> SEQUENCE: 621
taaggtttcc agacaattgt ggtctcagca atcatggatg taacagtgta gggatccatg      60
ttcgaagcag gcctcctgtc ctcgaaatat cccttccctg c                          101

<210> SEQ ID NO 622
<211> LENGTH: 101
<212> TYPE: DNA
<213> ORGANISM: Solanum lycopersicum

<400> SEQUENCE: 622
ttactatgca atttcaagaa aagggttcat gaactagaag ctgaagtagc aaatagacga      60
ttaacggagt ccaaaatatt cgattcgttg gcctcacaga c                          101

<210> SEQ ID NO 623
<211> LENGTH: 101
<212> TYPE: DNA
<213> ORGANISM: Solanum lycopersicum

<400> SEQUENCE: 623
ttactatgca atttcaagaa aagggttcat gaactagaag ctgaagtagc gaatagacga      60
ttaacggagt ccaaaatatt cgattcgttg gcctcacaga c                          101

<210> SEQ ID NO 624
<211> LENGTH: 101
<212> TYPE: DNA
<213> ORGANISM: Solanum lycopersicum

<400> SEQUENCE: 624
aattcaattg gtcttgtttg tttggcccaa taggccaatg tggagtgtta atataattgg      60
agattcgggg ttttttcttc ttcttttcaa ttgtggggga t                          101

<210> SEQ ID NO 625
<211> LENGTH: 101
<212> TYPE: DNA
<213> ORGANISM: Solanum lycopersicum

<400> SEQUENCE: 625
aattcaattg gtcttgtttg tttggcccaa taggccaatg tggagtgtta ctataattgg      60
agattcgggg ttttttcttc ttcttttcaa ttgtggggga t                          101

<210> SEQ ID NO 626
<211> LENGTH: 101
<212> TYPE: DNA
<213> ORGANISM: Solanum lycopersicum

<400> SEQUENCE: 626
caaagttatc ctcccggagt gcaatctcat aatagtgctc ctgttcaatc tcttcctagt      60
tatgcctatg gcaattccgt cgctgcaatg ccaccccata c                          101

<210> SEQ ID NO 627
<211> LENGTH: 101
<212> TYPE: DNA
<213> ORGANISM: Solanum lycopersicum

<400> SEQUENCE: 627
caaagttatc ctcccggagt gcaatctcat aatagtgctc ctgttcaatc gcttcctagt      60
tatgcctatg gcaattccgt cgctgcaatg ccaccccata c                          101
```

-continued

```
<210> SEQ ID NO 628
<211> LENGTH: 101
<212> TYPE: DNA
<213> ORGANISM: Solanum lycopersicum

<400> SEQUENCE: 628
ctaattccct gtttaactga aaaatgggga gatttaccac taaaagtcga tgattccgaa        60
gatatggtaa tttacggtct attaaaagac gctctaagcg t                          101

<210> SEQ ID NO 629
<211> LENGTH: 101
<212> TYPE: DNA
<213> ORGANISM: Solanum lycopersicum

<400> SEQUENCE: 629
ctaattccct gtttaactga aaaatgggga gatttaccac taaaagtcga cgattccgaa        60
gatatggtaa tttacggtct attaaaagac gctctaagcg t                          101

<210> SEQ ID NO 630
<211> LENGTH: 101
<212> TYPE: DNA
<213> ORGANISM: Solanum lycopersicum

<400> SEQUENCE: 630
tcggatgtta tcagtgtgtg tacagtaaaa cctctggtct tatgtgtact atggagtatc        60
attgtaatag cagtacaagc tttgaaatgg actctacttg t                          101

<210> SEQ ID NO 631
<211> LENGTH: 101
<212> TYPE: DNA
<213> ORGANISM: Solanum lycopersicum

<400> SEQUENCE: 631
tcggatgtta tcagtgtgtg tacagtaaaa cctctggtct tatgtgtact gtggagtatc        60
attgtaatag cagtacaagc tttgaaatgg actctacttg t                          101

<210> SEQ ID NO 632
<211> LENGTH: 101
<212> TYPE: DNA
<213> ORGANISM: Solanum lycopersicum

<400> SEQUENCE: 632
tacactttgt gctattttca gatgaaattt atgatgcatg ggtgacagca acgaatgaac        60
agttgaattg attagtatgt ttacgagtat ttgcaagacg g                          101

<210> SEQ ID NO 633
<211> LENGTH: 101
<212> TYPE: DNA
<213> ORGANISM: Solanum lycopersicum

<400> SEQUENCE: 633
tacactttgt gctattttca gatgaaattt atgatgcatg ggtgacagca gcgaatgaac        60
agttgaattg attagtatgt ttacgagtat ttgcaagacg g                          101

<210> SEQ ID NO 634
<211> LENGTH: 101
<212> TYPE: DNA
<213> ORGANISM: Solanum lycopersicum

<400> SEQUENCE: 634
```

-continued

```
taataaacct tagcaaagtt gccttgacct aataatctcc ccaaatcgta tttttccatc      60
agtacatttc cttttttctc catttgaacc aacaattctt g                        101

<210> SEQ ID NO 635
<211> LENGTH: 101
<212> TYPE: DNA
<213> ORGANISM: Solanum lycopersicum

<400> SEQUENCE: 635
taataaacct tagcaaagtt gccttgacct aataatctcc ccaaatcgta cttttccatc      60
agtacatttc cttttttctc catttgaacc aacaattctt g                        101

<210> SEQ ID NO 636
<211> LENGTH: 101
<212> TYPE: DNA
<213> ORGANISM: Solanum lycopersicum

<400> SEQUENCE: 636
caattttaac tcaataacag gaaatcacac ctaatccagg acacgacgct tgttcagatg      60
tatctacgga ataatagcaa ccacagataa cacgacccca a                        101

<210> SEQ ID NO 637
<211> LENGTH: 101
<212> TYPE: DNA
<213> ORGANISM: Solanum lycopersicum

<400> SEQUENCE: 637
caattttaac tcaataacag gaaatcacac ctaatccagg acacgacgct cgttcagatg      60
tatctacgga ataatagcaa ccacagataa cacgacccca a                        101

<210> SEQ ID NO 638
<211> LENGTH: 101
<212> TYPE: DNA
<213> ORGANISM: Solanum lycopersicum

<400> SEQUENCE: 638
ggccctagca aattattcgc catctccctt agcacatgct tcagttcatt cccatcatta      60
attactgaac acccgctcaa aggtgaacca taagtgttgt c                        101

<210> SEQ ID NO 639
<211> LENGTH: 101
<212> TYPE: DNA
<213> ORGANISM: Solanum lycopersicum

<400> SEQUENCE: 639
ggccctagca aattattcgc catctccctt agcacatgct tcagttcatt gccatcatta      60
attactgaac acccgctcaa aggtgaacca taagtgttgt c                        101

<210> SEQ ID NO 640
<211> LENGTH: 101
<212> TYPE: DNA
<213> ORGANISM: Solanum lycopersicum

<400> SEQUENCE: 640
aaattccggt tttgtatacc gatgatgaaa acactctagc taggtgtgtt atggggttta      60
aacttttttg gggtatttga tgtccattgt tgattttgaa c                        101

<210> SEQ ID NO 641
<211> LENGTH: 101
```

```
<212> TYPE: DNA
<213> ORGANISM: Solanum lycopersicum

<400> SEQUENCE: 641
aaattccggt tttgtatacc gatgatgaaa acactctagc taggtgtgtt gtggggttta      60 aactttttg gggtatttga tgtccattgt tgattttgaa c                         101

<210> SEQ ID NO 642
<211> LENGTH: 101
<212> TYPE: DNA
<213> ORGANISM: Solanum lycopersicum

<400> SEQUENCE: 642
tactctgttg aacctgctga aagcaggagg cctttccgtg ctctcttgga tgtcggcctc      60
ttaagaacta ctacagggaa ccgtgttttt ggtgctctca a                        101

<210> SEQ ID NO 643
<211> LENGTH: 101
<212> TYPE: DNA
<213> ORGANISM: Solanum lycopersicum

<400> SEQUENCE: 643
tactctgttg aacctgctga aagcaggagg cctttccgtg ctctcttgga cgtcggcctc      60
ttaagaacta ctacagggaa ccgtgttttt ggtgctctca a                        101

<210> SEQ ID NO 644
<211> LENGTH: 101
<212> TYPE: DNA
<213> ORGANISM: Solanum lycopersicum

<400> SEQUENCE: 644
atatagatct gtgtgaaagg catcatatgt tagctctctg ttattacgga aaaggagata      60
atttcaccgc cttgaacttg ttgcggaaac tattgagtag t                        101

<210> SEQ ID NO 645
<211> LENGTH: 101
<212> TYPE: DNA
<213> ORGANISM: Solanum lycopersicum

<400> SEQUENCE: 645
atatagatct gtgtgaaagg catcatatgt tagctctctg ttattacgga gaaggagata      60
atttcaccgc cttgaacttg ttgcggaaac tattgagtag t                        101

<210> SEQ ID NO 646
<211> LENGTH: 101
<212> TYPE: DNA
<213> ORGANISM: Solanum lycopersicum

<400> SEQUENCE: 646
cggcgaaatt ccagtagaca ttcagggtct gagtaatttg agagcattga acttggggag      60
aaataagttc atgggtgaaa ttccagatga aattggaggt t                        101

<210> SEQ ID NO 647
<211> LENGTH: 101
<212> TYPE: DNA
<213> ORGANISM: Solanum lycopersicum

<400> SEQUENCE: 647
cggcgaaatt ccagtagaca ttcagggtct gagtaatttg agagcattga gcttggggag      60
```

```
aaataagttc atgggtgaaa ttccagatga aattggaggt t                    101

<210> SEQ ID NO 648
<211> LENGTH: 101
<212> TYPE: DNA
<213> ORGANISM: Solanum lycopersicum

<400> SEQUENCE: 648
acaatacatg agaggaacaa attaagtaag atcatcttcc tcaagctcct tcgccttcaa     60
tgtttccttg actcttagaa gtagtgttgt cctccaagca t                    101

<210> SEQ ID NO 649
<211> LENGTH: 101
<212> TYPE: DNA
<213> ORGANISM: Solanum lycopersicum

<400> SEQUENCE: 649
acaatacatg agaggaacaa attaagtaag atcatcttcc tcaagctcct ccgccttcaa     60
tgtttccttg actcttagaa gtagtgttgt cctccaagca t                    101

<210> SEQ ID NO 650
<211> LENGTH: 101
<212> TYPE: DNA
<213> ORGANISM: Solanum lycopersicum

<400> SEQUENCE: 650
ataagtgtcc acttgaccat aatgcccttg tgagatgggt gtggaggatg agtcccacat     60
gttcaagggc ataggttggt gatgctgatg aggtggacca a                    101

<210> SEQ ID NO 651
<211> LENGTH: 101
<212> TYPE: DNA
<213> ORGANISM: Solanum lycopersicum

<400> SEQUENCE: 651
ataagtgtcc acttgaccat aatgcccttg tgagatgggt gtggaggatg ggtcccacat     60
gttcaagggc ataggttggt gatgctgatg aggtggacca a                    101

<210> SEQ ID NO 652
<211> LENGTH: 101
<212> TYPE: DNA
<213> ORGANISM: Solanum lycopersicum

<400> SEQUENCE: 652
cccattcttt gtttctacac acaattcaaa atccctcct ccctctcttt tccccccttt     60
gaactctgca gccgtacgcc actctcattt tcctgcgaat t                    101

<210> SEQ ID NO 653
<211> LENGTH: 101
<212> TYPE: DNA
<213> ORGANISM: Solanum lycopersicum

<400> SEQUENCE: 653
cccattcttt gtttctacac acaattcaaa atccctcct ccctctcttt ccccccttt     60 gaactctgca gccgtacgcc actctcattt tcctgcgaat t                    101

<210> SEQ ID NO 654
<211> LENGTH: 101
<212> TYPE: DNA
<213> ORGANISM: Solanum lycopersicum
```

<400> SEQUENCE: 654
cagtaaaaat gcttgcaaag ggcagaagac ctcccaccag agaaataaca tatggtctta      60
ggtaccattt cttctcaggg ataggacgcg gaatattctt a                         101

<210> SEQ ID NO 655
<211> LENGTH: 101
<212> TYPE: DNA
<213> ORGANISM: Solanum lycopersicum

<400> SEQUENCE: 655
cagtaaaaat gcttgcaaag ggcagaagac ctcccaccag agaaataaca gatggtctta      60
ggtaccattt cttctcaggg ataggacgcg gaatattctt a                         101

<210> SEQ ID NO 656
<211> LENGTH: 101
<212> TYPE: DNA
<213> ORGANISM: Solanum lycopersicum

<400> SEQUENCE: 656
atcatctttc ttctccggat tgggagaaaa tacccctgct gtaacaagtg tggtaagtac      60
aagagaaatg gcgaaaacat tcatcatctt ttccaattag t                         101

<210> SEQ ID NO 657
<211> LENGTH: 101
<212> TYPE: DNA
<213> ORGANISM: Solanum lycopersicum

<400> SEQUENCE: 657
atcatctttc ttctccggat tgggagaaaa tacccctgct gtaacaagtg cggtaagtac      60
aagagaaatg gcgaaaacat tcatcatctt ttccaattag t                         101

<210> SEQ ID NO 658
<211> LENGTH: 101
<212> TYPE: DNA
<213> ORGANISM: Solanum lycopersicum

<400> SEQUENCE: 658
tgggtgctca atggtcagat gaccatctga gtgtgagaaa tatgcactcc ttcacaagca      60
gcaggcctat cagagtgctg ctcatgcgtg gttcagcaga g                         101

<210> SEQ ID NO 659
<211> LENGTH: 101
<212> TYPE: DNA
<213> ORGANISM: Solanum lycopersicum

<400> SEQUENCE: 659
tgggtgctca atggtcagat gaccatctga gtgtgagaaa tatgcactcc gtcacaagca      60
gcaggcctat cagagtgctg ctcatgcgtg gttcagcaga g                         101

<210> SEQ ID NO 660
<211> LENGTH: 101
<212> TYPE: DNA
<213> ORGANISM: Solanum lycopersicum

<400> SEQUENCE: 660
gtgcattttt tccatgatgg acaaggtttc atgtctgttg agttgacacc aacagaggct      60
gagatcaaat attatgatgt ttttggtaga attagacata g                         101

<210> SEQ ID NO 661
<211> LENGTH: 101
<212> TYPE: DNA
<213> ORGANISM: Solanum lycopersicum

<400> SEQUENCE: 661
gtgcattttt tccatgatgg acaaggtttc atgtctgttg agttgacacc gacagaggct     60
gagatcaaat attatgatgt ttttggtaga attagacata g                        101

<210> SEQ ID NO 662
<211> LENGTH: 101
<212> TYPE: DNA
<213> ORGANISM: Solanum lycopersicum

<400> SEQUENCE: 662
agttaattct tgtgctgctt gctatatttt gaggcctgtt ggacgcaaca aactagtaaa     60
ataggatctt agtcatgtat tgcctcaaga atttgtgttt c                        101

<210> SEQ ID NO 663
<211> LENGTH: 101
<212> TYPE: DNA
<213> ORGANISM: Solanum lycopersicum

<400> SEQUENCE: 663
agttaattct tgtgctgctt gctatatttt gaggcctgtt ggacgcaaca tactagtaaa     60
ataggatctt agtcatgtat tgcctcaaga atttgtgttt c                        101

<210> SEQ ID NO 664
<211> LENGTH: 101
<212> TYPE: DNA
<213> ORGANISM: Solanum lycopersicum

<400> SEQUENCE: 664
ggcccggata agattagtaa aatatatggc gactggattg atgacatcga atgaaggagt     60
tgtcataatt agctactgat ctgtttagct agacacaaat a                        101

<210> SEQ ID NO 665
<211> LENGTH: 101
<212> TYPE: DNA
<213> ORGANISM: Solanum lycopersicum

<400> SEQUENCE: 665
ggcccggata agattagtaa aatatatggc gactggattg atgacatcga gtgaaggagt     60
tgtcataatt agctactgat ctgtttagct agacacaaat a                        101

<210> SEQ ID NO 666
<211> LENGTH: 101
<212> TYPE: DNA
<213> ORGANISM: Solanum lycopersicum

<400> SEQUENCE: 666
ggtcggaagc aattgatggg gcaagaatcg gtcggaaatg gagttctagg acatttatct     60
tcgtcgtctt gatgagaagg tagtggattt aaaccgttta a                        101

<210> SEQ ID NO 667
<211> LENGTH: 101
<212> TYPE: DNA
<213> ORGANISM: Solanum lycopersicum

<400> SEQUENCE: 667

-continued

```
ggtcggaagc aattgatggg gcaagaatcg gtcggaaatg gagttctagg gcatttatct        60
tcgtcgtctt gatgagaagg tagtggattt aaaccgttta a                           101

<210> SEQ ID NO 668
<211> LENGTH: 101
<212> TYPE: DNA
<213> ORGANISM: Solanum lycopersicum

<400> SEQUENCE: 668
tatgtagcta ggaagagagt tgaaaagacc tagcttacaa aagatggggg aaaaaagggg        60
gagatgataa ataaggtata agtttttgag agatgaatga a                           101

<210> SEQ ID NO 669
<211> LENGTH: 101
<212> TYPE: DNA
<213> ORGANISM: Solanum lycopersicum

<400> SEQUENCE: 669
tatgtagcta ggaagagagt tgaaaagacc tagcttacaa aagatggggg gaaaaagggg        60
gagatgataa ataaggtata agtttttgag agatgaatga a                           101

<210> SEQ ID NO 670
<211> LENGTH: 101
<212> TYPE: DNA
<213> ORGANISM: Solanum lycopersicum

<400> SEQUENCE: 670
caacacctgt acaggataca tctgcagaag aattgttgtc cagaaagatg acaggcaata        60
ggttggcaga atctttatgg ccctcaacaa tgaggagtct g                           101

<210> SEQ ID NO 671
<211> LENGTH: 101
<212> TYPE: DNA
<213> ORGANISM: Solanum lycopersicum

<400> SEQUENCE: 671
caacacctgt acaggataca tctgcagaag aattgttgtc cagaaagatg gcaggcaata        60
ggttggcaga atctttatgg ccctcaacaa tgaggagtct g                           101

<210> SEQ ID NO 672
<211> LENGTH: 101
<212> TYPE: DNA
<213> ORGANISM: Solanum lycopersicum

<400> SEQUENCE: 672
gtctcctatg ctcttcctgt ctcctttgtt tcaagtggta tcatgcgttc agagacagaa        60
gttgaggaga aatcaatcga aacaacccag acaaccacca t                           101

<210> SEQ ID NO 673
<211> LENGTH: 101
<212> TYPE: DNA
<213> ORGANISM: Solanum lycopersicum

<400> SEQUENCE: 673
gtctcctatg ctcttcctgt ctcctttgtt tcaagtggta tcatgcgttc ggagacagaa        60
gttgaggaga aatcaatcga aacaacccag acaaccacca t                           101

<210> SEQ ID NO 674
```

-continued

```
<211> LENGTH: 101
<212> TYPE: DNA
<213> ORGANISM: Solanum lycopersicum

<400> SEQUENCE: 674
atctcaggaa cttctctaaa gaacgtatct tgtcttccag gatttgcatg atctcaccag      60
gaagtcggca gacaactact acattgtcaa atgcttctga a                        101

<210> SEQ ID NO 675
<211> LENGTH: 101
<212> TYPE: DNA
<213> ORGANISM: Solanum lycopersicum

<400> SEQUENCE: 675
atctcaggaa cttctctaaa gaacgtatct tgtcttccag gatttgcatg gtctcaccag      60
gaagtcggca gacaactact acattgtcaa atgcttctga a                        101

<210> SEQ ID NO 676
<211> LENGTH: 101
<212> TYPE: DNA
<213> ORGANISM: Solanum lycopersicum

<400> SEQUENCE: 676
gacagctcca cttgcagcag aaagtgtgac tccaacaaag cgaaacagaa aatcttcagc      60
ttctaagaag gacgtgaaag acaaaaaaga acaggaagaa a                        101

<210> SEQ ID NO 677
<211> LENGTH: 101
<212> TYPE: DNA
<213> ORGANISM: Solanum lycopersicum

<400> SEQUENCE: 677
gacagctcca cttgcagcag aaagtgtgac tccaacaaag cgaaacagaa gatcttcagc      60
ttctaagaag gacgtgaaag acaaaaaaga acaggaagaa a                        101

<210> SEQ ID NO 678
<211> LENGTH: 101
<212> TYPE: DNA
<213> ORGANISM: Solanum lycopersicum

<400> SEQUENCE: 678
catgaagttg ggatacacga atgcatataa agcttttgat ccaagtcgat caaaatcttg      60
gtccttcccc gcactaccag tttcacatcg ttggatgctg a                        101

<210> SEQ ID NO 679
<211> LENGTH: 101
<212> TYPE: DNA
<213> ORGANISM: Solanum lycopersicum

<400> SEQUENCE: 679
catgaagttg ggatacacga atgcatataa agcttttgat ccaagtcgat gaaaatcttg      60
gtccttcccc gcactaccag tttcacatcg ttggatgctg a                        101

<210> SEQ ID NO 680
<211> LENGTH: 101
<212> TYPE: DNA
<213> ORGANISM: Solanum lycopersicum

<400> SEQUENCE: 680
tcttttgtca gaaggaatca actcgggggt tgatggagcc agaagcatct agtggtggtt      60
```

-continued

```
agctaggctg ttaatcatcc aacaaaagtt gttagatgat c                         101

<210> SEQ ID NO 681
<211> LENGTH: 101
<212> TYPE: DNA
<213> ORGANISM: Solanum lycopersicum

<400> SEQUENCE: 681
tcttttgtca gaaggaatca actcgggggt tgatggagcc agaagcatct cgtggtggtt      60
agctaggctg ttaatcatcc aacaaaagtt gttagatgat c                         101

<210> SEQ ID NO 682
<211> LENGTH: 101
<212> TYPE: DNA
<213> ORGANISM: Solanum lycopersicum

<400> SEQUENCE: 682
ctactctttc acaatacatt caagtggtga agttcacata gtgtgcctca tcacttttat      60
tcatgctaca tgcattactt aattttattc ataagttaca c                         101

<210> SEQ ID NO 683
<211> LENGTH: 101
<212> TYPE: DNA
<213> ORGANISM: Solanum lycopersicum

<400> SEQUENCE: 683
ctactctttc acaatacatt caagtggtga agttcacata gtgtgcctca ccacttttat      60
tcatgctaca tgcattactt aattttattc ataagttaca c                         101

<210> SEQ ID NO 684
<211> LENGTH: 101
<212> TYPE: DNA
<213> ORGANISM: Solanum lycopersicum

<400> SEQUENCE: 684
accttcctcc atgccacaaa gttcccagaa cctccaccac gataagttct agtatcacag      60
aagtcgaagt tgaagaaata actattttgg gagcttattg g                         101

<210> SEQ ID NO 685
<211> LENGTH: 101
<212> TYPE: DNA
<213> ORGANISM: Solanum lycopersicum

<400> SEQUENCE: 685
accttcctcc atgccacaaa gttcccagaa cctccaccac gataagttct ggtatcacag      60
aagtcgaagt tgaagaaata actattttgg gagcttattg g                         101

<210> SEQ ID NO 686
<211> LENGTH: 101
<212> TYPE: DNA
<213> ORGANISM: Solanum lycopersicum

<400> SEQUENCE: 686
ttgatcttta accctgcaac cgaagctatt gactgtgaaa acttcaccaa caagcatttg      60
atcaatgacc tcctccctct tcgacccagt caacttgtgc a                         101

<210> SEQ ID NO 687
<211> LENGTH: 101
<212> TYPE: DNA
```

-continued

<213> ORGANISM: Solanum lycopersicum

<400> SEQUENCE: 687
ttgatcttta acccctgcaac cgaagctatt gactgtgaaa acttcaccaa gaagcatttg      60
atcaatgacc tcctccctct tcgacccagt caacttgtgc a                          101

<210> SEQ ID NO 688
<211> LENGTH: 101
<212> TYPE: DNA
<213> ORGANISM: Solanum lycopersicum

<400> SEQUENCE: 688
cctgaagaag ctgtttcgac tgatactatt aatggtgggg ggcagaaccc agttttcgat      60
cagagtcttc gacttaatgt caagactatt gaaacatcag t                          101

<210> SEQ ID NO 689
<211> LENGTH: 101
<212> TYPE: DNA
<213> ORGANISM: Solanum lycopersicum

<400> SEQUENCE: 689
cctgaagaag ctgtttcgac tgatactatt aatggtgggg ggcagaaccc ggttttcgat      60
cagagtcttc gacttaatgt caagactatt gaaacatcag t                          101

<210> SEQ ID NO 690
<211> LENGTH: 101
<212> TYPE: DNA
<213> ORGANISM: Solanum lycopersicum

<400> SEQUENCE: 690
cactccgaaa ctttgtcaga acagggaagt gtcaaatcaa ttgggactac tccggtaacc      60
caactgccca ggctgcacaa gaatgtcagc gactcaatgt t                          101

<210> SEQ ID NO 691
<211> LENGTH: 101
<212> TYPE: DNA
<213> ORGANISM: Solanum lycopersicum

<400> SEQUENCE: 691
cactccgaaa ctttgtcaga acagggaagt gtcaaatcaa ttgggactac cccggtaacc      60
caactgccca ggctgcacaa gaatgtcagc gactcaatgt t                          101

<210> SEQ ID NO 692
<211> LENGTH: 101
<212> TYPE: DNA
<213> ORGANISM: Solanum lycopersicum

<400> SEQUENCE: 692
tcaggctgga ttcttggttt attcgaagcg gttagtcaca gtaagataag ttttgttgta      60
taagcggtgg gtaaagcggt tgtcggtttg ctgaacatgc c                          101

<210> SEQ ID NO 693
<211> LENGTH: 101
<212> TYPE: DNA
<213> ORGANISM: Solanum lycopersicum

<400> SEQUENCE: 693
tcaggctgga ttcttggttt attcgaagcg gttagtcaca gtaagataag ctttgttgta      60
taagcggtgg gtaaagcggt tgtcggtttg ctgaacatgc c                          101

-continued

<210> SEQ ID NO 694
<211> LENGTH: 101
<212> TYPE: DNA
<213> ORGANISM: Solanum lycopersicum

<400> SEQUENCE: 694
caactttaag tcgaggatga agggtggtgg tgatttggct gttgcatcta ttacgaatgg      60
aaaagataga tatgttccgt ttgatgtgga gaacggttct a                        101

<210> SEQ ID NO 695
<211> LENGTH: 101
<212> TYPE: DNA
<213> ORGANISM: Solanum lycopersicum

<400> SEQUENCE: 695
caactttaag tcgaggatga agggtggtgg tgatttggct gttgcatcta ctacgaatgg      60
aaaagataga tatgttccgt ttgatgtgga gaacggttct a                        101

<210> SEQ ID NO 696
<211> LENGTH: 101
<212> TYPE: DNA
<213> ORGANISM: Solanum lycopersicum

<400> SEQUENCE: 696
gtgaggctac tgtcgggtta cccggtgggt gtgacattgg ggcccgaccc attgattttt      60
acattcatgg tctacgtgct cttggtgcta cggttgagtt g                        101

<210> SEQ ID NO 697
<211> LENGTH: 101
<212> TYPE: DNA
<213> ORGANISM: Solanum lycopersicum

<400> SEQUENCE: 697
gtgaggctac tgtcgggtta cccggtgggt gtgacattgg ggcccgaccc gttgattttt      60
acattcatgg tctacgtgct cttggtgcta cggttgagtt g                        101

<210> SEQ ID NO 698
<211> LENGTH: 101
<212> TYPE: DNA
<213> ORGANISM: Solanum lycopersicum

<400> SEQUENCE: 698
cagacgacaa tactgttgga ccaacttgca ttttcgggat cacctttgtc tggcaagcaa      60 cctttctga aacttgctta ggtgattttc ttcttccctg t                        101

<210> SEQ ID NO 699
<211> LENGTH: 101
<212> TYPE: DNA
<213> ORGANISM: Solanum lycopersicum

<400> SEQUENCE: 699
cagacgacaa tactgttgga ccaacttgca ttttcgggat cacctttgtc cggcaagcaa      60 cctttctga aacttgctta ggtgattttc ttcttccctg t                        101

<210> SEQ ID NO 700
<211> LENGTH: 101
<212> TYPE: DNA
<213> ORGANISM: Solanum lycopersicum

<400> SEQUENCE: 700
caaaaagttt tcaaaccgtg tgatttctgg tgaacctgat ccagatcgtc atgtagttgc    60
accaatcaag tcagacaaaa agttttcata cccagatctt c                        101

<210> SEQ ID NO 701
<211> LENGTH: 101
<212> TYPE: DNA
<213> ORGANISM: Solanum lycopersicum

<400> SEQUENCE: 701
caaaaagttt tcaaaccgtg tgatttctgg tgaacctgat ccagatcgtc ctgtagttgc    60
accaatcaag tcagacaaaa agttttcata cccagatctt c                        101

<210> SEQ ID NO 702
<211> LENGTH: 101
<212> TYPE: DNA
<213> ORGANISM: Solanum lycopersicum

<400> SEQUENCE: 702
cggtggcggc aacagcggag gagaatcggc gtggtaggga gggtttgaag attgggttta    60
ccgttttgag tgatgaaggt tttggaattc gcggaagcag a                        101

<210> SEQ ID NO 703
<211> LENGTH: 101
<212> TYPE: DNA
<213> ORGANISM: Solanum lycopersicum

<400> SEQUENCE: 703
cggtggcggc aacagcggag gagaatcggc gtggtaggga gggtttgaag gttgggttta    60
ccgttttgag tgatgaaggt tttggaattc gcggaagcag a                        101

<210> SEQ ID NO 704
<211> LENGTH: 101
<212> TYPE: DNA
<213> ORGANISM: Solanum lycopersicum

<400> SEQUENCE: 704
gagttttttt tgcggagttg aacgaagtgc ttacaagaga gttggcggag aatggttact    60
cgggagttga agttagggtt actcccgtgc gaactgaaat c                        101

<210> SEQ ID NO 705
<211> LENGTH: 101
<212> TYPE: DNA
<213> ORGANISM: Solanum lycopersicum

<400> SEQUENCE: 705
gagttttttt tgcggagttg aacgaagtgc ttacaagaga gttggcggag gatggttact    60
cgggagttga agttagggtt actcccgtgc gaactgaaat c                        101

<210> SEQ ID NO 706
<211> LENGTH: 101
<212> TYPE: DNA
<213> ORGANISM: Solanum lycopersicum

<400> SEQUENCE: 706
aacaaaactt gaagagcaat ttaaggaagt gaagttggaa gaaagagcag tccgtaggga    60
agccagaagg aagatgtatg gttggtcacc aaaatcagag g                        101

-continued

<210> SEQ ID NO 707
<211> LENGTH: 101
<212> TYPE: DNA
<213> ORGANISM: Solanum lycopersicum

<400> SEQUENCE: 707
aacaaaactt gaagagcaat ttaaggaagt gaagttggaa gaaagagcag cccgtaggga      60
agccagaagg aagatgtatg gttggtcacc aaaatcagag g                         101

<210> SEQ ID NO 708
<211> LENGTH: 101
<212> TYPE: DNA
<213> ORGANISM: Solanum lycopersicum

<400> SEQUENCE: 708
caggaccaag tctccgatct ttctggatta aacgggaaac tgcatccata acctcattac      60
taatgtcaag aggcttagat gcagcccgaa cacttgggat a                         101

<210> SEQ ID NO 709
<211> LENGTH: 101
<212> TYPE: DNA
<213> ORGANISM: Solanum lycopersicum

<400> SEQUENCE: 709
caggaccaag tctccgatct ttctggatta aacgggaaac tgcatccata gcctcattac      60
taatgtcaag aggcttagat gcagcccgaa cacttgggat a                         101

<210> SEQ ID NO 710
<211> LENGTH: 101
<212> TYPE: DNA
<213> ORGANISM: Solanum lycopersicum

<400> SEQUENCE: 710
tctgtcatgc gttaatcgtg ttaacatttc ctttaaggta tgacgatgag ttctggcatc      60
cgatttacat gcccggactg tttttgatg gcaaagtttc t                          101

<210> SEQ ID NO 711
<211> LENGTH: 101
<212> TYPE: DNA
<213> ORGANISM: Solanum lycopersicum

<400> SEQUENCE: 711
tctgtcatgc gttaatcgtg ttaacatttc ctttaaggta tgacgatgag ctctggcatc      60
cgatttacat gcccggactg tttttgatg gcaaagtttc t                          101

<210> SEQ ID NO 712
<211> LENGTH: 101
<212> TYPE: DNA
<213> ORGANISM: Solanum lycopersicum

<400> SEQUENCE: 712
catattagta aaggcctaat ggaagggaca cgataaactt gctcctcaat tagctcgttg      60
cctgttgtgg ttccaagttg gtccctggtt gtctcagtct c                         101

<210> SEQ ID NO 713
<211> LENGTH: 101
<212> TYPE: DNA
<213> ORGANISM: Solanum lycopersicum

<400> SEQUENCE: 713

-continued

```
catattagta aaggcctaat ggaagggaca cgataaactt gctcctcaat cagctcgttg      60
cctgttgtgg ttccaagttg gtccctggtt gtctcagtct c                        101

<210> SEQ ID NO 714
<211> LENGTH: 101
<212> TYPE: DNA
<213> ORGANISM: Solanum lycopersicum

<400> SEQUENCE: 714
ttaataggtg ctactccgag gttcttcggt aggtattgct tgctagagga taaactcgaa      60
cggattaaaa tttattgcta caggcgctgt gcgtctatgt t                        101

<210> SEQ ID NO 715
<211> LENGTH: 101
<212> TYPE: DNA
<213> ORGANISM: Solanum lycopersicum

<400> SEQUENCE: 715
ttaataggtg ctactccgag gttcttcggt aggtattgct tgctagagga caaactcgaa      60
cggattaaaa tttattgcta caggcgctgt gcgtctatgt t                        101

<210> SEQ ID NO 716
<211> LENGTH: 101
<212> TYPE: DNA
<213> ORGANISM: Solanum lycopersicum

<400> SEQUENCE: 716
ccatccgcta aatccaaaaa tttcgttgaa tattaggtta cctgcaaaaa agcaaaaggc      60
aacccatctg aatcccttcg cggaactttc tatatttggt a                        101

<210> SEQ ID NO 717
<211> LENGTH: 101
<212> TYPE: DNA
<213> ORGANISM: Solanum lycopersicum

<400> SEQUENCE: 717
ccatccgcta aatccaaaaa tttcgttgaa tattaggtta cctgcaaaaa ggcaaaaggc      60
aacccatctg aatcccttcg cggaactttc tatatttggt a                        101

<210> SEQ ID NO 718
<211> LENGTH: 101
<212> TYPE: DNA
<213> ORGANISM: Solanum lycopersicum

<400> SEQUENCE: 718
tcatcgacta attcaaattc acgctccttg cctcagtcac attaaggact aggccggtgt      60
cgatccgcaa atcgattaac caaagcaagt gcattactag t                        101

<210> SEQ ID NO 719
<211> LENGTH: 101
<212> TYPE: DNA
<213> ORGANISM: Solanum lycopersicum

<400> SEQUENCE: 719
tcatcgacta attcaaattc acgctccttg cctcagtcac attaaggact tggccggtgt      60
cgatccgcaa atcgattaac caaagcaagt gcattactag t                        101

<210> SEQ ID NO 720
<211> LENGTH: 101
```

<212> TYPE: DNA
<213> ORGANISM: Solanum lycopersicum

<400> SEQUENCE: 720
atcaacgccg ccgacactga atgaagctcc gagtgtgatt cgggtcgggt tggaaacgac    60
atttccggtt cgagaaaatc acctaaacca aaaacagtga a                        101

<210> SEQ ID NO 721
<211> LENGTH: 101
<212> TYPE: DNA
<213> ORGANISM: Solanum lycopersicum

<400> SEQUENCE: 721
atcaacgccg ccgacactga atgaagctcc gagtgtgatt cgggtcgggt cggaaacgac    60
atttccggtt cgagaaaatc acctaaacca aaaacagtga a                        101

<210> SEQ ID NO 722
<211> LENGTH: 101
<212> TYPE: DNA
<213> ORGANISM: Solanum lycopersicum

<400> SEQUENCE: 722
gaacactatg aagatgagac cccagatgac accgaagatg acgatgaggg tggaaaagaa    60
gcatctcttg ggcgttattg tgtcttctgt agtaaacttg a                        101

<210> SEQ ID NO 723
<211> LENGTH: 101
<212> TYPE: DNA
<213> ORGANISM: Solanum lycopersicum

<400> SEQUENCE: 723
gaacactatg aagatgagac cccagatgac accgaagatg acgatgaggg gggaaaagaa    60
gcatctcttg ggcgttattg tgtcttctgt agtaaacttg a                        101

<210> SEQ ID NO 724
<211> LENGTH: 101
<212> TYPE: DNA
<213> ORGANISM: Solanum lycopersicum

<400> SEQUENCE: 724
actgcaagta aaatgtttc atatacggat gctgcagctg ttgaagaaaa aaaatcctgg    60
tcttcttctg catgcccata caacctgtag aggacacgca a                        101

<210> SEQ ID NO 725
<211> LENGTH: 101
<212> TYPE: DNA
<213> ORGANISM: Solanum lycopersicum

<400> SEQUENCE: 725
actgcaagta aaatgtttc atatacggat gctgcagctg ttgaagaaaa gaaatcctgg    60
tcttcttctg catgcccata caacctgtag aggacacgca a                        101

<210> SEQ ID NO 726
<211> LENGTH: 101
<212> TYPE: DNA
<213> ORGANISM: Solanum lycopersicum

<400> SEQUENCE: 726
gttcagtatc ccgaaattca aaggtttgct tttcggctcc ttagtcagac atgcaatggt    60

-continued

```
gcttcacatt ataggctgaa aaggagcttg gtcgagacat t                         101

<210> SEQ ID NO 727
<211> LENGTH: 101
<212> TYPE: DNA
<213> ORGANISM: Solanum lycopersicum

<400> SEQUENCE: 727
gttcagtatc ccgaaattca aaggtttgct tttcggctcc ttagtcagac ttgcaatggt      60
gcttcacatt ataggctgaa aaggagcttg gtcgagacat t                         101

<210> SEQ ID NO 728
<211> LENGTH: 101
<212> TYPE: DNA
<213> ORGANISM: Solanum lycopersicum

<400> SEQUENCE: 728
actatagcgt gcatgggaaa cagaaaattg agtttgatcc ttgatgattg aaaatgaagg      60
atcagcagaa ccgtctttgc tctgagaaac aacaaaaggt g                         101

<210> SEQ ID NO 729
<211> LENGTH: 101
<212> TYPE: DNA
<213> ORGANISM: Solanum lycopersicum

<400> SEQUENCE: 729
actatagcgt gcatgggaaa cagaaaattg agtttgatcc ttgatgattg gaaatgaagg      60
atcagcagaa ccgtctttgc tctgagaaac aacaaaaggt g                         101

<210> SEQ ID NO 730
<211> LENGTH: 101
<212> TYPE: DNA
<213> ORGANISM: Solanum lycopersicum

<400> SEQUENCE: 730
taaccacagc atcagacaaa gacataaaga ggctgcgatg aggagaaaaa aatatggagt      60
agacacacta ctcccaatat tccacttcaa attattaacc c                         101

<210> SEQ ID NO 731
<211> LENGTH: 101
<212> TYPE: DNA
<213> ORGANISM: Solanum lycopersicum

<400> SEQUENCE: 731
taaccacagc atcagacaaa gacataaaga ggctgcgatg aggagaaaaa catatggagt      60
agacacacta ctcccaatat tccacttcaa attattaacc c                         101

<210> SEQ ID NO 732
<211> LENGTH: 101
<212> TYPE: DNA
<213> ORGANISM: Solanum lycopersicum

<400> SEQUENCE: 732
tggtgttcta acatttgaaa gcaaattctg caacctttcc acactcattc tagcacatga      60
tgcgatgtct tctttggttg gatgacgatt gccttgtcga a                         101

<210> SEQ ID NO 733
<211> LENGTH: 101
<212> TYPE: DNA
<213> ORGANISM: Solanum lycopersicum
```

-continued

```
<400> SEQUENCE: 733
tggtgttcta acatttgaaa gcaaattctg caacctttcc acactcattc cagcacatga      60
tgcgatgtct tctttggttg gatgacgatt gccttgtcga a                          101

<210> SEQ ID NO 734
<211> LENGTH: 101
<212> TYPE: DNA
<213> ORGANISM: Solanum lycopersicum

<400> SEQUENCE: 734
cgtttgcatg accgtctgtg gctgcattcg tagatgttga atttgctttc agtaccaaac      60
ttttgtatga cagacgacat aacttctgtc atatttccag g                          101

<210> SEQ ID NO 735
<211> LENGTH: 101
<212> TYPE: DNA
<213> ORGANISM: Solanum lycopersicum

<400> SEQUENCE: 735
cgtttgcatg accgtctgtg gctgcattcg tagatgttga atttgctttc ggtaccaaac      60
ttttgtatga cagacgacat aacttctgtc atatttccag g                          101

<210> SEQ ID NO 736
<211> LENGTH: 101
<212> TYPE: DNA
<213> ORGANISM: Solanum lycopersicum

<400> SEQUENCE: 736
ccatcccaga agacataatt tgtagcattg gagcatgttc cgatggacct agcattacaa      60
aggaatgatg tttctagtgt accagtcccg cagcaagcct t                          101

<210> SEQ ID NO 737
<211> LENGTH: 101
<212> TYPE: DNA
<213> ORGANISM: Solanum lycopersicum

<400> SEQUENCE: 737
ccatcccaga agacataatt tgtagcattg gagcatgttc cgatggacct ggcattacaa      60
aggaatgatg tttctagtgt accagtcccg cagcaagcct t                          101

<210> SEQ ID NO 738
<211> LENGTH: 201
<212> TYPE: DNA
<213> ORGANISM: Solanum lycopersicum
<220> FEATURE:
<221> NAME/KEY: modified_base
<222> LOCATION: (75)..(75)
<223> OTHER INFORMATION: a, c, t, g, unknown or other
<220> FEATURE:
<221> NAME/KEY: modified_base
<222> LOCATION: (162)..(162)
<223> OTHER INFORMATION: a, c, t, g, unknown or other

<400> SEQUENCE: 738
gaattcttgc atttgaaatt gcaactttga tgtctaaggt ggttaacttg tggcagtgtc      60
taagtgaaag gcgantcgac aagttaagag aagaaatctc aagttcactt ggcattcaga      120
agcttgttgc tgaagatgac aaatatctta tggatcttgc tnttgctgag ataattgaca      180
atttgggatc tctgacgaag t                                               201
```

-continued

```
<210> SEQ ID NO 739
<211> LENGTH: 201
<212> TYPE: DNA
<213> ORGANISM: Solanum lycopersicum
<220> FEATURE:
<221> NAME/KEY: modified_base
<222> LOCATION: (75)..(75)
<223> OTHER INFORMATION: a, c, t, g, unknown or other
<220> FEATURE:
<221> NAME/KEY: modified_base
<222> LOCATION: (162)..(162)
<223> OTHER INFORMATION: a, c, t, g, unknown or other

<400> SEQUENCE: 739
gaattcttgc atttgaaatt gcaactttga tgtctaaggt ggttaacttg tggcagtgtc     60
taagtgaaag gcgantcgac aagttaagag aagaaatctc gagttcactt ggcattcaga    120
agcttgttgc tgaagatgac aaatatctta tggatcttgc tnttgctgag ataattgaca    180
atttgggatc tctgacgaag t                                               201

<210> SEQ ID NO 740
<211> LENGTH: 101
<212> TYPE: DNA
<213> ORGANISM: Solanum lycopersicum

<400> SEQUENCE: 740
cccacaaaat agctggtaga gaatcattga ttggctcaat ttagcctcta taacacattt     60
tgcaagaact gaaagattga taagtaacca tcccatcata c                        101

<210> SEQ ID NO 741
<211> LENGTH: 101
<212> TYPE: DNA
<213> ORGANISM: Solanum lycopersicum

<400> SEQUENCE: 741
cccacaaaat agctggtaga gaatcattga ttggctcaat ttagcctcta caacacattt     60
tgcaagaact gaaagattga taagtaacca tcccatcata c                        101

<210> SEQ ID NO 742
<211> LENGTH: 101
<212> TYPE: DNA
<213> ORGANISM: Solanum lycopersicum

<400> SEQUENCE: 742
aatgatgtca ttgagatctt tagtggatag taaaatggtg ggttcttaag taaaatggta     60
aagaggtgcg ctgttcgtga tgtgggcttg tagataaagc t                        101

<210> SEQ ID NO 743
<211> LENGTH: 101
<212> TYPE: DNA
<213> ORGANISM: Solanum lycopersicum

<400> SEQUENCE: 743
aatgatgtca ttgagatctt tagtggatag taaaatggtg ggttcttaag gaaaatggta     60
aagaggtgcg ctgttcgtga tgtgggcttg tagataaagc t                        101

<210> SEQ ID NO 744
<211> LENGTH: 101
<212> TYPE: DNA
<213> ORGANISM: Solanum lycopersicum

<400> SEQUENCE: 744
```

```
caaaacccgc atgctggtga cgttttggtt gattctatga aaaggtatta tggaaagtta      60
cctgcagtcg ttgaactgtt tagtcaagtt ggagcacagg t                         101

<210> SEQ ID NO 745
<211> LENGTH: 101
<212> TYPE: DNA
<213> ORGANISM: Solanum lycopersicum

<400> SEQUENCE: 745
caaaacccgc atgctggtga cgttttggtt gattctatga aaaggtatta cggaaagtta      60
cctgcagtcg ttgaactgtt tagtcaagtt ggagcacagg t                         101

<210> SEQ ID NO 746
<211> LENGTH: 101
<212> TYPE: DNA
<213> ORGANISM: Solanum lycopersicum

<400> SEQUENCE: 746
acactcatga acattgctga taacccgacg aatgtccaac tccccggtat atacaacaag      60
caagagaatg ccagggtacc tattattgtc actggtaacg a                         101

<210> SEQ ID NO 747
<211> LENGTH: 101
<212> TYPE: DNA
<213> ORGANISM: Solanum lycopersicum

<400> SEQUENCE: 747
acactcatga acattgctga taacccgacg aatgtccaac tccccggtat gtacaacaag      60
caagagaatg ccagggtacc tattattgtc actggtaacg a                         101

<210> SEQ ID NO 748
<211> LENGTH: 101
<212> TYPE: DNA
<213> ORGANISM: Solanum lycopersicum

<400> SEQUENCE: 748
ttaatgcatc acagacagga tgtaaaccac accctacgcg tatagatatt atcagcccat      60
tatccaattt gttgaagcgt ttgcaagtta gggatacaga g                         101

<210> SEQ ID NO 749
<211> LENGTH: 101
<212> TYPE: DNA
<213> ORGANISM: Solanum lycopersicum

<400> SEQUENCE: 749
ttaatgcatc acagacagga tgtaaaccac accctacgcg tatagatatt ctcagcccat      60
tatccaattt gttgaagcgt ttgcaagtta gggatacaga g                         101

<210> SEQ ID NO 750
<211> LENGTH: 101
<212> TYPE: DNA
<213> ORGANISM: Solanum lycopersicum

<400> SEQUENCE: 750
tcttttggta gaagagatgt gccatctttc caattttcat caatatattc aagaatcact      60
agagactcag gaattggatt tcccttgtgc aaaaatacag g                         101

<210> SEQ ID NO 751
```

-continued

```
<211> LENGTH: 101
<212> TYPE: DNA
<213> ORGANISM: Solanum lycopersicum

<400> SEQUENCE: 751
tcttttggta gaagagatgt gccatctttc caattttcat caatatattc cagaatcact        60
agagactcag gaattggatt tcccttgtgc aaaaatacag g                           101

<210> SEQ ID NO 752
<211> LENGTH: 101
<212> TYPE: DNA
<213> ORGANISM: Solanum lycopersicum

<400> SEQUENCE: 752
gagtagaaga agaatcaaaa agcaaaaatg gtgaaagaca gaaccattgg tgtggctgta        60 gattttttcaa agagcagcaa aacagctttg aaatgggcaa t                          101

<210> SEQ ID NO 753
<211> LENGTH: 101
<212> TYPE: DNA
<213> ORGANISM: Solanum lycopersicum

<400> SEQUENCE: 753
gagtagaaga agaatcaaaa agcaaaaatg gtgaaagaca gaaccattgg cgtggctgta        60 gattttttcaa agagcagcaa aacagctttg aaatgggcaa t                          101

<210> SEQ ID NO 754
<211> LENGTH: 101
<212> TYPE: DNA
<213> ORGANISM: Solanum lycopersicum

<400> SEQUENCE: 754
tcgctcatct acccttctcc acttaaatag tttacgggca agactcgtac agtgcatccc        60
gcagtgggga cacaagtatg tgtctttcat ttggttctta a                           101

<210> SEQ ID NO 755
<211> LENGTH: 101
<212> TYPE: DNA
<213> ORGANISM: Solanum lycopersicum

<400> SEQUENCE: 755
tcgctcatct acccttctcc acttaaatag tttacgggca agactcgtac cgtgcatccc        60
gcagtgggga cacaagtatg tgtctttcat ttggttctta a                           101

<210> SEQ ID NO 756
<211> LENGTH: 101
<212> TYPE: DNA
<213> ORGANISM: Solanum lycopersicum

<400> SEQUENCE: 756
tacagatcct ctgttttctt caaacaacaa atgtctctta ttccaagctt ttttggtggt        60
cggaggagca atatcttcga cccattttcc cttgacttat g                           101

<210> SEQ ID NO 757
<211> LENGTH: 101
<212> TYPE: DNA
<213> ORGANISM: Solanum lycopersicum

<400> SEQUENCE: 757
tacagatcct ctgttttctt caaacaacaa atgtctctta ttccaagctt ctttggtggt        60
```

-continued

```
cggaggagca atatcttcga cccattttcc cttgacttat g                          101

<210> SEQ ID NO 758
<211> LENGTH: 101
<212> TYPE: DNA
<213> ORGANISM: Solanum lycopersicum

<400> SEQUENCE: 758
tccaaatcca taagtggttg ttacttcact tgaacaccat tccccttctt agctgaattt       60
gtgttgcatc acctttttcc gtagtgcatg ctcctcttgg t                          101

<210> SEQ ID NO 759
<211> LENGTH: 101
<212> TYPE: DNA
<213> ORGANISM: Solanum lycopersicum

<400> SEQUENCE: 759
tccaaatcca taagtggttg ttacttcact tgaacaccat tccccttctt cgctgaattt       60
gtgttgcatc acctttttcc gtagtgcatg ctcctcttgg t                          101

<210> SEQ ID NO 760
<211> LENGTH: 101
<212> TYPE: DNA
<213> ORGANISM: Solanum lycopersicum

<400> SEQUENCE: 760
caggaagaca taatcacaac acttttgaat ctgtccatcc atgacaacaa taagaagctt       60
gtcgcggaga ctccaaaagt tattccactt cttgtggagg c                          101

<210> SEQ ID NO 761
<211> LENGTH: 101
<212> TYPE: DNA
<213> ORGANISM: Solanum lycopersicum

<400> SEQUENCE: 761
caggaagaca taatcacaac acttttgaat ctgtccatcc atgacaacaa caagaagctt       60
gtcgcggaga ctccaaaagt tattccactt cttgtggagg c                          101

<210> SEQ ID NO 762
<211> LENGTH: 101
<212> TYPE: DNA
<213> ORGANISM: Solanum lycopersicum

<400> SEQUENCE: 762
gatggaatta cacacaacct cagatgaata tgagagacag ctacatacct aattggtctg       60
catcgcgtaa tcctgggcat tattctggct atcgtggtcc t                          101

<210> SEQ ID NO 763
<211> LENGTH: 101
<212> TYPE: DNA
<213> ORGANISM: Solanum lycopersicum

<400> SEQUENCE: 763
gatggaatta cacacaacct cagatgaata tgagagacag ctacatacct gattggtctg       60
catcgcgtaa tcctgggcat tattctggct atcgtggtcc t                          101

<210> SEQ ID NO 764
<211> LENGTH: 101
<212> TYPE: DNA
```

<213> ORGANISM: Solanum lycopersicum

<400> SEQUENCE: 764
ccagcataaa tttaagaatg gagtagaatc caattgacaa aagagagcag ttattaacgc    60
acctaaacat ccttacccgc actgcaatta atgcatttat c                        101

<210> SEQ ID NO 765
<211> LENGTH: 101
<212> TYPE: DNA
<213> ORGANISM: Solanum lycopersicum

<400> SEQUENCE: 765
ccagcataaa tttaagaatg gagtagaatc caattgacaa aagagagcag ctattaacgc    60
acctaaacat ccttacccgc actgcaatta atgcatttat c                        101

<210> SEQ ID NO 766
<211> LENGTH: 101
<212> TYPE: DNA
<213> ORGANISM: Solanum lycopersicum

<400> SEQUENCE: 766
actgctggac ctggcattga catgtccatg gcacataatc atgctatttt tcagagtctc    60
ccggaagcta cgaggcaaaa tttacagatg gccgcagcag c                        101

<210> SEQ ID NO 767
<211> LENGTH: 101
<212> TYPE: DNA
<213> ORGANISM: Solanum lycopersicum

<400> SEQUENCE: 767
actgctggac ctggcattga catgtccatg gcacataatc atgctatttt ccagagtctc    60
ccggaagcta cgaggcaaaa tttacagatg gccgcagcag c                        101

<210> SEQ ID NO 768
<211> LENGTH: 101
<212> TYPE: DNA
<213> ORGANISM: Solanum lycopersicum

<400> SEQUENCE: 768
gatttattca cagataacga agaggatgat atggaaaatg ctgatatcag tatcaaggga    60
aggaggagag aagacgatgg catctttta cgactcagga t                         101

<210> SEQ ID NO 769
<211> LENGTH: 101
<212> TYPE: DNA
<213> ORGANISM: Solanum lycopersicum

<400> SEQUENCE: 769
gatttattca cagataacga agaggatgat atggaaaatg ctgatatcag catcaaggga    60
aggaggagag aagacgatgg catctttta cgactcagga t                         101

<210> SEQ ID NO 770
<211> LENGTH: 101
<212> TYPE: DNA
<213> ORGANISM: Solanum lycopersicum

<400> SEQUENCE: 770
aaatcggcag agaaggaagt cgagatattg accaaatttg ctccactcaa aggattctcc    60
atctaattga actttctgtt gtacagttta gttcagtatc t                        101

-continued

```
<210> SEQ ID NO 771
<211> LENGTH: 101
<212> TYPE: DNA
<213> ORGANISM: Solanum lycopersicum

<400> SEQUENCE: 771
aaatcggcag agaaggaagt cgagatattg accaaatttg ctccactcaa gggattctcc      60
atctaattga actttctgtt gtacagttta gttcagtatc t                        101

<210> SEQ ID NO 772
<211> LENGTH: 101
<212> TYPE: DNA
<213> ORGANISM: Solanum lycopersicum

<400> SEQUENCE: 772
agttcaagca aggtgacata ctaatcaaca cgttcgtgca atcgttgctc aattgagcaa      60
caactccaga acagatcatc gcaaacataa tcgcgaaaaa a                        101

<210> SEQ ID NO 773
<211> LENGTH: 101
<212> TYPE: DNA
<213> ORGANISM: Solanum lycopersicum

<400> SEQUENCE: 773
agttcaagca aggtgacata ctaatcaaca cgttcgtgca atcgttgctc gattgagcaa      60
caactccaga acagatcatc gcaaacataa tcgcgaaaaa a                        101

<210> SEQ ID NO 774
<211> LENGTH: 101
<212> TYPE: DNA
<213> ORGANISM: Solanum lycopersicum

<400> SEQUENCE: 774
caatacagat atgggagaaa actaaagatc tgaaggcaca agtggagacg tactataaat      60
ccttaaaatt cactccatcg caattcccca ctgttggtgg a                        101

<210> SEQ ID NO 775
<211> LENGTH: 101
<212> TYPE: DNA
<213> ORGANISM: Solanum lycopersicum

<400> SEQUENCE: 775
caatacagat atgggagaaa actaaagatc tgaaggcaca agtggagacg cactataaat      60
ccttaaaatt cactccatcg caattcccca ctgttggtgg a                        101

<210> SEQ ID NO 776
<211> LENGTH: 101
<212> TYPE: DNA
<213> ORGANISM: Solanum lycopersicum

<400> SEQUENCE: 776
gatgaaaaga ttgcaactca ttttcaagtt gccgtcagct caattgcaca atctctcaga      60
actcagatta ttaataggtc ttatgatgaa gtttctatat g                        101

<210> SEQ ID NO 777
<211> LENGTH: 101
<212> TYPE: DNA
<213> ORGANISM: Solanum lycopersicum
```

-continued

```
<400> SEQUENCE: 777
gatgaaaaga ttgcaactca ttttcaagtt gccgtcagct caattgcaca gtctctcaga        60
actcagatta ttaataggtc ttatgatgaa gtttctatat g                          101

<210> SEQ ID NO 778
<211> LENGTH: 101
<212> TYPE: DNA
<213> ORGANISM: Solanum lycopersicum

<400> SEQUENCE: 778
acaagttctt ctttgaaacg gagatattca ggaaccgtca attgttcaac actcagatca        60
tatacgttca cacgaacata ttcccaaaca cctggccttg g                          101

<210> SEQ ID NO 779
<211> LENGTH: 101
<212> TYPE: DNA
<213> ORGANISM: Solanum lycopersicum

<400> SEQUENCE: 779
acaagttctt ctttgaaacg gagatattca ggaaccgtca attgttcaac gctcagatca        60
tatacgttca cacgaacata ttcccaaaca cctggccttg g                          101

<210> SEQ ID NO 780
<211> LENGTH: 101
<212> TYPE: DNA
<213> ORGANISM: Solanum lycopersicum

<400> SEQUENCE: 780
gctcgagtcc tcaaatgagg aatcagctga ttcgaggggt ctcccttcaa tccacgttct        60
aacagacttg ttcttcagtt ggtaggtgta gtacacttct t                          101

<210> SEQ ID NO 781
<211> LENGTH: 101
<212> TYPE: DNA
<213> ORGANISM: Solanum lycopersicum

<400> SEQUENCE: 781
gctcgagtcc tcaaatgagg aatcagctga ttcgaggggt ctcccttcaa cccacgttct        60
aacagacttg ttcttcagtt ggtaggtgta gtacacttct t                          101

<210> SEQ ID NO 782
<211> LENGTH: 101
<212> TYPE: DNA
<213> ORGANISM: Solanum lycopersicum

<400> SEQUENCE: 782
gagtcaagat gagattgcaa aaaaggactc ttcaaccagg aagagaccgc tttttgtcaa        60
tcctcaaagg ccaatgagac caagtactat tgctgcagct a                          101

<210> SEQ ID NO 783
<211> LENGTH: 101
<212> TYPE: DNA
<213> ORGANISM: Solanum lycopersicum

<400> SEQUENCE: 783
gagtcaagat gagattgcaa aaaaggactc ttcaaccagg aagagaccgc tttttgtcaa        60
tcctcaaagg ccaatgagac caagtactat tgctgcagct a                          101
```

-continued

```
<210> SEQ ID NO 784
<211> LENGTH: 101
<212> TYPE: DNA
<213> ORGANISM: Solanum lycopersicum

<400> SEQUENCE: 784
tggagatgta ctctagatct taactgtgat gttctgagct gtaaaagtac taactccgat          60
catcagtcag atcaacgtcc ctattacttt gtaacgatgt c                             101

<210> SEQ ID NO 785
<211> LENGTH: 101
<212> TYPE: DNA
<213> ORGANISM: Solanum lycopersicum

<400> SEQUENCE: 785
tggagatgta ctctagatct taactgtgat gttctgagct gtaaaagtac caactccgat          60
catcagtcag atcaacgtcc ctattacttt gtaacgatgt c                             101

<210> SEQ ID NO 786
<211> LENGTH: 101
<212> TYPE: DNA
<213> ORGANISM: Solanum lycopersicum

<400> SEQUENCE: 786
tgaagattgt gtatggtgat actaaagtgg atttaaaagg cgaaaacgac ataaacatgg          60
gtgcagggga agttgttggt tttgttctgg agaataggaa g                             101

<210> SEQ ID NO 787
<211> LENGTH: 101
<212> TYPE: DNA
<213> ORGANISM: Solanum lycopersicum

<400> SEQUENCE: 787
tgaagattgt gtatggtgat actaaagtgg atttaaaagg cgaaaacgac gtaaacatgg          60
gtgcagggga agttgttggt tttgttctgg agaataggaa g                             101

<210> SEQ ID NO 788
<211> LENGTH: 101
<212> TYPE: DNA
<213> ORGANISM: Solanum lycopersicum

<400> SEQUENCE: 788
ggatatgaaa ggtaagaagt taaccgtcat tggtacagtt gatccagtga acgtagtgag          60
taggctacgt aagttttggt ggacagagat actcatagta g                             101

<210> SEQ ID NO 789
<211> LENGTH: 101
<212> TYPE: DNA
<213> ORGANISM: Solanum lycopersicum

<400> SEQUENCE: 789
ggatatgaaa ggtaagaagt taaccgtcat tggtacagtt gatccagtga gcgtagtgag          60
taggctacgt aagttttggt ggacagagat actcatagta g                             101

<210> SEQ ID NO 790
<211> LENGTH: 101
<212> TYPE: DNA
<213> ORGANISM: Solanum lycopersicum

<400> SEQUENCE: 790
```

-continued

```
aaagagtaaa ccggtgcaca aagtatccta cgtcaacaag cttcggggaa agccgcaccc      60
caagaagcat aagtagattc ataaccacaa agtgatacta t                         101

<210> SEQ ID NO 791
<211> LENGTH: 101
<212> TYPE: DNA
<213> ORGANISM: Solanum lycopersicum

<400> SEQUENCE: 791
aaagagtaaa ccggtgcaca aagtatccta cgtcaacaag cttcggggaa ggccgcaccc      60
caagaagcat aagtagattc ataaccacaa agtgatacta t                         101

<210> SEQ ID NO 792
<211> LENGTH: 101
<212> TYPE: DNA
<213> ORGANISM: Solanum lycopersicum

<400> SEQUENCE: 792
ctttagctgt cttgatcttc tgaagtctca cttacagtgc gtcaacttca ctcagctcta      60
gactgcccag ctcgggaaga caagataatg ccaacaataa g                         101

<210> SEQ ID NO 793
<211> LENGTH: 101
<212> TYPE: DNA
<213> ORGANISM: Solanum lycopersicum

<400> SEQUENCE: 793
ctttagctgt cttgatcttc tgaagtctca cttacagtgc gtcaacttca gtcagctcta      60
gactgcccag ctcgggaaga caagataatg ccaacaataa g                         101

<210> SEQ ID NO 794
<211> LENGTH: 101
<212> TYPE: DNA
<213> ORGANISM: Solanum lycopersicum

<400> SEQUENCE: 794
ccataagaga acaacagatt ggtggcattg ttcaggtgat tgattgattt attcctggat      60
gttttaaaca acttatcatg tcgatttctt gtggattact c                         101

<210> SEQ ID NO 795
<211> LENGTH: 101
<212> TYPE: DNA
<213> ORGANISM: Solanum lycopersicum

<400> SEQUENCE: 795
ccataagaga acaacagatt ggtggcattg ttcaggtgat tgattgattt gttcctggat      60
gttttaaaca acttatcatg tcgatttctt gtggattact c                         101

<210> SEQ ID NO 796
<211> LENGTH: 154
<212> TYPE: DNA
<213> ORGANISM: Solanum lycopersicum

<400> SEQUENCE: 796
aaacccttat cggcgcaaga atgggaaaat ctaatcgacg attacaacca cggtggttca      60
cggcggctcc ggtggacttc catcaactac gccgccgttc ctcttcttga cctcacactt     120
tcatcacttc tccggaaaga tatccctcac aatc                                 154
```

```
<210> SEQ ID NO 797
<211> LENGTH: 154
<212> TYPE: DNA
<213> ORGANISM: Solanum lycopersicum

<400> SEQUENCE: 797
aaacccttat cggcgcaaga atgggaaaat ctaatcgacg attacaacca cggcggttca      60
cggcggctcc ggtggacttc catcaactac gccgccgttc ctcttcttga cctcacactt     120
tcatcacttc tccggaaaga tatccctcac aatc                                 154

<210> SEQ ID NO 798
<211> LENGTH: 101
<212> TYPE: DNA
<213> ORGANISM: Solanum lycopersicum

<400> SEQUENCE: 798 gaaagggggga ttttggtaag agattgggca cctcaattgg agatcttgtc acattgttcg      60
actggtggat tcttgagtca ctgtgggtgg aattcatgca t                         101

<210> SEQ ID NO 799
<211> LENGTH: 101
<212> TYPE: DNA
<213> ORGANISM: Solanum lycopersicum

<400> SEQUENCE: 799 gaaagggggga ttttggtaag agattgggca cctcaattgg agatcttgtc gcattgttcg      60
actggtggat tcttgagtca ctgtgggtgg aattcatgca t                         101

<210> SEQ ID NO 800
<211> LENGTH: 101
<212> TYPE: DNA
<213> ORGANISM: Solanum lycopersicum

<400> SEQUENCE: 800
taaccaacca ctttggtatc tgttagtcca ccaacatgac tatgagtaat tcgactattg      60
aaactgaaga tacttttgcc agcttgcttg aacttgctgc c                         101

<210> SEQ ID NO 801
<211> LENGTH: 101
<212> TYPE: DNA
<213> ORGANISM: Solanum lycopersicum

<400> SEQUENCE: 801
taaccaacca ctttggtatc tgttagtcca ccaacatgac tatgagtaat ccgactattg      60
aaactgaaga tacttttgcc agcttgcttg aacttgctgc c                         101

<210> SEQ ID NO 802
<211> LENGTH: 101
<212> TYPE: DNA
<213> ORGANISM: Solanum lycopersicum

<400> SEQUENCE: 802
ccacgttgga ctaacgaaat tttaaccatc atagaaatga cttccgcgcg ttccttcact      60
ggaattcaat ttcttatagt gggacccact ttccgatctg t                        101

<210> SEQ ID NO 803
<211> LENGTH: 101
<212> TYPE: DNA
<213> ORGANISM: Solanum lycopersicum
```

-continued

<400> SEQUENCE: 803
ccacgttgga ctaacgaaat tttaaccatc atagaaatga cttccgcgcg ctccttcact      60
ggaattcaat ttcttatagt gggacccact ttccgatctg t                       101

<210> SEQ ID NO 804
<211> LENGTH: 101
<212> TYPE: DNA
<213> ORGANISM: Solanum lycopersicum

<400> SEQUENCE: 804
tttgctgaag agagcaggat ttttatgtgg cagttgctag actgcagtat aaactccttt      60
tgcagtttct ttcgttacat ttatgttgcc gtctttatca t                       101

<210> SEQ ID NO 805
<211> LENGTH: 101
<212> TYPE: DNA
<213> ORGANISM: Solanum lycopersicum

<400> SEQUENCE: 805
tttgctgaag agagcaggat ttttatgtgg cagttgctag actgcagtat gaactccttt      60
tgcagtttct ttcgttacat ttatgttgcc gtctttatca t                       101

<210> SEQ ID NO 806
<211> LENGTH: 101
<212> TYPE: DNA
<213> ORGANISM: Solanum lycopersicum

<400> SEQUENCE: 806
aagggaagag aatgtgcttt gctagtagtt tgaaggagtc tttttggtg ttttgagggt      60 ttgattcttt ttgtaatggg ctgtgaataa agtgaagtgc t                       101

<210> SEQ ID NO 807
<211> LENGTH: 101
<212> TYPE: DNA
<213> ORGANISM: Solanum lycopersicum

<400> SEQUENCE: 807
aagggaagag aatgtgcttt gctagtagtt tgaaggagtc tttttggtg ctttgagggt      60 ttgattcttt ttgtaatggg ctgtgaataa agtgaagtgc t                       101

<210> SEQ ID NO 808
<211> LENGTH: 201
<212> TYPE: DNA
<213> ORGANISM: Solanum lycopersicum
<220> FEATURE:
<221> NAME/KEY: modified_base
<222> LOCATION: (185)..(185)
<223> OTHER INFORMATION: a, c, t, g, unknown or other
<220> FEATURE:
<221> NAME/KEY: modified_base
<222> LOCATION: (199)..(199)
<223> OTHER INFORMATION: a, c, t, g, unknown or other

<400> SEQUENCE: 808
ttttgagtta aattcgaata atttcaaagt ttacacaata attttgatgt tggtggttgt      60
tcaggttcaa tgtaacaatg aggtaattca acagcattgt aacggacctg tacaaaaatt     120
aaagcgattt cttataaaga aattgaaacg taatgtttct gttgttcgac aaaagaaagg     180
taatnaatca tgcagccgnt a                                              201

```
<210> SEQ ID NO 809
<211> LENGTH: 201
<212> TYPE: DNA
<213> ORGANISM: Solanum lycopersicum
<220> FEATURE:
<221> NAME/KEY: modified_base
<222> LOCATION: (185)..(185)
<223> OTHER INFORMATION: a, c, t, g, unknown or other
<220> FEATURE:
<221> NAME/KEY: modified_base
<222> LOCATION: (199)..(199)
<223> OTHER INFORMATION: a, c, t, g, unknown or other

<400> SEQUENCE: 809
ttttgagtta aattcgaata atttcaaagt ttacacaata attttgatgt tggtggttgt      60
tcaggttcaa tgtaacaatg aggtaattca acagcattgt gacggacctg tacaaaaatt     120
aaagcgattt cttataaaga aattgaaacg taatgtttct gttgttcgac aaaagaaagg     180
taatnaatca tgcagccgnt a                                                201

<210> SEQ ID NO 810
<211> LENGTH: 101
<212> TYPE: DNA
<213> ORGANISM: Solanum lycopersicum

<400> SEQUENCE: 810
tcaccatata accacgaaat accttctgga tccttaacgc tgaagcagat cttctatcag      60
gcgcctccgc ctgcgccaac tcatcaggtt tctgtgaccg a                         101

<210> SEQ ID NO 811
<211> LENGTH: 101
<212> TYPE: DNA
<213> ORGANISM: Solanum lycopersicum

<400> SEQUENCE: 811
tcaccatata accacgaaat accttctgga tccttaacgc tgaagcagat gttctatcag      60
gcgcctccgc ctgcgccaac tcatcaggtt tctgtgaccg a                         101

<210> SEQ ID NO 812
<211> LENGTH: 101
<212> TYPE: DNA
<213> ORGANISM: Solanum lycopersicum

<400> SEQUENCE: 812
ccagcttgaa aagcagagac attaacgttt cattcacccg taccctttcc atttcgtctc      60
tccgaatcaa ctccgccgtt tcgccgaata aaagcttccg t                         101

<210> SEQ ID NO 813
<211> LENGTH: 101
<212> TYPE: DNA
<213> ORGANISM: Solanum lycopersicum

<400> SEQUENCE: 813
ccagcttgaa aagcagagac attaacgttt cattcacccg tacctttcc ctttcgtctc      60 tccgaatcaa ctccgccgtt tcgccgaata aaagcttccg t                         101

<210> SEQ ID NO 814
<211> LENGTH: 101
<212> TYPE: DNA
<213> ORGANISM: Solanum lycopersicum

<400> SEQUENCE: 814
```

-continued

```
gttgcgctct atgtatttta ctgtctatat acaccattca ctgctgcttc aacgtggact      60
gcgttaccat cttccatgat catcccgttg atttgtgttc t                        101

<210> SEQ ID NO 815
<211> LENGTH: 101
<212> TYPE: DNA
<213> ORGANISM: Solanum lycopersicum

<400> SEQUENCE: 815
gttgcgctct atgtatttta ctgtctatat acaccattca ctgctgcttc gacgtggact      60
gcgttaccat cttccatgat catcccgttg atttgtgttc t                        101

<210> SEQ ID NO 816
<211> LENGTH: 101
<212> TYPE: DNA
<213> ORGANISM: Solanum lycopersicum

<400> SEQUENCE: 816
atttgagctg tgaaaggagt tgcagatttg ggatagttag ggcttcttgt accgaggagg      60
tggtggtgga tgatcatgag attgatgacg tggagaggaa g                        101

<210> SEQ ID NO 817
<211> LENGTH: 101
<212> TYPE: DNA
<213> ORGANISM: Solanum lycopersicum

<400> SEQUENCE: 817
atttgagctg tgaaaggagt tgcagatttg ggatagttag ggcttcttgt gccgaggagg      60
tggtggtgga tgatcatgag attgatgacg tggagaggaa g                        101

<210> SEQ ID NO 818
<211> LENGTH: 101
<212> TYPE: DNA
<213> ORGANISM: Solanum lycopersicum

<400> SEQUENCE: 818
cctctctgca tcatacagtt gatcgtgggg gaacacacat atttctagtt tcagtaatat      60 tcctttttgta tcttgcatgc agtcattcag aaagagatag g                       101

<210> SEQ ID NO 819
<211> LENGTH: 101
<212> TYPE: DNA
<213> ORGANISM: Solanum lycopersicum

<400> SEQUENCE: 819
cctctctgca tcatacagtt gatcgtgggg gaacacacat atttctagtt ccagtaatat      60 tcctttttgta tcttgcatgc agtcattcag aaagagatag g                       101

<210> SEQ ID NO 820
<211> LENGTH: 101
<212> TYPE: DNA
<213> ORGANISM: Solanum lycopersicum

<400> SEQUENCE: 820
gtcgatcgaa cgttattgat aacgagaaca acgatctttt ctcatgtgca tgcaaatcag      60
gccttgatat acgagatgtg tctatttacg atggttttcc t                        101

<210> SEQ ID NO 821
<211> LENGTH: 101
```

-continued

```
<212> TYPE: DNA
<213> ORGANISM: Solanum lycopersicum

<400> SEQUENCE: 821
gtcgatcgaa cgttattgat aacgagaaca acgatctttt ctcatgtgca cgcaaatcag      60
gccttgatat acgagatgtg tctatttacg atggttttcc t                         101

<210> SEQ ID NO 822
<211> LENGTH: 101
<212> TYPE: DNA
<213> ORGANISM: Solanum lycopersicum

<400> SEQUENCE: 822
acttaatcca agaaagagag gaaattgtgg cttgtggaat ttcaaatcaa taataacccc      60
aaaaagaact gctaaaaacc gtaagcaaga taccacagag a                         101

<210> SEQ ID NO 823
<211> LENGTH: 101
<212> TYPE: DNA
<213> ORGANISM: Solanum lycopersicum

<400> SEQUENCE: 823
acttaatcca agaaagagag gaaattgtgg cttgtggaat ttcaaatcaa caataacccc      60
aaaaagaact gctaaaaacc gtaagcaaga taccacagag a                         101

<210> SEQ ID NO 824
<211> LENGTH: 101
<212> TYPE: DNA
<213> ORGANISM: Solanum lycopersicum

<400> SEQUENCE: 824
gtggagctca atttggggct tatttacaga ggagcacaga tactcctgca aatgggagtt      60
gcggtagaat tgaagccacc ggagaaaacc cagtttggga a                         101

<210> SEQ ID NO 825
<211> LENGTH: 101
<212> TYPE: DNA
<213> ORGANISM: Solanum lycopersicum

<400> SEQUENCE: 825
gtggagctca atttggggct tatttacaga ggagcacaga tactcctgca catgggagtt      60
gcggtagaat tgaagccacc ggagaaaacc cagtttggga a                         101

<210> SEQ ID NO 826
<211> LENGTH: 101
<212> TYPE: DNA
<213> ORGANISM: Solanum lycopersicum

<400> SEQUENCE: 826
tccttgtctt gaatcttagc tttgacatta tcaatggtgt cagaactctc aacctcaaga      60
gtgatggtct ttccggtgag tgtcttaaca aatatctgca t                         101

<210> SEQ ID NO 827
<211> LENGTH: 101
<212> TYPE: DNA
<213> ORGANISM: Solanum lycopersicum

<400> SEQUENCE: 827
tccttgtctt gaatcttagc tttgacatta tcaatggtgt cagaactctc gacctcaaga      60
```

```
gtgatggtct ttccggtgag tgtcttaaca aatatctgca t                        101
```

```
<210> SEQ ID NO 828
<211> LENGTH: 101
<212> TYPE: DNA
<213> ORGANISM: Solanum lycopersicum

<400> SEQUENCE: 828
atatctttgt tttgcaaaac tcatgaattt aagcttgttc aagcaaacga tggaagacgg      60
aggtcgtgaa attagagtcc ctgtggcatc aagcttctcc a                        101

<210> SEQ ID NO 829
<211> LENGTH: 101
<212> TYPE: DNA
<213> ORGANISM: Solanum lycopersicum

<400> SEQUENCE: 829
atatctttgt tttgcaaaac tcatgaattt aagcttgttc aagcaaacga cggaagacgg      60
aggtcgtgaa attagagtcc ctgtggcatc aagcttctcc a                        101

<210> SEQ ID NO 830
<211> LENGTH: 101
<212> TYPE: DNA
<213> ORGANISM: Solanum lycopersicum

<400> SEQUENCE: 830
ttgaagtttg tggattttgt cagtaggatg gtacttgtta ggacccgaaa tgccaagcaa      60
ctcgcgtctc atgatcataa gagcaatatc gtcaattata a                        101

<210> SEQ ID NO 831
<211> LENGTH: 101
<212> TYPE: DNA
<213> ORGANISM: Solanum lycopersicum

<400> SEQUENCE: 831
ttgaagtttg tggattttgt cagtaggatg gtacttgtta ggacccgaaa cgccaagcaa      60
ctcgcgtctc atgatcataa gagcaatatc gtcaattata a                        101

<210> SEQ ID NO 832
<211> LENGTH: 101
<212> TYPE: DNA
<213> ORGANISM: Solanum lycopersicum

<400> SEQUENCE: 832
tagtttgatt gtttgatcaa gcagcaagaa caagtgcttt tattgtccct tgactgtttg      60
ctgtaacaat ggttgggctg tcacgtttcc aacaaacagc a                        101

<210> SEQ ID NO 833
<211> LENGTH: 101
<212> TYPE: DNA
<213> ORGANISM: Solanum lycopersicum

<400> SEQUENCE: 833
tagtttgatt gtttgatcaa gcagcaagaa caagtgcttt tattgtccct cgactgtttg      60
ctgtaacaat ggttgggctg tcacgtttcc aacaaacagc a                        101

<210> SEQ ID NO 834
<211> LENGTH: 101
<212> TYPE: DNA
<213> ORGANISM: Solanum lycopersicum
```

-continued

<400> SEQUENCE: 834
atagagcaaa gaaccctgac cattctaagc agcaaccacc tcttgagcac atctagactc          60
caaccatgat gtagctgcaa ccttcgtggt caaaaaccac c                             101

<210> SEQ ID NO 835
<211> LENGTH: 101
<212> TYPE: DNA
<213> ORGANISM: Solanum lycopersicum

<400> SEQUENCE: 835
atagagcaaa gaaccctgac cattctaagc agcaaccacc tcttgagcac gtctagactc          60
caaccatgat gtagctgcaa ccttcgtggt caaaaaccac c                             101

<210> SEQ ID NO 836
<211> LENGTH: 101
<212> TYPE: DNA
<213> ORGANISM: Solanum lycopersicum

<400> SEQUENCE: 836
gcaacctcaa cttctaattg tttctctgtg tcacggactg aagtagttgg tgatgagtca          60
aattgctcgt ccacatcttg gacaactgac acatctggga t                             101

<210> SEQ ID NO 837
<211> LENGTH: 101
<212> TYPE: DNA
<213> ORGANISM: Solanum lycopersicum

<400> SEQUENCE: 837
gcaacctcaa cttctaattg tttctctgtg tcacggactg aagtagttgg cgatgagtca          60
aattgctcgt ccacatcttg gacaactgac acatctggga t                             101

<210> SEQ ID NO 838
<211> LENGTH: 101
<212> TYPE: DNA
<213> ORGANISM: Solanum lycopersicum

<400> SEQUENCE: 838
tcaaatgagg agcaaaaatt gggtttaaac accaaaaaaa tgcagcagca acagcagcct          60
taaaaggccg aaactgaaga gcaaaaaatg ggtttaaact c                             101

<210> SEQ ID NO 839
<211> LENGTH: 101
<212> TYPE: DNA
<213> ORGANISM: Solanum lycopersicum

<400> SEQUENCE: 839
tcaaatgagg agcaaaaatt gggtttaaac accaaaaaaa tgcagcagca gcagcagcct          60
taaaaggccg aaactgaaga gcaaaaaatg ggtttaaact c                             101

<210> SEQ ID NO 840
<211> LENGTH: 101
<212> TYPE: DNA
<213> ORGANISM: Solanum lycopersicum

<400> SEQUENCE: 840
cccattacca acacagtggc atcagcatgc cttgcagcca cttctgctaa tccaaagttt          60
tgattccctg gacaagctac tcccatacat ccttgttggt g                             101

-continued

```
<210> SEQ ID NO 841
<211> LENGTH: 101
<212> TYPE: DNA
<213> ORGANISM: Solanum lycopersicum

<400> SEQUENCE: 841
cccattacca acacagtggc atcagcatgc cttgcagcca cttctgctaa cccaaagttt      60
tgattccctg acaagctac tcccatacat ccttgttggt g                         101

<210> SEQ ID NO 842
<211> LENGTH: 101
<212> TYPE: DNA
<213> ORGANISM: Solanum lycopersicum

<400> SEQUENCE: 842
gctttaaagg gtcctaaaga tgtctctgat ggcctaagga aacttgataa actaatagag      60
aaaagtgatg gaccagaaaa gttccagctt gctcgtggac t                        101

<210> SEQ ID NO 843
<211> LENGTH: 101
<212> TYPE: DNA
<213> ORGANISM: Solanum lycopersicum

<400> SEQUENCE: 843
gctttaaagg gtcctaaaga tgtctctgat ggcctaagga aacttgataa gctaatagag      60
aaaagtgatg gaccagaaaa gttccagctt gctcgtggac t                        101

<210> SEQ ID NO 844
<211> LENGTH: 101
<212> TYPE: DNA
<213> ORGANISM: Solanum lycopersicum

<400> SEQUENCE: 844
ttctcaagtc atcccactca ttatagttat cattccacac atcatccagg acaacaagaa      60
acttcttccc ttcgggcttt ctttcaattg acctatagct t                        101

<210> SEQ ID NO 845
<211> LENGTH: 101
<212> TYPE: DNA
<213> ORGANISM: Solanum lycopersicum

<400> SEQUENCE: 845
ttctcaagtc atcccactca ttatagttat cattccacac atcatccagg gcaacaagaa      60
acttcttccc ttcgggcttt ctttcaattg acctatagct t                        101

<210> SEQ ID NO 846
<211> LENGTH: 101
<212> TYPE: DNA
<213> ORGANISM: Solanum lycopersicum

<400> SEQUENCE: 846
tattaggaga caggtgtgat ttcacctctg gaataatttt cttgtgaaac tgacgatcat      60
catgagattc aacaaaacgc tgggtcatat tggaggcttg a                        101

<210> SEQ ID NO 847
<211> LENGTH: 101
<212> TYPE: DNA
<213> ORGANISM: Solanum lycopersicum

<400> SEQUENCE: 847
```

-continued

```
tattaggaga caggtgtgat ttcacctctg gaataatttt cttgtgaaac cgacgatcat      60
catgagattc aacaaaacgc tgggtcatat tggaggcttg a                        101

<210> SEQ ID NO 848
<211> LENGTH: 101
<212> TYPE: DNA
<213> ORGANISM: Solanum lycopersicum

<400> SEQUENCE: 848
gatatgttgg aacaaagtcg gcacatgtcc tattacagag gagaagatgg tcactttgag      60
aaattgaaac aactctctga atcagagcag ctgaggacat t                        101

<210> SEQ ID NO 849
<211> LENGTH: 101
<212> TYPE: DNA
<213> ORGANISM: Solanum lycopersicum

<400> SEQUENCE: 849
gatatgttgg aacaaagtcg gcacatgtcc tattacagag gagaagatgg ccactttgag      60
aaattgaaac aactctctga atcagagcag ctgaggacat t                        101

<210> SEQ ID NO 850
<211> LENGTH: 101
<212> TYPE: DNA
<213> ORGANISM: Solanum lycopersicum

<400> SEQUENCE: 850
tgagtggatc tttgtcgtgt gcatctgtat gtgtgtggta catgcgtgct tttcttcatc      60
aatttagatg acagtgagac tactccaaag atcatgcatt a                        101

<210> SEQ ID NO 851
<211> LENGTH: 101
<212> TYPE: DNA
<213> ORGANISM: Solanum lycopersicum

<400> SEQUENCE: 851
tgagtggatc tttgtcgtgt gcatctgtat gtgtgtggta catgcgtgct cttcttcatc      60
aatttagatg acagtgagac tactccaaag atcatgcatt a                        101

<210> SEQ ID NO 852
<211> LENGTH: 101
<212> TYPE: DNA
<213> ORGANISM: Solanum lycopersicum

<400> SEQUENCE: 852
atactagagg gaggtatatg gcctattgtc caggtggcca acttccgcta tataccagtt      60
aggtatcagc tcctttacgt caatttcttc tgcttgcttg a                        101

<210> SEQ ID NO 853
<211> LENGTH: 101
<212> TYPE: DNA
<213> ORGANISM: Solanum lycopersicum

<400> SEQUENCE: 853
atactagagg gaggtatatg gcctattgtc caggtggcca acttccgcta cataccagtt      60
aggtatcagc tcctttacgt caatttcttc tgcttgcttg a                        101

<210> SEQ ID NO 854
```

-continued

```
<211> LENGTH: 101
<212> TYPE: DNA
<213> ORGANISM: Solanum lycopersicum

<400> SEQUENCE: 854
gggtctgggg aggactttac ccctaccttg ggaggtagag agttgttttc aatagaacct      60
cggctcaaaa ctaacttgaa aagatgcttg gtattactga g                         101

<210> SEQ ID NO 855
<211> LENGTH: 101
<212> TYPE: DNA
<213> ORGANISM: Solanum lycopersicum

<400> SEQUENCE: 855
gggtctgggg aggactttac ccctaccttg ggaggtagag agttgttttc tatagaacct      60
cggctcaaaa ctaacttgaa aagatgcttg gtattactga g                         101

<210> SEQ ID NO 856
<211> LENGTH: 101
<212> TYPE: DNA
<213> ORGANISM: Solanum lycopersicum

<400> SEQUENCE: 856
gaaaactgaa gtttgtcctc caagtttatg tgataaccca attatattat tgctgtcctc      60
atcttcttca tagtgttgca aactgtgacc actcaaacta t                         101

<210> SEQ ID NO 857
<211> LENGTH: 101
<212> TYPE: DNA
<213> ORGANISM: Solanum lycopersicum

<400> SEQUENCE: 857
gaaaactgaa gtttgtcctc caagtttatg tgataaccca attatattat cgctgtcctc      60
atcttcttca tagtgttgca aactgtgacc actcaaacta t                         101

<210> SEQ ID NO 858
<211> LENGTH: 101
<212> TYPE: DNA
<213> ORGANISM: Solanum lycopersicum

<400> SEQUENCE: 858
tccaggtcct caaggccttt gcgaatactg gaattgagct tatgattggg attccaaact      60
cagacttgtt ggcgttttct caattcgagt ctaatgccaa t                         101

<210> SEQ ID NO 859
<211> LENGTH: 101
<212> TYPE: DNA
<213> ORGANISM: Solanum lycopersicum

<400> SEQUENCE: 859
tccaggtcct caaggccttt gcgaatactg gaattgagct tatgattggg gttccaaact      60
cagacttgtt ggcgttttct caattcgagt ctaatgccaa t                         101

<210> SEQ ID NO 860
<211> LENGTH: 101
<212> TYPE: DNA
<213> ORGANISM: Solanum lycopersicum

<400> SEQUENCE: 860
agaaagcatt tcatatgggc aaagctacgt ttgattttat atgttctgaa atagaatcag      60
```

-continued

```
tagtgacaaa aaaggacacg atgttacgta tggcgatacc t                    101

<210> SEQ ID NO 861
<211> LENGTH: 101
<212> TYPE: DNA
<213> ORGANISM: Solanum lycopersicum

<400> SEQUENCE: 861
agaaagcatt tcatatgggc aaagctacgt ttgattttat atgttctgaa ttagaatcag    60
tagtgacaaa aaaggacacg atgttacgta tggcgatacc t                    101

<210> SEQ ID NO 862
<211> LENGTH: 101
<212> TYPE: DNA
<213> ORGANISM: Solanum lycopersicum

<400> SEQUENCE: 862
atggcaaggg tggttgtcga cccatatttc gtatttatgg acaggatcca ttcatagttt    60
ctgatcggtc tccgaaaagc ttgttctcaa cacaaaagaa a                    101

<210> SEQ ID NO 863
<211> LENGTH: 101
<212> TYPE: DNA
<213> ORGANISM: Solanum lycopersicum

<400> SEQUENCE: 863
atggcaaggg tggttgtcga cccatatttc gtatttatgg acaggatcca ctcatagttt    60
ctgatcggtc tccgaaaagc ttgttctcaa cacaaaagaa a                    101

<210> SEQ ID NO 864
<211> LENGTH: 101
<212> TYPE: DNA
<213> ORGANISM: Solanum lycopersicum

<400> SEQUENCE: 864
tctctaattg aaaaaccttg tccacctcca cctccacctc caccacttcc tgagaagcat    60
gtgaaggaag atttttctct aaccgaaaaa ctatgtccac c                    101

<210> SEQ ID NO 865
<211> LENGTH: 101
<212> TYPE: DNA
<213> ORGANISM: Solanum lycopersicum

<400> SEQUENCE: 865
tctctaattg aaaaaccttg tccacctcca cctccacctc caccacttcc cgagaagcat    60
gtgaaggaag atttttctct aaccgaaaaa ctatgtccac c                    101

<210> SEQ ID NO 866
<211> LENGTH: 101
<212> TYPE: DNA
<213> ORGANISM: Solanum lycopersicum

<400> SEQUENCE: 866
gagcttcacg aagttatggc aagcaaaacg aagatttact tcgccatgga atacgttaaa    60
ggcggtgaat tgttcgaaaa agtagctaaa ggtaagctta g                    101

<210> SEQ ID NO 867
<211> LENGTH: 101
<212> TYPE: DNA
```

-continued

<213> ORGANISM: Solanum lycopersicum

<400> SEQUENCE: 867
gagcttcacg aagttatggc aagcaaaacg aagatttact tcgccatgga gtacgttaaa        60
ggcggtgaat tgttcgaaaa agtagctaaa ggtaagctta g                          101

<210> SEQ ID NO 868
<211> LENGTH: 101
<212> TYPE: DNA
<213> ORGANISM: Solanum lycopersicum

<400> SEQUENCE: 868
tactatatct actactaatc ttggtccttc attcacttga gatgtctttg tgtagacctc        60
cacttcctcg acttctgctg aataacgtct cgtgtatgag a                          101

<210> SEQ ID NO 869
<211> LENGTH: 101
<212> TYPE: DNA
<213> ORGANISM: Solanum lycopersicum

<400> SEQUENCE: 869
tactatatct actactaatc ttggtccttc attcacttga gatgtctttg cgtagacctc        60
cacttcctcg acttctgctg aataacgtct cgtgtatgag a                          101

<210> SEQ ID NO 870
<211> LENGTH: 101
<212> TYPE: DNA
<213> ORGANISM: Solanum lycopersicum

<400> SEQUENCE: 870
caacaatata gggacgaggt caataacaac gagcacaaca acaacaacaa taatagtaac        60
gtttgggatc agagtgaaaa atacaaagcg gatattttaa a                          101

<210> SEQ ID NO 871
<211> LENGTH: 101
<212> TYPE: DNA
<213> ORGANISM: Solanum lycopersicum

<400> SEQUENCE: 871
caacaatata gggacgaggt caataacaac gagcacaaca acaacaacaa caatagtaac        60
gtttgggatc agagtgaaaa atacaaagcg gatattttaa a                          101

<210> SEQ ID NO 872
<211> LENGTH: 101
<212> TYPE: DNA
<213> ORGANISM: Solanum lycopersicum

<400> SEQUENCE: 872
ataataggag gccaacaagc cttataagac gcaactcgtg ctcttggtga tcctccctta        60
gctgttccat tgccatatcc gaaaatgtta gctccctcga c                          101

<210> SEQ ID NO 873
<211> LENGTH: 101
<212> TYPE: DNA
<213> ORGANISM: Solanum lycopersicum

<400> SEQUENCE: 873
ataataggag gccaacaagc cttataagac gcaactcgtg ctcttggtga ccctccctta        60
gctgttccat tgccatatcc gaaaatgtta gctccctcga c                          101

-continued

```
<210> SEQ ID NO 874
<211> LENGTH: 101
<212> TYPE: DNA
<213> ORGANISM: Solanum lycopersicum

<400> SEQUENCE: 874
cttgccaaac aagagtataa gttccacaat ggaaatgcca agagcagggg tcttctcaca      60
gcagcaagga accaggaatt ttcaatctgg aagttcaccg c                         101

<210> SEQ ID NO 875
<211> LENGTH: 101
<212> TYPE: DNA
<213> ORGANISM: Solanum lycopersicum

<400> SEQUENCE: 875
cttgccaaac aagagtataa gttccacaat ggaaatgcca agagcagggg ccttctcaca      60
gcagcaagga accaggaatt ttcaatctgg aagttcaccg c                         101

<210> SEQ ID NO 876
<211> LENGTH: 101
<212> TYPE: DNA
<213> ORGANISM: Solanum lycopersicum

<400> SEQUENCE: 876
attcagattt cgagctacaa cttttcttac tttccagtat cctctactgc ttgaacccga      60
gatttaacgt ctgattcgga cattggatcc cgaattgatc c                         101

<210> SEQ ID NO 877
<211> LENGTH: 101
<212> TYPE: DNA
<213> ORGANISM: Solanum lycopersicum

<400> SEQUENCE: 877
attcagattt cgagctacaa cttttcttac tttccagtat cctctactgc ctgaacccga      60
gatttaacgt ctgattcgga cattggatcc cgaattgatc c                         101

<210> SEQ ID NO 878
<211> LENGTH: 101
<212> TYPE: DNA
<213> ORGANISM: Solanum lycopersicum

<400> SEQUENCE: 878
catttagttc acactgatct gatcagctgc taaacacgcg agtacaagga agcagaggta      60
acatttcaga ttattcactt tcgagtacat tctgtctaag a                         101

<210> SEQ ID NO 879
<211> LENGTH: 101
<212> TYPE: DNA
<213> ORGANISM: Solanum lycopersicum

<400> SEQUENCE: 879
catttagttc acactgatct gatcagctgc taaacacgcg agtacaagga ggcagaggta      60
acatttcaga ttattcactt tcgagtacat tctgtctaag a                         101

<210> SEQ ID NO 880
<211> LENGTH: 101
<212> TYPE: DNA
<213> ORGANISM: Solanum lycopersicum
```

-continued

```
<400> SEQUENCE: 880
ttaacaatac cagcattaat gttgaacaga tcatcacggg tcataccagg tttccgtggc    60
acaccagctg gaataatgac aacatcagct ccctccaaag c                       101

<210> SEQ ID NO 881
<211> LENGTH: 101
<212> TYPE: DNA
<213> ORGANISM: Solanum lycopersicum

<400> SEQUENCE: 881
ttaacaatac cagcattaat gttgaacaga tcatcacggg tcataccagg cttccgtggc    60
acaccagctg gaataatgac aacatcagct ccctccaaag c                       101

<210> SEQ ID NO 882
<211> LENGTH: 101
<212> TYPE: DNA
<213> ORGANISM: Solanum lycopersicum

<400> SEQUENCE: 882
caatccaagt ttacattata aagatctgga agaagcctac ttgtggaagt aacattttca    60
tctttaccag gtacagatac tgagactgaa gaatcactcc a                       101

<210> SEQ ID NO 883
<211> LENGTH: 101
<212> TYPE: DNA
<213> ORGANISM: Solanum lycopersicum

<400> SEQUENCE: 883
caatccaagt ttacattata aagatctgga agaagcctac ttgtggaagt tacattttca    60
tctttaccag gtacagatac tgagactgaa gaatcactcc a                       101

<210> SEQ ID NO 884
<211> LENGTH: 101
<212> TYPE: DNA
<213> ORGANISM: Solanum lycopersicum

<400> SEQUENCE: 884
ttaaaatttg ttcattttgc ttggtagtga agttgaggcc tccgttaatc tgtggtcatc    60
aaacccgatt cttaacatac ctcatatatt tggcagaaga g                       101

<210> SEQ ID NO 885
<211> LENGTH: 101
<212> TYPE: DNA
<213> ORGANISM: Solanum lycopersicum

<400> SEQUENCE: 885
ttaaaatttg ttcattttgc ttggtagtga agttgaggcc tccgttaatc cgtggtcatc    60
aaacccgatt cttaacatac ctcatatatt tggcagaaga g                       101

<210> SEQ ID NO 886
<211> LENGTH: 101
<212> TYPE: DNA
<213> ORGANISM: Solanum lycopersicum

<400> SEQUENCE: 886
cagggtggtt tgcatggcta ttttccgtca tctaaggttc ttgtttggtg tgattccaag    60
tgatcacggt gcaaccgaga ctactgtgaa ccttggaagg a                       101
```

-continued

<210> SEQ ID NO 887
<211> LENGTH: 101
<212> TYPE: DNA
<213> ORGANISM: Solanum lycopersicum

<400> SEQUENCE: 887
cagggtggtt tgcatggcta ttttccgtca tctaaggttc ttgtttggtg ggattccaag      60
tgatcacggt gcaaccgaga ctactgtgaa ccttggaagg a                          101

<210> SEQ ID NO 888
<211> LENGTH: 101
<212> TYPE: DNA
<213> ORGANISM: Solanum lycopersicum

<400> SEQUENCE: 888
aataaaaaaa caaatcaaat cgacaaacaa tacatatctg gttaactgag tgaagatgag      60
atgccattct tgttgccact gacagacgag ggttttccaa c                          101

<210> SEQ ID NO 889
<211> LENGTH: 101
<212> TYPE: DNA
<213> ORGANISM: Solanum lycopersicum

<400> SEQUENCE: 889
aataaaaaaa caaatcaaat cgacaaacaa tacatatctg gttaactgag cgaagatgag      60
atgccattct tgttgccact gacagacgag ggttttccaa c                          101

<210> SEQ ID NO 890
<211> LENGTH: 101
<212> TYPE: DNA
<213> ORGANISM: Solanum lycopersicum

<400> SEQUENCE: 890
cagagagacc ggccagcatt gggaaccaaa aatgctctgt gacgtcacac ctctcatctt      60
cagtagtgtc aactggcttc agagcaccac caggtataag a                          101

<210> SEQ ID NO 891
<211> LENGTH: 101
<212> TYPE: DNA
<213> ORGANISM: Solanum lycopersicum

<400> SEQUENCE: 891
cagagagacc ggccagcatt gggaaccaaa aatgctctgt gacgtcacac gtctcatctt      60
cagtagtgtc aactggcttc agagcaccac caggtataag a                          101

<210> SEQ ID NO 892
<211> LENGTH: 101
<212> TYPE: DNA
<213> ORGANISM: Solanum lycopersicum

<400> SEQUENCE: 892
gaactaggag caggacatcc aagaagagca aagctttcag tattagtggt atcaataact      60
tcacttgtaa ttggtgcatt attgacaata ttactcttac t                          101

<210> SEQ ID NO 893
<211> LENGTH: 101
<212> TYPE: DNA
<213> ORGANISM: Solanum lycopersicum

<400> SEQUENCE: 893

-continued

```
gaactaggag caggacatcc aagaagagca aagctttcag tattagtggt gtcaataact          60
tcacttgtaa ttggtgcatt attgacaata ttactcttac t                            101

<210> SEQ ID NO 894
<211> LENGTH: 101
<212> TYPE: DNA
<213> ORGANISM: Solanum lycopersicum

<400> SEQUENCE: 894
tagagggtct tcaggagata aaggtagtcc gagtcaaact gtatcaagct tccatgcaac          60
accatatgaa gttccattac aaacccagaa tagatttctt t                            101

<210> SEQ ID NO 895
<211> LENGTH: 101
<212> TYPE: DNA
<213> ORGANISM: Solanum lycopersicum

<400> SEQUENCE: 895
tagagggtct tcaggagata aaggtagtcc gagtcaaact gtatcaagct cccatgcaac          60
accatatgaa gttccattac aaacccagaa tagatttctt t                            101

<210> SEQ ID NO 896
<211> LENGTH: 101
<212> TYPE: DNA
<213> ORGANISM: Solanum lycopersicum

<400> SEQUENCE: 896
gaggacatta tggagcgcat aacagccatg aacttgatga aacctcaaaa atgtaggctc          60
aaacgaacac caagtcatcc tcgaaaacag aaacaagtaa g                            101

<210> SEQ ID NO 897
<211> LENGTH: 101
<212> TYPE: DNA
<213> ORGANISM: Solanum lycopersicum

<400> SEQUENCE: 897
gaggacatta tggagcgcat aacagccatg aacttgatga aacctcaaaa ctgtaggctc          60
aaacgaacac caagtcatcc tcgaaaacag aaacaagtaa g                            101

<210> SEQ ID NO 898
<211> LENGTH: 101
<212> TYPE: DNA
<213> ORGANISM: Solanum lycopersicum

<400> SEQUENCE: 898
gatgaaagcc ctggcagaaa atcaattgtg ttctctcaat tcaggaagtt tttgctccta          60
cttgaagagc cgcttaaagc agctggtttt aagatattgc g                            101

<210> SEQ ID NO 899
<211> LENGTH: 101
<212> TYPE: DNA
<213> ORGANISM: Solanum lycopersicum

<400> SEQUENCE: 899
gatgaaagcc ctggcagaaa atcaattgtg ttctctcaat tcaggaagtt gttgctccta          60
cttgaagagc cgcttaaagc agctggtttt aagatattgc g                            101

<210> SEQ ID NO 900
<211> LENGTH: 101
```

```
<212> TYPE: DNA
<213> ORGANISM: Solanum lycopersicum

<400> SEQUENCE: 900
taacatctat ggtacgtttc aaagcacgcc aaagaattag tgcaaagaca actttagcac      60
atccatactt tgatagagaa ggtcttctag ccctgtcctt c                         101

<210> SEQ ID NO 901
<211> LENGTH: 101
<212> TYPE: DNA
<213> ORGANISM: Solanum lycopersicum

<400> SEQUENCE: 901
taacatctat ggtacgtttc aaagcacgcc aaagaattag tgcaaagaca gctttagcac      60
atccatactt tgatagagaa ggtcttctag ccctgtcctt c                         101

<210> SEQ ID NO 902
<211> LENGTH: 101
<212> TYPE: DNA
<213> ORGANISM: Solanum lycopersicum

<400> SEQUENCE: 902
ctttcttgag cctagctgcc tgaatgtcat caaacatgtg tgtccttctc tccttccttg      60
ttagcatgaa atatatatgt atacatctgt ttattttgtc t                         101

<210> SEQ ID NO 903
<211> LENGTH: 101
<212> TYPE: DNA
<213> ORGANISM: Solanum lycopersicum

<400> SEQUENCE: 903
ctttcttgag cctagctgcc tgaatgtcat caaacatgtg tgtccttctc cccttccttg      60
ttagcatgaa atatatatgt atacatctgt ttattttgtc t                         101

<210> SEQ ID NO 904
<211> LENGTH: 101
<212> TYPE: DNA
<213> ORGANISM: Solanum lycopersicum

<400> SEQUENCE: 904
caataggaac agaaattgat gggcactaag ctgtcacatc aaatgtaatg aaagctgtcc      60
aatgttcaac gtgttggcca cttatgcctt atcaagaaat a                         101

<210> SEQ ID NO 905
<211> LENGTH: 101
<212> TYPE: DNA
<213> ORGANISM: Solanum lycopersicum

<400> SEQUENCE: 905
caataggaac agaaattgat gggcactaag ctgtcacatc aaatgtaatg taagctgtcc      60
aatgttcaac gtgttggcca cttatgcctt atcaagaaat a                         101

<210> SEQ ID NO 906
<211> LENGTH: 101
<212> TYPE: DNA
<213> ORGANISM: Solanum lycopersicum

<400> SEQUENCE: 906
agggaggttg tttccgatag tcccatagtt tattccgaca ccatgaacat tgtagttaat      60
```

```
aagagagagg agaatgaaga gggataagac aagagtacaa a                        101

<210> SEQ ID NO 907
<211> LENGTH: 101
<212> TYPE: DNA
<213> ORGANISM: Solanum lycopersicum

<400> SEQUENCE: 907
agggaggttg tttccgatag tcccatagtt tattccgaca ccatgaacat cgtagttaat    60
aagagagagg agaatgaaga gggataagac aagagtacaa a                        101

<210> SEQ ID NO 908
<211> LENGTH: 101
<212> TYPE: DNA
<213> ORGANISM: Solanum lycopersicum

<400> SEQUENCE: 908
gaaaaggagc atcgaagcaa cagtaaagtt gtctctgagt gaattatagg taaggggttt    60
aagccgtcag aatagtcact aatacttgta attaggatag a                        101

<210> SEQ ID NO 909
<211> LENGTH: 101
<212> TYPE: DNA
<213> ORGANISM: Solanum lycopersicum

<400> SEQUENCE: 909
gaaaaggagc atcgaagcaa cagtaaagtt gtctctgagt gaattatagg caaggggttt    60
aagccgtcag aatagtcact aatacttgta attaggatag a                        101

<210> SEQ ID NO 910
<211> LENGTH: 101
<212> TYPE: DNA
<213> ORGANISM: Solanum lycopersicum

<400> SEQUENCE: 910
cagcggttga tgaaactgaa ctgctaggaa catctgacac ttctcctgcc acagttccca    60
catctttctt tttggtcatg aaaagataag ctacataaat t                        101

<210> SEQ ID NO 911
<211> LENGTH: 101
<212> TYPE: DNA
<213> ORGANISM: Solanum lycopersicum

<400> SEQUENCE: 911
cagcggttga tgaaactgaa ctgctaggaa catctgacac ttctcctgcc tcagttccca    60
catctttctt tttggtcatg aaaagataag ctacataaat t                        101

<210> SEQ ID NO 912
<211> LENGTH: 101
<212> TYPE: DNA
<213> ORGANISM: Solanum lycopersicum

<400> SEQUENCE: 912
aacttcactg aaacttcaat caaaaaaacc atcttcttcg gtaacccaac aaacaaactt    60
ctcagagtat tgccggtgca tctgcttact cactttagca t                        101

<210> SEQ ID NO 913
<211> LENGTH: 101
<212> TYPE: DNA
<213> ORGANISM: Solanum lycopersicum
```

-continued

```
<400> SEQUENCE: 913
aacttcactg aaacttcaat caaaaaaacc atcttcttcg gtaacccaac gaacaaactt        60
ctcagagtat tgccggtgca tctgcttact cactttagca t                          101

<210> SEQ ID NO 914
<211> LENGTH: 101
<212> TYPE: DNA
<213> ORGANISM: Solanum lycopersicum

<400> SEQUENCE: 914
cacctctata ctgctgtaga caagcagagt ccaatccaga ggatgtttct aagaacactt        60
gttagacaat caacatcaga tgacagttta ctagcgtatc a                          101

<210> SEQ ID NO 915
<211> LENGTH: 101
<212> TYPE: DNA
<213> ORGANISM: Solanum lycopersicum

<400> SEQUENCE: 915
cacctctata ctgctgtaga caagcagagt ccaatccaga ggatgtttct cagaacactt        60
gttagacaat caacatcaga tgacagttta ctagcgtatc a                          101

<210> SEQ ID NO 916
<211> LENGTH: 101
<212> TYPE: DNA
<213> ORGANISM: Solanum lycopersicum

<400> SEQUENCE: 916
gttcttcagc ttacgttctt cagctcagca acagttcgtc cgcaagagct aagctcagct        60
cagctcttca gtcttctgct tcctctcttc gatcttcagt a                          101

<210> SEQ ID NO 917
<211> LENGTH: 101
<212> TYPE: DNA
<213> ORGANISM: Solanum lycopersicum

<400> SEQUENCE: 917
gttcttcagc ttacgttctt cagctcagca acagttcgtc cgcaagagct gagctcagct        60
cagctcttca gtcttctgct tcctctcttc gatcttcagt a                          101

<210> SEQ ID NO 918
<211> LENGTH: 101
<212> TYPE: DNA
<213> ORGANISM: Solanum lycopersicum

<400> SEQUENCE: 918
cctgttttat ttgttggaca tctttcgaaa acttccacct tgatcataga taaaccttgg        60
attcaagtgg ttaaaactct tgatgctcaa ccagttcaca g                          101

<210> SEQ ID NO 919
<211> LENGTH: 101
<212> TYPE: DNA
<213> ORGANISM: Solanum lycopersicum

<400> SEQUENCE: 919
cctgttttat ttgttggaca tctttcgaaa acttccacct tgatcataga caaaccttgg        60
attcaagtgg ttaaaactct tgatgctcaa ccagttcaca g                          101
```

```
<210> SEQ ID NO 920
<211> LENGTH: 101
<212> TYPE: DNA
<213> ORGANISM: Solanum lycopersicum

<400> SEQUENCE: 920
tatccaggga ttaagggcga aggtcctgaa tcaggtgaga agtctctccg aagaggctgg      60
aggcaaaggg tctgccaaga aggacctaaa cagtcaaaga a                        101

<210> SEQ ID NO 921
<211> LENGTH: 101
<212> TYPE: DNA
<213> ORGANISM: Solanum lycopersicum

<400> SEQUENCE: 921
tatccaggga ttaagggcga aggtcctgaa tcaggtgaga agtctctccg tagaggctgg      60
aggcaaaggg tctgccaaga aggacctaaa cagtcaaaga a                        101

<210> SEQ ID NO 922
<211> LENGTH: 101
<212> TYPE: DNA
<213> ORGANISM: Solanum lycopersicum

<400> SEQUENCE: 922
tccgaaactg ttgaagtgtc tgcactattc atattttgat tcgaaccaac tgaaccttca      60
agccatacag ttggatttct tgacgccttt gtactggcac g                        101

<210> SEQ ID NO 923
<211> LENGTH: 101
<212> TYPE: DNA
<213> ORGANISM: Solanum lycopersicum

<400> SEQUENCE: 923
tccgaaactg ttgaagtgtc tgcactattc atattttgat tcgaaccaac cgaaccttca      60
agccatacag ttggatttct tgacgccttt gtactggcac g                        101

<210> SEQ ID NO 924
<211> LENGTH: 101
<212> TYPE: DNA
<213> ORGANISM: Solanum lycopersicum

<400> SEQUENCE: 924
gcaatcgggt atgggcaacg agtgcccata cgatttaagg ttgcggggcg agtggatata      60
aatttggtca cggtaacaat ggttgcacct ggatttaaca c                        101

<210> SEQ ID NO 925
<211> LENGTH: 101
<212> TYPE: DNA
<213> ORGANISM: Solanum lycopersicum

<400> SEQUENCE: 925
gcaatcgggt atgggcaacg agtgcccata cgatttaagg ttgcggggcg ggtggatata      60
aatttggtca cggtaacaat ggttgcacct ggatttaaca c                        101

<210> SEQ ID NO 926
<211> LENGTH: 101
<212> TYPE: DNA
<213> ORGANISM: Solanum lycopersicum

<400> SEQUENCE: 926
```

-continued

```
aaccaatggc cccaacctag gtgagagaac tcaggcaaac cagagagagg agatgggacg        60
tttgcaggat gtgaaggatg atttagtgtt ccggcaactt c                         101

<210> SEQ ID NO 927
<211> LENGTH: 101
<212> TYPE: DNA
<213> ORGANISM: Solanum lycopersicum

<400> SEQUENCE: 927
aaccaatggc cccaacctag gtgagagaac tcaggcaaac cagagagagg ggatgggacg        60
tttgcaggat gtgaaggatg atttagtgtt ccggcaactt c                         101

<210> SEQ ID NO 928
<211> LENGTH: 101
<212> TYPE: DNA
<213> ORGANISM: Solanum lycopersicum

<400> SEQUENCE: 928
caacaacaca aaaatggttt acgcacacgc catgggttag aaaataatca agaatttcaa        60
catcaaccgt ataaaaatgg tttaggccca cgtcacgggt t                         101

<210> SEQ ID NO 929
<211> LENGTH: 101
<212> TYPE: DNA
<213> ORGANISM: Solanum lycopersicum

<400> SEQUENCE: 929
caacaacaca aaaatggttt acgcacacgc catgggttag aaaataatca ggaatttcaa        60
catcaaccgt ataaaaatgg tttaggccca cgtcacgggt t                         101

<210> SEQ ID NO 930
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 930
tgtggcctgg agagggtagg                                                  20

<210> SEQ ID NO 931
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 931
tctccaccct tcaaaggtag agg                                              23

<210> SEQ ID NO 932
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 932
gatctgttgt acttctttct tgcagc                                           26
```

<210> SEQ ID NO 933
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 933
gtcgaaatta ttgattccta aatcttttcg tg                                       32

<210> SEQ ID NO 934
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 934
ggaggaaaaa gatacccttt gttgc                                               25

<210> SEQ ID NO 935
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 935
cttgcatccc ttcaaaaatg gcaa                                                24

<210> SEQ ID NO 936
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 936
gtggtgaggc tggaaatgta atcc                                                24

<210> SEQ ID NO 937
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 937
acgtcaagaa ccggaatgtt cc                                                  22

<210> SEQ ID NO 938
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 938
ccactataca agatggaggc tggtaag                                             27

-continued

```
<210> SEQ ID NO 939
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 939
atgtcctcat acctacattg caaaatc                                          27

<210> SEQ ID NO 940
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 940
cgcgtaacat ttgtgtccaa cg                                               22

<210> SEQ ID NO 941
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 941
gacagacaac agtacaatga tagcttgg                                         28

<210> SEQ ID NO 942
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 942
gacagtaaga tggagaattt tgttcctg                                         28

<210> SEQ ID NO 943
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 943
ctccacgcct ccatttctcg                                                  20

<210> SEQ ID NO 944
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 944
agtgaagata gcctccaagc atttc                                            25
```

-continued

```
<210> SEQ ID NO 945
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 945
atgttcgggg gtaatctcac tcc                                                 23

<210> SEQ ID NO 946
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 946
aacaacaaca acggggccc                                                      19

<210> SEQ ID NO 947
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 947
ggttgttgtt gttattgtta tcaaactgg                                           29

<210> SEQ ID NO 948
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 948
cccattgaac agcatggcaa tg                                                  22

<210> SEQ ID NO 949
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 949
ttagcaggaa tttccatcat tgcg                                                24

<210> SEQ ID NO 950
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 950
gctttgtgat taggtaaagg tgatcac                                             27

<210> SEQ ID NO 951
```

-continued

```
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 951
accatcttcg ccatccttgt ct                                            22

<210> SEQ ID NO 952
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 952
tttcgcttgt gcctcttctc cc                                            22

<210> SEQ ID NO 953
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 953
cccgttgcat tcctcttaca ctag                                          24

<210> SEQ ID NO 954
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 954
cagaaacaac tgcatccact gaag                                          24

<210> SEQ ID NO 955
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 955
actggaatat tctctacccc taatatttct g                                  31

<210> SEQ ID NO 956
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 956
gtcgtctcat ggatgatgat atctctaag                                     29

<210> SEQ ID NO 957
<211> LENGTH: 23
```

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 957
gcagatgcat cagttctgga aac                                                      23

<210> SEQ ID NO 958
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 958
gctgaacttc ttgccacctt ctg                                                      23

<210> SEQ ID NO 959
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 959
tcttcaatag cttcatcact caatttctca c                                             31

<210> SEQ ID NO 960
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 960
gagctgaagc agagtttccc ac                                                       22

<210> SEQ ID NO 961
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 961
caggacacaa ctggcatact tttg                                                     24

<210> SEQ ID NO 962
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 962
gtggaaggaa gtacagagaa gaagc                                                    25

<210> SEQ ID NO 963
<211> LENGTH: 24
<212> TYPE: DNA

<213> ORGANISM: Artificial Sequence
<220> FEATURE:
<223> OTHER INFORMATION: Description of Artificial Sequence: Synthetic
      primer

<400> SEQUENCE: 963
gctctggaaa aaacaatctc ccac                                            24

<210> SEQ ID NO 964
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 964
acaggaacat cgtcaacacc ttg                                             23

<210> SEQ ID NO 965
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 965
ttctggcgaa aatagttcct ccac                                            24

<210> SEQ ID NO 966
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 966
tgaagacatc aatgattgac agtgct                                          26

<210> SEQ ID NO 967
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 967
taggagcttc ttcccaccct gg                                              22

<210> SEQ ID NO 968
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 968
ttcatcttga gggagctcac atg                                             23

<210> SEQ ID NO 969
<211> LENGTH: 23
<212> TYPE: DNA
<213> ORGANISM: Artificial Sequence -continued

```
<220> FEATURE:
<223> OTHER INFORMATION: Description of Artificial Sequence: Synthetic
      primer

<400> SEQUENCE: 969
caccagctga tctgaaatcg ggg                                             23

<210> SEQ ID NO 970
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 970
aactctgtgt ggcctgacaa tg                                              22

<210> SEQ ID NO 971
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 971
gggaaattta ttttctgact gaacttttct c                                    31

<210> SEQ ID NO 972
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 972
tgtccaagta tccctcattg tggg                                            24

<210> SEQ ID NO 973
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 973
ttctacttca cagaactcat cggtc                                           25

<210> SEQ ID NO 974
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 974
acaatggcaa tttggagcaa tgg                                             23

<210> SEQ ID NO 975
<211> LENGTH: 25
<212> TYPE: DNA
<213> ORGANISM: Artificial Sequence
<220> FEATURE:
```

-continued

<223> OTHER INFORMATION: Description of Artificial Sequence: Synthetic
     primer

<400> SEQUENCE: 975
tcagtctgat ttcccaagtt agagg                                        25

<210> SEQ ID NO 976
<211> LENGTH: 27
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 976
cactgtgaag agaatatgat gagagga                                      27

<210> SEQ ID NO 977
<211> LENGTH: 26
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 977
gctctagcaa ataatgtcaa tgtgca                                       26

<210> SEQ ID NO 978
<211> LENGTH: 30
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 978
caactactaa acggtcaatt ttaagtgagc                                   30

<210> SEQ ID NO 979
<211> LENGTH: 31
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 979
tgttttctgg tttgatattt agagaaatgg g                                 31

<210> SEQ ID NO 980
<211> LENGTH: 24
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 980
cactgaagca ttagcctttg tctc                                         24

<210> SEQ ID NO 981
<211> LENGTH: 23
<212> TYPE: DNA
<213> ORGANISM: Artificial Sequence
<220> FEATURE:
<223> OTHER INFORMATION: Description of Artificial Sequence: Synthetic -continued primer

<400> SEQUENCE: 981
ggaacagaac atttggggct acc                                          23

<210> SEQ ID NO 982
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 982
atctcggcga gcttggtgac                                              20

<210> SEQ ID NO 983
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 983
cgcactctcc atggcatctt atg                                          23

<210> SEQ ID NO 984
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 984
tggtgattcc tgttcataga tttggc                                       26

<210> SEQ ID NO 985
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 985
cagtttttta tagtccatac acgaatttaa ggc                               33

<210> SEQ ID NO 986
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 986
ttcttacttc ttcaataaac ctcaggaatt c                                 31

<210> SEQ ID NO 987
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 987
atcggaatca acgtcaatgg cg                                    22

<210> SEQ ID NO 988
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 988
attggttgtt cgagtttgct cag                                   23

<210> SEQ ID NO 989
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 989
gggcatccgg atcaatgcc                                        19

<210> SEQ ID NO 990
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 990
agagtttaga tccaagactg tgaattagg                             29

<210> SEQ ID NO 991
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 991
tgacatactt tctatcttgc catgtgg                               27

<210> SEQ ID NO 992
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 992
gccaacaggg aacaagagac taaagg                                26

<210> SEQ ID NO 993
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 993
cagcttgaag ttcagcctct atcc                                          24

<210> SEQ ID NO 994
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 994
gacttgagaa taaagcgaaa ttcctctttg                                    30

<210> SEQ ID NO 995
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 995
tgtgcatgga ttcaactgtt aggttg                                        26

<210> SEQ ID NO 996
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 996
tgttgaaacc aaaattatac atagaatatc tgtcc                              35

<210> SEQ ID NO 997
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 997
gtgtaatctt caatgtccct catgagag                                      28

<210> SEQ ID NO 998
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 998
agtatcattt tgaaagatac aaagcaaaca ag                                 32

<210> SEQ ID NO 999
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 999
ttctagatat aaaaatctta caaattcgtg caag                                        34

<210> SEQ ID NO 1000
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1000
tccctggcca aacaacccc                                                        19

<210> SEQ ID NO 1001
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1001
aggcatggaa gcagatgtct tc                                                    22

<210> SEQ ID NO 1002
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1002
aaggattttg cgaaggaggc taaa                                                  24

<210> SEQ ID NO 1003
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1003
cctcttaatc ctactacatt aggatgcct                                            29

<210> SEQ ID NO 1004
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1004
caattgtcaa agactcgtaa cctgc                                                25

<210> SEQ ID NO 1005
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1005
gcaaaagaga agaaaaaaca cctgttc 27

<210> SEQ ID NO 1006
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1006
caagaggagg cagaggagtg g 21

<210> SEQ ID NO 1007
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1007
tttgcttcct tggcagcaat gc 22

<210> SEQ ID NO 1008
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1008
ggcagtacca cgaagcttga c 21

<210> SEQ ID NO 1009
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1009
aaacctttaa gaatggtgaa aactgtgc 28

<210> SEQ ID NO 1010
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1010
tgatgcaaaa gaagaatgtt gatgctg 27

<210> SEQ ID NO 1011
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1011
tcgcaaccaa tccttgtaat ctaatgg 27

-continued

```
<210> SEQ ID NO 1012
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1012
gttctgaacc agtgtaatta tgttgttctt g                                      31

<210> SEQ ID NO 1013
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1013
aggctcaaaa cccatgtcaa tcatac                                            26

<210> SEQ ID NO 1014
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1014
atcaaagagc gggaggatta agc                                               23

<210> SEQ ID NO 1015
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1015
ttgcttgttt gctactccat ttgatg                                            26

<210> SEQ ID NO 1016
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1016
gaagcaaaag tagatccaga atccag                                            26

<210> SEQ ID NO 1017
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1017
ggtcagaacc agaaatcttt tacaagc                                           27
```

-continued

```
<210> SEQ ID NO 1018
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1018
ggcaattggg agttgggcc                                                    19

<210> SEQ ID NO 1019
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1019
ggagcatcat ctcagattca ttgagc                                            26

<210> SEQ ID NO 1020
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1020
tggtgggcag gggattctg                                                    19

<210> SEQ ID NO 1021
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1021
tgtggaacaa attcaagtac tacatttcg                                         29

<210> SEQ ID NO 1022
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1022
actcttccaa acctaccgca aaaga                                             25

<210> SEQ ID NO 1023
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1023
tcctgacaac tcaagtcata tatagggg                                          28
```

-continued

```
<210> SEQ ID NO 1024
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1024
cccctctagt agccagccaa g                                                   21

<210> SEQ ID NO 1025
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1025
ggaagttttg atgcagttta catttcc                                             27

<210> SEQ ID NO 1026
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1026
ataagctttg ccattgtaag agataagatc                                          30

<210> SEQ ID NO 1027
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1027
agtctaagaa catattcaca gtccaatttg                                          30

<210> SEQ ID NO 1028
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1028
actgacaaaa aagggccttc aatgg                                               25

<210> SEQ ID NO 1029
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1029
ggcacagaga accaccaaat tc                                                  22

<210> SEQ ID NO 1030
```

-continued

```
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1030
gccagccatt tcttcgccg                                                        19

<210> SEQ ID NO 1031
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1031
gagttcctcc cctatttgat agataacg                                             28

<210> SEQ ID NO 1032
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1032
gctccgttca ttccttccta gc                                                   22

<210> SEQ ID NO 1033
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1033
gcagagtcaa gttgagaagc ttaagc                                               26

<210> SEQ ID NO 1034
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1034
cgcttgtgtt gttggtgcc                                                       19

<210> SEQ ID NO 1035
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1035
taagcttaaa ttttctaggc agcagc                                               26

<210> SEQ ID NO 1036
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1036
cagaaattcg ggtttcggtt cag                                                23

<210> SEQ ID NO 1037
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1037
aaggggtgcc attcaagtta attg                                               24

<210> SEQ ID NO 1038
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1038
attcatcaat tttttcctgc atcagtttc                                          29

<210> SEQ ID NO 1039
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1039
tcaagcgaag gcctgaagaa g                                                  21

<210> SEQ ID NO 1040
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1040
gcattatctt tcaggccaga gcg                                                23

<210> SEQ ID NO 1041
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1041
tgaactcgaa atcttgaccc ctga                                               24

<210> SEQ ID NO 1042
<211> LENGTH: 22
<212> TYPE: DNA
```

-continued

```
<213> ORGANISM: Artificial Sequence
<220> FEATURE:
<223> OTHER INFORMATION: Description of Artificial Sequence: Synthetic
      primer

<400> SEQUENCE: 1042
cttcgacgtc taaggctttt gc                                                22

<210> SEQ ID NO 1043
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1043
cagggatgcg atgagagaac aaatatg                                           27

<210> SEQ ID NO 1044
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1044
atcagcttat gaactccaaa cgttgtttg                                         29

<210> SEQ ID NO 1045
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1045
ctggtaaatg aactgatggt caaagag                                           27

<210> SEQ ID NO 1046
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1046
atccaatatc gaggcagggt tg                                                22

<210> SEQ ID NO 1047
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1047
tctcaccaga gtctgctaat ttagagtc                                          28

<210> SEQ ID NO 1048
<211> LENGTH: 26
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 1048
accacaagta cacaactaaa gctttg                                              26

<210> SEQ ID NO 1049
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1049
gttggtatgt tcgtcaagac tgaaac                                              26

<210> SEQ ID NO 1050
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1050
tgagctgata atgtactatc taaagcgg                                            28

<210> SEQ ID NO 1051
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1051
aatgttgagt tctgatatga cttcaaaaag g                                        31

<210> SEQ ID NO 1052
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1052
gttcacccaa ctcttcaatt cttgaatc                                            28

<210> SEQ ID NO 1053
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1053
acagattctc ctactttctt attcaacaag atttg                                    35

<210> SEQ ID NO 1054
<211> LENGTH: 29
<212> TYPE: DNA
<213> ORGANISM: Artificial Sequence
<220> FEATURE:
```

-continued

<223> OTHER INFORMATION: Description of Artificial Sequence: Synthetic
     primer

<400> SEQUENCE: 1054
tcacattttt cgtgcagata aagtatacc                                      29

<210> SEQ ID NO 1055
<211> LENGTH: 22
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 1055
gggagcaaag gatgagactt gc                                             22

<210> SEQ ID NO 1056
<211> LENGTH: 23
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 1056 agagtttttcc ttgggctcaa gca                                           23

<210> SEQ ID NO 1057
<211> LENGTH: 30
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 1057
aaaaattgtt tttgatcttg tcaaagtccg                                     30

<210> SEQ ID NO 1058
<211> LENGTH: 25
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 1058
gcaagggtac aattcctatc cctgg                                          25

<210> SEQ ID NO 1059
<211> LENGTH: 23
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 1059
ccaagggctc ctaggttctc ttc                                            23

<210> SEQ ID NO 1060
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 1060
ctgaacggcc aaccatttca g                                        21

<210> SEQ ID NO 1061
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1061
catgctggca gaggaagtga gag                                      23

<210> SEQ ID NO 1062
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1062
taagtttccg ttcgatgccg g                                        21

<210> SEQ ID NO 1063
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1063
tgatcaattc tcctcttccg gc                                       22

<210> SEQ ID NO 1064
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1064
tgcaagttgc tggttaagtg cc                                       22

<210> SEQ ID NO 1065
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1065
tcacccgaaa gagttaatta aacatgc                                  27

<210> SEQ ID NO 1066
<211> LENGTH: 27
<212> TYPE: DNA
<213> ORGANISM: Artificial Sequence
<220> FEATURE:
<223> OTHER INFORMATION: Description of Artificial Sequence: Synthetic
      primer 551                                                                               552

<400> SEQUENCE: 1066
tgatgggtgt tcaattattg agatgtg                                          27

<210> SEQ ID NO 1067
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1067
ggcagctttt catcttaaag tgagc                                            25

<210> SEQ ID NO 1068
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1068
gccatgtggt gagtgctgc                                                   19

<210> SEQ ID NO 1069
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1069
ttgttacagt aacccttctg cagatcc                                          27

<210> SEQ ID NO 1070
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1070
ctggggtggg aagtagggga at                                               22

<210> SEQ ID NO 1071
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1071
tatggagctc cagttcctcc cg                                               22

<210> SEQ ID NO 1072
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1072
aaatctacaa aacgaagcgg aactg                                          25

<210> SEQ ID NO 1073
<211> LENGTH: 25
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 1073
cgtcaatttc actccctaag aagcc                                          25

<210> SEQ ID NO 1074
<211> LENGTH: 27
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 1074
ctgttgcatt gtaggtctat catctgg                                        27

<210> SEQ ID NO 1075
<211> LENGTH: 30
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 1075
agaagcaatt atagaaatag ctgcaagatg                                     30

<210> SEQ ID NO 1076
<211> LENGTH: 22
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 1076
ctgagactca tcagaatccg cc                                             22

<210> SEQ ID NO 1077
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 1077
ccggcgaagg tgatggagac                                                20

<210> SEQ ID NO 1078
<211> LENGTH: 21
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 1078

-continued ctcgtggtgc aaaactcgga g                                                    21

<210> SEQ ID NO 1079
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1079
tcaaggagaa tctgttgtac gatctc                                               26

<210> SEQ ID NO 1080
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1080
gctgtgaaca ttgagacagt tgag                                                 24

<210> SEQ ID NO 1081
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1081
ctgagagcac ctgataactc actttatg                                             28

<210> SEQ ID NO 1082
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1082
aagccagaaa ttgtgattat tgattgtgg                                            29

<210> SEQ ID NO 1083
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1083
ggccctccaa ttattcccat cc                                                   22

<210> SEQ ID NO 1084
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1084
cggcgaccgg agaatcctac                                                    20

<210> SEQ ID NO 1085
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1085
tcgagacact cacggtcgg                                                     19

<210> SEQ ID NO 1086
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1086
agaagcagaa gagactatga caggag                                             26

<210> SEQ ID NO 1087
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1087
cggctgtggc ttctactcct ac                                                 22

<210> SEQ ID NO 1088
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1088
ttccctgctc atgatctgca ag                                                 22

<210> SEQ ID NO 1089
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1089
aggatcgtct gaacatcctt ccac                                               24

<210> SEQ ID NO 1090
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1090
caccagaaaa tcgatctgtt ctgtg                                              25

-continued

```
<210> SEQ ID NO 1091
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1091
cgggtggggg taagtttatc c                                           21

<210> SEQ ID NO 1092
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1092
cgtgccttca ggaaatgcag c                                           21

<210> SEQ ID NO 1093
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1093
tgtgcaatgc ctgtttccct tc                                          22

<210> SEQ ID NO 1094
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1094
ccatcttcat tcactttatt cttccctttg                                  30

<210> SEQ ID NO 1095
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1095
tcagggtcca aaactgaatg acac                                        24

<210> SEQ ID NO 1096
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1096
tcttaaaagt tgtgagccat caaatctc                                    28
```

```
<210> SEQ ID NO 1097
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1097
gtagagtccg aaaactacaa cccc                                            24

<210> SEQ ID NO 1098
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1098
tacttcctgg acaaccatca acc                                             23

<210> SEQ ID NO 1099
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1099
ggtgagggct acacaaaggc ag                                              22

<210> SEQ ID NO 1100
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1100
accacacaga tgccgacgg                                                  19

<210> SEQ ID NO 1101
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1101
gcatggacga tgagagcttc ag                                              22

<210> SEQ ID NO 1102
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1102
cagccaaacg ataaatattc cttcgag                                         27
```

```
<210> SEQ ID NO 1103
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1103
taggttcaga tagccagacg agg                                                23

<210> SEQ ID NO 1104
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1104
cgcactgatg gtggcaaatt c                                                  21

<210> SEQ ID NO 1105
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1105
tccagtgccc actttggata gc                                                 22

<210> SEQ ID NO 1106
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1106
tttatcttta aattccatgc cacccc                                             26

<210> SEQ ID NO 1107
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1107
gcttcgtcag agaggtactt ctg                                                23

<210> SEQ ID NO 1108
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1108
gccatttgca atgttttagt tggtg                                              25

<210> SEQ ID NO 1109
```

```
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1109
ctgaattaga caacgcatgc ttgc                                              24

<210> SEQ ID NO 1110
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1110
gacatggtca atatcgatgc atcgc                                             25

<210> SEQ ID NO 1111
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1111
aaatcataat tgaacaatca ccaagggg                                          28

<210> SEQ ID NO 1112
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1112
agcagacatc tttatacaag aaaatgtggc                                        30

<210> SEQ ID NO 1113
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1113
ttttgttgtg ccaatttgtt atttatttga c                                      31

<210> SEQ ID NO 1114
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1114
gccgcatcta cataatgccc ag                                                22

<210> SEQ ID NO 1115
<211> LENGTH: 25
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1115
ggttgtggac tgacttttag gtttg                                        25

<210> SEQ ID NO 1116
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1116
gcttcctgct agcattattg agatga                                       26

<210> SEQ ID NO 1117
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1117
aggtaaatag agttgaagaa aatactatcg acat                              34

<210> SEQ ID NO 1118
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1118
cttggaatga ctcctcttca tctgg                                        25

<210> SEQ ID NO 1119
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1119
aagatttctc ttcgtgttaa gttctcttta c                                 31

<210> SEQ ID NO 1120
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1120
ggagctttcg agtgcttcaa ttgttc                                       26

<210> SEQ ID NO 1121
<211> LENGTH: 22
<212> TYPE: DNA
```

-continued

```
<213> ORGANISM: Artificial Sequence
<220> FEATURE:
<223> OTHER INFORMATION: Description of Artificial Sequence: Synthetic
      primer

<400> SEQUENCE: 1121
cagatgggag ccagccaata ag                                               22

<210> SEQ ID NO 1122
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1122
tgccacctat gacagtaaag acatg                                            25

<210> SEQ ID NO 1123
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1123
ctctccaaca tctcgaagtt gcttc                                            25

<210> SEQ ID NO 1124
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1124
gagtcaggta ttaagaaagt ggcaaag                                          27

<210> SEQ ID NO 1125
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1125
acaactctca gctttaccag gc                                               22

<210> SEQ ID NO 1126
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1126
actgatggta aattgagcaa gagaatcg                                         28

<210> SEQ ID NO 1127
<211> LENGTH: 28
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 1127
gcaattagca gtctcaatac aaatggag                                          28

<210> SEQ ID NO 1128
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1128
gggagaaata atattgtgat atatgaagaa gagc                                   34

<210> SEQ ID NO 1129
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1129
ttggttcatc tgtgacttcc acc                                               23

<210> SEQ ID NO 1130
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1130
ggaaacaatt ggagtacttt gaacaatatc                                        30

<210> SEQ ID NO 1131
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1131
gtttgtgctg ctccaattaa accac                                             25

<210> SEQ ID NO 1132
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1132
tgcatgtcta agcttaagcc taattgac                                          28

<210> SEQ ID NO 1133
<211> LENGTH: 22
<212> TYPE: DNA
<213> ORGANISM: Artificial Sequence
<220> FEATURE:
```

-continued

```
<223> OTHER INFORMATION: Description of Artificial Sequence: Synthetic
      primer

<400> SEQUENCE: 1133
atatgctgtt accggtgtct gg                                             22

<210> SEQ ID NO 1134
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1134
gcagcatgta tttaacaaac aaggaac                                        27

<210> SEQ ID NO 1135
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1135
cagtgacttc atcttgactg acagc                                          25

<210> SEQ ID NO 1136
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1136
cagatatttt gaattcgagc tttgttcg                                       28

<210> SEQ ID NO 1137
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1137
tcatttcaaa tatacattag cataaaacgt tccc                                34

<210> SEQ ID NO 1138
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1138
actagcagca acagaagcag c                                              21

<210> SEQ ID NO 1139
<211> LENGTH: 28
<212> TYPE: DNA
<213> ORGANISM: Artificial Sequence
<220> FEATURE:
<223> OTHER INFORMATION: Description of Artificial Sequence: Synthetic
```

-continued

```
    primer

<400> SEQUENCE: 1139
ccttcattct tatggtattt tctcagcc                                      28

<210> SEQ ID NO 1140
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1140
gtctccttga gcactagttc taagtattc                                     29

<210> SEQ ID NO 1141
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1141
acttgataga atggttgagg aagatgac                                      28

<210> SEQ ID NO 1142
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1142
taacactata ctagtctttt tgccgcc                                       27

<210> SEQ ID NO 1143
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1143
acccttttcc cttttacctg aataaac                                       27

<210> SEQ ID NO 1144
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1144
cccttgatcg ccattgtaga cc                                            22

<210> SEQ ID NO 1145
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 1145
ctcagaagta aaacgtaaag tgagtgg                                      27

<210> SEQ ID NO 1146
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1146
ttcagaaggt tttggaattc actgtag                                      27

<210> SEQ ID NO 1147
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1147
gaaggggaca gagtgggatc c                                            21

<210> SEQ ID NO 1148
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1148
gtgtgcagag gaagagaaaa tagagatg                                     28

<210> SEQ ID NO 1149
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1149
ggtaagtctc ttttggccta cagg                                         24

<210> SEQ ID NO 1150
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1150
gaaaagaagg tccctccaac tgg                                          23

<210> SEQ ID NO 1151
<211> LENGTH: 31
<212> TYPE: DNA
<213> ORGANISM: Artificial Sequence
<220> FEATURE:
<223> OTHER INFORMATION: Description of Artificial Sequence: Synthetic
      primer
```

-continued

```
<400> SEQUENCE: 1151
tgacattatt attgtcacct gagaaatctc c                              31

<210> SEQ ID NO 1152
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1152
cctttaccac tattataaag aaaaaggaca acc                            33

<210> SEQ ID NO 1153
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1153
gaccatgcgt gaacatgtga tg                                        22

<210> SEQ ID NO 1154
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1154
tgaagtagga gcaatgttgg tgatg                                     25

<210> SEQ ID NO 1155
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1155
catttttctt aggaggaagt aggctaac                                  28

<210> SEQ ID NO 1156
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1156
tgttcatttt aagatgaata aagaattaag tctgc                          35

<210> SEQ ID NO 1157
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1157
```
aatgagttcc aagggtagtg gtttg                                                    25

<210> SEQ ID NO 1158
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1158
aagtactatc tgctgcaagt tgttttttc                                                29

<210> SEQ ID NO 1159
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1159
tatggttttt tgtgttctaa ataaacttga tctg                                          34

<210> SEQ ID NO 1160
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1160
cgtgcaatcc tctggagaag c                                                        21

<210> SEQ ID NO 1161
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1161
gttggtctgc tttttgttgc gac                                                      23

<210> SEQ ID NO 1162
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1162
tggtgccttt atacttgctg tgtatg                                                   26

<210> SEQ ID NO 1163
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1163

-continued

```
agtaacaaga actgtaacta acgtaggac                                       29

<210> SEQ ID NO 1164
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1164
ttgctctgaa aaacaaaata tggagtgatg                                      30

<210> SEQ ID NO 1165
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1165 ttggatggg tggagtttac ttg                                              23

<210> SEQ ID NO 1166
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1166
ttcgagtgat tttgggcgtt cc                                              22

<210> SEQ ID NO 1167
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1167
tgcattggtc agatcaaaca gagga                                           25

<210> SEQ ID NO 1168
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1168
tccatttcag atagtgtgct ggc                                             23

<210> SEQ ID NO 1169
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1169
atgcacaaat caaattttca aggcag                                          26
```

<210> SEQ ID NO 1170
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1170
ttcagctaaa tctctggcca aagttg                                         26

<210> SEQ ID NO 1171
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1171
gagatcggaa ggagcaaagg ag                                             22

<210> SEQ ID NO 1172
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1172
tgatttttgg agctcagaag aaagaaga                                       28

<210> SEQ ID NO 1173
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1173
tctagaagga aaaggaatcg accct                                          25

<210> SEQ ID NO 1174
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1174
gttctctgat ttgagccatg atgag                                          25

<210> SEQ ID NO 1175
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1175
gcaactcttg atcaactttc agtcc                                          25

-continued

<210> SEQ ID NO 1176
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1176
caagcaggtg cagctgcttt tag                                                23

<210> SEQ ID NO 1177
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1177
tcacaaccag tcaatgaaag agggg                                              25

<210> SEQ ID NO 1178
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1178
aggatcgtac gtgtatggtt caaagg                                             26

<210> SEQ ID NO 1179
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1179
agcccgtcgt ccagttattt tc                                                 22

<210> SEQ ID NO 1180
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1180
ggacgaagaa tgctcaaaac aataagg                                            27

<210> SEQ ID NO 1181
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1181
acgcttggaa ctgaaaagat gc                                                 22

```
<210> SEQ ID NO 1182
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1182
acgatagaac agaaaacatt gcactg                                            26

<210> SEQ ID NO 1183
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1183
gttgcagaga agattgctga ttttgg                                            26

<210> SEQ ID NO 1184
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1184
gttgtgtggg caaaggcaga g                                                 21

<210> SEQ ID NO 1185
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1185
gaacttgttg tcttgtacgc gtag                                              24

<210> SEQ ID NO 1186
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1186
ctcctacacc gccctatcct ac                                                22

<210> SEQ ID NO 1187
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1187
agttggagac agtgagactc agattg                                            26

<210> SEQ ID NO 1188
```

```
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1188
tccataaccc attgtgttca attggac                                         27

<210> SEQ ID NO 1189
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1189
tctaatcgaa agctctggcg attc                                            24

<210> SEQ ID NO 1190
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1190
gaagttgaag caatatcttt cgagaatgat g                                    31

<210> SEQ ID NO 1191
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1191
gataagtgat ccaacgacag aactttc                                         27

<210> SEQ ID NO 1192
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1192
aatcctcatc gatccgatca aatcg                                           25

<210> SEQ ID NO 1193
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1193
ccgcacggaa atagagatgt tcg                                             23

<210> SEQ ID NO 1194
<211> LENGTH: 28
```

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1194
gctgaagcaa ggaaaaaatc gaaaattc                                         28

<210> SEQ ID NO 1195
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1195
tttcaagaat gtaaggttct ttgtttctca cc                                    32

<210> SEQ ID NO 1196
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1196
agtttgcata ttttcgtcca tgttttttaat c                                    31

<210> SEQ ID NO 1197
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1197
aaccaatgat tgcatagaaa gtcatatcac                                       30

<210> SEQ ID NO 1198
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1198
gtgggtagct gaagggtttg tacaag                                           26

<210> SEQ ID NO 1199
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1199
caagaaacct tgtgcggtat cttc                                             24

<210> SEQ ID NO 1200
<211> LENGTH: 26
<212> TYPE: DNA

-continued

```
<213> ORGANISM: Artificial Sequence
<220> FEATURE:
<223> OTHER INFORMATION: Description of Artificial Sequence: Synthetic
      primer

<400> SEQUENCE: 1200
gcctatattt cctctcacta ctgtgc                                        26

<210> SEQ ID NO 1201
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1201
ggaatatcta agacaatgcc cgagc                                         25

<210> SEQ ID NO 1202
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1202
gaaaagtcta cttccacttc tcctgtg                                       27

<210> SEQ ID NO 1203
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1203
catcctcatc atctgacgca tagttag                                       27

<210> SEQ ID NO 1204
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1204
tccaccatag aagccccaaa tcc                                           23

<210> SEQ ID NO 1205
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1205
ggattgttaa tgaagagaag catagggg                                      28

<210> SEQ ID NO 1206
<211> LENGTH: 23
<212> TYPE: DNA
<213> ORGANISM: Artificial Sequence
```

-continued

```
<220> FEATURE:
<223> OTHER INFORMATION: Description of Artificial Sequence: Synthetic
      primer

<400> SEQUENCE: 1206
tcagcatttt caaatctggt ggc                                                  23

<210> SEQ ID NO 1207
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1207
aggttaaccc cttggatgat ctcc                                                 24

<210> SEQ ID NO 1208
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1208
gcttccaaac tatgtcgtct atcatg                                               26

<210> SEQ ID NO 1209
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1209
catctcaact gcacatacat tacgc                                                25

<210> SEQ ID NO 1210
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1210
ccctggtaat acagcaagta cgac                                                 24

<210> SEQ ID NO 1211
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1211
ggtagctatt acttgcatca tgccag                                               26

<210> SEQ ID NO 1212
<211> LENGTH: 26
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 1212
tcaatcgatt cgggaatatc tgcttg                                            26

<210> SEQ ID NO 1213
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1213
aagcagcgca gaaagagaat acc                                               23

<210> SEQ ID NO 1214
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1214
gagacgagtg agatttcaaa ttacaagtc                                         29

<210> SEQ ID NO 1215
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1215
catgttgttc gttactagcc aacttag                                           27

<210> SEQ ID NO 1216
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1216
tggagaaaac aagaggtggt aagg                                              24

<210> SEQ ID NO 1217
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1217
gctccaccag ccattactac acg                                               23

<210> SEQ ID NO 1218
<211> LENGTH: 25
<212> TYPE: DNA
<213> ORGANISM: Artificial Sequence
<220> FEATURE:
<223> OTHER INFORMATION: Description of Artificial Sequence: Synthetic -continued primer

<400> SEQUENCE: 1218
atgcacttcc ttcatcacat tgttg                                              25

<210> SEQ ID NO 1219
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1219 ggctttctt cgaaatgtt gcattaatcc                                          30

<210> SEQ ID NO 1220
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1220
ttgtggtctc agcaatcatg gatg                                               24

<210> SEQ ID NO 1221
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1221
aggcctgctt cgaacatgg                                                     19

<210> SEQ ID NO 1222
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1222
gaaaagggtt catgaactag aagctg                                             26

<210> SEQ ID NO 1223
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1223
atcgaatatt ttggactccg ttaatcg                                            27

<210> SEQ ID NO 1224
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1224
tggtcttgtt tgtttggccc aatag                                           25

<210> SEQ ID NO 1225
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1225
agaagaagaa aaaccccga atctcc                                           26

<210> SEQ ID NO 1226
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1226
ggagtgcaat ctcataatag tgctcctg                                        28

<210> SEQ ID NO 1227
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1227
agcgacggaa ttgccatagg                                                 20

<210> SEQ ID NO 1228
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1228
tttaactgaa aaatggggag atttaccac                                       29

<210> SEQ ID NO 1229
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1229
tttaatagac cgtaaattac catatcttcg g                                    31

<210> SEQ ID NO 1230
<211> LENGTH: 25
<212> TYPE: DNA
<213> ORGANISM: Artificial Sequence
<220> FEATURE:
<223> OTHER INFORMATION: Description of Artificial Sequence: Synthetic
      primer -continued

```
<400> SEQUENCE: 1230
tgtgtgtaca gtaaaacctc tggtc                                         25

<210> SEQ ID NO 1231
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1231
gagtccattt caaagcttgt actgc                                         25

<210> SEQ ID NO 1232
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1232
ttcagatgaa atttatgatg catgggtg                                      28

<210> SEQ ID NO 1233
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1233
gcaaatactc gtaaacatac taatcaattc aac                                33

<210> SEQ ID NO 1234
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1234
aagttgcctt gacctaataa tctccc                                        26

<210> SEQ ID NO 1235
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1235
atggagaaaa aaggaaatgt actgatgg                                      28

<210> SEQ ID NO 1236
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1236
```

```
ctcaataaca ggaaatcaca cctaatcc                                        28

<210> SEQ ID NO 1237
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1237
tgtggttgct attattccgt agatacatc                                       29

<210> SEQ ID NO 1238
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1238
tcgccatctc ccttagcaca tg                                              22

<210> SEQ ID NO 1239
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1239
ttgagcgggt gttcagtaat taatg                                           25

<210> SEQ ID NO 1240
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1240
taccgatgat gaaaacactc tagctag                                         27

<210> SEQ ID NO 1241
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1241
aatcaacaat ggacatcaaa tacccc                                          26

<210> SEQ ID NO 1242
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1242
```

```
gaggcctttc cgtgctctc                                                  19

<210> SEQ ID NO 1243
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1243
acggttccct gtagtagttc ttaagag                                          27

<210> SEQ ID NO 1244
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1244
tgtgaaaggc atcatatgtt agctctc                                          27

<210> SEQ ID NO 1245
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1245
acaagttcaa ggcggtgaaa ttatc                                            25

<210> SEQ ID NO 1246
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1246
tcagggtctg agtaatttga gagc                                             24

<210> SEQ ID NO 1247
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1247
gaatttcacc catgaactta tttctccc                                         28

<210> SEQ ID NO 1248
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1248
ggaacaaatt aagtaagatc atcttcctca ag                                    32
```

```
<210> SEQ ID NO 1249
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1249
aggacaacac tacttctaag agtcaagg                                        28

<210> SEQ ID NO 1250
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1250
atgcccttgt gagatgggtg tg                                              22

<210> SEQ ID NO 1251
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1251
caacctatgc ccttgaacat gtg                                             23

<210> SEQ ID NO 1252
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1252
acacaattca aaatcccctc ctcc                                            24

<210> SEQ ID NO 1253
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1253
cgtacggctg cagagttcaa ag                                              22

<210> SEQ ID NO 1254
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1254
gcagaagacc tcccaccaga g                                               21
```

<210> SEQ ID NO 1255
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1255
atccctgaga agaaatggta cctaag                                                            26

<210> SEQ ID NO 1256
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1256
ttgggagaaa atacccctgc tg                                                                22

<210> SEQ ID NO 1257
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1257
tgaatgtttt cgccatttct cttgtac                                                           27

<210> SEQ ID NO 1258
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1258
tgaccatctg agtgtgagaa atatgc                                                            26

<210> SEQ ID NO 1259
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1259
agcactctga taggcctgct g                                                                 21

<210> SEQ ID NO 1260
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1260
gacaaggttt catgtctgtt gagttg                                                            26

```
<210> SEQ ID NO 1261
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1261
ctaccaaaaa catcataata tttgatctca gc                                   32

<210> SEQ ID NO 1262
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1262
gctatatttt gaggcctgtt ggac                                            24

<210> SEQ ID NO 1263
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1263
aaacacaaat tcttgaggca atacatgac                                       29

<210> SEQ ID NO 1264
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1264
taaaatatat ggcgactgga ttgatgac                                        28

<210> SEQ ID NO 1265
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1265
acagatcagt agctaattat gacaactcc                                       29

<210> SEQ ID NO 1266
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1266
gggcaagaat cggtcggaaa tg                                               22

<210> SEQ ID NO 1267
```

<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1267
ccactacctt ctcatcaaga cgac                                                                                     24

<210> SEQ ID NO 1268
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1268
ctaggaagag agttgaaaag acctagc                                                                                  27

<210> SEQ ID NO 1269
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1269
aaaaacttat accttattta tcatctcccc c                                                                             31

<210> SEQ ID NO 1270
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1270
catctgcaga agaattgttg tccag                                                                                    25

<210> SEQ ID NO 1271
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1271
ggccataaag attctgccaa cc                                                                                       22

<210> SEQ ID NO 1272
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1272
tgtctccttt gtttcaagtg gtatcatg                                                                                 28

<210> SEQ ID NO 1273
<211> LENGTH: 27

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1273
tgtttcgatt gatttctcct caacttc                                        27

<210> SEQ ID NO 1274
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1274
tagttgtctg ccgacttcct gg                                             22

<210> SEQ ID NO 1275
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1275
ctcaggaact tctctaaaga acgtatcttg                                     30

<210> SEQ ID NO 1276
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1276
agaaagtgtg actccaacaa agcg                                           24

<210> SEQ ID NO 1277
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1277
tctttcacgt ccttcttaga agctg                                          25

<210> SEQ ID NO 1278
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1278
cgaatgcata taaagctttt gatccaag                                       28

<210> SEQ ID NO 1279
<211> LENGTH: 20
<212> TYPE: DNA
```

-continued

```
<213> ORGANISM: Artificial Sequence
<220> FEATURE:
<223> OTHER INFORMATION: Description of Artificial Sequence: Synthetic
      primer

<400> SEQUENCE: 1279
tagtgcgggg aaggaccaag                                               20

<210> SEQ ID NO 1280
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1280
cagaaggaat caactcgggg gt                                            22

<210> SEQ ID NO 1281
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1281
taacagccta gctaaccacc ac                                            22

<210> SEQ ID NO 1282
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1282
ttcaagtggt gaagttcaca tagtgtg                                       27

<210> SEQ ID NO 1283
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1283
aaaattaagt aatgcatgta gcatgaataa aagtg                              35

<210> SEQ ID NO 1284
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1284
acaaagttcc cagaacctcc ac                                            22

<210> SEQ ID NO 1285
<211> LENGTH: 29
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 1285
tagttatttc ttcaacttcg acttctgtg                                      29

<210> SEQ ID NO 1286
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1286
ctgcaaccga agctattgac tgtg                                           24

<210> SEQ ID NO 1287
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1287
cgaagaggga ggaggtcatt gatc                                           24

<210> SEQ ID NO 1288
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1288
gctgtttcga ctgatactat taatggtgg                                      29

<210> SEQ ID NO 1289
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1289
tgacattaag tcgaagactc tgatcga                                        27

<210> SEQ ID NO 1290
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1290
gaacagggaa gtgtcaaatc aattggg                                        27

<210> SEQ ID NO 1291
<211> LENGTH: 17
<212> TYPE: DNA
<213> ORGANISM: Artificial Sequence
<220> FEATURE:
```

-continued

<223> OTHER INFORMATION: Description of Artificial Sequence: Synthetic
     primer

<400> SEQUENCE: 1291
tgcagcctgg gcagttg                                                17

<210> SEQ ID NO 1292
<211> LENGTH: 24
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 1292
ttcgaagcgg ttagtcacag taag                                        24

<210> SEQ ID NO 1293
<211> LENGTH: 18
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 1293
aaccgcttta cccaccgc                                               18

<210> SEQ ID NO 1294
<211> LENGTH: 21
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 1294
gaagggtggt ggtgatttgg c                                           21

<210> SEQ ID NO 1295
<211> LENGTH: 29
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 1295
acatcaaacg gaacatatct atcttttcc                                   29

<210> SEQ ID NO 1296
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 1296
gtgggtgtga cattggggcc                                             20

<210> SEQ ID NO 1297
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 1297
caccaagagc acgtagacca tg                                                      22

<210> SEQ ID NO 1298
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1298
ttggaccaac ttgcattttc ggg                                                     23

<210> SEQ ID NO 1299
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1299
cacctaagca agtttcagaa aaggttg                                                  27

<210> SEQ ID NO 1300
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1300
gtgatttctg gtgaacctga tccag                                                   25

<210> SEQ ID NO 1301
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1301
tttgtctgac ttgattggtg caac                                                    24

<210> SEQ ID NO 1302
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1302
gaatcggcgt ggtagggagg                                                         20

<210> SEQ ID NO 1303
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1303
aaccttcatc actcaaaacg gtaaac                                    26

<210> SEQ ID NO 1304
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1304
tgaacgaagt gcttacaaga gagttg                                    26

<210> SEQ ID NO 1305
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1305
gagtaaccct aacttcaact cccg                                      24

<210> SEQ ID NO 1306
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1306
aggaagtgaa gttggaagaa agagcag                                   27

<210> SEQ ID NO 1307
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1307
accaaccata catcttcctt ctggc                                     25

<210> SEQ ID NO 1308
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1308
gatctttctg gattaaacgg gaaactg                                   27

<210> SEQ ID NO 1309
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1309
gctgcatcta agcctcttga cattag                                          26

<210> SEQ ID NO 1310
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1310
tcgtgttaac atttccttta aggtatgacg                                      30

<210> SEQ ID NO 1311
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1311
tccgggcatg taaatcggat gc                                              22

<210> SEQ ID NO 1312
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1312
aagggacacg ataaacttgc tcc                                             23

<210> SEQ ID NO 1313
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1313
accaacttgg aaccacaaca gg                                              22

<210> SEQ ID NO 1314
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1314
gaggttcttc ggtaggtatt gcttg                                           25

<210> SEQ ID NO 1315
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1315

-continued gcgcctgtag caataaattt taatccg                                    27

<210> SEQ ID NO 1316
<211> LENGTH: 33
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 1316
atccaaaaat ttcgttgaat attaggttac ctg                             33

<210> SEQ ID NO 1317
<211> LENGTH: 22
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 1317
gcgaagggat tcagatgggt tg                                         22

<210> SEQ ID NO 1318
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 1318
acgctccttg cctcagtcac                                            20

<210> SEQ ID NO 1319
<211> LENGTH: 25
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 1319
gctttggtta atcgatttgc ggatc                                      25

<210> SEQ ID NO 1320
<211> LENGTH: 23
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 1320
gacactgaat gaagctccga gtg                                        23

<210> SEQ ID NO 1321
<211> LENGTH: 24
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 1321

```
gattttctcg aaccggaaat gtcg                                          24

<210> SEQ ID NO 1322
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1322
accccagatg acaccgaaga tg                                            22

<210> SEQ ID NO 1323
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1323
agacacaata acgcccaaga gatg                                          24

<210> SEQ ID NO 1324
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1324
tcatatacgg atgctgcagc tg                                            22

<210> SEQ ID NO 1325
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1325
gggcatgcag aagaagacca g                                             21

<210> SEQ ID NO 1326
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1326
caaaggtttg cttttcggct cc                                            22

<210> SEQ ID NO 1327
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1327
ttttcagcct ataatgtgaa gcacc                                         25
```

-continued

```
<210> SEQ ID NO 1328
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1328
gcatgggaaa cagaaaattg agtttg                                          26

<210> SEQ ID NO 1329
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1329
aaagacggtt ctgctgatcc ttc                                            23

<210> SEQ ID NO 1330
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1330
cataaagagg ctgcgatgag gag                                            23

<210> SEQ ID NO 1331
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1331
agtggaatat tgggagtagt gtgtc                                          25

<210> SEQ ID NO 1332
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1332
caaattctgc aacctttcca cact                                           24

<210> SEQ ID NO 1333
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1333
ccaaccaaag aagacatcgc atc                                            23
```

<210> SEQ ID NO 1334
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1334
tggctgcatt cgtagatgtt gaatttg                                        27

<210> SEQ ID NO 1335
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1335
agttatgtcg tctgtcatac aaaagtttg                                      29

<210> SEQ ID NO 1336
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1336
tgtagcattg gagcatgttc cg                                             22

<210> SEQ ID NO 1337
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1337
cgggactggt acactagaaa catc                                           24

<210> SEQ ID NO 1338
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1338
cagcaacaag cttctgaatg cca                                            23

<210> SEQ ID NO 1339
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1339
ggcagtgtct aagtgaaagg cga                                            23

```
<210> SEQ ID NO 1340
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1340
gctggtagag aatcattgat tggctc                                           26

<210> SEQ ID NO 1341
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1341
tggttactta tcaatctttc agttcttgc                                        29

<210> SEQ ID NO 1342
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1342
tctttagtgg atagtaaaat ggtgggttc                                        29

<210> SEQ ID NO 1343
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1343
catcacgaac agcgcacctc                                                  20

<210> SEQ ID NO 1344
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1344
tggtgacgtt ttggttgatt ctatg                                            25

<210> SEQ ID NO 1345
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1345
ctaaacagtt caacgactgc agg                                              23

<210> SEQ ID NO 1346
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1346
aacccgacga atgtccaact c                                          21

<210> SEQ ID NO 1347
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1347
aggtaccctg gcattctctt gc                                         22

<210> SEQ ID NO 1348
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1348
taaaccacac cctacgcgta tag                                        23

<210> SEQ ID NO 1349
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1349
acgcttcaac aaattggata atggg                                      25

<210> SEQ ID NO 1350
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1350
atgtgccatc tttccaattt tcatca                                     26

<210> SEQ ID NO 1351
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1351
ggaaatccaa ttcctgagtc tctagtg                                    27

<210> SEQ ID NO 1352
<211> LENGTH: 25
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1352
agcaaaaatg gtgaaagaca gaacc                                        25

<210> SEQ ID NO 1353
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1353
ctgttttgct gctctttgaa aaatctac                                     28

<210> SEQ ID NO 1354
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1354
ccacttaaat agtttacggg caagac                                       26

<210> SEQ ID NO 1355
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1355
tacttgtgtc cccactgcgg                                              20

<210> SEQ ID NO 1356
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1356
gttttcttca acaacaaat gtctcttatt cc                                 32

<210> SEQ ID NO 1357
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1357
cgaagatatt gctcctccga ccac                                         24

<210> SEQ ID NO 1358
<211> LENGTH: 25
<212> TYPE: DNA
```

-continued

```
<213> ORGANISM: Artificial Sequence
<220> FEATURE:
<223> OTHER INFORMATION: Description of Artificial Sequence: Synthetic
      primer

<400> SEQUENCE: 1358
gttacttcac ttgaacacca ttccc                                        25

<210> SEQ ID NO 1359
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1359
caagaggagc atgcactacg g                                            21

<210> SEQ ID NO 1360
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1360
acacttttga atctgtccat ccatgac                                      27

<210> SEQ ID NO 1361
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1361
ttggagtctc cgcgacaagc                                              20

<210> SEQ ID NO 1362
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1362
cccaggatta cgcgatgcag                                              20

<210> SEQ ID NO 1363
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1363
gatggaatta cacacaacct cagatg                                       26

<210> SEQ ID NO 1364
<211> LENGTH: 23
<212> TYPE: DNA
<213> ORGANISM: Artificial Sequence
```

-continued

```
<220> FEATURE:
<223> OTHER INFORMATION: Description of Artificial Sequence: Synthetic
      primer

<400> SEQUENCE: 1364
cgggtaagga tgtttaggtg cgt                                              23

<210> SEQ ID NO 1365
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1365
ccagcataaa tttaagaatg gagtagaatc c                                     31

<210> SEQ ID NO 1366
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1366
gacctggcat tgacatgtcc atg                                              23

<210> SEQ ID NO 1367
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1367
cctcgtagct tccgggagac                                                  20

<210> SEQ ID NO 1368
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1368
aacgaagagg atgatatgga aaatgc                                           26

<210> SEQ ID NO 1369
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1369
atcgtcttct ctcctccttc cc                                               22

<210> SEQ ID NO 1370
<211> LENGTH: 26
<212> TYPE: DNA
<213> ORGANISM: Artificial Sequence
<220> FEATURE:
```

-continued

<223> OTHER INFORMATION: Description of Artificial Sequence: Synthetic
     primer

<400> SEQUENCE: 1370
agtcgagata ttgaccaaat ttgctc                                          26

<210> SEQ ID NO 1371
<211> LENGTH: 29
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 1371
tgtacaacag aaagttcaat tagatggag                                       29

<210> SEQ ID NO 1372
<211> LENGTH: 22
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 1372
aatcaacacg ttcgtgcaat cg                                              22

<210> SEQ ID NO 1373
<211> LENGTH: 24
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 1373
gatgatctgt tctggagttg ttgc                                            24

<210> SEQ ID NO 1374
<211> LENGTH: 25
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 1374
actaaagatc tgaaggcaca agtgg                                           25

<210> SEQ ID NO 1375
<211> LENGTH: 28
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 1375
gggaattgcg atggagtgaa ttttaagg                                        28

<210> SEQ ID NO 1376
<211> LENGTH: 22
<212> TYPE: DNA
<213> ORGANISM: Artificial Sequence
<220> FEATURE:
<223> OTHER INFORMATION: Description of Artificial Sequence: Synthetic -continued

```
    primer

<400> SEQUENCE: 1376
tcattttcaa gttgccgtca gc                                           22

<210> SEQ ID NO 1377
<211> LENGTH: 35
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 1377
aacttcatca taagacctat taataatctg agttc                             35

<210> SEQ ID NO 1378
<211> LENGTH: 26
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 1378
cggagatatt caggaaccgt caattg                                       26

<210> SEQ ID NO 1379
<211> LENGTH: 23
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 1379
gccaggtgtt tgggaatatg ttc                                          23

<210> SEQ ID NO 1380
<211> LENGTH: 20
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 1380
cagctgattc gaggggtctc                                              20

<210> SEQ ID NO 1381
<211> LENGTH: 28
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 1381
accaactgaa gaacaagtct gttagaac                                     28

<210> SEQ ID NO 1382
<211> LENGTH: 24
<212> TYPE: DNA
<213> ORGANISM: Artificial Sequence
<220> FEATURE:
<223> OTHER INFORMATION: Description of Artificial Sequence: Synthetic
    primer
```

-continued

```
<400> SEQUENCE: 1382
tgcaaaaaag gactcttcaa ccag                                          24

<210> SEQ ID NO 1383
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1383
ggtctcattg gcctttgagg attg                                          24

<210> SEQ ID NO 1384
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1384
ctagatctta actgtgatgt tctgagctg                                     29

<210> SEQ ID NO 1385
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1385
acgttgatct gactgatgat cgg                                           23

<210> SEQ ID NO 1386
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1386
ggtgatacta aagtggattt aaaaggcg                                      28

<210> SEQ ID NO 1387
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1387
accaacaact tcccctgcac c                                             21

<210> SEQ ID NO 1388
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 1388
accgtcattg gtacagttga tcc                                              23

<210> SEQ ID NO 1389
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1389
ccaccaaaac ttacgtagcc tactc                                            25

<210> SEQ ID NO 1390
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1390
aagtatccta cgtcaacaag cttcg                                            25

<210> SEQ ID NO 1391
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1391
tgaatctact tatgcttctt ggggtg                                           26

<210> SEQ ID NO 1392
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1392
tgtcttgatc ttctgaagtc tcacttac                                         28

<210> SEQ ID NO 1393
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1393
ccgagctggg cagtctagag                                                  20

<210> SEQ ID NO 1394
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1394

```
tggtggcatt gttcaggtga ttg                                        23
```

```
<210> SEQ ID NO 1395
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1395
agaaatcgac atgataagtt gtttaaaaca tc                              32
```

```
<210> SEQ ID NO 1396
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1396
tgggaaaatc taatcgacga ttacaac                                    27
```

```
<210> SEQ ID NO 1397
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1397
ggcggcgtag ttgatggaag                                            20
```

```
<210> SEQ ID NO 1398
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1398
ggggattttg gtaagagatt gggc                                       24
```

```
<210> SEQ ID NO 1399
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1399
cacagtgact caagaatcca ccag                                       24
```

```
<210> SEQ ID NO 1400
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1400
```

-continued

```
tatctgttag tccaccaaca tgactatg                                          28

<210> SEQ ID NO 1401
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1401
caagctggca aaagtatctt cagtttc                                           27

<210> SEQ ID NO 1402
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1402
taacgaaatt ttaaccatca tagaaatgac ttcc                                   34

<210> SEQ ID NO 1403
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1403
tgggtcccac tataagaaat tgaattcc                                          28

<210> SEQ ID NO 1404
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1404
ggatttttat gtggcagttg ctagac                                            26

<210> SEQ ID NO 1405
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1405
acataaatgt aacgaaagaa actgcaaaag                                        30

<210> SEQ ID NO 1406
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1406
gtgctttgct agtagtttga aggag                                             25
```

```
<210> SEQ ID NO 1407
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1407
cagcccatta caaaaagaat caaaccc                                          27

<210> SEQ ID NO 1408
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1408
caatgtaaca atgaggtaat tcaacagc                                         28

<210> SEQ ID NO 1409
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1409
tctttataag aaatcgcttt aatttttgta cagg                                  34

<210> SEQ ID NO 1410
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1410
taccttctgg atccttaacg ctg                                              23

<210> SEQ ID NO 1411
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1411
acctgatgag ttggcgcagg                                                  20

<210> SEQ ID NO 1412
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1412
aacgtttcat tcacccgtac cc                                               22
```

-continued

```
<210> SEQ ID NO 1413
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1413
acggcggagt tgattcggag                                                      20

<210> SEQ ID NO 1414
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1414
attttactgt ctatatacac cattcactgc                                           30

<210> SEQ ID NO 1415
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1415
gatcatggaa gatggtaacg cagtc                                                25

<210> SEQ ID NO 1416
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1416
ttgcagattt gggatagtta gggc                                                 24

<210> SEQ ID NO 1417
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1417
catgatcatc caccaccacc tcc                                                  23

<210> SEQ ID NO 1418
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1418
gcatcataca gttgatcgtg ggg                                                  23
```

<210> SEQ ID NO 1419
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1419
atgactgcat gcaagataca aaagg                                                  25

<210> SEQ ID NO 1420
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1420
attgataacg agaacaacga tcttttctc                                              29

<210> SEQ ID NO 1421
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1421
gacacatctc gtatatcaag gcctg                                                  25

<210> SEQ ID NO 1422
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1422
gaaagagagg aaattgtggc ttgtg                                                  25

<210> SEQ ID NO 1423
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1423 cggttttag cagttctttt tgggg                                                   25

<210> SEQ ID NO 1424
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1424
ttggggctta tttacagagg agc                                                    23

<210> SEQ ID NO 1425

```
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1425
tggcttcaat tctaccgcaa ctc                                             23

<210> SEQ ID NO 1426
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1426
tcaccggaaa gaccatcact cttg                                            24

<210> SEQ ID NO 1427
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1427
ccttgtcttg aatcttagct ttgacattat c                                    31

<210> SEQ ID NO 1428
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1428
aaactcatga atttaagctt gttcaagc                                        28

<210> SEQ ID NO 1429
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1429
acagggactc taatttcacg acc                                             23

<210> SEQ ID NO 1430
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1430
tgtcagtagg atggtacttg ttaggac                                         27

<210> SEQ ID NO 1431
<211> LENGTH: 24
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1431
ttgctcttat gatcatgaga cgcg                                              24

<210> SEQ ID NO 1432
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1432
atcaagcagc aagaacaagt gc                                                22

<210> SEQ ID NO 1433
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1433
gtgacagccc aaccattgtt acag                                              24

<210> SEQ ID NO 1434
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1434
ccattctaag cagcaaccac ctc                                               23

<210> SEQ ID NO 1435
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1435
tgcagctaca tcatggttgg ag                                                22

<210> SEQ ID NO 1436
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1436
taattgtttc tctgtgtcac ggactg                                            26

<210> SEQ ID NO 1437
<211> LENGTH: 24
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 1437
caagatgtgg acgagcaatt tgac                                                              24

<210> SEQ ID NO 1438
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1438
ggagcaaaaa ttgggtttaa acacc                                                             25

<210> SEQ ID NO 1439
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1439
ttgctcttca gtttcggcct tttaag                                                            26

<210> SEQ ID NO 1440
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1440
ccaacacagt ggcatcagca tg                                                                22

<210> SEQ ID NO 1441
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1441
gggagtagct tgtccaggga atc                                                               23

<210> SEQ ID NO 1442
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1442
tgtctctgat ggcctaagga aac                                                               23

<210> SEQ ID NO 1443
<211> LENGTH: 24
<212> TYPE: DNA
<213> ORGANISM: Artificial Sequence -continued

```
<220> FEATURE:
<223> OTHER INFORMATION: Description of Artificial Sequence: Synthetic
      primer

<400> SEQUENCE: 1443
gctggaactt ttctggtcca tcac                                              24

<210> SEQ ID NO 1444
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1444
cactcattat agttatcatt ccacacatca t                                      31

<210> SEQ ID NO 1445
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1445
aggtcaattg aaagaaagcc cgaag                                             25

<210> SEQ ID NO 1446
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1446
tgtgatttca cctctggaat aattttcttg                                        30

<210> SEQ ID NO 1447
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1447
atgacccagc gttttgttga atctc                                             25

<210> SEQ ID NO 1448
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1448
gtcggcacat gtcctattac agagg                                             25

<210> SEQ ID NO 1449
<211> LENGTH: 29
<212> TYPE: DNA
<213> ORGANISM: Artificial Sequence
<220> FEATURE:
```

-continued

```
<223> OTHER INFORMATION: Description of Artificial Sequence: Synthetic
      primer

<400> SEQUENCE: 1449
tctgattcag agagttgttt caatttctc                                    29

<210> SEQ ID NO 1450
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1450
gcatctgtat gtgtgtggta catg                                         24

<210> SEQ ID NO 1451
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1451
ttggagtagt ctcactgtca tctaaattg                                    29

<210> SEQ ID NO 1452
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1452
cctattgtcc aggtggccaa c                                            21

<210> SEQ ID NO 1453
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1453
acgtaaagga gctgatacct aactg                                        25

<210> SEQ ID NO 1454
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1454
ggaggacttt acccctacct tgg                                          23

<210> SEQ ID NO 1455
<211> LENGTH: 29
<212> TYPE: DNA
<213> ORGANISM: Artificial Sequence
<220> FEATURE:
<223> OTHER INFORMATION: Description of Artificial Sequence: Synthetic
```

-continued

```
      primer

<400> SEQUENCE: 1455
catcttttca agttagtttt gagccgagg                              29

<210> SEQ ID NO 1456
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1456
tgtcctccaa gtttatgtga taaccc                                 26

<210> SEQ ID NO 1457
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1457
gtggtcacag tttgcaacac tatgaag                                27

<210> SEQ ID NO 1458
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1458
gcctttgcga atactggaat tgag                                   24

<210> SEQ ID NO 1459
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1459
ttgagaaaac gccaacaagt ctgag                                  25

<210> SEQ ID NO 1460
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1460
atgggcaaag ctacgtttga ttttatatg                              29

<210> SEQ ID NO 1461
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 1461
catcgtgtcc ttttttgtca ctactg                                          26

<210> SEQ ID NO 1462
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1462
gtcgacccat atttcgtatt tatggacag                                       29

<210> SEQ ID NO 1463
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1463
tgagaacaag cttttcggag acc                                             23

<210> SEQ ID NO 1464
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1464
tccacctcca cctccacctc                                                 20

<210> SEQ ID NO 1465
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1465
cggttagaga aaaatcttcc ttcacatg                                        28

<210> SEQ ID NO 1466
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1466
acgaagttat ggcaagcaaa acg                                             23

<210> SEQ ID NO 1467
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
```

-continued

```
<400> SEQUENCE: 1467
agctactttt tcgaacaatt caccg                                                  25

<210> SEQ ID NO 1468
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1468
cttggtcctt cattcacttg agatg                                                  25

<210> SEQ ID NO 1469
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1469
agcagaagtc gaggaagtgg ag                                                     22

<210> SEQ ID NO 1470
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1470
ggacgaggtc aataacaacg agc                                                    23

<210> SEQ ID NO 1471
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1471
tttttcactc tgatcccaaa cgttac                                                 26

<210> SEQ ID NO 1472
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1472
acaagcctta taagacgcaa ctcg                                                   24

<210> SEQ ID NO 1473
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1473
```

```
aacattttcg gatatggcaa tggaac                                        26

<210> SEQ ID NO 1474
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1474
tcctggttcc ttgctgctgt g                                             21

<210> SEQ ID NO 1475
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1475
ttgccaaaca agagtataag ttccac                                        26

<210> SEQ ID NO 1476
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1476
gctacaactt ttcttacttt ccagtatcct c                                  31

<210> SEQ ID NO 1477
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1477
ccgaatcaga cgttaaatct cggg                                          24

<210> SEQ ID NO 1478
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1478
tgatcagctg ctaaacacgc g                                             21

<210> SEQ ID NO 1479
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1479
```

```
gtactcgaaa gtgaataatc tgaaatgtta cc                                            32
```

```
<210> SEQ ID NO 1480
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1480
tgttgaacag atcatcacgg gtc                                                      23
```

```
<210> SEQ ID NO 1481
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1481
attattccag ctggtgtgcc ac                                                       22
```

```
<210> SEQ ID NO 1482
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1482
agatctggaa gaagcctact tgtg                                                     24
```

```
<210> SEQ ID NO 1483
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1483
cagtctcagt atctgtacct ggtaaag                                                  27
```

```
<210> SEQ ID NO 1484
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1484
ttggtagtga agttgaggcc tc                                                       22
```

```
<210> SEQ ID NO 1485
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1485
tgaggtatgt taagaatcgg gtttgatg                                                 28
```

-continued

```
<210> SEQ ID NO 1486
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1486
tgcatggcta ttttccgtca tctaagg                                          27

<210> SEQ ID NO 1487
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1487
ggttgcaccg tgatcacttg g                                                21

<210> SEQ ID NO 1488
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1488
tcaaatcgac aaacaataca tatctggtta                                       30

<210> SEQ ID NO 1489
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1489
aaccctcgtc tgtcagtggc                                                  20

<210> SEQ ID NO 1490
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1490
tgaagccagt tgacactact gaag                                             24

<210> SEQ ID NO 1491
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1491
gagagaccgg ccagcattg                                                   19
```

-continued

```
<210> SEQ ID NO 1492
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1492
gcaggacatc caagaagagc aaag                                                   24

<210> SEQ ID NO 1493
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1493
tgtcaataat gcaccaatta caagtgaag                                             29

<210> SEQ ID NO 1494
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1494
aaggtagtcc gagtcaaact gtatc                                                 25

<210> SEQ ID NO 1495
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1495
tctgggtttg taatggaact tcatatgg                                             28

<210> SEQ ID NO 1496
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1496
gcataacagc catgaacttg atgaaac                                              27

<210> SEQ ID NO 1497
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1497
gacttggtgt tcgtttgagc c                                                    21
```

```
<210> SEQ ID NO 1498
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1498
cagaaaatca attgtgttct ctcaattcag                                        30

<210> SEQ ID NO 1499
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1499
gctttaagcg gctcttcaag tagg                                              24

<210> SEQ ID NO 1500
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1500
ttcaaagcac gccaaagaat tagtg                                             25

<210> SEQ ID NO 1501
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1501
accttctcta tcaaagtatg gatgtgc                                           27

<210> SEQ ID NO 1502
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1502
ctgcctgaat gtcatcaaac atgtg                                             25

<210> SEQ ID NO 1503
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1503
acagatgtat acatatatt ttcatgctaa caagg                                   35

<210> SEQ ID NO 1504
```

```
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1504
atgggcacta agctgtcaca tc                                               22

<210> SEQ ID NO 1505
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1505
gccaacacgt tgaacattgg ac                                               22

<210> SEQ ID NO 1506
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1506
agtcccatag tttattccga cacc                                             24

<210> SEQ ID NO 1507
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1507
tcttgtctta tccctcttca ttctcctc                                        28

<210> SEQ ID NO 1508
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1508
tagtgactat tctgacggct taaacc                                           26

<210> SEQ ID NO 1509
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1509
aaaggagcat cgaagcaaca gtaaag                                           26

<210> SEQ ID NO 1510
<211> LENGTH: 26
```

-continued

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1510
gaactgctag gaacatctga cacttc                                          26

<210> SEQ ID NO 1511
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1511
tcatgaccaa aaagaaagat gtggg                                           25

<210> SEQ ID NO 1512
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1512
aaccatcttc ttcggtaacc caac                                            24

<210> SEQ ID NO 1513
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1513
aagcagatgc accggcaata ct                                              22

<210> SEQ ID NO 1514
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1514
gcagagtcca atccagagga tg                                              22

<210> SEQ ID NO 1515
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1515
gtcatctgat gttgattgtc taacaagtg                                       29

<210> SEQ ID NO 1516
<211> LENGTH: 21
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 1516
cagctcagca acagttcgtc c                                            21

<210> SEQ ID NO 1517
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1517
agcagaagac tgaagagctg agc                                          23

<210> SEQ ID NO 1518
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1518
acatctttcg aaaacttcca ccttgatc                                     28

<210> SEQ ID NO 1519
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1519
gcatcaagag ttttaaccac ttgaatcc                                     28

<210> SEQ ID NO 1520
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1520
gggcgaaggt cctgaatcag                                              20

<210> SEQ ID NO 1521
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1521
gcagaccctt tgcctccagc                                              20

<210> SEQ ID NO 1522
<211> LENGTH: 29
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 1522
gtgtctgcac tattcatatt ttgattcga                                           29

<210> SEQ ID NO 1523
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1523
gtcaagaaat ccaactgtat ggcttg                                              26

<210> SEQ ID NO 1524
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1524
tgcccatacg atttaaggtt gcg                                                 23

<210> SEQ ID NO 1525
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1525
caggtgcaac cattgttacc gtg                                                 23

<210> SEQ ID NO 1526
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1526
ccccaaccta ggtgagagaa ctc                                                 23

<210> SEQ ID NO 1527
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1527
tccttcacat cctgcaaacg tcc                                                 23

<210> SEQ ID NO 1528
<211> LENGTH: 22
<212> TYPE: DNA
<213> ORGANISM: Artificial Sequence
<220> FEATURE:
```

-continued

```
<223> OTHER INFORMATION: Description of Artificial Sequence: Synthetic
      primer

<400> SEQUENCE: 1528
ttacgcacac gccatgggtt ag                                          22

<210> SEQ ID NO 1529
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1529
cgtgacgtgg gcctaaacc                                              19
```